(12) United States Patent
Diener et al.

(10) Patent No.: US 12,410,255 B2
(45) Date of Patent: Sep. 9, 2025

(54) NATRIURETIC PEPTIDE RECEPTOR 1 ANTIBODIES AND METHODS OF USE

(71) Applicant: NOVARTIS AG, Basel (CH)

(72) Inventors: John Louis Diener, Cambridge, MA (US); Lars Gadtke, Munich (DE); Felix Hartlepp, Munich (DE); Tiancen Hu, Woodbridge, CT (US); Kathrin Ladetzki-Baehs, Planegg (DE); Michael John Romanowski, Lexington, MA (US); Cesare Russo, Bachlettenstrasse (CH); Xenia Wezler, Munich (DE); Xiaoling Xie, Cambridge, MA (US)

(73) Assignee: NOVARTIS AG, Basel (CH)

(*) Notice: Subject to any disclaimer, the term of this patent is extended or adjusted under 35 U.S.C. 154(b) by 66 days.

(21) Appl. No.: 18/193,581

(22) Filed: Mar. 30, 2023

(65) Prior Publication Data

US 2023/0365674 A1    Nov. 16, 2023

Related U.S. Application Data

(62) Division of application No. 17/348,949, filed on Jun. 16, 2021, now abandoned, which is a division of application No. 16/897,935, filed on Jun. 10, 2020, now Pat. No. 11,066,469.

(60) Provisional application No. 62/860,508, filed on Jun. 12, 2019.

(51) Int. Cl.
| | | |
|---|---|---|
| *C07K 16/28* | (2006.01) | |
| *C12N 15/63* | (2006.01) | |
| *A61K 39/00* | (2006.01) | |
| *A61K 39/395* | (2006.01) | |
| *A61K 45/06* | (2006.01) | |
| *A61P 9/00* | (2006.01) | |
| *A61P 13/12* | (2006.01) | |
| *C07K 14/58* | (2006.01) | |
| *C07K 14/72* | (2006.01) | |

(52) U.S. Cl.
CPC .......... *C07K 16/2869* (2013.01); *C12N 15/63* (2013.01); *A61K 39/3955* (2013.01); *A61K 2039/505* (2013.01); *A61K 45/06* (2013.01); *A61P 9/00* (2018.01); *A61P 13/12* (2018.01); *C07K 14/58* (2013.01); *C07K 14/72* (2013.01); *C07K 2317/50* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/75* (2013.01)

(58) Field of Classification Search
CPC . C07K 16/2869; A61K 39/3955; C12N 15/63
See application file for complete search history.

(56) References Cited

U.S. PATENT DOCUMENTS

| | | |
|---|---|---|
| 9,090,695 B2 | 7/2015 | Waterman et al. |
| 9,987,330 B2 | 6/2018 | Hoon et al. |
| 10,184,942 B2 | 1/2019 | Mohapatra et al. |
| 2004/0253242 A1 | 12/2004 | Bowdish et al. |
| 2008/0181903 A1 | 7/2008 | Bhaskar et al. |
| 2008/0214437 A1 | 9/2008 | Mohapatra et al. |
| 2012/0270923 A1 | 10/2012 | Mohapatra et al. |
| 2014/0343120 A1 | 11/2014 | Mohapatra et al. |
| 2016/0168251 A1 | 6/2016 | Waterman et al. |

FOREIGN PATENT DOCUMENTS

| | | |
|---|---|---|
| CN | 104059154 A | 9/2014 |
| WO | 9100292 A1 | 1/1991 |
| WO | 0179231 A2 | 10/2001 |
| WO | 0236688 A2 | 5/2002 |
| WO | 0246238 A2 | 6/2002 |
| WO | 02078683 A1 | 10/2002 |
| WO | 2004050017 A2 | 6/2004 |
| WO | 2004108078 A2 | 12/2004 |
| WO | 2005060642 A2 | 7/2005 |
| WO | 2007070175 A2 | 6/2007 |
| WO | 2007115164 A2 | 10/2007 |
| WO | 2007115175 A2 | 10/2007 |
| WO | 2007115182 A2 | 10/2007 |
| WO | 2008151257 A2 | 12/2008 |
| WO | 2009006732 A1 | 1/2009 |
| WO | 2009015011 A1 | 1/2009 |
| WO | 2009036448 A2 | 3/2009 |
| WO | 2009073527 A2 | 6/2009 |
| WO | 2009142307 A1 | 11/2009 |
| WO | 2009149278 A1 | 12/2009 |
| WO | 2009149279 A1 | 12/2009 |
| WO | 2010009319 A2 | 1/2010 |
| WO | 2010065293 A1 | 6/2010 |
| WO | 2010135541 A2 | 11/2010 |
| WO | 2011069038 A2 | 6/2011 |
| WO | 2012019237 A1 | 2/2012 |
| WO | 2012088608 A1 | 7/2012 |

(Continued)

OTHER PUBLICATIONS

Badri, et al., Optimization of radiation dosing schedulesfor proneural glioblastoma, J. Math. Biol., 2016, 1301-1336, 72.

(Continued)

*Primary Examiner* — Zachary C Howard
(74) *Attorney, Agent, or Firm* — Sansun Yeh

(57) ABSTRACT

This disclosure relates to anti-Natriuretic Peptide Receptor 1 (NPR1) antibodies including agonist antibodies which are able to activate the NPR1 receptor, pharmaceutical compositions comprising the same, and methods of treatment comprising the same.

12 Claims, 40 Drawing Sheets

Specification includes a Sequence Listing.

(56) References Cited

FOREIGN PATENT DOCUMENTS

| WO | 2012110842 A1 | 8/2012 |
|---|---|---|
| WO | 2012118042 A1 | 9/2012 |
| WO | 2013027680 A1 | 2/2013 |
| WO | 2014115797 A1 | 7/2014 |
| WO | 2015085055 A2 | 6/2015 |
| WO | 2016033699 A1 | 3/2016 |
| WO | 2016131943 A1 | 8/2016 |
| WO | 2017082186 A1 | 5/2017 |
| WO | 2017156310 A1 | 9/2017 |
| WO | 2018034622 A1 | 2/2018 |
| WO | 2020086406 A2 | 4/2020 |
| WO | 2020236690 A1 | 11/2020 |
| WO | 2020250159 A1 | 12/2020 |

OTHER PUBLICATIONS

Baylot, et al., Chapter 13: TCTP Has a Crucial Role in the Different Stages of Prostate Cancer Malignant Progression, TCTP/tpt1—Remodeling Signaling from Stem Cell to Disease, 2017, 255-261, 64.

Maslov, et al., The Role of Natriuretic Peptides and Erythropoietin in the Regulation of Cardiac Tolerance to the Impact of Ischemia and Reperfusion. Analysis of Experimental and Clinical Data, Russian Journal of Physiology, Feb. 1, 2019, 24-35, 105(1).

Muller, et al., Spliceosomal peptide P140 for immunotherapy of systemic lupus erythematosus: results of an early phase II clinical trial, Arthritis & Rheumatism, Dec. 2008, 3873-3883, 58(12).

Arora, P et al., Atrial nalriuretic peptide is negatively regulated by microRNA-425, The Journal of Clinical Investigation, 2013, 3378-3382, 123(8).

Blech, M. et al., Structure of a Therapeutic Full-Length Anti-NPRA IgG4 Antibody: Dissecting Conformational Diversity, Biophysical Journal, May 1, 2019, 1637-1649, 11(9).

Cui, Y et al., Role of corin in trophoblast invasion and uterine spiral artery remodelling in pregnancy, Nature, 2012, 246-252, 484.

Dries, D. L. et al., Corin Gene Minor Allele Defined by 2 Missense Mutations Is Common in Blacks and Associated with High Blood Pressure and Hypertension, Circulation, 2005, 2403-2410, 112.

Ellmers L. J. et al., Npr1-regulated gene pathways contributing to cardiac hypertrophy and fibrosis, Journal of Molecular Endocrinology, Feb. 2007, 245-57, 38(1-2).

Hodgson-Zingman, D. M. et al., Atrial Nalriuretic Peptide Frameshift Mutation in Familial Atrial Fibrillation, The New England Journal of Medicine, 2008, 158-165, 359(2).

Kitano K. et al., Production and characterization of monoclonal antibodies against human nalriuretic peptide receptor-A or-B, Immunol. Lett., Sep. 1995, 215-22, 47(3).

List, K. et al., Different mechanisms are involved in the antibody mediated inhibition of ligand binding to the urokinase receptor: a study based on biosenser technology, Journal of Immunological Methods, 1999, 125-133, 222.

Lowe D. G. et al., Human atrial natriuretic peptide receptor defines a new paradigm for second messenger signal transduction, The EMBO Journal, 1989, 1377-1384., 8(5).

Lowe D. G. et al., Human natriuretic peptide receptor-A guanylyl cyclase. Hormone cross-linking and antibody reactivity distinguish receptor glycoforms, Journal Biol. Chem., Oct. 25, 1992, 21691-7., 267(30).

Lui, C. et al., Meta-analysis identifies common and rare variants influencing blood pressure and overlapping with metabolic trait loci, Nature Genetics, Oct. 2016, 1162-1170, 48(10).

Ma et al., Atrial natriuretic peptide/natriuretic peptide receptor A (ANP/NPRA) signaling pathway: A potential therapeutic target for allergic asthma, Medical Hypotheses, 2011, 832-33, 77.

Mezo, Adam R. et al., Atrial Natriuretic Peptide-Fc, ANP-Fc, Fusion Proteins: Semisynthesis, In Vitro Activity and Pharmacokinelics in Rais, Bioconjugate Chemistry, 2012, 518-526., 23(3).

Mumey, Brendan M. et al., A New Method for Mapping Discontinuous Antibody Epilopes to Reveal Structural Features of Proteins, Journal of Computational Biology, 2003, 555-567, 10(3-4).

Notification of Transmittal of The International Search Report and The Written Opinion of The International Searching Authority, or The Declaration, Mailed on Sep. 16, 2020, issued in International Patent Application No. PCT/IB2020/055468, filed Jun. 10, 2020.

Oliver P. M. et al., Hypertension, cardiac hypertrophy, and sudden death in mice lacking natriurelic peptide receptor A, Proc. Nall. Acad. Sci.US A., Dec. 23, 1997, 14730-5., 94(26).

Potter, L. et al., Natriurelic Peptides: Their Structures, Receptors, Physiologic Functions and Therapeutic Applications, Handbook of Experimental Pharmacology, 2009, 341-66., 191.

Rame, J. E. et al., Dysfunctional Corin I555(P568) Allele Is Associated With Impaired Brain Natriuretic Peptide Processing and Adverse Outcomes in Blacks With Systolic Heart Failure (Results From the Genetic Risk Assessment in Heart Failure Substudy), Cir. Heart Fail., 2009, 541-548, 2.

Rondeau, Jean Jacques et al_, Production of polyclonal antibody to the bovine adrenal atrial natriurelic factor-R1 receptor, Journal of Receptor Research, 1992, 485-505., 12(4).

Saito, Yoshihiko, Roles of atrial natriuretic peptide and its therapeutic use, Journal of Cardiology, 2010, 262-270, 56.

Vellaichamy, E. et al., Genetically Altered Mutant Mouse Models of Guanylyl Cyclase/Natriurelic Peptide Receptor-A Exhibit the Cardiac Expression of Proinflammatory Mediators in a Gene-Dose-Dependent Manner, Endocrinology, Mar. 2014, 1045-1056., 155(3).

Vellaichamy, et al., Reduced cGMP signaling activates NF-kB in hypertrophied hearts of mice lacking natriuretic peptide receptor-A, Biochemical and Biophysical Research Communications, 327, 106-111, 2005.

U.S. Appl. No. 18/193,581, filed Mar. 30, 2023, Natriuretic Peptide Receptor 1 Antibodies and Methods of Use.

NATRIURETIC PEPTIDE RECEPTOR 1 ANTIBODIES AND METHODS OF USE

RELATED APPLICATIONS

This application is a divisional of U.S. patent application Ser. No. 17/348,949, filed Jun. 16, 2021, which is a direct filing of U.S. patent application Ser. No. 16/897,935, filed Jun. 10, 2020, which claims the benefit of and priority to U.S. Provisional Application No. 62/860,508 filed Jun. 12, 2019, the entire contents of each of which are incorporated herein by reference in its entirety.

SEQUENCE LISTING

The instant application contains a Sequence Listing which has been submitted electronically herewith and is hereby incorporated by reference in its entirety. This sequence listing is named PAT058321-US-DIV02_SL.

BACKGROUND

Heart failure is a major public health problem concerning more than 20 million patients around the world (Orso et al., 2014, Expert Opin Pharmacother. 15 (13): 1849-1861) and is associated with high morbidity (Ibebuogu et al., 2011, Circulation. Heart failure 4 (2): 114-120). Natriuretic Peptide Receptor 1 (NPR1; also known as NPRA) is a receptor guanylate cyclase, which is activated by Atrial Natriuretic Peptide (ANP) resulting in lowering of blood pressure and blood volume (Chen & Burnett, 2006, European Heart Journal Supplements 8 (Suppl E): E18-E25; Ibebuogu et al. 2011, supra; Mani et al. 2015, Bioscience Reports 35 (5): e00260). ANP binding induces dimerization and twisting of the receptor that induces activation of the guanylate cyclase domain and conversion of GTP into cGMP (Misono et al., 2011, The FEBS journal 278 (11): 1818-1829). ANP is cleared by NPR3, a natriuretic peptide receptor that lacks the guanylate cyclase domain, and degraded by Neutral Endopeptidase (NEP) (Chen & Burnett 2006, supra; Schmitt et al., 2003, Clin Sci (Lond). 105 (2): 141-160). Certain antibodies against NPR1 have been described, for example, in WO2010/065293 (including antibody 5591-IgG). However, these antibodies appeared to have no functional activity in the absence of ANP in vitro and no functional activity in vivo.

It has been shown that an increase in ANP may be beneficial for patients with heart failure with reduced ejection fraction (outbound pumping of blood by heart). See McMurray et al., N. Engl. J. Med.; Vol. 371, No. 11, pp 993-1004 (2014); and Nougué et al., Eur J Heart Fail. 2019 May; 21 (5): 598-605. However, there is a need for further longer acting agents that have an alternative mode of action to supplement or replace existing therapies.

SUMMARY OF THE DISCLOSURE

Herein is demonstrated that it is possible to activate NPR1 by the use of agonistic anti-NPR1 antibodies or antigen binding fragments thereof. Furthermore, the present disclosure demonstrates that there are two types of such antibodies. While one type binds to NPR1 and competes with ANP binding (yet still activates NPR1; hereinafter "ANP competitive" anti-NPR1 antibodies), the second type is able to bind and activate NPR1 while not competing with ANP (hereinafter "ANP non-competitive" anti-NPR1 antibodies). Such antibodies (e.g., ANP non-competitive anti-NPR1 antibodies) may be used to bolster the body's natural system and/or existing treatment rationales. Furthermore, certain NPR1 agonist antibodies that are able to activate NPR1 in the absence of ANP have been found to be functionally equivalent to ANP.

The antibodies of the instant application show in vivo activity in both mouse and rat. Furthermore, the unique epitope binding of the antibodies described herein has been demonstrated using crystal structure data.

Thus the disclosure provides anti-NPR1 antibodies (e.g., human monoclonal antibodies) or antigen-binding fragments thereof that (i) bind to natriuretic peptide receptor 1 (NPR1); and (ii) are capable of activating NPR1 in the absence of ANP. Such antibodies are agonistic anti-NPR1 antibodies. In some embodiments of the invention, the disclosure also provides anti-NPR1 antibodies or antigen binding fragments thereof that (i) bind to natriuretic peptide receptor 1 (NPR1); and (ii) activate NPR1 in the absence of ANP. In some embodiments of the invention, the disclosure also provides antibodies or antigen binding fragments thereof that (i) bind to natriuretic peptide receptor 1 (NPR1); and (ii) activate NPR1 in both the presence and absence of ANP. Also provided are nucleic acids encoding said antibodies, vectors comprising said nucleic acids, host cells comprising said nucleic acids and/or vectors, and methods of manufacture of said antibodies using said nucleic acids, vectors and/or host cells. Also provided are pharmaceutical compositions and combinations comprising said antibodies, nucleic acids, vectors or host cells, as well as methods of treatment using said antibodies, nucleic acids, vectors, host cells or pharmaceutical compositions. The use of said antibodies, nucleic acids, vectors, host cells or pharmaceutical compositions or combinations in treating disease is also disclosed herein.

Thus, in one aspect of the invention, herein is provided an isolated antibody or antigen binding fragment that (i) binds to natriuretic peptide receptor 1 (NPR1); and (ii) is capable of activating NPR1 in the absence of atrial natriuretic peptide (ANP). In some embodiments of the invention, the isolated antibody or antigen binding fragment does not bind to and/or does not activate natriuretic peptide receptor 2 (NPR2) and/or natriuretic peptide receptor 3 (NPR3). In some embodiments of the invention, the isolated antibody or antigen binding fragment binds to (a) human NPR1; and (b) mouse NPR1 and/or rat NPR1.

In some embodiments of the invention, the antibody or antigen binding fragment binds to (a) human NPR1; and (b) cyno NPR1. In some embodiments of the invention, the antibody or antigen binding fragment is ANP non-competitive. In some embodiments of the invention, the antibody or antigen binding fragment is ANP competitive. In some embodiments of the invention, the antibody or antigen binding fragment is capable of stabilizing the ANP-NPR1 complex.

In some embodiments of the invention, the antibody or antigen binding fragment binds to an epitope within amino acids 99-133 of SEQ ID NO: 1, e.g., within a region of human NPR1 encompassed by amino acids 99-133 of SEQ ID NO: 1. In some embodiments of the invention, the antibody or antigen binding fragment binds to an epitope comprising at least two amino acid residues within amino acids 99-133 of SEQ ID NO: 1. In some embodiments of the invention, the antibody or antigen binding fragment binds to an epitope comprising at least 3, 4, 5, 6, 7, or 8 amino acid residues within amino acids 99-133 of SEQ ID NO: 1.

In some embodiments of the invention, the antibody or antigen binding fragment binds to an epitope within amino acids 99-111 of SEQ ID NO: 1. In some embodiments of the invention, the antibody or antigen binding fragment binds to an epitope within amino acids 99-103 of SEQ ID NO: 1. In some embodiments of the invention, the antibody or antigen binding fragment binds to an epitope within amino acids 105-111 of SEQ ID NO: 1. In some embodiments of the invention, the antibody or antigen binding fragment binds to an epitope comprising at least 2, 3, or 4 amino acid residues within amino acids 105-111 of SEQ ID NO: 1. In some embodiments of the invention, the antibody or antigen binding fragment binds to a conformational epitope of human NPR1, and wherein the conformational epitope comprises at least one amino acid residue within each of (i) amino acids 99-103 of SEQ ID NO: 1, (ii) 105-111 of SEQ ID NO: 1, (iii) 131-134 of SEQ ID NO: 1, and additionally binds to amino acid 375 and/or 378 of SEQ ID NO: 1. In some embodiments of the invention, the epitope is a conformational epitope, and the conformational epitope additionally comprises at least one amino acid residue selected from the group consisting of amino acids 33, 34, 76, 82, and 104 of SEQ ID NO: 1. In some embodiments of the invention, the conformational epitope additionally comprises at least one amino acid residue selected from the group consisting of amino acids 33, 34, 76, 82, 104, 374, and 375 of SEQ ID NO: 1.

In some embodiments of the invention, the antibody or antigen binding fragment binds to at least amino acids 82, 102, 103, 105, 106, 109, 132, and 375 of SEQ ID NO: 1. In some embodiments of the invention, the antibody or antigen binding fragment binds to at least amino acids 34, 82, 102, 103, 105, 106, 107, 109, 132, 133, 375, and 378 of SEQ ID NO: 1. In some embodiments of the invention, the antibody or antigen binding fragment binds to at least amino acids 79, 82, 99, 102, 103, 105, 106, 109, 131, 132, and 375 of SEQ ID NO: 1.

In some embodiments of the invention, the antibody or antigen binding fragment binds to an epitope within amino acids 188-219 of SEQ ID NO: 1. In some embodiments of the invention, the antibody or antigen binding fragment binds to an epitope comprising at least 2, 3, 4, 5, 6, or 7 amino acids within amino acids 188-219 of SEQ ID NO: 1. In some embodiments of the invention, the antibody or antigen binding fragment binds to a conformational epitope within NPR1, and the conformational epitope comprises at least one amino acid residue within each of (i) amino acids 188-198 of SEQ ID NO: 1, (ii) 201-208 of SEQ ID NO: 1, (iii) 215-238 of SEQ ID NO: 1, and (iv) 294-297 of SEQ ID NO: 1. In some embodiments of the invention, the antibody or antigen binding fragment binds to at least amino acids 188, 192, 194, 197, 201, 208, and 219 of SEQ ID NO: 1. In some embodiments of the invention, the antibody or antigen binding fragment binds to at least amino acids 188, 192, 194, 197, 201, 208, 219, and 295 of SEQ ID NO: 1.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $Y_1QY_2Y_3Y_4Y 5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1Y_2Y_3Y_4PR$ (SEQ ID NO: 432); wherein $Y_1$ is S, E, T, or I, $Y_2$ is Y or W, $Y_3$ is E, V, R, A, T, or M, and $Y_4$ is K, V, R, or A; or (IV) HCDR1 comprises or consists of an amino acid sequence as set forth in SEQ ID NO: 34, HCDR2 comprises or consists of an amino acid sequence as set forth in $IX_1SX_2GX_3YX_4$ (SEQ ID NO: 433), wherein $X_1$ is S or E, $X_2$ is D or K, $X_3$ is S or N, and $X_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (b) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A; (II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (III) HCDR1 comprises or consists of an amino acid sequence as set forth in SEQ ID NO: 32, HCDR2 comprises or consists of an amino acid sequence as set forth in X$_1$SX$_2$GX$_3$Y (SEQ ID NO: 431), wherein X$_1$ is S or E, X$_2$ is D or K, or X$_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in IX$_1$SX$_2$GX$_3$YX$_4$ (SEQ ID NO: 433), wherein X$_1$ is S or E, X$_2$ is D or K, X$_3$ is S or N, and X$_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (c) (I) HCDR1 comprises or consists of an amino acid sequence as set forth in SEQ ID NO: 28; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (II) HCDR1 comprises or consists of an amino acid sequence as set forth in SEQ ID NO: 31; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (III) HCDR1 comprises or consists of an amino acid sequence as set forth in SEQ ID NO: 32, HCDR2 comprises or consists of an amino acid sequence as set forth in SEQ ID NO: 120, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in SEQ ID NO: 121, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (d) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in Y$_1$Y$_2$Y$_3$GY$_4$Y$_5$ (SEQ ID NO: 439), wherein Y$_1$ is S or G, Y$_2$ is S or G, Y$_3$ is S or Q, Y$_4$ is S, Q, or G, and Y$_5$ is S, N, or M, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in IY$_1$Y$_2$Y$_3$GY$_4$Y$_5$T (SEQ ID NO: 441), wherein Y$_1$ is S or G, Y$_2$ is S or G, Y$_3$ is S or Q, Y$_4$ is S, Q, or G, and Y$_5$ is S, N, or M, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; (e) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SISY$_1$SGY$_2$Y$_3$TYYADSVKG (SEQ ID NO: 442), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in SISY$_1$SGY$_2$Y$_3$TYYADSVKG (SEQ ID NO: 442), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in SY$_1$SGY$_2$Y$_3$ (SEQ ID NO: 443), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in ISY$_1$SGY$_2$Y$_3$T (SEQ ID NO: 444), wherein Y$_1$ is S or G, Y$_2$ is S or Q, and Y$_3$ is S or N, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; (f) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in Y$_1$QY$_2$Y$_3$Y$_4$E (SEQ ID NO: 449), wherein Y$_1$ is K or H, Y$_2$ is S, Q, or H, Y$_3$ is G or A, and Y$_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IY$_1$QY$_2$Y$_3$Y$_4$EY$_5$ (SEQ ID NO: 451), wherein Y$_1$ is K or H, Y$_2$ is S, Q, or H, Y$_3$ is G or A, Y$_4$ is S, H, or L, and Y$_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; (g) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in HQY$_1$Y$_2$Y$_3$E (SEQ ID NO: 456), wherein Y$_1$ is Q or H, Y$_2$ is G or A, and Y$_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IHQY$_1$Y$_2$Y$_3$EY$_4$ (SEQ ID NO: 458), wherein Y$_1$ is Q or H, Y$_2$ is G or A, Y$_3$ is H or L, and Y$_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; (h) (I) HCDR1 comprises or consists of an amino acid sequence as set forth in GFTFSX$_1$YX$_2$IX$_3$ (SEQ ID NO: 452), wherein $X_1$ is S or R, $X_2$ is W or Y, and $X_3$ is S or N, HCDR2 comprises or consists of an amino acid sequence as set forth in $Y_1IY_2QY_3Y_4Y_5EY_6Y_7YVESVKG$ (SEQ ID NO: 446), wherein $Y_1$ is S or N, $Y_2$ is K or H, $Y_3$ is S, Q, or H, $Y_4$ is G or A, $Y_5$ is S, H, or L, $Y_6$ is T or K, and $Y_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in $X_1YX_2IX_3$ (SEQ ID NO: 454), wherein $X_1$ is S or R, $X_2$ is W or Y, and $X_3$ is S or N, HCDR2 comprises or consists of an amino acid sequence as set forth in $Y_1IY_2QY_3Y_4Y_5EY_6Y_7YVESVKG$ (SEQ ID NO: 446), wherein $Y_1$ is S or N, $Y_2$ is K or H, $Y_3$ is S, Q, or H, $Y_4$ is G or A, $Y_5$ is S, H, or L, $Y_6$ is T or K, and $Y_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in $GFTFSX_1Y$ (SEQ ID NO: 455), wherein $X_1$ is S or R, HCDR2 comprises or consists of an amino acid sequence as set forth in $Y_1QY_2Y_3Y_4E$ (SEQ ID NO: 449), wherein $Y_1$ is K or H, $Y_2$ is S, Q, or H, $Y_3$ is G or A, and $Y_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in $GFTFSX_1YX_2$ (SEQ ID NO: 457), wherein $X_1$ is S or R, and $X_2$ is W or Y, HCDR2 comprises or consists of an amino acid sequence as set forth in $IY_1QY_2Y_3Y_4EY_5$ (SEQ ID NO: 451), wherein $Y_1$ is K or H, $Y_2$ is S, Q, or H, $Y_3$ is G or A, $Y_4$ is S, H, or L, and $Y_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; or (i) (I) HCDR1 comprises or consists of an amino acid sequence as set forth in $GFTFSX_1YX_2IX_3$ (SEQ ID NO: 452), wherein $X_1$ is S or R, $X_2$ is W or Y, and $X_3$ is S or N, HCDR2 comprises or consists of an amino acid sequence as set forth in $SIHQY_1Y_2Y_3EY_4Y_5YVESVKG$ (SEQ ID NO: 453), wherein $Y_1$ is Q or H, $Y_2$ is G or A, $Y_3$ is H or L, $Y_4$ is T or K, and $Y_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in $X_1YX_2IX_3$ (SEQ ID NO: 454), wherein $X_1$ is S or R, $X_2$ is W or Y, and $X_3$ is S or N, HCDR2 comprises or consists of an amino acid sequence as set forth in $SIHQY_1Y_2Y_3EY_4Y_5YVESVKG$ (SEQ ID NO: 453), wherein $Y_1$ is Q or H, $Y_2$ is G or A, $Y_3$ is H or L, $Y_4$ is T or K, and $Y_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in $GFTFSX_1Y$ (SEQ ID NO: 455), wherein $X_1$ is S or R, HCDR2 comprises or consists of an amino acid sequence as set forth in $HQY_1Y_2Y_3E$ (SEQ ID NO: 456), wherein $Y_1$ is Q or H, $Y_2$ is G or A, and $Y_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in $GFTFSX_1YX_2$ (SEQ ID NO: 457), wherein $X_1$ is S or R, and $X_2$ is W or Y, HCDR2 comprises or consists of an amino acid sequence as set forth in $IHQY_1Y_2Y_3EY_4$ (SEQ ID NO: 458), wherein $Y_1$ is Q or H, $Y_2$ is G or A, $Y_3$ is H or L, and $Y_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 320, LCDR2 comprises or consists of an amino acid sequence as set forth in $GNSNRPY_1$ (SEQ ID NO: 460), wherein $Y_1$ is S or N, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; (II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 320, LCDR2 comprises or consists of an amino acid sequence as set forth in $GNSNRPY_1$ (SEQ ID NO: 460), wherein $Y_1$ is S or N, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; (III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in $GX_1X_2X_3GX_4LGFDH$ (SEQ ID NO: 459), wherein $X_1$ is A or S, $X_2$ is V or L, $X_3$ is A or P, and $X_4$ is Q or L, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in $YZ_1Z_2Z_3Z_4Z_5Z_6Z_7$ (SEQ ID NO: 462), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in $ARGX_1X_2X_3GX_4LGFDH$ (SEQ ID NO: 463), wherein $X_1$ is A or S, $X_2$ is V or L, $X_3$ is A or P, and $X_4$ is Q or L, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in $QSYZ_1Z_2Z_3Z_4Z_5Z_6Z_7V$ (SEQ ID NO: 461), wherein $Z_1$ is Y, D, or G, $Z_2$ is T, S, or A, $Z_3$ is S, P, or F, $Z_4$ is S, T, or P, $Z_5$ is H, S, or R, $Z_6$ is G, S, or F, and $Z_7$ is P, S, or V; (b) (I) HCDR1 comprises or consists of an amino acid sequence as set forth in $GFTFX_1X_2YAX_3X_4$ (SEQ ID NO: 464), wherein $X_1$ is S or G, $X_2$ is S or T, $X_3$ is I or M, and $X_4$ is S or T, HCDR2 comprises or consists of an amino acid sequence as set forth in $Y_1ISY_2Y_3GY_4Y_5Y_6Y_7YAY_8SVKG$ (SEQ ID NO: 465), wherein $Y_1$ is A or S, $Y_2$ is A, S, or G, $Y_3$ is S or H, $Y_4$ is G or Y, $Y_5$ is S or Y, $Y_6$ is T or A, $Y_7$ is Y, R, or N, and $Y_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in $X_1YAX_2X_3$ (SEQ ID NO: 466), wherein $X_1$ is S or T, $X_2$ is I or M, and $X_3$ is S or T, HCDR2 comprises or consists of an amino acid sequence as set forth in $Y_1ISY_2Y_3GY_4Y_5Y_6Y_7YAY_8SVKG$ (SEQ ID NO: 465), wherein $Y_1$ is A or S, $Y_2$ is A, S, or G, $Y_3$ is S or H, $Y_4$ is G or Y, $Y_5$ is S or Y, $Y_6$ is T or A, $Y_7$ is Y, R, or N, and $Y_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in $GFTFX_1X_2Y$ (SEQ ID NO: 467), wherein $X_1$ is S or G, and $X_2$ is S or T, HCDR2 comprises or consists of an amino acid sequence as set forth in $SY_1Y_2GY_3Y_4$ (SEQ ID NO: 468), wherein $Y_1$ is A, S, or G, $Y_2$ is S or H, $Y_3$ is G or Y, and $Y_4$ is S or Y, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in $GFTFX_1X_2YA$ (SEQ ID NO: 469), wherein $X_1$ is S or G, and $X_2$ is S or T, HCDR2 comprises or consists of an amino acid sequence as set forth in $ISY_1Y_2GY_3Y_4T$ (SEQ ID NO: 470), wherein $Y_1$ is S or G, $Y_2$ is S or H, $Y_3$ is G or Y, and $Y_4$ is S or Y, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339; or (c) (I) HCDR1 comprises or consists of an amino acid sequence as set forth in $GFTFX_1X_2YAX_3X_4$ (SEQ ID NO: 464), wherein $X_1$ is S or G, $X_2$ is S or T, $X_3$ is I or M, and $X_4$ is S or T, HCDR2 comprises or consists of an amino acid sequence as set forth in $SISY_1Y_2GYYY_3Y_4YAY_5SVKG$ (SEQ ID NO: 471), wherein $Y_1$ is A or S, $Y_2$ is S or H, $Y_3$ is T or A, $Y_4$ is R or N, and $Y_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in $X_1YAX_2X_3$ (SEQ ID NO: 466), wherein $X_1$ is S or T, $X_2$ is I or M, and $X_3$ is S or T, HCDR2 comprises or consists of an amino acid sequence as set forth in $SISY_1Y_2GYYY_3Y_4YAY_5SVKG$ (SEQ ID NO: 471), wherein $Y_1$ is A or S, $Y_2$ is S or H, $Y_3$ is T or A, $Y_4$ is R or N, and $Y_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in $GFTFX_1X_2Y$ (SEQ ID NO: 467), wherein $X_1$ is S or G, and $X_2$ is S or T, HCDR2 comprises or consists of an amino acid sequence as set forth in $SY_1Y_2GYY$ (SEQ ID NO: 472), wherein $Y_1$ is A or S, and $Y_2$ is S or H, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in $GFTFX_1X_2YA$ (SEQ ID NO: 469), wherein $X_1$ is S or G, and $X_2$ is S or T, HCDR2 comprises or consists of an amino acid sequence as set forth in $ISY_1Y_2G$ (SEQ ID NO: 473), wherein $Y_1$ is A, S, or G, and $Y_2$ is S or H, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 28, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (II) HCDR1 comprises or consists of an amino acid sequence as set forth in SEQ ID NO: 31, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (III) HCDR1 comprises or consists of an amino acid sequence as set forth in SEQ ID NO: 32, HCDR2 comprises or consists of an amino acid sequence as set forth in any one of SEQ ID NOs: 33, 120, and 191, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in any one of SEQ ID NOs: 46, 127, 135, 146, 173, 179, and 185; or (IV) HCDR1 comprises or consists of an amino acid sequence as set forth in SEQ ID NO: 34, HCDR2 comprises or consists of an amino acid sequence as set forth in any one of SEQ ID NOs: 35, 121, and 192, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in any one of SEQ ID NOs: 43, 126, 134, 145, 172, 178, and 184; (b) (I) HCDR1 comprises or consists of an amino acid sequence as set forth in any one of SEQ ID NOs: 4, 112, and 165, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in any one of SEQ ID NOs: 8, 113, and 166, HCDR2 comprises or consists of an amino acid sequence as set forth in any one of SEQ ID NOs: 9, 101, and 152, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in any one of SEQ ID NOs: 10, 114, and 167, HCDR2 comprises or consists of an amino acid sequence as set forth in any one of SEQ ID NOs: 11, 102, and 153, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; or (c) (I) HCDR1 comprises or consists of an amino acid sequence as set forth in any one of SEQ ID NOs: 226, 367, and 378, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in any one of SEQ ID NOs: 229, 369, and 380, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in any one of SEQ ID NOs: 32, 370, and 381, HCDR2 comprises or consists of an amino acid sequence as set forth in any one of SEQ ID NOs: 230, 371, and 382, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in any one of SEQ ID NOs: 34, 372, and 383, HCDR2 comprises or consists of an amino acid sequence as set forth in any one of SEQ ID NOs: 231, 373, and 384, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in any one of SEQ ID NOs: 312 and 348, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in any one of SEQ ID NOs: 325, 356, and 362; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in any one of SEQ ID NOs: 315 and 349, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in any one of SEQ ID NOs: 322, 355, and 361; or (b) (I) HCDR1 comprises or consists of an amino acid sequence as set forth in any one of SEQ ID NOs: 270 and 407, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in any one of SEQ ID NOs: 273 and 409, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in any one of SEQ ID NOs: 32 and 410, HCDR2 comprises or consists of an amino acid sequence as set forth in any one of SEQ ID NOs: 274, 390, and 411, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in any one of SEQ ID NOs: 275 and 412, HCDR2 comprises or consists of an amino acid sequence as set forth in any one of SEQ ID NOs: 276, 391, and 413, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (a) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3); (b) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3); (c) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3); (d) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3); (e) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120

(HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3); (f) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3); (g) (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3); (h) (I) SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3); (i) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3); (j) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3); (k) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3); (1) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3); (m) (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3); (n) (I) SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3); (o) (I) SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3); (p) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173

(LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3); (q) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3); (r) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3); (s) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3); (t) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3); (u) (I) SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3); (v) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3); (w) (I) SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3); (x) (I) SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3); (y) (I) SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3); (z) (I) SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (II) SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (III) SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3); or (IV) SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3); or (aa) (I) SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (II) SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (III) SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3); or (IV)

SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3).

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (a) (I) SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (II) SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (III) SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3); or (IV) SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3); (b) (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3); (c) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3); (d) (I) SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3); (e) (I) SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3); (f) (I) SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (II) SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (III) SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3); or (IV) SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3); (g) (I) SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3); or (h) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3).

In some embodiments of the invention, the antibody or antigen binding fragment comprises: (a) a heavy chain variable region comprising an amino acid sequence of SEQ ID NO: 201, and a light chain variable region comprising an amino acid sequence of SEQ ID NO: 136; (b) a heavy chain variable region comprising an amino acid sequence of SEQ ID NO: 122, and a light chain variable region comprising an amino acid sequence of SEQ ID NO: 136; (c) a heavy chain variable region comprising an amino acid sequence of SEQ ID NO: 201, and a light chain variable region comprising an amino acid sequence of SEQ ID NO: 128; (d) a heavy chain variable region comprising an amino acid sequence of SEQ ID NO: 122, and a light chain variable region comprising an amino acid sequence of SEQ ID NO: 128; (e) a heavy chain variable region comprising an amino acid sequence of SEQ ID NO: 201, and a light chain variable region comprising an amino acid sequence of SEQ ID NO: 147; (f) a heavy chain variable region comprising an amino acid sequence of SEQ ID NO: 122, and a light chain variable region comprising an amino acid sequence of SEQ ID NO: 147; (g) a heavy chain variable region comprising an amino acid sequence of SEQ ID NO: 201, and a light chain variable region comprising an amino acid sequence of SEQ ID NO: 174; (h) a heavy chain variable region comprising an amino acid sequence of SEQ ID NO: 122, and a light chain variable region comprising an amino acid sequence of SEQ ID NO: 174; (i) a heavy chain variable region comprising an amino acid sequence of SEQ ID NO: 201, and a light chain variable region comprising an amino acid sequence of SEQ ID NO: 180; (j) a heavy chain variable region comprising an amino acid sequence of SEQ ID NO: 122, and a light chain variable region comprising an amino acid sequence of SEQ ID NO: 180; (k) a heavy chain variable region comprising an amino acid sequence of SEQ ID NO: 201, and a light chain variable region comprising an amino acid sequence of SEQ ID NO: 186; (l) a heavy chain variable region comprising an amino acid sequence of SEQ ID NO: 122, and a light chain variable region comprising an amino acid sequence of SEQ ID NO: 186; (m) a heavy chain variable region comprising an amino acid sequence of SEQ ID NO: 103, and a light chain variable region comprising an amino acid sequence of SEQ ID NO: 24; (n) a heavy chain variable region comprising an amino acid sequence of SEQ ID NO: 115, and a light chain variable region comprising an amino acid sequence of SEQ ID NO: 24; (0) a heavy chain variable region comprising an amino acid sequence of SEQ ID NO: 122, and a light chain variable region comprising an amino acid sequence of SEQ ID NO: 48; (p) a heavy chain variable region comprising an amino acid sequence of SEQ ID NO: 37, and a light chain variable region comprising an amino acid sequence of SEQ ID NO: 128; (q) a heavy chain variable region comprising an amino acid sequence of SEQ ID NO: 37, and a light chain variable region comprising an amino acid sequence of SEQ ID NO: 136; (r) a heavy chain variable region comprising an amino acid sequence of SEQ ID NO: 37, and a light chain variable region comprising an amino acid sequence of SEQ ID NO: 147; (s) a heavy chain variable region comprising an amino acid sequence of SEQ ID NO: 154, and a light chain variable region comprising an amino acid sequence of SEQ ID NO: 24; (t) a heavy chain variable region comprising an amino acid sequence of SEQ ID NO: 161, and a light chain variable region comprising an amino acid sequence of SEQ ID NO: 24; (u) a heavy chain variable region comprising an amino acid sequence of SEQ ID NO: 168, and a light chain variable region comprising an amino acid sequence of SEQ ID NO: 24; (v) a heavy chain variable region comprising an amino acid sequence of SEQ ID NO: 37, and a light chain variable region comprising an amino acid sequence of SEQ ID NO: 174; (w) a heavy chain variable region comprising an amino acid sequence of SEQ ID NO: 37, and a light chain variable region comprising an amino acid sequence of SEQ ID NO: 180; (x) a heavy chain variable region comprising an amino acid sequence of SEQ ID NO: 37, and a light chain variable region comprising an amino acid sequence of SEQ ID NO: 186; (y) a heavy chain variable region comprising an amino acid sequence of SEQ ID NO: 193, and a light chain variable region comprising an amino acid sequence of SEQ ID NO: 136; (z) a heavy chain variable region comprising an amino acid sequence of SEQ ID NO: 193, and a light chain variable region comprising an amino acid sequence of SEQ ID NO: 174; (aa) a heavy chain variable region comprising an amino acid sequence of SEQ ID NO: 13, and a light chain variable region comprising an amino acid sequence of SEQ ID NO: 24; (bb) a heavy chain variable region comprising an amino acid sequence of SEQ ID NO: 37, and a light chain variable region comprising an amino acid sequence of SEQ ID NO: 48; (cc) a heavy chain variable region comprising an amino acid sequence of SEQ ID NO: 374, and a light chain variable region comprising an amino acid sequence of SEQ ID NO: 244; (dd) a heavy chain variable region comprising an amino acid sequence of SEQ ID NO: 385, and a light chain variable region comprising an amino acid sequence of SEQ ID NO: 244; (ee) a heavy chain variable region comprising an amino acid sequence of SEQ ID NO: 233, and a light chain variable region comprising an amino acid sequence of SEQ ID NO: 244; (ff) a heavy chain variable region comprising an amino acid sequence of SEQ ID NO: 278, and a light chain variable region comprising an amino acid sequence of SEQ ID NO: 287; or (gg) a heavy chain variable region comprising an amino acid sequence of SEQ ID NO: 300, and a light chain variable region comprising an amino acid sequence of SEQ ID NO: 306.

In some embodiments of the invention, the antibody or antigen binding fragment comprises: (a) a heavy chain variable region comprising an amino acid sequence of SEQ ID NO: 61, and a light chain variable region comprising an amino acid sequence of SEQ ID NO: 72; (b) a heavy chain variable region comprising an amino acid sequence of SEQ ID NO: 85, and a light chain variable region comprising an amino acid sequence of SEQ ID NO: 96; (c) a heavy chain variable region comprising an amino acid sequence of SEQ ID NO: 350, and a light chain variable region comprising an amino acid sequence of SEQ ID NO: 363; (d) a heavy chain variable region comprising an amino acid sequence of SEQ ID NO: 392, and a light chain variable region comprising an amino acid sequence of SEQ ID NO: 344; (e) a heavy chain variable region comprising an amino acid sequence of SEQ ID NO: 414, and a light chain variable region comprising an amino acid sequence of SEQ ID NO: 344; (f) a heavy chain variable region comprising an amino acid sequence of SEQ ID NO: 316, and a light chain variable region comprising an amino acid sequence of SEQ ID NO: 327; (g) a heavy chain variable region comprising an amino acid sequence of SEQ ID NO: 333, and a light chain variable region comprising an amino acid sequence of SEQ ID NO: 344; or (h) a heavy chain variable region comprising an amino acid sequence of SEQ ID NO: 350, and a light chain variable region comprising an amino acid sequence of SEQ ID NO: 357.

In some embodiments of the invention, the antibody or antigen binding fragment comprises: (a) a heavy chain comprising an amino acid sequence of SEQ ID NO: 203, and a light chain comprising an amino acid sequence of SEQ ID NO: 138; (b) a heavy chain comprising an amino acid sequence of SEQ ID NO: 208, and a light chain comprising an amino acid sequence of SEQ ID NO: 138; (c) a heavy chain comprising an amino acid sequence of SEQ ID NO: 203, and a light chain comprising an amino acid sequence of SEQ ID NO: 130; (d) a heavy chain comprising an amino acid sequence of SEQ ID NO: 208, and a light chain comprising an amino acid sequence of SEQ ID NO: 130; (e) a heavy chain comprising an amino acid sequence of SEQ ID NO: 203, and a light chain comprising an amino acid sequence of SEQ ID NO: 149; (f) a heavy chain comprising an amino acid sequence of SEQ ID NO: 208, and a light chain comprising an amino acid sequence of SEQ ID NO: 149; (g) a heavy chain comprising an amino acid sequence of SEQ ID NO: 203, and a light chain comprising an amino acid sequence of SEQ ID NO: 176; (h) a heavy chain comprising an amino acid sequence of SEQ ID NO: 208, and a light chain comprising an amino acid sequence of SEQ ID NO: 176; (i) a heavy chain comprising an amino acid sequence of SEQ ID NO: 203, and a light chain comprising an amino acid sequence of SEQ ID NO: 182; (j) a heavy chain comprising an amino acid sequence of SEQ ID NO: 208, and a light chain comprising an amino acid sequence of SEQ ID NO: 182; (k) a heavy chain comprising an amino acid sequence of SEQ ID NO: 203, and a light chain comprising an amino acid sequence of SEQ ID NO: 188; (l) a heavy chain comprising an amino acid sequence of SEQ ID NO: 208, and a light chain comprising an amino acid sequence of SEQ ID NO: 188; (m) a heavy chain comprising an amino acid sequence of SEQ ID NO: 105, and a light chain comprising an amino acid sequence of SEQ ID NO:

26; (n) a heavy chain comprising an amino acid sequence of SEQ ID NO: 108, and a light chain comprising an amino acid sequence of SEQ ID NO: 26; (o) a heavy chain comprising an amino acid sequence of SEQ ID NO: 117, and a light chain comprising an amino acid sequence of SEQ ID NO: 26; (p) a heavy chain comprising an amino acid sequence of SEQ ID NO: 124, and a light chain comprising an amino acid sequence of SEQ ID NO: 50; (q) a heavy chain comprising an amino acid sequence of SEQ ID NO: 39, and a light chain comprising an amino acid sequence of SEQ ID NO: 130; (r) a heavy chain comprising an amino acid sequence of SEQ ID NO: 39, and a light chain comprising an amino acid sequence of SEQ ID NO: 138; (s) a heavy chain comprising an amino acid sequence of SEQ ID NO: 141, and a light chain comprising an amino acid sequence of SEQ ID NO: 138; (t) a heavy chain comprising an amino acid sequence of SEQ ID NO: 39, and a light chain comprising an amino acid sequence of SEQ ID NO: 149; (u) a heavy chain comprising an amino acid sequence of SEQ ID NO: 156, and a light chain comprising an amino acid sequence of SEQ ID NO: 26; (v) a heavy chain comprising an amino acid sequence of SEQ ID NO: 159, and a light chain comprising an amino acid sequence of SEQ ID NO: 26; (w) a heavy chain comprising an amino acid sequence of SEQ ID NO: 163, and a light chain comprising an amino acid sequence of SEQ ID NO: 26; (x) a heavy chain comprising an amino acid sequence of SEQ ID NO: 170, and a light chain comprising an amino acid sequence of SEQ ID NO: 26; (y) a heavy chain comprising an amino acid sequence of SEQ ID NO: 39, and a light chain comprising an amino acid sequence of SEQ ID NO: 176; (z) a heavy chain comprising an amino acid sequence of SEQ ID NO: 39, and a light chain comprising an amino acid sequence of SEQ ID NO: 182; (aa) a heavy chain comprising an amino acid sequence of SEQ ID NO: 39, and a light chain comprising an amino acid sequence of SEQ ID NO: 188; (bb) a heavy chain comprising an amino acid sequence of SEQ ID NO: 195, and a light chain comprising an amino acid sequence of SEQ ID NO: 138; (cc) a heavy chain comprising an amino acid sequence of SEQ ID NO: 195, and a light chain comprising an amino acid sequence of SEQ ID NO: 176; (dd) a heavy chain comprising an amino acid sequence of SEQ ID NO: 15, and a light chain comprising an amino acid sequence of SEQ ID NO: 26; (ee) a heavy chain comprising an amino acid sequence of SEQ ID NO: 39, and a light chain comprising an amino acid sequence of SEQ ID NO: 50; (ff) a heavy chain comprising an amino acid sequence of SEQ ID NO: 376, and a light chain comprising an amino acid sequence of SEQ ID NO: 246; (gg) a heavy chain comprising an amino acid sequence of SEQ ID NO: 387, and a light chain comprising an amino acid sequence of SEQ ID NO: 246; (hh) a heavy chain comprising an amino acid sequence of SEQ ID NO: 235, and a light chain comprising an amino acid sequence of SEQ ID NO: 246; (ii) a heavy chain comprising an amino acid sequence of SEQ ID NO: 280, and a light chain comprising an amino acid sequence of SEQ ID NO: 289; or (jj) a heavy chain comprising an amino acid sequence of SEQ ID NO: 302, and a light chain comprising an amino acid sequence of SEQ ID NO: 308.

In some embodiments of the invention, the antibody or antigen binding fragment comprises: (a) a heavy chain comprising an amino acid sequence of SEQ ID NO: 63, and a light chain comprising an amino acid sequence of SEQ ID NO: 74; (b) a heavy chain comprising an amino acid sequence of SEQ ID NO: 87, and a light chain comprising an amino acid sequence of SEQ ID NO: 98; (c) a heavy chain comprising an amino acid sequence of SEQ ID NO: 352, and a light chain comprising an amino acid sequence of SEQ ID NO: 365; (d) a heavy chain comprising an amino acid sequence of SEQ ID NO: 394, and a light chain comprising an amino acid sequence of SEQ ID NO: 346; (e) a heavy chain comprising an amino acid sequence of SEQ ID NO: 416, and a light chain comprising an amino acid sequence of SEQ ID NO: 346; (f) a heavy chain comprising an amino acid sequence of SEQ ID NO: 318, and a light chain comprising an amino acid sequence of SEQ ID NO: 329; (g) a heavy chain comprising an amino acid sequence of SEQ ID NO: 335, and a light chain comprising an amino acid sequence of SEQ ID NO: 346; or (h) a heavy chain comprising an amino acid sequence of SEQ ID NO: 352, and a light chain comprising an amino acid sequence of SEQ ID NO: 359.

In some embodiments of the invention, the antibody or antigen binding fragment is an antigen binding fragment selected from the group consisting of a Fab, Fab', F(ab')$_2$, Fv, single domain antibody (dAb), and a single chain variable fragment (scFv). In some embodiments of the invention, the antibody or antigen binding fragment is an antigen binding fragment selected from the group consisting of a Fab, Fab', Fv, single domain antibody (dAb), and a single chain variable fragment (scFv).

In some embodiments of the invention, the antibody or antigen binding fragment is monoclonal. In some embodiments of the invention, the antibody or antigen binding fragment is fully human. In some embodiments of the invention, the antibody or antigen binding fragment is an IgG antibody. In some embodiments of the invention, the antibody or antigen binding fragment is an IgG1 antibody. In some embodiments of the invention, the antibody or antigen binding fragment is an IgG1 antibody having a kappa light chain. In some embodiments of the invention, the antibody or antigen binding fragment is a fully human antibody of the IgG1 isotype and has a kappa light chain.

In some embodiments of the invention, the antibody or antigen binding fragment additionally has mutations in the Fc region according to the EU index of Kabat, wherein the mutations comprise at least D265A and P329A.

In some embodiments of the invention, the antibody or antigen binding fragment additionally has mutations in the Fc region according to the EU index of Kabat, wherein the mutations comprise at least L234A and L235A.

In some embodiments of the invention, the antibody or antigen binding fragment is therapeutic.

In some embodiments of the invention, the antibody or antigen binding fragment binds to the same epitope on human NPR1 as any of the antibodies or antigen binding fragments or groups defined herein (e.g., XX16). In some embodiments of the invention, the antibody or antigen binding fragment competes for binding to human NPR1 with any of the antibodies or antigen binding fragments or groups defined herein (e.g., XX16).

In one aspect of the invention, provided herein is an isolated nucleic acid or nucleic acids encoding the amino acid sequence of any of the antibodies or antigen binding fragments or groups defined herein. In one aspect of the invention, provided herein is a vector comprising the isolated nucleic acid(s). In one aspect of the invention, provided herein is a host cell comprising the isolated nucleic acid(s) or the vector.

In one aspect of the invention, provided herein is a method of producing any of the antibodies or antigen binding fragments described herein, comprising culturing the host cell described herein under conditions suitable to produce the antibody or antigen binding fragment. In some embodiments of the invention, the method additionally comprises purification of the antibody or antigen binding fragment.

In one aspect of the invention, provided herein is pharmaceutical composition comprising a purified antibody or antigen binding fragment produced by the method described herein and a pharmaceutically acceptable carrier.

In one aspect of the invention, provided herein is pharmaceutical composition comprising any of the antibodies or antigen binding fragments described herein and a pharmaceutically acceptable carrier.

In one aspect of the invention, provided herein is pharmaceutical composition comprising: a) means for binding natriuretic peptide receptor 1 (NPR1) and activating NPR1 in the absence of ANP; and b) a pharmaceutically acceptable excipient. In some embodiments of the invention, said means for binding and activating is ANP non-competitive. In some embodiments of the invention, said means for binding and activating is ANP competitive. In some embodiments of the invention, said means for binding and activating is additionally capable of stabilizing the ANP-NPR1 complex. In some embodiments of the invention, the composition further comprises an additional therapeutic agent.

In some embodiments of the invention, the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), and combinations thereof. In some embodiments of the invention, the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, and combinations thereof. In some embodiments of the invention, the additional therapeutic agent is selected from chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof. In some embodiments of the invention, the additional therapeutic agent is an angiotensin receptor-neprilysin inhibitor (ARNi).

In some embodiments of the invention, the additional therapeutic agent is selected from a corticosteroid, a leukotriene modifier, a bronchodilator, and combinations thereof. In some embodiments of the invention, the additional therapeutic agent is selected from fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline and ipratropium, and combinations thereof. In some embodiments of the invention, the additional therapeutic agent is selected from salmeterol, formoterol, albuterol, and levalbuterol, and combinations thereof.

In some embodiments of the invention, the additional therapeutic agent is selected from a beta-adrenoceptor antagonist, a carbonic anhydrase inhibitor, an alpha 2-adrenoceptor agonist, a parasympathomimetic, a prostaglandin analog, a rho kinase inhibitor, and combinations thereof, and combinations thereof. In some embodiments of the invention, the additional therapeutic agent is selected from timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil and ripasudil, and combinations thereof.

In one aspect of the invention, provided herein is a method of treating a disorder or a disease associated with natriuretic peptide receptor activity in a subject in need thereof, the method comprising administering to the subject a therapeutically effective amount of any of the antibodies or antigen binding fragments described herein or a pharmaceutical composition or combination as described herein.

In one aspect of the invention, provided herein is a method of treating a cardiovascular disorder in a subject in need thereof, the method comprising administering to the subject a therapeutically effective amount of any one of the antibodies or antigen binding fragments thereof described herein or any one of the pharmaceutical compositions or combinations described herein.

In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is a method of treating heart failure, hypertrophic cardiomyopathy (HCM), hypertension, preeclampsia, asthma, glaucoma, and/or cytokine release syndrome in a subject in need thereof, comprising administering to the subject a therapeutically effective amount of any one of the antibodies or antigen binding fragments thereof described herein or any one of the pharmaceutical compositions or combinations described herein.

In some embodiments of the invention, the subject has heart failure, wherein the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is a method of treating a kidney disorder in a subject in need thereof, the method comprising administering to the subject a therapeutically effective amount of any one of the antibodies or antigen binding fragments thereof described herein or any one of the pharmaceutical compositions or combinations described herein. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In one aspect of the invention, provided herein is a use of any one of the antibodies or antigen binding fragments thereof described herein or any one of the pharmaceutical compositions or combinations described herein, for the manufacture of a medicament for the treatment of a disorder or disease associated with natriuretic peptide receptor activity in a subject in need of such treatment.

In one aspect of the invention, provided herein is a use of any one of the antibodies or antigen binding fragments thereof described herein or any one of the pharmaceutical compositions or combinations described herein, for the manufacture of a medicament for the treatment of a cardiovascular disorder in a subject in need of such treatment.

In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is a use of any one of the antibodies or antigen binding fragments thereof described herein or any one of the pharmaceutical compositions or combinations described herein, for the manufacture of a medicament for the treatment of heart failure, hypertrophic cardiomyopathy (HCM), hypertension, preeclampsia, asthma, glaucoma, and/or cytokine release syndrome in a subject in need of such treatment.

In some embodiments of the invention, the subject has heart failure, and the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is a use of any one of the antibodies or antigen binding fragments thereof described herein or any one of the pharmaceutical compositions or combinations described herein, for the manufacture of a medicament for the treatment of a kidney disorder in a subject in need of such treatment. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In one aspect of the invention, provided herein is an antibody or antigen binding fragment thereof described herein or any one of the pharmaceutical compositions or combinations described herein, for use in the treatment of a disorder or disease associated with natriuretic peptide receptor activity in a subject in need of such treatment.

In one aspect of the invention, provided herein is an antibody or antigen binding fragment thereof described herein or any one of the pharmaceutical compositions or combinations described herein, for use in the treatment of a cardiovascular disorder in a subject in need of such treatment.

In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is an antibody or antigen binding fragment thereof described herein or any one of the pharmaceutical compositions or combinations described herein, for use in the treatment of heart failure, hypertrophic cardiomyopathy (HCM), hypertension, preeclampsia, asthma, glaucoma, and/or cytokine release syndrome in a subject in need of such treatment.

In some embodiments of the invention, the subject has heart failure, and the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is an antibody or antigen binding fragment thereof described herein or any one of the pharmaceutical compositions or combinations described herein, for use in the treatment of a kidney disorder in a subject in need of such treatment. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In one aspect of the invention, provided herein is a method of treating a disorder or a disease associated with natriuretic peptide receptor activity in a subject in need thereof, comprising administering a pharmaceutical composition comprising: means for binding natriuretic peptide receptor 1 (NPR1) and activating NPR1 in the absence of ANP; and a pharmaceutically acceptable excipient.

In one aspect of the invention, provided herein is a method of treating a cardiovascular disorder in a subject in need thereof, comprising administering a pharmaceutical composition comprising: means for binding natriuretic peptide receptor 1 (NPR1) and activating NPR1 in the absence of ANP; and a pharmaceutically acceptable excipient. In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In one aspect of the invention, provided herein is a method of treating heart failure, hypertrophic cardiomyopathy (HCM), hypertension, preeclampsia, asthma, glaucoma, and/or cytokine release syndrome in a subject in need thereof, comprising administering a pharmaceutical composition comprising: means for binding natriuretic peptide receptor 1 (NPR1) and activating NPR1 in the absence of ANP; and a pharmaceutically acceptable excipient. In some embodiments of the invention, the subject has heart failure, wherein the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, wherein the hypertrophic cardiomyopathy is ventricular hypertrophy. In some embodiments of the invention, the subject has hypertension, wherein the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, wherein the hypertension is selected from resistant hypertension or hypertensive heart disease.

In one aspect of the invention, provided herein is a method of treating a kidney disorder in a subject in need thereof, comprising administering a pharmaceutical composition comprising: means for binding natriuretic peptide receptor 1 (NPR1) and activating NPR1 in the absence of ANP; and a pharmaceutically acceptable excipient. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD). In some embodiments of the invention, said means for binding and activating is ANP non-competitive. In some embodiments of the invention, said means for binding and activating is ANP competitive. In some embodiments of the invention, said means for binding and activating is additionally capable of stabilizing the ANP-NPR1 complex.

In one aspect of the invention, herein is provided an isolated anti-NPR1 antibody or antigen binding fragment, wherein the antibody or antigen binding fragment thereof binds to a conformational epitope of human NPR1, and wherein the conformational epitope comprises at least one amino acid residue within each of (i) amino acids 99-103 of SEQ ID NO: 1, (ii) 105-111 of SEQ ID NO: 1, (iii) 131-134 of SEQ ID NO: 1, and additionally binds to amino acid 375 and/or 378 of SEQ ID NO: 1.

In one aspect of the invention, herein is provided an isolated anti-NPR1 antibody or antigen binding fragment, wherein the antibody or antigen binding fragment thereof binds to a conformational epitope within NPR1, and wherein the conformational epitope comprises at least one amino acid residue within each of (i) amino acids 188-198 of SEQ ID NO: 1, (ii) 201-208 of SEQ ID NO: 1, (iii) 215-238 of SEQ ID NO: 1, and (iv) 294-297 of SEQ ID NO: 1, optionally wherein the antibody or antigen binding fragment thereof binds to at least amino acids 188, 192, 194, 197, 201, 208, and 219 of SEQ ID NO: 1.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3), wherein: (a) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $Y_1QY_2Y_3Y_4Y$ 5PRT (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $Y_1QY_2Y_3Y_4Y_5PRT$ (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A; (III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1Y_2Y_3Y_4PR$ (SEQ ID NO: 432); wherein $Y_1$ is S, E, T, or I, $Y_2$ is Y or W, $Y_3$ is E, V, R, A, T, or M, and $Y_4$ is K, V, R, or A; or (IV) HCDR1 comprises or consists of an amino acid sequence as set forth in SEQ ID NO: 34, HCDR2 comprises or consists of an amino acid sequence as set forth in IX$_1$SX$_2$GX$_3$YX$_4$ (SEQ ID NO: 433), wherein X$_1$ is S or E, X$_2$ is D or K, X$_3$ is S or N, and X$_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in Y$_1$QY$_2$Y$_3$Y$_4$Y$_5$PRT (SEQ ID NO: 430); wherein Y$_1$ is M or Q, Y$_2$ is S, E, T, or I, Y$_3$ is Y or W, Y$_4$ is E, V, R, A, T, or M, and Y$_5$ is K, V, R, or A; (b) (I) HCDR1 comprises or consists of an amino acid sequence as set forth in SEQ ID NO: 28; HCDR2 comprises or consists of an amino acid sequence as set forth in X$_1$IX$_2$SX$_3$GX$_4$YXX$_6$YADSVKG (SEQ ID NO: 429), wherein X$_1$ is A or V, X$_2$ is S or E, X$_3$ is D or K, X$_4$ is S or N, X$_5$ is I or T, and X$_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (II) HCDR1 comprises or consists of an amino acid sequence as set forth in SEQ ID NO: 31; HCDR2 comprises or consists of an amino acid sequence as set forth in X$_1$IX$_2$SX$_3$GX$_4$YXX$_6$YADSVKG (SEQ ID NO: 429), wherein X$_1$ is A or V, X$_2$ is S or E, X$_3$ is D or K, X$_4$ is S or N, X$_5$ is I or T, and X$_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (III) HCDR1 comprises or consists of an amino acid sequence as set forth in SEQ ID NO: 32, HCDR2 comprises or consists of an amino acid sequence as set forth in X$_1$SX$_2$GX$_3$Y (SEQ ID NO: 431), wherein X$_1$ is S or E, X$_2$ is D or K, or X$_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in IX$_1$SX$_2$GX$_3$YX$_4$ (SEQ ID NO: 433), wherein X$_1$ is S or E, X$_2$ is D or K, X$_3$ is S or N, and X$_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (c) (I) HCDR1 comprises or consists of an amino acid sequence as set forth in SEQ ID NO: 28; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (II) HCDR1 comprises or consists of an amino acid sequence as set forth in SEQ ID NO: 31; HCDR2 comprises or consists of an amino acid sequence as set forth in SEQ ID NO: 119; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (III) HCDR1 comprises or consists of an amino acid sequence as set forth in SEQ ID NO: 32, HCDR2 comprises or consists of an amino acid sequence as set forth in SEQ ID NO: 120, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in SEQ ID NO: 121, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A; (d) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in Y$_1$Y$_2$Y$_3$GY$_4$Y$_5$ (SEQ ID NO: 439), wherein Y$_1$ is S or G, $Y_2$ is S or G, $Y_3$ is S or Q, $Y_4$ is S, Q, or G, and $Y_5$ is S, N, or M, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein $X_1$ is N, S, or Q, HCDR2 comprises or consists of an amino acid sequence as set forth in IY$_1$Y$_2$Y 3GY$_4$Y ST (SEQ ID NO: 441), wherein $Y_1$ is S or G, $Y_2$ is S or G, $Y_3$ is S or Q, $Y_4$ is S, Q, or G, and $Y_5$ is S, N, or M, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; or (e) (I) HCDR1 comprises or consists of an amino acid sequence as set forth in GFTFX$_1$THYIH (SEQ ID NO: 436), wherein $X_1$ is N, S, or Q, HCDR2 comprises or consists of an amino acid sequence as set forth in SISY$_1$SGY$_2$Y$_3$TYYADSVKG (SEQ ID NO: 442), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in SISY$_1$SGY$_2$Y$_3$TYYADSVKG (SEQ ID NO: 442), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in GFTFX$_1$TH (SEQ ID NO: 438), wherein $X_1$ is N, S, or Q, HCDR2 comprises or consists of an amino acid sequence as set forth in SY$_1$SGY$_2$Y$_3$ (SEQ ID NO: 443), wherein $Y_1$ is S or G, $Y_2$ is S or Q, and $Y_3$ is S or N, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein $X_1$ is N, S, or Q, HCDR2 comprises or consists of an amino acid sequence as set forth in ISY$_1$SGY$_2$Y$_3$T (SEQ ID NO: 444), wherein $Y_1$ is S or G, $Y_2$ is S or Q, and $Y_3$ is S or N, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19.

In some aspects and embodiments of the invention, herein is provided an isolated anti-NPR1 antibody or antigen binding fragment, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein: (I) HCDR1 comprises or consists of an amino acid sequence as set forth in SEQ ID NO: 28, HCDR2 comprises or consists of an amino acid sequence as set forth in any one of comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (II) HCDR1 comprises or consists of an amino acid sequence as set forth in SEQ ID NO: 31, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (III) HCDR1 comprises or consists of an amino acid sequence as set forth in SEQ ID NO: 32, HCDR2 comprises or consists of an amino acid sequence as set forth in any one of SEQ ID NOs: 33, 120, and 191, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in any one of SEQ ID NOs: 46, 127, 135, 146, 173, 179, and 185; or (IV) HCDR1 comprises or consists of an amino acid sequence as set forth in SEQ ID NO: 34, HCDR2 comprises or consists of an amino acid sequence as set forth in any one of SEQ ID NOs: 35, 121, and 192, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in any one of SEQ ID NOs: 43, 126, 134, 145, 172, 178, and 184.

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (a) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (LCDR1), SEQ ID NO: 36 (HCDR3), SEQ ID NO: 47 (LCDR1), SEQ ID NO: 45 (LCDR2), and SEQ ID NO: 134 (LCDR3); (b) (I) SEQ ID NO: 28 (HCDR1), SEQ ID NO: 119 (HCDR2), SEQ ID NO: 30 (HCDR3), SEQ ID NO: 41

(LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3); (c) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3); (d) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3); (e) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3); (f) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3); (g) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3); (h) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3); (i) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3); (j) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3); (k) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3); (1) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3); (m) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29

(HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3); (n) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3); (0) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3); (p) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3).

In some embodiments of the invention, the antibody or antigen binding fragment comprises three heavy chain complementarity determining regions (HCDR1, HCDR2, and HCDR3) and three light chain complementarity determining regions (LCDR1, LCDR2, and LCDR3) selected from: (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3).

In some embodiments of the invention, the antibody or antigen binding fragment comprises: (a) a heavy chain variable region comprising an amino acid sequence of SEQ ID NO: 201, and a light chain variable region comprising an amino acid sequence of SEQ ID NO: 136; (b) a heavy chain variable region comprising an amino acid sequence of SEQ ID NO: 122, and a light chain variable region comprising an amino acid sequence of SEQ ID NO: 136; or (c) a heavy chain variable region comprising an amino acid sequence of SEQ ID NO: 37, and a light chain variable region comprising an amino acid sequence of SEQ ID NO: 48.

In some embodiments of the invention, the antibody or antigen binding fragment comprises: a heavy chain variable region comprising an amino acid sequence of SEQ ID NO: 85, and a light chain variable region comprising an amino acid sequence of SEQ ID NO: 96.

In some embodiments of the invention, the antibody or antigen binding fragment comprises: (a) a heavy chain comprising an amino acid sequence of SEQ ID NO: 203, and a light chain comprising an amino acid sequence of SEQ ID NO: 138; (b) a heavy chain comprising an amino acid sequence of SEQ ID NO: 208, and a light chain comprising an amino acid sequence of SEQ ID NO: 138; or (c) a heavy chain comprising an amino acid sequence of SEQ ID NO: 39, and a light chain comprising an amino acid sequence of SEQ ID NO: 50.

In some embodiments of the invention, the antibody or antigen binding fragment comprises: a heavy chain comprising an amino acid sequence of SEQ ID NO: 87, and a light chain comprising an amino acid sequence of SEQ ID NO: 98.

In some embodiments of the invention, the antigen binding fragment is selected from the group consisting of a Fab, Fab', F(ab')$_2$, Fv, single domain antibody (dAb), and a single chain variable fragment (scFv). In some embodiments of the invention, the antibody or antigen binding fragment is therapeutic.

In some aspects of the invention, provided herein is an isolated nucleic acid or nucleic acids encoding the amino acid sequence of any of the antibodies or antigen binding fragments described herein. In some aspects of the invention, provided herein is a vector comprising any of the isolated nucleic acid(s) described herein. In some aspects of the invention, provided herein is a host cell comprising any of the isolated nucleic acid(s) described herein. In some aspects of the invention, provided herein is a method of producing an isolated anti-NPR1 antibody or antigen binding fragment, comprising culturing any of the host cells described herein under conditions suitable for producing the antibody or antigen binding fragment.

In some aspects of the invention, provided herein is a pharmaceutical composition comprising any of the antibodies or antigen binding fragments described herein and a pharmaceutically acceptable carrier. In some embodiments of the invention, the composition further comprises an additional therapeutic agent. In some embodiments of the invention, the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), an angiotensin receptor-neprilysin inhibitor (ARNi), a corticosteroid, a leukotriene modifier, a bronchodilator, a beta-adrenoceptor antagonist, a carbonic anhydrase inhibitor, an alpha 2-adrenoceptor agonist, a parasympathomimetic, a prostaglandin analog, a rho kinase inhibitor, and combinations thereof. In some embodiments of the invention, the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline, ipratropium, salmeterol, formoterol, albuterol, levalbuterol, timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil, ripasudil, and combinations thereof.

In some aspects of the invention, provided herein is a method of treating a disorder or a disease associated with natriuretic peptide receptor activity in a subject in need thereof, the method comprising administering to the subject a therapeutically effective amount of any of the antibodies or antigen binding fragments described herein.

In some aspects of the invention, provided herein is a method of treating a cardiovascular disorder in a subject in need thereof, the method comprising administering to the subject a therapeutically effective amount of any of the antibodies or antigen binding fragments described herein. In some embodiments of the invention, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

In some aspects of the invention, provided herein is a method of treating heart failure, hypertrophic cardiomyopathy (HCM), hypertension, preeclampsia, asthma, glaucoma, and/or cytokine release syndrome in a subject in need thereof, comprising administering to the subject a therapeutically effective amount of any of the antibodies or antigen binding fragments described herein. In some embodiments of the invention, the subject has heart failure, and the heart failure is selected from a heart failure with reduced ejection fraction (HFrEF), heart failure with preserved ejection fraction (HFpEF), heart failure after acute myocardial infarct, or acute decompensated heart failure. In some embodiments of the invention, the subject has hypertrophic cardiomyopathy, and wherein the hypertrophic cardiomyopathy is ventricular hypertrophy. In some embodiments of the invention, the subject has hypertension, and the hypertension is selected from resistant hypertension, hypertensive heart disease, pulmonary hypertension, pulmonary arterial hypertension, isolated systolic hypertension, resistant hypertension, and pulmonary arterial hypertension. In some embodiments of the invention, the subject has hypertension, and the hypertension is selected from resistant hypertension or hypertensive heart disease.

In some aspects of the invention, provided herein is a method of treating a kidney disorder in a subject in need thereof, the method comprising administering to the subject a therapeutically effective amount of any of the antibodies or antigen binding fragments described herein. In some embodiments of the invention, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

GENERAL DEFINITIONS

Figure 1:
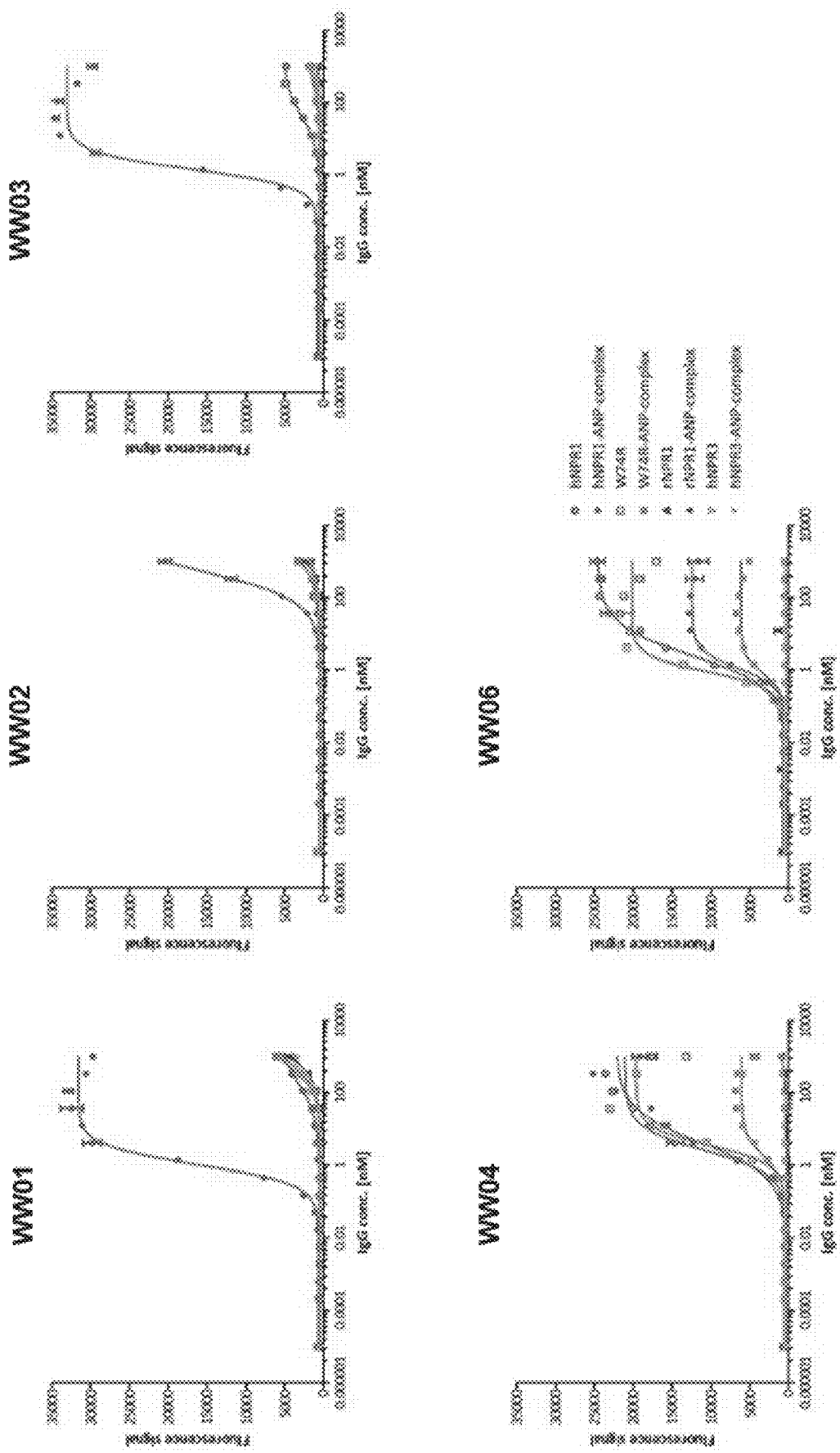
FIG. 1 is a set of graphs displaying the results of antibody candidates WW01, WW02, WW03, WW04, and WW06 binding to the following antigens (ELISA analysis): human NPR1, constitutively active human NPR1 mutant (W74R), rat NPR1, and human NPR3 (counter target) both in the absence of and presence of a 250 fold molar excess of ANP.

In order that the present disclosure may be more readily understood, certain terms are first defined. Additional definitions are set forth throughout the detailed description as required.

Throughout the description and claims of this specification, the words "comprise" and "contain" and variations of the words, for example "comprising" and "comprises", mean "including but not limited to", and do not exclude other components, integers, or steps. Moreover the singular encompasses the plural unless the context otherwise requires: in particular, where the indefinite article is used, the specification is to be understood as contemplating plurality as well as singularity, unless the context requires otherwise.

As used herein, "NPR1" and "NPR1 protein" refers to Natriuretic Peptide Receptor 1. This protein is also known as Atrial natriuretic peptide receptor type A (ANP-A, ANPR-A or NPR-A) and Guanylate cyclase A (GC-A). In some embodiments, the NPR1 referred to is human NPR1. In some embodiments the human NPR1 is has UniProt accession number P16066 or GenBank Accession number EAW53284.1 (SEQ ID NO: 1). In some embodiments, the NPR1 referred to is mouse (*Mus musculus*) NPR1. In some embodiments the mouse NPR1 has NCBI Reference Sequence number NP_032753.5 (SEQ ID NO: 2). In some embodiments, the NPR1 referred to is rat (*Rattus norvegicus*) NPR1. In some embodiments the rat NPR1 has NCBI Reference Sequence number NP_036745.1 (SEQ ID NO: 3). Exemplary NPR1 proteins are shown in Table 1. Where a constitutively active or W74R mutant is discussed herein, this mutant refers to Trp at amino acid 74 of the mature human NPR1 protein, which may also be referred to as the Trp at amino acid 106 of the hNPR1 protein shown in SEQ ID NO: 1.

TABLE 1

NPR1 Protein Sequences

| SEQ ID NO: | Animal | Sequence (amino acid) |
|---|---|---|
| 1 | Human | MPGPRRPAGSRLRLLLLLLPPLLLLLRGSHAGNLTVAVVLPLANTSYPWS WARVGPAVELALAQVKARPDLLPGWTVRTVLGSSENALGVCSDTAAPLA AVDLKWEHNPAVFLGPGCVYAAAPVGRFTAHWRVPLLTAGAPALGFGV KDEYALTTRAGPSYAKLGDFVAALHRRLGWERQALMLYAYRPGDEEHC FFLVEGLFMRVRDRLNITVDHLEFAEDDLSHYTRLLRTMPRKGRVIYICSS PDAFRTLMLLALEAGLCGEDYVFFHLDIFGQSLQGGQGPAPRRPWERGDG QDVSARQAFQAAKIITYKDPDNPEYLEFLKQLKHLAYEQFNFTMEDGLVN TIPASFHDGLLLYIQAVTETLAHGGTVTDGENITQRMWNRSFQGVTGYLK IDSSGDRETDFSLWDMDPENGAFRVVLNYNGTSQELVAVSGRKLNWPLG YPPPDIPKCGFDNEDPACNQDHLSTLEVLALVGSLSLLGIL-IVSFFIYRKMQ LEKELASELWRVRWEDVEPSSLERHLRSAGSRLTLSGRGSNYGSLLTTEG QFQVFAKTAYYKGNLVAVKRVNRKRIELTRKVLFELKHMRDVQNEHLTR FVGACTDPPNICILTEYCPRGSLQDILENESITLDWMFRYSLTNDI-VKGMLF LHNGAICSHGNLKSSNCVVDGRFVLKITDYGLESFRDLDPEQGHTVYAKK LWTAPELLRMASPPVRGSQAGDVYSFGIILQEIALRSGVFHVEGLDL-SPKEI IERVTRGEQPPFRPSLALQSHLEELGLLMQRCWAEDPQERPPFQQIRLTLR KFNRENSSNILDNLLSRMEQYANNLEELVEERTQAYLEEKRKAEALLYQI LPHSVAEQLKRGETVQAEAFDSVTIYFSDIVGFTALSAESTPMQVVTLLND LYTCFDAVIDNFDVYKVETIGDAYMVVSGLPVRNGRLHACEVARMALAL LDAVRSFRIRHRPQEQLRLRIGIHTGPVCAGVVGLKMPRYCLFGDTVNTA SRMESNGEALKIHLSSETKAVLEEFGGFELELRGDVEMKGKGKVRTYWL LGERGSSTRG |
| 2 | Mouse | MPGSRRVRPRLRALLLLPPLLLLRSGHASDLTVAVVLPLTNTSYPWSWAR VGPAVELALGRVKARPDLLPGWTVRMVLGSSENAAGVCSDTAAPLAAV DLKWEHSPAVFLGPGCVYSAAPVGRFTAHWRVPLLTAGAPALGIGVKDE YALTTRTGPSHVKLGDFVTALHRRLGWEHQALVLYADRLGDDRPCFFIV EGLYMRVRERLNITVNHQEFVEGDPDHYTKLLRTVQRKGRVIYICSSPDA FRNLMLLALDAGLTGEDYVFFHLDVFGQSLQGAQGPVPRKPWERDDGQ DRRARQAFQAAKIITYKEPDNPEYLEFLKQLKLLADKKFNFTMEDGLKNII PASFHDGLLLYVQAVTETLAQGGTVTDGENITQRMWNRSFQGVTGYLKI DRNGDRDTDFSLWDMDPETGAFRVVLNFNGTSQELMAVSEHRLYWPLG YPPPDIPKCGFDNEDPACNQDHFSTLEVLA-LVGSLSLVSFLIVSFFIYRKMQ LEKELVSELWRVRWEDLQPSSLERHLRSAGSRLTLSGRGSNYGSLLTTEG QFQVFAKTAYYKGNLVAVKRVNRKRIELTRKVLFELKHMRDVQNEHLTR FVGACTDPPNICILTEYCPRGSLQDILENESITLDWMFRYSLTNDI-VKGMLF LHNGAIGSHGNLKSSNCVVDGRFVLKITDYGLESFRDPEPEQGHTLFAKK LWTAPELLRMASPPARGSQAGDVYSFGIILQEIALRSGVFYVEGLDL-SPKEI IERVTRGEQPPFRPSMDLQSHLEELGQLMQRCWAEDPQERPPFQQIRLALR KFNKENSSNILDNLLSRMEQYANNLEELVEERTQAYLEEKRKAEALLYQI LPHSVAEQLKRGETVQAEAFDSVTIYFSDIVGFTALSAESTPMQVVTLLND LYTCFDAVIDNFDVYKVETIGDAYMVVSGLPVRNGQLHAREVARMALAL LDAVRSFRIRHRPQEQLRLRIGIHTGPVCAGVVGLKMPRYCLFGDTVNTA SRMESNGEALRIHLSSETKAVLEEFDGFELELRGDVEMKGKGKVRTYWL LGERGCSTRG |
| 3 | Rat | MPGSRRVRPRLRALLLLPPLLLLRGGHASDLTVAVVLPLTNTSYPWSWAR VGPAVELALARVKARPDLLPGWTVRMVLGSSENAAGVCSDTAAPLAAV DLKWEHSPAVFLGPGCVYSAAPVGRFTAHWRVPLLTAGAPALGIGVKDE YALTTRTGPSHVKLGDFVTALHRRLGWEHQALVLYADRLGDDRPCFFIV EGLYMRVRERLNITVNHQEFVEGDPDHYPKLLRAVRRKGRVIYICSSPDA FRNLMLLALNAGLTGEDYVFFHLDVFGQSLKSAQGLVPQKPWERGDGQD RSARQAFQAAKIITYKEPDNPEYLEFLKQLKLLADKKFNFTVEDGLKNIIP ASFHDGLLLYVQAVTETLAQGGTVTDGENITQRMWNRSFQGVTGYLKID RNGDRDTDFSLWDMDPETGAFRVVLNYNGTSQELMAVSEHKLYWPLGY PPPDVPKCGFDNEDPACNQDHFSTLEVLALVGSLSLIS-FLIVSFFIYRKMQL EKELVSELWRVRWEDLQPSSLERHLRSAGSRLTLSGRGSNYGSLLTTEGQ FQVFAKTAYYKGNLVAVKRVNRKRIELTRKVLFELKHMRDVQNEHLTRF VGACTDPPNICILTEYCPRGSLQDILENESITLDWMFRYSLTNDI-VKGMLFL |

TABLE 1-continued

NPR1 Protein Sequences

SEQ ID NO: Animal   Sequence (amino acid)

```
HNGAICSHGNLKSSNCVVDGRFVLKITDYGLESFRDPEPEQGHTLFAKKL
WTAPELLRMASPPARGSQAGDVYSFGIILQEIALRSGVFYVEGLDL-
SPKEII
ERVTRGEQPPFRPSMDLQSHLEELGQLMQRCWAEDPQERPPFQQIRLALR
KFNKENSSNILDNLLSRMEQYANNLEELVEERTQAYLEEKRKAEALLYQI
LPHSVAEQLKRGETVQAEAFDSVTIYFSDIVGFTALSAESTPMQVVTLLND
LYTCFDAVIDNFDVYKVETIGDAYMVVSGLPVRNGQLHAREVARMALAL
LDAVRSFRIRHRPQEQLRLRIGIHTGPVCAGVVGLKMPRYCLFGDTVNTA
SRMESNGEALKIHLSSETKAVLEEFDGFELELRGDVEMKGKGKVRTYWL
LGERGCSTRG
```

In various embodiments, the anti-NPR1 antibodies and antigen binding fragments disclosed herein are capable of binding to NPR1 and activating NPR1 in the absence of ANP. By virtue of this activity, the disclosed anti-NPR1 antibodies and antigen binding fragments may be useful in treating undesirable conditions, diseases and disorders including cardiovascular disorders (e.g., hypertension, peripheral vascular disease, heart failure (including but not limited to heart failure with reduced ejection fraction (HFrEF), heart failure with preserved ejection fraction (HFpEF), heart failure after acute myocardial infarct, or acute decompensated heart failure), coronary artery disease (CAD), ischemic heart disease (IHD), mitral stenosis and regurgitation, angina, hypertrophic cardiomyopathy (e.g., ventricular hypertrophy), diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, or myocardial infarction (MI)), hypertension (e.g., resistant hypertension, hypertensive heart disease, pulmonary hypertension, pulmonary arterial hypertension, isolated systolic hypertension, resistant hypertension, or pulmonary arterial hypertension), preeclampsia, asthma, glaucoma, cytokine release syndrome, and/or a kidney disorder (e.g., diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD)).

The term "antibody" as used herein refers to a whole antibody or antigen binding fragment thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes, but is not limited to, monoclonal antibodies, human antibodies, humanized antibodies, camelised antibodies, and chimeric antibodies. The antibodies can be of any isotype/class (e.g., IgG, IgE, IgM, IgD, IgA and IgY) or subclass (e.g., $IgG_1$, $IgG_2$, $IgG_3$, $IgG_4$, $IgA_1$, and $IgA_2$).

The term "antigen binding fragment" refers to a fragment of an intact antibody that retains the ability to specifically bind to a given antigen (e.g., NPR1) and/or provide a function of the intact antibody. Such fragments include Fab fragments, Fab' fragments, monovalent fragments consisting of the VL, VH, CL and CH1 domains; F (ab') 2 fragments, bivalent fragments comprising two Fab fragments linked by a disulfide bridge at the hinge region; an Fd fragment consisting of the VH and CH1 domains; an Fv fragment consisting of the VL and VH domains, a single chain Fv fragment (scFv) consisting of the VL and VH domains connected by a linker sequence; and a single domain antibody (dAb) fragment (Ward et al., 1989 Nature 341:544-546), which consists of a VH domain or a VL domain.

The term "single chain antibody", "single chain Fv" or "scFv" is refers to a molecule comprising an antibody heavy chain variable domain (or region; VH) and an antibody light chain variable domain (or region; VL) connected by a linker. Such scFv molecules can have the general structures: NH2-VL-linker-VH-COOH or NH2-VH-linker-VL-COOH. Any suitable linker may be used. A non-limiting set of linkers that can be used in such single chain antibodies are described by Holliger et al. (1993), Proc. Natl. Acad. Sci. USA 90:6444-6448, Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol; the contents of each of which are herein incorporated by reference for this purpose. Such single chain antibodies are also intended to be encompassed within the term "antigen binding fragment" of an antibody. These antibody fragments are obtained using techniques known to those of skill in the art, and the fragments are screened for utility in the same manner as are intact antibodies. Without limitation, an antigen binding fragment can be produced by any suitable method known in the art. For instance, the various antigen binding fragments described herein can be produced by enzymatic or chemical modification of intact antibodies, synthesized de novo using recombinant DNA methodologies (e.g., single chain Fv), or identified using phage display libraries (see, e.g., Pini and Bracci, Curr Protein Pept Sci 2000; 1(2):155-69, the contents of which are herein incorporated by reference for this purpose). Antigen binding fragments are screened for utility (e.g., binding affinity, activity) in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136, the contents of which are herein incorporated by reference for this purpose). Antigen binding portions of antibodies can be grafted into scaffolds based on polypeptides such as Fibronectin type III (Fn3) (see e.g., U.S. Pat. No. 6,703,199, which describes fibronectin polypeptide monobodies, the contents of which are herein incorporated by reference for this purpose).

Antigen binding fragments can be incorporated into single chain molecules comprising a pair of tandem Fv segments (VH-CH1-VH-CH1) which, together with complementary light chain polypeptides, form a pair of antigen binding regions (see Zapata et al., 1995 Protein Eng. 8 (10): 1057-1062; and U.S. Pat. No. 5,641,870; the contents of each of which are herein incorporated by reference for this purpose).

The term "isolated" means throughout this specification, that the immunoglobulin, antibody or polynucleotide, as the case may be, exists in a physical milieu distinct from that in which it may occur in nature. For example, a naturally-occurring polynucleotide or polypeptide present in a living organism is not isolated, but the same polynucleotide or polypeptide separated from some or all of the coexisting materials in the living organism, is isolated.

The term "isolated antibody," as used herein, refers to an antibody that has been identified and separated from one or more (e.g., the majority) of the components (by weight) of its source environment, e.g., from the components of a hybridoma cell culture or a different cell culture that was used for its production (e.g., producer cells including but not limited to the exemplary host cells described herein that recombinantly express the antibody). The separation is performed such that it sufficiently removes components that may otherwise interfere with the suitability of the antibody for the desired applications (e.g., for therapeutic use of an anti-NPR1 antibody). Methods for preparing isolated antibodies are known in the art and include Protein A chromatography, anion exchange chromatography, cation exchange chromatography, virus retentive filtration, and ultrafiltration.

Throughout this specification, complementarity determining regions ("CDR") are defined according to the Kabat definition unless specified that the CDR are defined according to another definition. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme); the contents of each of which are herein incorporated by reference for this purpose. For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

By convention, the CDR regions in the heavy chain are typically referred to as HCDR1, HCDR2 and HCDR3 and in the light chain as LCDR1, LCDR2 and LCDR3. They are numbered sequentially in the direction from the amino terminus to the carboxy terminus.

The term "antibody framework" as used herein refers to the part of the variable domain, either VL or VH, which serves as a scaffold for the antigen binding loops (CDRs) of this variable domain. In essence, it is the variable domain without the CDRs.

The terms "constant region" or "constant domain" refer to a carboxy terminal portion of the light and heavy chain which is not directly involved in binding of the antibody to antigen but exhibits various effector functions, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The term "epitope" or "antigenic determinant" refers to a site on an antigen to which an immunoglobulin or antibody specifically binds (e.g., a specific site on the target molecule). An epitope typically includes at least 3, 4, 5, 6, 7, 8, 9, 10, 11, 12, 13, 14, or 15 consecutive or non-consecutive amino acids in a unique spatial conformation. See, e.g., *Epitope Mapping Protocols in Methods in Molecular Biology*, Vol. 66, G. E. Morris, Ed. (1996), the contents of which are herein incorporated by reference for this purpose. In addition, as used herein, an epitope can comprise one or more monosaccharide units of a polysaccharide to which an antibody specifically binds. In specific aspects, an epitope can be a conformational epitope. See, e.g., Thompson et al., 2009, *J. of Biol. Chem.* 51:35621-35631, the contents of which are herein incorporated by reference for this purpose.

The terms "monoclonal antibody" or "monoclonal antibody composition" as used herein refers to an antibody obtained from a population of substantially homogeneous antibodies produced by a particular cell or cell line, wherein the individual antibodies comprising the population are essentially identical in sequence except for possible naturally-occurring mutations that may be present in minor amounts. A monoclonal antibody preparation displays a single binding specificity and affinity for a particular epitope. In contrast, conventional (polyclonal) antibody preparations typically include a multitude of antibodies directed against or specific for different epitopes. The modifier "monoclonal" indicates the character of the antibody as being obtained from a substantially homogeneous population of antibodies and is not to be construed as requiring production of the antibody by any particular method. Monoclonal antibodies (mAbs) can be produced by a variety of techniques, including conventional methodology, e.g., the standard somatic cell hybridization technique of Kohler and Milstein (Nature 1975; 256(5517):495-7), the contents of which are herein incorporated by reference for this purpose. A monoclonal antibody may also be obtained from other suitable methods, including phage display techniques such as those described in Clackson et al. (Nature 1991; 352 (6336):624-8) or Marks et al. (J Mol Biol 1991; 222(3):581-97), the contents of each of which are herein incorporated by reference for this purpose. The term "monoclonal antibody" is also not limited to antibody sequences from particular species of origin or from one single species of origin. Thus, the meaning of the term "monoclonal antibody" encompasses chimeric monoclonal antibodies such as humanized monoclonal antibodies.

The term "chimeric antibody," as used herein, refers to antibodies in which (a) the constant region is altered, replaced, or exchanged such that the antigen binding site (variable region) is linked to a constant region of a different or altered class, effector function, and/or species; or (b) the variable region, or a portion thereof, is altered, replaced, or exchanged with a variable region, or a portion thereof, having a different or altered antigen specificity. To create a chimeric antibody, the variable region sequences from a non-human donor antibody (e.g., a mouse, rabbit, or rat donor antibody) can be linked to human constant regions using methods known in the art (see, e.g., U.S. Pat. No. 4,816,567 (Cabilly et al.), the contents of which are herein incorporated by reference for this purpose). For instance, a mouse anti-NPR1 antibody can be modified by replacing its constant region with the constant region from a human immunoglobulin. Due to the replacement with a human constant region, the chimeric antibody can retain its specificity in recognizing human NPR1 while having reduced immunogenicity in human as compared to the original mouse antibody.

As used herein, the term "humanized antibody" refers to forms of antibodies that contain at least some human sequence and at least some non-human sequence. Typically, the antibody contains human sequences and a minor portion of non-human sequences which confer binding specificity to the target antigen. Such antibodies are chimeric antibodies which contain minimal sequence derived from a non-human immunoglobulin and retain the reactivity of a non-human antibody while being less immunogenic in humans. Typically, humanized antibodies are generated by replacing hypervariable region sequences from a human acceptor antibody with hypervariable region sequences from a non-human donor antibody (e.g., a mouse, rabbit, or rat donor antibody) that binds to an antigen of interest (e.g., NPR1). In some cases, framework region sequences of the acceptor antibody may also be replaced with the corresponding sequences of the donor antibody (e.g., via affinity maturation). In addition to the sequences derived from the donor and acceptor antibodies, the humanized antibody can be further modified by the substitution of residues, either in the framework region and/or within the replaced non-human residues to refine and optimize antibody specificity, affinity, and/or activity, as discussed herein. Methods to generate humanized antibodies are known in the art. See, e.g., Riechmann et al. (Nature 1988; 332(6162):323-7); Jones et al. (Nature 1986; 321(6069):522-5); U.S. Pat. No. 5,225,539 (Winter); and U.S. Pat. Nos. 5,530,101; 5,585,089; 5,693, 762, and 6,180,370 (Queen et al.), the contents of each of which are herein incorporated by reference for this purpose.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al., (2000) J Mol Biol; 296:57-86, the contents of which are herein incorporated by reference for this purpose). Human antibodies may include amino acid residues not encoded by human sequences (e.g., mutations introduced by random or site-specific mutagenesis in vitro or by somatic mutation in vivo).

The antibodies or antigen binding fragments of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "peptide," "polypeptide," and "protein" are used interchangeably herein to refer to a polymer of amino acid residues. The terms encompass amino acid polymers in which one or more amino acid residues is an artificial chemical mimetic of a corresponding naturally-occurring amino acid, as well as naturally-occurring amino acid polymers and non-naturally-occurring amino acid polymers. Unless otherwise indicated, a particular polypeptide sequence also implicitly encompasses conservatively modified variants thereof.

The term "conservatively modified variant" applies to both amino acid and nucleic acid sequences. For nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence. For polypeptide sequences, conservatively modified variants include individual substitutions, deletions, or additions to a polypeptide sequence which result in the substitution of an amino acid with a chemically similar amino acid. Conservative substitution tables providing functionally similar amino acids are well known in the art. The following eight groups contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine(S), Threonine (T); and
8) Cysteine (C), Methionine (M).

The term "identity" or "homology" refers to a relationship between the sequences of two or more polypeptides, as determined by comparing the sequences. "Identity" also means the degree of sequence relatedness between polypeptides, as determined by the number of matches between strings of two or more amino acid residues. The percent "identity" between the two sequences is a function of the number of identical positions shared by the sequences (i.e., percent identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Additionally, or alternatively, the protein sequences of the present disclosure can further be used as a "query sequence" to perform a search against public databases to, for example, identify related sequences. For example, such searches can be performed using the BLAST program of Altschul et al. (J Mol Biol 1990; 215(3):403-10), the contents of which are herein incorporated by reference for this purpose.

Two sequences are "substantially identical" if two sequences have a specified percentage of amino acid residues or nucleotides that are the same (e.g., 60% identity, 65% identity, 70% identity, 75% identity, 80% identity, 85% identity, 90% identity, 95% identity, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or exists over a region that is 100 to 500 or 1000 or more nucleotides (or 20, 50, 200 or more amino acids) in length.

Binding "affinity" refers to the strength of interaction between antibody and antigen at single antigenic sites. Within each antigenic site, the variable region of the antibody "arm" interacts through weak non-covalent forces with antigen at numerous sites. In general, the more interactions, the stronger the affinity. Generally, such determinations can be made using a cell-based assay.

The term "Kassoc" or "Ka", as used herein, is intended to refer to the association rate of a particular binding molecule-antigen interaction, whereas the term "Kdis" or "Kd," as used herein, is intended to refer to the dissociation rate of a particular binding molecule-antigen interaction. The term "KD", as used herein, is intended to refer to the equilibrium dissociation constant, which is obtained from the ratio of Kd to Ka (i.e., Kd/Ka) and is expressed as a molar concentration (M). $K_D$ values for antibodies can be determined using methods well established in the art. A method for determining the $K_D$ of an antibody is by using surface plasmon resonance, such as a Biacore® system, or solution equilibrium titration (SET) (see Friguet et al., (1985) J. Immunol. Methods, 77 (2): 305-319, and Hanel et al., (2005) Anal. Biochem., 339 (1): 182-184), the contents of each of which are herein incorporated by reference for this purpose.

As used herein, the term "specific," "specifically binds," and "binds specifically" refers to a binding reaction between an antibody or antigen binding fragment (e.g., an anti-NPR1 antibody) and a target antigen (e.g., NPR1) in a heterogeneous population of proteins and other biologics. Antibodies can be tested for specificity of binding by comparing binding to an appropriate antigen to binding to an irrelevant antigen or antigen mixture under a given set of conditions. If the antibody binds to the appropriate antigen with at least 2, 5, 7, and preferably 10 or more times more affinity than to the irrelevant antigen or antigen mixture, then it is considered to be specific. A "specific antibody" or a "target-specific antibody" is one that only binds the target antigen (e.g., NPR1), but does not bind (or exhibits minimal binding) to other antigens. In certain embodiments, an antibody or antigen binding fragment that specifically binds the target antigen (e.g., NPR1) has a $K_D$ of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In certain embodiments, the $K_D$ is about 1 pM to about 600 pM. In certain embodiments, the $K_D$ is between 600 pM to 1 μM, 1 μM to 100 nM, or 100 mM to 10 nM (inclusive).

In some embodiments, the antibodies or antigen binding fragments thereof act as non-competitive agonists. A "non-competitive agonist" refers to a molecule which binds to an enzyme or receptor at a site distant from the binding sites of its natural ligands. The non-competitive or allosteric agonism is generally independent of the association or concentration of the natural ligands for the enzyme or receptor. Such non-competitive agonists can, for example, provide for a level of activation that can be substantially independent of natural ligands. In a specific embodiment, the anti-NPR1 antibodies or antigen binding fragments described herein are ANP non-competitive, meaning that the antibody or antigen binding fragment acts as an agonist which binds at site away from ANP binding site of NPR1 and effect agonistic activity regardless of whether or not NPR1 is bound to ANP.

In some embodiments, the antibodies or antigen binding fragments thereof act as competitive agonists. A "competitive agonist" refers to an agonist which interferes or competes with a natural ligand for its binding site on an enzyme or receptor. In a specific embodiment, the anti-NPR1 antibodies or antigen binding fragments described herein are ANP competitive, meaning that the antibody or antigen binding fragment acts as an agonist which competes with ANP at the ANP binding site of NPR1.

In some embodiments, the activation of NPR1 by an antibody or antigen binding fragment may be determined by any suitable assay. An exemplary assay for determination of NPR1 activation is the production of cGMP by mammalian cells (e.g., CHO cells or a human cell line) expressing hNPR1.

Figure 3:
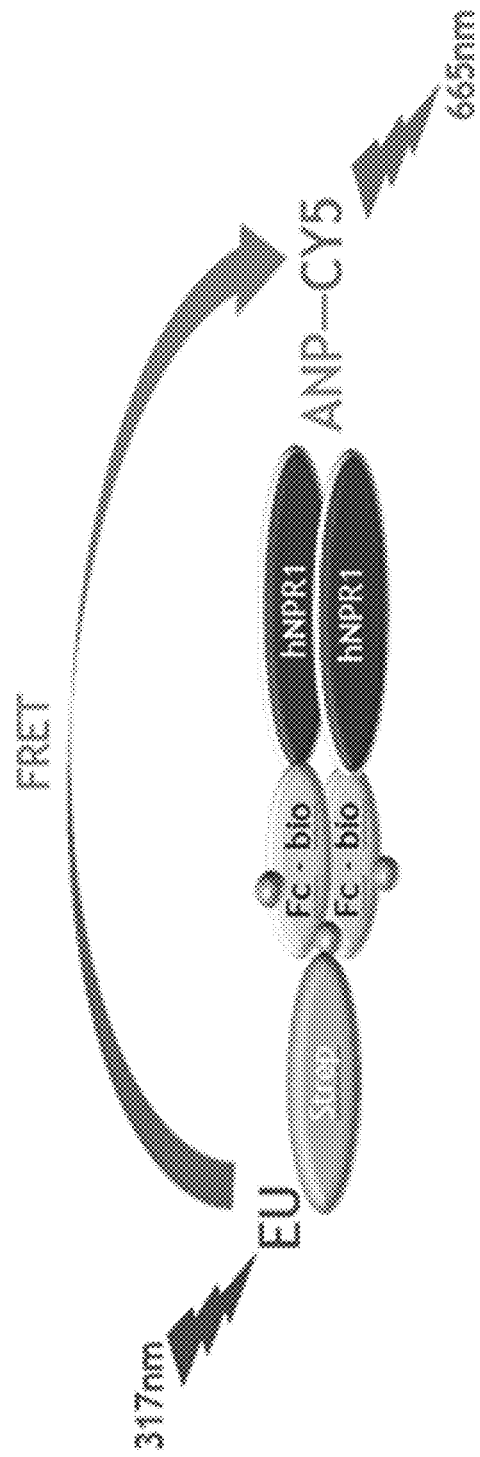
FIG. 3 is a graphical representation of a Fluorescence Resonance Energy Transfer (FRET)-based assay in which the NPR1-specific antibodies competed with ANP for binding to NPR1. In this FRET based assay, Eu-labeled Streptavidin (for measurement of IgGs) or Eu-labeled anti-hFc antibody (for measurement of FabCys) was used as an energy donor, while Cy5-labeled ANP was used as an acceptor.

In some embodiments, the stabilization of the ANP-NPR1 complex may be determined by any suitable assay. An exemplary assay for determination of the stability of the ANP-NPR1 complex is the FRET assay described herein (see, e.g., FIG. 3).

The term "about" in relation to a numerical value x means, for example, x±10%.

Antibodies of the Disclosure

Below are disclosed certain specific anti-NPR1 antibody sequences of the disclosure. As used herein, the term "anti-NPR1 antibody" or "antibody that binds to NPR1" refers to any form of an antibody or antigen binding fragment that specifically binds to NPR1, e.g., those binding with a $K_D$ of less than $1 \times 10^{-8}$ M, as determined by, e.g., surface plasmon resonance (SPR) spectroscopy (using Biacore™) or solution equilibrium titration (SET). The term encompasses monoclonal antibodies (including intact monoclonal antibodies), polyclonal antibodies, and biologically functional antigen binding fragments so long as they specifically bind to NPR1.

Amino acid and nucleic acid sequences of exemplary anti-NPR1 antibodies of the present disclosure are set forth in Table 2. In some embodiments, the antibody has the heavy and light chain CDRs, VH and VL sequence, and/or the heavy and light chain sequence of any of the antibodies described in Table 2. In some embodiments, the anti-NPR1 antibody is a four-chain antibody (also referred to as an intact antibody), comprising two heavy chains and two light chains. In some embodiments, the anti-NPR1 antibody is an antigen binding fragment of an intact antibody, e.g., a functional fragment of an intact antibody selected from any of those set forth in Table 2 that retains the ability to bind NPR1 and/or provide a function of the intact antibody (e.g., activating NPR1 in the absence of ANP). In some embodiments, the anti-NPR1 antibody is an antibody having the CDRs of any heavy chain variable region and light chain variable region pair shown in Table 2. In some embodiments, the anti-NPR1 antibody is an antibody having the CDRs of any heavy and light chain pair shown in Table 2.

TABLE 2

Exemplary anti-NPR1 antibody sequences

WW01_LALA

| | | |
|---|---|---|
| SEQ ID NO: 4 | HCDR1 (Combined) | GFTFNTHYIH |
| SEQ ID NO: 5 | HCDR2 (Combined) | SISGSGSNTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 5 | HCDR2 (Kabat) | SISGSGSNTYYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 9 | HCDR2 (Chothia) | SGSGSN |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 11 | HCDR2 (IMGT) | ISGSGSNT |
| SEQ ID NO: 12 | HCDR3 (IMGT) | ARERGYVYYHMFDP |
| SEQ ID NO: 13 | VH | QVQLLESGGGLVQPGGSLRLSCAASGFTFNTHYIHWVRQAPGKGLEWVSSI SGSGSNTYYADSVKGRFTISRDNSKNTLYLQMNSLRAEDTAVYYCARERG YVYYHMFDPWGQGTLVTVSS |
| SEQ ID NO: 14 | DNA VH | caggtgcaattgctggaaagcggcggtggcctggtgcagccgggtggcagcctgcgtctgagctgcgcggcgtccg gattcacctttaacactcattacatccattgggtgcgccaggcccccggcaaaggtctcgagtgggtttcctctatctctgg ttctggttctaacacctactatgcggatagcgtgaaaggccgctttaccatcagccgcgataattcgaaaaacaccctgta tctgcaaatgaacagcctgcgtgcggaagatacggccgtgtattattgcgcgcgtgaacgtggttacgtttactaccatat gttcgatccgtggggccaaggcaccctggtgactgttagctca |
| SEQ ID NO: 15 | Heavy Chain | QVQLLESGGGLVQPGGSLRLSCAASGFTFNTHYIHWVRQAPGKGLEWVSSI SGSGSNTYYADSVKGRFTISRDNSKNTLYLQMNSLRAEDTAVYYCARERG YVYYHMFDPWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI |

TABLE 2-continued

Exemplary anti-NPR1 antibody sequences

|  |  |  |
|---|---|---|
|  |  | CNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID<br>NO: 16 | DNA<br>Heavy<br>Chain | caggtgcaattgctggaaagcggcggtggcctggtgcagccgggtggcagcctgcgtctgagctgcgcggcgtccg<br>gattcacctttaacactcattacatccattgggtgcgccaggcccccggcaaaggtctcgagtgggtttcctctatctctgg<br>ttctggttctaacacctactatgcggatagcgtgaaaggccgctttaccatcagccgcgataattcgaaaaacaccctgta<br>tctgcaaatgaacagcctgcgtgcggaagatacggccgtgtattattgcgcgcgtgaacgtggttacgtttactaccatat<br>gttcgatccgtggggccaaggcaccctggtgactgttagctcagcctccaccaagggtccatcggtcttccccctggca<br>ccctcctccaagagcacctctgggggcacagcggccctgggctgcctggtcaaggactacttccccgaaccggtgac<br>ggtgtcgtggaactcaggcgccctgaccagcggcgtgcacaccttcccggctgtcctacagtcctcaggactctactcc<br>ctcagcagcgtggtgaccgtgccctccagcagcttgggcacccagacctacatctgcaacgtgaatcacaagcccag<br>caacaccaaggtggacaagagagttgagcccaaatcttgtgacaaaactcacacatgcccaccgtgcccagcacctg<br>aagcagcggggggaccgtcagtcttcctcttccccccaaaacccaaggacacccctcatgatctcccgacccctgagg<br>tcacatgcgtggtggtggacgtgagccacgaagaccctgaggtcaagttcaactggtacgtggacggcgtggaggtg<br>cataatgccaagacaaagccgcgggaggagcagtacaacagcacgtaccgggtggtcagcgtcctcaccgtcctgc<br>accaggactggctgaatggcaaggagtacaagtgcaaggtctccaacaaagccctcccagccccatcgagaaaac<br>catctccaaagccaaagggcagccccgagaaccacaggtgtacaccctgcccccatcccgggaggagatgaccaag<br>aaccaggtcagcctgacctgcctggtcaaaggcttctatcccagcgacatcgccgtggagtgggagagcaatgggca<br>gccggagaacaactacaagaccacgcctcccgtgctggactccgacggctccttcttcctctacagcaagctcaccgt<br>ggacaagagcaggtggcagcaggggaacgtcttctcatgctccgtgatgcatgaggctctgcacaaccactacacgc<br>agaagagcctctccctgtctccgggtaaa |
| SEQ ID<br>NO: 17 | LCDR1<br>(Combined) | RASQSITRNYLA |
| SEQ ID<br>NO: 18 | LCDR2<br>(Combined) | GASSRAT |
| SEQ ID<br>NO: 19 | LCDR3<br>(Combined) | QQHSMYPRT |
| SEQ ID<br>NO: 17 | LCDR1<br>(Kabat) | RASQSITRNYLA |
| SEQ ID<br>NO: 18 | LCDR2<br>(Kabat) | GASSRAT |
| SEQ ID<br>NO: 19 | LCDR3<br>(Kabat) | QQHSMYPRT |
| SEQ ID<br>NO: 20 | LCDR1<br>(Chothia) | SQSITRNY |
| SEQ ID<br>NO: 21 | LCDR2<br>(Chothia) | GAS |
| SEQ ID<br>NO: 22 | LCDR3<br>(Chothia) | HSMYPR |
| SEQ ID<br>NO: 23 | LCDR1<br>(IMGT) | QSITRNY |
| SEQ ID<br>NO: 21 | LCDR2<br>(IMGT) | GAS |
| SEQ ID<br>NO: 19 | LCDR3<br>(IMGT) | QQHSMYPRT |
| SEQ ID<br>NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID<br>NO: 25 | DNA VL | gatatcgtgctgacccagagcccggcgacccgagcctgagcccgggtgaacgtgccacccgagctgcagagcga<br>gccagtctatcactcgtaactacctggcttggtaccagcagaaacgggccaggccccgcgtctattaatctacgtgct<br>tcttctcgtgcgaccggcattccggcgcgttttagcggcagcggatccggcaccgatttcaccctgaccattagcagcct<br>ggaaccggaagactttgcggtgtattattgccagcagcattctatgtacccgcgtacctttggccagggcacgaaagttg<br>aaattaaa |
| SEQ ID<br>NO: 26 | Light<br>Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |

TABLE 2-continued

Exemplary anti-NPR1 antibody sequences

| SEQ ID NO: 27 | DNA Light Chain | gatatcgtgctgacccagagcccggcgaccctgagcctgagcccgggtgaacgtgccaccctgagctgcagagcga
gccagtctctatcactcgtggcattccggcgcgttttagcggcagcggatccggcaccgattttcaccctgaccattagcagcct
ggaaccggaagactttgcggtgtattattgccagcagcattctatgtacccggtacctttggccagggcacgaaagttg
aaattaaacgtacggtggccgctcccagcgtgttcatcttccccccagcgacgagcagctgaagagcggcaccgcc
agcgtggtgtgcctgctgaacaacttctaccccggggaggccaaggtgcagtggaaggtggacaacgccctgcaga
gcggcaacagccaggaaaagcgtcaccgagcaggacagcaaggactccacctacagcctgagcagcaccctgacc
tgagcaaggccgactacgagaagcacaaggtgtacgcctgcgaggtgacccaccagggcctgtccagccccgtgac
caagagcttcaaccggggcgagtgt |

WW03_LALA

| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS
AISSDGSYTYYADSVKGRFTISRDNSKNTLYLQMNSLRAEDTAVYYCARD
RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcggcgtccg
gattcaccttttcttcttactggatgaactgggtgcgccaggcccccgggcaaaggtctcgagtgggtttccgctatctcttc
tgacggttcttacacctactatgcggatagcgtgaaaggccgctttaccatcagccgcgataattcgaaaaacacctgt
atctgcaaatgaacagcctgcgtgcggaagatacggccgtgtattattgcgcgcgtgaccgttactctatgatctactctt
acggtgctggtgctttcgattactggggccaaggcaccctggtgactgttagctca |
| SEQ ID NO: 39 | Heavy Chain | QVQLLESGGGLVQPGGSLRLSCAASGFTFSSYWMNWVRQAPGKGLEWVS
AISSDGSYTYYADSVKGRFTISRDNSKNTLYLQMNSLRAEDTAVYYCARD
RYSMIYSYGAGAFDYWGQGTLVTVSSASTKGPSVFPLAPSSKSTSGGTAAL
GCLVKDYFPEPVTVSWNSGALTSGVHTFPAVLQSSGLYSLSSVVTVPSSSL
GTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSP
GK |
| SEQ ID NO: 40 | DNA Heavy Chain | caggtgcaattgctggaaagcggcggtggcctggtgcagccgggtggcagcctgcgtctgagctgcgcggcgtccg
gattcaccttttcttcttactggatgaactgggtgcgccaggcccccgggcaaaggtctcgagtgggtttccgctatctcttc
tgacggttcttacacctactatgcggatagcgtgaaaggccgctttaccatcagccgcgataattcgaaaaacacctgt
atctgcaaatgaacagcctgcgtgcggaagatacggccgtgtattattgcgcgcgtgaccgttactctatgatctactctt
acggtgctggtgctttcgattactggggccaaggcaccctggtgactgttagctcagcctccaccaagggtccatcggt
cttcccctggcaccctcctccaagagcacctctgggggcacagcggccctgggctgcctggtcaaggactacttccc
cgaaccggtgacggtgtcgtggaactcaggcgccctgaccagcggcgtgcacaccttcccggctgtcctacagtcctc
aggactctactccctcagcagcgtggtgaccgtgccctccagcagcttgggcacccagacctacatctgcaacgtgaat |

TABLE 2-continued

Exemplary anti-NPR1 antibody sequences

```
cacaagcccagcaacaccaaggtggacaagagagttgagcccaaatcttgtgacaaaactcacacatgcccaccgtg
cccagcacctgaagcagcggggggaccgtcagtcttcctcttccccccaaaacccaaggacacccctcatgatctcccg
gaccctgaggtcacatgcgtggtggtggacgtgagccacgaagaccctgaggtcaagttcaactggtacgtggacg
gcgtggaggtgcataatgccaagacaaagccgcgggaggagcagtacaacagcacgtaccgggtggtcagcgtcct
caccgtcctgcaccaggactggctgaatggcaaggagtacaagtgcaaggtctccaacaaagcccctcccagcccca
tcgagaaaaccatctccaaagccaaagggcagccccgagaaccacaggtgtacaccctgcccccatcccgggagga
gatgaccaagaaccaggtcagcctgacctgcctggtcaaaggcttctatcccagcgacatcgccgtggagtgggaga
gcaatgggcagccggagaacaactacaagaccacgcctcccgtgctggactccgacggctccttcttcctctacagca
agctcaccgtggacaagagcaggtggcagcaggggaacgtcttctcatgctccgtgatgcatgaggctctgcacaacc
actacacgcagaagagcctctccctgtctccgggtaaa
```

| SEQ ID NO: 41 | LCDR1 (Combined) | RASQGISSYLA |
|---|---|---|
| SEQ ID NO: 42 | LCDR2 (Combined) | TASTLQS |
| SEQ ID NO: 43 | LCDR3 (Combined) | MQSYEKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 43 | LCDR3 (Kabat) | MQSYEKPRT |
| SEQ ID NO: 44 | LCDR1 (Chothia) | SQGISSY |
| SEQ ID NO: 45 | LCDR2 (Chothia) | TAS |
| SEQ ID NO: 46 | LCDR3 (Chothia) | SYEKPR |
| SEQ ID NO: 47 | LCDR1 (IMGT) | QGISSY |
| SEQ ID NO: 45 | LCDR2 (IMGT) | TAS |
| SEQ ID NO: 43 | LCDR3 (IMGT) | MQSYEKPRT |
| SEQ ID NO: 48 | VL | DIQMTQSPSSLSASVGDRVTITCRASQGISSYLAWYQQKPGKAPKLLIYTASTLQSGVPSRFSGSGSGTDFTLTISSLQPEDFATYYCMQSYEKPRTFGQGTKVEIK |
| SEQ ID NO: 49 | DNA VL | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgcatgcagtcttacgaaaaaccgcgtacctttggccagggcacgaaagttgaa ttaaa |
| SEQ ID NO: 50 | Light Chain | DIQMTQSPSSLSASVGDRVTITCRASQGISSYLAWYQQKPGKAPKLLIYTASTLQSGVPSRFSGSGSGTDFTLTISSLQPEDFATYYCMQSYEKPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 51 | DNA Light Chain | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgcatgcagtcttacgaaaaaccgcgtacctttggccagggcacgaaagttgaa ttaaacgtacggtggccgctcccagcgtgttcatcttccccccagcgacgagcagctgaagagcggcaccgccagc gtggtgtgcctgctgaacaacttctaccccagggaggccaaggtgcagtggaaggtggacaacgccctgcagagcg gcaacagccaggaaagcgtcaccgagcaggacagcaaggactccacctacagcctgagcagcacccctgacctga gcaaggccgactacgagaagcacaaggtgtacgccgcggtgacccaccagggcctgtccagcccgtgacca agagcttcaaccggggcgagtgt |

WW05_LALA

| SEQ ID NO: 52 | HCDR1 (Combined) | GYSFSNYWIG |

TABLE 2-continued

Exemplary anti-NPR1 antibody sequences

| SEQ ID NO: 53 | HCDR2 (Combined) | IIYPDVSYTRYSPSFQG |
|---|---|---|
| SEQ ID NO: 54 | HCDR3 (Combined) | YWSEAYTFDY |
| SEQ ID NO: 55 | HCDR1 (Kabat) | NYWIG |
| SEQ ID NO: 53 | HCDR2 (Kabat) | IIYPDVSYTRYSPSFQG |
| SEQ ID NO: 54 | HCDR3 (Kabat) | YWSEAYTFDY |
| SEQ ID NO: 56 | HCDR1 (Chothia) | GYSFSNY |
| SEQ ID NO: 57 | HCDR2 (Chothia) | YPDVSY |
| SEQ ID NO: 54 | HCDR3 (Chothia) | YWSEAYTFDY |
| SEQ ID NO: 58 | HCDR1 (IMGT) | GYSFSNYW |
| SEQ ID NO: 59 | HCDR2 (IMGT) | IYPDVSYT |
| SEQ ID NO: 60 | HCDR3 (IMGT) | ARYWSEAYTFDY |
| SEQ ID NO: 61 | VH | QVQLVQSGAEVKKPGESLKISCKGSGYSFSNYWIGWVRQMPGKGLEWMG<br>IIYPDVSYTRYSPSFQGQVTISADKSISTAYLQWSSLKASDTAMYYCARYWS<br>EAYTFDYWGQGTLVTVSS |
| SEQ ID NO: 62 | DNA VH | caggtgcaattggtgcagagcggtgcggaagtgaaaaaaccgggcgaaagcctgaaaattagctgcaaaggctccg<br>gatatagcttctctaactactggatcggttgggtgcgccagatgccgggcaaaggtctcgagtggatgggcatcatctac<br>ccggacgttagctacacccgttatagcccgagctttcagggccaggtgaccattagcgcggataaaagcatcagcacc<br>gcgtatctgcaatggagcagcctgaaagcgagcgataccgcgatgtattattgcgcgcgttactggtctgaagcttacac<br>tttcgattactgggccaaggcaccctggtgactgttagctca |
| SEQ ID NO: 63 | Heavy Chain | QVQLVQSGAEVKKPGESLKISCKGSGYSFSNYWIGWVRQMPGKGLEWMG<br>IIYPDVSYTRYSPSFQGQVTISADKSISTAYLQWSSLKASDTAMYYCARYWS<br>EAYTFDYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| SEQ ID NO: 64 | DNA Heavy Chain | caggtgcaattggtgcagagcggtgcggaagtgaaaaaaccgggcgaaagcctgaaaattagctgcaaaggctccg<br>gatatagcttctctaactactggatcggttgggtgcgccagatgccgggcaaaggtctcgagtggatgggcatcatctac<br>ccggacgttagctacacccgttatagcccgagctttcagggccaggtgaccattagcgcggataaaagcatcagcacc<br>gcgtatctgcaatggagcagcctgaaagcgagcgataccgcgatgtattattgcgcgcgttactggtctgaagcttacac<br>tttcgattactgggccaaggcaccctggtgactgttagctcagcctccaccaagggtccatcggtcttccccctggcac<br>cctcctccaagagcacctctggggggcacagcggccctgggctgcctggtcaaggactacttccccgaaccggtgacg<br>gtgtcgtggaactcaggcgccctgaccagcggcgtgcacaccttcccggctgtcctacagtcctcaggactctactccc<br>tcagcagcgtggtgaccgtgccctccagcagcttgggcacccagacctacatctgcaacgtgaatcacaagcccagc<br>aacaccaaggtggacaagagagttgagcccaaatcttgtgacaaaactcacacatgcccaccgtgcccagcacctga<br>agcagcggggggaccgtcagtcttcctcttccccccaaaacccaaggacaccctcatgatctcccggacccctgaggt<br>cacatgcgtggtggtggacgtgagccacgaagaccctgaggtcaagttcaactggtacgtggacggcgtggaggtgc<br>ataatgccaagacaaagccgcgggaggagcagtacaacagcacgtaccgggtggtcagcgtcctcaccgtcctgca<br>ccaggactggctgaatggcaaggagtacaagtgcaaggtctccaacaaagccctcccagcccccatcgagaaaacc<br>atctccaaagccaaagggcagccccgagaaccacaggtgtacaccctgccccatcccgggaggagatgaccaaga<br>accaggtcagcctgacctgcctggtcaaaggcttctatcccagcgacatcgccgtggagtgggagagcaatgggcag<br>ccggagaacaactacaagaccacgcctcccgtgctggactccgacggctccttcttcctctacagcaagctcaccgtg<br>gacaagagcaggtggcagcaggggaacgtcttctcatgctccgtgatgcatgaggctctgcacaaccactacacgca<br>gaagagcctctccctgtctccgggtaaa |
| SEQ ID NO: 65 | LCDR1 (Combined) | SGDNIRKKYVF |
| SEQ ID NO: 66 | LCDR2 (Combined) | GDNDRPS |

TABLE 2-continued

Exemplary anti-NPR1 antibody sequences

| SEQ ID NO: 67 | LCDR3 (Combined) | GTYTLLFTSKV |
| SEQ ID NO: 65 | LCDR1 (Kabat) | SGDNIRKKYVF |
| SEQ ID NO: 66 | LCDR2 (Kabat) | GDNDRPS |
| SEQ ID NO: 67 | LCDR3 (Kabat) | GTYTLLFTSKV |
| SEQ ID NO: 68 | LCDR1 (Chothia) | DNIRKKY |
| SEQ ID NO: 69 | LCDR2 (Chothia) | GDN |
| SEQ ID NO: 70 | LCDR3 (Chothia) | YTLLFTSK |
| SEQ ID NO: 71 | LCDR1 (IMGT) | NIRKKY |
| SEQ ID NO: 69 | LCDR2 (IMGT) | GDN |
| SEQ ID NO: 67 | LCDR3 (IMGT) | GTYTLLFTSKV |
| SEQ ID NO: 72 | VL | DIELTQPPSVSVSPGQTASITCSGDNIRKKYVFWYQQKPGQAPVLVIYGDND RPSGIPERFSGSNSGNTATLTISGTQAEDEADYYCGTYTLLFTSKVFGGGTK LTVL |
| SEQ ID NO: 73 | DNA VL | gatatcgaactgacccagccgccgagcgtgagcgtgagtccgggccagaccgcgagcattacctgtagcggcgata acatccgtaaaaaatacgttttctggtaccagcagaaaccgggccaggcgccggtgctggtgatctacggtgacaacg accgtccgagcggcatcccggaacgttttagcggatccaacagcggcaacaccgcgaccctgaccattagcggcacc caggcggaagacgaagcggattattactgcggtacttacactctgctgttcacttctaaagtgtttggcggcggcacgaa gttaaccgtccta |
| SEQ ID NO: 74 | Light Chain | DIELTQPPSVSVSPGQTASITCSGDNIRKKYVFWYQQKPGQAPVLVIYGDND RPSGIPERFSGSNSGNTATLTISGTQAEDEADYYCGTYTLLFTSKVFGGGTK LTVLGQPKAAPSVTLFPPSSEELQANKATLVCLISDFYPGAVTVAWKADSS PVKAGVETTTPSKQSNNKYAASSYLSLTPEQWKSHRSYSCQVTHEGSTVEK TVAPTECS |
| SEQ ID NO: 75 | DNA Light Chain | gatatcgaactgacccagccgccgagcgtgagcgtgagtccgggccagaccgcgagcattacctgtagcggcgata acatccgtaaaaaatacgttttctggtaccagcagaaaccgggccaggcgccggtgctggtgatctacggtgacaacg accgtccgagcggcatcccggaacgttttagcggatccaacagcggcaacaccgcgaccctgaccattagcggcacc caggcggaagacgaagcggattattactgcggtacttacactctgctgttcacttctaaagtgtttggcggcggcacgaa gttaaccgtcctaggtcagcccaaggctgcccctcggtcactctgttcccgccctcctctgaggagcttcaagccaaca aggcacactggtgtgtctcataagtgacttctacccgggagccgtgacagtggcctggaaggcagatagcagcccc gtcaaggcgggagtggagaccaccacaccctccaaacaaagcaacaacaagtacgcggccagcagctatctgagcc tgacgcctgagcagtggaagtcccacagaagctacagctgccaggtcacgcatgaagggagcaccgtggagaagac agtggcccctacagaatgttca |

WW06_LALA

| SEQ ID NO: 76 | HCDR1 (Combined) | GYSFTSYWIA |
| SEQ ID NO: 77 | HCDR2 (Combined) | RIDPDNSYTRYSPSFQG |
| SEQ ID NO: 78 | HCDR3 (Combined) | WLSPGYALGEQPAGMDH |
| SEQ ID NO: 79 | HCDR1 (Kabat) | SYWIA |
| SEQ ID NO: 77 | HCDR2 (Kabat) | RIDPDNSYTRYSPSFQG |
| SEQ ID NO: 78 | HCDR3 (Kabat) | WLSPGYALGEQPAGMDH |

TABLE 2-continued

Exemplary anti-NPR1 antibody sequences

| SEQ ID NO: 80 | HCDR1 (Chothia) | GYSFTSY |
| --- | --- | --- |
| SEQ ID NO: 81 | HCDR2 (Chothia) | DPDNSY |
| SEQ ID NO: 78 | HCDR3 (Chothia) | WLSPGYALGEQPAGMDH |
| SEQ ID NO: 82 | HCDR1 (IMGT) | GYSFTSYW |
| SEQ ID NO: 83 | HCDR2 (IMGT) | IDPDNSYT |
| SEQ ID NO: 84 | HCDR3 (IMGT) | ARWLSPGYALGEQPAGMDH |
| SEQ ID NO: 85 | VH | QVQLVQSGAEVKKPGESLKISCKGSGYSFTSYWIAWVRQMPGKGLEWMG RIDPDNSYTRYSPSFQGQVTISADKSISTAYLQWSSLKASDTAMYYCARWL SPGYALGEQPAGMDHWGQGTLVTVSS |
| SEQ ID NO: 86 | DNA VH | caggtgcaattggtgcagagcggtgcggaagtgaaaaaaccgggcgaaagcctgaaaattagctgcaaaggctccg gatatagcttcacttcttactggatcgcttgggtgcgccagatgccgggcaaaggtctcgagtggatgggccgtatcgac ccggacaacagctacacccgttatagcccgagctttcagggccaggtgaccattagcgcggataaaagcatcagcac cgcgtatctgcaatggagcagcctgaaagcgagcgataccgcgatgtattattgcgcgcgttggctgtctccgggttac gctctgggtgaacagccggctggtatggatcattgggggccaaggcacccctggtgactgttagctca |
| SEQ ID NO: 87 | Heavy Chain | QVQLVQSGAEVKKPGESLKISCKGSGYSFTSYWIAWVRQMPGKGLEWMG RIDPDNSYTRYSPSFQGQVTISADKSISTAYLQWSSLKASDTAMYYCARWL SPGYALGEQPAGMDHWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 88 | DNA Heavy Chain | caggtgcaattggtgcagagcggtgcggaagtgaaaaaaccgggcgaaagcctgaaaattagctgcaaaggctccg gatatagcttcacttcttactggatcgcttgggtgcgccagatgccgggcaaaggtctcgagtggatgggccgtatcgac ccggacaacagctacacccgttatagcccgagctttcagggccaggtgaccattagcgcggataaaagcatcagcac cgcgtatctgcaatggagcagcctgaaagcgagcgataccgcgatgtattattgcgcgcgttggctgtctccgggttac gctctgggtgaacagccggctggtatggatcattgggggccaaggcacccctggtgactgttagctcagcctccaccaag ggtccatcggtcttccccctggcaccctcctccaagagcacctctgggggcacagcggccctgggctgcctggtcaag gactacttccccgaaccggtgacggtgtcgtggaactcaggcgccctgaccagcggcgtgcacaccttcccggctgtc ctacagtcctcaggactctactccctcagcagcgtggtgaccgtgccctccagcagcttgggcacccagacctacatct gcaacgtgaatcacaagcccagcaacaccaaggtggacaagagagttgagcccaaatcttgtgacaaaactcacaca tgcccaccgtgcccagcacctgaagcagcggggggaccgtcagtcttcctcttccccccaaaacccaaggacaccct catgatctcccggacccctgaggtcacatgcgtggtggtggacgtgagccacgaagaccctgaggtcaagttcaactg gtacgtggacggcgtggaggtgcataatgccaagacaaagccgcgggaggagcagtacaacagcacgtaccgggtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtgtacaccctgcccca tcccgggaggagatgaccaagaaccaggtcagcctgacctgcctggtcaaaggcttctatcccagcgacatcgccgt ggagtgggagagcaatgggcagccggagaacaactacaagaccacgcctcccgtgctggactccgacggctccttc ttcctctacagcaagctcaccgtggacaagagcaggtggcagcaggggaacgtcttctcatgctccgtgatgcatgag gctctgcacaaccactacacgcagaagagcctctccctgtctccgggtaaa |
| SEQ ID NO: 89 | LCDR1 (Combined) | TGSSSNIGAGYAVH |
| SEQ ID NO: 90 | LCDR2 (Combined) | SNNKRPS |
| SEQ ID NO: 91 | LCDR3 (Combined) | QSYDLQKSSRV |
| SEQ ID NO: 89 | LCDR1 (Kabat) | TGSSSNIGAGYAVH |
| SEQ ID NO: 90 | LCDR2 (Kabat) | SNNKRPS |
| SEQ ID NO: 91 | LCDR3 (Kabat) | QSYDLQKSSRV |
| SEQ ID NO: 92 | LCDR1 (Chothia) | SSSNIGAGYA |

TABLE 2-continued

Exemplary anti-NPR1 antibody sequences

| SEQ ID NO: 93 | LCDR2 (Chothia) | SNN |
| --- | --- | --- |
| SEQ ID NO: 94 | LCDR3 (Chothia) | YDLQKSSR |
| SEQ ID NO: 95 | LCDR1 (IMGT) | SSNIGAGYA |
| SEQ ID NO: 93 | LCDR2 (IMGT) | SNN |
| SEQ ID NO: 91 | LCDR3 (IMGT) | QSYDLQKSSRV |
| SEQ ID NO: 96 | VL | DIVLTQPPSVSGAPGQRVTISCTGSSSNIGAGYAVHWYQQLPGTAPKLLIYS<br>NNKRPSGVPDRFSGSKSGTSASLAITGLQAEDEADYYCQSYDLQKSSRVFG<br>GGTKLTVL |
| SEQ ID NO: 97 | DNA VL | gatatcgtgctgacccagccgccgagcgtgagcggtgcaccgggccagcgcgtgaccattagctgtaccggcagca<br>gcagcaacattggtgctggttacgctgtgcattggtaccagcagctgccgggcacggcgccgaaactgctgatctactc<br>taacaacaaacgcccgagcggcgtgccggatcgctttagcggatccaaaagcggcaccagcgccagcctggcgatt<br>accggcctgcaagcagaagacgaagcggattattactgccagtcttacgacctgcagaaatcttctcgtgtgtttggcgg<br>cggcacgaagttaaccgtccta |
| SEQ ID NO: 98 | Light Chain | DIVLTQPPSVSGAPGQRVTISCTGSSSNIGAGYAVHWYQQLPGTAPKLLIYS<br>NNKRPSGVPDRFSGSKSGTSASLAITGLQAEDEADYYCQSYDLQKSSRVFG<br>GGTKLTVLGQPKAAPSVTLFPPSSEELQANKATLVCLISDFYPGAVTVAWK<br>ADSSPVKAGVETTTPSKQSNNKYAASSYLSLTPEQWKSHRSYSCQVTHEGS<br>TVEKTVAPTECS |
| SEQ ID NO: 99 | DNA Light Chain | gatatcgtgctgacccagccgccgagcgtgagcggtgcaccgggccagcgcgtgaccattagctgtaccggcagca<br>gcagcaacattggtgctggttacgctgtgcattggtaccagcagctgccgggcacggcgccgaaactgctgatctactc<br>taacaacaaacgcccgagcggcgtgccggatcgctttagcggatccaaaagcggcaccagcgccagcctggcgatt<br>accggcctgcaagcagaagacgaagcggattattactgccagtcttacgacctgcagaaatcttctcgtgtgtttggcgg<br>cggcacgaagttaaccgtcctaggtcagcccaaggctgcccctcggtcactctgttccgccctcctctgaggagctt<br>caagccaacaaggccacactggtgtgtctcataagtgacttctacccgggagccgtgacagtggcctggaaggcagat<br>agcagccccgtcaaggcgggagtggagaccaccacacctccaaacaaagcaacaacaagtacgcggccagcag<br>ctatctgagcctgacgcctgagcagtggaagtccacagaagctacagctgccaggtcacgcatgaagggagcaccg<br>tggagaagacagtggcccctacagaatgttca |

XX01_LALA

| SEQ ID NO: 4 | HCDR1 (Combined) | GFTFNTHYIH |
| --- | --- | --- |
| SEQ ID NO: 100 | HCDR2 (Combined) | SISSSGQSTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 100 | HCDR2 (Kabat) | SISSSGQSTYYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 101 | HCDR2 (Chothia) | SSSGQS |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 102 | HCDR2 (IMGT) | ISSSGQST |

TABLE 2-continued

Exemplary anti-NPR1 antibody sequences

| SEQ ID NO: 12 | HCDR3 (IMGT) | ARERGYVYYHMFDP |
|---|---|---|
| SEQ ID NO: 103 | VH | EVQLLESGGGLVQPGGSLRLSCAASGFTFNTHYIHWVRQAPGKGLEWVSSI SSSGQSTYYADSVKGRFTISRDNSKNTLYLQMNSLRAEDTAVYYCARERG YVYYHMFDPWGQGTLVTVSS |
| SEQ ID NO: 104 | DNA VH | gaggtgcaattgctggaaagcggcggtggcctggtgcagccgggtggcagcctgcgtctgagctgcgcggcgtccg gattcacctttaacactcattacatccattgggtgcgccaggcccccggcaaaggtctcgagtgggtttcctctatctcttct tctggccagtctacttactatgcggatagcgtgaaaggccgctttaccatcagccgcgataattcgaaaaacaccctgtat ctgcaaatgaacagcctgcgtgcggaagatacggccgtgtattattgcgcgcgtgaacgtggttacgtttactaccatat gttcgatccgtggggccaaggcacccctggtgactgttagctca |
| SEQ ID NO: 105 | Heavy Chain | EVQLLESGGGLVQPGGSLRLSCAASGFTFNTHYIHWVRQAPGKGLEWVSSI SSSGQSTYYADSVKGRFTISRDNSKNTLYLQMNSLRAEDTAVYYCARERG YVYYHMFDPWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 106 | DNA Heavy Chain | gaggtgcaattgctggaaagcggcggtggcctggtgcagccgggtggcagcctgcgtctgagctgcgcggcgtccg gattcacctttaacactcattacatccattgggtgcgccaggcccccggcaaaggtctcgagtgggtttcctctatctcttct tctggccagtctacttactatgcggatagcgtgaaaggccgctttaccatcagccgcgataattcgaaaaacaccctgtat ctgcaaatgaacagcctgcgtgcggaagatacggccgtgtattattgcgcgcgtgaacgtggttacgtttactaccatat gttcgatccgtggggccaaggcacccctggtgactgttagctcagcctccaccaagggtccatcggtcttcccctggca ccctcctccaagagcacctctgggggcacagcggccctgggctgcctggtcaaggactacttccccgaaccggtgac ggtgtcgtggaactcaggcgccctgaccagcggcgtgcacaccttcccggctgtcctacagtcctcaggactctactcc ctcagcagcgtggtgaccgtgccctccagcagcttgggcacccagacctacatctgcaacgtgaatcacaagcccag caacaccaaggtggacaagagagttgagcccaaatcttgtgacaaaactcacacatgcccaccgtgcccagcacctg aagcagcggggggaccgtcagtcttcctcttccccccaaaacccaaggacaccctcatgatctcccggacccctgagg tcacatgcgtggtggtggacgtgagccacgaagaccctgaggtcaagttcaactggtacgtggacggcgtggaggtg cataatgccaagacaaagccgcgggaggagcagtacaacagcacgtaccgggtggtcagcgtcctcaccgtcctgc accaggactggctgaatggcaaggagtacaagtgcaaggtctccaacaaagcccctcccagccccatcgagaaaac catctccaaagccaaagggcagccccgagaaccacaggtgtacaccctgcccccatcccgggaggagatgaccaag aaccaggtcagcctgacctgcctggtcaaaggcttctatcccagcgacatcgccgtggagtgggagagcaatgggca gccggagaacaactacaagaccacgcctcccgtgctggactccgacggctccttcttcctctacagcaagctcaccgt ggacaagagcaggtggcagcaggggaacgtcttctcatgctccgtgatgcatgaggctctgcacaaccactacacgc agaagagcctctccctgtctccgggtaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |

TABLE 2-continued

Exemplary anti-NPR1 antibody sequences

| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
|---|---|---|
| SEQ ID NO: 25 | DNA VL | gatatcgtgctgacccagagcccggcgaccctgagcctgagcccgggtgaacgtgccaccctgagctgcagagcga gccagtctatcactcgtaactacctggcttggtaccagcagaaaccgggccaggccccgcgtctattaatctacggtgct tcttctcgtgcgaccggcattccggcgcgttttagcggcagcggatccggcaccgatttcaccctgaccattagcagcct ggaaccggaagactttgcggtgtattattgccagcagcattctatgtacccgcgtacctttggccagggcacgaaagttg aaattaaa |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 27 | DNA Light Chain | gatatcgtgctgacccagagcccggcgaccctgagcctgagcccgggtgaacgtgccaccctgagctgcagagcga gccagtctatcactcgtaactacctggcttggtaccagcagaaaccgggccaggccccgcgtctattaatctacggtgct tcttctcgtgcgaccggcattccggcgcgttttagcggcagcggatccggcaccgatttcaccctgaccattagcagcct ggaaccggaagactttgcggtgtattattgccagcagcattctatgtacccgcgtacctttggccagggcacgaaagttg aaattaaacgtacggtggccgctcccagcgtgttcatcttccccccagcgacgagcagctgaagagcggcaccgcc agcgtggtgtgcctgctgaacaacttctaccccggggaggccaaggtgcagtggaaggtggacaacgccctgcaga gcggcaacagccaggaaagcgtcaccgagcaggacagcaaggactccacctacagcctgagcagcaccctgaccc tgagcaaggccgactacgagaagcacaaggtgtacgcctgcgaggtgacccaccagggcctgtccagcccgtgac caagagcttcaaccggggcgagtgt |

XX01_DAPA

| SEQ ID NO: 4 | HCDR1 (Combined) | GFTFNTHYIH |
|---|---|---|
| SEQ ID NO: 100 | HCDR2 (Combined) | SISSSGQSTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 100 | HCDR2 (Kabat) | SISSSGQSTYYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 101 | HCDR2 (Chothia) | SSSGQS |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 102 | HCDR2 (IMGT) | ISSSGQST |
| SEQ ID NO: 12 | HCDR3 (IMGT) | ARERGYVYYHMFDP |
| SEQ ID NO: 103 | VH | EVQLLESGGGLVQPGGSLRLSCAASGFTFNTHYIHWVRQAPGKGLEWVSSI SSSGQSTYYADSVKGRFTISRDNSKNTLYLQMNSLRAEDTAVYYCARERG YVYYHMFDPWGQGTLVTVSS |
| SEQ ID NO: 107 | DNA VH | gaagtgcagctgcttgagtccggggggtggactggtgcagcccggaggatccctgcgcctgagctgcgctgcatccgg cttcaccttcaacacgcactacatccattgggtcagacaggcccaggaaaaggcctggaatgggtgtcctccatctcct cgtcggggcagtcaacctactacgcggactccgtcaagggccggtttaccattagccgggacaacagcaagaatacc ctgtacctccaaatgaactcgctgagggcgaagataccgccgtgtattactgtgcccgcgagagggctacgtgtact accacatgttcgacccgtggggacagggtactctcgtgactgtgtcttct |
| SEQ ID NO: 108 | Heavy Chain | EVQLLESGGGLVQPGGSLRLSCAASGFTFNTHYIHWVRQAPGKGLEWVSSI SSSGQSTYYADSVKGRFTISRDNSKNTLYLQMNSLRAEDTAVYYCARERG YVYYHMFDPWGQGTLVTVSSASTKGPSVFPLAPSSKSTSGGTAALGCLVK |

TABLE 2-continued

Exemplary anti-NPR1 antibody sequences

|  |  |  |
|---|---|---|
|  |  | DYFPEPVTVSWNSGALTSGVHTFPAVLQSSGLYSLSSVVTVPSSSLGTQTYI<br>CNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID<br>NO: 109 | DNA<br>Heavy<br>Chain | gaagtgcagctgcttgagtccggggggtggactggtgcagcccggaggatccctgcgcctgagctgcgctgcatccgg<br>cttcaccttcaacacgcactacatccattgggtcagacaggcccaggaaaaggcctggaatgggtgtcctccatctcct<br>cgtcggggcagtcaacctactacgcggactccgtcaagggccggtttaccattagccgggacaacagcaagaatacc<br>ctgtacctccaaatgaactcgctgagggccgaagataccgccgtgtattactgtgcccgcgagagaggctacgtgtact<br>accacatgttcgacccgtggggacagggtactctcgtgactgtgtcttctgcgagcactaagggcccgtcagtgttccc<br>gctggctccatcgtcgaagtccacctccgaggaaccgcagcactcggttgctggtcaaggactacttccctgagcc<br>agtgaccgtgtcgtggaacagcggagccctgacttccggcgtgcacacttttccgcggtgctgcagtcctccggtctg<br>tactccctttcgtccgtggtcaccgtgccgtcgtctagcctgggcaccagaccctacatctgcaacgtgaaccacaagcc<br>gtccaacaccaaagtggataagcgggtggagccgaagtcctgcgataagacacacacgtgcccgccatgtccagcg<br>cctgaattgcttggcggaccttccgtgttcctgttcccgcctaagcccaaggacaccttgatgattagcggactcccga<br>gtcacctgtgtggtggtggcagtgtcccacgaggaccccgaggtcaagtttaattggtacgtggacggcgtcgaagt<br>gcacaacgccaagactaagccccgggaggaacagtacaacagcacctaccgggtcgtgtccgtgctgaccgtgctg<br>caccaggactggctgaatgggaaagagtacaagtgcaaagtgtccaacaaggccttggccgctcctatcgaaaaaact<br>atcagcaaggctaagggacagccgagggaaccccaagtctacaccctgccccttcacgcgaagagatgaccaaga<br>atcaagtgtcgctgacctgcctcgtcaagggattctacccctcgacattgcggtggagtgggagtccaacggccagc<br>ccgagaacaactacaagactactccgcccgtgctggactccgacggcagcttcttcctgtattccaagctgaccgtgga<br>caagtcccggtggcagcaaggaaacgtgttcctcctgctcggtcatgcacgaagccctgcacaaccactatacgcagaa<br>gtccctgtccttgagcccggggaaa |
| SEQ ID<br>NO: 17 | LCDR1<br>(Combined) | RASQSITRNYLA |
| SEQ ID<br>NO: 18 | LCDR2<br>(Combined) | GASSRAT |
| SEQ ID<br>NO: 19 | LCDR3<br>(Combined) | QQHSMYPRT |
| SEQ ID<br>NO: 17 | LCDR1<br>(Kabat) | RASQSITRNYLA |
| SEQ ID<br>NO: 18 | LCDR2<br>(Kabat) | GASSRAT |
| SEQ ID<br>NO: 19 | LCDR3<br>(Kabat) | QQHSMYPRT |
| SEQ ID<br>NO: 20 | LCDR1<br>(Chothia) | SQSITRNY |
| SEQ ID<br>NO: 21 | LCDR2<br>(Chothia) | GAS |
| SEQ ID<br>NO: 22 | LCDR3<br>(Chothia) | HSMYPR |
| SEQ ID<br>NO: 23 | LCDR1<br>(IMGT) | QSITRNY |
| SEQ ID<br>NO: 21 | LCDR2<br>(IMGT) | GAS |
| SEQ ID<br>NO: 19 | LCDR3<br>(IMGT) | QQHSMYPRT |
| SEQ ID<br>NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID<br>NO: 110 | DNA VL | gacatcgtgctgactcagtcccctgcgactctgagcctgtcaccgggagaacgggccaccctctcttgccgcgcctcc<br>caatccattactcggaactacctggcctggtatcagcagaagccaggacaggcccctaggcttctgatctacggggcc<br>agctcaagagcaactggcatcccggctcgcttctccggttcgggaagcggcaccgacttcaccctgacaatttcgtccc<br>tcgaacccgaggattttgccgtgtactactgccaacagcactccatgtaccccggaccttggcagggaaccaaagt<br>cgagatcaag |
| SEQ ID<br>NO: 26 | Light<br>Chain | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |

TABLE 2-continued

Exemplary anti-NPR1 antibody sequences

| SEQ ID NO: 111 | DNA Light Chain | gacatcgtgctgactcagtccctgcgactctgagcctgtcaccgggagaacgggccaccctctcttgccgcgcctcc
caatccattactcggaactacctggcctggtatcagcagaagccaggacaggcccctaggcttctgatctacgggcc
agctcaagagcaactggcatcccggctcgcttctccggttcgggaagcggcactgacttcaccctgacaatttcgtccc
tcgaacccgaggatttcgccgtgtactactgccaacagcactccatgtaccccggacctttgggcagggaaccaaagt
cgagatcaagcgtacggtggccgctcccagcgtgttcatcttcccccccagcgacgagcagctgaagagcggcaccg
ccagcgtggtgtgcctgctgaacaacttctaccccccgggaggccaaggtgcagtggaaggtggacaacgccctgcag
agcggcaacagccaggagagcgtcaccgagcaggacagcaaggactccacctacagcctgagcagcaccctgacc
ctgagcaaggccgactacgagaagcataaggtgtacgcctgcgaggtgacccaccagggcctgtccagccccgtga
ccaagagcttcaacaggggcgagtgc |

XX01_N30S_DAPA

| SEQ ID NO: 112 | HCDR1 (Combined) | GFTFSTHYIH |
| SEQ ID NO: 100 | HCDR2 (Combined) | SISSSGQSTYYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 100 | HCDR2 (Kabat) | SISSSGQSTYYADSVKG |
| SEQ ID NO: 6 | HCDR3 (Kabat) | ERGYVYYHMFDP |
| SEQ ID NO: 113 | HCDR1 (Chothia) | GFTFSTH |
| SEQ ID NO: 101 | HCDR2 (Chothia) | SSSGQS |
| SEQ ID NO: 6 | HCDR3 (Chothia) | ERGYVYYHMFDP |
| SEQ ID NO: 114 | HCDR1 (IMGT) | GFTFSTHY |
| SEQ ID NO: 102 | HCDR2 (IMGT) | ISSSGQST |
| SEQ ID NO: 12 | HCDR3 (IMGT) | ARERGYVYYHMFDP |
| SEQ ID NO: 115 | VH | EVQLLESGGGLVQPGGSLRLSCAASGFTFSTHYIHWVRQAPGKGLEWVSSI
SSSGQSTYYADSVKGRFTISRDNSKNTLYLQMNSLRAEDTAVYYCARERG
YVYYHMFDPWGQGTLVTVSS |
| SEQ ID NO: 116 | DNA VH | gaagtgcagctgcttgagtccggggggtggactggtgcagcccggaggatccctgcgcctgagctgcgctgcatccgg
cttcaccttcagcacgcactacatccattgggtcagacaggcccaggaaaaggcctggaatgggtgtcctccatctcc
tcgtcggggcagtcaacctactacgcggactccgtcaagggccggtttaccattagcggacaacagcaagaatacc
ctgtacctccaaatgaactcgctgagggccgaagataccgccgtgtattactgtgcccgcgagagaggctacgtgtact
accacatgttcgacccgtggggacagggtactctcgtgactgtgtcttct |
| SEQ ID NO: 117 | Heavy Chain | EVQLLESGGGLVQPGGSLRLSCAASGFTFSTHYIHWVRQAPGKGLEWVSSI
SSSGQSTYYADSVKGRFTISRDNSKNTLYLQMNSLRAEDTAVYYCARERG
YVYYHMFDPWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDT
LMISRTPEVTCVVVAVSHEDPEVKFNWYVDGVEVHNAKTKPREEQYNSTY
RVVSVLTVLHQDWLNGKEYKCKVSNKALAAPIEKTISKAKGQPREPQVYT
LPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK |
| SEQ ID NO: 118 | DNA Heavy Chain | gaagtgcagctgcttgagtccggggggtggactggtgcagcccggaggatccctgcgcctgagctgcgctgcatccgg
cttcaccttcagcacgcactacatccattgggtcagacaggcccaggaaaaggcctggaatgggtgtcctccatctcc
tcgtcggggcagtcaacctactacgcggactccgtcaagggccggtttaccattagcggacaacagcaagaatacc
ctgtacctccaaatgaactcgctgagggccgaagataccgccgtgtattactgtgcccgcgagagaggctacgtgtact
accacatgttcgacccgtggggacagggtactctcgtgactgtgtcttctgcgcactaagggcccgtcagtgttccc
gctggctccatcgtcgaagtccacctccgaggaaccgcagcactcggttgcctggtcaaggactacttccctgagcc
agtgaccgtgtcgtggaacagcggagccctgacttccggcgtgcacacttttccgcggtgctgcagtcctccggtctg
tactcccttttcgtccgtggtcaccgtgccgtcgtctagcctgggcacccagacctacatctgcaacgtgaaccacaagcc |

TABLE 2-continued

Exemplary anti-NPR1 antibody sequences

```
                      gtccaacaccaaagtggataagcgggtggagccgaagtcctgcgataagacacacgtgcccgccatgtccagcg
                      cctgaattgcttggcggaccttccgtgttcctgttcccgcctaagcccaaggacaccttgatgattagcggactcccga
                      agtcacctgtgtggtggtggcagtgtcccacgaggacccccgaggtcaagtttaattggtacgtggacggcgtcgaagt
                      gcacaacgccaagactaagcccgggaggaacagtacaacagcacctaccgggtcgtgtccgtgctgaccgtgctg
                      caccaggactggctgaatgggaaagagtacaagtgcaaagtgtccaacaaggccttggccgctcctatcgaaaaaact
                      atcagcaaggctaagggacagccgagggaaccccaagtctacaccctgccccttcacgcgaagagatgaccaaga
                      tcaagtgtcgctgacctgcctcgtcaagggattctaccccgacattgcggtggagtggggagtccaacggccagc
                      ccgagaacaactacaagactactccgcccgtgctggactccgacggcagcttcttcctgtattccaagctgaccgtgga
                      caagtcccggtggcagcaaggaaacgtgttctcctgctcggtcatgcacgaagccctgcacaaccactatacgcagaa
                      gtccctgtccttgagcccggggaaa
```

| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 110 | DNA VL | gacatcgtgctgactcagtcccctgcgactctgagcctgtcaccggagaacgggccacccctctcttgccgcgcctcc caatccattactcggaactacctggcctggtatcagcagaagccaggacaggcccctaggcttctgatctacggggcc agctcaagagcaactggcatcccggctcgcttctccggttcgggaagcggcaccgacttcaccctgacaatttcgtccc tcgaacccgaggattcgccgtgtactactgccaacagcactccatgtaccccggaccttgggcagggaaccaaagt cgagatcaag |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 111 | DNA Light Chain | gacatcgtgctgactcagtcccctgcgactctgagcctgtcaccggagaacgggccacccctctcttgccgcgcctcc caatccattactcggaactacctggcctggtatcagcagaagccaggacaggcccctaggcttctgatctacggggcc agctcaagagcaactggcatcccggctcgcttctccggttcgggaagcggcaccgacttcaccctgacaatttcgtccc tcgaacccgaggattcgccgtgtactactgccaacagcactccatgtaccccggaccttgggcagggaaccaaagt cgagatcaagcgtacggtggccgctcccagcgtgttcatcttcccccccagcgacgagcagctgaagagcggcaccg ccagcgtggtgtgcctgctgaacaacttctacccccgagggccaaggtgcagtggaaggtggacaacgccctgcag agcggcaacagccaggagagcgtcaccgagcaggacagcaaggactccacctacagcctgagcagcacctgacc ctgagcaaggccgactacgagaagcataaggtgtacgcctgcgaggtgacccaccagggcctgtccagccccgtga ccaagagcttcaacaggggcgagtgc |
| XX03_LALA | | |
| SEQ ID NO: 28 | HCDR1 (Combined) | GFTFSSYWMN |

TABLE 2-continued

Exemplary anti-NPR1 antibody sequences

| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 123 | DNA VH | gaggtgcaattgctggaaagcggcggtggcctggtgcagccgggtggcagcctgcgtctgagctgcgcggcgtccg gattcacctttttcttcttactggatgaactgggtgcgccaggcccgggcaaaggtctcgagtgggtttccgttatcgaat ctaaaggcaactacatcttctatgcggatagcgtgaaaggccgctttaccatcagccgcgataattcgaaaaacaccctg tatctgcaaatgaacagcctgcgtgcggaagatacggccgtgtattattgcgcgcgtgaccgttactctatgatctactctt acggtgctggtgctttcgattactggggccaaggcaccctggtgactgttagctca |
| SEQ ID NO: 124 | Heavy Chain | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPEAAGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 125 | DNA Heavy Chain | gaggtgcaattgctggaaagcggcggtggcctggtgcagccgggtggcagcctgcgtctgagctgcgcggcgtccg gattcacctttttcttcttactggatgaactgggtgcgccaggcccgggcaaaggtctcgagtgggtttccgttatcgaat ctaaaggcaactacatcttctatgcggatagcgtgaaaggccgctttaccatcagccgcgataattcgaaaaacaccctg tatgcaaatgaacagcctgcgtgcggaagatacggccgtgtattattgcgcgcgtgaccgttactctatgatctactctt acggtgctggtgctttcgattactggggccaaggcaccctggtgactgttagctcagcctccaccaagggtccatcggt cttccccctggcaccctcctccaagagcacctctgggggcacagcggccctgggctgcctggtcaaggactacttccc cgaaccggtgacggtgtcgtggaactcaggcgccctgaccagcggcgtgcacaccttcccggctgtcctacagtcctc aggactctactccctcagcagcgtggtgaccgtgccctccagcagcttgggcacccagacctacatctgcaacgtgaat cacaagcccagcaacaccaaggtggacaagagagttgagcccaaatcttgtgacaaaactcacacatgcccaccgtg cccagcacctgaagcagcggggggaccgtcagtcttcctcttccccccaaaacccaaggacaccctcatgatctcccg gacccctgaggtcacatgcgtggtggtggacgtgagccacgaagaccctgaggtcaagttcaactggtacgtggacg gcgtggaggtgcataatgccaagacaaagccgcgggaggagcagtacaacagcacgtaccgggtggtcagcgtcct caccgtcctgcaccaggactggctgaatggcaaggagtacaagtgcaaggtctccaacaaagccctcccagccccca tcgagaaaaccatctccaaagccaaagggcagccccgagaaccacaggtgtacaccctgcccccatcccgggagga tgaccaagaaccaggtcagcctgacctgcctggtcaaaggcttctatcccagcgacatcgccgtggagtgggagagc aatgggcagccggagaacaactacaagaccacgcctcccgtgctggactccgacggctccttcttcctctacagca agctcaccgtggacaagagcaggtggcagcaggggaacgtcttctcatgctccgtgatgcatgaggctctgcacaacc actacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |

TABLE 2-continued

Exemplary anti-NPR1 antibody sequences

| SEQ ID NO: 43 | LCDR3 (Combined) | MQSYEKPRT |
|---|---|---|
| SEQ ID NO: 41 | LCDR1 (Kabat) | RASQGISSYLA |
| SEQ ID NO: 42 | LCDR2 (Kabat) | TASTLQS |
| SEQ ID NO: 43 | LCDR3 (Kabat) | MQSYEKPRT |
| SEQ ID NO: 44 | LCDR1 (Chothia) | SQGISSY |
| SEQ ID NO: 45 | LCDR2 (Chothia) | TAS |
| SEQ ID NO: 46 | LCDR3 (Chothia) | SYEKPR |
| SEQ ID NO: 47 | LCDR1 (IMGT) | QGISSY |
| SEQ ID NO: 45 | LCDR2 (IMGT) | TAS |
| SEQ ID NO: 43 | LCDR3 (IMGT) | MQSYEKPRT |
| SEQ ID NO: 48 | VL | DIQMTQSPSSLSASVGDRVTITCRASQGISSYLAWYQQKPGKAPKLLIYTAS TLQSGVPSRFSGSGSGTDFTLTISSLQPEDFATYYCMQSYEKPRTFGQGTKV EIK |
| SEQ ID NO: 49 | DNA VL | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgcatgcagtcttacgaaaaaccgcgtaccttggccagggcacgaaagttgaaa ttaaa |
| SEQ ID NO: 50 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCMQSYEKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 51 | DNA Light Chain | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgcatgcagtcttacgaaaaaccgcgtaccttggccagggcacgaaagttgaaa ttaaacgtacggtggccgctcccagcgtgttcatcttcccccccagcgacgagcagctgaagagcggcaccgccagc gtggtgtgcctgctgaacaacttctaccccegggaggccaaggtgcagtggaaggtggacaacgccctgcagagcg gcaacagccaggaaagcgtcaccgagcaggacagcaaggactccacctacagcctgagcagcaccctgaccctga gcaaggccgactacgagaagcacaaggtgtacgcctgcgaggtgacccaccagggcctgtccagccccgtgacca gagcttcaaccggggcgagtgt |

XX04_LALA

| SEQ ID NO: 28 | HCDR1 (Combined) | GFTFSSYWMN |
|---|---|---|
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |

TABLE 2-continued

Exemplary anti-NPR1 antibody sequences

| SEQ ID NO: 32 | HCDR1 (Chothia) | GFTFSSY |
|---|---|---|
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcggcgtccg gattcacctttttcttcttactggatgaactgggtgcgccaggcccccgggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcacccctggtgactgttagctca |
| SEQ ID NO: 39 | Heavy Chain | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 40 | DNA Heavy Chain | caggtgcaattgctggaaagcggcggtggcctggtgcagccgggtggcagcctgcgtctgagctgcgcggcgtccg gattcacctttttcttcttactggatgaactgggtgcgccaggcccccgggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcacccctggtgactgttagctcagcctccaccaagggtccatcggt cttccccctggcacccctcctccaagagcacctctgggggcacagcggccctgggctgcctggtcaaggactacttccc cgaaccggtgacggtgtcgtggaactcaggcgccctgaccagcggcgtgcacaccttcccggctgtcctacagtcctc aggactctactccctcagcagcgtggtgaccgtgccctccagcagcttgggcacccagacctacatctgcaacgtgaat cacaagcccagcaacaccaaggtggacaagagagttgagcccaaatcttgtgacaaaactcacacatgcccaccgtg cccagcacctgaagcagcgggggggaccgtcagtcttcctcttccccccaaaacccaaggacaccctcatgatctccg gacccctgaggtcacatgcgtggtggtggacgtgagccacgaagaccctgaggtcaagttcaactggtacgtggacg gcgtggaggtgcataatgccaagacaaagccgcgggaggagcagtacaacagcacgtaccgggtggtcagcgtcct caccgtcctgcaccaggactggctgaatggcaaggagtacaagtgcaaggtctccaacaaagcccctcccagccccca tcgagaaaaccatctccaaagccaaagggcagccccgagaaccacaggtgtacaccctgcccccatcccgggaggg gatgaccaagaaccaggtcagcctgacctgcctggtcaaaggcttctatcccagcgacatcgccgtggagtgggaga gcaatgggcagccggagaacaactacaagaccacgcctcccgtgctggactccgacggctccttcttcctctacagca agctcaccgtggacaagagcaggtggcagcaggggaacgtcttctcatgctccgtgatgcatgaggctctgcacaacc actacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 126 | LCDR3 (Combined) | QQEWVKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 126 | LCDR3 (Kabat) | QQEWVKPRT |
| SEQ ID NO: 44 | LCDR1 (Chothia) | SQGISSY |

TABLE 2-continued

Exemplary anti-NPR1 antibody sequences

| SEQ ID NO: 45 | LCDR2 (Chothia) | TAS |
|---|---|---|
| SEQ ID NO: 127 | LCDR3 (Chothia) | EWVKPR |
| SEQ ID NO: 47 | LCDR1 (IMGT) | QGISSY |
| SEQ ID NO: 45 | LCDR2 (IMGT) | TAS |
| SEQ ID NO: 126 | LCDR3 (IMGT) | QQEWVKPRT |
| SEQ ID NO: 128 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWVKPRTFGQGTKV EIK |
| SEQ ID NO: 129 | DNA VL | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgccagcaggaatgggttaaaccgcgtaccttggccagggcacgaaagttgaa attaaa |
| SEQ ID NO: 130 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWVKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 131 | DNA Light Chain | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgccagcaggaatgggttaaaccgcgtaccttggccagggcacgaaagttgaa attaaacgtacggtggccgctcccagcgtgttcatcttccccccagcgacgagcagctgaagagcggcaccgccag cgtggtgtgcctgctgaacaacttctaccccggggaggccaaggtgcagtggaaggtggacaacgccctgcagagc ggcaacagccaggaaagcgtcaccgagcaggacagcaaggactccacctacagcctgagcagcacctgaccctg agcaaggccgactacgagaagcacaaggtgtacgcctgcgaggtgacccaccagggcctgtccagccccgtgacc aagagcttcaaccggggcgagtgt |

XX06_LALA

| SEQ ID NO: 28 | HCDR1 (Combined) | GFTFSSYWMN |
|---|---|---|
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |

TABLE 2-continued

Exemplary anti-NPR1 antibody sequences

| SEQ ID NO: 36 | HCDR3 (IMGT) | ARDRYSMIYSYGAGAFDY |
|---|---|---|
| SEQ ID NO: 37 | VH | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSS |
| SEQ ID NO: 132 | DNA VH | caggtgcaattgctggaaagcggcggtggcctggtgcagccgggtggcagcctgcgtctgagctgcgcggcgtccg gattcaccttttcttcttactggatgaactgggtgcgccaggccccaggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcacccctggtgactgttagctca |
| SEQ ID NO: 39 | Heavy Chain | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 133 | DNA Heavy Chain | caggtgcaattgctggaaagcggcggtggcctggtgcagccgggtggcagcctgcgtctgagctgcgcggcgtccg gattcaccttttcttcttactggatgaactgggtgcgccaggccccaggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcacccctggtgactgttagctcagcctccaccaagggtccatcggt cttccccctggcaccctcctccaagagcacctctgggggcacagcggccctgggctgcctggtcaaggactacttccc cgaaccggtgacggtgtcgtggaactcaggcgccctgaccagcggcgtgcacaccttcccggctgtcctacagtcctc aggactctactccctcagcagcgtggtgaccgtgccctccagcagcttgggcacccagacctacatctgcaacgtgaat cacaagcccagcaacaccaaggtggacaagagagttgagcccaaatcttgtgacaaaactcacacatgcccaccgtg cccagcacctgaagcagcggggggaccgtcagtcttcctcttccccccaaaacccaaggacaccctcatgatctcccg gacccctgaggtcacatgcgtggtggtggacgtgagccacgaagaccctgaggtcaagttcaactggtacgtggacg gcgtggaggtgcataatgccaagacaaagccgcgggaggagcagtacaacagcacgtaccgggtggtcagcgtcct caccgtcctgcaccaggactggctgaatggcaaggagtacaagtgcaaggtctccaacaaagccctcccagccccca tcgagaaaaccatctccaaagccaaagggcagccccgagaaccacaggtgtacaccctgcccccatcccgggagga gatgaccaagaaccaggtcagcctgacctgcctggtcaaaggcttctatcccagcgacatcgccgtggagtgggaga gcaatgggcagccggagaacaactacaagaccacgcctcccgtgctggactccgacggctccttcttcctctacagca gctccaccgtggacaagagcaggtggcagcaggggaacgtcttctcatgctccgtgatgcatgaggctctgcacaacc actacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |

TABLE 2-continued

Exemplary anti-NPR1 antibody sequences

SEQ ID NO: 136  VL
DIQMTQSPSSLSASVGDRVTITCRASQGISSYLAWYQQKPGKAPKLLIYTAS
TLQSGVPSRFSGSGSGTDFTLTISSLQPEDFATYYCQQTWRKPRTFGQGTKV
EIK

SEQ ID NO: 137  DNA VL
gatatccagatgacccagagcccgagcagcctgagcgccagcgtgggcgatcgcgtgaccattacctgcagagcca
gccagggtattttcttcttacctggcttggtaccagcagaaaccgggcaaagcgccgaaactattaatctacactgcttcta
ctctgcaaagcggcgtgccgagccgctttagcggcagcggatccggcaccgatttcaccctgaccattagctctctgca
accggaagactttgcgacctattattgccagcagacttggcgtaaaccgcgtaccttggccagggcacgaaagttgaa
attaaa SEQ ID NO: 138  Light Chain
DIQMTQSPSSLSASVGDRVTITCRASQGISSYLAWYQQKPGKAPKLLIYTAS
TLQSGVPSRFSGSGSGTDFTLTISSLQPEDFATYYCQQTWRKPRTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC SEQ ID NO: 139  DNA Light Chain
gatatccagatgacccagagcccgagcagcctgagcgccagcgtgggcgatcgcgtgaccattacctgcagagcca
gccagggtattttcttcttacctggcttggtaccagcagaaaccgggcaaagcgccgaaactattaatctacactgcttcta
ctctgcaaagcggcgtgccgagccgctttagcggcagcggatccggcaccgatttcaccctgaccattagctctctgca
accggaagactttgcgacctattattgccagcagacttggcgtaaaccgcgtaccttggccagggcacgaaagttgaa
attaaacgtacggtggccgctcccagcgtgttcatcttcccccccagcgacgagcagctgaagagcggcaccgccag
cgtggtgtgcctgctgaacaacttctaccccccgggaggccaaggtgcagtggaaggtggacaacgccctgcagagc
ggcaacagccaggaaagcgtcaccgagcaggacagcaaggactccacctacagcctgagcagcaccctgaccctg
agcaaggccgactacgagaagcacaaggtgtacgcctgcgaggtgacccaccagggcctgtccagcccgtgacc
aagagcttcaaccggggcgagtgt

XX06_DAPA

SEQ ID NO: 28  HCDR1 (Combined)
GFTFSSYWMN

SEQ ID NO: 29  HCDR2 (Combined)
AISSDGSYTYYADSVKG

SEQ ID NO: 30  HCDR3 (Combined)
DRYSMIYSYGAGAFDY

SEQ ID NO: 31  HCDR1 (Kabat)
SYWMN

SEQ ID NO: 29  HCDR2 (Kabat)
AISSDGSYTYYADSVKG

SEQ ID NO: 30  HCDR3 (Kabat)
DRYSMIYSYGAGAFDY

SEQ ID NO: 32  HCDR1 (Chothia)
GFTFSSY

SEQ ID NO: 33  HCDR2 (Chothia)
SSDGSY

SEQ ID NO: 30  HCDR3 (Chothia)
DRYSMIYSYGAGAFDY

SEQ ID NO: 34  HCDR1 (IMGT)
GFTFSSYW

SEQ ID NO: 35  HCDR2 (IMGT)
ISSDGSYT

SEQ ID NO: 36  HCDR3 (IMGT)
ARDRYSMIYSYGAGAFDY

SEQ ID NO: 37  VH
QVQLLESGGGLVQPGGSLRLSCAASGFTFSSYWMNWVRQAPGKGLEWVS
AISSDGSYTYYADSVKGRFTISRDNSKNTLYLQMNSLRAEDTAVYYCARD
RYSMIYSYGAGAFDYWGQGTLVTVSS

SEQ ID NO: 140  DNA VH
caagtgcagctgcttgagagcggtggcggactggtgcagccaggggatccttgcgcctgtcatgcgctgcgtcgg
gttcaccttctcgtcctactggatgaactgggtcagacaggctccggggaagggactcgaatgggtgtccgccatttcct
ccgacggctcctacacttactacgccgatagcgtcaagggccggttcaccatctcccgggacaattcgaagaacaccc
tgtacctccaaatgaactcactgcgcgccgaggacactgcggtgtattactgtgcccgggataggacagcatgatcta
ctccgtacggtgccggagcctttgactactggggacagggaaccctttgtgaccgtgtctagc SEQ ID NO: 141  Heavy Chain
QVQLLESGGGLVQPGGSLRLSCAASGFTFSSYWMNWVRQAPGKGLEWVS
AISSDGSYTYYADSVKGRFTISRDNSKNTLYLQMNSLRAEDTAVYYCARD TABLE 2-continued Exemplary anti-NPR1 antibody sequences

|  |  |  |
|---|---|---|
|  |  | RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFLFPP KPKDTLMISRTPEVTCVVVAVSHEDPEVKFNWYVDGVEVHNAKTKPREEQ YNSTYRVVSVLTVLHQDWLNGKEYKCKVSNKALAAPIEKTISKAKGQPRE PQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG K |
| SEQ ID NO: 142 | DNA Heavy Chain | caagtgcagctgcttgagagcggtggcggactggtgcagcaggggggatccttgcgcctgtcatgcgctgcgtcggg gttcacctttctcgtcctactggatgaactgggtcagacaggctccgggaaggactcgaatgggtgtccgccatttcct ccgacggctcctacacttactacgccgatagcgtcaagggccggttcaccatctcccgggacaattcgaagaacaccc tgtacctccaaatgaactcactgcgcgccgaggacactgcggtgtattactgtgcccgggataggtacagcatgatcta ctcctacggtgccggagcctttgactactggggacagggaaccttgtgaccgtgtctagcgcgtccactaagggccc gtcagtgttcccgctggctccatcgtcgaagtccacctccggggggaaccgcagaccctcggttgcctggtcaaggactac ttccctgagccagtgaccgtgtcgtgaacagcggagccctgacttccggcgtgcacacttttcccgcggtgctgcagt cctccggtctgtactccctttcgtccgtggtcaccgtgccgtcgtctagcctgggcacccagacctacatctgcaacgtg aaccacaagccgtccaacaccaaagtggataagcgggtggagccgaagtcctgcgataagacacacgtgcccgc catgtccagcgctgaattgcttggcgaccttccgtgttcctgttcccgcctaagcccaaggacaccttgatgattagcc ggactcccgaagtcacctgtgtggtggtggcagtgtcccacgaggaccccgaggtcaagtttaattggtacgtggacg gcgtcgaagtgcacaacgccaagactaagcccgggaggaacagtacaacagcacctaccgggtcgtgtccgtgct gaccgtgctgcaccaggactggctgaatgggaaagagtacaagtgcaaagtgtccaacaaggccttggccgctcctat cgaaaaaactatcagcaaggctaagggacagccgagggaacccaagtctacaccctgccccccttcacgcgaagag atgaccaagaatcaagtgtcgctgacctgcctcgtcaaggattctacccctccgacattgcggtgagtgggagtcca acggccagcccgagaacaactacaagactactccgcccgtgctggactccgacggcagcttcttcctgtattccaagct gaccgtggacaagtcccggtggcagcaaggaaacgtgttctcctgctcggtcatgcacgaagccctgcacaaccacta tacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIK |
| SEQ ID NO: 143 | DNA VL | gacatccagatgacccagtctccgtcctccctgtccgcatcagtgggggacagagtgaccatcacttgtcgggcctcc aaggcatctcgtcataccaggcctggtatcagcagaaacccggaaaggctcaaagctgctcatctacaccgcctcga ctctgcaatccggagtgccttcccgctttctccggatccggttcgggaaccgacttcacccttccaccattagcagcttcag ccggaagatttcgcgacctactactgccagcaaacctggcggaagcccaggacatttggccagggcactaaggtcga gattaag |
| SEQ ID NO: 138 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIKRTVAAPSVIFPPSDEQLKSGTASVVCLLNNFYPREAKVQWKVDNALQ SGNSQESVTEQDSKDSTYSLSSTLTLSKADYEKHKVYACEVTHQGLSSPVT |

TABLE 2-continued

Exemplary anti-NPR1 antibody sequences

|  |  |  |
|---|---|---|
|  |  | KSFNRGEC |
| SEQ ID NO: 144 | DNA Light Chain | gacatccagatgacccagtctccgtcctccctgtccgcatcagtgggggacagagtgaccatcacttgtcgggcctcc<br>aaggcatctcgtcatacctggcctggtatcagcagaaacccggaaaggctccaaagctgctcatctacaccgcctcga<br>ctctgcaatccggagtgcctttccgcttctccggatccggttcgggaaccgacttcacccctcaccattagcagccttcag<br>ccggaagatttcgcgacctactactgccagcaaacctggcggaagcccaggacatttggccaggcactaaggtcga<br>gattaagcgtacggtggccgctcccagcgtgttcatcttccccccagcgacgagcagctgaagagcggcaccgcca<br>gcgtggtgtgcctgctgaacaacttctaccccgggaggcaagtgcagtggaaggtggacaacgcccctgcagag<br>cggcaacagccaggagagcgtcaccgagcaggacagcaaggactccacctacagcctgagcagcaccctgaccct<br>gagcaaggccgactacgagaagcataaggtgtacgcctgcgaggtgacccaccagggcctgtccagcccgtgacc<br>aagagcttcaacaggggcgagtgc |

XX07_LALA

| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcggcgtccg<br>gattcacctttcttcttactggatgaactgggtgcgccaggcccccgggcaaaggtctcgagtgggtttccgctatctcttc<br>tgacggttcttacacctactatgcggatagcgtgaaaggccgctttaccatcagccgcgataattcgaaaaacaccctgt<br>atctgcaaatgaacagcctgcgtgcggaagatacggccgtgtattattgcgcgcgtgaccgttactctatgatctactctt<br>acggtgctggtgctttcgattactggggccaaggcacccctggtgactgttagctca |
| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 40 | DNA Heavy Chain | caggtgcaattgctggaaagcggcggtggcctggtgcagccgggtggcagcctgcgtctgagctgcgcggcgtccg<br>gattcacctttcttcttactggatgaactgggtgcgccaggcccccgggcaaaggtctcgagtgggtttccgctatctcttc<br>tgacggttcttacacctactatgcggatagcgtgaaaggccgctttaccatcagccgcgataattcgaaaaacaccctgt<br>atctgcaaatgaacagcctgcgtgcggaagatacggccgtgtattattgcgcgcgtgaccgttactctatgatctactctt<br>acggtgctggtgctttcgattactggggccaaggcacccctggtgactgttagctcagcctccaccaagggtccatcggt<br>cttccccctggcaccctcctccaagagcacctctgggggcacagcggccctgggctgcctggtcaaggactacttccc |

TABLE 2-continued

Exemplary anti-NPR1 antibody sequences

```
cgaaccggtgacggtgtcgtggaactcaggcgccctgaccagcggcgtgcacaccttcccggctgtcctacagtcctc
aggactctactccctcagcagcgtggtgaccgtgccctccagcagcttgggcacccagacctacatctgcaacgtgaat
cacaagcccagcaacaccaaggtggacaagagagttgagcccaaatcttgtgacaaaactcacacatgcccaccgtg
cccagcacctgaagcagcggggggaccgtcagtcttcctcttccccccaaaacccaaggacaccctcatgatctcccg
gacccctgaggtcacatgcgtggtggtggacgtgagccacgaagaccctgaggtcaagttcaactggtacgtggacg
gcgtggaggtgcataatgccaagacaaagccgcgggaggagcagtacaacagcacgtaccgggtggtcagcgtcct
caccgtcctgcaccaggactggctgaatggcaaggagtacaagtgcaaggtctccaacaaagccctcccagccccca
tcgagaaaaccatctccaaagccaaagggcagccccgagaaccacaggtgtaccctgcccccatcccgggagga
gatgaccaagaaccaggtcagcctgacctgcctggtcaaaggcttctatcccagcgacatcgccgtggagtgggaga
gcaatgggcagccggagaacaactacaagaccacgcctcccgtgctggactccgacggctccttcttcctctacagca
agctcaccgtggacaagagcaggtggcagcaggggaacgtcttctcatgctccgtgatgcatgaggctctgcacaacc
actacacgcagaagagcctctccctgtctccgggtaaa
```

| SEQ ID NO: 41 | LCDR1 (Combined) | RASQGISSYLA |
|---|---|---|
| SEQ ID NO: 42 | LCDR2 (Combined) | TASTLQS |
| SEQ ID NO: 145 | LCDR3 (Combined) | QQIWTVPRT |
| SEQ ID NO: 41 | LCDR1 (Kabat) | RASQGISSYLA |
| SEQ ID NO: 42 | LCDR2 (Kabat) | TASTLQS |
| SEQ ID NO: 145 | LCDR3 (Kabat) | QQIWTVPRT |
| SEQ ID NO: 44 | LCDR1 (Chothia) | SQGISSY |
| SEQ ID NO: 45 | LCDR2 (Chothia) | TAS |
| SEQ ID NO: 146 | LCDR3 (Chothia) | IWTVPR |
| SEQ ID NO: 47 | LCDR1 (IMGT) | QGISSY |
| SEQ ID NO: 45 | LCDR2 (IMGT) | TAS |
| SEQ ID NO: 145 | LCDR3 (IMGT) | QQIWTVPRT |
| SEQ ID NO: 147 | VL | DIQMTQSPSSLSASVGDRVTITCRASQGISSYLAWYQQKPGKAPKLLIYTASTLQSGVPSRFSGSGSGTDFTLTISSLQPEDFATYYCQQIWTVPRTFGQGTKVEIK |
| SEQ ID NO: 148 | DNA VL | gatatccagatgacccagagcccgagcagcctgagcgccagcgtgggcgatcgcgtgaccattacctgcagagcca gcagggtatttcttcttacctggcttggtaccagcagaaaccgggcaaagcgccgaaactattaatctacactgcttcta ctctgcaaagcggcgtgccgagccgctttagcggcagcggatccggcaccgattcaccctgaccattagctctctgca accggaagactttgcgacctattattgccagcagatctggactgttccgcgtacctttggccagggcacgaaagttgaaa ttaaa |
| SEQ ID NO: 149 | Light Chain | DIQMTQSPSSLSASVGDRVTITCRASQGISSYLAWYQQKPGKAPKLLIYTASTLQSGVPSRFSGSGSGTDFTLTISSLQPEDFATYYCQQIWTVPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 150 | DNA Light Chain | gatatccagatgacccagagcccgagcagcctgagcgccagcgtgggcgatcgcgtgaccattacctgcagagcca gcagggtatttcttcttacctggcttggtaccagcagaaaccgggcaaagcgccgaaactattaatctacactgcttcta ctctgcaaagcggcgtgccgagccgctttagcggcagcggatccggcaccgattcaccctgaccattagctctctgca accggaagactttgcgacctattattgccagcagatctggactgttccgcgtacctttggccagggcacgaaagttgaaa ttaaacgtacggtggcgctcccacgtcgttcatcttcccccgggaggagcaaggtgcagtggaaggtggacaacgcccagagcg gcaacagccaggaaagcgtcaccgagcaggacagcaaggactccacctacagcctgagcagcaccctgacctga gcaaggccgactacgagaagcacaaggtgtacgcctgcgaggtgacccaccaggggcctgtccagccccgtgacca agagcttcaaccggggcgagtgt |

TABLE 2-continued

Exemplary anti-NPR1 antibody sequences

XX08_LALA

| SEQ ID NO: 4 | HCDR1 (Combined) | GFTFNTHYIH |
|---|---|---|
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 8 | HCDR1 (Chothia) | GFTFNTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 154 | VH | EVQLLESGGGLVQPGGSLRLSCAASGFTFNTHYIHWVRQAPGKGLEWVSSI GGQGGMTLYADSVKGRFTISRDNSKNTLYLQMNSLRAEDTAVYYCARER GYVYYHMFDPWGQGTLVTVSS |
| SEQ ID NO: 155 | DNA VH | gaggtgcaattgctggaaagcggcggtggcctggtgcagccgggtggcagcctgcgtctgagctgcgcggcgtccg gattcacctttaacactcattacatccattgggtgcgccaggcccccggcaaaggtctcgagtgggtttcctctatcggtg gtcaggcggtatgactctgtatgcggatagcgtgaaaggccgctttaccatcagccgcgataattcgaaaaacaccct gtatctgcaaatgaacagcctgcgtgcggaagatacggccgtgtattattgcgcgcgtgaacgtggttacgtttactacc atatgttcgatccgtggggccaaggcaccctggtgactgttagctca |
| SEQ ID NO: 156 | Heavy Chain | EVQLLESGGGLVQPGGSLRLSCAASGFTFNTHYIHWVRQAPGKGLEWVSSI GGQGGMTLYADSVKGRFTISRDNSKNTLYLQMNSLRAEDTAVYYCARER GYVYYHMFDPWGQGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 157 | DNA Heavy Chain | gaggtgcaattgctggaaagcggcggtggcctggtgcagccgggtggcagcctgcgtctgagctgcgcggcgtccg gattcacctttaacactcattacatccattgggtgcgccaggcccccggcaaaggtctcgagtgggtttcctctatcggtg gtcaggcggtatgactctgtatgcggatagcgtgaaaggccgctttaccatcagccgcgataattcgaaaaacaccct gtatctgcaaatgaacagcctgcgtgcggaagatacggccgtgtattattgcgcgcgtgaacgtggttacgtttactacc atatgttcgatccgtggggccaaggcaccctggtgactgttagctcagcctccaccaagggtccatcggtcttccccctg gcaccctcctccaagagcacctctgggggcacagcggccctgggctgcctggtcaaggactacttccccgaaccggt gacggtgtcgtggaactcaggcgccctgaccagcggcgtgcacaccttcccggctgtcctacagtcctcaggactcta ctccctcagcagcgtggtgaccgtgccctccagcagcttgggcacccagacctacatctgcaacgtgaatcacaagcc cagcaacaccaaggtggacaagagagttgagcccaaatcttgtgacaaaactcacacatgcccaccgtgcccagcac ctgaagcagcggggggaccgtcagtcttcctcttccccccaaaacccaaggacaccctcatgatctcccggacccctg aggtcacatgcgtggtggtggacgtgagccacgaagaccctgaggtcaagttcaactggtacgtggacggcgtggag gtgcataatgccaagacaaagccgcgggaggagcagtacaacagcacgtaccgggtggtcagcgtcctcaccgtcct gcaccaggactggctgaatggcaaggagtacaagtgcaaggtctccaacaaagccctcccagcccccatcgagaaa accatctccaaagccaaagggcagccccgagaaccacaggtgtacaccctgcccccatcccgggaggagatgacca agaaccaggtcagcctgacctgcctggtcaaaggcttctatcccagcgacatcgccgtggagtgggagagcaatggg cagccggagaacaactacaagaccacgcctcccgtgctggactccgacggctccttcttcctctacagcaagctcacc gtggacaagagcaggtggcagcaggggaacgtcttctcatgctccgtgatgcatgaggctctgcacaaccactacacg cagaagagcctctccctgtctccgggtaaa |

TABLE 2-continued

Exemplary anti-NPR1 antibody sequences

| SEQ ID NO: 17 | LCDR1 (Combined) | RASQSITRNYLA |
|---|---|---|
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 25 | DNA VL | gatatcgtgctgacccagagcccggcgaccctgagcctgagcccgggtgaacgtgccaccctgagctgcagagcga gccagtctatcactcgtaactacctggcttggtaccagcagaaaccgggccaggcccccgcgtctattaatctacggtgct tcttctcgtgcgaccggcattccggcgcgttttagcggcagcggatccggcaccgatttcaccctgaccattagcagcct ggaaccggaagactttgcggtgtattattgccagcagcattctatgtacccgcgtacctttggccagggcacgaaagttg aaattaaa |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 27 | DNA Light Chain | gatatcgtgctgacccagagcccggcgaccctgagcctgagcccgggtgaacgtgccaccctgagctgcagagcga gccagtctatcactcgtaactacctggcttggtaccagcagaaaccgggccaggcccccgcgtctattaatctacggtgct tcttctcgtgcgaccggcattccggcgcgttttagcggcagcggatccggcaccgatttcaccctgaccattagcagcct ggaaccggaagactttgcggtgtattattgccagcagcattctatgtacccgcgtacctttggccagggcacgaaagttg aaattaaacgtacggtggccgctcccagcgtgttcatcttccccccagcgacgagcagctgaagagcggcaccgcc agcgtggtgtgcctgctgaacaacttctaccccggggaggccaaggtgcagtggaaggtggacaacgccctgcaga gcggcaacagccaggaaagcgtcaccgagcaggacagcaaggactccacctacagcctgagcagcaccctgaccc tgagcaaggccgactacgagaagcacaaggtgtacgcctgcgaggtgacccaccagggcctgtccagccccgtgac caagagcttcaaccggggcgagtgt |

XX08_DAPA

| SEQ ID NO: 4 | HCDR1 (Combined) | GFTFNTHYIH |
|---|---|---|
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |

TABLE 2-continued

Exemplary anti-NPR1 antibody sequences

| SEQ ID NO: 151 | HCDR2 (Kabat) | SIGGQGGMTLYADSVKG |
|---|---|---|
| SEQ ID NO: 6 | HCDR3 (Kabat) | ERGYVYYHMFDP |
| SEQ ID NO: 8 | HCDR1 (Chothia) | GFTFNTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 10 | HCDR1 (IMGT) | GFTFNTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 154 | VH | EVQLLESGGGLVQPGGSLRLSCAASGFTFNTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSS |
| SEQ ID NO: 158 | DNA VH | gaagtgcagctcctggagtcgggtggcggactggtgcagcctggcggatcactgcggctgtcatgtgccgcgagcg<br>gtttactttcaacacccactacatccactgggtccgccaagctcccggaaagggactcgaatgggtgtcctccattggt<br>ggacagggcggcatgaccctttacgcggatagcgtgaaggggaggttcaccatctcccgcgacaacagcaagaaca<br>ccctgtacctccaaatgaactcgcttcgggccgaggacactgccgtgtactattgcgcaagagagcggggctacgtgt<br>actaccacatgttcgacccatggggacagggaacgctggtcaccgtgtcctcc |
| SEQ ID NO: 159 | Heavy Chain | EVQLLESGGGLVQPGGSLRLSCAASGFTFNTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 160 | DNA Heavy Chain | gaagtgcagctcctggagtcgggtggcggactggtgcagcctggcggatcactgcggctgtcatgtgccgcgagcg<br>gtttactttcaacacccactacatccactgggtccgccaagctcccggaaagggactcgaatgggtgtcctccattggt<br>ggacagggcggcatgaccctttacgcggatagcgtgaaggggaggttcaccatctcccgcgacaacagcaagaaca<br>ccctgtacctccaaatgaactcgcttcgggccgaggacactgccgtgtactattgcgcaagagagcggggctacgtgt<br>actaccacatgttcgacccatggggacagggaacgctggtcaccgtgtcctccgcctccactaagggccgtcagtgtt<br>cccgctggctccatcgtcgaagtccacctccggaggaaccgcagcactcggttgctggtcaaggactacttccctga<br>gccagtgaccgtgtcgtggaacagcggagccctgacttccggcgtgcacactttttcccgcggtgctgcagtcctccggt<br>ctgtactcccttccgtccgtggtcaccgtgccgtcgtctagcctgggcacccagacctacatctgcaacgtgaaccacaa<br>gccgtccaacaccaaagtggataagcgggtggagccgaagtcctgcgataagacacacgtgcccgccatgtcca<br>gcgcctgaattgcttggcggaccttccgtgttcctgttcccgcctaagcccaaggacaccttgatgattagccggactcc<br>cgaagtcacctgtgtggtggtggcagtgtcccacgaggaccccgaggtcaagtttaattggtacgtggacggcgtcga<br>agtgcacaacgccaagactaagccccgggaggaacagtacaacagcacctaccgggtcgtgtccgtgctgaccgtg<br>ctgcaccaggactggctgaattggaaaagagtacaagtgcaaggtgtccaacaaggcctttggccgctcctatcgaaaaa<br>actatcagcaaggctaagggacagccgagggaaccccaagtctacaccctgccccttcacgcgaagagatgacca<br>agaatcaagtgtcgctgacctgcctcgtcaagggattctaccctccgacattgcggtggagtgggagtccaacggcc<br>agcccgagaacaactacaagactactccgcccgtgctggactccgacggcagcttcttcctgtattccaagctgaccgt<br>ggacaagtcccggtggcagcaaggaaacgtgttctcctgctcggtcatgcacgaagccctgcacaaccactatacgca<br>gaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |

TABLE 2-continued

Exemplary anti-NPR1 antibody sequences

| SEQ ID NO: 19 | LCDR3 (Kabat) | QQHSMYPRT |
|---|---|---|
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |
| SEQ ID NO: 21 | LCDR2 (IMGT) | GAS |
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 110 | DNA VL | gacatcgtgctgactcagtcccctgcgactctgagcctgtcaccgggagaacgggccaccctctcttgccgcgcctcc caatccattactcggaactacctggcctggtatcagcagaagccaggacaggcccctaggcttctgatctacggggcc agctcaagagcaactggcatcccggctcgcttctccggttcgggaagcggcaccgacttcaccctgacaatttcgtccc tcgaacccgaggatttcgccgtgtactactgccaacagcactccatgtaccccggaccttttgggcagggaaccaaagt cgagatcaag |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 111 | DNA Light Chain | gacatcgtgctgactcagtcccctgcgactctgagcctgtcaccgggagaacgggccaccctctcttgccgcgcctcc caatccattactcggaactacctggcctggtatcagcagaagccaggacaggcccctaggcttctgatctacggggcc agctcaagagcaactggcatcccggctcgcttctccggttcgggaagcggcaccgacttcaccctgacaatttcgtccc tcgaacccgaggatttcgccgtgtactactgccaacagcactccatgtaccccggaccttttgggcagggaaccaaagt cgagatcaagcgtacggtggccgctcccagcgtgttcatcttcccccccagcgacgagcagctgaagagcggcaccg ccagcgtggtgtgcctgctgaacaacttctaccccggggaggccaaggtgcagtggaaggtggacaacgccctgcag agcggcaacagccaggagagcgtcaccgagcaggacagcaaggactccacctacagcctgagcagcaccctgacc ctgagcaaggccgactacgagaagcataaggtgtacgcctgcgaggtgacccaccagggcctgtccagccccgtga ccaagagcttcaacaggggcgagtgc |

XX08_N30S_DAPA

| SEQ ID NO: 112 | HCDR1 (Combined) | GFTFSTHYIH |
|---|---|---|
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 113 | HCDR1 (Chothia) | GFTFSTH |
| SEQ ID NO: 152 | HCDR2 (Chothia) | GGQGGM |
| SEQ ID NO: 6 | HCDR3 (Chothia) | ERGYVYYHMFDP |

TABLE 2-continued

Exemplary anti-NPR1 antibody sequences

| SEQ ID NO: 114 | HCDR1 (IMGT) | GFTFSTHY |
|---|---|---|
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 161 | VH | EVQLLESGGGLVQPGGSLRLSCAASGFTFSTHYIHWVRQAPGKGLEWVSSI GGQGGMTLYADSVKGRFTISRDNSKNTLYLQMNSLRAEDTAVYYCARER GYVYYHMFDPWGQGTLVTVSS |
| SEQ ID NO: 162 | DNA VH | gaagtgcagctcctggagtcgggtggcggactggtgcagcctggcggatcactgcggctgtcatgtgccgcgagcg ggtttactttctccacccactacatccactgggtccgccaagctcccggaaagggactcgaatgggtgtcctccattggt ggacagggcggcatgacccttacgcggatagcgtgaaggggaggttcaccatctcccgcgacaacagcaagaaca ccctgtacctccaaatgaactcgcttcgggccgaggacactgccgtgtactattgcgcaagagagcggggctacgtgt actaccacatgttcgacccatggggacagggaacgctggtcaccgtgtcctcc |
| SEQ ID NO: 163 | Heavy Chain | EVQLLESGGGLVQPGGSLRLSCAASGFTFSTHYIHWVRQAPGKGLEWVSSI GGQGGMTLYADSVKGRFTISRDNSKNTLYLQMNSLRAEDTAVYYCARER GYVYYHMFDPWGQGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSCDKTHTCPPCPAPELLGGPSVFLFPPKPKDT LMISRTPEVTCVVVAVSHEDPEVKFNWYVDGVEVHNAKTKPREEQYNSTY RVVSVLTVLHQDWLNGKEYKCKVSNKALAAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 164 | DNA Heavy Chain | gaagtgcagctcctggagtcgggtggcggactggtgcagcctggcggatcactgcggctgtcatgtgccgcgagcg ggtttactttctccacccactacatccactgggtccgccaagctcccggaaagggactcgaatgggtgtcctccattggt ggacagggcggcatgacccttacgcggatagcgtgaaggggaggttcaccatctcccgcgacaacagcaagaaca ccctgtacctccaaatgaactcgcttcgggccgaggacactgccgtgtactattgcgcaagagagcggggctacgtgt actaccacatgttcgacccatggggacagggaacgctggtcaccgtgtcctccgcctccactaagggcccgtcagtgtt cccgctggctccatcgtcgaagtccacctccggaggaaccgcagcactcggttgcctggtcaaggactacttccctga gccagtgaccgtgtcgtggaacagcggagccctgacttccggcgtgcacacttttccccgcggtgctgcagtcctccggt ctgtactccctttcgtccgtggtcaccgtgccgtcgtctagcctgggcacccagacctacatctgcaacgtgaaccacaa gccgtccaacaccaaagtggataagcgggtggagccgaagtcctgcgataagacacacacgtgcccgccatgtcca gcgcctgaattgcttggcggaccttccgtgttcctgttcccgcctaagcccaaggacaccttgatgattagccggactcc cgaagtcacctgtgtggtggtgcagtcccacgaggacccgaggtcaagtttaattggtacgtggacggcgtcga agtgcacaacgccaagactaagccccgggaggaacagtacaacagcacctaccgggtcgtgtccgtgctgaccgtg ctgcaccaggactggctgaatgggaaagagtacaagtgcaaagtgtccaacaaggccttggccgctcctatcgaaaaa actatcagcaaggctaagggacagccgagggaaccccaagtctacacccgtgccccttcacgcgaagagatgacca agaatcaagtgtcgctgacctgcctcgtcaagggattctaccccctccgacattgcggtggagtgggagtccaacggcc agcccgagaacaactacaagactactccgcccgtgctgtacctccgacggcagcttcttcctgtattccaagctgaccgt ggacaagtcccggtggcagcaaggaaacgtgttctcctgctcggtcatgcacgaagccctgcacaaccactatcgca gaagtccctgtccttgagcccggggaaa |
| SEQ ID NO: 17 | LCDR1 (Combined) | RASQSITRNYLA |
| SEQ ID NO: 18 | LCDR2 (Combined) | GASSRAT |
| SEQ ID NO: 19 | LCDR3 (Combined) | QQHSMYPRT |
| SEQ ID NO: 17 | LCDR1 (Kabat) | RASQSITRNYLA |
| SEQ ID NO: 18 | LCDR2 (Kabat) | GASSRAT |
| SEQ ID NO: 19 | LCDR3 (Kabat) | QQHSMYPRT |
| SEQ ID NO: 20 | LCDR1 (Chothia) | SQSITRNY |
| SEQ ID NO: 21 | LCDR2 (Chothia) | GAS |
| SEQ ID NO: 22 | LCDR3 (Chothia) | HSMYPR |
| SEQ ID NO: 23 | LCDR1 (IMGT) | QSITRNY |

TABLE 2-continued

Exemplary anti-NPR1 antibody sequences

| SEQ ID NO: 21 | LCDR2 (IMGT) | GAS |
|---|---|---|
| SEQ ID NO: 19 | LCDR3 (IMGT) | QQHSMYPRT |
| SEQ ID NO: 24 | VL | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIK |
| SEQ ID NO: 110 | DNA VL | gacatcgtgctgactcagtcccctgcgactctgagcctgtcaccggagaacgggccacccctctcttgccgcgcctcc caatccattactcggaactacctggcctggtatcagcagaagccaggacaggcccctaggcttctgatctacggggcc agctcaagagcaactggcatcccggctcgcttctccggttcggggaagcggcaccgacttcaccctgacaatttcgtccc tcgaacccgaggatttcgccgtgtactactgccaacagcactccatgtaccccggaccttttgggcagggaaccaaagt cgagatcaag |
| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 111 | DNA Light Chain | gacatcgtgctgactcagtcccctgcgactctgagcctgtcaccggagaacgggccacccctctcttgccgcgcctcc caatccattactcggaactacctggcctggtatcagcagaagccaggacaggcccctaggcttctgatctacggggcc agctcaagagcaactggcatcccggctcgcttctccggttcggggaagcggcaccgacttcaccctgacaatttcgtccc tcgaacccgaggatttcgccgtgtactactgccaacagcactccatgtaccccggaccttttgggcagggaaccaaagt cgagatcaagcgtacggtggccgctcccagcgtgttcatcttcccccccagcgacgagcagctgaagagcggcaccg ccagcgtggtcgtgcctgctgaacaacttctacccccggagccaaggtgcagtggaaggtggacaacgccctgcag agcggcaacagccaggagagcgtcacccgagcaggacagcaaggactccacctacagcctgagcagcaccctgacc ctgagcaaggccgactacgagaagcataaggtgtacgcctgcgaggtgacccaccagggcctgtccagccccgtga ccaagagcttcaacaggggcgagtgc |
| XX08_N30Q_DAPA | | |
| SEQ ID NO: 165 | HCDR1 (Combined) | GFTFQTHYIH |
| SEQ ID NO: 151 | HCDR2 (Combined) | SIGGQGGMTLYADSVKG |
| SEQ ID NO: 6 | HCDR3 (Combined) | ERGYVYYHMFDP |
| SEQ ID NO: 7 | HCDR1 (Kabat) | THYIH |
| SEQ ID NO: 151 | HCDR2 (Kabat) | SIGGQGGMTLYADSVKG |
| SEQ ID NO: 6 | HCDR3 (Kabat) | ERGYVYYHMFDP |
| SEQ ID NO: 166 | HCDR1 (Chothia) | GFTFQTH |
| SEQ ID NO: 152 | HCDR2 (Chothia) | GGQGGM |
| SEQ ID NO: 6 | HCDR3 (Chothia) | ERGYVYYHMFDP |
| SEQ ID NO: 167 | HCDR1 (IMGT) | GFTFQTHY |
| SEQ ID NO: 153 | HCDR2 (IMGT) | IGGQGGMT |
| SEQ ID NO: 12 | HCDR3 (IMGT) | ARERGYVYYHMFDP |
| SEQ ID NO: 168 | VH | EVQLLESGGGLVQPGGSLRLSCAASGFTFQTHYIHWVRQAPGKGLEWVSSI GGQGGMTLYADSVKGRFTISRDNSKNTLYLQMNSLRAEDTAVYYCARER GYVYYHMFDPWGQGTLVTSS |
| SEQ ID NO: 169 | DNA VH | gaagtgcagctcctggagtcgggtggcggactggtgcagcctggcggatcactgcggctgtcatgtgccgcgagcg ggtttactttccagacccactacatccactgggtccgccaagctcccggaaagggactcgaatggtgtcctccattggt |

TABLE 2-continued

Exemplary anti-NPR1 antibody sequences

|  |  |  |
|---|---|---|
|  |  | ggacagggcggcatgacccttacgcggatagcgtgaaggggaggttcaccatctcccgcgacaacagcaagaaca<br>ccctgtacctccaaatgaactcgcttcgggccgaggacactgccgtgtactattgcgcaagagagcggggctacgtgt<br>actaccacatgttcgacccatggggacagggaacgctggtcaccgtgtcctcc |
| SEQ ID<br>NO: 170 | Heavy<br>Chain | EVQLLESGGGLVQPGGSLRLSCAASGFTFQTHYIHWVRQAPGKGLEWVSSI<br>GGQGGMTLYADSVKGRFTISRDNSKNTLYLQMNSLRAEDTAVYYCARER<br>GYVYYHMFDPWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPELLGGPSVFLFPPKPKDT<br>LMISRTPEVTCVVVAVSHEDPEVKFNWYVDGVEVHNAKTKPREEQYNSTY<br>RVVSVLTVLHQDWLNGKEYKCKVSNKALAAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID<br>NO: 171 | DNA<br>Heavy<br>Chain | gaagtgcagctcctggagtcgggtggcggactggtgcagcctggcggatcactgcggctgtcatgtgccgcagcg<br>ggtttactttccagacccactacatccactgggtccgccaagctcccggaaagggactcgaatgggtgtcctccattggt<br>ggacagggcggcatgacccttacgcggatagcgtgaaggggaggttcaccatctcccgcgacaacagcaagaaca<br>ccctgtacctccaaatgaactcgcttcgggccgaggacactgccgtgtactattgcgcaagagagcggggctacgtgt<br>actaccacatgttcgacccatggggacagggaacgctggtcaccgtgtcctcgagtgtt<br>cccgctggctccatcgtcgaagtccacctccggaggaaccgcagcactcggttgcctggtcaaggactacttccctga<br>gccagtgaccgtgtcgtggaacagcggagccctgacttcggcgtgcacacttttccgcggtgctgcagtcctccggt<br>ctgtactcccttcgtccgtggtcaccgtgccgtcgtctagcctgggcacccagacctacatctgcaacgtgaaccacaa<br>gccgtccaacaccaaagtggataagcgggtggaacccaagtcctgcgataagcacacacacctgcccgccatgtcca<br>gcgcctgaattgcttggcgaccttccgtgttcctgttcccgcctaagcccaaggcaccttgatgattagccggactcc<br>cgaagtcacctgtgtggtggtggcagtgtcccacgaggaccccgaggtcaagtttaattggtacgtggacggcgtcga<br>agtgcacaacgccaagactaagccccgggaggaacagtacaacagcacctaccgggtcgtgtccgtgctgaccgtg<br>ctgcaccaggactggctgaatgggaaagagtacaagtgcaaagtgtccaacaaggccctggccgctcctatcgaaaaa<br>actatcagcaaggctaagggacagccgagggaacccaagtctacaccctgcccctccacgcgaagatgacca<br>agaatcaagtgtcgctgacctgcctcgtcaagggattctacccctccgacattgcggtggagtgggagtccaacggcc<br>agcccgagaacaactacaagactactccgcccgtgctggactcgacggcagcttcttcctgtattccaagctgaccgt<br>ggacaagtcccggtggcagcaaggaaacgtgttctcctgctcggtcatgcacgaagccctgcacaaccactacgca<br>gaagtccctgtccttgagcccggggaaa |
| SEQ ID<br>NO: 17 | LCDR1<br>(Combined) | RASQSITRNYLA |
| SEQ ID<br>NO: 18 | LCDR2<br>(Combined) | GASSRAT |
| SEQ ID<br>NO: 19 | LCDR3<br>(Combined) | QQHSMYPRT |
| SEQ ID<br>NO: 17 | LCDR1<br>(Kabat) | RASQSITRNYLA |
| SEQ ID<br>NO: 18 | LCDR2<br>(Kabat) | GASSRAT |
| SEQ ID<br>NO: 19 | LCDR3<br>(Kabat) | QQHSMYPRT |
| SEQ ID<br>NO: 20 | LCDR1<br>(Chothia) | SQSITRNY |
| SEQ ID<br>NO: 21 | LCDR2<br>(Chothia) | GAS |
| SEQ ID<br>NO: 22 | LCDR3<br>(Chothia) | HSMYPR |
| SEQ ID<br>NO: 23 | LCDR1<br>(IMGT) | QSITRNY |
| SEQ ID<br>NO: 21 | LCDR2<br>(IMGT) | GAS |
| SEQ ID<br>NO: 19 | LCDR3<br>(IMGT) | QQHSMYPRT |
| SEQ ID<br>NO: 24 | VL | DIVLTQSPATLSLSPGERATLSCRASQSITRNYLAWYQQKPGQAPRLLIYGA<br>SSRATGIPARFSGSGSGTDFTLTISSLEPEDFAVYYCQQHSMYPRTFGQGTK<br>VEIK |
| SEQ ID<br>NO: 110 | DNA VL | gacatcgtgctgactcagtccctgcgactctgagcctgtcaccgggagaacgggccaccctctcttgccgcgcctcc<br>caatccattactcggaactacctggctggtatcagcagaagccaggacaggcccctaggttctgatctacggggcc<br>agctcaagagcaactggcatcccggctcgcttctccggttcgggaagcggcaccgacttcaccctgacaatttcgtccc<br>tcgaacccgaggattcgccgtgtactactgccaacagcactccatgtaccccggaccttgggcagggaaccaaagt<br>cgagatcaag |

TABLE 2-continued

Exemplary anti-NPR1 antibody sequences

| SEQ ID NO: 26 | Light Chain | DIVLTQSPATLSLSPGERATLSCRASQSITRNYLAWYQQKPGQAPRLLIYGA SSRATGIPARFSGSGSGTDFTLTISSLEPEDFAVYYCQQHSMYPRTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| --- | --- | --- |
| SEQ ID NO: 111 | DNA Light Chain | gacatcgtgctgactcagtccctgcgactctgagcctgtcaccgggagaacgggccaccctctcttgccgcgcctcc caatccattactcggaactacctggcctggtatcagcagaagccaggacaggcccctaggttctgatctacggggcc agctcaagagcaactggcatcccggctcgcttctccggttcgggaagcggcaccgacttcaccctgacaatttcgtccc tcgaacccgaggatttcgccgtgtactactgccaacagcactccatgtaccccccgacctttgggcagggaaccaaagt cgagatcaagcgtacggtggccgctcccagcgtgttcatcttcccccccagcgacgagcagctgaagagcggcaccg ccagcgtggtgtgcctgctgaacaacttctacccccgggaggccaaggtgcagtggaaggtggacaacgccctgcag agcggcaacagccaggagagcgtcaccgagcaggacagcaaggactccacctacagcctgagcagcaccctgacc ctgagcaaggccgactacgagaagcataaggtgtacgcctgcgaggtgacccaccagggcctgtccagcccgtga ccaagagcttcaacaggggcgagtgc |

XX09_LALA

| SEQ ID NO: 28 | HCDR1 (Combined) | GFTFSSYWMN |
| --- | --- | --- |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcggcgtccg gattcaccttttcttcttactggatgaactgggtgcgccaggcccccgggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcaccctggtgactgttagctca |
| SEQ ID NO: 39 | Heavy Chain | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |

TABLE 2-continued

Exemplary anti-NPR1 antibody sequences

| SEQ ID NO: 40 | DNA Heavy Chain | caggtgcaattgctggaaagcggcggtggcctggtgcagccgggtggcagcctgcgtctgagctgcgcggcgtccg gattcaccttttcttcttactggatgaactgggtgcgccaggccccgggcaaaggtctcgagtgggtttccgctatctcttc tgacggttcttacacctactactggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgcttcgattactggggccaaggcacccgtggtgactgttagctcagcctccaccaagggtccatcggt cttcccctggcaccctcctccaagagcacctctggggcacagcggccctgggctgcctggtcaaggactacttcc cgaaccggtgacggtgtcgtggaactcaggcgccctgaccagcggcgtgcacaccttcccggctgtcctacagtcctc aggactctactccctcagcagcgtggtgaccgtgccctccagcagcttgggcacccagacctacatctgcaacgtgaat cacaagcccagcaacaccaaggtggacaagagagttgagcccaaatcttgtgacaaaactcacacatgcccaccgtg cccagcacctgaagcagcggggggaccgtcagtcttcctcttccccccaaaacccaaggacaccctcatgatctcccg gacccctgaggtcacatgcgtggtggtggacgtgagccacgaagaccctgaggtcaagttcaactggtacgtggacg gcgtggaggtgcataatgccaagacaaagccgcgggaggagcagtacaacagcacgtaccgggtggtcagcgtcct caccgtcctgcaccaggactggctgaatggcaaggagtacaagtgcaaggtctccaacaaagccctcccagcccca tcgagaaaaccatctccaaagccaaagggcagccccgagaaccacaggtgtacaccctgcccccatcccgggagga tgatgaccaagaaccaggtcagcctgacctgcctggtcaaaggcttctatcccagcgacatcgccgtggagtgggaga gcaatgggcagccggagaacaactacaagaccacgcctcccgtgctggactccgacggctccttcttcctctacagca agctcaccgtggacaagagcaggtggcagcaggggaacgtcttctcatgctccgtgatgcatgaggctctgcacaacc actacacgcagaagagcctctccctgtctccgggtaaa |
| --- | --- | --- |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIK |
| SEQ ID NO: 175 | DNA VL | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgccagcaggaatgggctaaaccgcgtaccttcggccagggcacgaaagttgaa attaaa |
| SEQ ID NO: 176 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 177 | DNA Light Chain | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgccagcaggaatgggctaaaccgcgtaccttcggccagggcacgaaagttgaa attaaacgtacggtggccgctcccagcgtgttcatcttcccccccagcgacgagcagctgaagagcggcaccgccag cgtggtgtgcctgctgaacaacttctaccccggggaggccaaggtgcagtggaaggtggacaacgccctgcagagc ggcaacagccaggaaagcgtcaccgagcaggacagcaaggactccacctacagcctgagcagcaccctgaccctg |

TABLE 2-continued

Exemplary anti-NPR1 antibody sequences agcaaggccgactacgagaagcacaaggtgtacgcctgcgaggtgacccaccagggcctgtccagccccgtgacc
aagagcttcaaccggggcgagtgt

XX11_LALA

| SEQ ID NO: 28 | HCDR1 (Combined) | GFTFSSYWMN |
| SEQ ID NO: 29 | HCDR2 (Combined) | AISSDGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcggcgtccg<br>gattcacctttttcttcttactggatgaactgggtgcgccaggcccggggcaaaggtctcgagtgggtttccgctatctcttc<br>tgacggttcttacacctactatgcggatagcgtgaaaggccgctttaccatcagccgcgataattcgaaaaacaccctgt<br>atctgcaaatgaacagcctgcgtgcggaagatacggccgtgtattattgcgcgcgtgaccgttactctatgatctactctt<br>acggtgctggtgctttcgattactggggccaaggcaccctggtgactgttagctca |
| SEQ ID NO: 39 | Heavy Chain | QVQLLESGGGLVQPGGSLRLSCAASGFTFSSYWMNWVRQAPGKGLEWVS<br>AISSDGSYTYYADSVKGRFTISRDNSKNTLYLQMNSLRAEDTAVYYCARD<br>RYSMIYSYGAGAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| SEQ ID NO: 40 | DNA Heavy Chain | caggtgcaattgctggaaagcggcggtggcctggtgcagccgggtggcagcctgcgtctgagctgcgcggcgtccg<br>gattcacctttttcttcttactggatgaactgggtgcgccaggcccggggcaaaggtctcgagtgggtttccgctatctcttc<br>tgacggttcttacacctactatgcggatagcgtgaaaggccgctttaccatcagccgcgataattcgaaaaacaccctgt<br>atctgcaaatgaacagcctgcgtgcggaagatacggccgtgtattattgcgcgcgtgaccgttactctatgatctactctt<br>acggtgctggtgctttcgattactggggccaaggcaccctggtgactgttagctcagcctccaccaagggtccatcggt<br>cttcccctggcacctctggggggcacagcggcctgggctgcctggtcaaggactacttccc<br>cgaaccggtgacggtgtcgtggaactcaggcgccctgaccagcggcgtgcacaccttcccggctgtcctacagtcctc<br>aggactctactccctcagcagcgtggtgaccgtgccctccagcagcttgggcacccagacctacatctgcaacgtaat<br>cacaagcccagcaacaccaaggtggacaagagagttgagcccaaatcttgtgacaaaactcacacatgcccaccgtg<br>cccagcacctgaagcgcggggggaccgtcagtcttcctcttccccccaaaacccaaggacaccctcatgatctccacg<br>gacccctgaggtcacatgcgtggtggtggacgtgagccacgaagaccctgaggtcaagttcaactgtacgtggacg<br>gcgtggaggtgcataatgccaagacaaagccgcgggaggagcagtacaacagcacgtaccgggtggtcagcgtcct<br>caccgtcctgcaccaggactggctgaatggcaaggagtacaagtgcaaggtctccaacaaagcccctcccagccccca<br>tcgagaaaaccatctccaaagccaaagggcagccccgagaaccacaggtgtacaccctgcccccatcccgggagga<br>gatgaccaagaaccaggtcagcctgacctgcctggtcaaaggcttctatcccagcgacatcgccgtggagtgggaga TABLE 2-continued Exemplary anti-NPR1 antibody sequences

```
                            gcaatgggcagccggagaacaactacaagaccacgcctcccgtgctggactccgacggctccttcttcctctacagca
                            agctcaccgtggacaagagcaggtggcagcaggggaacgtcttctcatgctccgtgatgcatgaggctctgcacaacc
                            actacacgcagaagagcctctcccctgtctccgggtaaa
```

| SEQ ID NO: 41 | LCDR1 (Combined) | RASQGISSYLA |
|---|---|---|
| SEQ ID NO: 42 | LCDR2 (Combined) | TASTLQS |
| SEQ ID NO: 178 | LCDR3 (Combined) | QQSWTRPRT |
| SEQ ID NO: 41 | LCDR1 (Kabat) | RASQGISSYLA |
| SEQ ID NO: 42 | LCDR2 (Kabat) | TASTLQS |
| SEQ ID NO: 178 | LCDR3 (Kabat) | QQSWTRPRT |
| SEQ ID NO: 44 | LCDR1 (Chothia) | SQGISSY |
| SEQ ID NO: 45 | LCDR2 (Chothia) | TAS |
| SEQ ID NO: 179 | LCDR3 (Chothia) | SWTRPR |
| SEQ ID NO: 47 | LCDR1 (IMGT) | QGISSY |
| SEQ ID NO: 45 | LCDR2 (IMGT) | TAS |
| SEQ ID NO: 178 | LCDR3 (IMGT) | QQSWTRPRT |
| SEQ ID NO: 180 | VL | DIQMTQSPSSLSASVGDRVTITCRASQGISSYLAWYQQKPGKAPKLLIYTAS TLQSGVPSRFSGSGSGTDFTLTISSLQPEDFATYYCQQSWTRPRTFGQGTKV EIK |
| SEQ ID NO: 181 | DNA VL | gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgccagcagtcttggactcgtccgcgtaccttggccagggcacgaaagttgaaa ttaaa |
| SEQ ID NO: 182 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQSWTRPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 183 | DNA Light Chain | Gatatccagatgacccagagcccgagcagcctgagcgccagcgtgggcgatcgcgtgaccattacctgcagagcca gccagggtatttcttcttacctggcttggtaccagcagaaaccgggcaaagcgccgaaactattaatctacactgcttcta ctctgcaaagcggcgtgccgagccgctttagcggcagcggatccggcaccgatttcaccctgaccattagctctctgca accggaagactttgcgacctattattgccagcagtcttggactcgtccgcgtaccttggccagggcacgaaagttgaaa ttaaacgtacggtggccgctcccagcgtgttcatcttccccccagcgacgagcagctgaagagcggcaccgccagc gtggtgtgcctgctgaacaacttctaccccccgggaggccaaggtgcagtggaaggtggacaacgccctgcagagcg gcaacagccaggaaagcgtcaccgagcaggacagcaaggactccacctacagcctgagcagcaccctgaccctga gcaaggccgactacgagaagcacaaggtgtacgcctgcgaggtgaccccaccagggcctgtccagcccgtgacca agagcttcaaccggggcgagtgt |

XX12_LALA

| SEQ ID NO: 28 | HCDR1 (Combined) | GFTFSSYWMN |
|---|---|---|
| SEQ ID NO: 29 | HCDR2 (Combined) | AISSDGSYTYYADSVKG |
| SEQ ID NO: 30 | HCDR3 (Combined) | DRYSMIYSYGAGAFDY |

TABLE 2-continued

Exemplary anti-NPR1 antibody sequences

| SEQ ID NO: 31 | HCDR1 (Kabat) | SYWMN |
|---|---|---|
| SEQ ID NO: 29 | HCDR2 (Kabat) | AISSDGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 33 | HCDR2 (Chothia) | SSDGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 35 | HCDR2 (IMGT) | ISSDGSYT |
| SEQ ID NO: 36 | HCDR3 (IMGT) | ARDRYSMIYSYGAGAFDY |
| SEQ ID NO: 37 | VH | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSS |
| SEQ ID NO: 38 | DNA VH | caggtgcaattgctggaaagcggcggtggcctggtgcagccgggtggcagcctgcgtctgagctgcgcggcgtccg gattcacctttcttcttactggatgaactgggtgcgccaggcccccgggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcaccctggtgactgttagctca |
| SEQ ID NO: 39 | Heavy Chain | QVQLLESGGGLVQPGGSLRLSCAASGFTFSSYWMNWVRQAPGKGLEWVS AISSDGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 40 | DNA Heavy Chain | caggtgcaattgctggaaagcggcggtggcctggtgcagccgggtggcagcctgcgtctgagctgcgcggcgtccg gattcacctttcttcttactggatgaactgggtgcgccaggcccccgggcaaaggtctcgagtgggtttccgctatctcttc tgacggttcttacacctactatgcggatagcgtgaaaggccgctttaccatcagccgcgataattcgaaaaacaccctgt atctgcaaatgaacagcctgcgtgcggaagatacggccgtgtattattgcgcgcgtgaccgttactctatgatctactctt acggtgctggtgctttcgattactggggccaaggcaccctggtgactgttagctcagcctccaccaagggtccatcggt cttccccctggcaccctcctccaagagcacctctgggggcacagcggccctgggctgcctggtcaaggactacttccc cgaaccggtgacggtgtcgtggaactcaggcgccctgaccagcggcgtgcacaccttcccggctgtcctacagtcctc aggactctactccctcagcagcgtggtgaccgtgccctccagcagcttgggcacccagacctacatctgcaacgtgaat cacaagcccagcaacaccaaggtggacaagagagttgagcccaaatcttgtgacaaaactcacacatgcccaccgtg cccagcacctgaagcagcggggggaccgtcagtcttcctcttccccccaaaacccaaggacaccctcatgatctcccg gacccctgaggtcacatgcgtggtggtggacgtgagccacgaagaccctgaggtcaagttcaactggtacgtggacg gcgtggaggtgcataatgccaagacaaagccgcgggaggagcagtacaacagcacgtaccgggtggtcagcgtcct caccgtcctgcaccaggactggctgaatggcaaggagtacaagtgcaaggtctccaacaaagccctcccagccccca tcgagaaaaccatctccaaagccaaagggcagccccgagaaccacaggtgtacaccctgcccccatcccgggagga gatgaccaagaaccaggtcagcctgacctgcctggtcaaaggcttctatcccagcgacatcgccgtggagtgggaga gcaatgggcagccggagaacaactacaagaccacgcctcccgtgctggactccgacggctccttcttcctctacagca agctcaccgtggacaagagcaggtggcagcaggggaacgtcttctcatgctccgtgatgcatgaggctctgcacaacc actacacgcagaagagcctctccctgtctccgggtaaa |
| SEQ ID NO: 41 | LCDR1 (Combined) | RASQGISSYLA |
| SEQ ID NO: 42 | LCDR2 (Combined) | TASTLQS |
| SEQ ID NO: 184 | LCDR3 (Combined) | QQIWMAPRT |
| SEQ ID NO: 41 | LCDR1 (Kabat) | RASQGISSYLA |

TABLE 2-continued

Exemplary anti-NPR1 antibody sequences

| SEQ ID NO: 42 | LCDR2 (Kabat) | TASTLQS |
| SEQ ID NO: 184 | LCDR3 (Kabat) | QQIWMAPRT |
| SEQ ID NO: 44 | LCDR1 (Chothia) | SQGISSY |
| SEQ ID NO: 45 | LCDR2 (Chothia) | TAS |
| SEQ ID NO: 185 | LCDR3 (Chothia) | IWMAPR |
| SEQ ID NO: 47 | LCDR1 (IMGT) | QGISSY |
| SEQ ID NO: 45 | LCDR2 (IMGT) | TAS |
| SEQ ID NO: 184 | LCDR3 (IMGT) | QQIWMAPRT |
| SEQ ID NO: 186 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIK |
| SEQ ID NO: 187 | DNA VL | gatatccagatgacccagagcccgagcagcctgagcgccagcgtgggcgatcgcgtgaccattacctgcagagcca<br>gccagggtatttcttcttacctggcttggtaccagcagaaaccgggcaaagcgccgaaactattaatctacactgcttcta<br>ctctgcaaagcggcgtgccgagccgctttagcggcagcggatccggcaccgatttcaccctgaccattagctctctgca<br>accggaagactttgcgacctattattgccagcagatctggatggctccgcgtaccttggccagggcacgaaagttgaa<br>attaaa |
| SEQ ID NO: 188 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 189 | DNA Light Chain | gatatccagatgacccagagcccgagcagcctgagcgccagcgtgggcgatcgcgtgaccattacctgcagagcca<br>gccagggtatttcttcttacctggcttggtaccagcagaaaccgggcaaagcgccgaaactattaatctacactgcttcta<br>ctctgcaaagcggcgtgccgagccgctttagcggcagcggatccggcaccgatttcaccctgaccattagctctctgca<br>accggaagactttgcgacctattattgccagcagatctggatggctccgcgtaccttggccagggcacgaaagttgaa<br>attaaacgtacggtggccgctcccagcgtgttcatcttccccccagcgacgagcagctgaagagcggcaccgccag<br>cgtggtgtgcctgctgaacaacttctaccccggggaggccaaggtgcagtggaaggtggacaacgccctgcagagc<br>ggcaacagccaggaaagcgtcaccgagcaggacagcaaggactccacctacagcctgagcagcaccctgaccctg<br>agcaaggccgactacgagaagcacaaggtgtacgcctgcgaggtgacccaccagggcctgtccagccccgtgacc<br>aagagcttcaaccggggcgagtgt |

XX13_<br>LALA

| SEQ ID NO: 28 | HCDR1 (Combined) | GFTFSSYWMN |
| SEQ ID NO: 190 | HCDR2 (Combined) | AISSKGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 190 | HCDR2 (Kabat) | AISSKGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 191 | HCDR2 (Chothia) | SSKGSY |

TABLE 2-continued

Exemplary anti-NPR1 antibody sequences

| SEQ ID NO: 30 | HCDR3 (Chothia) | DRYSMIYSYGAGAFDY |
|---|---|---|
| SEQ ID NO: 34 | HCDR1 (IMGT) | GFTFSSYW |
| SEQ ID NO: 192 | HCDR2 (IMGT) | ISSKGSYT |
| SEQ ID NO: 36 | HCDR3 (IMGT) | ARDRYSMIYSYGAGAFDY |
| SEQ ID NO: 193 | VH | QVQLLESGGGLVQPGGSLRLSCAASGFTFSSYWMNWVRQAPGKGLEWVS AISSKGSYTYYADSVKGRFTISRDNSKNTLYLQMNSLRAEDTAVYYCARD RYSMIYSYGAGAFDYWGQGTLVTVSS |
| SEQ ID NO: 194 | DNA VH | caagttcagctccttgagtctggggggggcctggtgcaacctggggggctctctgcggctttcatgtgcggcctcagggt tcactttcagctcatactggatgaattgggtacgccaagctccaggcaaaggactcgaatgggtaagcgctatatccagc aaagggagctataacctattacgcggattccgttaagggcaggttcactatatcccgcgacaactccaaaaatactttgtat ctgcaaatgaattccctccgagccgaagataccgcagtatattactgtgcgagggacaggtactccatgatttacagcta cggtgccggtgctttcgattattggggacaggggacacttgtgaccgtcagttct |
| SEQ ID NO: 195 | Heavy Chain | QVQLLESGGGLVQPGGSLRLSCAASGFTFSSYWMNWVRQAPGKGLEWVS AISSKGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 196 | DNA Heavy Chain | caagttcagctccttgagtctggggggggcctggtgcaacctggggggctctctgcggctttcatgtgcggcctcagggt tcactttcagctcatactggatgaattgggtacgccaagctccaggcaaaggactcgaatgggtaagcgctatatccagc aaagggagctataacctattacgcggattccgttaagggcaggttcactatatcccgcgacaactccaaaaatactttgtat ctgcaaatgaattccctccgagccgaagataccgcagtatattactgtgcgagggacaggtactccatgatttacagcta cggtgccggtgctttcgattattggggacaggggacacttgtgaccgtcagttctgcaagtaccaaagggccgtctgttttt cccattggctccctcatccaagagcacgagtggaggcaccgcgcgctgggatgccttgtgaaagactatttccgga gccgtgaccgttagctggaacagcggcgctcttaccagtggcgttcacacattcccagctgttttgcagtcatccgggc tctactctctctcatccgtggtcaccgtgccgtctagttctttgggcacccagacctacatctgtaacgtaaatcacaaacct agtaatactaaggtggacaagcgagttgaaccgaagagctgtgataagacacatacttgtccaccatgtccggcaccc gaggcagcgggggccccagtgtttttctcttcccacccaagcccaaagacacattgatgatctcacgaaccccagag gtaacttgtgtcgtggtagatgtaagcatgaggaccccgaagttaagttcaattggtatgtgtgacggtgtagaggtgcac aatgccaaaactaaaccccgggaggagcaatacaactcaactacagagtcgtatccgtgctgaccgtttgcaccagg attggttgaatggtaaggaatacaaatgtaaagtgagcaataaagctctcccagcgcccatcgagaagaccattagcaa agccaagggtcaacccagggaaccccaggtatatacgctgccacccctcaaggggaagagatgacaaagaatcaagtgt cactgacgtgtcttgtcaagggtttctatcctagcgacattgcggtggaatgggagtcaaatgggcaacccgagaacaa ctacaagactactcctccccgtcctggacagcgacggctccttcttcctgtatagtaaactgaccgtcgataaaagtaggtg gcagcaggggaatgtcttagttgctgctcatgcatgaggcgctccataaccactacacccaaaatctttgagcttgag ccctgggaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |

TABLE 2-continued

Exemplary anti-NPR1 antibody sequences

| SEQ ID NO: 47 | LCDR1 (IMGT) | QGISSY |
|---|---|---|
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIK |
| SEQ ID NO: 197 | DNA VL | gacattcaaatgacacaaagtccgtccagtcttagtgcttctgtgggcgatagggtcaccatcacttgtcgggcgtctcag gggatcagctcttacttggcatggtatcaacaaaagccaggaaaagcacctaaattgcttatttatacagcgtccaccctc cagtcaggagtgcctagtaggttctcaggctctgggtccggtactgacttcacgctgactatatcaagcttgcaacccga agattttgcaacatactactgccaacagacatggaggaagccaagaactttcggtcagggaacgaaagttgagataaa g |
| SEQ ID NO: 138 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 198 | DNA Light Chain | gacattcaaatgacacaaagtccgtccagtcttagtgcttctgtgggcgatagggtcaccatcacttgtcgggcgtctcag gggatcagctcttacttggcatggtatcaacaaaagccaggaaaagcacctaaattgcttatttatacagcgtccaccctc cagtcaggagtgcctagtaggttctcaggctctgggtccggtactgacttcacgctgactatatcaagcttgcaacccga agattttgcaacatactactgccaacagacatggaggaagccaagaactttcggtcagggaacgaaagttgagataaa gcgcactgtcgcagcaccttccgtgttcatttttcccgccttccgacgagcagcttaaatcagggaccgcgagtgttgtttg cttgcttaataacttttacccacgggaagccaaagttcagtggaaggtggacaatgcactccaaagcgggaatagtcag gagtcagttactgagcaagatagtaaagactctacttactctttgagttcaaccttgaccctctcaaaagcggactacgag aagcataaagtgtacgcctgcgaggtgacgcatcaaggtttgtcttcccggttacgaagtccttaataggggggaatg t |

XX14_ LALA

| SEQ ID NO: 28 | HCDR1 (Combined) | GFTFSSYWMN |
|---|---|---|
| SEQ ID NO: 190 | HCDR2 (Combined) | AISSKGSYTYYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 190 | HCDR2 (Kabat) | AISSKGSYTYYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 191 | HCDR2 (Chothia) | SSKGSY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 192 | HCDR2 (IMGT) | ISSKGSYT |
| SEQ ID NO: 36 | HCDR3 (IMGT) | ARDRYSMIYSYGAGAFDY |
| SEQ ID NO: 193 | VH | QVQLLESGGGLVQPGGSLRLSCAASGFTFSSYWMNWVRQAPGKGLEWVS AISSKGSYTYYADSVKGRFTISRDNSKNTLYLQMNSLRAEDTAVYYCARD RYSMIYSYGAGAFDYWGQGTLVTVSS |

TABLE 2-continued

Exemplary anti-NPR1 antibody sequences

| | | |
|---|---|---|
| SEQ ID NO: 194 | DNA VH | caagttcagctccttgagtctggggggggcctggtgcaacctgggggctctctgcggcctttcatgtgcggcctcagggt tcactttcagctcatactggatgaattgggtacgccaagctccaggcaaaggactcgaatgggtaagcgctatatccagc aaagggagctatacctattacgcggattccgttaagggcaggttcactatatcccgcgacaactccaaaaatactttgtat ctgcaaatgaattccctccgagccgaagataccgcagtatattactgtgcgagggacaggtactccatgatttacagcta cggtgccggtgctttcgattattggggacaggggacacttgtgaccgtcagttct |
| SEQ ID NO: 195 | Heavy Chain | QVQLLESGGGLVQPGGSLRLSCAASGFTFSSYWMNWVRQAPGKGLEWVS AISSKGSYTYYADSVKGRFTISRDNSKNTLYLQMNSLRAEDTAVYYCARD RYSMIYSYGAGAFDYWGQGTLVTVSSASTKGPSVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK |
| SEQ ID NO: 196 | DNA Heavy Chain | caagttcagctccttgagtctggggggggcctggtgcaacctgggggctctctgcggcctttcatgtgcggcctcagggt tcactttcagctcatactggatgaattgggtacgccaagctccaggcaaaggactcgaatgggtaagcgctatatccagc aaagggagctatacctattacgcggattccgttaagggcaggttcactatatcccgcgacaactccaaaaatactttgtat ctgcaaatgaattccctccgagccgaagataccgcagtatattactgtgcgagggacaggtactccatgatttacagcta cggtgccggtgctttcgattattggggacaggggacacttgtgaccgtcagttctgcaagtaccaaagggcgtctgtttt cccattggctccctcatccaagagcacgagtggaggcaccgccgcgctgggatgcctgtgaaagactatttcccgga gcccgtgaccgttagctggaacagcggcgctcttaccagtggcgttcacacattcccagctgtttttgcagtcatccggc tctactctctctcatccgtggtcaccgtgccgtctagttctttgggcacccagacctacatctgtaacgtaaatcacaaacct agtaatactaaggtggacaagcgagttgaaccgaagagctgtgataagcacatacttgtccaccatgtccggcaccc gaggcagcgggggccagtgttttctcttcccaccaagcccaaagacacattgatgatctcacgaaccccagag gtaacttgtgtcgtggtagatgtaagccatgaggaccccgaagttaagttcaattggtatgttgacggtgtagaggtgcac aatgccaaaactaaaccccgggaggagcaatacaactcaacttacagagtcgtatccgtgctgaccgttttgcaccagg attggttgaatggtaaggaatacaaatgtaaagtgagcaataaagctctcccagcgcccatcgagaagaccattagcaa agccaaggtcaacccaggggaaccccaggtatatacgttgccaccctcaaggggaagagatgacaaagaatcaagtgt cactgacgtgtcttgtcaagggtttctatcctagcgacattgcggtggaatgggagtcaaatgggcaacccgagaacaa ctacaagactactcctcccgtcctggacagcgacggctccttcttcctgtatagtaaactgaccgtcgataaaagtaggtg gcagcaggggaatgtctttagttgctctgtcatgcatgaggcgctccataaccactacacccaaaaatctttgagcttgag ccctgggaaa |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIK |

TABLE 2-continued

Exemplary anti-NPR1 antibody sequences

| SEQ ID NO: 199 | DNA VL | gatatacagatgacgcaaagtccctctagtctttctgcaagtgtcggggacagagttaccattacctgcagagcgtcaca aggcatctctagttatctcgcgtggtaccaacagaagccaggtaaagcacctaaactgttgatttacacggcatcaacatt gcagtcaggtgtcccctcccgatttagtggcagtggtagcggtacagatttttactcttaccattcatctcttcagccagaa gattttgctacgtactactgtcaacaagaatgggctaaaccacgaacctttggacagggtacgaaggtcgaaataaaa |
|---|---|---|
| SEQ ID NO: 176 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 200 | DNA Light Chain | gatatacagatgacgcaaagtccctctagtctttctgcaagtgtcggggacagagttaccattacctgcagagcgtcaca aggcatctctagttatctcgcgtggtaccaacagaagccaggtaaagcacctaaactgttgatttacacggcatcaacatt gcagtcaggtgtcccctcccgatttagtggcagtggtagcggtacagatttttactcttaccattcatctcttcagccagaa gattttgctacgtactactgtcaacaagaatgggctaaaccacgaacctttggacagggtacgaaggtcgaaataaaac ggaccgttgccgcccctccgtcttcatcttcccccgtctgacgagcagctcaaatccggcacagcttctgtagtctgct tgctgaataacttctacccaagagaagccaaagttcagtggaaggtcgataatgcattgcaatctggtaatagtcaggaa tctgtgactgagcaggatagcaaagactcaacttacagcctctcttcaaccttgacgttgtccaaagcggattatgagaaa cacaaggtgtacgcttgcgaggtgacgcatcaagggcttagttccccggtaaccaaatcttttcaaccgaggtgaatgc |

XX15_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 202 | DNA VH | caagttcaattgctggaaagcggaggtggacttgtccaacctggagggtcactccgactgtcttcgcgctgcatcaggatt cacctttagtagctattggatgaactgggtccggcaggctcctgggaaagggcttgagtgggtaagtgtcattgaatcaa aagggcaactacatcttttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactgggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPEAAAGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |

TABLE 2-continued

Exemplary anti-NPR1 antibody sequences

| SEQ ID NO: 204 | DNA Heavy Chain | caagttcaattgctggaaagcggaggtggacttgtccaacctggagggtcactccgactgtcttgcgctgcatcaggatt
cacctttagtagctattggatgaactgggtccggcaggctcctgggaaagggcttgagtgggtaagtgtcattgaatcaa
agggcaactacatcttttatgctgattctgtaaagggtaggttcaccatctccagggacaattcaaaaaatactttgtatctg
cagatgaactctctcagggcagaagacacggccgtttattactgcgcccgcgatcgatacagcatgatatactcctacg
gcgcaggagcttttgactactggggtcaaggcacacttgttactgtcagtagcgcctcaacgaaaggaccgtccgtgttt
cctcttgctcctagctccaaatccacctcaggtggaacgccgccctgggggtgcctggtaaggactatttcccagagc
cagttactgtgtcttggaattctggtgcattgacaagtggcgtacacacttttcccgcggtcctccaatctagtggtctgtac
tcactgtcctccgttgtgactgtcccaagtagctcacttggcacacagacttacatctgtaatgttaatcataagccgtcaaa
cacgaaggtggataagagggtagaacctaagtcatgtgacaaaacgcatacttgccccccctgccctgcgccggaag
ccgctggcggaccctccgtattcttgttccctccaaagccaaaggacactctgatgattagccggacaccggaggtcac
ttgtgttgtagttgacgtcagccatgaggatcctgaggtgaaatttaattggtacgtggacggggttgaagtccacaatgc
taaaactaaacctaggaagagcaatataatagtacatacagggttgtcagtgtgctgaccgttctccatcaggactggc
tgaacggcaaggaatacaagtgcaaggtcagcaacaaggccttgccggcccccatcgagaagacgatctccaaagc
caagggcaaccccgagaaccgcaggtatacacgctcccccctagtagagaaggagatgacaaagaatcaagtttcctt
gacgtgcctgtgaaaggcttctaccctagtgacatcgcagtcgaatgggagagcaacgggcagccggagaataacta
taaaacaacccccccgtgcttgactcagacgggtcattttttctgtatagcaaattgactgttgataaatcacggtggcaa
caaggaaacgtgttagttgcagcgtaatgcacgaagctctccacaatcactatactcaaaagtcactgtcactctcccct
ggcaag |
| SEQ ID NO: 41 | LCDR1 (Combined) | RASQGISSYLA |
| SEQ ID NO: 42 | LCDR2 (Combined) | TASTLQS |
| SEQ ID NO: 126 | LCDR3 (Combined) | QQEWVKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 126 | LCDR3 (Kabat) | QQEWVKPRT |
| SEQ ID NO: 44 | LCDR1 (Chothia) | SQGISSY |
| SEQ ID NO: 45 | LCDR2 (Chothia) | TAS |
| SEQ ID NO: 127 | LCDR3 (Chothia) | EWVKPR |
| SEQ ID NO: 47 | LCDR1 (IMGT) | QGISSY |
| SEQ ID NO: 45 | LCDR2 (IMGT) | TAS |
| SEQ ID NO: 126 | LCDR3 (IMGT) | QQEWVKPRT |
| SEQ ID NO: 128 | VL | DIQMTQSPSSLSASVGDRVTITCRASQGISSYLAWYQQKPGKAPKLLIYTAS
TLQSGVPSRFSGSGSGTDFTLTISSLQPEDFATYYCQQEWVKPRTFGQGTKV
EIK |
| SEQ ID NO: 205 | DNA VL | gacatacaaatgacgcaatctccgagtagcttgtcagcgtccgtaggcgaccgagtaacgattacgtgtagagcgagc
cagggaatttcatcttatttggcttggtatcagcaaaagccgggaaaagcacccaaactcctcatttatactgccagcacg
ttgcaaagcggcgttccgagtcggtctctggatcagggtccgggacggacttcaccttgacgatttcatctttgcaacct
gaagattttgcaacatactactgtcaacaggagtgggtgaagccaaggaccttcggacaaggcacgaaggtcgaaatc
aag |
| SEQ ID NO: 130 | Light Chain | DIQMTQSPSSLSASVGDRVTITCRASQGISSYLAWYQQKPGKAPKLLIYTAS
TLQSGVPSRFSGSGSGTDFTLTISSLQPEDFATYYCQQEWVKPRTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC |
| SEQ ID NO: 206 | DNA Light Chain | gacatacaaatgacgcaatctccgagtagcttgtcagcgtccgtaggcgaccgagtaacgattacgtgtagagcgagc
cagggaatttcatcttatttggcttggtatcagcaaaagccgggaaaagcacccaaactcctcatttatactgccagcacg
ttgcaaagcggcgttccgagtcggtctctggatcagggtccgggacggacttcaccttgacgatttcatctttgcaacct
gaagattttgcaacatactactgtcaacaggagtgggtgaagccaaggaccttcggacaaggcacgaaggtcgaaatc
aagcgaaccgtggcagctccgtccgtgtttatttttccgcctccgacgaacaacttaaagtggaacagcctctgtcgtc
tgtctcccttaacaacttctaccccaggaagctaaagtacagtggaaggtagataacgctctgcaaagtggtaattctcag |

TABLE 2-continued

Exemplary anti-NPR1 antibody sequences gagagcgtcacggaacaggactccaaagactccacctattctctgagctctacactgacgctcagcaaggcagactac
gaaaagcacaaagtatatgcgtgtgaggtgacgcatcaaggccttagcagtccagttacaaaaagttttaacaggggag
aatgc

XX15_DAPA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgcagcctccgg attcaccttttcgtcgtactggatgaactgggtcagacaggtcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactgggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKP KDTLMISRTPEVTCVVVAVSHEDPEVKFNWYVDGVEVHNAKTKPREEQY NSTYRVVSVLTVLHQDWLNGKEYKCKVSNKALAAPIEKTISKAKGQPREP QVYTLPPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgcagcctccgg attcaccttttcgtcgtactggatgaactgggtcagacaggtcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactgggacagggaaccctcgtgaccgtcagctccgcctcaaccaagggccc gtcagtgttcccgctggtcccatcgtcgaagtccacctccggagggaaccgcagcactcggttgcctggtcaaggactac ttccctgagccagtgaccgtgtcgtgaacagcggagccctgacttccggcgtgcacacttttcccgcggtgctgcagt cctccggtctgtactcccttttcgtccgtggtcaccgtgccgtcgtctagcctgggcacccagacctacatctgcaacgtg aaccacaagccgtccaacaccaaagtggataagcgggtggagccgaagtcctgcgataagacacacacgtgcccgc catgtccagccgtccgaattgcttggcggaccttccgtgttcctgttcccgcctaagccaaggacaccttgatgattagc cggactcccgaagtcacctgtgtggtggcagtgtcccacgaggaccccgaggtcaagtttaattggtacgtggacg gcgtcgaagtgcacaacgccaagactaagccccgggaggaacagtacaacagcacctaccgggtcgtgtccgtgct gaccgtgctgcaccaggactggctgaatgggaaagagtacaagtgcaaagtgtccaacaaggccttggccgctcctat cgaaaaaactatcagcaaggctaagggacagccgagggaaccccaagtctacaccctgccccttcacgcgaagag atgaccaagaatcaagtgtcgctgacctgcctcgtcaaggattctaccctctccgacattgcggtggagtgggagtcca |

TABLE 2-continued

Exemplary anti-NPR1 antibody sequences

```
acggccagcccgagaacaactacaagactactccgcccgtgctggactccgacggcagcttcttcctgtattccaagct
gaccgtggacaagtcccggtggcagcaaggaaacgtgttctcctgctcggtcatgcacgaagccctgcacaaccacta
tacgcagaagtccctgtccttgagcccggggaaa
```

| SEQ ID NO: 41 | LCDR1 (Combined) | RASQGISSYLA |
|---|---|---|
| SEQ ID NO: 42 | LCDR2 (Combined) | TASTLQS |
| SEQ ID NO: 126 | LCDR3 (Combined) | QQEWVKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 126 | LCDR3 (Kabat) | QQEWVKPRT |
| SEQ ID NO: 44 | LCDR1 (Chothia) | SQGISSY |
| SEQ ID NO: 45 | LCDR2 (Chothia) | TAS |
| SEQ ID NO: 127 | LCDR3 (Chothia) | EWVKPR |
| SEQ ID NO: 47 | LCDR1 (IMGT) | QGISSY |
| SEQ ID NO: 45 | LCDR2 (IMGT) | TAS |
| SEQ ID NO: 126 | LCDR3 (IMGT) | QQEWVKPRT |
| SEQ ID NO: 128 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWVKPRTFGQGTKV EIK |
| SEQ ID NO: 210 | DNA VL | gacatccagatgacccagtctccgtcctccctgtccgcatcagtgggggacagagtgaccatcacttgtcgggcctcc caaggcatctcgtcataccctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaagaatgggtgaagcccaggacatttggccagggcactaaggtcga gattaag |
| SEQ ID NO: 130 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWVKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 211 | DNA Light Chain | gacatccagatgacccagtctccgtcctccctgtccgcatcagtgggggacagagtgaccatcacttgtcgggcctcc caaggcatctcgtcataccctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaagaatgggtgaagcccaggacatttggccagggcactaaggtcga gattaagcgtacggtggccgctcccagcgtgttcatcttcccccccgacgacgagcagctgaagagcggcaccgcca gcgtggtgtgcctgctgaacaacttctacccccgggaggccaaggtgcagtggaaggtggacaacgccctgcagag cggcaacagccaggagagcgtcaccgagcaggacagcaaggactccacctacagcctgagcagcaccctgaccct gagcaaggccgactacgagaagcataaggtgtacgcctgcgaggtgacccacccagggctgtccagcccgtgacc aagagcttcaacaggggcgagtgc |

XX16_LALA

| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |

TABLE 2-continued

Exemplary anti-NPR1 antibody sequences

| SEQ ID NO: 31 | HCDR1 (Kabat) | SYWMN |
|---|---|---|
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 202 | DNA VH | caagttcaattgctggaaagcggaggtggacttgtccaacctggagggtcactccgactgtcttgcgctgcatcaggatt cacctttagtagctattggatgaactgggtccggcaggctcctgggaaagggcttgagtgggtaagtgtcattgaatcaa agggcaactacatctttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactggggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPEAAGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgctgcatcaggatt cacctttagtagctattggatgaactgggtccggcaggctcctgggaaagggcttgagtgggtaagtgtcattgaatcaa agggcaactacatctttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactggggtcaaggcacacttgttactgtcagtagcgctagcaccaaaggaccgtccgtgttt cctctgctcctagctccaaatccacctcaggtggaacggccgcctggggtgcctggtcaaaggactatttcccagagc cagttactgtgtcttggaattctggtgcattgacaagtggcgtacacacttttcccgcggtcctccaatctagtggtctgtac tcactgtcctccgttgtgactgtcccaagtagctcacttggcacacagacttacatctgtaatgttaatcataagccgtcaaa cacgaaggtggataagagggtagaaccaagtcatgtgacaaaacgcatacttgccccctgccctgcgccggaag ccgctggcggaccctccgtattcttgttccctccaaagccaaagacactctgatgattagccggacaccggaggtcac ttgtgttgtagttgacgtcagccatgaggatcctgaggtgaaatttaattggtacgtggacggggttgaagtccacaatgc taaaactaaacctaggaagagcaatataatagtacatacaggggttgtcagtgtgctgaccgttctccatcaggactggc tgaacggcaaggaatacaagtgcaaggtcagcaacaaggccttgccggccccatcgagaagacgatctccaaagc caaggggcaaccccgagaaccgcaggtatacacgctccccctagtagagaaggagatgacaaagaatcaagtttcctt gacgtgcccttgtgaaaggcttctaccctagtgacatcgcagtcgaatgggagagcaacgggcagccggagaataacta taaaacaaccccccccgtgcttgactcagacgggtcatttttctgtatagcaaattgactgttgataaatcacggtggcaa caaggaaacgtgtttagttgcagcgtaatgcacgaagctctccacaatcactatactcaaaagtcactgtcactctcccct ggcaag |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |

TABLE 2-continued

Exemplary anti-NPR1 antibody sequences

| SEQ ID NO: 42 | LCDR2 (Kabat) | TASTLQS |
| --- | --- | --- |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |
| SEQ ID NO: 47 | LCDR1 (IMGT) | QGISSY |
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIK |
| SEQ ID NO: 197 | DNA VL | gacattcaaatgacacaaagtccgtccagtcttagtgcttctgtgggcgatagggtcaccatcacttgtcgggcgtctcag gggatcagctccttacttggcatggtatcaacaaaagccaggaaaagcacctaaattgcttatttatacagcgtccaccctc cagtcaggagtgcctagtaggttctcaggctctgggtccggtactgacttcacgctgactatatcaagcttgcaacccga agattttgcaacatactactgccaacagacatggaggaagccaagaactttcggtcagggaacgaaagttgagataaa g |
| SEQ ID NO: 138 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 198 | DNA Light Chain | gacattcaaatgacacaaagtccgtccagtcttagtgcttctgtgggcgatagggtcaccatcacttgtcgggcgtctcag gggatcagctccttacttggcatggtatcaacaaaagccaggaaaagcacctaaattgcttatttatacagcgtccaccctc cagtcaggagtgcctagtaggttctcaggctctgggtccggtactgacttcacgctgactatatcaagcttgcaacccga agattttgcaacatactactgccaacagacatggaggaagccaagaactttcggtcagggaacgaaagttgagataaa gcgcactgtcgcagcaccttccgtgttcattttcccgccttccgacgagcagcttaaatcagggaccgcgagtgttgtttg cttgcttaataacttttacccacgggaagccaaagttcagtggaaggtggacaatgcactccaaagcggaatagtcag gagtcagttactgagcaagatagtaaagactctacttactctttgagttcaaccttgaccctctcaaaagcggactacgag aagcataaagtgtacgcctgcgaggtgacgcatcaaggtttgtcttcccggttacgaagtcctttaatagggggaatg t |

XX16_DAPA

| SEQ ID NO: 28 | HCDR1 (Combined) | GFTFSSYWMN |
| --- | --- | --- |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |

TABLE 2-continued

Exemplary anti-NPR1 antibody sequences

| SEQ ID NO: 30 | HCDR3 (Chothia) | DRYSMIYSYGAGAFDY |
|---|---|---|
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgcagcctccgg attcaccttttcgtcgtactggatgaactgggtcagacaggctcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactggggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKP KDTLMISRTPEVTCVVVAVSHEDPEVKFNWYVDGVEVHNAKTKPREEQY NSTYRVVSVLTVLHQDWLNGKEYKCKVSNKALAAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgcagcctccgg attcaccttttcgtcgtactggatgaactgggtcagacaggctcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactggggacagggaaccctcgtgaccgtcagctccgcctcaaccaagggccc gtcagtgttcccgctggctccatcgtcgaagtccacctccggaggaaccgcagcactcggttgcctggtcaaggactac ttccctgagccagtgaccgtgtcgtggaacagcggagccctgacttccggcgtgcacacttttcccgcggtgctgcagt cctccggtctgtactccctttcgtcggtggtcaccgtgccgtcgtctagcctgggcacccagacctacatctgcaacgtg aaccacaagccgtccaacaccaaagtggataagcgggtggagccgaagtcctgcgataagacacacacgtgcccgc catgtccagcgcctgaattgcttggcggaccttcgtgttcctgtttcccgcctaagcccaaggacaccttgatgattagcc ggactcccgaagtcacctgtgtggtggtggcagtgtcccacgaggaccccgaggtcaagtttaattggtacgtggacg gcgtcgaagtgcacaacgccaagactaagccccgggaggaacagtacaacagcacctaccgggtgtgtcccgtgct gaccgtgctgcaccaggactggctgaatgggaaagagtacaagtgcaaagtgtccaacaaggccttggccgctcctat cgaaaaaactatcagcaaggctaagggacagccgagggaaccccaagtctacaccctgccccctcacgcgaagag atgaccaagaatcaagtgtcgctgacctgcctcgtcaagggattctacccctccgacattgcggtggagtgggagtcca acggccagcccgagaacaactacaagactactccgcccgtgctggactccgacggcagcttcttcctgtattccaagct gaccgtggacaagtcccggtggcagcaaggaaacgtgttctcctgctcggtcatgcacgaagcccctgcacaaccacta tacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 134 | LCDR3 (Combined) | QQTWRKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 134 | LCDR3 (Kabat) | QQTWRKPRT |
| SEQ ID NO: 44 | LCDR1 (Chothia) | SQGISSY |
| SEQ ID NO: 45 | LCDR2 (Chothia) | TAS |
| SEQ ID NO: 135 | LCDR3 (Chothia) | TWRKPR |

TABLE 2-continued

Exemplary anti-NPR1 antibody sequences

| SEQ ID NO: 47 | LCDR1 (IMGT) | QGISSY |
|---|---|---|
| SEQ ID NO: 45 | LCDR2 (IMGT) | TAS |
| SEQ ID NO: 134 | LCDR3 (IMGT) | QQTWRKPRT |
| SEQ ID NO: 136 | VL | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIK |
| SEQ ID NO: 143 | DNA VL | gacatccagatgacccagtctccgtcctccctgtccgcatcagtgggggacagagtgaccatcacttgtcgggcctcc aaggcatctcgtcatacctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaaacctggcggaagcccaggacatttggccagggcactaaggtcga gattaag |
| SEQ ID NO: 138 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQTWRKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 144 | DNA Light Chain | gacatccagatgacccagtctccgtcctccctgtccgcatcagtgggggacagagtgaccatcacttgtcgggcctcc aaggcatctcgtcatacctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaaacctggcggaagcccaggacatttggccagggcactaaggtcga gattaagcgtacggtgccgctcccagcgtgttcatcttcccccccagcgacgagcagctgaagagcggcaccgcca gcgtggtgtgcctgctgaacaacttctaccccgggaggccaaggtgcagtggaaggtggacaacgcccctgcagag cggcaacagccaggagagcgtcaccgagcaggacagcaaggactccacctacagcctgagcagcaccctgaccct gagcaaggccgactacgagaagcataaggtgtacgcctgcgaggtgacccaccagggcctgtccagcccgtgacc aagagcttcaacaggggcgagtgc |

XX17_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |

TABLE 2-continued

Exemplary anti-NPR1 antibody sequences

| SEQ ID NO: 202 | DNA VH | caagttcaattgctggaaagcggaggtggacttgtccaacctggagggtcactccgactgtcttgcgctgcatcaggatt cacctttagtagctattggatgaactgggtccggcaggctcctgggaaagggcttgagtgggtaagtgtcattgaatcaa agggcaactacatctttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactggggtcaaggcacacttgttactgtcagtagc |
|---|---|---|
| SEQ ID NO: 203 | Heavy Chain | QVQLLESGGGLVQPGGSLRLSCAASGFTSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPEAAGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgctgcatcaggatt cacctttagtagctattggatgaactgggtccggcaggctcctgggaaagggcttgagtgggtaagtgtcattgaatcaa agggcaactacatctttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactggggtcaaggcacacttgttactgtcagtagcgcctcaacgaaaggaccgtccgtgttt cctcttgctcctagctccaaatccacctcaggtggaacgccgcctgggtgcctggtaaaggactatttcccagagc cagttactgtcttggaattctggtgcattgacaagtggcgtcacacttttcccgcggtcctccaatctagtggtctgtac tcactgtcctccgttgtgactgtcccaagtagctcacttggcacacagacttactactgtaatgttaatcataagccgtcaaa cacgaaggtggataagagggtagaacctaagtcatgtgacaaaacgcatacttgccccccctgccctgcgccggaag ccgctggcggaccctccgtattcttgttccctccaaagccaaggacactctgatgattagccgacaccggaggtcac ttgtgttgtagttgacgtcagccatgaggatcctgaggtgaaatttaattggtacgtggacggggttgaagtccacaatgc taaaactaaacctagggaagaagcaatataatagtacatacagggtttgtcagtgtgctgaccgttctccatcaggactggc tgaacgcaaggaatacaagtgcaaggtcagcaacaaggccttgccggcccccatcgagaagacgatctccaaagc caaggggcaaccccgagaaccgcaggtatacacgctccccccctagtagagaagagatgacaaagaatcaagtttcctt gacgtgcctctgtgaaaggcttctaccctagtgacatcgcagtcgaatgggagagcaacgggcagccggagaataacta taaacaaccccccgtgcttgactcagacgggtcattttttctgtatagcaaattgactgttgataaatcacggtggcaa caaggaaacgtgtttagttgcagcgtaatgcacgaagctctccacaatcactatactcaaaagtcactgtcactctccct ggcaag |
| SEQ ID NO: 41 | LCDR1 (Combined) | RASQGISSYLA |
| SEQ ID NO: 42 | LCDR2 (Combined) | TASTLQS |
| SEQ ID NO: 145 | LCDR3 (Combined) | QQIWTVPRT |
| SEQ ID NO: 41 | LCDR1 (Kabat) | RASQGISSYLA |
| SEQ ID NO: 42 | LCDR2 (Kabat) | TASTLQS |
| SEQ ID NO: 145 | LCDR3 (Kabat) | QQIWTVPRT |
| SEQ ID NO: 44 | LCDR1 (Chothia) | SQGISSY |
| SEQ ID NO: 45 | LCDR2 (Chothia) | TAS |
| SEQ ID NO: 146 | LCDR3 (Chothia) | IWTVPR |
| SEQ ID NO: 47 | LCDR1 (IMGT) | QGISSY |
| SEQ ID NO: 45 | LCDR2 (IMGT) | TAS |
| SEQ ID NO: 145 | LCDR3 (IMGT) | QQIWTVPRT |
| SEQ ID NO: 147 | VL | DIQMTQSPSSLSASVGDRVTITCRASQGISSYLAWYQQKPGKAPKLLIYTAS TLQSGVPSRFSGSGSGTDFTLTISSLQPEDFATYYCQQIWTVPRTFGQGTKV EIK |

TABLE 2-continued

Exemplary anti-NPR1 antibody sequences

| SEQ ID NO: 212 | DNA VL | gacatacagatgactcagagtccttcctccctcagtgcttcagtgggtgatcgcgtgacgatcacgtgcagagcctcaca
aggatctccagttacctggcctggtatcaacaaaaaccaggcaaggcgcctaagctgttgatatatacggcatctacat
tgcagtctggggtaccaagtcgattcagtggttctggctcaggcactgactttacccttacaatatcaagtcttcagccgg
aggatttcgcaacttactattgccagcagatttggacggtgccgcgcactttcggtcagggaacaaaggtggaaataaa
a |
| SEQ ID NO: 149 | Light Chain | DIQMTQSPSSLSASVGDRVTITCRASQGISSYLAWYQQKPGKAPKLLIYTAS
TLQSGVPSRFSGSGSGTDFTLTISSLQPEDFATYYCQQIWTVPRTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC |
| SEQ ID NO: 213 | DNA Light Chain | gacatacagatgactcagagtccttcctccctcagtgcttcagtgggtgatcgcgtgacgatcacgtgcagagcctcaca
aggatctccagttacctggcctggtatcaacaaaaaccaggcaaggcgcctaagctgttgatatatacggcatctacat
tgcagtctggggtaccaagtcgattcagtggttctggctcaggcactgactttacccttacaatatcaagtcttcagccgg
aggatttcgcaacttactattgccagcagatttggacggtgccgcgcactttcggtcagggaacaaaggtggaaataaa
aagaacggtcgcagcaccgagtgttttcatcttcctccctccgacgagcagcttaaaagcggtacagccagcgtagtg
tgtttgttgaataatttttatccacgcgaagcaaaagttcagtggaaggtagacaacgcattgcaaagcggaaatttcccaa
gaaagtgttacggagcaagacagtaaggactctacatattccttgtcatcaaacactcacccttagtaaagcagattacga
gaaacacaaggtctatgcatgtgaggtaacgcatcagggcctctccagtcccgtcaccaagtccttcaacagggtgta
gtgc |

XX17_DAPA

| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS
VIESKGNYIFYADSVKGRFTISRDNSKNTLYLQMNSLRAEDTAVYYCARDR
YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgcagcctccgg
attcaccttttcgtcgtactggatgaactgggtcagacaggctcctggaaagggcctggaatgggtgtctgtgattgaatc
caaggggaactacatcttctacgcggacagcgtgaagggccggttcactatcagcagagacaacagcaagaacaccc
tgtacctccaaatgaactgctgagggccgaagatactgccgtgtactactgtgcccgcgatcgctactcgatgatctac
agctatggtgccggagcgttcgattactggggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS
VIESKGNYIFYADSVKGRFTISRDNSKNTLYLQMNSLRAEDTAVYYCARDR
YSMIYSYGAGAFDYWGQGTLVTVSSASTKGPSVFPLAPSSKSTSGGTAALG
CLVKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPPKP
KDTLMISRTPEVTCVVVAVSHEDPEVKFNWYVDGVEVHNAKTKPREEQY
NSTYRVVSVLTVLHQDWLNGKEYKCKVSNKALAAPIEKTISKAKGQPREP |

TABLE 2-continued

Exemplary anti-NPR1 antibody sequences

| | | |
|---|---|---|
| | | QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID<br>NO: 209 | DNA<br>Heavy<br>Chain | gaagtgcagctgctggaatccggcggaggtctggtccagcctggaggttccctgcgcctgtcatgcgcagcctccgg<br>attcacctttcgtcgtactggatgaactgggtcagacaggctcctggaaagggcctggaatgggtgtctgtgattgaatc<br>caaggggaactacatcttctacgcggacagcgtgaagggccggttcactatcagcagagacaacagcaagaaccacc<br>tgtacctccaaatgaactcgctgagggccgaagatactgccgtgtactactgtgcccgcgatcgctactcgatgatctac<br>agctatggtgccggagcgttcgattactgggacagggaaccctcgtgaccgtcagctccgcctcaaccaagggccc<br>gtcagtgttcccgctggctccatcgtcgaagtccacctccggaggaaccgcagcactcggttgcctggtcaaggactac<br>ttccctgagccagtgaccgtgtcgtggaacagcggagccctgacttccggcgtgcacacttttcccgcggtgctgcagt<br>cctccggtctgtactcccttcgtcgtggtcaccgtgcctcgtctagcctgggcacccagacctacatctgcaacgtg<br>aaccacaagccgtccaacaccaaagtggataagcgggtggagccgaagtcctgcgataagacacacacgtgcccgc<br>catgtccagcgcctgaattgcttggcggaccttccgtgttcctgttcccgcctaagcccaaggcaccttgatgattagcc<br>ggactcccgaagtcacctgtgtggtggtggcagtgtcccacgaggaccccgaggtcaagtttaattggtacgtggacg<br>gcgtcgaagtgcacaacgccaagactaagccgggaggaacagtacaacagcaccaccgggtcgtgtccgtgct<br>gaccgtgctgcaccaggactggctgaatgggaaagagtacaagtgcaaagtgtccaacaaggccttggccgctcctat<br>cgaaaaaactatcagcaaggctaagggacagccgagggaaccccaagtctacaccctgccccctctcacgcgaagag<br>atgaccaagaatcaagtgtcgctgacctgcctcgtcaagggattctacccctccgacattgcggtggagtgggagtcca<br>acggccagcccgagaacaactacaagactactccgcccgtgctggactcgacggcagcttcttcctgtattccaagct<br>gaccgtggacaagtcccggtggcagcaaggaaacgtgttctcctgctcggtcatgcacgaagccctgcacaaccacta<br>tacgcagaagtccctgtccttgagcccggggaaa |
| SEQ ID<br>NO: 41 | LCDR1<br>(Combined) | RASQGISSYLA |
| SEQ ID<br>NO: 42 | LCDR2<br>(Combined) | TASTLQS |
| SEQ ID<br>NO: 145 | LCDR3<br>(Combined) | QQIWTVPRT |
| SEQ ID<br>NO: 41 | LCDR1<br>(Kabat) | RASQGISSYLA |
| SEQ ID<br>NO: 42 | LCDR2<br>(Kabat) | TASTLQS |
| SEQ ID<br>NO: 145 | LCDR3<br>(Kabat) | QQIWTVPRT |
| SEQ ID<br>NO: 44 | LCDR1<br>(Chothia) | SQGISSY |
| SEQ ID<br>NO: 45 | LCDR2<br>(Chothia) | TAS |
| SEQ ID<br>NO: 146 | LCDR3<br>(Chothia) | IWTVPR |
| SEQ ID<br>NO: 47 | LCDR1<br>(IMGT) | QGISSY |
| SEQ ID<br>NO: 45 | LCDR2<br>(IMGT) | TAS |
| SEQ ID<br>NO: 145 | LCDR3<br>(IMGT) | QQIWTVPRT |
| SEQ ID<br>NO: 147 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWTVPRTFGQGTKV<br>EIK |
| SEQ ID<br>NO: 214 | DNA VL | gacatccagatgacccagtctccgtcctccctgtccgcatcagtgggggacagagtgaccatcacttgtcgggcctccc<br>aaggcatctcgtcatacctggcctggtatcagcagaaacccggaaaggctccaaagctgctcatctacaccgcctcga<br>ctctgcaatccggagtgccttcccgcttctccggatccggttcgggaaccgacttcacccctcaccattagcagccttcag<br>ccggaagatttcgcgacctactactgccagcaaatctggaccgtgcccaggacatttggccagggcactaaggtcgag<br>attaag |
| SEQ ID<br>NO: 149 | Light<br>Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWTVPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID<br>NO: 215 | DNA<br>Light<br>Chain | gacatccagatgacccagtctccgtcctccctgtccgcatcagtgggggacagagtgaccatcacttgtcgggcctccc<br>aaggcatctcgtcatacctggcctggtatcagcagaaacccggaaaggctccaaagctgctcatctacaccgcctcga<br>ctctgcaatccggagtgccttcccgcttctccggatccggttcgggaaccgacttcacccctcaccattagcagccttcag<br>ccggaagatttcgcgacctactactgccagcaaatctggaccgtgcccaggacatttggccagggcactaaggtcgag |

TABLE 2-continued

Exemplary anti-NPR1 antibody sequences attaagcgtacggtggccgctcccagcgtgttcatcttcccccccagcgacgagcagctgaagagcggcaccgccag
cgtggtgtgcctgctgaacaacttctaccccgggaggcaaggtgcagtggaaggtggacaacgccctgcagagc
ggcaacagccaggagagcgtcaccgagcaggacagcaaggactccacctacagcctgagcagcaccctgaccctg
agcaaggccgactacgagaagcataaggtgtacgcctgcgaggtgacccaccagggcctgtccagcccgtgacca
agagcttcaacaggggcgagtgc

XX18_LALA

| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 202 | DNA VH | caagttcaattgctggaaagcggaggtggacttgtccaacctggagggtcactccgactgtcttgcgctgcatcaggatt<br>cacctttagtagctattggatgaactgggtccggcaggcctctgggaaagggcttgagtgggtaagtgtcattgaatcaa<br>aggggcaactacatctttttatgctgattctgtaaagggtaggttcaccatctccagggacaattcaaaaaatactttgtatctg<br>cagatgaactctctcagggcagaagacacggccgtttattactgcgcccgcgatcgatacagcatgatatactcctacg<br>gcgcaggagcttttgactactgggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgctgcatcaggatt<br>cacctttagtagctattggatgaactgggtccggcaggcctctgggaaagggcttgagtgggtaagtgtcattgaatcaa<br>aggggcaactacatctttttatgctgattctgtaaagggtaggttcaccatctccagggacaattcaaaaaatactttgtatctg<br>cagatgaactctctcagggcagaagacacggccgtttattactgcgcccgcgatcgatacagcatgatatactcctacg<br>gcgcaggagcttttgactactgggtcaaggcacacttgttactgtcagtagcgcctcaacgaaaggaccgtccgtgttt<br>cctcttgctcctagctccaaatccacctcaggtgaacgccgccctggggtgcctggtaaaggactattcccagagc<br>cagttactgtgtcttggaattctggtgcattgacaagtggcgtacacacttttccgcggtcctccaatctagtggtctgtac<br>tcactgtcctccgttgtgactgtcccaagtagctcacttggcaccagattacatctgtaatgttaatcataagcgtcaaa<br>cacgaaggtggataagagggtagaacctaagtcatgtgacaaaacgcatacttgccccccctgccctgcgccggaag<br>ccgctggcggacccctcgtattcttgttccctccaaagccaaaggacactctgatgattagccgacaccggaggtcac<br>ttgtgttgtagttgacgtcagccatgaggatcctgaggtgaaatttaattggtacgtggacggggttgaagtccacaatgc<br>taaaactaaacctagggaagagcaatataatagtacatacagggttgtcagtgtgctgaccgttctccatcaggactggc<br>tgaacggcaaggaatacaagtgcaaggtcagcaacaaggccttgccggccccatcgagaagacgatctccaaagc |

TABLE 2-continued

Exemplary anti-NPR1 antibody sequences

```
                        caaggggcaaccccgagaaccgcaggtatacacgctcccccctagtagaagagatgacaaagaatcaagtttcctt
                        gacgtgccttgtgaaaggcttctaccctagtgacatcgcagtcgaatgggagagcaacgggcagccggagaataacta
                        taaaacaaccccccccgtgcttgactcagacgggtcatttttctgtatagcaaattgactgttgataaatcacggtggcaa
                        caaggaaacgtgtttagttgcagcgtaatgcacgaagctctccacaatcactatactcaaaagtcactgtcactctcccct
                        ggcaag
```

| SEQ ID NO: 41 | LCDR1 (Combined) | RASQGISSYLA |
|---|---|---|
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |
| SEQ ID NO: 42 | LCDR2 (Kabat) | TASTLQS |
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |

SEQ ID NO: 174  VL

DIQMTQSPSSLSASVGDRVTITCRASQGISSYLAWYQQKPGKAPKLLIYTAS
TLQSGVPSRFSGSGSGTDFTLTISSLQPEDFATYYCQQEWAKPRTFGQGTKV
EIK

SEQ ID NO: 199  DNA VL

```
gatatacagatgacgcaaagtccctctagtctttctgcaagtgtcggggacagagttaccattacctgcagagcgtcaca
aggcatctctagttatctcgcgtggtaccaacagaagccaggtaaagcacctaaactgttgatttacacggcatcaacatt
gcagtcaggtgtccctcccgatttagtggcagtggtagcggtacagattttactcttaccatttcatctcttcagccagaa
gattttgctacgtactactgtcaacaagaatgggctaaaccacgaaccttggacaggggtacgaaggtcgaaataaaa
```

SEQ ID NO: 176  Light Chain

DIQMTQSPSSLSASVGDRVTITCRASQGISSYLAWYQQKPGKAPKLLIYTAS
TLQSGVPSRFSGSGSGTDFTLTISSLQPEDFATYYCQQEWAKPRTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC

SEQ ID NO: 200  DNA Light Chain

```
gatatacagatgacgcaaagtccctctagtctttctgcaagtgtcggggacagagttaccattacctgcagagcgtcaca
aggcatctctagttatctcgcgtggtaccaacagaagccaggtaaagcacctaaactgttgatttacacggcatcaacatt
gcagtcaggtgtccctcccgatttagtggcagtggtagcggtacagattttactcttaccatttcatctcttcagccagaa
gattttgctacgtactactgtcaacaagaatgggctaaaccacgaaccttggacaggggtacgaaggtcgaaataaaac
ggaccgttgccgcccctccgtcttcatcttcccccgtctgacgagcagctcaaatccggcacagcttctgtagtctgct
tgctgaataacttctacccaagagaagccaaagttcagtggaaggtcgataatgcattgcaatctggtaatagtcaggaa
tctgtgactgagcaggatagcaaagactcaacttacagcctctcttcaaccttgacgttgtccaaagcggattatgagaaa
cacaaggtgtacgcttgcgaggtgacgcatcaagggcttagttcccggtaaccaaatctttcaaccgaggtgaatgc
```

XX18_DAPA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |

TABLE 2-continued

Exemplary anti-NPR1 antibody sequences

| SEQ ID NO: 31 | HCDR1 (Kabat) | SYWMN |
|---|---|---|
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgcagcctccgg attcaccttttcgtcgtactggatgaactgggtcagacaggctcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactggggacagggaaccctcgtgaccgtcagctcc |
| SEQ ID NO: 208 | Heavy Chain | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKP KDTLMISRTPEVTCVVVAVSHEDPEVKFNWYVDGVEVHNAKTKPREEQY NSTYRVVSVLTVLHQDWLNGKEYKCKVSNKALAAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgcagcctccgg attcaccttttcgtcgtactggatgaactgggtcagacaggctcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactggggacagggaaccctcgtgaccgtcagctcctccgcctcaaccaagggccc gtcagtgtttcccgctggctccatcgtcgaagtccacctccggaggaaccgcagcactcggttgcctggtcaaggactac ttccctgagccagtgaccgtgtcgtggaacagccgagccctgacttccggcgtgcacacttttcccgcggtgctgcagt cctccggtctgtactccctttcgtccgtggtcaccgtgccgtcgtctagcctgggcacccagacctacatctgcaacgtg aaccacaagccgtccaacaccaaagtggataagcgggtggagccgaagtcctgcgataagacacacacgtgccccgc catgtccagcgcctgaattgcttggcggaccttccgtgttcctgttccccccaaagcccaaggacaccttgatgattagcc ggactcccgaagtcacctgtgtggtggtggcagtgtcccacgaggaccccgaggtcaagtttaattggtacgtggacg gcgtcgaagtgcacaacgccaagactaagccccgggaggaacagtacaacagcacctaccgggtcgtgtccgtgct gaccgtgctgcaccaggactggctgaatgggaaagagtacaagtgcaaagtgtccaacaaggccttggccgctcctat cgaaaaaactatcagcaaggctaagggacagccgagggaacccaagtctacaccctgccccctttcacgcggaagag atgaccaagaatcaagtgtcgctgacctgcctcgtcaaggggattctaccctccgacattgcggtggagtgggagtcca acggccagcccgagaacaactacaagactactccgcccgtgctggactccgacggcagcttcttcctgtattccaagct gaccgtggacaagtcccggtggcagcaaggaaacgtgttctcctgctcggtcatgcacgaagcccgcacaaccacta tacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 172 | LCDR3 (Combined) | QQEWAKPRT |
| SEQ ID NO: 41 | LCDR1 (Kabat) | RASQGISSYLA |

TABLE 2-continued

Exemplary anti-NPR1 antibody sequences

| SEQ ID NO: 42 | LCDR2 (Kabat) | TASTLQS |
|---|---|---|
| SEQ ID NO: 172 | LCDR3 (Kabat) | QQEWAKPRT |
| SEQ ID NO: 44 | LCDR1 (Chothia) | SQGISSY |
| SEQ ID NO: 45 | LCDR2 (Chothia) | TAS |
| SEQ ID NO: 173 | LCDR3 (Chothia) | EWAKPR |
| SEQ ID NO: 47 | LCDR1 (IMGT) | QGISSY |
| SEQ ID NO: 45 | LCDR2 (IMGT) | TAS |
| SEQ ID NO: 172 | LCDR3 (IMGT) | QQEWAKPRT |
| SEQ ID NO: 174 | VL | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIK |
| SEQ ID NO: 216 | DNA VL | gacatccagatgacccagtctccgtcctccctgtccgcatcagtgggggacagagtgaccatcacttgtcgggcctcc aaggcatctcgtcatacctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaagaatgggccaagcccaggacatttggccagggcactaaggtcga gattaag |
| SEQ ID NO: 176 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQEWAKPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 217 | DNA Light Chain | gacatccagatgacccagtctccgtcctccctgtccgcatcagtgggggacagagtgaccatcacttgtcgggcctcc aaggcatctcgtcatacctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaagaatgggccaagcccaggacatttggccagggcactaaggtcga gattaagcgtacggtggccgctcccagcgtgttcatcttccccccagcgacgagcagctgaagagcggcaccgcca gcgtggtgtgcctgctgaacaacttctaccccgggaggccaaggtgcagtggaaggtggacaacgcgctgcagag cggcaacagccaggagagcgtcaccgagcaggacagcaaggactccacctacagcctgagcagcaccctgaccct gagcaaggccgactacgagaagcataaggtgtacgcctgcgaggtgacccaccagggcctgtccagcccgtgacc aagagcttcaacaggggcgagtgc |

XX19_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |

TABLE 2-continued

Exemplary anti-NPR1 antibody sequences

| SEQ ID NO: 30 | HCDR3 (Chothia) | DRYSMIYSYGAGAFDY |
|---|---|---|
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 202 | DNA VH | caagttcaattgctggaaagcggaggtggacttgtccaacctggagggtcactccgactgtcttgcgctgcatcaggatt cacctttagtagctattggatgaactgggtccggcaggtcctgggaaagggcttgagtgggtaagtgtcattgaatcaa agggcaactacatcttttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactggggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPEAAGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 204 | DNA Heavy Chain | caagttcaattgctggaaagcggaggtggacttgtccaacctggagggtcactccgactgtcttgcgctgcatcaggatt cacctttagtagctattggatgaactgggtccggcaggtcctgggaaagggcttgagtgggtaagtgtcattgaatcaa agggcaactacatctttatgctgattctgtaaagggtaggttcaccatctccagggacaattcaaaaaatactttgtatctg cagatgaactctctcagggcagaagacacggccgtttattactgcgcccgcgatcgatacagcatgatatactcctacg gcgcaggagcttttgactactggggtcaaggcacacttgttactgtcagtagcgcctcaacgaaaggaccgtccgtgttt cctcttgctcctagctccaaatccacctcaggtggaacgccgcctgggggtgcctggtaaaggactatttcccagagc cagttactgtgtcttggaattctggtgcattgacaagtggcgtacacactttccgcggtcctccaatctagtggtctgtac tcactgtcctccgttgtgactgtcccaagtagctcacttgcacagacttacatctgtaatgttaatcataagccgtcaaa cacgaaggtggataagagggtagaacctaagtcatgtgacaaaacgcatcttgccccccctgcctgcgccggaag ccgctggcggacccttgtattcttgttccctccaaagccaaggacactctgatgattagccggacaccggaggtcac ttgtgttgtagttgacgtcagccatgaggatcctgaggtgaaatttaattggtacgtggacgggggttgaagtccacaatgc taaaactaaacctagggaagagcaatataatagtacatacagggtttgtcagtgtgctgaccgttctccatcaggactggc tgaacgcaaggaatacaagtgcaaggtcagcaacaaggcctgccggcccccatcgagaagacgatctccaaagc caaggggcaaccccgagaaccgcaggtatacacgctccccccagtagagaagagatgacaaagaatcaagtttcctt gacgtgccttgtgaaaggcttctaccctagtgacatcgcagtcgaatgggagagcaacgggcagccggagaataacta taaaacaaccccccccgtgcttgactcagacgggtcattttttctgtatagcaaattgactgttgataaatcacggtggcaa caaggaaacgtgtttagttgcagcgtaatgcacgaagctctccacaatcactatactcaaaagtcactgtcactctcccct ggcaag |
| SEQ ID NO: 41 | LCDR1 (Combined) | RASQGISSYLA |
| SEQ ID NO: 42 | LCDR2 (Combined) | TASTLQS |
| SEQ ID NO: 178 | LCDR3 (Combined) | QQSWTRPRT |
| SEQ ID NO: 41 | LCDR1 (Kabat) | RASQGISSYLA |
| SEQ ID NO: 42 | LCDR2 (Kabat) | TASTLQS |
| SEQ ID NO: 178 | LCDR3 (Kabat) | QQSWTRPRT |
| SEQ ID NO: 44 | LCDR1 (Chothia) | SQGISSY |
| SEQ ID NO: 45 | LCDR2 (Chothia) | TAS |
| SEQ ID NO: 179 | LCDR3 (Chothia) | SWTRPR |

TABLE 2-continued

Exemplary anti-NPR1 antibody sequences

| SEQ ID NO: 47 | LCDR1 (IMGT) | QGISSY |
| SEQ ID NO: 45 | LCDR2 (IMGT) | TAS |
| SEQ ID NO: 178 | LCDR3 (IMGT) | QQSWTRPRT |
| SEQ ID NO: 180 | VL | DIQMTQSPSSLSASVGDRVTITCRASQGISSYLAWYQQKPGKAPKLLIYTAS TLQSGVPSRFSGSGSGTDFTLTISSLQPEDFATYYCQQSWTRPRTFGQGTKV EIK |
| SEQ ID NO: 218 | DNA VL | gatattcagatgacgcaatctccgtcttccttgtcagctagtgtaggagaccgcgtcacaattacctgtagagccagcca ggggatttcctcatacctttgcatggtaccagcaaaagccaggcaaagcccccaaactgctgatctacaccgcgtctacc ttgcaatctggtgtgccgtcacgcttttccggctctggctcaggtactgatttcacattgacgatctcaagtctccagccgg aagacttcgcaacttactactgccaacaatcctggacgaggccgaggactttcgggcagggaacaaaggttgaaatta aa |
| SEQ ID NO: 182 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQSWTRPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 219 | DNA Light Chain | gatattcagatgacgcaatctccgtcttccttgtcagctagtgtaggagaccgcgtcacaattacctgtagagccagcca ggggatttcctcatacctttgcatggtaccagcaaaagccaggcaaagcccccaaactgctgatctacaccgcgtctacc ttgcaatctggtgtgccgtcacgcttttccggctctggctcaggtactgatttcacattgacgatctcaagtctccagccgg aagacttcgcaacttactactgccaacaatcctggacgaggccgaggactttcgggcagggaacaaaggttgaaatta aagaacagtcgcagcaccaagtgtttttattttttccaccctcagacgagcagctcaagtctggcaccgcgagcgtagta tgtttgttgaataatttttaccctaggggaagctaaggtacagtggaaagtggataatgctctccaaagtggcaactcccag gaatcagtgactgagcaagattcaaaggacagcacgtattctctttcttctacgcttactctctctaaggccgactacgaaa aacacaaagtttacgcttgcgaggttacccaccaggggctgtcctcaccagtaacgaaaagttttaaccggggcgagtg t |
| XX19_DAPA | | |
| SEQ ID NO: 28 | HCDR1 (Combined) | GFTFSSYWMN |
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |

TABLE 2-continued

Exemplary anti-NPR1 antibody sequences

| SEQ ID NO: 207 | DNA VH | gaagtgcagctgctggaatccggcggaggtctggtccagcctggaggttccctgcgcctgtcatgcgcagcctccgg attcacctttcgtcgtactggatgaactgggtcagacaggctcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactggggacagggaaccctcgtgaccgtcagctcc |
| SEQ ID NO: 208 | Heavy Chain | EVQLLESGGGLVQPGGSLRLSCAASGFTSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKP KDTLMISRTPEVTCVVVAVSHEDPEVKFNWYVDGVEVHNAKTKPREEQY NSTYRVVSVLTVLHQDWLNGKEYKCKVSNKALAAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgcagcctccgg attcacctttcgtcgtactggatgaactgggtcagacaggctcctggaaagggcctggaatgggtgtctgtgattgaatc caaggggaactacatcttctacgcggacagcgtgaagggccggttcactatcagcagagacaacagcaagaacaccc tgtacctccaaatgaactcgctgagggccgaagatactgccgtgtactactgtgcccgcgatcgctactcgatgatctac agctatggtgccggagcgttcgattactggggacagggaaccctcgtgaccgtcagctccgcctcaaccaagggccc gtcagtgttcccgctggctccatcgtcgaagtccacctccggaggaaccgcagcactcggttgcctggtcaaggactac ttccctgagccagtgaccgtgtcgtggaacagcggagccctcgacttccggcggcacactttccccgcggtgctgcagt cctccggtctgtactcccttttcgtccgtggtcaccgtgccgtcgtctagcctgggcacccagacctacatctgcaacgtg aaccacaagccgtccaacaccaaagtggataagcgggtggagccgaagtcctgcgataagacacacacgtgcccgc catgtccagcgcctgaattgcttggcggaccttccgtgttcctgttcccgcctaagcccaaggacaccttgatgattagcc ggactcccgaagtcacctgtgtggtggtggcagtgtcccacgaggaccccgaggtcaagtttaattggtacgtggacg gcgtcgaagtgcacaacgccaagactaagccccgggaggaacagtacaacagcacctaccgggtcgtgtccgtgct gaccgtgctgcaccaggactggctgaatgggaaagagtacaagtgcaaagtgtccaacaaggccttggccgctcctat cgaaaaaactatcagcaaggctaagggacagccgagggaaccccaagtctacaccctgcccccttcacgcgaagag atgaccaagaatcaagtgtcgctgacctgcctcgtcaagggattctaccctccgacattgcggtggagtgggagtcca acggccagcccgagaacaactacaagactactccgcccgtgctggactccgacggcagcttcttcctgtattccaagct gaccgtggacaagtcccggtggcagcaaggaaacgtgttcctcctgctcggtcatgcacgaagccctgcacaaccacta tacgcagaagtccctgtccttgagcccggggaaa |
| SEQ ID NO: 41 | LCDR1 (Combined) | RASQGISSYLA |
| SEQ ID NO: 42 | LCDR2 (Combined) | TASTLQS |
| SEQ ID NO: 178 | LCDR3 (Combined) | QQSWTRPRT |
| SEQ ID NO: 41 | LCDR1 (Kabat) | RASQGISSYLA |
| SEQ ID NO: 42 | LCDR2 (Kabat) | TASTLQS |
| SEQ ID NO: 178 | LCDR3 (Kabat) | QQSWTRPRT |
| SEQ ID NO: 44 | LCDR1 (Chothia) | SQGISSY |
| SEQ ID NO: 45 | LCDR2 (Chothia) | TAS |
| SEQ ID NO: 179 | LCDR3 (Chothia) | SWTRPR |
| SEQ ID NO: 47 | LCDR1 (IMGT) | QGISSY |
| SEQ ID NO: 45 | LCDR2 (IMGT) | TAS |
| SEQ ID NO: 178 | LCDR3 (IMGT) | QQSWTRPRT |
| SEQ ID NO: 180 | VL | DIQMTQSPSSLSASVGDRVTITCRASQGISSYLAWYQQKPGKAPKLLIYTAS TLQSGVPSRFSGSGSGTDFTLTISSLQPEDFATYYCQQSWTRPRTFGQGTKV EIK |

TABLE 2-continued

Exemplary anti-NPR1 antibody sequences

| SEQ ID NO: 220 | DNA VL | gacatccagatgacccagtctccgtcctccctgtccgcatcagtgggggacagagtgaccatcacttgtcgggcctccc<br>aaggcatctcgtcatacctggcctggtatcagcagaaacccggaaaggctccaaagctgctcatctacaccgcctcga<br>ctctgcaatccggagtgccttcccgcttctccggatccggttcgggaaccgacttcaccctcaccattagcagccttcag<br>ccggaagatttcgcgacctactactgccagcaaagctggaccaggcccaggacatttggccagggcactaaggtcga<br>gattaag |
|---|---|---|
| SEQ ID NO: 182 | Light Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQSWTRPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 221 | DNA Light Chain | gacatccagatgacccagtctccgtcctccctgtccgcatcagtgggggacagagtgaccatcacttgtcgggcctccc<br>aaggcatctcgtcatacctggcctggtatcagcagaaacccggaaaggctccaaagctgctcatctacaccgcctcga<br>ctctgcaatccggagtgccttcccgcttctccggatccggttcgggaaccgacttcaccctcaccattagcagccttcag<br>ccggaagatttcgcgacctactactgccagcaaagctggaccaggcccaggacatttggccagggcactaaggtcga<br>gattaagcgtacggtggccgctcccagcgtgttcatcttccccccagcgacgagcagctgaagagcggcaccgcca<br>gcgtggtgtgcctgctgaacaacttctaccccgggaggccaaggtgcagtggaaggtggacaacgcctgcagag<br>cggcaacagccaggagagcgtcaccgagcaggacagcaaggactccacctacagcctgagcagcaccctgaccct<br>gagcaaggccgactacgagaagcataaggtgtacgcctgcgaggtgacccaccagggcctgtccagccccgtgacc<br>aagagcttcaacaggggcgagtgc |

XX20_LALA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 201 | VH | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSS |
| SEQ ID NO: 202 | DNA VH | caagttcaattgctggaaagcggaggtggacttgtccaacctggagggtcactccgactgtcttgcgctgcatcaggatt<br>cacctttagtagctattggatgaactgggtccggcaggctcctgggaaagggcttgagtgggtaagtgtcattgaatcaa<br>agggcaactacatcttttatgctgattctgtaaagggtaggttcaccatctccagggacaattcaaaaaatactttgtatctg<br>cagatgaactctctcagggcagaagacacggccgtttattactgcgcccgcgatcgatacagcatgatatactcctacg<br>gcgcaggagcttttgactactggggtcaaggcacacttgttactgtcagtagc |
| SEQ ID NO: 203 | Heavy Chain | QVQLLESGGGLVQPGGSLRLSCAASGFTFSSYWMNWVRQAPGKGLEWVS<br>VIESKGNYIFYADSVKGRFTISRDNSKNTLYLQMNSLRAEDTAVYYCARDR<br>YSMIYSYGAGAFDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREP |

TABLE 2-continued

Exemplary anti-NPR1 antibody sequences

|  |  |  |
|---|---|---|
|  |  | QVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID<br>NO: 204 | DNA<br>Heavy<br>Chain | caagttcaattgctggaaagcggaggtggacttgtccaacctggagggtcactccgactgtcttgcgctgcatcaggatt<br>cacctttagtagctattggatgaactgggtccggcaggcctctgggaaagggcttgagtgggtaagtgtcattgaatcaa<br>agggcaactacatctttatgctgattctgtaaagggtaggttcaccatctccagggacaattcaaaaaatactttgtatctg<br>cagatgaactctctcagggcagaagacacggccgtttattactgcgcccgcgatcgatacagcatgatatactcctacg<br>gcgcaggagcttttgactactggggtcaaggcacacttgttactgtcagtagccgcctcaacgaaaggaccgtccgtgttt<br>cctcttgctcctagctccaaatccacctcaggtggaacgccgccctgggggcctggtaaaggactattccccagagc<br>cagttactgtgtcttggaattctggtgcattgacaagtggcgtacacacttttcccgcggtcctccaatctagtggtctgtac<br>tcactgtcctccgttgtgactgtcccaagtagctcacttggcacacagacttacatctgtaatgttaatcataagccgtcaaa<br>cacgaaggtggataagagggtagaacctaagtcatgtgacaaaacgcatacttgcccccctgccctgcgccggaag<br>ccgctggcggacccctccgtattcttgttccctccaaagccaaaggacactctgatgattagccggacaccggaggtcac<br>ttgtgttgtagttgacgtcagccatgaggatcctgaggtgaaatttaattggtacgtggacggggttgaagtccacaatgc<br>taaaactaaacctagggagaagcaatataatagtacatacagggtttgtcagtgtgctgaccgttctccatcaggactggc<br>tgaacggcaaggaatacaagtgcaaggtcagcaacaaggcctgccggccccatcgagaagacgatctccaaagc<br>caaggggcaaccccgagaaccgcaggtatacacgctcccccctagtagagaagagatgacaaagaatcaagtttcctt<br>gacgtgccttgtgaaaggcttctaccctagtgacatcgcagtcgaatgggagagcaacgggcagccggagaataacta<br>taaaacaaccccccccgtgcttgactcagacgggtcatttttctgtatagcaaattgactgttgataaatcacggtggcaa<br>caaggaaacgtgtttagttgcagcgtaatgcacgaagctctccacaatcactatactcaaaagtcactgtcactctcccct<br>ggcaag |
| SEQ ID<br>NO: 41 | LCDR1<br>(Combined) | RASQGISSYLA |
| SEQ ID<br>NO: 42 | LCDR2<br>(Combined) | TASTLQS |
| SEQ ID<br>NO: 184 | LCDR3<br>(Combined) | QQIWMAPRT |
| SEQ ID<br>NO: 41 | LCDR1<br>(Kabat) | RASQGISSYLA |
| SEQ ID<br>NO: 42 | LCDR2<br>(Kabat) | TASTLQS |
| SEQ ID<br>NO: 184 | LCDR3<br>(Kabat) | QQIWMAPRT |
| SEQ ID<br>NO: 44 | LCDR1<br>(Chothia) | SQGISSY |
| SEQ ID<br>NO: 45 | LCDR2<br>(Chothia) | TAS |
| SEQ ID<br>NO: 185 | LCDR3<br>(Chothia) | IWMAPR |
| SEQ ID<br>NO: 47 | LCDR1<br>(IMGT) | QGISSY |
| SEQ ID<br>NO: 45 | LCDR2<br>(IMGT) | TAS |
| SEQ ID<br>NO: 184 | LCDR3<br>(IMGT) | QQIWMAPRT |
| SEQ ID<br>NO: 186 | VL | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIK |
| SEQ ID<br>NO: 222 | DNA VL | gacattcaaatgactcagtctccctcatctttgtcagcatcagttggggacagggtgacaatacatgccgagcctcaca<br>ggggatttctagctatcttgcatggtaccaacagaagcccggcaaagcccccaagcttttgatatatacggcatccactct<br>tcagagcggagtacccagtaggtttagtggctccgggagtggtacggactttactctgacgatttcctccttcaacctga<br>gactttgcaacgtattactgtcagcaaatatggatggctcccagaacgtttggtcaaggtactaaagttgaaataaag |
| SEQ ID<br>NO: 188 | Light<br>Chain | DIQMTQSPSSLSASVGDRVTITCRASQGISSYLAWYQQKPGKAPKLLIYTAS<br>TLQSGVPSRFSGSGSGTDFTLTISSLQPEDFATYYCQQIWMAPRTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID<br>NO: 223 | DNA<br>Light<br>Chain | gacattcaaatgactcagtctccctcatctttgtcagcatcagttggggacagggtgacaatacatgccgagcctcaca<br>ggggatttctagctatcttgcatggtaccaacagaagcccggcaaagcccccaagcttttgatatatacggcatccactct<br>tcagagcggagtacccagtaggtttagtggctccgggagtggtacggactttactctgacgatttcctccttcaacctga<br>gactttgcaacgtattactgtcagcaaatatggatggctcccagaacgtttggtcaaggtactaaagttgaaataaagcg<br>aactgtagcagcaccctagtgtatttatcttccccccctctgatgaacagttgaagtccgggacggcttccgtcgtatgtctc |

TABLE 2-continued

Exemplary anti-NPR1 antibody sequences

```
                    ctgaacaacttttacccaagggaggcaaaggtgcaatggaaggtggataatgcactccagagtggcaatagccaaga
                    atcagtaaccgaacaggattccaaggattctacctacagcctttcctctacgcttacattgagcaaggcggactatgaaaa
                    gcataaggtgtatgcgtgcgaagtaacacaccagggtctcagcagtccagttacgaagtctttcaatcggggagaatgt
```

XX20_DAPA

| SEQ ID NO: 28 | HCDR1 (Combined) | GFTFSSYWMN |
|---|---|---|
| SEQ ID NO: 119 | HCDR2 (Combined) | VIESKGNYIFYADSVKG |
| SEQ ID NO: 30 | HCDR3 (Combined) | DRYSMIYSYGAGAFDY |
| SEQ ID NO: 31 | HCDR1 (Kabat) | SYWMN |
| SEQ ID NO: 119 | HCDR2 (Kabat) | VIESKGNYIFYADSVKG |
| SEQ ID NO: 30 | HCDR3 (Kabat) | DRYSMIYSYGAGAFDY |
| SEQ ID NO: 32 | HCDR1 (Chothia) | GFTFSSY |
| SEQ ID NO: 120 | HCDR2 (Chothia) | ESKGNY |
| SEQ ID NO: 30 | HCDR3 (Chothia) | DRYSMIYSYGAGAFDY |
| SEQ ID NO: 34 | HCDR1 (IMGT) | GFTFSSYW |
| SEQ ID NO: 121 | HCDR2 (IMGT) | IESKGNYI |
| SEQ ID NO: 36 | HCDR3 (IMGT) | ARDRYSMIYSYGAGAFDY |
| SEQ ID NO: 122 | VH | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSS |
| SEQ ID NO: 207 | DNA VH | gaagtgcagctgctggaatccggcggaggtctggtccagcctggaggttccctgcgcctgtcatgcgcagcctccgg<br>attcacctttcgtcgtactggatgaactgggtcagacaggtcctggaaagggcctggaatgggtgtctgtgattgaatc<br>caaggggaactacatcttctacgcggacagcgtgaagggccggttcactatcagcagagacaacagcaagaacaccc<br>tgtacctccaaatgaactcgctgagggccgaagatactgccgtgtactactgtgcccgcgatcgctactcgatgatctac<br>agctatggtgccggagcgttcgattactgggacagggaacccctcgtgaccgtcagctcc |
| SEQ ID NO: 208 | Heavy Chain | EVQLLESGGGLVQPGGSLRLSCAASGFTFSSYWMNWVRQAPGKGLEWVS VIESKGNYIFYADSVKGRFTISRDNSKNTLYLQMNSLRAEDTAVYYCARDR YSMIYSYGAGAFDYWGQGTLVTVSSASTKGPSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKP KDTLMISRTPEVTCVVVAVSHEDPEVKFNWYVDGVEVHNAKTKPREEQY NSTYRVVSVLTVLHQDWLNGKEYKCKVSNKALAAPIEKTISKAKGQPREP QVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| SEQ ID NO: 209 | DNA Heavy Chain | gaagtgcagctgctggaatccggcggaggtctggtccagcctggaggttccctgcgcctgtcatgcgcagcctccgg<br>attcacctttcgtcgtactggatgaactgggtcagacaggtcctggaaagggcctggaatgggtgtctgtgattgaatc<br>caaggggaactacatcttctacgcggacagcgtgaagggccggttcactatcagcagagacaacagcaagaacaccc<br>tgtacctccaaatgaactcgctgagggccgaagatactgccgtgtactactgtgcccgcgatcgctactcgatgatctac<br>agctatggtgccggagcgttcgattactgggacagggaacccctcgtgaccgtcagctccgcctcaaccaagggccc<br>gtcagtgttcccgctggtcccatcgtcaagtccacctccgggagcaccgcagccctcggttgcctggtcaaggactac<br>ttccctgagccagtgaccgtgtcgtgaacagcggagccctgacttccggcgtgcacactttttccccgcggtgctgcagt<br>cctccggtctgtactcccttttcgtccgtggtcaccgtgccgtcgtctagcctgggcacccagacctacatctgcaacgtg<br>aaccacaagccgtccaacaccaaagtggataagcgggtggagccgaagtcctgcgataagacacacacgtgcccgc<br>catgtccagcgcctgaattgctggcggaccttccgtgttcctgttcccgcctaagcccaaggacaccttgatgattagcc<br>ggactcccgaagtcacctgtgtggtggcagtgtcccacgaggaccccgaggtcaagtttaattggtacgtggacg<br>gcgtcgaagtgcacaacgccaagactaagcccgggaggaacagtacaacagcacctaccgggtcgtgtccgtgct<br>gaccgtgctgcaccaggactggctgaatgggaaagagtacaagtgcaaagtgtccaacaaggccttggccgctcctat<br>cgaaaaaactatcagcaaggctaagggacagccgagggaaccccaagtctacaccctgccccttcacgcgaagag<br>atgaccaagaatcaagtgtcgtgacctgcctcgtcaagggattctaccctccgacattgcggtggagtgggagtcca |

TABLE 2-continued

Exemplary anti-NPR1 antibody sequences

```
acggccagcccgagaacaactacaagactactccgcccgtgctggactccgacggcagcttcttcctgtattccaagct
gaccgtggacaagtcccggtggcagcaaggaaacgtgttctcctgctcggtcatgcacgaagccctgcacaaccacta
tacgcagaagtccctgtccttgagcccggggaaa
```

| SEQ ID NO: 41 | LCDR1 (Combined) | RASQGISSYLA |
|---|---|---|
| SEQ ID NO: 42 | LCDR2 (Combined) | TASTLQS |
| SEQ ID NO: 184 | LCDR3 (Combined) | QQIWMAPRT |
| SEQ ID NO: 41 | LCDR1 (Kabat) | RASQGISSYLA |
| SEQ ID NO: 42 | LCDR2 (Kabat) | TASTLQS |
| SEQ ID NO: 184 | LCDR3 (Kabat) | QQIWMAPRT |
| SEQ ID NO: 44 | LCDR1 (Chothia) | SQGISSY |
| SEQ ID NO: 45 | LCDR2 (Chothia) | TAS |
| SEQ ID NO: 185 | LCDR3 (Chothia) | IWMAPR |
| SEQ ID NO: 47 | LCDR1 (IMGT) | QGISSY |
| SEQ ID NO: 45 | LCDR2 (IMGT) | TAS |
| SEQ ID NO: 184 | LCDR3 (IMGT) | QQIWMAPRT |
| SEQ ID NO: 186 | VL | DIQMTQSPSSLSASVGDRVTITCRASQGISSYLAWYQQKPGKAPKLLIYTAS TLQSGVPSRFSGSGSGTDFTLTISSLQPEDFATYYCQQIWMAPRTFGQGTKV EIK |
| SEQ ID NO: 224 | DNA VL | gacatccagatgacccagtctccgtcctccctgtccgcatcagtgggggacagagtgaccatcacttgtcgggcctcc aaggcatctcgtcatacctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaaatctggatggcccccaggacatttggccagggcactaaggtcgag attaag |
| SEQ ID NO: 188 | Light Chain | DIQMTQSPSSLSASVGDRVTITCRASQGISSYLAWYQQKPGKAPKLLIYTAS TLQSGVPSRFSGSGSGTDFTLTISSLQPEDFATYYCQQIWMAPRTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 225 | DNA Light Chain | gacatccagatgacccagtctccgtcctccctgtccgcatcagtgggggacagagtgaccatcacttgtcgggcctcc aaggcatctcgtcatacctggcctggtatcagcagaaacccggaaaggctccaaagctgctcatctacaccgcctcga ctctgcaatccggagtgccttcccgcttctccggatccggttcgggaaccgacttcaccctcaccattagcagccttcag ccggaagatttcgcgacctactactgccagcaaatctggatggcccccaggacatttggccagggcactaaggtcgag attaagcgtacggtggccgctcccagcgtgttcatcttccccccctcagacgagcagctgaagaagtggacaacgccctgcagagc ggcaacagccaggagagcgtcaccgagcaggacagcaaggactccacctacagcctgagcagcaccctgacccctg agcaaggccgactacgagaagcataaggtgtacgcctgcgaggtgacccaccagggcctgtccagccccgtgacca agagcttcaacaggggcgagtgc |

YY01_LALA

| SEQ ID NO: 226 | HCDR1 (Combined) | GFTFSSYWIS |
| SEQ ID NO: 227 | HCDR2 (Combined) | NIKQSGSETYYVESVKG |
| SEQ ID NO: 228 | HCDR3 (Combined) | SLRRRSTEHAGFDV |

TABLE 2-continued

Exemplary anti-NPR1 antibody sequences

| SEQ ID NO: 229 | HCDR1 (Kabat) | SYWIS |
|---|---|---|
| SEQ ID NO: 227 | HCDR2 (Kabat) | NIKQSGSETYYVESVKG |
| SEQ ID NO: 228 | HCDR3 (Kabat) | SLRRRSTEHAGFDV |
| SEQ ID NO: 32 | HCDR1 (Chothia) | GFTFSSY |
| SEQ ID NO: 230 | HCDR2 (Chothia) | KQSGSE |
| SEQ ID NO: 228 | HCDR3 (Chothia) | SLRRRSTEHAGFDV |
| SEQ ID NO: 34 | HCDR1 (IMGT) | GFTFSSYW |
| SEQ ID NO: 231 | HCDR2 (IMGT) | IKQSGSET |
| SEQ ID NO: 232 | HCDR3 (IMGT) | ARSLRRRSTEHAGFDV |
| SEQ ID NO: 233 | VH | EVQLVESGGGLVQPGGSLRLSCAASGFTFSSYWISWVRQAPGKGLEWVAN IKQSGSETYYVESVKGRFTISRDNAKNSLYLQMNSLRAEDTAVYYCARSLR RRSTEHAGFDVWGQGTLVTVSS |
| SEQ ID NO: 234 | DNA VH | gaagtgcagctggtggaaagcggcggtggcctggtgcagccaggtggtagcctgcgcctgagctgcgccgccagc ggctttacctttagcagctattggattagctgggttcgccaggcccaggcaaaggcctggaatgggtggcgaacatca aacagagcggcagcgagacctactatgtggagagcgtgaaaggccgctttaccattagccgcgataacgccaaaaac agcctgtatctgcaaatgaacagcctgcgggccgaagataccgccgtgtattattgcgcgcgtagcctgcgtcgtcgta gcactgagcacgcaggattcgacgtttggggccagggcacccgtggttactgtctcgagc |
| SEQ ID NO: 235 | Heavy Chain | EVQLVESGGGLVQPGGSLRLSCAASGFTFSSYWISWVRQAPGKGLEWVAN IKQSGSETYYVESVKGRFTISRDNAKNSLYLQMNSLRAEDTAVYYCARSLR RRSTEHAGFDVWGQGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 236 | DNA Heavy Chain | gaagtgcagctggtggaaagcggcggtggcctggtgcagccaggtggtagcctgcgcctgagctgcgccgccagc ggctttacctttagcagctattggattagctgggttcgccaggcccaggcaaaggcctggaatgggtggcgaacatca aacagagcggcagcgagacctactatgtggagagcgtgaaaggccgctttaccattagccgcgataacgccaaaaac agcctgtatctgcaaatgaacagcctgcgggccgaagataccgccgtgtattattgcgcgcgtagcctgcgtcgtcgta gcactgagcacgcaggattcgacgtttggggccagggcacccgtggttactgtctcgagcgcgtccgaccaaaggccc agcgtgttccctctggcccccagcagcaagagcacctctgggtgcgcgaacagccgccctctgggctgcctggtcaaggacta cttccccgagcccgtgaccgtgtcctggaactctggcgccctgaccagcggcgtgcacacctttccagccgtgctcca gagcagcggcctgtacagcctgagcagcgtcgtgaccgtgcccagcagcagcctgggcacccagacctacatctgc aacgtgaaccacaagcccagcaacacaaaggtggacaagcgggtggaacccaagagctgcgacaagacccacac ctgtccccccgccctgcccctgaagcggcgggaggcccctcgctgttcctgttccccccaaagccctaaggacaccct gatgatcagccggacccccgaagtgacctgcgtggtggtggacgtgtcccacgaggaccctgaagtgaagtttaattg gtacgtggacggcgtggaagtgcacaacgccaagaccaagccagaggagaacagtacaacagcacctaccgggt ggtgtccgtgctgaccgtgctgcaccaggactggctgaacggcaaagagtacaagtgcaaggtgtccaacaaggccc tgcctgccccccatcgagaaaaccatcagcaaggccaaagggccaaggcccgagccccaggtgtacaccctgcccc tagccggaagagatgaccaagaaccaggtgtccctgacctgcctcgtgaaggcttctaccccagcgacattgccgt ggaatgggagagcaacggccagcccgagaacaactacaagaccaccccccctgtgctggacagcgacggctcattc ttcctgtacagcaagctgaccgtggacaagagccggtggcagcagggcaacgtgttcagctgctccgtgatgcacga ggcccctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 239 | LCDR3 (Combined) | QQADKFPYT |
| SEQ ID NO: 237 | LCDR1 (Kabat) | RASQGISNYLA |

TABLE 2-continued

Exemplary anti-NPR1 antibody sequences

| SEQ ID NO: 238 | LCDR2 (Kabat) | AASTLQS |
| --- | --- | --- |
| SEQ ID NO: 239 | LCDR3 (Kabat) | QQADKFPYT |
| SEQ ID NO: 240 | LCDR1 (Chothia) | SQGISNY |
| SEQ ID NO: 241 | LCDR2 (Chothia) | AAS |
| SEQ ID NO: 242 | LCDR3 (Chothia) | ADKFPY |
| SEQ ID NO: 243 | LCDR1 (IMGT) | QGISNY |
| SEQ ID NO: 241 | LCDR2 (IMGT) | AAS |
| SEQ ID NO: 239 | LCDR3 (IMGT) | QQADKFPYT |
| SEQ ID NO: 244 | VL | DIQMTQSPSSLSASVGDRVTITCRASQGISNYLAWYQQKPGKVPKLLIYAAS TLQSGVPSRFSGSGSGTDFTLTISSLQPEDVATYYCQQADKFPYTFGQGTKV EIK |
| SEQ ID NO: 245 | DNA VL | gatattcagatgacccagagcccgagcagcctgagcgcaagcgtgggcgatcgcgtgaccattacctgccgcgcca gccagggcattagcaactatctggcctggtatcagcagaaaccgggcaaagtgccgaaactgctgatctatgccgcca gcaccctgcaaagcggcgtgccaagtcgctttagcggcagcggtagcggcaccgatttcaccctgaccattagcagc ctgcaaccggaagacgtggcgacctattattgccagcaggctgacaaattcccgtacaccttcggccagggtaccaaa gtggaaatcaag |
| SEQ ID NO: 246 | Light Chain | DIQMTQSPSSLSASVGDRVTITCRASQGISNYLAWYQQKPGKVPKLLIYAAS TLQSGVPSRFSGSGSGTDFTLTISSLQPEDVATYYCQQADKFPYTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 247 | DNA Light Chain | gatattcagatgacccagagcccgagcagcctgagcgcaagcgtgggcgatcgcgtgaccattacctgccgcgcca gccagggcattagcaactatctggcctggtatcagcagaaaccgggcaaagtgccgaaactgctgatctatgccgcca gcaccctgcaaagcggcgtgccaagtcgctttagcggcagcggtagcggcaccgatttcaccctgaccattagcagc ctgcaaccggaagacgtggcgacctattattgccagcaggctgacaaattcccgtacaccttcggccagggtaccaaa gtggaaatcaagcggaccgtggccgctcccctccgtgttcatcttcccaccagcgacgagcagctgaagtccggcaca gccagcgtcgtgtgcctgctgaacaacttctaccccgcgaggccaaagtgcagtggaaggtggacaacgccctcca gagcggcaacagccaggaaagcgtcaccgagcaggacagcaaggactccacctacagcctgagcagcaccctgac cctgagcaaggccgactacgagaagcacaaggtgtacgcctgcgaagtgacccaccagggcctgtccagcccgtg accaagagcttcaaccggggcgagtgt |

YY02_LALA

| SEQ ID NO: 248 | HCDR1 (Combined) | GFTFSSYSMN |
| --- | --- | --- |
| SEQ ID NO: 249 | HCDR2 (Combined) | SISSSSSYIYYADSVKG |
| SEQ ID NO: 250 | HCDR3 (Combined) | SGYRGVYGFDY |
| SEQ ID NO: 251 | HCDR1 (Kabat) | SYSMN |
| SEQ ID NO: 249 | HCDR2 (Kabat) | SISSSSSYIYYADSVKG |
| SEQ ID NO: 250 | HCDR3 (Kabat) | SGYRGVYGFDY |
| SEQ ID NO: 32 | HCDR1 (Chothia) | GFTFSSY |
| SEQ ID NO: 252 | HCDR2 (Chothia) | SSSSSY |

TABLE 2-continued

Exemplary anti-NPR1 antibody sequences

| SEQ ID NO: 250 | HCDR3 (Chothia) | SGYRGVYGFDY |
|---|---|---|
| SEQ ID NO: 253 | HCDR1 (IMGT) | GFTFSSYS |
| SEQ ID NO: 254 | HCDR2 (IMGT) | ISSSSSYI |
| SEQ ID NO: 255 | HCDR3 (IMGT) | ARSGYRGVYGFDY |
| SEQ ID NO: 256 | VH | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSGY RGVYGFDYWGQGTLVTVSS |
| SEQ ID NO: 257 | DNA VH | gaagtgcagctggtggaaagcggcggtggcctggtgaaaccaggcgtagcctgcgcctgagctgcgccgccagc ggctttacctttagcagctatagcatgaactgggttcgccaggccccaggcaaaggcctggaatgggttagcagcatca gcagcagtagcagctatatctattacgccgatagcgtgaaaggccgctttaccattagccgcgataacgccaaaaacag cctgtatctgcaaatgaacagcctgcgggccgaagataccgccgtgtattattgcgcgcgaagcggatatcgtggagtt tacggatttgattattgggccagggcaccctggttactgtctcgagc |
| SEQ ID NO: 258 | Heavy Chain | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSGY RGVYGFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCDKTHTCPPCPAPEAAGGPSVFLFPPKPKDTL MISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| SEQ ID NO: 259 | DNA Heavy Chain | gaagtgcagctggtggaaagcggcggtggcctggtgaaaccaggcgtagcctgcgcctgagctgcgccgccagc ggctttacctttagcagctatagcatgaactgggttcgccaggccccaggcaaaggcctggaatgggttagcagcatca gcagcagtagcagctatatctattacgccgatagcgtgaaaggccgctttaccattagccgcgataacgccaaaaacag cctgtatctgcaaatgaacagcctgcgggccgaagataccgccgtgtattattgcgcgcgaagcggatatcgtggagtt tacggatttgattattgggccagggcaccctggttactgtctcgagcgcgtcgaccaaaggcccagcgtgttccctct ggcccccagcagcaagagcacctctggcgcaacagcgccctgggctgcctggtcaaggactacttccccgagccc gtgaccgtgtcctggaactctggcgccctgaccagcggcgtgcacacctttccagccgtgctccagagcagcggcctg tacagcctgagcagcgtcgtgaccgtgccccagcagcagcctgggcacccagacctacatctgcaacgtgaaccacaa gcccagcaacacaaaggtggacaagcgggtggaacccaagagctgcgacaagacccacacctgtccccctgccct gcccctgaagcggcggaggccctccgtgttcctgttcccccaaagcctaaggacaccctgatgatcagccgac ccccgaagtgacctgcgtggtggtggacgtgtcccacgaggaccctgaagtgaagtttaattggtacgtggacggcgt ggaagtgcacaacgccaagacccagagaggaacagtacaacgccacctaccgggtggtgtccgtgctgacc gtgctgcaccaggactggctgaacggcaaagagtacaagtgcaaggtgtccaacaaggcctgcctgccccatcga gaaaaccatcagcaaggccaaaggccagccccgcgagccccaggtgtacacactgcccccctagccgggaagagat gaccaagaaccaggtgtccctgacctgctcgtgaagggcttctaccccagcgacattgccgtggaatgggagagca acggccagcccgagaacaactacaagaccaccccccctgtgctggacagcgacggctcattcttcctgtacagcaag ctgaccgtggacaagagccggtggcagcagggcaacgtgttcagctgctccgtgatgcacgaggcctgcacaacc actacacccagaagtccctgagcctgagccccggcaag |
| SEQ ID NO: 260 | LCDR1 (Combined) | RASQGISSWLA |
| SEQ ID NO: 261 | LCDR2 (Combined) | AASSLQS |
| SEQ ID NO: 262 | LCDR3 (Combined) | QQYYHSPLT |
| SEQ ID NO: 260 | LCDR1 (Kabat) | RASQGISSWLA |
| SEQ ID NO: 261 | LCDR2 (Kabat) | AASSLQS |
| SEQ ID NO: 262 | LCDR3 (Kabat) | QQYYHSPLT |
| SEQ ID NO: 263 | LCDR1 (Chothia) | SQGISSW |
| SEQ ID NO: 241 | LCDR2 (Chothia) | AAS |
| SEQ ID NO: 264 | LCDR3 (Chothia) | YYHSPL |

TABLE 2-continued

Exemplary anti-NPR1 antibody sequences

| SEQ ID NO: 265 | LCDR1 (IMGT) | QGISSW |
|---|---|---|
| SEQ ID NO: 241 | LCDR2 (IMGT) | AAS |
| SEQ ID NO: 262 | LCDR3 (IMGT) | QQYHSPLT |
| SEQ ID NO: 266 | VL | DIQMTQSPSSVSASVGDRVTITCRASQGISSWLAWYQQKPGKAPKLLIYAA SSLQSGVPSRFSGSGSGTDFTLTISSLQPEDFATYYCQQYYHSPLTFGQGTK VEIK |
| SEQ ID NO: 267 | DNA VL | gatattcagatgacccagagcccgagcagcgttagcgccagcgtgggcgatcgcgtgaccattacctgccgcgccag tcagggcattagcagctggctggcctggtatcagcagaaacccggcaaagccccgaaactgctgatctatgccgcca gcagcctgcaaagcggcgtgccaagtcgctttagcggcagcggtagcggcaccgatttcaccctgaccattagcagtc tgcaaccggaagactttgccacctattattgccagcagtactaccattctccgctgaccttcggccagggtaccaaagtg gaaatcaag |
| SEQ ID NO: 268 | Light Chain | DIQMTQSPSSVSASVGDRVTITCRASQGISSWLAWYQQKPGKAPKLLIYAA SSLQSGVPSRFSGSGSGTDFTLTISSLQPEDFATYYCQQYYHSPLTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 269 | DNA Light Chain | gatattcagatgacccagagcccgagcagcgttagcgccagcgtgggcgatcgcgtgaccattacctgccgcgccag tcagggcattagcagctggctggcctggtatcagcagaaacccggcaaagccccgaaactgctgatctatgccgcca gcagcctgcaaagcggcgtgccaagtcgctttagcggcagcggtagcggcaccgatttcaccctgaccattagcagtc tgcaaccggaagactttgccacctattattgccagcagtactaccattctccgctgaccttcggccagggtaccaaagtg gaaatcaagcggaccgtggccgctcccctcgtgttcatcttcccaccagcgacgagcagctgaagtccggcacagc cagcgtcgtgtgcctgctgaacaacttctaccccgcgaggccaaagtgcagtggaaggtggacaacgccctccaga gcggcaacagccaggaaagcgtcaccgagcaggacagcaaggactccacctacagcctgagcagcaccctgaccc tgagcaaggccgactacgagaagcacaaggtgtacgcctgcgaagtgacccaccagggcctgtccagcccgtgac caagagcttcaaccggggcgagtgt |

YY03_ LALA

| SEQ ID NO: 270 | HCDR1 (Combined) | GFTFSSYAIS |
|---|---|---|
| SEQ ID NO: 271 | HCDR2 (Combined) | AISGSGGSTYYAESVKG |
| SEQ ID NO: 272 | HCDR3 (Combined) | ESGYVYYLKFDY |
| SEQ ID NO: 273 | HCDR1 (Kabat) | SYAIS |
| SEQ ID NO: 271 | HCDR2 (Kabat) | AISGSGGSTYYAESVKG |
| SEQ ID NO: 272 | HCDR3 (Kabat) | ESGYVYYLKFDY |
| SEQ ID NO: 32 | HCDR1 (Chothia) | GFTFSSY |
| SEQ ID NO: 274 | HCDR2 (Chothia) | SGSGGS |
| SEQ ID NO: 272 | HCDR3 (Chothia) | ESGYVYYLKFDY |
| SEQ ID NO: 275 | HCDR1 (IMGT) | GFTFSSYA |
| SEQ ID NO: 276 | HCDR2 (IMGT) | ISGSGGST |
| SEQ ID NO: 277 | HCDR3 (IMGT) | ARESGYVYYLKFDY |
| SEQ ID NO: 278 | VH | EVQLLESGGGLVQPGGSLRLSCAASGFTFSSYAISWVRQAPGKGLEWVSAI SGSGGSTYYAESVKGRFTISRDNSKNTLYLQMNSLRAEDTAVYYCARESG YVYYLKFDYWGQGTLVTVSS |

TABLE 2-continued

Exemplary anti-NPR1 antibody sequences

| SEQ ID NO: 279 | DNA VH | gaagtgcagctgctggaaagcggtggcggtctggtgcagccaggtggtagcctgcgcctgagctgtgccgcaagcg gctttacctttagcagctatgccattagctgggtgcgccaagcaccaggcaaaggcctggaatgggtgagcgccattag cggcagcggtggcagcacctattatgccgagagcgtgaaaggtcgctttaccattagtcgcgataacagcaaaaacac cctgtatctgcaaatgaacagcctgcgggcagaagataccgcagtttattattgcgcgcgtgagagcggatacgtttact atctgaaattcgattattgggccagggcacccctggttactgtctcgagc |
|---|---|---|
| SEQ ID NO: 280 | Heavy Chain | EVQLLESGGGLVQPGGSLRLSCAASGFTFSSYAISWVRQAPGKGLEWVSAI SGSGGSTYYAESVKGRFTISRDNSKNTLYLQMNSLRAEDTAVYYCARESG YVYYLKFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 281 | DNA Heavy Chain | gaagtgcagctgctggaaagcggtggcggtctggtgcagccaggtggtagcctgcgcctgagctgtgccgcaagcg gctttacctttagcagctatgccattagctgggtgcgccaagcaccaggcaaaggcctggaatgggtgagcgccattag cggcagcggtggcagcacctattatgccgagagcgtgaaaggtcgctttaccattagtcgcgataacagcaaaaacac cctgtatctgcaaatgaacagcctgcgggcagaagataccgcagtttattattgcgcgcgtgagagcggatacgtttact atctgaaattcgattattgggccagggcacccctggttactgtctcgagcgcgtcgaccaaaggcccagcgtgttccct ctggcccccagcagcaagagcacctctggcggaacagccgccctgggctgcctggtcaaggactacttccccgagc ccgtgacctgtgtcctggaactctggcgccctgaccagcggcgtgcacaccttccagcccgtgctgcagagcagcggc ctgtacagcctgagcagcgtcgtgaccgtgccagcagcgcctgggcacccagacctacatctgcaacgtgaacca caagcccagcaacacaaaggtggacaagcggtggaacccaaagagctgcgacaagacccacacctgtcccccctg ccctgcccctgaagcggaggaggccctcgtgttcctgttccccaaagcctaaggacaccctgatgatcagccg gaccccgaagtgacctgcgtggtggtggacgtgtcccacgaggaccctgaagtgaagttcaattggtacgtggacgg cgtggaagtgcacaacgccaagaccaagcccagagaggaacagtacaacagcaccctaccgggtggtcagcgtgctg accgtgctgcaccaggactggctgaacggcaaagagtacaagtgcaaggtgtccaacaaggcctgcctgcccccat cgagaaaaccatcagcaaggccaaggccagccccgcgagccccaggtgtacacactgcccctagccgggaaga gatgaccaagaaccaggtgtccctgacctgcctcgtgaagggcttctaccccagcgacattgccgtggaatgggagag caacggccagcccgagaacaactacaagaccacccccctgtgctggacagcgacggctcattcttcctgtacagca agctgaccgtggacaagagccggtggcagcagggcaacgtgttcagctgctccgtgatgcacgaggccctgcacaa ccactacacccagaagtcccctgagcctgagccccggcaag |
| SEQ ID NO: 282 | LCDR1 (Combined) | RASQSISSYLN |
| SEQ ID NO: 261 | LCDR2 (Combined) | AASSLQS |
| SEQ ID NO: 283 | LCDR3 (Combined) | QQHVRVPIT |
| SEQ ID NO: 282 | LCDR1 (Kabat) | RASQSISSYLN |
| SEQ ID NO: 261 | LCDR2 (Kabat) | AASSLQS |
| SEQ ID NO: 283 | LCDR3 (Kabat) | QQHVRVPIT |
| SEQ ID NO: 284 | LCDR1 (Chothia) | SQSISSY |
| SEQ ID NO: 241 | LCDR2 (Chothia) | AAS |
| SEQ ID NO: 285 | LCDR3 (Chothia) | HVRVPI |
| SEQ ID NO: 286 | LCDR1 (IMGT) | QSISSY |
| SEQ ID NO: 241 | LCDR2 (IMGT) | AAS |
| SEQ ID NO: 283 | LCDR3 (IMGT) | QQHVRVPIT |
| SEQ ID NO: 287 | VL | DIQMTQSPSSLSASVGDRVTITCRASQSISSYLNWYQQKPGKAPKLLIYAAS SLQSGVPSRFSGSGSGTDFTLTISSLQPEDFATYYCQQHVRVPITFGQGTKVE IK |
| SEQ ID NO: 288 | DNA VL | gatattcagatgacccagagcccgagcagcctgagcgccagcgtgggtgatcgcgtgaccattacctgtcgcgcaag ccagagcattagcagctatctgaactggtatcagcagaaaccaggcaaagcccccaaaactgctgatttatgccgcaag cagcctgcaaagcggtgtgccgagccgctttagcggcagcggtagcggcaccgatttcaccctgaccattagtagcct |

TABLE 2-continued

Exemplary anti-NPR1 antibody sequences

| | | |
|---|---|---|
| | | gcaaccggaagactttgccacctattattgccagcagcatgttcgtgttccgatcaccttcggccagggtaccaaagtgg<br>aaatcaag |
| SEQ ID<br>NO: 289 | Light<br>Chain | DIQMTQSPSSLSASVGDRVTITCRASQSISSYLNWYQQKPGKAPKLLIYAAS<br>SLQSGVPSRFSGSGSGTDFTLTISSLQPEDFATYYCQQHVRVPITFGQGTKVE<br>IKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTK<br>SFNRGEC |
| SEQ ID<br>NO: 290 | DNA<br>Light<br>Chain | gatattcagatgacccagagcccgagcagcctgagcgccagcgtgggtgatcgcgtgaccattacctgtcgcgcaag<br>ccagagcattagcagctatctgaactggtatcagcagaaaccaggcaaagcccaaaactgctgatttatgccgcaag<br>cagcctgcaaagcggtgtgccgagccgctttagcggcagcggtagcggcaccgattttaccctgaccattagtagcct<br>gcaaccggaagactttgccacctattattgccagcagcatgttcgtgttccgatcaccttcggccagggtaccaaagtgg<br>aaatcaagcggaccgtggccgctcccctcgtgttcatcttcccaccagcgacgagcagctgaagtccggcacagcc<br>agcgtcgtgtgcctgctgaacaacttctacccccgcgaggccaaagtgcagtggaaggtggacaacgccctccagag<br>cggcaacagccaggaaagcgtcaccgagcaggacagcaaggactccacctacagcctgagcagcaccctgaccct<br>gagcaaggccgactacgagaagcacaaggtgtacgcctgcgaagtgacccaccagggcctgtccagccccgtgac<br>caagagcttcaaccggggcgagtgt |
| YY04_<br>LALA | | |
| SEQ ID<br>NO: 291 | HCDR1<br>(Combined) | GFTFSNYWIS |
| SEQ ID<br>NO: 292 | HCDR2<br>(Combined) | RIKSKTYGGTTDYAEPVKG |
| SEQ ID<br>NO: 293 | HCDR3<br>(Combined) | EKYSIRARGHGDYGFDV |
| SEQ ID<br>NO: 294 | HCDR1<br>(Kabat) | NYWIS |
| SEQ ID<br>NO: 292 | HCDR2<br>(Kabat) | RIKSKTYGGTTDYAEPVKG |
| SEQ ID<br>NO: 293 | HCDR3<br>(Kabat) | EKYSIRARGHGDYGFDV |
| SEQ ID<br>NO: 295 | HCDR1<br>(Chothia) | GFTFSNY |
| SEQ ID<br>NO: 296 | HCDR2<br>(Chothia) | KSKTYGGT |
| SEQ ID<br>NO: 293 | HCDR3<br>(Chothia) | EKYSIRARGHGDYGFDV |
| SEQ ID<br>NO: 297 | HCDR1<br>(IMGT) | GFTFSNYW |
| SEQ ID<br>NO: 298 | HCDR2<br>(IMGT) | IKSKTYGGTT |
| SEQ ID<br>NO: 299 | HCDR3<br>(IMGT) | AREKYSIRARGHGDYGFDV |
| SEQ ID<br>NO: 300 | VH | EVQLVESGGGLVKPGGSLRLSCAASGFTFSNYWISWVRQAPGKGLEWVGR<br>IKSKTYGGTTDYAEPVKGRFTISRDDSKNTLYLQMNSLKTEDTAVYYCARE<br>KYSIRARGHGDYGFDVWGQGTLVTVSS |
| SEQ ID<br>NO: 301 | DNA VH | gaagtgcagctggtggaaagcggcggtggcctggtgaaaccaggcggtagcctgcgcctgagctgcgccgccagc<br>ggctttacctttagcaactattggattagctgggttcgccaggcccaggcaaaggcctggaatgggttggccgcatca<br>aaagcaaaacctatggcggcaccaccgattatgccgagccagtgaaaggccgcttttaccattagccgcgacgatagc<br>aaaaacacctgtacctgcaaatgaacagcctgaaaaccgaagataccgccgtgtattattgcgcgcgtgagaaatatt<br>ccatccgtgcacgtggtcacggagactacggatttgatgtgtggggccagggcaccctggttactgtctcgagc |
| SEQ ID<br>NO: 302 | Heavy<br>Chain | EVQLVESGGGLVKPGGSLRLSCAASGFTFSNYWISWVRQAPGKGLEWVGR<br>IKSKTYGGTTDYAEPVKGRFTISRDDSKNTLYLQMNSLKTEDTAVYYCARE<br>KYSIRARGHGDYGFDVWGQGTLVTVSSASTKGPSVFPLAPSSKSTSGGTAA<br>LGCLVKDYFPEPVTVSWNSGALTSGVHTFPAVLQSSGLYSLSSVVTVPSSSL<br>GTQTYICNVNHKPSNTKVDKRVEPKSCDKTHTCPPCPAPEAAGGPSVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |

TABLE 2-continued

Exemplary anti-NPR1 antibody sequences

| SEQ ID NO: 303 | DNA Heavy Chain | gaagtgcagctggtggaaagcggcggtggcctggtgaaaccaggcggtagcctgcgcctgagctgcgccgccagc
ggctttacctttagcaactattggattagctgggttcgccaggcccaggcaaaggcctggaatgggttggccgcatca
aaagcaaaacctatggcggcaccaccgattatgccgagccagtgaaaggccgctttaccattagccgcgacgatagc
aaaaacaccctgtacctgcaaatgaacagcctgaaaaccgaagataccgccgtgtattattgcgcgcgtgagaaatatt
ccatccgtgcacgtggtcacggagactacggatttgatgtgtggggccagggcaccctggttactgtctcgagcgcgtc
gaccaaaggcccagcgtgttccctctggccccagcgcagcaagagcacctctggcggaacagccgccctgggctgc
ctggtcaaggactactcccccgagcccgtgaccgtgtcctggaactctggcgccctgaccagcggcgtgcacacctttc
cagccgtgctccagagcagcggcctgtacagcctgagcagcgtcgtgaccgtgcccagcagcagcctgggcaccca
gacctacatctgcaacgtgaaccacaagcccagcaacacaaaggtggacaagcgggtggaacccaagagctgcga
caagacccacacctgtcccccctgccctgcccctgaagcggcgggaggcccctccgtgttcctgttcccccaaagcc
taaggacacccctgatgatcagccggacccccgaagtgacctgcgtggtggtggacgtgtcccacgaggaccctgaag
tgaagtttaattggtacgtggacggcgtgaagtgcacaacgccaagaccaagcccagagaggaacagtacaacagc
acctaccgggtggtgtccgtgctgaccgtgctgcaccaggactggctgaacggcaaagagtacaagtgcaaggtgtc
caacaaggccctgcctgcccccatcgagaaaaccatcagcaaggccaaaggccaaagccccgcgagcccaggtgta
cacactgcccctagccggaagagatgaccaagaaccaggtgtccctgacctgcctcgtgaaggcttctacccca
gcgacattgccgtggaatgggagagcaacggccagcccgagaacaactacaagaccacccccctgtgctggacag
cgacggctcattcttcctgtacagcaagctgaccgtggacaagagccggtggcagcagggcaacgtgttcagctgctc
cgtgatgcacgaggccctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 304 | LCDR3 (Combined) | QQGYHAPFT |
| SEQ ID NO: 237 | LCDR1 (Kabat) | RASQGISNYLA |
| SEQ ID NO: 238 | LCDR2 (Kabat) | AASTLQS |
| SEQ ID NO: 304 | LCDR3 (Kabat) | QQGYHAPFT |
| SEQ ID NO: 240 | LCDR1 (Chothia) | SQGISNY |
| SEQ ID NO: 241 | LCDR2 (Chothia) | AAS |
| SEQ ID NO: 305 | LCDR3 (Chothia) | GYHAPF |
| SEQ ID NO: 243 | LCDR1 (IMGT) | QGISNY |
| SEQ ID NO: 241 | LCDR2 (IMGT) | AAS |
| SEQ ID NO: 304 | LCDR3 (IMGT) | QQGYHAPFT |
| SEQ ID NO: 306 | VL | DIQMTQSPSSLSASVGDRVTITCRASQGISNYLAWYQQKPGKVPKLLIYAAS
TLQSGVPSRFSGSGSGTDFTLTISSLQPEDVATYYCQQGYHAPFTFGQGTKV
EIK |
| SEQ ID NO: 307 | DNA VL | gatattcagatgacccagagcccgagcagcctgagcgcaagcgtgggcgatcgcgtgaccattacctgccgcgcca
gccaggggcattagcaactatctggcctggtatcagcagaaaccgggcaaagtgccgaaactgctgatctatgccgcca
gcaccctgcaaagcggcgtgccaagtcgctttagcggcagcggtagcggcaccgatttcaccctgaccattagcagc
ctgcaaccggaagacgtggcgacctattattgccagcaggggttaccatgctccgttcaccttcggccagggtaccaaag
tggaaatcaag |
| SEQ ID NO: 308 | Light Chain | DIQMTQSPSSLSASVGDRVTITCRASQGISNYLAWYQQKPGKVPKLLIYAAS
TLQSGVPSRFSGSGSGTDFTLTISSLQPEDVATYYCQQGYHAPFTFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGEC |
| SEQ ID NO: 309 | DNA Light Chain | gatattcagatgacccagagcccgagcagcctgagcgcaagcgtgggcgatcgcgtgaccattacctgccgcgcca
gccaggggcattagcaactatctggcctggtatcagcagaaaccgggcaaagtgccgaaactgctgatctatgccgcca
gcaccctgcaaagcggcgtgccaagtcgctttagcggcagcggtagcggcaccgatttcaccctgaccattagcagc
ctgcaaccggaagacgtggcgacctattattgccagcaggggttaccatgctccgttcaccttcggccagggtaccaaag
tggaaatcaagcggaccgtggccgctcccccgtgttcatcttcccaccagcgacgagcagctgaagtccggcacag
ccagcgtcgtgtgcctgctgaacaacttctaccccgcgaggccaaagtgcagtggaaggtggacaacgcccctgcag |

TABLE 2-continued

Exemplary anti-NPR1 antibody sequences agcggcaacagccaggaaagcgtcaccgagcaggacagcaaggactccacctacagcctgagcagcaccctgacc
ctgagcaaggccgactacgagaagcacaaggtgtacgcctgcgaagtgacccaccagggcctgtccagccccgtga
ccaagagcttcaaccggggcgagtgt

YY05_LALA

| SEQ ID NO: 310 | HCDR1 (Combined) | GYSFTSYWIS |
| SEQ ID NO: 311 | HCDR2 (Combined) | IIYPGTSYTRYSPSFQG |
| SEQ ID NO: 312 | HCDR3 (Combined) | GAVAGQLGFDH |
| SEQ ID NO: 229 | HCDR1 (Kabat) | SYWIS |
| SEQ ID NO: 311 | HCDR2 (Kabat) | IIYPGTSYTRYSPSFQG |
| SEQ ID NO: 312 | HCDR3 (Kabat) | GAVAGQLGFDH |
| SEQ ID NO: 80 | HCDR1 (Chothia) | GYSFTSY |
| SEQ ID NO: 313 | HCDR2 (Chothia) | YPGTSY |
| SEQ ID NO: 312 | HCDR3 (Chothia) | GAVAGQLGFDH |
| SEQ ID NO: 82 | HCDR1 (IMGT) | GYSFTSYW |
| SEQ ID NO: 314 | HCDR2 (IMGT) | IYPGTSYT |
| SEQ ID NO: 315 | HCDR3 (IMGT) | ARGAVAGQLGFDH |

SEQ ID NO: 316  VH

EVQLVQSGAEVKKPGESLKISCKGSGYSFTSYWISWVRQMPGKGLEWMGII
YPGTSYTRYSPSFQGQVTISADKSISTAYLQWSSLKASDTAMYYCARGAVA
GQLGFDHWGQGTLVTVSS

SEQ ID NO: 317  DNA VH gaagtgcagctggtgcagagcggtgccgaagtgaaaaaaccgggcgaaagcctgaaaatcagctgcaaaggcagc
ggctatagctttaccagctattggattagctgggttcgccagatgccgggcaaaggcctggaatggatgggcattatcta
tccgggcaccagctatacccgctatagcccgagctttcagggccaggttacaattagcgccgacaaaagcatcagcac
cgcctatctgcaatggagcagcctgaaagccagcgataccgccatgtattattgcgcgcgtggtgcagttgcaggaca
actgggatttgatcactggggccagggcaccctggttactgtctcgagc SEQ ID NO: 318  Heavy Chain EVQLVQSGAEVKKPGESLKISCKGSGYSFTSYWISWVRQMPGKGLEWMGII
YPGTSYTRYSPSFQGQVTISADKSISTAYLQWSSLKASDTAMYYCARGAVA
GQLGFDHWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNV
NHKPSNTKVDKRVEPKSCDKTHTCPPCPAPEAAGGPSVFLFPPKPKDTLMIS
RTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID NO: 319  DNA Heavy Chain gaagtgcagctggtgcagagcggtgccgaagtgaaaaaaccgggcgaaagcctgaaaatcagctgcaaaggcagc
ggctatagctttaccagctattggattagctgggttcgccagatgccgggcaaaggcctggaatggatgggcattatcta
tccgggcaccagctatacccgctatagcccgagctttcagggccaggttacaattagcgccgacaaaagcatcagcac
cgcctatctgcaatggagcagcctgaaagccagcgataccgccatgtattattgcgcgcgtggtgcagttgcaggaca
actgggatttgatcactggggccagggcaccctggttactgtctcgagcgcgtcgaccaaaggcccagcgtgttccct
ctggccccagcagcaagagcacctctggcggaacagccgccctgggctgcctggtcaaggactacttcccgagc
ccgtgaccgtgtcctggaactctggcgccctgaccagcggcgtgcacacctttccagccgtgctgcagagcagcggc
ctgtacagcctgagcagcgtcgtgaccgtgcccagcagcagcctgggcacccagacctacatctgcaacgtgaacca
caagcccagcaacacaaaggtggacaaggggtggaacccaagagctgcgacaagacccacacctgtcccctg
ccctgccctgaagcggagggcccctcctgtcttcctgttccccccaaagcctaaggacaccctcatgatcagccg
gacccccgaagtgacctgcgtggtggtggacgtgtcccacgaggaccctgaagtgaagtttaattggtacgtggacgg
cgtggaagtgcacaacgccaagaccaagcccagagaggaacagtacaacagcacctaccgggtggtgtccgtgctg
accgtgctgcaccaggactggctgaacggcaaagagtacaagtgcaaggtgtccaacaaggcctgcctgccccat
cgagaaaaccatcagcaaggccaaaggccagccccgcgagccccaggtgtacacactgccccctagccgggaaga
gatgaccaagaaccaggtgtccctgacctgcctcgtgaagggcttctaccccagcgacattgccgtggaatgggagag TABLE 2-continued Exemplary anti-NPR1 antibody sequences

```
caacggccagcccgagaacaactacaagaccaccccctgtgctggacagcgacggctcattcttcctgtacagca
agctgaccgtggacaagagccggtggcagcagggcaacgtgttcagctgctccgtgatgcacgaggccctgcacaa
ccactacacccagaagtccctgagcctgagccccggcaag
```

| | | |
|---|---|---|
| SEQ ID NO: 320 | LCDR1 (Combined) | TGSSSNIGAGYDVH |
| SEQ ID NO: 321 | LCDR2 (Combined) | GNSNRPS |
| SEQ ID NO: 322 | LCDR3 (Combined) | QSYYTSSHGPV |
| SEQ ID NO: 320 | LCDR1 (Kabat) | TGSSSNIGAGYDVH |
| SEQ ID NO: 321 | LCDR2 (Kabat) | GNSNRPS |
| SEQ ID NO: 322 | LCDR3 (Kabat) | QSYYTSSHGPV |
| SEQ ID NO: 323 | LCDR1 (Chothia) | SSSNIGAGYD |
| SEQ ID NO: 324 | LCDR2 (Chothia) | GNS |
| SEQ ID NO: 325 | LCDR3 (Chothia) | YYTSSHGP |
| SEQ ID NO: 326 | LCDR1 (IMGT) | SSNIGAGYD |
| SEQ ID NO: 324 | LCDR2 (IMGT) | GNS |
| SEQ ID NO: 322 | LCDR3 (IMGT) | QSYYTSSHGPV |
| SEQ ID NO: 327 | VL | QSVLTQPPSVSGAPGQRVTISCTGSSSNIGAGYDVHWYQQLPGTAPKLLIYG<br>NSNRPSGVPDRFSGSKSGTSASLAITGLQAEDEADYYCQSYYTSSHGPVFG<br>GGTKLTVL |
| SEQ ID NO: 328 | DNA VL | cagagcgtgctgacccagccaccaagcgtgagcggtgcaccaggtcagcgcgtgaccattagctgcaccggcagca<br>gcagcaacattggcgcaggctatgatgtgcattggtatcagcagctgccaggcaccgcaccgaaactgctgatttatgg<br>caacagcaatcgcccaagcggtgtgccggatcgctttagcggcagcaaaagcggcaccagcgccagcctggcgatt<br>accggtctgcaagccgaagacgaagccgattattactgccagtcttactacacttcttctcatggtccggtgtttggcggc<br>ggtaccaagctgaccgtgctg |
| SEQ ID NO: 329 | Light Chain | QSVLTQPPSVSGAPGQRVTISCTGSSSNIGAGYDVHWYQQLPGTAPKLLIYG<br>NSNRPSGVPDRFSGSKSGTSASLAITGLQAEDEADYYCQSYYTSSHGPVFG<br>GGTKLTVLGQPKAAPSVTLFPPSSEELQANKATLVCLISDFYPGAVTVAWK<br>ADSSPVKAGVETTTPSKQSNNKYAASSYLSLTPEQWKSHRSYSCQVTHEGS<br>TVEKTVAPTECS |
| SEQ ID NO: 330 | DNA Light Chain | cagagcgtgctgacccagccaccaagcgtgagcggtgcaccaggtcagcgcgtgaccattagctgcaccggcagca<br>gcagcaacattggcgcaggctatgatgtgcattggtatcagcagctgccaggcaccgcaccgaaactgctgatttatgg<br>caacagcaatcgcccaagcggtgtgccggatcgctttagcggcagcaaaagcggcaccagcgccagcctggcgatt<br>accggtctgcaagccgaagacgaagccgattattactgccagtcttactacacttcttctcatggtccggtgtttggcggc<br>ggtaccaagctgaccgtgctgggcagccaaagccgcccctagcgtgaccctgttccccccaagcagcgaggaac<br>tccaggccaacaaggccaccctcgtgtgcctgatcagcgacttctacccggcgccgtgaccgtggcctggaaggcc<br>gatagcagccctgtgaaggccggcgtggaaaccaccaccccagcaagcagagcaacaacaaatacgccgccagc<br>agctacctgagcctgaccccgagcagtggaagtcccacagatcctacagctgccaggtcacacacgagggcagca<br>ccgtggaaaagaccgtggccccaccgagtgcagc |

YY06_LALA

| | | |
|---|---|---|
| SEQ ID NO: 270 | HCDR1 (Combined) | GFTFSSYAIS |
| SEQ ID NO: 271 | HCDR2 (Combined) | AISGSGGSTYYAESVKG |
| SEQ ID NO: 331 | HCDR3 (Combined) | PYLGDRRSYGFDH |

TABLE 2-continued

Exemplary anti-NPR1 antibody sequences

| SEQ ID NO: 273 | HCDR1 (Kabat) | SYAIS |
|---|---|---|
| SEQ ID NO: 271 | HCDR2 (Kabat) | AISGSGGSTYYAESVKG |
| SEQ ID NO: 331 | HCDR3 (Kabat) | PYLGDRRSYGFDH |
| SEQ ID NO: 32 | HCDR1 (Chothia) | GFTFSSY |
| SEQ ID NO: 274 | HCDR2 (Chothia) | SGSGGS |
| SEQ ID NO: 331 | HCDR3 (Chothia) | PYLGDRRSYGFDH |
| SEQ ID NO: 275 | HCDR1 (IMGT) | GFTFSSYA |
| SEQ ID NO: 276 | HCDR2 (IMGT) | ISGSGGST |
| SEQ ID NO: 332 | HCDR3 (IMGT) | ARPYLGDRRSYGFDH |
| SEQ ID NO: 333 | VH | EVQLLESGGGLVQPGGSLRLSCAASGFTFSSYAISWVRQAPGKGLEWVSAI SGSGGSTYYAESVKGRFTISRDNSKNTLYLQMNSLRAEDTAVYYCARPYL GDRRSYGFDHWGQGTLVTVSS |
| SEQ ID NO: 334 | DNA VH | gaagtgcagctgctggaaagcggtggcggtctggtgcagccaggtggtagcctgcgcctgagctgtgccgcaagcg gcttttacctttagcagctatgccattagctgggtgcgccaagcaccaggcaaaggcctggaatgggtgagcgccattag cggcagcggtggcagcacctattatgccgagagcgtgaaaggtcgctttaccattagtcgcgataacagcaaaaacac cctgtatctgcaaatgaacagcctgcgggcagaagataccgcagtttattattgcgcgcgaccttatctgggtgaccgtc gtagctatggtttcgaccactggggccagggcaccctggttactgtctcgagc |
| SEQ ID NO: 335 | Heavy Chain | EVQLLESGGGLVQPGGSLRLSCAASGFTFSSYAISWVRQAPGKGLEWVSAI SGSGGSTYYAESVKGRFTISRDNSKNTLYLQMNSLRAEDTAVYYCARPYL GDRRSYGFDHWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 336 | DNA Heavy Chain | gaagtgcagctgctggaaagcggtggcggtctggtgcagccaggtggtagcctgcgcctgagctgtgccgcaagcg gcttttacctttagcagctatgccattagctgggtgcgccaagcaccaggcaaaggcctggaatgggtgagcgccattag cggcagcggtggcagcacctattatgccgagagcgtgaaaggtcgctttaccattagtcgcgataacagcaaaaacac cctgtatctgcaaatgaacagcctgcgggcagaagataccgcagtttattattgcgcgcgaccttatctgggtgaccgtc gtagctatggtttcgaccactggggccagggcaccctggttactgtctcgagcgcgtcgaccaaaggcccagcgtgtt cctctggccccctgcagcagcaagacacctctggcggacagcgccctgggctgcctggtcaaggactacttcccg agcccgtgaccgtgtcctggaactctggcgccctgaccagcggcgtgcacacctttccagccgtgctgcagagcagc ggcctgtacagcctgagcagcgtcgtgaccgtgccccagcagcagcctgggcacccagacctacatctgcaacgtgaa ccacaagcccagcaacacaaaggtggacaagcgggtggaacccaagagctgcgacaagacccacacctgtccccc ctgccctgccccgtgaagcggcggaggcccctccgtgttcctgttccccccaaagcctaaggacacctgatgatcag ccggacccccgaagtgacctgcgtggtggtggacgtgtcccacgaggaccctgaagtgaagtttaattggtacgtgga cggcgtggaagtgcacaacgccaagaccaagcccagagaggaacagtacaacagcacctaccggggtggtgtccgt gctgaccgtgctgcaccaggactggctgaacggcaaagagtacaagtgcaaggtgtccaacaaggccctgcctgcc ccatcgagaaaaccatcagcaaggccaaaggccagccccgcgagcccaggtgtacaccctgccccctagccggg aagagatgaccaagaaccaggtgtccctgacctgcctcgtgaaggcttctacccagcgacattgccgtggaatggg agagcaacggccagcccgagaacaactacaagaccacccccctgtgctggacagcgacggctcattcttcctgtac agcaagctgaccgtggacaagagccggtggcagcagggcaacgtgttcagctgctccgtgatgcacgaggccctgc acaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |

TABLE 2-continued

Exemplary anti-NPR1 antibody sequences

| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVL |
| SEQ ID NO: 345 | DNA VL | cagagcgccctgacccagccagccagcgttagcggtagcccaggccagagcattaccattagctgcaccggcacca gcagcgacgtgggcagctataaacctggttagctggtatcagcagcatccgggcaaagcccccgaaactgatgatctatg aaggcagcaaacgcccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctg |
| SEQ ID NO: 346 | Light Chain | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 347 | DNA Light Chain | cagagcgccctgacccagccagccagcgttagcggtagcccaggccagagcattaccattagctgcaccggcacca gcagcgacgtgggcagctataaacctggttagctggtatcagcagcatccgggcaaagcccccgaaactgatgatctatg aaggcagcaaacgcccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctgggcagcccaaaagccgcccctagcgtgaccctgttcccccccaagcagcgaggaac tccaggccaacaaggccaccctcgtgtgcctgatcagcgacttctaccctggcgccgtgaccgtggcctggaaggcc gatagcagccctgtgaaggccggcgtggaaaccaccacccccagcaagcagagcaacaacaaatacgccgccagc agctacctgagcctgacccccgagcagtgaaagtcccacagatcctacagctgccaggtcacacacgagggcagca ccgtggaaaagaccgtggcccccaccgagtgcagc |

YY07_LALA

| SEQ ID NO: 310 | HCDR1 (Combined) | GYSFTSYWIS |
| SEQ ID NO: 311 | HCDR2 (Combined) | IIYPGTSYTRYSPSFQG |
| SEQ ID NO: 348 | HCDR3 (Combined) | GSLPGLLGFDH |
| SEQ ID NO: 229 | HCDR1 (Kabat) | SYWIS |
| SEQ ID NO: 311 | HCDR2 (Kabat) | IIYPGTSYTRYSPSFQG |
| SEQ ID NO: 348 | HCDR3 (Kabat) | GSLPGLLGFDH |
| SEQ ID NO: 80 | HCDR1 (Chothia) | GYSFTSY |
| SEQ ID NO: 313 | HCDR2 (Chothia) | YPGTSY |

TABLE 2-continued

Exemplary anti-NPR1 antibody sequences

| SEQ ID NO: 348 | HCDR3 (Chothia) | GSLPGLLGFDH |
|---|---|---|
| SEQ ID NO: 82 | HCDR1 (IMGT) | GYSFTSYW |
| SEQ ID NO: 314 | HCDR2 (IMGT) | IYPGTSYT |
| SEQ ID NO: 349 | HCDR3 (IMGT) | ARGSLPGLLGFDH |
| SEQ ID NO: 350 | VH | EVQLVQSGAEVKKPGESLKISCKGSYSFTSYWISWVRQMPGKGLEWMGII YPGTSYTRYSPSFQGQVTISADKSISTAYLQWSSLKASDTAMYYCARGSLP GLLGFDHWGQGTLVTVSS |
| SEQ ID NO: 351 | DNA VH | gaagtgcagctggtgcagagcggtgccgaagtgaaaaaaccgggcgaaagcctgaaaatcagctgcaaaggcagc ggctatagctttaccagctattggattagctgggttcgccagatgccgggcaaaggcctggaatggatgggcattatcta tccgggcaccagctatacccgctatagccccgagctttcagggccaggttacaattagcgccgacaaaagcatcagcac cgcctatctgcaatggagcagcctgaaagccagcgataccgccatgtattattgcgcgcgtggaagcctgcctggtctg ctgggttttgatcactgggccagggcaccctggttactgtctcgagc |
| SEQ ID NO: 352 | Heavy Chain | EVQLVQSGAEVKKPGESLKISCKGSYSFTSYWISWVRQMPGKGLEWMGII YPGTSYTRYSPSFQGQVTISADKSISTAYLQWSSLKASDTAMYYCARGSLP GLLGFDHWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKRVEPKSCDKTHTCPPCPAPEAAGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| SEQ ID NO: 353 | DNA Heavy Chain | gaagtgcagctggtgcagagcggtgccgaagtgaaaaaaccgggcgaaagcctgaaaatcagctgcaaaggcagc ggctatagctttaccagctattggattagctgggttcgccagatgccgggcaaaggcctggaatggatgggcattatcta tccgggcaccagctatacccgctatagccccgagctttcagggccaggttacaattagcgccgacaaaagcatcagcac cgcctatctgcaatggagcagcctgaaagccagcgataccgccatgtattattgcgcgcgtggaagcctgcctggtctg ctgggttttgatcactgggccagggcaccctggttactgtctcgagcgcgtcgaccaaaggcccagcgtgttccctc tggccccagcagcaagagcacctctggcggaacagccgccctgggctgcctggtcaaggactacttccccgagcc cgtgaccgtgtcctggaactctggcgccctgaccagcggcgtgcacacctttccagccgtgctcagagcagcggcct gtacagcctgagcagcgtcgtgaccgtgccacagcagcgcgggcacccagacctacatctgcaacgtgaaccaca agcccagcaacacaaaggtggacaaggggtggaacccaagagctgcgacaagacccacacctgtccccctgcc ctgcccctgaagcgggaggaggcccctccgtgttcctgttccccccaaagcctaaggacaccctgatgatcagccgga cccccgaagtgacctgcgtggtggtggacgtgtcccacgaggaccctgaagtgaagtttaattggtacgtggacggcg tggaagtgcacaacgccaagaccaagcccagagaggaacagtacaacagcacctaccgggtggtgtccgtgctgac cgtgctgcaccaggactggctgaacggcaaagagtacaagtgcaaggtgtccaacaaggcctgcctgcccccatcg agaaaaccatcagcaaggccaaggccagcccgcgagcccaggtgtacacactgcccctagccgggaagaga tgaccaagaaccaggtgtccctgacctgcctcgtgaagggcttctacccagcgacattgccgtggaatgggagagca acggccagcccgagaacaactacaagaccaccccccctgtgctggacagcgacggctcattcttcctgtacagcaag ctgaccgtggacaagagccggtggcagcagggcaacgtgttcagctgctccgtgatgcacgaggcctgcacaacc actacacccagaagtccctgagcctgagccccggcaag |
| SEQ ID NO: 320 | LCDR1 (Combined) | TGSSSNIGAGYDVH |
| SEQ ID NO: 354 | LCDR2 (Combined) | GNSNRPN |
| SEQ ID NO: 355 | LCDR3 (Combined) | QSYDSPTSSSV |
| SEQ ID NO: 320 | LCDR1 (Kabat) | TGSSSNIGAGYDVH |
| SEQ ID NO: 354 | LCDR2 (Kabat) | GNSNRPN |
| SEQ ID NO: 355 | LCDR3 (Kabat) | QSYDSPTSSSV |
| SEQ ID NO: 323 | LCDR1 (Chothia) | SSSNIGAGYD |
| SEQ ID NO: 324 | LCDR2 (Chothia) | GNS |
| SEQ ID NO: 356 | LCDR3 (Chothia) | YDSPTSSS |

TABLE 2-continued

Exemplary anti-NPR1 antibody sequences

| SEQ ID NO: 326 | LCDR1 (IMGT) | SSNIGAGYD |
|---|---|---|
| SEQ ID NO: 324 | LCDR2 (IMGT) | GNS |
| SEQ ID NO: 355 | LCDR3 (IMGT) | QSYDSPTSSSV |
| SEQ ID NO: 357 | VL | QSVLTQPPSVSGAPGQRVTISCTGSSSNIGAGYDVHWYQQLPGTAPKLLIYG NSNRPNGVPDRFSGSKSGTSASLAITGLQAEDEADYYCQSYDSPTSSSVFGG GTKLTVL |
| SEQ ID NO: 358 | DNA VL | cagagcgtgctgacccagccaccaagcgtgagcggtgcaccaggtcagcgcgtgaccattagctgcaccggcagca gcagcaacattggcgcgcaggctatgatgtgcattggtatcagcagctgccaggcaccgcaccgaaactgctgatttatgg caacagcaatcgcccaaacggtgtgccggatcgctttagcggcagcaaaagcggcaccagcgccagcctggcgatt accggtctgcaagccgaagacgaagccgattattactgccagtcttacgactctccgacttcttcttctgtgtttggcggc ggtaccaagctgaccgtgctg |
| SEQ ID NO: 359 | Light Chain | QSVLTQPPSVSGAPGQRVTISCTGSSSNIGAGYDVHWYQQLPGTAPKLLIYG NSNRPNGVPDRFSGSKSGTSASLAITGLQAEDEADYYCQSYDSPTSSSVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 360 | DNA Light Chain | cagagcgtgctgacccagccaccaagcgtgagcggtgcaccaggtcagcgcgtgaccattagctgcaccggcagca gcagcaacattggcgcgcaggctatgatgtgcattggtatcagcagctgccaggcaccgcaccgaaactgctgatttatgg caacagcaatcgcccaaacggtgtgccggatcgctttagcggcagcaaaagcggcaccagcgccagcctggcgatt accggtctgcaagccgaagacgaagccgattattactgccagtcttacgactctccgacttcttcttctgtgtttggcggc ggtaccaagctgaccgtgctgggccagcccaaagccgcccctagcgtgaccctgttcccccccaagcagcgaggaac tccaggccaacaaggccaccctcgtgtgcctgatcagcgacttctacccgggcgccgtgaccgtggcctggaaggcc gatagcagccctgtgaaggccggcgtggaaaccaccacccccagcaagcagagcaacaacaaatacgccgccagc agctacctgagcctgaccccccgagcagtggaagtcccacagatcctacagctgccaggtcacacacgagggcagca ccgtggaaaagaccgtggccccccaccgagtgcagc |

ZZ05_LALA

| SEQ ID NO: 310 | HCDR1 (Combined) | GYSFTSYWIS |
|---|---|---|
| SEQ ID NO: 311 | HCDR2 (Combined) | IIYPGTSYTRYSPSFQG |
| SEQ ID NO: 348 | HCDR3 (Combined) | GSLPGLLGFDH |
| SEQ ID NO: 229 | HCDR1 (Kabat) | SYWIS |
| SEQ ID NO: 311 | HCDR2 (Kabat) | IIYPGTSYTRYSPSFQG |
| SEQ ID NO: 348 | HCDR3 (Kabat) | GSLPGLLGFDH |
| SEQ ID NO: 80 | HCDR1 (Chothia) | GYSFTSY |
| SEQ ID NO: 313 | HCDR2 (Chothia) | YPGTSY |
| SEQ ID NO: 348 | HCDR3 (Chothia) | GSLPGLLGFDH |
| SEQ ID NO: 82 | HCDR1 (IMGT) | GYSFTSYW |
| SEQ ID NO: 314 | HCDR2 (IMGT) | IYPGTSYT |
| SEQ ID NO: 349 | HCDR3 (IMGT) | ARGSLPGLLGFDH |
| SEQ ID NO: 350 | VH | EVQLVQSGAEVKKPGESLKISCKGSGYSFTSYWISWVRQMPGKGLEWMGII YPGTSYTRYSPSFQGQVTISADKSISTAYLQWSSLKASDTAMYYCARGSLP GLLGFDHWGQGTLVTVSS |

TABLE 2-continued

Exemplary anti-NPR1 antibody sequences

| SEQ ID NO: 351 | DNA VH | gaagtgcagctggtgcagagcggtgccgaagtgaaaaaaccgggcgaaagcctgaaaatcagctgcaaaggcagc ggctatagcttttaccagctattggattagctgggtttcgccagatgccgggcaaaggcctggaatggatgggcattatcta tccgggcaccagctataccccgctatagcccgagcttttcagggccaggttacaattagcgccgacaaaagcatcagctc cgcctatctgcaatggagcagcctgaaagccagcgataccgccatgtattattgcgcgcgtggaagcctgcctggtctg ctgggttttgatcactgggggccagggcaccctggttactgtctcgagc |
| SEQ ID NO: 352 | Heavy Chain | EVQLVQSGAEVKKPGESLKISCKGSGYSFTSYWISWVRQMPGKGLEWMGII YPGTSYTRYSPSFQGQVTISADKSISTAYLQWSSLKASDTAMYYCARGSLP GLLGFDHWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKRVEPKSCDKTHTCPPCPAPEAAGGPSVFLFPPKPKDTLMIS RTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| SEQ ID NO: 353 | DNA Heavy Chain | gaagtgcagctggtgcagagcggtgccgaagtgaaaaaaccgggcgaaagcctgaaaatcagctgcaaaggcagc ggctatagctttaccagctattggattagctgggttcgccagatgccgggcaaaggcctggaatggatgggcattatcta tccgggcaccagctataccccgctatagcccgagcttttcagggccaggttacaattagcgccgacaaaagcatcagctc cgcctatctgcaatggagcagcctgaaagccagcgataccgccatgtattattgcgcgcgtggaagcctgcctggtctg ctgggttttgatcactgggccagggcaccctggttactgtctcgagcgcgtcgaccaaaggcccagcgtgttcctc tggccccagcagcaagagcacctctggcggaacagccgcctgggctgctggtcaaggactacttccccgagcc cgtgaccgtgtcctggaactctggcgccctgaccagcggcgtgcacacctttccagccgtcctgcagagcagcggcct gtacagcctgagcagcgtcgtgaccgtgccagcagcagcctgggcacccagacctacatctgcaacgtgaaccaca agccagcaacacaaaggtggacaagcgggtggaacccaagagctgcgacaagacccacacctgtcccccctgcc ctgcccctgaagcggcgggaggcccctccgtgttcctgttccccccaaagcctaaggacaccctgatgatcagccgga ccccgaagtgacctgcgtggtggtggacgtgtcccacgaggaccctgaagtgaagtttaattggtacgtggacggcg tggaagtgcacaacgccaagaccaagcccagaggaacagtacaacagcacctaccgggtggtgtcgtgctgac cgtgctgcaccaggactggctgaacggcaaagagtacaagtgcaaggtgtccaacaaggcctgcctgccccatcg agaaaaccatcagcaaggccaaggccagccccgcgagcccaggtgtacacactgccccctagccgggaagaga tgaccaagaaccaggtgtccctgacctgcctcgtgaagggcttctacccagcgacattgccgtggaatgggagagca acggccagcccgagaacaactacaagaccaccccccctgtgctggacagcgacggctcattcttcctgtacagcaag ctgaccgtggacaagagccggtggcagggcaacgtgttcagctgctccgtgatgcacgaggccctgcacaacc actacacccagaagtccctgagcctgagccccggcaag |
| SEQ ID NO: 320 | LCDR1 (Combined) | TGSSSNIGAGYDVH |
| SEQ ID NO: 354 | LCDR2 (Combined) | GNSNRPN |
| SEQ ID NO: 361 | LCDR3 (Combined) | QSYGAFPRFVV |
| SEQ ID NO: 320 | LCDR1 (Kabat) | TGSSSNIGAGYDVH |
| SEQ ID NO: 354 | LCDR2 (Kabat) | GNSNRPN |
| SEQ ID NO: 361 | LCDR3 (Kabat) | QSYGAFPRFVV |
| SEQ ID NO: 323 | LCDR1 (Chothia) | SSSNIGAGYD |
| SEQ ID NO: 324 | LCDR2 (Chothia) | GNS |
| SEQ ID NO: 362 | LCDR3 (Chothia) | YGAFPRFV |
| SEQ ID NO: 326 | LCDR1 (IMGT) | SSNIGAGYD |
| SEQ ID NO: 324 | LCDR2 (IMGT) | GNS |
| SEQ ID NO: 361 | LCDR3 (IMGT) | QSYGAFPRFVV |
| SEQ ID NO: 363 | VL | QSVLTQPPSVSGAPGQRVTISCTGSSSNIGAGYDVHWYQQLPGTAPKLLIYG NSNRPNGVPDRFSGSKSGTSASLAITGLQAEDEADYYCQSYGAFPRFVVFG GGTKLTVL |
| SEQ ID NO: 364 | DNA VL | cagagcgtgctgacccagccaccaagcgtgagcggtgcaccaggtcagcgcgtgaccattagctgcaccggcagca gcagcaacattggcgcaggctatgatgtgcattggtatcagcagctgccaggcaccgcaccgaaactgctgatttatgg caacagcaatcgcccaaacggtgtgccggatcgctttagcggcagcaaaagcggcaccagcgccagcctggcgatt |

TABLE 2-continued

Exemplary anti-NPR1 antibody sequences

| | | |
|---|---|---|
| | | accggtctgcaagccgaagacgaagccgattattactgccaatcctatggtgccttccctcgtttcgttgttttttggcggcg<br>gtaccaagctgaccgtgctg |
| SEQ ID<br>NO: 365 | Light<br>Chain | QSVLTQPPSVSGAPGQRVTISCTGSSSNIGAGYDVHWYQQLPGTAPKLLIYG<br>NSNRPNGVPDRFSGSKSGTSASLAITGLQAEDEADYYCQSYGAFPRFVVFG<br>GGTKLTVLGQPKAAPSVTLFPPSSEELQANKATLVCLISDFYPGAVTVAWK<br>ADSSPVKAGVETTTPSKQSNNKYAASSYLSLTPEQWKSHRSYSCQVTHEGS<br>TVEKTVAPTECS |
| SEQ ID<br>NO: 366 | DNA<br>Light<br>Chain | cagagcgtgctgacccagccaccaagcgtgagcggtgcaccaggtcagcgcgtgaccattagctgcaccggcagca<br>gcaacattggcgcaggctatgatgtgcattggtatcagcagctgccaggcaccgccaccgaaactgctgatttatgg<br>caacagcaatcgcccaaacggtgtgccggatcgctttagcggcagcaaaagcggcaccagcgccagcctggcgatt<br>accggtctgcaagccgaagacgaagccgattattactgccaatcctatggtgccttccctcgtttcgttgttttttggcggcg<br>gtaccaagctgaccgtgctgggccagcccaaagccgcccctagcgtgaccctgttccccccaagcagcgaggaactc<br>caggccaacaaggccaccctcgtgtgcctgatcagcgacttctaccctggcgccgtgaccgtggcctggaaggccga<br>tagcagccctgtgaaggccggcgtggaaaccaccaccccagcaagcagagcaacaacaaatacgccgccagcag<br>ctacctgagcctgacccccgagcagtggaagtcccacagatcctacagctgccaggtcacacacgagggcagcacc<br>gtggaaaagaccgtggcccccaccgagtgcagc |
| ZZ12_<br>LALA | | |
| SEQ ID<br>NO: 367 | HCDR1<br>(Combined) | GFSFSKYYLN |
| SEQ ID<br>NO: 368 | HCDR2<br>(Combined) | SIHQQAHEKKYVESVKG |
| SEQ ID<br>NO: 228 | HCDR3<br>(Combined) | SLRRRSTEHAGFDV |
| SEQ ID<br>NO: 369 | HCDR1<br>(Kabat) | KYYLN |
| SEQ ID<br>NO: 368 | HCDR2<br>(Kabat) | SIHQQAHEKKYVESVKG |
| SEQ ID<br>NO: 228 | HCDR3<br>(Kabat) | SLRRRSTEHAGFDV |
| SEQ ID<br>NO: 370 | HCDR1<br>(Chothia) | GFSFSKY |
| SEQ ID<br>NO: 371 | HCDR2<br>(Chothia) | HQQAHE |
| SEQ ID<br>NO: 228 | HCDR3<br>(Chothia) | SLRRRSTEHAGFDV |
| SEQ ID<br>NO: 372 | HCDR1<br>(IMGT) | GFSFSKYY |
| SEQ ID<br>NO: 373 | HCDR2<br>(IMGT) | IHQQAHEK |
| SEQ ID<br>NO: 232 | HCDR3<br>(IMGT) | ARSLRRRSTEHAGFDV |
| SEQ ID<br>NO: 374 | VH | EVQLVESGGGLVQPGGSLRLSCAASGFSFSKYYLNWVRQAPGKGLEWVAS<br>IHQQAHEKKYVESVKGRFTISRDNAKNSLYLMNSLRAEDTAVYYCARSL<br>RRRSTEHAGFDVWGQGTLVTVSS |
| SEQ ID<br>NO: 375 | DNA VH | gaagtgcagctggtggaaagcggcggtggcctggtgcagccaggtggtagcctgcgcctgagctgcgccgccagc<br>ggctttagcttcagcaaatattacttgaactgggttcgccaggcccaggcaaaggcctggaatgggtggccagcattc<br>accagcaagcacacgagaaaaaatacgtgaagtccgtgaaaggccgcttttaccattagccgcgataacgccaaaag<br>agcctgtatctgcaaatgaacagcctgcgggccgaagataccgccgtgtattattgcgcgcgtagcctgcgtcgtcgta<br>gcactgagcacgcaggattcgactttggggccagggcaccctggttactgtctcgagc |
| SEQ ID<br>NO: 376 | Heavy<br>Chain | EVQLVESGGGLVQPGGSLRLSCAASGFSFSKYYLNWVRQAPGKGLEWVAS<br>IHQQAHEKKYVESVKGRFTISRDNAKNSLYLMNSLRAEDTAVYYCARSL<br>RRRSTEHAGFDVWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQT<br>YICNVNHKPSNTKVDKRVEPKSCDKTHTCPPCPAPEAAGGPSVFLFPPKPK<br>DTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVLD<br>SDGSFFLYSKLTVDKSRWQQGNVFSCSVMHEALHNHYTQKSLSLSPGK |

TABLE 2-continued

Exemplary anti-NPR1 antibody sequences

| SEQ ID NO: 377 | DNA Heavy Chain | gaagtgcagctggtggaaagcggcggtggcctggtgcagccaggtggtagcctgcgcctgagctgcgccgccagc ggctttagcttcagcaaatattacttgaactgggttcgccaggccccaggcaaaggcctggaatgggtggccagcattc accagcagcacacgagaaaaaatacgtggagtccgtgaaaggccgctttaccattagccgcgataacgccaaaaac agcctgtatctgcaaatgaacagcctgcgggccgaagataccgccgtgtattattgcgcgcgtagcctgcgtcgtcgta gcactgagcacgcaggattcgacgtttggggccagggcaccctggttactgtctcgagcgcgtcgaccaaaggcccc agcgtgttccctctggccccagcagcaagagcacctctggcggaacagccgccctgggctgcctggtcaaggacta cttccccgagccgtgaccgtgtcctggaactctggggcccctgaccagcggcgtgcacaccttccagccgtgctcca gagcagcggcctgtacagcctgagcagcgtcgtgaccgtgcccagcagcagcctgggcacccagacctacatctgc aacgtgaaccacaagcccagcaacacaaaggtggacaagcgggtggaacccaagagctgcgacaagacccacac ctgtccccctgccctgcccctgaagcggcggaggcccctccgtgttcctgttcccccaaagcctaaggacacccct gatgatcagccggacccccgaagtgacctgcgtggtggtggacgtgtcccacgaggaccctgaagtgaagtttaattg gtacgtggacggcgtggaagtgcacaacgccaagaccaagcccagagaggaacagtacaacagcacctaccgggt ggtgtccgtgctgaccgtgctgcaccaggactggctgaacggcaaagagtacaagtgcaaggtgtccaacaaggcc tgcctgccccatcgagaaaaccatcagcaaggccaaaggccagccccgcgagcccagggtgtacacactgccccc tagccgggaagatgatgaccaagaaccaggtgtccctgacctgcctcgtgaaggggcttctacccagcgacattgccgt ggaatgggagagcaacggccagcccgagaacaactacaagaccaccccccctgtgctggacagcgacggctcattc ttcctgtacagcaagctgaccgtggacaagagccggtggcagcagggcaacgtgttcagctgctccgtgatgcacga ggcccttgcacaaccactacacccagaagtccctgagcctgagccccggcaag |
| --- | --- | --- |
| SEQ ID NO: 237 | LCDR1 (Combined) | RASQGISNYLA |
| SEQ ID NO: 238 | LCDR2 (Combined) | AASTLQS |
| SEQ ID NO: 239 | LCDR3 (Combined) | QQADKFPYT |
| SEQ ID NO: 237 | LCDR1 (Kabat) | RASQGISNYLA |
| SEQ ID NO: 238 | LCDR2 (Kabat) | AASTLQS |
| SEQ ID NO: 239 | LCDR3 (Kabat) | QQADKFPYT |
| SEQ ID NO: 240 | LCDR1 (Chothia) | SQGISNY |
| SEQ ID NO: 241 | LCDR2 (Chothia) | AAS |
| SEQ ID NO: 242 | LCDR3 (Chothia) | ADKFPY |
| SEQ ID NO: 243 | LCDR1 (IMGT) | QGISNY |
| SEQ ID NO: 241 | LCDR2 (IMGT) | AAS |
| SEQ ID NO: 239 | LCDR3 (IMGT) | QQADKFPYT |
| SEQ ID NO: 244 | VL | DIQMTQSPSSLSASVGDRVTITCRASQGISNYLAWYQQKPGKVPKLLIYAAS TLQSGVPSRFSGSGSGTDFTLTISSLQPEDVATYYCQQADKFPYTFGQGTKV EIK |
| SEQ ID NO: 245 | DNA VL | gatattcagatgacccagagcccgagcagcctgagcgcaagcgtgggcgatcgcgtgaccattacctgccgcgcca gccagggcattagcaactatctggcctggtatcagcagaaaccggggcaaagtgccgaaactgctgatctatgccgcca gcaccctgcaaagcggcgtgccaagtcgctttagcggcagcggtagcggcaccgatttcaccctgaccattagcagc ctgcaaccggaagacgtggccacctattattgccagcaggctgacaaattcccgtacaccttcggccagggtaccaaa gtggaaatcaag |
| SEQ ID NO: 246 | Light Chain | DIQMTQSPSSLSASVGDRVTITCRASQGISNYLAWYQQKPGKVPKLLIYAAS TLQSGVPSRFSGSGSGTDFTLTISSLQPEDVATYYCQQADKFPYTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC |
| SEQ ID NO: 247 | DNA Light Chain | gatattcagatgacccagagcccgagcagcctgagcgcaagcgtgggcgatcgcgtgaccattacctgccgcgcca gccagggcattagcaactatctggcctggtatcagcagaaaccggggcaaagtgccgaaactgctgatctatgccgcca gcaccctgcaaagcggcgtgccaagtcgctttagcggcagcggtagcggcaccgatttcaccctgaccattagcagc ctgcaaccggaagacgtggccacctattattgccagcaggctgacaaattcccgtacaccttcggccagggtaccaaa gtggaaatcaagcggaccgtggccgctcccctcgtgttcatcttcccaccagcgacgagcagctgaagtccggcaca gccagcgtcgtgtgcctgctgaacaacttctaccccgcgaggccaaagtgcagtggaaggtggacaacgccctcca gagcggcaacagccaggaaagcgtcaccgagcaggacagcaaggactccacctcagcctgagcagcaccctgac |

TABLE 2-continued

Exemplary anti-NPR1 antibody sequences cctgagcaaggccgactacgagaagcacaaggtgtacgcctgcgaagtgacccaccagggcctgtccagccccgtg
accaagagcttcaaccggggcgagtgt

ZZ13_LALA

| SEQ ID NO: 378 | HCDR1 (Combined) | GFTFSRYYIN |
| --- | --- | --- |
| SEQ ID NO: 379 | HCDR2 (Combined) | SIHQHGLETRYVESVKG |
| SEQ ID NO: 228 | HCDR3 (Combined) | SLRRRSTEHAGFDV |
| SEQ ID NO: 380 | HCDR1 (Kabat) | RYYIN |
| SEQ ID NO: 379 | HCDR2 (Kabat) | SIHQHGLETRYVESVKG |
| SEQ ID NO: 228 | HCDR3 (Kabat) | SLRRRSTEHAGFDV |
| SEQ ID NO: 381 | HCDR1 (Chothia) | GFTFSRY |
| SEQ ID NO: 382 | HCDR2 (Chothia) | HQHGLE |
| SEQ ID NO: 228 | HCDR3 (Chothia) | SLRRRSTEHAGFDV |
| SEQ ID NO: 383 | HCDR1 (IMGT) | GFTFSRYY |
| SEQ ID NO: 384 | HCDR2 (IMGT) | IHQHGLET |
| SEQ ID NO: 232 | HCDR3 (IMGT) | ARSLRRRSTEHAGFDV |

SEQ ID NO: 385   VH

EVQLVESGGGLVQPGGSLRLSCAASGFTFSRYYINWVRQAPGKGLEWVASI
HQHGLETRYVESVKGRFTISRDNAKNSLYLQMNSLRAEDTAVYYCARSLR
RRSTEHAGFDVWGQGTLVTVSS

SEQ ID NO: 386   DNA VH gaagtgcagctggtggaaagcggcggtggcctggtgcagccaggtggtagcctgcgcctgagctgcgccgccagc
gggtttacttttccagatattacattaattgggttcgccaggccccaggcaaaggcctggaatgggtggcgagcatcca
ccagcacggcctggagaccagatatgtggaatctgtcaaagggcgctttaccattagccgcgataacgccaaaaacag
cctgtatctgcaaatgaacagcctgcgggccgaagataccgccgtgtattattgcgcgcgtagcctgcgtcgtcgtagc
actgagcacgcaggattcgacgtttggggccagggcaccctggttactgtctcgagc SEQ ID NO: 387   Heavy Chain EVQLVESGGGLVQPGGSLRLSCAASGFTFSRYYINWVRQAPGKGLEWVASI
HQHGLETRYVESVKGRFTISRDNAKNSLYLQMNSLRAEDTAVYYCARSLR
RRSTEHAGFDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQTY
ICNVNHKPSNTKVDKRVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 388   DNA Heavy Chain gaagtgcagctggtggaaagcggcggtggcctggtgcagccaggtggtagcctgcgcctgagctgcgccgccagc
gggtttacttttccagatattacattaattgggttcgccaggccccaggcaaaggcctggaatgggtggcgagcatcca
ccagcacggcctggagaccagatatgtggaatctgtcaaagggcgctttaccattagccgcgataacgccaaaaacag
cctgtatctgcaaatgaacagcctgcgggccgaagataccgccgtgtattattgcgcgcgtagcctgcgtcgtcgtagc
actgagcacgcaggattcgacgtttggggccagggcaccctggttactgtctcgagcgcgtcgaccaaaggcccag
cgtgttccctctggccccagcagcaagagcacctctggcggaacagccgccctgggctgcctggtcaaggactactt
ccccgagcccgtgaccgtgtcctggaactctggcgccctgaccagcggcgtgcacaccttccagccgtgctccaga
gcagcggcctgtacagcctgagcagcgtcgtgaccgtgccagcagcagcctgggcacccagacctacatctgcaa
cgtgaaccacaagcccagcaacacaaaggtggacaagcgggtggaacccaagagctgcgacaagacccacacctg
tccccctgccctgcccctgaagcggcggaggccctccgtgttcctgttcccccaaagcctaaggacaccctgat
gatcagccggacccccgaagtgacctgcgtggtggtggacgtgtcccacgaggaccccgaagtgaagttcaattggta
cgtcgacggcgtggaagtgcacaacgccaagaccaagccagagaggaacagtacaacagcacctacgggtggt
gtccgtgctgaccgtgctgcaccaggactggctgaacggcaaagagtacaagtgcaaggtgtccaacaaggcctgc
ctgcccccatgagaaaccatcagcaaggccaaaggccagccccgcgagccccaggtgtacacactgcccccctag
ccgggaagagatgaccaagaaccaggtgtcctgacctgcctcgtgaagggcttctaccccagcgacattgccgtgg
aatgggagagcaacggccagccccgagaacaactacaagaccacccccccctgtgctggacagcgacggctcattcttc TABLE 2-continued Exemplary anti-NPR1 antibody sequences

|  |  |  |
|---|---|---|
|  |  | ctgtacagcaagctgaccgtggacaagagccggtggcagcagggcaacgtgttcagctgctccgtgatgcacgagg<br>ccctgcacaaccactacacccagaagtccctgagcctgagccccggcaag |
| SEQ ID NO: 237 | LCDR1 (Combined) | RASQGISNYLA |
| SEQ ID NO: 238 | LCDR2 (Combined) | AASTLQS |
| SEQ ID NO: 239 | LCDR3 (Combined) | QQADKFPYT |
| SEQ ID NO: 237 | LCDR1 (Kabat) | RASQGISNYLA |
| SEQ ID NO: 238 | LCDR2 (Kabat) | AASTLQS |
| SEQ ID NO: 239 | LCDR3 (Kabat) | QQADKFPYT |
| SEQ ID NO: 240 | LCDR1 (Chothia) | SQGISNY |
| SEQ ID NO: 241 | LCDR2 (Chothia) | AAS |
| SEQ ID NO: 242 | LCDR3 (Chothia) | ADKFPY |
| SEQ ID NO: 243 | LCDR1 (IMGT) | QGISNY |
| SEQ ID NO: 241 | LCDR2 (IMGT) | AAS |
| SEQ ID NO: 239 | LCDR3 (IMGT) | QQADKFPYT |
| SEQ ID NO: 244 | VL | DIQMTQSPSSLSASVGDRVTITCRASQGISNYLAWYQQKPGKVPKLLIYAAS<br>TLQSGVPSRFSGSGSGTDFTLTISSLQPEDVATYYCQQADKFPYTFGQGTKV<br>EIK |
| SEQ ID NO: 245 | DNA VL | gatattcagatgacccagagcccgagcagcctgagcgcaagcgtgggcgatcgcgtgaccattacctgccgcgcca<br>gccagggcattagcaactatctggcctggtatcagcagaaaccgggcaaagtgccgaaactgctgatctatgccgcca<br>gcaccctgcaaagcggcgtgccaagtcgctttagcggcagcggtagcggcaccgatttcaccctgaccattagcagc<br>ctgcaaccggaagacgtggcgacctattattgccagcaggctgacaaattcccgtacaccttcggccagggtaccaaa<br>gtggaaatcaag |
| SEQ ID NO: 246 | Light Chain | DIQMTQSPSSLSASVGDRVTITCRASQGISNYLAWYQQKPGKVPKLLIYAAS<br>TLQSGVPSRFSGSGSGTDFTLTISSLQPEDVATYYCQQADKFPYTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC |
| SEQ ID NO: 247 | DNA Light Chain | gatattcagatgacccagagcccgagcagcctgagcgcaagcgtgggcgatcgcgtgaccattacctgccgcgcca<br>gccagggcattagcaactatctggcctggtatcagcagaaaccgggcaaagtgccgaaactgctgatctatgccgcca<br>gcaccctgcaaagcggcgtgccaagtcgctttagcggcagcggtagcggcaccgatttcaccctgaccattagcagc<br>ctgcaaccggaagacgtggcgacctattattgccagcaggctgacaaattcccgtacaccttcggccagggtaccaaa<br>gtggaaatcaagcggaccgtggccgctcccctccgtgttcatcttcccaccagcgacgagcagctgaagtccggcaca<br>gccagcgtcgtgtgcctgctgaacaacttctaccccgcgaggcaaagtgcagtggaaggtggacaacgccctcca<br>gagcggcaacagccaggaaagcgtcaccgagcaggacagcaaggactccacctacagcctgagcagcaccctgac<br>cctgagcaaggccgactacgagaagcacaaggtgtacgcctgcgaagtgacccaccagggcctgtccagcccgtg<br>accaagagcttcaaccggggcgagtgt |

ZZ14_LALA

| SEQ ID NO: 270 | HCDR1 (Combined) | GFTFSSYAIS |
| SEQ ID NO: 389 | HCDR2 (Combined) | SISSHGYYTRYAESVKG |
| SEQ ID NO: 331 | HCDR3 (Combined) | PYLGDRRSYGFDH |

TABLE 2-continued

Exemplary anti-NPR1 antibody sequences

| SEQ ID NO: 273 | HCDR1 (Kabat) | SYAIS |
|---|---|---|
| SEQ ID NO: 389 | HCDR2 (Kabat) | SISSHGYYTRYAESVKG |
| SEQ ID NO: 331 | HCDR3 (Kabat) | PYLGDRRSYGFDH |
| SEQ ID NO: 32 | HCDR1 (Chothia) | GFTFSSY |
| SEQ ID NO: 390 | HCDR2 (Chothia) | SSHGYY |
| SEQ ID NO: 331 | HCDR3 (Chothia) | PYLGDRRSYGFDH |
| SEQ ID NO: 275 | HCDR1 (IMGT) | GFTFSSYA |
| SEQ ID NO: 391 | HCDR2 (IMGT) | ISSHGYYT |
| SEQ ID NO: 332 | HCDR3 (IMGT) | ARPYLGDRRSYGFDH |
| SEQ ID NO: 392 | VH | EVQLLESGGGLVQPGGSLRLSCAASGFTFSSYAISWVRQAPGKGLEWVSSIS SHGYYTRYAESVKGRFTISRDNSKNTLYLQMNSLRAEDTAVYYCARPYLG DRRSYGFDHWGQGTLVTVSS |
| SEQ ID NO: 393 | DNA VH | gaagtgcagctgctggaaagcggtggcggtctggtgcagccaggtggtagcctgcgcctgagctgtgccgcaagcg gtttacattttccagctatgctatcagctgggtgcgccaagcaccaggcaaaggcctggaatgggtgagcagcattag ctccacatggatattacacccggtatgccgagtccgtgaaaggtcgctttaccattagtcgcgataacagcaaaaacaccc tgtatctgcaaatgaacagcctgcgggcagaagataccgcagtttattattgcgcgcgaccttatctgggtgaccgtcgt agctatggtttcgaccactggggccagggcaccctggttactgtctcgagc |
| SEQ ID NO: 394 | Heavy Chain | EVQLLESGGGLVQPGGSLRLSCAASGFTFSSYAISWVRQAPGKGLEWVSSIS SHGYYTRYAESVKGRFTISRDNSKNTLYLQMNSLRAEDTAVYYCARPYLG DRRSYGFDHWGQGTLVTVSSASTKGPSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCDKTHTCPPCPAPEAAGGPSVFLFPPKPKDTL MISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| SEQ ID NO: 395 | DNA Heavy Chain | gaagtgcagctgctggaaagcggtggcggtctggtgcagccaggtggtagcctgcgcctgagctgtgccgcaagcg gtttacattttccagctatgctatcagctgggtgcgccaagcaccaggcaaaggcctggaatgggtgagcagcattag ctccacatggatattacacccggtatgccgagtccgtgaaaggtcgctttaccattagtcgcgataacagcaaaaacaccc tgtatctgcaaatgaacagcctgcgggcagaagataccgcagtttattattgcgcgcgaccttatctgggtgaccgtcgt agctatggtttcgaccactggggccagggcaccctggttactgtctcgagcgcgtcgaccaagggcccagcgtgttc cctctgccccagcagcaagagcacctctggcggaacagccgccctgggctgcctggtcaaggactacttccccga gcccgtgaccgtgtcctggaactctggcgcctgaccagcggcgtgcacacctttccagccgtgctccagagcagcg gcctgtacagcctgagcagcgtcgtgaccgtgcccagcagcagcctgggcacccagacctacatctgcaacgtgaac cacaagcccagcaacacaaaggtggacaagcgggtggaacccaagagctgcgacaagacccacacctgtccccc ctgccctgccctgaacggcggcgggagggccccgtgttcctgttccccccaaagcctaaggacaccctcatgatcagc cggacccccgaagtgacctgcgtggtggtggacgtgtcccacgaggaccctgaagtgaagtttaattggtacgtggac ggcgtggaagtgcacaacgccaagaccaagcccagagaggaacagtacaacagcacctaccgggtggtgtccgtg ctgaccgtgctgcaccaggactggctgaacggcaaagagtacaagtgcaaggtgtccaacaaggcccctgcctgccc catcgagaaaaccatcagcaaggcccaaggcccaggtgtacacactgccccctagccgggga agagatgaccaagaaccaggtgtccctgacctgcctcgtgaagggcttctaccccagcgacattgccgtggaatggga gagcaacggccagcccgagaacaactacaagaccacccccctgtgctggacagcgacggctcattcttcctgtaca gcaagctgaccgtggacaagagccggtggcagcagggcaacgtgttcagctgctccgtgatgcacgaggccctgca caaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |

TABLE 2-continued

Exemplary anti-NPR1 antibody sequences

| SEQ ID NO: 338 | LCDR2 (Kabat) | EGSKRPS |
|---|---|---|
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVL |
| SEQ ID NO: 345 | DNA VL | cagagcgccctgacccagccagccagcgttagcggtagcccaggccagagcattaccattagctgcaccggcacca gcagcgacgtgggcagctataaacctggttagctggtatcagcagcatccggggcaaagcccccgaaactgatgatctatg aaggcagcaaacgccccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctg |
| SEQ ID NO: 346 | Light Chain | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 347 | DNA Light Chain | cagagcgccctgacccagccagccagcgttagcggtagcccaggccagagcattaccattagctgcaccggcacca gcagcgacgtgggcagctataaacctggttagctggtatcagcagcatccggggcaaagcccccgaaactgatgatctatg aaggcagcaaacgccccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctgggcagcccaaagccgcccctagcgtgaccctgttcccccaagcagcgaggaac tccaggccaacaaggccacccctcgtgtgcctgatcagcgacttctacccctggcgccgtgaccgtggcctggaaggcc gatagcagccctgtgaaggccggcgtggaaaccaccacccccagcaagcagagcaacaacaaatacgccgccagc agctacctgagcctgacccccgagcagtgaaagtcccacagatcctacagctgccaggtcacacacgagggcagca ccgtggaaaagaccgtggccccaccgagtgcagc |

ZZ15_LALA

| SEQ ID NO: 396 | HCDR1 (Combined) | GFTFASYAIT |
|---|---|---|
| SEQ ID NO: 397 | HCDR2 (Combined) | TISGSGVYTYYAESVKG |
| SEQ ID NO: 331 | HCDR3 (Combined) | PYLGDRRSYGFDH |
| SEQ ID NO: 398 | HCDR1 (Kabat) | SYAIT |
| SEQ ID NO: 397 | HCDR2 (Kabat) | TISGSGVYTYYAESVKG |
| SEQ ID NO: 331 | HCDR3 (Kabat) | PYLGDRRSYGFDH |
| SEQ ID NO: 399 | HCDR1 (Chothia) | GFTFASY |
| SEQ ID NO: 400 | HCDR2 (Chothia) | SGSGVY |

TABLE 2-continued

Exemplary anti-NPR1 antibody sequences

| SEQ ID NO: 331 | HCDR3 (Chothia) | PYLGDRRSYGFDH |
|---|---|---|
| SEQ ID NO: 401 | HCDR1 (IMGT) | GFTFASYA |
| SEQ ID NO: 402 | HCDR2 (IMGT) | ISGSGVYT |
| SEQ ID NO: 332 | HCDR3 (IMGT) | ARPYLGDRRSYGFDH |
| SEQ ID NO: 403 | VH | EVQLLESGGGLVQPGGSLRLSCAASGFTFASYAITWVRQAPGKGLEWVSTI SGSGVYTYYAESVKGRFTISRDNSKNTLYLQMNSLRAEDTAVYYCARPYL GDRRSYGFDHWGQGTLVTVSS |
| SEQ ID NO: 404 | DNA VH | gaagtgcagctgctggaaagcggtggcggtctggtgcagccaggtggtagcctgcgcctgagctgtgccgcaagcg ggttcacattcgcatcctatgcaattacttggtgcgccaagcaccaggcaaaggcctggaatgggtgagcaccatttc cggtgtccggtgtgtacacctattacgccgagtccgtcaaaggccgctttaccattagtcgcgataacagcaaaaacacc ctgtatctgcaaatgaacagcctgcgggcagaagataccgcagtttattattgcgcgcgacccttatctgggtgaccgtcg tagctatggtttcgaccactggggccagggcaccctggttactgtctcgagc |
| SEQ ID NO: 405 | Heavy Chain | EVQLLESGGGLVQPGGSLRLSCAASGFTFASYAITWVRQAPGKGLEWVSTI SGSGVYTYYAESVKGRFTISRDNSKNTLYLQMNSLRAEDTAVYYCARPYL GDRRSYGFDHWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKRVEPKSCDKTHTCPPCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO: 406 | DNA Heavy Chain | gaagtgcagctgctggaaagcggtggcggtctggtgcagccaggtggtagcctgcgcctgagctgtgccgcaagcg ggttcacattcgcatcctatgcaattacttggtgcgccaagcaccaggcaaaggcctggaatgggtgagcaccatttc cggtgtccggtgtgtacacctattacgccgagtccgtcaaaggccgctttaccattagtcgcgataacagcaaaaacacc ctgtatctgcaaatgaacagcctgcgggcagaagataccgcagtttattattgcgcgcgacccttatctgggtgaccgtcg tagctatggtttcgaccactggggccagggcaccctggttactgtctcgagcgcgtcgaccaaaggcccatcggtgttc cctctggcccccagcagcaagagcacctctggcgcgaacagccgccctgggctgcctggtcaaggactacttcccga gcccgtgaccgtgtcctggaactctggcgccctgaccagcggcgtgcacacctttccagccgtgctgcagagcagcg gcctgtacagcctgagcagcgtcgtgaccgtgccgcagcagtacatcaacaccacatctgcaacgtgaac cacaagcccagcaacacaaaggtggacaagcgggtggaacccaagagctgcgacaagacccacacctgtccccccc tgccctgccctgaagcggcgggaggcccctccgtgttcctgttccccccaaagcctaaggacaccctgatgatcagc cggaccccggaagtgacctgcgtggtggtggacgtgtcccacgaggaccctgaagtgaagtttaattggtacgtggac ggcgtggaagtgcacaacgccaagaccaagcccagagagagaacagtacaacagcacctaccgggtggtgtccgtg ctgaccgtgctgcaccaggactggctgaacggcaaagagtacaagtgcaaggtgtccaacaaggcccctgcctgccc catcgagaaaaccatcagcaaggccaaggccagccccgcgagccccaggtgtacacactgcccccagccggga agagatgaccaagaaccaggtgtccctgacctgcctcgtgaagggcttctacccagcgacattgccgtggaatggga gagcaacggccagcccgagaacaactacaagaccaccccccgtgctggacagcgacggctcattcttcctgtaca gcaagctgaccgtggacaagagccggtggcagcagggcaacgtgttcagctgctccgtgatgcacgaggcctgca caaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |

TABLE 2-continued

Exemplary anti-NPR1 antibody sequences

| SEQ ID NO: 343 | LCDR1 (IMGT) | SSDVGSYNL |
|---|---|---|
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVL |
| SEQ ID NO: 345 | DNA VL | cagagcgccctgacccagccagccagcgttagcggtagcccaggccagagcattaccattagctgcaccggcacca gcagcgacgtgggcagctataaacctggttagctggtatcagcagcatccgggcaaagccccgaaactgatgatctatg aaggcagcaaacgcccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctg |
| SEQ ID NO: 346 | Light Chain | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 347 | DNA Light Chain | cagagcgccctgacccagccagccagcgttagcggtagcccaggccagagcattaccattagctgcaccggcacca gcagcgacgtgggcagctataaacctggttagctggtatcagcagcatccgggcaaagccccgaaactgatgatctatg aaggcagcaaacgcccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctgggccagcccaaagccgcccctagcgtgaccctgttcccccccaagcagcgaggaac tccaggccaacaaggccacccctcgtgtgcctgatcagcgacttctacccctggcgccgtgaccgtggcctggaaggcc gatagcagccctgtgaaggccggcgtggaaaccaccacccccagcaagcagagcaacaacaaatacgccgccagc agctacctgagcctgaccccccgagcagtggaagtcccacagatcctacagctgccaggtcacacacgagggcagca ccgtggaaaagaccgtggccccaccgagtgcagc |

ZZ16_LALA

| SEQ ID NO: 407 | HCDR1 (Combined) | GFTFGTYAMT |
|---|---|---|
| SEQ ID NO: 408 | HCDR2 (Combined) | SISASGYYANYAGSVKG |
| SEQ ID NO: 331 | HCDR3 (Combined) | PYLGDRRSYGFDH |
| SEQ ID NO: 409 | HCDR1 (Kabat) | TYAMT |
| SEQ ID NO: 4080 | HCDR2 (Kabat) | SISASGYYANYAGSVKG |
| SEQ ID NO: 331 | HCDR3 (Kabat) | PYLGDRRSYGFDH |
| SEQ ID NO: 410 | HCDR1 (Chothia) | GFTFGTY |
| SEQ ID NO: 411 | HCDR2 (Chothia) | SASGYY |
| SEQ ID NO: 331 | HCDR3 (Chothia) | PYLGDRRSYGFDH |
| SEQ ID NO: 412 | HCDR1 (IMGT) | GFTFGTYA |
| SEQ ID NO: 413 | HCDR2 (IMGT) | ISASG |
| SEQ ID NO: 332 | HCDR3 (IMGT) | ARPYLGDRRSYGFDH |
| SEQ ID NO: 414 | VH | EVQLLESGGGLVQPGGSLRLSCAASGFTFGTYAMTWVRQAPGKGLEWVSS ISASGYYANYAGSVKGRFTISRDNSKNTLYLQMNSLRAEDTAVYYCARPY LGDRRSYGFDHWGQGTLVTVSS |

TABLE 2-continued

Exemplary anti-NPR1 antibody sequences

| SEQ ID NO: 415 | DNA VH | gaagtgcagctgctggaaagcggtggcggtctggtgcagccaggtggtagcctgcgcctgagctgtgccgcaagcg ggtttacattcggcacctatgcaatgacttgggtgcgccaaggccaggcaaaggcctggaatgggtgagtagcattag cgcatccggatatattacgctaactacgcaggcagcgtcaaaggccgctttaccattagtcgcgataacagcaaaaacacc ctgtatctgcaaatgaacagcctgcgggcagaagataccgcagtttattattgcgcgcgaccttatctgggtgaccgtcg tagctatggtttcgaccactggggccagggcaccctggttactgtctcgagc |
|---|---|---|
| SEQ ID NO: 416 | Heavy Chain | EVQLLESGGGLVQPGGSLRLSCAASGFTFGTYAMTWVRQAPGKGLEWVSS<br>ISASGYYANYAGSVKGRFTISRDNSKNTLYLQMNSLRAEDTAVYYCARPY<br>LGDRRSYGFDHWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 417 | DNA Heavy Chain | gaagtgcagctgctggaaagcggtggcggtctggtgcagccaggtggtagcctgcgcctgagctgtgccgcaagcg ggtttacattcggcacctatgcaatgacttgggtgcgccaagcaccaggcaaaggcctggaatgggtgagtagcattag cgcatccggatatattacgctaactacgcaggcagcgtcaaaggccgctttaccattagtcgcgataacagcaaaaacacc ctgtatctgcaaatgaacagcctgcgggcagaagataccgcagtttattattgcgcgcgaccttatctgggtgaccgtcg tagctatggtttcgaccactggggccagggcaccctggttactgtctcgagcgcgtcgaccaaaggcccagcgttc cctctggccccagcagcaagagcacctctggcgaacgccgcctgggctgcctggtcaaggactacttcccga gcccgtgaccgtgtcctggaactctggcgcctgaccagcggcgtgcacacctttccagccgtgctccagagcagcg gcctgtacagcctgagcagcgtcgtgaccgtgcccagcagcagcctgggcacccagacctacatctgcaacgtgaac cacaagcccagcaacacaaaggtggacaagcgggtggaacccaagagctgcgacaagacccacacctgtccccc tgccctgccctgaagcggcggaggcccctccgtgttcctgttccccccaaagcctaaggacaccctgatgatcagc cggacccccgaagtgacctgcgtggtggtggacgtgtcccacgaggaccctgaagtgaagtttaattggtacgtggac ggcgtggaagtgcacaacgccaagaccaagcccagagaggaacagtacaacagcacctaccgggtggtgtccgtg ctgaccgtgctgcaccaggactggctgaacggcaaagagtacaagtgcaaggtgtccaacaaggcccctgcctgccc catcgagaaaaccatcagcaaggccaaggccagccccgcgagcccaggtgtacacactgcccctagccggga agagatgaccaagaaccaggtgtccctgacctgcctcgtgaagggcttctacccagcgacattgccgtggaatggga gagcaacggccagcccgagaacaactacaagaccacccccccctgtgctggacagcgacggctcattcttcctgtaca gcaagctgaccgtggacaagagccggtggcagcagggcaacgtgttcagctgctccgtgatgcacgaggcctgca caaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE<br>GSKRPSGVSNRFSGSKSGNTASLTISGLQAEDEADYYCSSYGFHIVVVVFGG<br>GTKLTVL |
| SEQ ID NO: 345 | DNA VL | cagagcgccctgacccagccagccagcgttagcggtagcccaggccagagcattaccattagctgcaccggcacca gcagcgacgtgggcagctataacctggttagctggtatcagcagcatccgggcaaagcccgaaactgatgatctatg aaggcagcaaacgcccgagcggcgtagcaaccgctttagtggcagcaaaagcggcaacaccgccagcctgaccat |

TABLE 2-continued

Exemplary anti-NPR1 antibody sequences

| | | |
|---|---|---|
| | | tagcggcctgcaagccgaagacgaagccgattattactgctcctcttacggtttccatatcgttgttgttgtgtttggcggc<br>ggtaccaagctgaccgtgctg |
| SEQ ID<br>NO: 346 | Light<br>Chain | QSALTQPASVSGSPGQSITISCTGTSSDVGSYNLVSWYQQHPGKAPKLMIYE<br>GSKRPSGVSNRFSGSKSGNTASLTISGLQAEDEADYYCSSYGFHIVVVVFGG<br>GTKLTVLGQPKAAPSVTLFPPSSEELQANKATLVCLISDFYPGAVTVAWKA<br>DSSPVKAGVETTTPSKQSNNKYAASSYLSLTPEQWKSHRSYSCQVTHEGST<br>VEKTVAPTECS |
| SEQ ID<br>NO: 347 | DNA<br>Light<br>Chain | cagagcgccctgacccagccagccagcgttagcggtagcccaggccagagcattaccattagctgcaccggcacca<br>gcagcgacgtgggcagctataaacctggttagctggtatcagcagcatccggcaaagccccgaaactgatgatcatg<br>aaggcagcaaacgcccgagcggcgttagcaaccgctttagtggcagcaaaagcggcaacaccgccagcctgaccat<br>tagcggcctgcaagccgaagacgaagccgattattactgctcctcttacggtttccatatcgttgttgttgtgtttggcggc<br>ggtaccaagctgaccgtgctgggcagcccaaagccgcccctagcgtgaccctgttcccccaagcagcgaggaac<br>tccaggccaacaaggccaccctcgtgtgcctgatcagcgactttctaccctggcgccgtgaccgtggcctggaaggcc<br>gatagcagcctgtgaaggccggcgtggaaaccaccaccccagcaagcagagcaacaacaaatacgccgccagc<br>agctacctgagcctgacccccgagcagtggaagtcccacagatcctacagctgccaggtcacacacgagggcagca<br>ccgtggaaaagaccgtggcccccaccgagtgcagc |

ZZ17_<br>LALA

| | | |
|---|---|---|
| SEQ ID<br>NO: 418 | HCDR1<br>(Combined) | GFTFSDYAIS |
| SEQ ID<br>NO: 419 | HCDR2<br>(Combined) | SISGGGYHTQYAGSVKG |
| SEQ ID<br>NO: 331 | HCDR3<br>(Combined) | PYLGDRRSYGFDH |
| SEQ ID<br>NO: 420 | HCDR1<br>(Kabat) | DYAIS |
| SEQ ID<br>NO: 419 | HCDR2<br>(Kabat) | SISGGGYHTQYAGSVKG |
| SEQ ID<br>NO: 331 | HCDR3<br>(Kabat) | PYLGDRRSYGFDH |
| SEQ ID<br>NO: 421 | HCDR1<br>(Chothia) | GFTFSDY |
| SEQ ID<br>NO: 422 | HCDR2<br>(Chothia) | SGGGYH |
| SEQ ID<br>NO: 331 | HCDR3<br>(Chothia) | PYLGDRRSYGFDH |
| SEQ ID<br>NO: 423 | HCDR1<br>(IMGT) | GFTFSDYA |
| SEQ ID<br>NO: 424 | HCDR2<br>(IMGT) | ISGGGYHT |
| SEQ ID<br>NO: 332 | HCDR3<br>(IMGT) | ARPYLGDRRSYGFDH |
| SEQ ID<br>NO: 425 | VH | EVQLLESGGGLVQPGGSLRLSCAASGFTFSDYAISWVRQAPGKGLEWVSSI<br>SGGGYHTQYAGSVKGRFTISRDNSKNTLYLQMNSLRAEDTAVYYCARPYL<br>GDRRSYGFDHWGQGTLVTVSS |
| SEQ ID<br>NO: 426 | DNA VH | gaagtgcagctgctggaaagcggtggcggtctggtgcagccaggtggtagcctgcgcctgagctgtgccgcaagcg<br>gctttacctttccgactatgcaatcagctgggtgcgccaagcaccaggcaaaggcctggaatgggtgagcagcatttc<br>cggggggtatcatacacaatatgcaggatccgtgaaaggccgctttaccattagtcgcgataacagcaaaaacac<br>cctgtatctgcaaatgaacagcctgcgggcagaagataccgcagtttattattgcgcgcgaccttatctgggtgaccgtc<br>gtagctatggtttcgaccactgggccagggcaccctggttactgtctcgagc |
| SEQ ID<br>NO: 427 | Heavy<br>Chain | EVQLLESGGGLVQPGGSLRLSCAASGFTFSDYAISWVRQAPGKGLEWVSSI<br>SGGGYHTQYAGSVKGRFTISRDNSKNTLYLQMNSLRAEDTAVYYCARPYL<br>GDRRSYGFDHWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQTYI<br>CNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |

TABLE 2-continued

Exemplary anti-NPR1 antibody sequences

| SEQ ID NO: 428 | DNA Heavy Chain | gaagtgcagctgctggaaagcggtggcggtctggtgcagccaggtggtagcctgcgcctgagctgtgccgcaagcg gctttacctttccgactatgcaatcagctgggtgcgccaagcaccaggcaaaggcctggaatgggtgagcagcattc cgggggggggtatcatacacaatatgcaggatccgtgaaaggccgcttaccattagtcgcgataacagcaaaaacac cctgtatctgcaaatgaacagcctgcgggcagaagataccgcagtttattattgcgcgcgacctatctgggtgaccgtc gtagctatggtttcgaccactggggccagggcaccctggttactgtctcgagcgcgtcgaccaaaggccccagcgtgtt ccctctggccccagcagcaagagcacctctggcggaacagccgccctgggctgcctggtcaaggactacttcccg agcccgtgaccgtgtcctggaactctggcgccctgaccagcggcgtgcacacctttccagccgtgctcagagcag ggcctgtacagcctgagcagcgtcgtgaccgtgcccagcagcagcctgggcacccagacctacatctgcaacgtgaa ccacaagcccagcaacacaaaggtggacaagggggtggaacccaagagctgcgacaagacccacacctgtccccc ctgccctgccctgaagcggcgggaggcccctccgtgttcctgttcccccaaagcctaaggacaccctgatgatcag ccggacccccgaagtgacctgcgtggtggtggacgtgtcccacgaggaccctgaagtgaagtttaattggtacgtgga cggcgtggaagtgcacaacgccaagaccaagcccagagaggaacagtacaacagcacctaccgggtggtgtccgt gctgaccgtgctgcaccaggactggctgaacggcaaagagtacaagtgcaaggtgtccaacaaggccctgcctgccc ccatcgagaaaaccatcagcaaggccaaaggccagccccgcgagcccaggtgtacacactgccccctagccggg aagagatgaccaagaaccaggtgtccctgacctgcctcgtgaaggcttctacccccagcgacattgccgtggaatggg agagcaacggccagcccgagaacaactacaagaccacccccctgtgctggacagcgacgctcattcttctgtac agcaagctgaccgtggacaagagccggtggcagcagggcaacgtgttcagctgctccgtgatgcacgaggccctgc acaaccactacacccagaagtccctgagcctgagccccggcaag |
| SEQ ID NO: 337 | LCDR1 (Combined) | TGTSSDVGSYNLVS |
| SEQ ID NO: 338 | LCDR2 (Combined) | EGSKRPS |
| SEQ ID NO: 339 | LCDR3 (Combined) | SSYGFHIVVVV |
| SEQ ID NO: 337 | LCDR1 (Kabat) | TGTSSDVGSYNLVS |
| SEQ ID NO: 338 | LCDR2 (Kabat) | EGSKRPS |
| SEQ ID NO: 339 | LCDR3 (Kabat) | SSYGFHIVVVV |
| SEQ ID NO: 340 | LCDR1 (Chothia) | TSSDVGSYNL |
| SEQ ID NO: 341 | LCDR2 (Chothia) | EGS |
| SEQ ID NO: 342 | LCDR3 (Chothia) | YGFHIVVV |
| SEQ ID NO: 343 | LCDR1 (IMGT) | SSDVGSYNL |
| SEQ ID NO: 341 | LCDR2 (IMGT) | EGS |
| SEQ ID NO: 339 | LCDR3 (IMGT) | SSYGFHIVVVV |
| SEQ ID NO: 344 | VL | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVL |
| SEQ ID NO: 345 | DNA VL | cagagcgccctgacccagccagccagcgttagcggtagcccaggccagagcattaccattagctgcaccggcacca gcagcgacgtgggcagctataaacctggttagctggtatcagcagcatccgggcaaagcccccgaaactgatgatctatg aaggcagcaaacgcccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctg |
| SEQ ID NO: 346 | Light Chain | QSALTQPASVSGSPGQSITISCTGTSSDVGSYNLVSWYQQHPGKAPKLMIYE GSKRPSGVSNRFSGSKSGNTASLTISGLQAEDEADYYCSSYGFHIVVVVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS |
| SEQ ID NO: 347 | DNA Light Chain | cagagcgccctgacccagccagccagcgttagcggtagcccaggccagagcattaccattagctgcaccggcacca gcagcgacgtgggcagctataaacctggttagctggtatcagcagcatccgggcaaagcccccgaaactgatgatctatg aaggcagcaaacgcccgagcggcgttagcaaccgctttagtggcagcaaaagcggcaacaccgccagcctgaccat tagcggcctgcaagccgaagacgaagccgattattactgctcctcttacggtttccatatcgttgttgttgtgtttggcggc ggtaccaagctgaccgtgctgggcagcccaaagccgcccctagcgtgaccctgttccccccaagcagcgaggaac tccaggccaacaaggccaccctcgtgtgcctgatcagcgacttctaccctggcgccgtgaccgtggcctggaaggcc gatagcagccctgtgaaggccggcgtggaaaccaccacccccagcaagcagagcaacaacaaatacgccgccagc |

TABLE 2-continued

Exemplary anti-NPR1 antibody sequences

```
agctacctgagcctgacccccgagcagtggaagtcccacagatcctacagctgccaggtcacacacgagggcagca
ccgtggaaaagaccgtggcccccaccgagtgcagc
```

For example, WW01_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, WW01_LALA may be defined as comprising or having amino acid sequences of SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, WW01_LALA may be defined as comprising or having amino acid sequences of SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, WW01_LALA may be defined as comprising or having amino acid sequences of SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, WW01_LALA may be defined as comprising or having amino acid sequences of SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, WW01_LALA may be defined as comprising or having a heavy chain variable region comprising or having an amino acid sequence of SEQ ID NO: 13, and a light chain variable region comprising or having an amino acid sequence of SEQ ID NO: 24. In some embodiments, WW01_LALA may be defined as comprising or having a heavy chain comprising or having an amino acid sequence of SEQ ID NO: 15, and a light chain comprising or having an amino acid sequence of SEQ ID NO: 26.

For example, WW03_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, WW03_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, WW03_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, WW03_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3). In some embodiments, WW03_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, WW03_LALA may be defined as comprising or having a heavy chain variable region comprising or having an amino acid sequence of SEQ ID NO: 37, and a light chain variable region comprising or having an amino acid sequence of SEQ ID NO: 48. In some embodiments, WW03_LALA may be defined as comprising or having a heavy chain comprising or having an amino acid sequence of SEQ ID NO: 39, and a light chain comprising or having an amino acid sequence of SEQ ID NO: 50.

For example, WW05_LALA may be defined as having three heavy chain complementarity regions (LCDR1, LCDR2, and LCDR3) selected from: (I) SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (II) SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (III) SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3); or (IV) SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3). In some embodiments, WW05_LALA may be defined as comprising or having amino acid sequences of SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3). In some embodiments, WW05_LALA may be defined as comprising or having amino acid sequences of SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3). In some embodiments, WW05_LALA may be defined as comprising or having amino acid sequences of SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3). In some embodiments, WW05_LALA may be defined as comprising or having amino acid sequences of SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3). In some embodiments, WW05_LALA may be defined as comprising or having a heavy chain variable region comprising or having an amino acid sequence of SEQ ID NO: 61, and a light chain variable region comprising or having an amino acid sequence of SEQ ID NO: 72. In some embodiments, WW05_LALA may be defined as comprising or having a heavy chain comprising or having an amino acid sequence of SEQ ID NO: 63, and a light chain comprising or having an amino acid sequence of SEQ ID NO: 74.

For example, WW06_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3). In some embodiments, WW06_LALA may be defined as comprising or having amino acid sequences of SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3). In some embodiments, WW06_LALA may be defined as comprising or having amino acid sequences of SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3). In some embodiments, WW06_LALA may be defined as comprising or having amino acid sequences of SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3). In some embodiments, WW06_LALA may be defined as comprising or having amino acid sequences of SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3). In some embodiments, WW06_LALA may be defined as comprising or having a heavy chain variable region comprising or having an amino acid sequence of SEQ ID NO: 85, and a light chain variable region comprising or having an amino acid sequence of SEQ ID NO: 96. In some embodiments, WW06_LALA may be defined as comprising or having a heavy chain comprising or having an amino acid sequence of SEQ ID NO: 87, and a light chain comprising or having an amino acid sequence of SEQ ID NO: 98.

For example, XX01_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_LALA may be defined as comprising or having amino acid sequences of SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_LALA may be defined as comprising or having amino acid sequences of SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_LALA may be defined as comprising or having amino acid sequences of SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX01_LALA may be defined as comprising or having amino acid sequences of SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_LALA may be defined as comprising or having a heavy chain variable region comprising or having an amino acid sequence of SEQ ID NO: 103, and a light chain variable region comprising or having an amino acid sequence of SEQ ID NO: 24. In some embodiments, XX01_LALA may be defined as comprising or having a heavy chain comprising or having an amino acid sequence of SEQ ID NO: 105, and a light chain comprising or having an amino acid sequence of SEQ ID NO: 26.

For example, XX01_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_DAPA may be defined as comprising or having amino acid sequences of SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_DAPA may be defined as comprising or having amino acid sequences of SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_DAPA may be defined as comprising or having amino acid sequences of SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX01_DAPA may be defined as comprising or having amino acid sequences of SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_DAPA may be defined as comprising or having a heavy chain variable region comprising or having an amino acid sequence of SEQ ID NO: 103, and a light chain variable region comprising or having an amino acid sequence of SEQ ID NO: 24. In some embodiments, XX01_DAPA may be defined as comprising or having a heavy chain comprising or having an amino acid sequence of SEQ ID NO: 108, and a light chain comprising or having an amino acid sequence of SEQ ID NO: 26.

For example, XX01_N30S_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_N30S_DAPA may be defined as comprising or having amino acid sequences of SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_N30S_DAPA may be defined as comprising or having amino acid sequences of SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX01_N30S_DAPA may be defined as comprising or having amino acid sequences of SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX01_N30S_DAPA may be defined as comprising or having amino acid sequences of SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX01_N30S_DAPA may be defined as comprising or having a heavy chain variable region comprising or having an amino acid sequence of SEQ ID NO: 115, and a light chain variable region comprising or having an amino acid sequence of SEQ ID NO: 24. In some embodiments, XX01_N30S_DAPA may be defined as comprising or having a heavy chain comprising or having an amino acid sequence of SEQ ID NO: 117, and a light chain comprising or having an amino acid sequence of SEQ ID NO: 26.

For example, XX03_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, XX03_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, XX03_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3). In some embodiments, XX03_LALA may be defined as ID NO: 30 (HCDR3), SEQ ID NO: 44 (LCDR1), SEQ ID NO: 45 (LCDR2), and SEQ ID NO: 46 (LCDR3). In some embodiments, XX03_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3). In some embodiments, XX03_LALA may be defined as comprising or having a heavy chain variable region comprising or having an amino acid sequence of SEQ ID NO: 122, and a light chain variable region comprising or having an amino acid sequence of SEQ ID NO: 48. In some embodiments, XX03_LALA may be defined as comprising or having a heavy chain comprising or having an amino acid sequence of SEQ ID NO: 124, and a light chain comprising or having an amino acid sequence of SEQ ID NO: 50.

For example, XX04_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX04_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX04_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX04_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3). In some embodiments, XX04_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47

(LCDR1), SEQ ID NO: 45 (LCDR2), and SEQ ID NO: 126 (LCDR3). In some embodiments, XX04_LALA may be defined as comprising or having a heavy chain variable region comprising or having an amino acid sequence of SEQ ID NO: 37, and a light chain variable region comprising or having an amino acid sequence of SEQ ID NO: 128. In some embodiments, XX04_LALA may be defined as comprising or having a heavy chain comprising or having an amino acid sequence of SEQ ID NO: 39, and a light chain comprising or having an amino acid sequence of SEQ ID NO: 130.

For example, XX06_LALA may be defined as having three heavy chain complementarity regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX06_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_LALA may be defined as comprising or having a heavy chain variable region comprising or having an amino acid sequence of SEQ ID NO: 37, and a light chain variable region comprising or having an amino acid sequence of SEQ ID NO: 136. In some embodiments, XX06_LALA may be defined as comprising or having a heavy chain comprising or having an amino acid sequence of SEQ ID NO: 39, and a light chain comprising or having an amino acid sequence of SEQ ID NO: 138.

For example, XX06_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_DAPA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_DAPA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX06_DAPA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX06_DAPA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX06_DAPA may be defined as comprising or having a heavy chain variable region comprising or having an amino acid sequence of SEQ ID NO: 37, and a light chain variable region comprising or having an amino acid sequence of SEQ ID NO: 136. In some embodiments, XX06_DAPA may be defined as comprising or having a heavy chain comprising or having an amino acid sequence of SEQ ID NO: 141, and a light chain comprising or having an amino acid sequence of SEQ ID NO: 138.

For example, XX07_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX07_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX07_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX07_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3). In some embodiments, XX07_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX07_LALA may be defined as comprising or having a heavy chain variable region comprising or having an amino acid sequence of SEQ ID NO: 37, and a light chain variable region comprising or having an amino acid sequence of SEQ ID NO: 147. In some embodiments, XX07_LALA may be defined as comprising or having a heavy chain comprising or having an amino acid sequence of SEQ ID NO: 39, and a light chain comprising or having an amino acid sequence of SEQ ID NO: 149.

For example, XX08_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_LALA may be defined as comprising or having amino acid sequences of SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_LALA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_LALA may be defined as comprising or having amino acid sequences of SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_LALA may be defined as comprising or having amino acid sequences of SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_LALA may be defined as comprising or having a heavy chain variable region comprising or having an amino acid sequence of SEQ ID NO: 154, and a light chain variable region comprising or having an amino acid sequence of SEQ ID NO: 24. In some embodiments, XX08_LALA may be defined as comprising or having a heavy chain comprising or having an amino acid sequence of SEQ ID NO: 156, and a light chain comprising or having an amino acid sequence of SEQ ID NO: 26.

For example, XX08_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_DAPA may be defined as comprising or having amino acid sequences of SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_DAPA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_DAPA may be defined as comprising or having amino acid sequences of SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_DAPA may be defined as comprising or having amino acid sequences of SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_DAPA may be defined as comprising or having a heavy chain variable region comprising or having an amino acid sequence of SEQ ID NO: 154, and a light chain variable region comprising or having an amino acid sequence of SEQ ID NO: 24. In some embodiments, XX08_DAPA may be defined as comprising or having a heavy chain comprising or having an amino acid sequence of SEQ ID NO: 159, and a light chain comprising or having an amino acid sequence of SEQ ID NO: 26.

For example, XX08_N30S_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30S_DAPA may be defined as comprising or having amino acid sequences of SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08 N30S_DAPA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30S_DAPA may be defined as comprising or having amino acid sequences of SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_N30S_DAPA may be defined as comprising or having amino acid sequences of SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30S_DAPA may be defined as comprising or having a heavy chain variable region comprising or having an amino acid sequence of SEQ ID NO: 161, and a light chain variable region comprising or having an amino acid sequence of SEQ ID NO: 24. In some embodiments, XX08_N30S_DAPA may be defined as comprising or having a heavy chain comprising or having an amino acid sequence of SEQ ID NO: 163, and a light chain comprising or having an amino acid sequence of SEQ ID NO: 26.

For example, XX08_N30Q_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30Q_DAPA may be defined as comprising or having amino acid sequences of SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30Q_DAPA may be defined as comprising or having amino acid sequences of SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3). In some embodiments, XX08_N30Q_DAPA may be defined as comprising or having amino acid sequences of SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3). In some embodiments, XX08_N30Q_DAPA may be defined as comprising or having amino acid sequences of SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3). In some embodiments, XX08_N30Q_DAPA may be defined as comprising or having a heavy chain variable region comprising or having an amino acid sequence of SEQ ID NO: 168, and a light chain variable region comprising or having an amino acid sequence of SEQ ID NO: 24. In some embodiments, XX08_N30Q_DAPA may be defined as comprising or having a heavy chain comprising or having an amino acid sequence of SEQ ID NO: 170, and a light chain comprising or having an amino acid sequence of SEQ ID NO: 26.

For example, XX09_LALA may be defined as having three heavy chain complementarity regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX09_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX09_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX09_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX09_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX09_LALA may be defined as comprising or having a heavy chain variable region comprising or having an amino acid sequence of SEQ ID NO: 37, and a light chain variable region comprising or having an amino acid sequence of SEQ ID NO: 174. In some embodiments, XX09_LALA may be defined as comprising or having a heavy chain comprising or having an amino acid sequence of SEQ ID NO: 39, and a light chain comprising or having an amino acid sequence of SEQ ID NO: 176.

For example, XX11_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX11_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX11_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX11_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3). In some embodiments, XX11_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX11_LALA may be defined as comprising or having a heavy chain variable region comprising or having an amino acid sequence of SEQ ID NO: 37, and a light chain variable region comprising or having an amino acid sequence of SEQ ID NO: 180. In some embodiments, XX11_LALA may be defined as comprising or having a heavy chain comprising or having an amino acid sequence of SEQ ID NO: 39, and a light chain comprising or having an amino acid sequence of SEQ ID NO: 182.

For example, XX12_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX12_LALA may be defined as comprising or having amino acid sequences of SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX12_LALA may be defined as comprising or having amino acid sequences of SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX12_LALA may be defined as comprising or having amino acid sequences of SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3). In some embodiments, XX12_LALA may be defined as comprising or having amino acid sequences of SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX12_LALA may be defined as comprising or having a heavy chain variable region comprising or having an amino acid sequence of SEQ ID NO: 37, and a light chain variable region comprising or having an amino acid sequence of SEQ ID NO: 186. In some embodiments, XX12_LALA may be defined as comprising or having a heavy chain comprising or having an amino acid sequence of SEQ ID NO: 39, and a light chain comprising or having an amino acid sequence of SEQ ID NO: 188.

For example, XX13_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX13_LALA may be defined as comprising or having amino acid sequences of SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX13_LALA may be defined as comprising or having amino acid sequences of SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX13_LALA may be defined as comprising or having amino acid sequences of SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX13_LALA may be defined as comprising or having amino acid sequences of SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX13_LALA may be defined as comprising or having a heavy chain variable region comprising or having an amino acid sequence of SEQ ID NO: 193, and a light chain variable region comprising or having an amino acid sequence of SEQ ID NO: 136. In some embodiments, XX13_LALA may be defined as comprising or having a heavy chain comprising or having an amino acid sequence of SEQ ID NO: 195, and a light chain comprising or having an amino acid sequence of SEQ ID NO: 138.

For example, XX14_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX14_LALA may be defined as comprising or having amino acid sequences of SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX14_LALA may be defined as comprising or having amino acid sequences of SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX14_LALA may be defined as comprising or having amino acid sequences of SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX14_LALA may be defined as comprising or having amino acid sequences of SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX14_LALA may be defined as comprising or having a heavy chain variable region comprising or having an amino acid sequence of SEQ ID NO: 193, and a light chain variable region comprising or having an amino acid sequence of SEQ ID NO: 174. In some embodiments, XX14_LALA may be defined as comprising or having a heavy chain comprising or having an amino acid sequence of SEQ ID NO: 195, and a light chain comprising or having an amino acid sequence of SEQ ID NO: 176.

For example, XX15_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_LALA may be defined as ID NO: 30 (HCDR3), SEQ ID NO: 44 (LCDR1), SEQ ID NO: 45 (LCDR2), and SEQ ID NO: 127 (LCDR3). In some embodiments, XX15_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_LALA may be defined as comprising or having a heavy chain variable region comprising or having an amino acid sequence of SEQ ID NO: 201, and a light chain variable region comprising or having an amino acid sequence of SEQ ID NO: 128. In some embodiments, XX15_LALA may be defined as comprising or having a heavy chain comprising or having an amino acid sequence of SEQ ID NO: 203, and a light chain comprising or having an amino acid sequence of SEQ ID NO: 130.

For example, XX15_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3). In some embodiments, XX15_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3). In some embodiments, XX15_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3). In some embodiments, XX15_DAPA may be defined as comprising or having a heavy chain variable region comprising or having an amino acid sequence of SEQ ID NO: 122, and a light chain variable region comprising or having an amino acid sequence of SEQ ID NO: 128. In some embodiments, XX15_DAPA may be defined as comprising or having a heavy chain comprising or having an amino acid sequence of SEQ ID NO: 208, and a light chain comprising or having an amino acid sequence of SEQ ID NO: 130.

For example, XX16_LALA may be defined as having three heavy chain complementarity regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX16_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_LALA may be defined as comprising or having a heavy chain variable region comprising or having an amino acid sequence of SEQ ID NO: 201, and a light chain variable region comprising or having an amino acid sequence of SEQ ID NO: 136. In some embodiments, XX16_LALA may be defined as comprising or having a heavy chain comprising or having an amino acid sequence of SEQ ID NO: 203, and a light chain comprising or having an amino acid sequence of SEQ ID NO: 138.

For example, XX16_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3). In some embodiments, XX16_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3). In some embodiments, XX16_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3). In some embodiments, XX16_DAPA may be defined as comprising or having a heavy chain variable region comprising or having an amino acid sequence of SEQ ID NO: 122, and a light chain variable region comprising or having an amino acid sequence of SEQ ID NO: 136. In some embodiments, XX16_DAPA may be defined as comprising or having a heavy chain comprising or having an amino acid sequence of SEQ ID NO: 208, and a light chain comprising or having an amino acid sequence of SEQ ID NO: 138.

For example, XX17_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3). In some embodiments, XX17_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_LALA may be defined as comprising or having a heavy chain variable region comprising or having an amino acid sequence of SEQ ID NO: 201, and a light chain variable region comprising or having an amino acid sequence of SEQ ID NO: 147. In some embodiments, XX17_LALA may be defined as comprising or having a heavy chain comprising or having an amino acid sequence of SEQ ID NO: 203, and a light chain comprising or having an amino acid sequence of SEQ ID NO: 149.

For example, XX17_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3). In some embodiments, XX17_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3). In some embodiments, XX17_DAPA may be defined as comprising or having amino acid sequences of (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3). In some embodiments, XX17_DAPA may be defined as comprising or having a heavy chain variable region comprising or having an amino acid sequence of SEQ ID NO: 122, and a light chain variable region comprising or having an amino acid sequence of SEQ ID NO: 147. In some embodiments, XX17_DAPA may be defined as comprising or having a heavy chain comprising or having an amino acid sequence of SEQ ID NO: 208, and a light chain comprising or having an amino acid sequence of SEQ ID NO: 149.

For example, XX18_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3). In some embodiments, XX18_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_LALA may be defined as comprising or having a heavy chain variable region comprising or having an amino acid sequence of SEQ ID NO: 201, and a light chain variable region comprising or having an amino acid sequence of SEQ ID NO: 174. In some embodiments, XX18_LALA may be defined as comprising or having a heavy chain comprising or having an amino acid sequence of SEQ ID NO: 203, and a light chain comprising or having an amino acid sequence of SEQ ID NO: 176.

For example, XX18_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3). In some embodiments, XX18_DAPA may be defined as ID NO: 30 (HCDR3), SEQ ID NO: 44 (LCDR1), SEQ ID NO: 45 (LCDR2), and SEQ ID NO: 173 (LCDR3). In some embodiments, XX18_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3). In some embodiments, XX18_DAPA may be defined as comprising or having a heavy chain variable region comprising or having an amino acid sequence of SEQ ID NO: 122, and a light chain variable region comprising or having an amino acid sequence of SEQ ID NO: 174. In some embodiments, XX18_DAPA may be defined as comprising or having a heavy chain comprising or having an amino acid sequence of SEQ ID NO: 208, and a light chain comprising or having an amino acid sequence of SEQ ID NO: 176.

For example, XX19_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3). In some embodiments, XX19_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_LALA may be defined as comprising or having a heavy chain variable region comprising or having an amino acid sequence of SEQ ID NO: 201, and a light chain variable region comprising or having an amino acid sequence of SEQ ID NO: 180. In some embodiments, XX19_LALA may be defined as comprising or having a heavy chain comprising or having an amino acid sequence of SEQ ID NO: 203, and a light chain comprising or having an amino acid sequence of SEQ ID NO: 182.

For example, XX19_DAPA may be defined as having three heavy chain complementarity regions (LCDR1, LCDR2, and LCDR3) selected from: (I) SEQ ID NO: 28

(HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3). In some embodiments, XX19_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3). In some embodiments, XX19_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3). In some embodiments, XX19_DAPA may be defined as comprising or having a heavy chain variable region comprising or having an amino acid sequence of SEQ ID NO: 122, and a light chain variable region comprising or having an amino acid sequence of SEQ ID NO: 180. In some embodiments, XX19_DAPA may be defined as comprising or having a heavy chain comprising or having an amino acid sequence of SEQ ID NO: 208, and a light chain comprising or having an amino acid sequence of SEQ ID NO: 182.

For example, XX20_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_LALA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_LALA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_LALA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3). In some embodiments, XX20_LALA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_LALA may be defined as comprising or having a heavy chain variable region comprising or having an amino acid sequence of SEQ ID NO: 201, and a light chain variable region comprising or having an amino acid sequence of SEQ ID NO: 186. In some embodiments, XX20_LALA may be defined as comprising or having a heavy chain comprising or having an amino acid sequence of SEQ ID NO: 203, and a light chain comprising or having an amino acid sequence of SEQ ID NO: 188.

For example, XX20_DAPA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_DAPA may be defined as comprising or having amino acid sequences of SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_DAPA may be defined as comprising or having amino acid sequences of SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3). In some embodiments, XX20_DAPA may be defined as comprising or having amino acid sequences of SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3). In some embodiments, XX20_DAPA may be defined as comprising or having amino acid sequences of SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3). In some embodiments, XX20_DAPA may be defined as comprising or having a heavy chain variable region comprising or having an amino acid sequence of SEQ ID NO: 122, and a light chain variable region comprising or having an amino acid sequence of SEQ ID NO: 186. In some embodiments, XX20_DAPA may be defined as comprising or having a heavy chain comprising or having an amino acid sequence of SEQ ID NO: 208, and a light chain comprising or having an amino acid sequence of SEQ ID NO: 188.

For example, YY01_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, YY01_LALA may be defined as comprising or having amino acid sequences of SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, YY01_LALA may be defined as comprising or having amino acid sequences of SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, YY01_LALA may be defined as comprising or having amino acid sequences of SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3). In some embodiments, YY01_LALA may be defined as comprising or having amino acid sequences of SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, YY01_LALA may be defined as comprising or having a heavy chain variable region comprising or having an amino acid sequence of SEQ ID NO: 233, and a light chain variable region comprising or having an amino acid sequence of SEQ ID NO: 244. In some embodiments, YY01_LALA may be defined as comprising or having a heavy chain comprising or having an amino acid sequence of SEQ ID NO: 235, and a light chain comprising or having an amino acid sequence of SEQ ID NO: 246.

For example, YY02_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 248 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3); (II) SEQ ID NO: 251 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3); (III) SEQ ID NO: 32 (HCDR1), SEQ ID NO: 252 (HCDR2), SEQ ID NO: 250 (HCDR3), SEQ ID NO: 263 (LCDR1), SEQ ID NO: 241 (LCDR2), and SEQ ID NO: 264 (LCDR3); or (IV) SEQ ID NO: 253 (HCDR1), SEQ ID NO: 254 (HCDR2), SEQ ID NO: 255 (HCDR3), SEQ ID NO: 265 (LCDR1), SEQ ID NO: 241 (LCDR2), and SEQ ID NO: 262 (LCDR3). In some embodiments, YY02_LALA may be defined as comprising or having amino acid sequences of SEQ ID NO: 248 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3). In some embodiments, YY02_LALA may be defined as comprising or having amino acid sequences of SEQ ID NO: 251 (HCDR1), SEQ ID NO: 249 (HCDR2), SEQ ID NO: 250 (HCDR3), SEQ ID NO: 260 (LCDR1), SEQ ID NO: 261 (LCDR2), and SEQ ID NO: 262 (LCDR3). In some embodiments, YY02_LALA may be defined as comprising or having amino acid sequences of SEQ ID NO: 32 (HCDR1), SEQ ID NO: 252 (HCDR2), SEQ ID NO: 250 (HCDR3), SEQ ID NO: 263 (LCDR1), SEQ ID NO: 241 (LCDR2), and SEQ ID NO: 264 (LCDR3). In some embodiments, YY02_LALA may be defined as comprising or having amino acid sequences of SEQ ID NO: 253 (HCDR1), SEQ ID NO: 254 (HCDR2), SEQ ID NO: 255 (HCDR3), SEQ ID NO: 265 (LCDR1), SEQ ID NO: 241 (LCDR2), and SEQ ID NO: 262 (LCDR3). In some embodiments, YY02_LALA may be defined as comprising or having a heavy chain variable region comprising or having an amino acid sequence of SEQ ID NO: 256, and a light chain variable region comprising or having an amino acid sequence of SEQ ID NO: 266. In some embodiments, YY02_LALA may be defined as comprising or having a heavy chain comprising or having an amino acid sequence of SEQ ID NO: 258, and a light chain comprising or having an amino acid sequence of SEQ ID NO: 268.

For example, YY03_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (II) SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (III) SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3); or (IV) SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3). In some embodiments, YY03_LALA may be defined as comprising or having amino acid sequences of SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3). In some embodiments, YY03_LALA may be defined as comprising or having amino acid sequences of SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3). In some embodiments, YY03_LALA may be defined as comprising or having amino acid sequences of SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3). In some embodiments, YY03_LALA may be defined as comprising or having amino acid sequences of SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3). In some embodiments, YY03_LALA may be defined as comprising or having a heavy chain variable region comprising or having an amino acid sequence of SEQ ID NO: 278, and a light chain variable region comprising or having an amino acid sequence of SEQ ID NO: 287. In some embodiments, YY03_LALA may be defined as comprising or having a heavy chain comprising or having an amino acid sequence of SEQ ID NO: 280, and a light chain comprising or having an amino acid sequence of SEQ ID NO: 289.

For example, YY04_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (II) SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (III) SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3); or (IV) SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3). In some embodiments, YY04_LALA may be defined as comprising or having amino acid sequences of SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3). In some embodiments, YY04_LALA may be defined as comprising or having amino acid sequences of SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3). In some embodiments, YY04_LALA may be defined as comprising or having amino acid sequences of SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3). In some embodiments, YY04_LALA may be defined as comprising or having amino acid sequences of SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3). In some embodiments, YY04_LALA may be defined as comprising or having a heavy chain variable region comprising or having an amino acid sequence of SEQ ID NO: 300, and a light chain variable region comprising or having an amino acid sequence of SEQ ID NO: 306. In some embodiments, YY04_LALA may be defined as comprising or having a heavy chain comprising or having an amino acid sequence of SEQ ID NO: 302, and a light chain comprising or having an amino acid sequence of SEQ ID NO: 308.

For example, YY05_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (II) SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (III) SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3); or (IV) SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3). In some embodiments, YY05_LALA may be defined as comprising or having amino acid sequences of SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3). In some embodiments, YY05_LALA may be defined as comprising or having amino acid sequences of SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3). In some embodiments, YY05_LALA may be defined as comprising or having amino acid sequences of SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3). In some embodiments, YY05_LALA may be defined as comprising or having amino acid sequences of SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3). In some embodiments, YY05_LALA may be defined as comprising or having a heavy chain variable region comprising or having an amino acid sequence of SEQ ID NO: 316, and a light chain variable region comprising or having an amino acid sequence of SEQ ID NO: 327. In some embodiments, YY05_LALA may be defined as comprising or having a heavy chain comprising or having an amino acid sequence of SEQ ID NO: 318, and a light chain comprising or having an amino acid sequence of SEQ ID NO: 329.

For example, YY06_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, YY06_LALA may be defined as comprising or having amino acid sequences of SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, YY06_LALA may be defined as comprising or having amino acid sequences of SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, YY06_LALA may be defined as comprising or having amino acid sequences of SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, YY06_LALA may be defined as comprising or having amino acid sequences of SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, YY06_LALA may be defined as comprising or having a heavy chain variable region comprising or having an amino acid sequence of SEQ ID NO: 333, and a light chain variable region comprising or having an amino acid sequence of SEQ ID NO: 344. In some embodiments, YY06_LALA may be defined as comprising or having a heavy chain comprising or having an amino acid sequence of SEQ ID NO: 335, and a light chain comprising or having an amino acid sequence of SEQ ID NO: 346.

For example, YY07_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3). In some embodiments, YY07_LALA may be defined as comprising or having amino acid sequences of SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3). In some embodiments, YY07_LALA may be defined as comprising or having amino acid sequences of SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3). In some embodiments, YY07_LALA may be defined as comprising or having amino acid sequences of SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3). In some embodiments, YY07_LALA may be defined as comprising or having amino acid sequences of SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3). In some embodiments, YY07_LALA may be defined as comprising or having a heavy chain variable region comprising or having an amino acid sequence of SEQ ID NO: 350, and a light chain variable region comprising or having an amino acid sequence of SEQ ID NO: 357. In some embodiments, YY07_LALA may be defined as comprising or having a heavy chain comprising or having an amino acid sequence of SEQ ID NO: 352, and a light chain comprising or having an amino acid sequence of SEQ ID NO: 359.

For example, ZZ05_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3). In some embodiments, ZZ05_LALA may be defined as comprising or having amino acid sequences of SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3). In some embodiments, ZZ05_LALA may be defined as comprising or having amino acid sequences of SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3). In some embodiments, ZZ05_LALA may be defined as comprising or having amino acid sequences of SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3). In some embodiments, ZZ05_LALA may be defined as comprising or having amino acid sequences of SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3). In some embodiments, ZZ05_LALA may be defined as comprising or having a heavy chain variable region comprising or having an amino acid sequence of SEQ ID NO: 350, and a light chain variable region comprising or having an amino acid sequence of SEQ ID NO: 363. In some embodiments, ZZ05_LALA may be defined as comprising or having a heavy chain comprising or having an amino acid sequence of SEQ ID NO: 352, and a light chain comprising or having an amino acid sequence of SEQ ID NO: 365.

For example, ZZ12_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ12_LALA may be defined as comprising or having amino acid sequences of SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ12_LALA may be defined as comprising or having amino acid sequences of SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ12_LALA may be defined as comprising or having amino acid sequences of SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3). In some embodiments, ZZ12_LALA may be defined as comprising or having amino acid sequences of SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ12_LALA may be defined as comprising or having a heavy chain variable region comprising or having an amino acid sequence of SEQ ID NO: 374, and a light chain variable region comprising or having an amino acid sequence of SEQ ID NO: 244. In some embodiments, ZZ12_LALA may be defined as comprising or having a heavy chain comprising or having an amino acid sequence of SEQ ID NO: 376, and a light chain comprising or having an amino acid sequence of SEQ ID NO: 246.

For example, ZZ13_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ13_LALA may be defined as comprising or having amino acid sequences of SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ13_LALA may be defined as comprising or having amino acid sequences of SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3). In some embodiments, ZZ13_LALA may be defined as comprising or having amino acid sequences of SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3). In some embodiments, ZZ13_LALA may be defined as comprising or having amino acid sequences of (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3). In some embodiments, ZZ13_LALA may be defined as comprising or having a heavy chain variable region comprising or having an amino acid sequence of SEQ ID NO: 385, and a light chain variable region comprising or having an amino acid sequence of SEQ ID NO: 244. In some embodiments, ZZ13_LALA may be defined as comprising or having a heavy chain comprising or having an amino acid sequence of SEQ ID NO: 387, and a light chain comprising or having an amino acid sequence of SEQ ID NO: 246.

For example, ZZ14_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ14_LALA may be defined as comprising or having amino acid sequences of SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ14_LALA may be defined as comprising or having amino acid sequences of SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ14_LALA may be defined as comprising or having amino acid sequences of SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ14_LALA may be defined as comprising or having amino acid sequences of SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ14_LALA may be defined as comprising or having a heavy chain variable region comprising or having an amino acid sequence of SEQ ID NO: 392, and a light chain variable region comprising or having an amino acid sequence of SEQ ID NO: 344. In some embodiments, ZZ14_LALA may be defined as comprising or having a heavy chain comprising or having an amino acid sequence of SEQ ID NO: 394, and a light chain comprising or having an amino acid sequence of SEQ ID NO: 346.

For example, ZZ15_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 396 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 398 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 399 (HCDR1), SEQ ID NO: 400 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 401 (HCDR1), SEQ ID NO: 402 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ15_LALA may be defined as comprising or having amino acid sequences of SEQ ID NO: 396 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ15_LALA may be defined as comprising or having amino acid sequences of SEQ ID NO: 398 (HCDR1), SEQ ID NO: 397 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ15_LALA may be defined as comprising or having amino acid sequences of SEQ ID NO: 399 (HCDR1), SEQ ID NO: 400 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ15_LALA may be defined as comprising or having amino acid sequences of SEQ ID NO: 401 (HCDR1), SEQ ID NO: 402 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ15_LALA may be defined as comprising or having a heavy chain variable region comprising or having an amino acid sequence of SEQ ID NO: 403, and a light chain variable region comprising or having an amino acid sequence of SEQ ID NO: 344. In some embodiments, ZZ15_LALA may be defined as comprising or having a heavy chain comprising or having an amino acid sequence of SEQ ID NO: 405, and a light chain comprising or having an amino acid sequence of SEQ ID NO: 346.

For example, ZZ16_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ16_LALA may be defined as comprising or having amino acid sequences of SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ16_LALA may be defined as comprising or having amino acid sequences of SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ16_LALA may be defined as comprising or having amino acid sequences of SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ16_LALA may be defined as comprising or having amino acid sequences of SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ16_LALA may be defined as comprising or having a heavy chain variable region comprising or having an amino acid sequence of SEQ ID NO: 414, and a light chain variable region comprising or having an amino acid sequence of SEQ ID NO: 344. In some embodiments, ZZ16_LALA may be defined as comprising or having a heavy chain comprising or having an amino acid sequence of SEQ ID NO: 416, and a light chain comprising or having an amino acid sequence of SEQ ID NO: 346.

For example, ZZ17_LALA may be defined as having three heavy chain complementarity determining regions (HCDR1, HCDR2, and HCDR3) and three light chain complimentarity determining regions (LCDR1, LCDR2, and LCDR3) selected from: (I) SEQ ID NO: 418 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 420 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 421 (HCDR1), SEQ ID NO: 422 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 423 (HCDR1), SEQ ID NO: 424 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ17_LALA may be defined as comprising or having amino acid sequences of SEQ ID NO: 418 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ17_LALA may be defined as comprising or having amino acid sequences of SEQ ID NO: 420 (HCDR1), SEQ ID NO: 419 (HCDR2), SEQ ID NO: 331 (HCDR3), SEQ ID NO: 337 (LCDR1), SEQ ID NO: 338 (LCDR2), and SEQ ID NO: 339 (LCDR3). In some embodiments, ZZ17_LALA may be defined as comprising or having amino acid sequences of SEQ ID NO: 421 (HCDR1), SEQ ID NO: 422 (HCDR2), SEQ ID NO: 331 (HCDR3), SEQ ID NO: 340 (LCDR1), SEQ ID NO: 341 (LCDR2), and SEQ ID NO: 342 (LCDR3). In some embodiments, ZZ17_LALA may be defined as comprising or having amino acid sequences of SEQ ID NO: 423 (HCDR1), SEQ ID NO: 424 (HCDR2), SEQ ID NO: 332 (HCDR3), SEQ ID NO: 343 (LCDR1), SEQ ID NO: 341 (LCDR2), and SEQ ID NO: 339 (LCDR3). In some embodiments, ZZ17_LALA may be defined as comprising or having a heavy chain variable region comprising or having an amino acid sequence of SEQ ID NO: 425, and a light chain variable region comprising or having an amino acid sequence of SEQ ID NO: 344. In some embodiments, ZZ17_LALA may be defined as comprising or having a heavy chain comprising or having an amino acid sequence of SEQ ID NO: 427, and a light chain comprising or having an amino acid sequence of SEQ ID NO: 346.

In some embodiments, the antibody or antigen binding fragment comprises a heavy chain variable region comprising or having an amino acid sequence of SEQ ID NO: 13 or a sequence having at least 95%, 96%, 97%, 98%, or 99% identity with SEQ ID NO: 13, and a light chain variable region comprising or having an amino acid sequence of SEQ ID NO: 24 or a sequence having at least 95%, 96%, 97%, 98%, or 99% identity with SEQ ID NO: 24. In some other embodiments, the antibody or antigen binding fragment comprises a heavy chain comprising or having an amino acid sequence of SEQ ID NO: 15 or a sequence having at least 95%, 96%, 97%, 98%, or 99% identity with SEQ ID NO: 15, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 48 or a sequence having at least 95%, 96%, 97%, 98%, or 99% identity with SEQ ID NO: 48. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 50 or a sequence having at least 95%, 96%, 97%, 98%, or 99% identity with SEQ ID NO: 50.

In some embodiments, the antibody or antigen binding fragment comprises a heavy chain variable region comprising or having an amino acid sequence of SEQ ID NO: 61 or a sequence having at least 95%, 96%, 97%, 98%, or 99% identity with SEQ ID NO: 61, and a light chain variable region comprising or having an amino acid sequence of SEQ ID NO: 72 or a sequence having at least 95%, 96%, 97%, 98%, or 99% identity with SEQ ID NO: 72. In some embodiments, the antibody or antigen binding fragment comprises a heavy chain comprising or having an amino acid sequence of SEQ ID NO: 63 or a sequence having at least 95%, 96%, 97%, 98%, or 99% identity with SEQ ID NO: 63, and a light chain comprising or having an amino acid sequence of SEQ ID NO: 74 or a sequence having at least 95%, 96%, 97%, 98%, or 99% identity with SEQ ID NO: 74.

In some embodiments, the antibody or antigen binding fragment comprises a heavy chain variable region comprising or having an amino acid sequence of SEQ ID NO: 85 or a sequence having at least 95%, 96%, 97%, 98%, or 99% identity with SEQ ID NO: 85, and a light chain variable region comprising or having an amino acid sequence of SEQ ID NO: 96 or a sequence having at least 95%, 96%, 97%, 98%, or 99% identity with SEQ ID NO: 96. In some embodiments, the antibody or antigen binding fragment comprises a heavy chain comprising or having an amino acid sequence of SEQ ID NO: 87 or a sequence having at least 95%, 96%, 97%, 98%, or 99% identity with SEQ ID NO: 87, and a light chain comprising or having an amino acid sequence of SEQ ID NO: 98 or a sequence having at least 95%, 96%, 97%, 98%, or 99% identity with SEQ ID NO: 98.

In some embodiments, the antibody or antigen binding fragment comprises a heavy chain variable region comprising or having an amino acid sequence of SEQ ID NO: 103 or a sequence having at least 95%, 96%, 97%, 98%, or 99% identity with SEQ ID NO: 103, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 105 or a sequence having at least 95%, 96%, 97%, 98%, or 99% identity with SEQ ID NO: 105, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 103 or a sequence having at least 95%, 96%, 97%, 98%, or 99% identity with SEQ ID NO: 103, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 108 or a sequence having at least 95%, 96%, 97%, 98%, or 99% identity with SEQ ID NO: 108, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 115 or a sequence having at least 95%, 96%, 97%, 98%, or 99% identity with SEQ ID NO: 115, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 117 or a sequence having at least 95%, 96%, 97%, 98%, or 99% identity with SEQ ID NO: 117, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 48 or a sequence having at least 95%, 96%, 97%, 98%, or 99% identity with SEQ ID NO: 48. In some embodiments, the antibody or antigen binding fragment comprises a heavy chain comprising or having an amino acid sequence of SEQ ID NO: 124 or a sequence having at least 95%, 96%, 97%, 98%, or 99% identity with SEQ ID NO: 124, and a light chain comprising or having an amino acid sequence of SEQ ID NO: 50 or a sequence having at least 95%, 96%, 97%, 98%, or 99% identity with SEQ ID NO: 50.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 128 or a sequence having at least 95%, 96%, 97%, 98%, or 99% identity with SEQ ID NO: 128. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 130 or a sequence having at least 95%, 96%, 97%, 98%, or 99% identity with SEQ ID NO: 130.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 141 or a sequence having at least 95%, 96%, 97%, 98%, or 99% identity with SEQ ID NO: 141, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 147 or a sequence having at least 95%, 96%, 97%, 98%, or 99% identity with SEQ ID NO: 147. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 149 or a sequence having at least 95%, 96%, 97%, 98%, or 99% identity with SEQ ID NO: 149.

In some embodiments, the antibody or antigen binding fragment comprises a heavy chain variable region comprising or having an amino acid sequence of SEQ ID NO: 154 or a sequence having at least 95%, 96%, 97%, 98%, or 99% identity with SEQ ID NO: 154, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 156 or a sequence having at least 95%, 96%, 97%, 98%, or 99% identity with SEQ ID NO: 156, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 154 or a sequence having at least 95%, 96%, 97%, 98%, or 99% identity with SEQ ID NO: 154, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 159 or a sequence having at least 95%, 96%, 97%, 98%, or 99% identity with SEQ ID NO: 159, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 161 or a sequence having at least 95%, 96%, 97%, 98%, or 99% identity with SEQ ID NO: 161, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 163 or a sequence having at least 95%, 96%, 97%, 98%, or 99% identity with SEQ ID NO: 163, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 168 or a sequence having at least 95%, 96%, 97%, 98%, or 99% identity with SEQ ID NO: 168, and a light chain variable region comprising or having an amino acid sequence of SEQ ID NO: 24 or a sequence having at least 95%, 96%, 97%, 98%, or 99% identity with SEQ ID NO: 24. In some embodiments, the antibody or antigen binding fragment comprises a heavy chain comprising or having an amino acid sequence of SEQ ID NO: 170 or a sequence having at least 95%, 96%, 97%, 98%, or 99% identity with SEQ ID NO: 170, and a light chain comprising or having an amino acid sequence of SEQ ID NO: 26 or a sequence having at least 95%, 96%, 97%, 98%, or 99% identity with SEQ ID NO: 26.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 180 or a sequence having at least 95%, 96%, 97%, 98%, or 99% identity with SEQ ID NO: 180. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 182 or a sequence having at least 95%, 96%, 97%, 98%, or 99% identity with SEQ ID NO: 182.

In some embodiments, the antibody or antigen binding fragment comprises a heavy chain variable region comprising or having an amino acid sequence of SEQ ID NO: 37 or a sequence having at least 95%, 96%, 97%, 98%, or 99% identity with SEQ ID NO: 37, and a light chain variable region comprising or having an amino acid sequence of SEQ ID NO: 186 or a sequence having at least 95%, 96%, 97%, 98%, or 99% identity with SEQ ID NO: 186. In some embodiments, the antibody or antigen binding fragment comprises a heavy chain comprising or having an amino acid sequence of SEQ ID NO: 39 or a sequence having at least 95%, 96%, 97%, 98%, or 99% identity with SEQ ID NO: 39, and a light chain comprising or having an amino acid sequence of SEQ ID NO: 188 or a sequence having at least 95%, 96%, 97%, 98%, or 99% identity with SEQ ID NO: 188.

In some embodiments, the antibody or antigen binding fragment comprises a heavy chain variable region comprising or having an amino acid sequence of SEQ ID NO: 193 or a sequence having at least 95%, 96%, 97%, 98%, or 99% identity with SEQ ID NO: 193, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 195 or a sequence having at least 95%, 96%, 97%, 98%, or 99% identity with SEQ ID NO: 195, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 193 or a sequence having at least 95%, 96%, 97%, 98%, or 99% identity with SEQ ID NO: 193, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 195 or a sequence having at least 95%, 96%, 97%, 98%, or 99% identity with SEQ ID NO: 195, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 128 or a sequence having at least 95%, 96%, 97%, 98%, or 99% identity with SEQ ID NO: 128. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 130 or a sequence having at least 95%, 96%, 97%, 98%, or 99% identity with SEQ ID NO: 130.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 128 or a sequence having at least 95%, 96%, 97%, 98%, or 99% identity with SEQ ID NO: 128. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 130 or a sequence having at least 95%, 96%, 97%, 98%, or 99% identity with SEQ ID NO: 130.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 136 or a sequence having at least 95%, 96%, 97%, 98%, or 99% identity with SEQ ID NO: 136. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 138 or a sequence having at least 95%, 96%, 97%, 98%, or 99% identity with SEQ ID NO: 138.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 147 or a sequence having at least 95%, 96%, 97%, 98%, or 99% identity with SEQ ID NO: 147. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 149 or a sequence having at least 95%, 96%, 97%, 98%, or 99% identity with SEQ ID NO: 149.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 147 or a sequence having at least 95%, 96%, 97%, 98%, or 99% identity with SEQ ID NO: 147. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 149 or a sequence having at least 95%, 96%, 97%, 98%, or 99% identity with SEQ ID NO: 149.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 174 or a sequence having at least 95%, 96%, 97%, 98%, or 99% identity with SEQ ID NO: 174. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 176 or a sequence having at least 95%, 96%, 97%, 98%, or 99% identity with SEQ ID NO: 176.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 180 or a sequence having at least 95%, 96%, 97%, 98%, or 99% identity with SEQ ID NO: 180. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 182 or a sequence having at least 95%, 96%, 97%, 98%, or 99% identity with SEQ ID NO: 182.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 180 or a sequence having at least 95%, 96%, 97%, 98%, or 99% identity with SEQ ID NO: 180. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 182 or a sequence having at least 95%, 96%, 97%, 98%, or 99% identity with SEQ ID NO: 182.

In some embodiments, the antibody or antigen binding fragment comprises a heavy chain variable region comprising or having an amino acid sequence of SEQ ID NO: 201 or a sequence having at least 95%, 96%, 97%, 98%, or 99% identity with SEQ ID NO: 201, and a light chain variable region comprising or having an amino acid sequence of SEQ ID NO: 186 or a sequence having at least 95%, 96%, 97%, 98%, or 99% identity with SEQ ID NO: 186. In some embodiments, the antibody or antigen binding fragment comprises a heavy chain comprising or having an amino acid sequence of SEQ ID NO: 203 or a sequence having at least 95%, 96%, 97%, 98%, or 99% identity with SEQ ID NO: 203, and a light chain comprising or having an amino acid sequence of SEQ ID NO: 188 or a sequence having at least 95%, 96%, 97%, 98%, or 99% identity with SEQ ID NO: 188.

In some embodiments, the antibody or antigen binding fragment comprises a heavy chain variable region comprising or having an amino acid sequence of SEQ ID NO: 122 or a sequence having at least 95%, 96%, 97%, 98%, or 99% identity with SEQ ID NO: 122, and a light chain variable region comprising or having an amino acid sequence of SEQ ID NO: 186 or a sequence having at least 95%, 96%, 97%, 98%, or 99% identity with SEQ ID NO: 186. In some embodiments, the antibody or antigen binding fragment comprises a heavy chain comprising or having an amino acid sequence of SEQ ID NO: 208 or a sequence having at least 95%, 96%, 97%, 98%, or 99% identity with SEQ ID NO: 208, and a light chain comprising or having an amino acid sequence of SEQ ID NO: 188 or a sequence having at least 95%, 96%, 97%, 98%, or 99% identity with SEQ ID NO: 188.

In some embodiments, the antibody or antigen binding fragment comprises a heavy chain variable region comprising or having an amino acid sequence of SEQ ID NO: 233 or a sequence having at least 95%, 96%, 97%, 98%, or 99% identity with SEQ ID NO: 233, and a light chain variable region comprising or having an amino acid sequence of SEQ ID NO: 244 or a sequence having at least 95%, 96%, 97%, 98%, or 99% identity with SEQ ID NO: 244. In some embodiments, the antibody or antigen binding fragment comprises a heavy chain comprising or having an amino acid sequence of SEQ ID NO: 235 or a sequence having at least 95%, 96%, 97%, 98%, or 99% identity with SEQ ID NO: 235, and a light chain comprising or having an amino acid sequence of SEQ ID NO: 246 or a sequence having at least 95%, 96%, 97%, 98%, or 99% identity with SEQ ID NO: 246.

In some embodiments, the antibody or antigen binding fragment comprises a heavy chain variable region comprising or having an amino acid sequence of SEQ ID NO: 256 or a sequence having at least 95%, 96%, 97%, 98%, or 99% identity with SEQ ID NO: 256, and a light chain variable region comprising or having an amino acid sequence of SEQ ID NO: 266 or a sequence having at least 95%, 96%, 97%, 98%, or 99% identity with SEQ ID NO: 266. In some embodiments, the antibody or antigen binding fragment comprises a heavy chain comprising or having an amino acid sequence of SEQ ID NO: 258 or a sequence having at least 95%, 96%, 97%, 98%, or 99% identity with SEQ ID NO: 258, and a light chain comprising or having an amino acid sequence of SEQ ID NO: 268 or a sequence having at least 95%, 96%, 97%, 98%, or 99% identity with SEQ ID NO: 268.

In some embodiments, the antibody or antigen binding fragment comprises a heavy chain variable region comprising or having an amino acid sequence of SEQ ID NO: 278 or a sequence having at least 95%, 96%, 97%, 98%, or 99% identity with SEQ ID NO: 278, and a light chain variable region comprising or having an amino acid sequence of SEQ ID NO: 287 or a sequence having at least 95%, 96%, 97%, 98%, or 99% identity with SEQ ID NO: 287. In some embodiments, the antibody or antigen binding fragment comprises a heavy chain comprising or having an amino acid sequence of SEQ ID NO: 280 or a sequence having at least 95%, 96%, 97%, 98%, or 99% identity with SEQ ID NO: 280, and a light chain comprising or having an amino acid sequence of SEQ ID NO: 289 or a sequence having at least 95%, 96%, 97%, 98%, or 99% identity with SEQ ID NO: 289.

In some embodiments, the antibody or antigen binding fragment comprises a heavy chain variable region comprising or having an amino acid sequence of SEQ ID NO: 300 or a sequence having at least 95%, 96%, 97%, 98%, or 99% identity with SEQ ID NO: 300, and a light chain variable region comprising or having an amino acid sequence of SEQ ID NO: 306 or a sequence having at least 95%, 96%, 97%, 98%, or 99% identity with SEQ ID NO: 306. In some embodiments, the antibody or antigen binding fragment comprises a heavy chain comprising or having an amino acid sequence of SEQ ID NO: 302 or a sequence having at least 95%, 96%, 97%, 98%, or 99% identity with SEQ ID NO: 302, and a light chain comprising or having an amino acid sequence of SEQ ID NO: 308 or a sequence having at least 95%, 96%, 97%, 98%, or 99% identity with SEQ ID NO: 308.

In some embodiments, the antibody or antigen binding fragment comprises a heavy chain variable region comprising or having an amino acid sequence of SEQ ID NO: 316 or a sequence having at least 95%, 96%, 97%, 98%, or 99% identity with SEQ ID NO: 316, and a light chain variable region comprising or having an amino acid sequence of SEQ ID NO: 327 or a sequence having at least 95%, 96%, 97%, 98%, or 99% identity with SEQ ID NO: 327. In some embodiments, the antibody or antigen binding fragment comprises a heavy chain comprising or having an amino acid sequence of SEQ ID NO: 318 or a sequence having at least 95%, 96%, 97%, 98%, or 99% identity with SEQ ID NO: 318, and a light chain comprising or having an amino acid sequence of SEQ ID NO: 329 or a sequence having at least 95%, 96%, 97%, 98%, or 99% identity with SEQ ID NO: 329.

In some embodiments, the antibody or antigen binding fragment comprises a heavy chain variable region comprising or having an amino acid sequence of SEQ ID NO: 333 or a sequence having at least 95%, 96%, 97%, 98%, or 99% identity with SEQ ID NO: 333, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 335 or a sequence having at least 95%, 96%, 97%, 98%, or 99% identity with SEQ ID NO: 335, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 350 or a sequence having at least 95%, 96%, 97%, 98%, or 99% identity with SEQ ID NO: 350, and a light chain variable region comprising or having an amino acid sequence of SEQ ID NO: 357 or a sequence having at least 95%, 96%, 97%, 98%, or 99% identity with SEQ ID NO: 357. In some embodiments, the antibody or antigen binding fragment comprises a heavy chain comprising or having an amino acid sequence of SEQ ID NO: 352 or a sequence having at least 95%, 96%, 97%, 98%, or 99% identity with SEQ ID NO: 352, and a light chain comprising or having an amino acid sequence of SEQ ID NO: 359 or a sequence having at least 95%, 96%, 97%, 98%, or 99% identity with SEQ ID NO: 359.

In some embodiments, the antibody or antigen binding fragment comprises a heavy chain variable region comprising or having an amino acid sequence of SEQ ID NO: 350 or a sequence having at least 95%, 96%, 97%, 98%, or 99% identity with SEQ ID NO: 350, and a light chain variable region comprising or having an amino acid sequence of SEQ ID NO: 363 or a sequence having at least 95%, 96%, 97%, 98%, or 99% identity with SEQ ID NO: 363. In some embodiments, the antibody or antigen binding fragment comprises a heavy chain comprising or having an amino acid sequence of SEQ ID NO: 352 or a sequence having at least 95%, 96%, 97%, 98%, or 99% identity with SEQ ID NO: 352, and a light chain comprising or having an amino acid sequence of SEQ ID NO: 365 or a sequence having at least 95%, 96%, 97%, 98%, or 99% identity with SEQ ID NO: 365.

In some embodiments, the antibody or antigen binding fragment comprises a heavy chain variable region comprising or having an amino acid sequence of SEQ ID NO: 374 or a sequence having at least 95%, 96%, 97%, 98%, or 99% identity with SEQ ID NO: 374, and a light chain variable region comprising or having an amino acid sequence of SEQ ID NO: 244 or a sequence having at least 95%, 96%, 97%, 98%, or 99% identity with SEQ ID NO: 244. In some embodiments, the antibody or antigen binding fragment comprises a heavy chain comprising or having an amino acid sequence of SEQ ID NO: 376 or a sequence having at least 95%, 96%, 97%, 98%, or 99% identity with SEQ ID NO: 376, and a light chain comprising or having an amino acid sequence of SEQ ID NO: 246 or a sequence having at least 95%, 96%, 97%, 98%, or 99% identity with SEQ ID NO: 246.

In some embodiments, the antibody or antigen binding fragment comprises a heavy chain variable region comprising or having an amino acid sequence of SEQ ID NO: 385 or a sequence having at least 95%, 96%, 97%, 98%, or 99% identity with SEQ ID NO: 385, and a light chain variable region comprising or having an amino acid sequence of SEQ ID NO: 244 or a sequence having at least 95%, 96%, 97%, 98%, or 99% identity with SEQ ID NO: 244. In some embodiments, the antibody or antigen binding fragment comprises a heavy chain comprising or having an amino acid sequence of SEQ ID NO: 387 or a sequence having at least 95%, 96%, 97%, 98%, or 99% identity with SEQ ID NO: 387, and a light chain comprising or having an amino acid sequence of SEQ ID NO: 246 or a sequence having at least 95%, 96%, 97%, 98%, or 99% identity with SEQ ID NO: 246.

In some embodiments, the antibody or antigen binding fragment comprises a heavy chain variable region comprising or having an amino acid sequence of SEQ ID NO: 392 or a sequence having at least 95%, 96%, 97%, 98%, or 99% identity with SEQ ID NO: 392, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 394 or a sequence having at least 95%, 96%, 97%, 98%, or 99% identity with SEQ ID NO: 394, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 403 or a sequence having at least 95%, 96%, 97%, 98%, or 99% identity with SEQ ID NO: 403, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 405 or a sequence having at least 95%, 96%, 97%, 98%, or 99% identity with SEQ ID NO: 405, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 414 or a sequence having at least 95%, 96%, 97%, 98%, or 99% identity with SEQ ID NO: 414, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 416 or a sequence having at least 95%, 96%, 97%, 98%, or 99% identity with SEQ ID NO: 416, and a light chain comprising or having an amino acid sequence of SEQ ID NO: 346 or a sequence having at least 95%, 96%, 97%, 98%, or 99% identity with SEQ ID NO: 346.

In some embodiments, the antibody or antigen binding fragment comprises a heavy chain variable region comprising or having an amino acid sequence of SEQ ID NO: 425 or a sequence having at least 95%, 96%, 97%, 98%, or 99% identity with SEQ ID NO: 425, and a light chain variable region comprising or having an amino acid sequence of SEQ ID NO: 344 or a sequence having at least 95%, 96%, 97%, 98%, or 99% identity with SEQ ID NO: 344. In some embodiments, the antibody or antigen binding fragment comprises a heavy chain comprising or having an amino acid sequence of SEQ ID NO: 427 or a sequence having at least 95%, 96%, 97%, 98%, or 99% identity with SEQ ID NO: 427, and a light chain comprising or having an amino acid sequence of SEQ ID NO: 346 or a sequence having at least 95%, 96%, 97%, 98%, or 99% identity with SEQ ID NO: 346.

Groups of exemplary anti-NPR1 antibodies of the present disclosure are set forth in Table 3 or Table 4 by CDR (i.e., numerical values in these tables represent sequence identifiers such that "28" represents "SEQ ID NO: 28") or amino acid consensus sequences. When multiple numerical values are presented in Table 3, they may be used in the alternative for that CDR (i.e., when SEQ ID Nos: 29, 119, and 190 are listed for HCDR2, they may be used in the alternative for that CDR). In Table 4, those amino acids presented in parentheses and separated by a slash represent alternative amino acids in that position (e.g., "(A/V)" represents a position at which the amino acid may be alanine or valine). In some embodiments, the antibody has the heavy and light chain CDRs of any of the antibodies described in Table 3 or Table 4. In some embodiments, the anti-NPR1 antibody is a four-chain antibody (also referred to as an intact antibody), comprising two heavy chains and two light chains. In some embodiments, the anti-NPR1 antibody is an antigen binding fragment of an intact antibody, e.g., a functional fragment of an intact antibody selected from any of those set forth in Table 3 or Table 4 that retains the ability to bind NPR1 and/or provide a function of the intact antibody (e.g., activating NPR1 in the absence of ANP).

TABLE 3

Exemplary anti-NPR1 antibody groups by CDR

| | HCDR1 | HCDR2 | HCDR3 | LCDR1 | LCDR2 | LCDR3 |
|---|---|---|---|---|---|---|
| ANP non-competitive group 1 | | | | | | |
| Combined | 28 | 29 | 30 | 41 | 42 | 43 |
| | | 119 | | | | 126 |
| | | 190 | | | | 134 |
| | | | | | | 145 |
| | | | | | | 172 |
| | | | | | | 178 |
| | | | | | | 184 |
| Kabat | 31 | 29 | 30 | 41 | 42 | 43 |
| | | 119 | | | | 126 |
| | | 190 | | | | 134 |
| | | | | | | 145 |
| | | | | | | 172 |
| | | | | | | 178 |
| | | | | | | 184 |
| Chothia | 32 | 33 | 30 | 44 | 45 | 46 |
| | | 120 | | | | 127 |
| | | 191 | | | | 135 |
| | | | | | | 146 |
| | | | | | | 173 |
| | | | | | | 179 |
| | | | | | | 185 |
| IMGT | 34 | 35 | 36 | 47 | 45 | 43 |
| | | 121 | | | | 126 |
| | | 192 | | | | 134 |
| | | | | | | 145 |

TABLE 3-continued

| | Exemplary anti-NPR1 antibody groups by CDR | | | | | |
|---|---|---|---|---|---|---|
| | HCDR1 | HCDR2 | HCDR3 | LCDR1 | LCDR2 | LCDR3 |
| | | | | | | 172 |
| | | | | | | 178 |
| | | | | | | 184 |
| ANP non-competitive group 2 | | | | | | |
| Combined | 28 | 119 | 30 | 41 | 42 | 126 |
| | | | | | | 134 |
| | | | | | | 145 |
| | | | | | | 172 |
| | | | | | | 178 |
| | | | | | | 184 |
| Kabat | 31 | 119 | 30 | 41 | 42 | 126 |
| | | | | | | 134 |
| | | | | | | 145 |
| | | | | | | 172 |
| | | | | | | 178 |
| | | | | | | 184 |
| Chothia | 32 | 120 | 30 | 44 | 45 | 127 |
| | | | | | | 135 |
| | | | | | | 146 |
| | | | | | | 173 |
| | | | | | | 179 |
| | | | | | | 185 |
| IMGT | 34 | 121 | 36 | 47 | 45 | 126 |
| | | | | | | 134 |
| | | | | | | 145 |
| | | | | | | 172 |
| | | | | | | 178 |
| | | | | | | 184 |
| ANP non-competitive group 3 | | | | | | |
| Combined | 4 | 5 | 6 | 17 | 18 | 19 |
| | 112 | 100 | | | | |
| | 165 | 151 | | | | |
| Kabat | 7 | 5 | 6 | 17 | 18 | 19 |
| | | 100 | | | | |
| | | 151 | | | | |
| Chothia | 8 | 9 | 6 | 20 | 21 | 22 |
| | 113 | 101 | | | | |
| | 166 | 152 | | | | |
| IMGT | 10 | 11 | 12 | 23 | 21 | 19 |
| | 114 | 102 | | | | |
| | 167 | 153 | | | | |
| ANP non-competitive group 4 | | | | | | |
| Combined | 4 | 5 | 6 | 17 | 18 | 19 |
| | 112 | 100 | | | | |
| | 165 | | | | | |
| Kabat | 7 | 5 | 6 | 17 | 18 | 19 |
| | | 100 | | | | |
| Chothia | 8 | 9 | 6 | 20 | 21 | 22 |
| | 113 | 101 | | | | |
| | 166 | | | | | |
| IMGT | 10 | 11 | 12 | 23 | 21 | 19 |
| | 114 | 102 | | | | |
| | 167 | | | | | |
| ANP non-competitive group 5 | | | | | | |
| Combined | 226 | 227 | 228 | 237 | 238 | 239 |
| | 367 | 368 | | | | |
| | 378 | 379 | | | | |
| Kabat | 229 | 227 | 228 | 237 | 238 | 239 |
| | 369 | 368 | | | | |
| | 380 | 379 | | | | |

TABLE 3-continued

Exemplary anti-NPR1 antibody groups by CDR

| | HCDR1 | HCDR2 | HCDR3 | LCDR1 | LCDR2 | LCDR3 |
|---|---|---|---|---|---|---|
| Chothia | 32<br>370<br>381 | 230<br>371<br>382 | 228 | 240 | 241 | 242 |
| IMGT | 34<br>372<br>383 | 231<br>373<br>384 | 232 | 243 | 241 | 239 |
| ANP non-competitive group 6 | | | | | | |
| Combined | 226<br>378 | 227<br>368<br>379 | 228 | 237 | 238 | 239 |
| Kabat | 229<br>380 | 227<br>368<br>379 | 228 | 237 | 238 | 239 |
| Chothia | 32<br>381 | 230<br>371<br>382 | 228 | 240 | 241 | 242 |
| IMGT | 34<br>383 | 231<br>373<br>384 | 232 | 243 | 241 | 239 |
| ANP non-competitive group 7 | | | | | | |
| Combined | 226<br>367<br>378 | 368<br>379 | 228 | 237 | 238 | 239 |
| Kabat | 229<br>369<br>380 | 368<br>379 | 228 | 237 | 238 | 239 |
| Chothia | 32<br>370<br>381 | 371<br>382 | 228 | 240 | 241 | 242 |
| IMGT | 34<br>372<br>383 | 373<br>384 | 232 | 243 | 241 | 239 |
| ANP non-competitive group 8 | | | | | | |
| Combined | 226<br>378 | 368<br>379 | 228 | 237 | 238 | 239 |
| Kabat | 229<br>380 | 368<br>379 | 228 | 237 | 238 | 239 |
| Chothia | 32<br>381 | 371<br>382 | 228 | 240 | 241 | 242 |
| IMGT | 34<br>383 | 373<br>384 | 232 | 243 | 241 | 239 |
| ANP competitive group 1 | | | | | | |
| Combined | 310 | 311 | 312<br>348 | 320 | 321<br>354 | 322<br>355<br>361 |
| Kabat | 229 | 311 | 312<br>348 | 320 | 321<br>354 | 322<br>355<br>361 |
| Chothia | 80 | 313 | 312<br>348 | 323 | 324 | 325<br>356<br>362 |
| IMGT | 82 | 314 | 315<br>349 | 326 | 324 | 322<br>355<br>361 |
| ANP competitive group 2 | | | | | | |
| Combined | 270<br>407 | 271<br>389<br>408 | 331 | 337 | 338 | 339 |
| Kabat | 273<br>409 | 271<br>389<br>408 | 331 | 337 | 338 | 339 |

TABLE 3-continued

Exemplary anti-NPR1 antibody groups by CDR

|  | HCDR1 | HCDR2 | HCDR3 | LCDR1 | LCDR2 | LCDR3 |
|---|---|---|---|---|---|---|
| Chothia | 32 | 274 | 331 | 340 | 341 | 342 |
|  | 410 | 390 |  |  |  |  |
|  |  | 411 |  |  |  |  |
| IMGT | 275 | 276 | 332 | 343 | 341 | 339 |
|  | 412 | 391 |  |  |  |  |
|  |  | 413 |  |  |  |  |
| ANP competitive group 3 |  |  |  |  |  |  |
| Combined | 270 | 389 | 331 | 337 | 338 | 339 |
|  | 407 | 408 |  |  |  |  |
| Kabat | 273 | 389 | 331 | 337 | 338 | 339 |
|  | 409 | 408 |  |  |  |  |
| Chothia | 32 | 390 | 331 | 340 | 341 | 342 |
|  | 410 | 411 |  |  |  |  |
| IMGT | 275 | 276 | 332 | 343 | 341 | 339 |
|  | 412 | 391 |  |  |  |  |
|  |  | 413 |  |  |  |  |

TABLE 4

Exemplary anti-NPR1 antibody groups by consensus sequence

|  | HCDR1 | HCDR2 | HCDR3 | LCDR1 | LCDR2 | LCDR3 |
|---|---|---|---|---|---|---|
| ANP non-competitive group A |  |  |  |  |  |  |
| Combined | 28 | (A/V)I(S/E)S(D/K)G(S/N)Y(I/T)(Y/F)YADSVKG (SEQ ID NO: 429) | 30 | 41 | 42 | (M/Q)Q(S/E/T/I)(Y/W)(E/V/R/A/T/M)(K/V/R/A)PRT (SEQ ID NO: 430) |
| Kabat | 31 | (A/V)I(S/E)S(D/K)G(S/N)Y(I/T)(Y/F)YADSVKG (SEQ ID NO: 429) | 30 | 41 | 42 | (M/Q)Q(S/E/T/I)(Y/W)(E/V/R/A/T/M)(K/V/R/A)PRT (SEQ ID NO: 430) |
| Chothia | 32 | (E/S)S(D/K)G(S/N)Y (SEQ ID NO: 431) | 30 | 44 | 45 | (S/E/T/I)(Y/W)(E/V/R/A/T/M)(K/V/R/A)PR (SEQ ID NO: 432) |
| IMGT | 34 | I(S/E)S(D/K)G(S/N)Y(I/T) (SEQ ID NO: 433) | 36 | 47 | 45 | (M/Q)Q(S/E/T/I)(Y/W)(E/V/R/A/T/M)(K/V/R/A)PRT (SEQ ID NO: 430) |
| ANP non-competitive group B |  |  |  |  |  |  |
| Combined | 28 | (A/V)I(S/E)S(D/K)G(S/N)Y(I/T)(Y/F)YADSVKG (SEQ ID NO: 429) | 30 | 41 | 42 | QQ(S/E/T/I)W(V/R/A/T/M)(K/V/R/A)PRT (SEQ ID NO: 434) |
| Kabat | 31 | (A/V)I(S/E)S(D/K)G(S/N)Y(I/T)(Y/F)YADSVKG (SEQ ID NO: 429) | 30 | 41 | 42 | QQ(S/E/T/I)W(V/R/A/T/M)(K/V/R/A)PRT (SEQ ID NO: 434) |
| Chothia | 32 | (E/S)S(D/K)G(S/N)Y (SEQ ID NO: 431) | 30 | 44 | 45 | (S/E/T/I)W(V/R/A/T/M)(K/V/R/A)PR (SEQ ID NO: 435) |

TABLE 4-continued

Exemplary anti-NPR1 antibody groups by consensus sequence

| | HCDR1 | HCDR2 | HCDR3 | LCDR1 | LCDR2 | LCDR3 |
|---|---|---|---|---|---|---|
| IMGT | 34 | I(S/E)S(D/K)G(S/N)Y(I/T) (SEQ ID NO: 433) | 36 | 47 | 45 | QQ(S/E/T/I)W(V/R/A/T/M)(K/V/R/A)PRT (SEQ ID NO: 434) |
| ANP non-competitive group C | | | | | | |
| Combined | 28 | 119 | 30 | 41 | 42 | QQ(S/E/T/I)W(V/R/A/T/M)(K/V/R/A)PRT (SEQ ID NO: 434) |
| Kabat | 31 | 119 | 30 | 41 | 42 | QQ(S/E/T/I)W(V/R/A/T/M)(K/V/R/A)PRT (SEQ ID NO: 434) |
| Chothia | 32 | 120 | 30 | 44 | 45 | (S/E/T/I)W(V/R/A/T/M)(K/V/R/A)PR (SEQ ID NO: 435) |
| IMGT | 34 | 121 | 36 | 47 | 45 | QQ(S/E/T/I)W(V/R/A/T/M)(K/V/R/A)PRT (SEQ ID NO: 434) |
| ANP non-competitive group D | | | | | | |
| Combined | GFTF(N/S/Q)THYIH (SEQ ID NO: 436) | SI(S/G)(S/G)(S/Q)G(S/Q/G)(S/N/M)T(Y/L)YADSVKG (SEQ ID NO: 437) | 6 | 17 | 18 | 19 |
| Kabat | 7 | SI(S/G)(S/G)(S/Q)G(S/Q/G)(S/N/M)T(Y/L)YADSVKG (SEQ ID NO: 437) | 6 | 17 | 18 | 19 |
| Chothia | GFTF(N/S/Q)TH (SEQ ID NO: 438) | (S/G)(S/G)(S/Q)G(S/Q/G)(S/N/M) (SEQ ID NO: 439) | 6 | 20 | 21 | 22 |
| IMGT | GFTF(N/S/Q)THY (SEQ ID NO: 440) | I(S/G)(S/G)(S/Q)G(S/Q/G)(S/N/M)T (SEQ ID NO: 441) | 12 | 23 | 21 | 19 |
| ANP non-competitive group E | | | | | | |
| Combined | GFTF(N/S/Q)THYIH (SEQ ID NO: 436) | SIS(S/G)SG(S/Q)(S/N)TYYADSVKG (SEQ ID NO: 442) | 6 | 17 | 18 | 19 |
| Kabat | 7 | SIS(S/G)SG(S/Q)(S/N)TYYADSVKG (SEQ ID NO: 442) | 6 | 17 | 18 | 19 |
| Chothia | GFTF(N/S/Q)TH (SEQ ID NO: 438) | S(S/G)SG(S/Q)(S/N) (SEQ ID NO: 443) | 6 | 20 | 21 | 22 |
| IMGT | GFTF(N/S/Q)THY (SEQ ID NO: 440) | IS(S/G)SG(S/Q)(S/N)T (SEQ ID NO: 444) | 12 | 23 | 21 | 19 |
| ANP non-competitive group F | | | | | | |
| Combined | GF(S/T)FS(S/K/R)Y(W/Y)(I/L)(S/N) (SEQ ID NO: 445) | (N/S)I(K/H)Q(S/Q/H)(G/A)(S/H/L)E(T/K)(Y/K/R)YVESVKG (SEQ ID NO: 446) | 228 | 237 | 238 | 239 |

TABLE 4-continued

Exemplary anti-NPR1 antibody groups by consensus sequence

| | HCDR1 | HCDR2 | HCDR3 | LCDR1 | LCDR2 | LCDR3 |
|---|---|---|---|---|---|---|
| Kabat | (S/K/R)Y(W/Y)(I/L)(S/N) (SEQ ID NO: 447) | (N/S)I(K/H)Q(S/Q/H)(G/A)(S/H/L)E(T/K)(Y/K/R)YVESVKG (SEQ ID NO: 446) | 228 | 237 | 238 | 239 |
| Chothia | GF(S/T)FS(S/K/R)Y (SEQ ID NO: 448) | (K/H)Q(S/Q/H)(G/A)(S/H/L)E (SEQ ID NO: 449) | 228 | 240 | 241 | 242 |
| IMGT | GF(S/T)FS(S/K/R)Y(W/Y) (SEQ ID NO: 450) | I(K/H)Q(S/Q/H)(G/A)(S/H/L)E(T/K) (SEQ ID NO: 451) | 232 | 243 | 241 | 239 |
| ANP non-competitive group G | | | | | | |
| Combined | GFTFS(S/R)Y(W/Y)I(S/N) (SEQ ID NO: 452) | (N/S)I(K/H)Q(S/Q/H)(G/A)(S/H/L)E(T/K)(Y/K/R)YVESVKG (SEQ ID NO: 446) | 228 | 237 | 238 | 239 |
| Kabat | (S/R)Y(W/Y)I(S/N) (SEQ ID NO: 454) | (N/S)I(K/H)Q(S/Q/H)(G/A)(S/H/L)E(T/K)(Y/K/R)YVESVKG (SEQ ID NO: 446) | 228 | 237 | 238 | 239 |
| Chothia | GFTFS(S/R)Y (SEQ ID NO: 455) | (K/H)Q(S/Q/H)(G/A)(S/H/L)E (SEQ ID NO: 449) | 228 | 240 | 241 | 242 |
| IMGT | GFTFS(S/R)Y(W/Y) (SEQ ID NO: 457) | I(K/H)Q(S/Q/H)(G/A)(S/H/L)E(T/K) (SEQ ID NO: 451) | 232 | 243 | 241 | 239 |
| ANP non-competitive group H | | | | | | |
| Combined | GF(S/T)FS(S/K/R)Y(W/Y)(I/L)(S/N) (SEQ ID NO: 445) | SIHQ(Q/H)(G/A)(H/L)E(T/K)(K/R)YVESVKG (SEQ ID NO: 453) | 228 | 237 | 238 | 239 |
| Kabat | (S/K/R)Y(W/Y)(I/L)(S/N) (SEQ ID NO: 447) | SIHQ(Q/H)(G/A)(H/L)E(T/K)(K/R)YVESVKG (SEQ ID NO: 453) | 228 | 237 | 238 | 239 |
| Chothia | GF(S/T)FS(S/K/R)Y (SEQ ID NO: 448) | HQ(Q/H)(G/A)(H/L)E (SEQ ID NO: 456) | 228 | 240 | 241 | 242 |
| IMGT | GF(S/T)FS(S/K/R)Y(W/Y) (SEQ ID NO: 450) | IHQ(Q/H)(G/A)(H/L)E(T/K) (SEQ ID NO: 458) | 232 | 243 | 241 | 239 |
| ANP non-competitive group I | | | | | | |
| Combined | GFTFS(S/R)Y(W/Y)I(S/N) (SEQ ID NO: 452) | SIHQ(Q/H)(G/A)(H/L)E(T/K)(K/R)YVESVKG (SEQ ID NO: 453) | 228 | 237 | 238 | 239 |
| Kabat | (S/R)Y(W/Y)I(S/N) (SEQ ID NO: 454) | SIHQ(Q/H)(G/A)(H/L)E(T/K)(K/R)YVESVKG (SEQ ID NO: 453) | 228 | 237 | 238 | 239 |
| Chothia | GFTFS(S/R)Y (SEQ ID NO: 455) | HQ(Q/H)(G/A)(H/L)E (SEQ ID NO: 456) | 228 | 240 | 241 | 242 |
| IMGT | GFTFS(S/R)Y(W/Y) (SEQ ID NO: 457) | IHQ(Q/H)(G/A)(H/L)E(T/K) (SEQ ID NO: 458) | 232 | 243 | 241 | 239 |
| ANP competitive group A | | | | | | |
| Combined | 310 | 311 | G(A/S)(V/L)(A/P)G(Q/L)L GFDH (SEQ ID NO: 459) | 320 | GNSNRP(S/N) (SEQ ID NO: 460) | QSY(Y/D/G)(T/S/A)(S/P/F)(S/T/P)(H/S/R)(G/S/F)(P/S/V)V (SEQ ID NO: 461) |

TABLE 4-continued

Exemplary anti-NPR1 antibody groups by consensus sequence

| | HCDR1 | HCDR2 | HCDR3 | LCDR1 | LCDR2 | LCDR3 |
|---|---|---|---|---|---|---|
| Kabat | 229 | 311 | G(A/S)(V/L)(A/P)G(Q/L)LGFDH (SEQ ID NO: 459) | 320 | GNSNRP(S/N) (SEQ ID NO: 460) | QSY(Y/D/G)(T/S/A)(S/P/F)(S/T/P)(H/S/R)(G/S/F)(P/S/V)V (SEQ ID NO: 461) |
| Chothia | 80 | 313 | G(A/S)(V/L)(A/P)G(Q/L)LGFDH (SEQ ID NO: 459) | 323 | 324 | Y(Y/D/G)(T/S/A)(S/P/F)(S/T/P)(H/S/R)(G/S/F)(P/S/V) (SEQ ID NO: 462) |
| IMGT | 82 | 314 | ARG(A/S)(V/L)(A/P)G(Q/L)LGFDH (SEQ ID NO: 463) | 326 | 324 | QSY(Y/D/G)(T/S/A)(S/P/F)(S/T/P)(H/S/R)(G/S/F)(P/S/V)V (SEQ ID NO: 461) |
| ANP competitive group B | | | | | | |
| Combined | GFTF(S/G)(S/T)YA(I/M)(S/T) (SEQ ID NO: 464) | (A/S)IS(A/S/G)(S/H)G(G/Y)(S/Y)(T/A)(Y/R/N)YA(E/G)SVKG (SEQ ID NO: 465) | 331 | 337 | 338 | 339 |
| Kabat | (S/T)YA(I/M)(S/T) (SEQ ID NO: 466) | (A/S)IS(A/S/G)(S/H)G(G/Y)(S/Y)(T/A)(Y/R/N)YA(E/G)SVKG (SEQ ID NO: 465) | 331 | 337 | 338 | 339 |
| Chothia | GFTF(S/G)(S/T)Y (SEQ ID NO: 467) | S(A/S/G)(S/H)G(G/Y)(S/Y) (SEQ ID NO: 468) | 331 | 340 | 341 | 342 |
| IMGT | GFTF(S/G)(S/T)YA (SEQ ID NO: 469) | IS(S/G)(S/H)G(G/Y)(S/Y)T (SEQ ID NO: 470) | 332 | 343 | 341 | 339 |
| ANP competitive group C | | | | | | |
| Combined | GFTF(S/G)(S/T)YA(I/M)(S/T) (SEQ ID NO: 464) | SIS(A/S)(S/H)GYY(T/A)(R/N)YA(E/G)SVKG (SEQ ID NO: 471) | 331 | 337 | 338 | 339 |
| Kabat | (S/T)YA(I/M)(S/T) (SEQ ID NO: 466) | SIS(A/S)(S/H)GYY(T/A)(R/N)YA(E/G)SVKG (SEQ ID NO: 471) | 331 | 337 | 338 | 339 |
| Chothia | GFTF(S/G)(S/T)Y (SEQ ID NO: 467) | S(A/S)(S/H)GYY (SEQ ID NO: 472) | 331 | 340 | 341 | 342 |
| IMGT | GFTF(S/G)(S/T)YA (SEQ ID NO: 469) | IS(A/S/G)(S/H)G (SEQ ID NO: 473) | 332 | 343 | 341 | 339 |

In some embodiments, an antibody or antigen-binding fragment thereof as provided herein binds to (a) human NPR1; and (b) mouse NPR1 and/or rat NPR1.

In some embodiments, an antibody or antigen-binding fragment thereof as provided herein binds to (a) human NPR1; and (b) cyno NPR1. In some embodiments, the antibody or antigen binding fragment thereof is therapeutic. A therapeutic antibody, as defined herein, is an antibody that is both efficacious and stable.

Antibodies that Bind to the Same Epitope as Anti-NPR1 Antibodies of the Disclosure In another embodiment, the disclosure provides antibodies or antigen-binding fragments thereof that bind to the same epitope as one or more of the anti-NPR1 antibodies described herein (e.g., WW06). Such antibodies:
 (i) bind NPR1;
 (ii) are agonists of NPR1;
 (iii) are ANP competitive; and
 bind the same epitope in NPR1 as antibody WW06.

In another embodiment, the disclosure provides antibodies or antigen-binding fragments thereof that bind to the same epitope as one or more of the anti-NPR1 antibodies described herein (e.g., XX16). Such antibodies:
 (i) bind NPR1;
 (ii) are agonists of NPR1;
 (iii) are ANP non-competitive; and
 bind the same epitope in NPR1 as XX16.

In another embodiment, the disclosure provides antibodies or antigen-binding fragments thereof that bind to the same epitope as one or more of the anti-NPR1 antibodies described herein (e.g., WW03). Such antibodies:
 (i) bind NPR1;
 (ii) are agonists of NPR1;
 (iii) are ANP non-competitive; and
 bind the same epitope in NPR1 as WW03.

Following the crystallisation and structure determination, the binding regions of the preferred antibodies of the disclosure have been more clearly defined. Such binding is defined herein as being inclusive of both covalent and non-covalent bonds.

Thus, the disclosure provides an ANP competitive antibody that binds the same epitope as WW06. In some embodiments, the disclosure provides an antibody that binds to an epitope of human NPR1 protein (Accession no. P16066; SEQ ID NO: 1) comprising amino acids 188, 192, 194, 197, 201, 208, and 219. In some embodiments, the disclosure provides an antibody that binds to an epitope of human NPR1 protein (Accession no. P16066; SEQ ID NO: 1) comprising amino acids 188, 192, 194, 197, 201, 208, 219, and 295. In some embodiments, the disclosure provides an antibody that binds to an epitope within amino acid numbers 188-198 of SEQ ID NO: 1. In some embodiments, the disclosure provides an antibody that binds to at least 2, 3, or 4 amino acid residues within amino acid numbers 188-198 of SEQ ID NO: 1. In some embodiments, the disclosure provides an antibody that binds to an epitope within amino acid numbers 201-208 of SEQ ID NO: 1. In some embodiments, the disclosure provides an antibody that binds to at least 2 amino acids within amino acid numbers 201-208 of SEQ ID NO: 1. In some embodiments, the disclosure provides an antibody that binds to at least 2, 3, or 4 amino acid residues within amino acid numbers 188-198 of SEQ ID NO: 1, and binds to at least 2 amino acids within amino acid numbers 201-208 of SEQ ID NO: 1. In some embodiments, the disclosure provides an antibody that binds to an epitope comprising at least one amino acid residue within each of (i) amino acids 188-198 of SEQ ID NO: 1, (ii) amino acids 201-208 of SEQ ID NO: 1, (iii) amino acids 215-238 of SEQ ID NO: 1, and (iv) amino acids 294-297 of SEQ ID NO: 1.

The disclosure provides an ANP non-competitive antibody that binds the same epitope as WW03. In some embodiments, the disclosure provides an antibody that binds to an epitope of human NPR1 protein (Accession no. P16066; SEQ ID NO: 1) comprising amino acids 82, 102, 103, 105, 106, 109, 132, and 375. In some embodiments, the disclosure provides an antibody that binds to an epitope of human NPR1 protein (Accession no. P16066; SEQ ID NO: 1) comprising amino acids 79, 82, 99, 102, 103, 105, 106, 109, 131, 132, and 375. In some embodiments, the disclosure provides an antibody that binds to an epitope within amino acid numbers 99-111 of SEQ ID NO: 1. In some embodiments, the disclosure provides an antibody that binds to at least 2, 3, 4, 5, or 6 amino acids within amino acid numbers 99-111 of SEQ ID NO: 1. In some embodiments, the disclosure provides an antibody that binds to at least 2, 3, 4, 5, 6, 7, or 8 amino acid residues within amino acid numbers 99-133 of SEQ ID NO: 1. In some embodiments, the disclosure provides an antibody that binds to an epitope within amino acid numbers 131-134 of SEQ ID NO: 1. In some embodiments, the disclosure provides an antibody that binds to at least 2 amino acids within amino acid numbers 131-134 of SEQ ID NO: 1. In some embodiments, the disclosure provides an antibody that binds to at least 2, 3, 4, 5, or 6 amino acids within amino acid numbers 99-111 of SEQ ID NO: 1, and binds to at least 2 amino acids within amino acid numbers 131-134 of SEQ ID NO: 1. In some embodiments, the disclosure provides an antibody that binds to an epitope comprising at least one amino acid residue within each of (i) amino acids 99-111 of SEQ ID NO: 1, (ii) amino acids 131-134 of SEQ ID NO: 1, and (iii) amino acids 374-375 of SEQ ID NO: 1. Optionally, the antibody may additionally bind to amino acids 79 and/or 82 of SEQ ID NO: 1.

The disclosure additionally provides an ANP non-competitive antibody that binds the same epitope as XX16. In some embodiments, the disclosure provides an antibody that binds to an epitope of human NPR1 protein (Accession no. P16066; SEQ ID NO: 1) comprising amino acids 82, 102, 103, 105, 106, 109, 132, and 375. In some embodiments, the disclosure provides an antibody that binds to an epitope of human NPR1 protein (Accession no. P16066; SEQ ID NO: 1) comprising amino acids 34, 82, 102, 103, 105, 106, 107, 109, 132, 133, 375, and 378. In some embodiments, the disclosure provides an antibody that binds to an epitope within amino acid numbers 102-111 of SEQ ID NO: 1. In some embodiments, the disclosure provides an antibody that binds to at least 2, 3, 4, 5, or 6 amino acids within amino acid numbers 102-111 of SEQ ID NO: 1. In some embodiments, the disclosure provides an antibody that binds to an epitope within amino acid numbers 131-134 of SEQ ID NO: 1. In some embodiments, the disclosure provides an antibody that binds to at least 2 amino acids within amino acid numbers 131-134 of SEQ ID NO: 1. In some embodiments, the disclosure provides an antibody that binds to at least 2, 3, 4, 5, or 6 amino acids within amino acid numbers 102-111 of SEQ ID NO: 1, and binds to at least 2 amino acids within amino acid numbers 131-134 of SEQ ID NO: 1. In some embodiments, the disclosure provides an antibody that binds to an epitope comprising at least one amino acid residue within each of (i) amino acids 102-111 of SEQ ID NO: 1, (ii) amino acids 131-134 of SEQ ID NO: 1, and (iii) amino acids 374-378 of SEQ ID NO: 1. Optionally, the antibody may additionally bind to amino acids 34, 76, and/or 82 of SEQ ID NO: 1.

Additional antibodies can be identified based on their ability to cross-compete (e.g., to competitively inhibit the binding of, in a statistically significant manner) with other antibodies of the disclosure in standard NPR1 binding assays (e.g., XX16, WW06, or WW03). The ability of a test antibody to inhibit the binding of antibodies of the present disclosure to human NPR1 demonstrates that the test antibody can compete with that antibody for binding to human NPR1; such an antibody may, according to non-limiting theory, bind to the same or a related (e.g., a structurally similar or spatially proximal) epitope on human NPR1 as the antibody with which it competes. In a certain embodiment, the antibody that binds to the same epitope on human NPR1 as the antibodies of the present disclosure is a human antibody (e.g., a human monoclonal antibody or antigen binding fragment thereof). Such antibodies can be prepared and isolated as described herein.

Engineered and Modified Antibodies

An antibody of the disclosure can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is antibody binding region/paratope or CDR grafting. Because paratope sequences are responsible for most antibody-antigen interactions, it is possible to express recombinant antibodies that mimic the properties of specific naturally occurring antibodies by constructing expression vectors that include CDR/paratope sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. Nos. 5,225,539, and 5,530,101; 5,585,089; 5,693,762 and 6,180,370; the contents of each of which are herein incorporated by reference for this purpose).

Accordingly, another embodiment of the disclosure pertains to an isolated anti-NPR1 antibody, or a antigen-binding fragment thereof, comprising an antigen binding portion thereof, comprising a heavy chain variable region comprising the CDR sequences of an antibody or group of antibodies shown in Table 2, Table 3, or Table 4. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www [dot] mrc-cpe [dot] cam [dot] ac [dot] uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are herein incorporated by reference for this purpose.

An example of framework sequences for use in the antibodies or antigen binding fragments of the disclosure are those that are structurally similar to the framework sequences used by selected antibodies of the disclosure, e.g., consensus sequences and/or framework sequences used by the antibodies or antigen binding fragments of the disclosure. The VH CDR1, 2 and 3 sequences, and the VL CDR1, 2 and 3 sequences, can be grafted onto framework regions that have an identical sequence to that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370; the contents of each of which are herein incorporated by reference for this purpose).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein. Conservative modifications (as discussed above) can also be introduced. The mutations may be amino acid substitutions, additions or deletions. Moreover, typically no more than one, two, three, four or five residues within a CDR region are altered.

Grafting Antigen Binding Domains into Alternative Frameworks or Scaffolds

A wide variety of antibody/immunoglobulin frameworks or scaffolds can be employed so long as the resulting polypeptide includes at least one binding region which specifically binds to NPR1. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the disclosure pertains to generating non-immunoglobulin based antibodies using non-immunoglobulin scaffolds onto which CDRs of the disclosure can be grafted. Known or future non-immunoglobulin frameworks and scaffolds may be employed, as long as they comprise a binding region specific for NPR1, e.g., such as those disclosed for an antibody described herein including, but not limited to, XX16, WW03, or WW06. Such compounds are known herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary (*Camelus bactrianus* and *Camelus dromaderius*) family including new world members such as llama species (*Lama paccos, Lama glama*, and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals, see WO94/04678, the contents of which are herein incorporated by reference for this purpose.

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808; see also Stijlemans, B. et al., 2004 J Biol Chem 279:1256-1261; Dumoulin, M. et al., 2003 Nature 424:783-788; Pleschberger, M. et al. 2003 Bioconjugate Chem 14:440-448; Cortez-Retamozo, V. et al. 2002 Int J Cancer 89:456-62; and Lauwereys, M. et al. 1998 EMBO J 17:3512-3520; the contents of each of which are herein incorporated by reference for this purpose. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier, see US2004/0161738, the contents of which are herein incorporated by reference for this purpose. These features combined with the low antigenicity to humans indicate great therapeutic potential. Further, these molecules can be fully expressed in prokaryotic cells such as *E. coli* and may be expressed as functional fusion proteins with bacteriophage.

Accordingly, a feature of the present disclosure is a camelid antibody or nanobody having high affinity for NPR1. In one embodiment, the camelid antibody or nanobody is obtained by grafting the CDRs sequences of the heavy or light chain of the human antibodies of the disclosure into nanobody or single domain antibody framework sequences as described, for example, in WO94/04678 (the contents of which are herein incorporated by reference for this purpose).

Framework or Fc Engineering

Engineered antibodies of the disclosure include those in which modifications have been made to framework residues within VH and/or VL, e.g., to improve one or more properties of the antibody. Typically such framework modifications are made to decrease the immunogenicity of the antibody. Antibodies of the disclosure may be modified in one or more ways, including each of the ways described herein.

For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies and additional modifications described herein are also intended to be encompassed by the disclosure.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in US2003/0153043, the contents of which are herein incorporated by reference for this purpose.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CHI is modified such that the number of cysteine residues in the hinge region is altered, e.g., increased or decreased. This approach is described further in U.S. Pat. No. 5,677,425, the contents of which are herein incorporated by reference for this purpose. The number of cysteine residues in the hinge region of CHI is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745, the contents of which are herein incorporated by reference for this purpose.

In another embodiment, the antibody is modified to increase its biological half-life. Various approaches are possible. For example, one or more of the following mutations can be introduced: T252L, T254S, T256F, as described in U.S. Pat. No. 6,277,375, the contents of which are herein incorporated by reference for this purpose. Alternatively, to increase the biological half life, the antibody can be altered within the CHI or CL region to contain a salvage receptor binding epitope taken from two loops of a CH2 domain of an Fc region of an IgG, as described in U.S. Pat. Nos. 5,869,046 and 6,121,022, the contents of each of which are herein incorporated by reference for this purpose.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, the contents of each of which are herein incorporated by reference for this purpose.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies. See, for example, LALA and N297A (Strohl, W., 2009, Curr. Opin. Biotechnol. vol. 20(6):685-691); and D265A (Baudino et al., 2008, J. Immunol. 181:6664-69) see also Heusser et al., WO2012065950;, the contents of each of which are herein incorporated by reference for this purpose. In particular, residues 234 and/or 235 may be mutated, optionally to alanine. Thus, in one embodiment, an antibody according to the disclosure has a mutation in the Fc region at one or both of amino acids 234 and 235. Such substitution of both amino acids 234 and 235 results in reduced ADCC activity. One example of such a mutation is the LALA mutant comprising L234A and L235A mutation in the IgG1 Fc amino acid sequence. Another example of a silent IgG1 antibody is the DAPA (D265A, P329A) mutation (U.S. Pat. No. 6,737,056, the contents of which are herein incorporated by reference for this purpose). Another silent IgG1 antibody comprises the N297A mutation, which results in aglycosylated/non-glycosylated antibodies. Fc silent antibodies result in no or low ADCC activity, meaning that an Fc silent antibody exhibits an ADCC activity that is below 50% specific cell lysis. No ADCC activity means that the Fc silent antibody exhibits an ADCC activity (specific cell lysis) that is below 1%.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551, the contents of which are herein incorporated by reference for this purpose.

In another embodiment, one or more amino acid residues are altered to thereby alter the ability of the antibody to fix complement. This approach is described further in WO94/29351, the contents of which are herein incorporated by reference for this purpose.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in WO00/42072, the contents of which are herein incorporated by reference for this purpose. Moreover, the binding sites on human $IgG_1$ for FcγRI, FcγRII, FcγRIII and FcRn have been mapped and variants with improved binding have been described (see Shields, R. L. et al., 2001 J. Biol. Chen. 276:6591-6604, the contents of which are herein incorporated by reference for this purpose).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861, the contents of each of which are herein incorporated by reference for this purpose.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1,176,195 (the contents of which are herein incorporated by reference for this purpose) describes a cell line with a functionally disrupted FUT8 gene, which encodes a fucosyl transferase, such that antibodies expressed in such a cell line exhibit hypofucosylation. WO03/035835 describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). WO99/54342 describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). The contents of each of the foregoing applications and references are herein incorporated by reference for this purpose Another modification of the antibodies herein that is contemplated by the disclosure is pegylation. An antibody can be pegylated, for example, to increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, for example, EP0154316 and EP0401384, the contents of each of which are herein incorporated by reference for this purpose.

Another modification of the antibodies that is contemplated by the disclosure is a conjugate or a protein fusion of at least the antigen-binding region of the antibody of the disclosure to serum protein, such as human serum albumin or a fragment thereof to increase half-life of the resulting molecule. Such an approach is described, for example, in EP0322094, the contents of which are herein incorporated by reference for this purpose.

Another possibility is a fusion of at least the antigen-binding region of the antibody of the disclosure to proteins capable of binding to serum proteins, such human serum albumin to increase half-life of the resulting molecule. Such approach is described, for example, in EP0486525, the contents of which are herein incorporated by reference for this purpose.

Nucleic Acid Molecules Encoding Antibodies of the Disclosure

Another aspect of the disclosure pertains to nucleic acid molecules that encode the antibodies of the disclosure. The term "nucleic acid" is used herein interchangeably with the term "polynucleotide," and refers to deoxyribonucleotides or ribonucleotides and polymers thereof in either single- or double-stranded form. The term encompasses nucleic acids containing known nucleotide analogs or modified backbone residues or linkages, which are synthetic, naturally-occurring, and non-naturally-occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). In some embodiments, the nucleic acid may be an mRNA.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (See: Batzer et al., Nucleic Acids Res 1991; 25(19):5081; Ohtsuka et al., J Biol Chem 1985; 260(5):2605-8; Rossolini et al., Mol Cell Probes 1994; 8(2):91-8; the contents of each of which are herein incorporated by reference for this purpose).

Provided herein are exemplary full length heavy and light chain nucleotide sequences of anti-NPR1 antibodies. In some embodiments, the nucleic acid molecules are one or more of those identified in Table 2, e.g., those encoding an anti-NPR1 antibody or antigen binding fragment thereof. In some other embodiments, the nucleic acid molecules described herein comprise nucleotide sequences that are substantially identical (e.g., at least 80%, 85%, 90%, 91%, 92%, 93%, 94%, 95%, 96%, 97%, 98%, or 99%) to the nucleotide sequences of those identified in Table 2. When expressed from appropriate expression vectors, polypeptides encoded by these polynucleotides are capable of binding to a NPR1 protein (e.g., human NPR1).

Also provided herein are polynucleotides which encode at least one CDR region, and usually all three CDR regions, from the heavy and/or light chain of an anti-NPR1 antibody or antigen binding fragment of the disclosure. Further provided herein are polynucleotides which encode all or substantially all of the variable region sequence of the heavy chain and/or the light chain of an exemplary anti-NPR1 antibody or antigen binding fragment of the disclosure. Because of the degeneracy of the genetic code, a variety of nucleic acid sequences will encode each of the immunoglobulin amino acid sequences.

In some embodiments, the nucleic acid molecules disclosed herein encode both a variable region and a constant region of an antibody. In some embodiments, the nucleic acid molecules disclosed herein comprise nucleotides encoding a full-length heavy chain sequence that is substantially identical (e.g., at least 80%, 85%, 90%, 91%, 92%, 93%, 94%, 95%, 96%, 97%, 98%, or 99%) to the heavy chain sequence of one of the antibodies described herein including those in Table 2. In some embodiments, the nucleic acid molecules disclosed herein comprise nucleotides encoding a full-length light chain sequence that is substantially identical (e.g., at least 80%, 85%, 90%, 91%, 92%, 93%, 94%, 95%, 96%, 97%, 98%, or 99%) to the light chain sequence of one of the antibodies described herein including those in Table 2.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York, the contents of which are herein incorporated by reference for this purpose. A nucleic acid of the disclosure can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the disclosure can be obtained using standard molecular biology techniques. For antibodies expressed by hybridomas (e.g., hybridomas prepared from transgenic mice carrying human immunoglobulin genes as described further herein), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

The polynucleotide sequences can be produced by de novo solid-phase DNA synthesis or by PCR mutagenesis of an existing sequence (e.g., sequences as described herein in, for example, Table 2). Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066 (the contents of each of which are herein incorporated by reference for this purpose). Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif, 1990; Mattila et al., Nucleic Acids Res. 19:967, 1991; and Eckert et al., PCR Methods and Applications 1:17, 1991.

Once DNA fragments encoding VH and VL segments are obtained, these DNA fragments can be further manipulated by standard recombinant DNA techniques, for example to convert the variable region genes to full-length antibody chain genes, to Fab fragment genes or to an scFv gene. In these manipulations, a VL- or VH-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al., 1991 Sequences of Proteins of Immunological Interest, Fifth Edition, U.S. Department of Health and Human Services, NIH Publication No. 91-3242, the contents of which are herein incorporated by reference for this purpose) and DNA fragments encompassing these regions can be obtained by standard PCR amplification. The heavy chain constant region can be an IgG1, IgG2, IgG3, IgG4, IgA, IgE, IgM, or IgD constant region. In some embodiments, the heavy chain constant region is an IgG1 isotype. For a Fab fragment heavy chain gene, the VH-encoding DNA can be operatively linked to another DNA molecule encoding only the heavy chain CHI constant region.

The isolated DNA encoding the VL region can be converted to a full-length light chain gene (as well as to a Fab light chain gene) by operatively linking the VL-encoding DNA to another DNA molecule encoding the light chain constant region, CL. The sequences of human light chain constant region genes are known in the art (see, e.g., Kabat, E. A., et al., 1991 Sequences of Proteins of Immunological Interest, Fifth Edition, U.S. Department of Health and Human Services, NIH Publication No. 91-3242, the contents of which are herein incorporated by reference for this purpose) and DNA fragments encompassing these regions can be obtained by standard PCR amplification. The light chain constant region can be a kappa or a lambda constant region.

To create an scFv gene, the VH- and VL-encoding DNA fragments are operatively linked to another fragment encoding a flexible linker, such that the VH and VL sequences can be expressed as a contiguous single-chain protein, with the VL and VH regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554; the contents of each of which are herein incorporated by reference for this purpose).

Vectors

Various expression vectors can be employed to express the polynucleotides encoding the antibody of the disclosure or antigen-binding fragment thereof. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997, the contents of which are herein incorporated by reference for this purpose). For example, nonviral vectors useful for expression of the polynucleotides and polypeptides of the multispecific antibody of the disclosure or domains thereof in mammalian (e.g., human) cells include pThioHis A, B and C, pcDNA3.1/His, pEBVHis A, B and C, (Invitrogen, San Diego, Calif.), MPS V vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992, the contents of each of which are herein incorporated by reference for this purpose.

The choice of expression vector depends on the intended host cells in which the vector is to be expressed. Expression vectors for mammalian host cells can include expression control sequences, such as an origin of replication, a promoter, and an enhancer (see, e.g., Queen, et al., Immunol. Rev. 89:49-68, 1986, the contents of which are herein incorporated by reference for this purpose), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPS V promoter, the tetracycline-inducible CMV promoter (such as the human immediate-early CMV promoter), the constitutive CMV promoter, and known promoter-enhancer combinations.

Cultures of transformed organisms can be expanded under non-inducing conditions without biasing the population for coding sequences whose expression products are better tolerated by the host cells. In addition to promoters, other regulatory elements may also be required or desired for efficient expression of the antibody of the disclosure or fragments thereof. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987; the contents of each of which are herein incorporated by reference for this purpose). For example, the SV40 enhancer or CMV enhancer may be used to increase expression in mammalian host cells.

Accordingly, the disclosure provides a cloning or expression vector comprising one or more of the nucleic acid sequences of the antibodies shown in Table 2. Furthermore, the disclosure provides a cloning or expression vector comprising a nucleic acid encoding one or more of the nucleotide sequences shown in Table 2.

Host Cells

For expression of the light and heavy chains, the expression vector or expression vectors encoding the heavy and light chains may be transferred into a host cell by standard techniques.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra, the contents of which are herein incorporated by reference for this purpose). Other methods include, e.g., electroporation, calcium phosphate treatment, liposome-mediated transformation, injection and microinjection, ballistic methods, virosomes, immunoliposomes, polycatiomnucleic acid conjugates, naked DNA, artificial virions, fusion to the herpes virus structural protein VP22 (Elliot and O'Hare, Cell 88:223, 1997, the contents of which are herein incorporated by reference for this purpose), agent-enhanced uptake of DNA, and ex vivo transduction.

It is theoretically possible to express the antibodies of the disclosure in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13, the contents of which are herein incorporated by reference for this purpose).

For long-term, high-yield production of recombinant proteins, stable expression will often be desired. For example, cell lines which stably express the antibodies or antigen-binding fragments thereof of the disclosure can be prepared using expression vectors of the disclosure which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present disclosure thus provides a method of producing the antibodies or antigen-binding fragments of the disclosure, wherein said method comprises the step of culturing a host cell comprising a nucleic acid encoding the antibodies or antigen-binding fragments.

In some embodiments, mammalian host cells are used to express and produce the anti-NPR1 antibodies or antigen binding fragments of the present disclosure. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various COS cell lines, HeLa cells, myeloma cell lines, transformed B-cells, and hybridomas. Exemplary host cells include but are not limited to Chinese hamster ovary (CHO) cells, human embryonic kidney (HEK) cells (e.g., HEK293, HEK293T, HEK293F), monkey kidney (COS) cells (e.g., COS-1, COS-7), baby hamster kidney (BHK) cells (e.g., BHK-21), African green monkey kidney cells (e.g. BSC-1), HeLa cells, human hepatocellular carcinoma cells (e.g., Hep G2), myeloma cells (e.g., NS0, 653, SP2/0), lymphoma cells, oocyte cells, and cells from a transgenic animal (e.g., mammary epithelial cells), or any derivative, immortalized, or transformed cell thereof. In particular, for use with NS0 myeloma cells, another expression system is the GS gene expression system shown in WO87/04462, WO89/01036 and EP0338841, the contents of each of which are herein incorporated by reference for this purpose. When recombinant expression vectors encoding antibody nucleic acid are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Such purified antibodies of the disclosure may be used for any purpose including, but not limited to, the methods and uses described herein, and/or as part of a pharmaceutical composition as described herein.

In a further alternative, the host cell may be a yeast or a filamentous fungi engineered for mammalian-like glycosylation pattern, and capable for producing antibodies lacking fucose as glycosylation pattern (see, for example, EP1297172, the contents of which are herein incorporated by reference for this purpose).

Accordingly, the disclosure provides a host cell comprising one or more of the vectors, or nucleic acid sequences of the disclosure described above.

Generation of Monoclonal Antibodies of the Disclosure

Monoclonal antibodies (mAbs) can be produced by a variety of techniques, including conventional monoclonal antibody methodology e.g., the somatic cell hybridization technique of Kohler and Milstein, 1975 Nature 256:495, the contents of which are herein incorporated by reference for this purpose. Many techniques for producing monoclonal antibody can be employed e.g., viral or oncogenic transformation of B lymphocytes.

Hybridomas may be prepared using, for example, the murine system. Immunization protocols and isolation of immunized splenocytes for fusion may be performed according to any appropriate procedure. Chimeric or humanized antibodies can be prepared based on the sequence of a murine monoclonal antibody prepared as described herein. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using any known methods (see e.g., U.S. Pat. No. 4,816,567, the contents of which are herein incorporated by reference for this purpose). To create a humanized antibody, the murine CDR regions can be inserted into a human framework using any known methods. See e.g., U.S. Pat. Nos. 5,225,539, and 5,530,101; 5,585,089; 5,693,762 and 6,180,370, the contents of each of which are herein incorporated by reference for this purpose.

Human monoclonal antibodies can also be generated using transgenic or transchromosomic mice carrying parts of the human immune system rather than the mouse system. These transgenic and transchromosomic mice include mice referred to herein as HuMAb Mice® and KM mice, respectively, and are collectively referred to herein as "human Ig mice."

The HuMAb Mouse® (Medarex, Inc.) contains human immunoglobulin gene miniloci that encode un-rearranged human heavy (u and y) and K light chain immunoglobulin sequences, together with targeted mutations that inactivate the endogenous u and K chain loci (see e.g., Lonberg, et al., 1994 Nature 368(6474):856-859, the contents of which are herein incorporated by reference for this purpose). Accordingly, the mice exhibit reduced expression of mouse IgM or K, and in response to immunization, the introduced human heavy and light chain transgenes undergo class switching and somatic mutation to generate high affinity human IgGK monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13:65-93, and Harding, F. and Lonberg, N., 1995 Ann. N. Y. Acad. Sci. 764:536-546; the contents of each of which are herein incorporated by reference for this purpose). The preparation and use of HuMAb Mice®, and the genomic modifications carried by such mice, is further described in Taylor, L. et al., 1992 Nucleic Acids Research 20:6287-6295; Chen, J. et al., 1993 International Immunology 5:647-656; Tuaillon et al., 1993 Proc. Natl. Acad. Sci. USA 94:3720-3724; Choi et al., 1993 Nature Genetics 4:117-123; Chen, J. et al., 1993 EMBO J. 12:821-830; Tuaillon et al., 1994 J. Immunol. 152:2912-2920; Taylor, L. et al., 1994 International Immunology 579-591; and Fishwild, D. et al., 1996 Nature Biotechnology 14:845-851, the contents of each of which are hereby incorporated by reference for this purpose. See further, U.S. Pat. Nos. 5,545,806; 5,569,825; 5,625,126; 5,633,425; 5,789,650; 5,877,397; 5,661,016; 5,814,318; 5,874,299; and 5,770,429; U.S. Pat. No. 5,545,807; WO92/103918, WO93/12227, WO94/25585, WO97/113852, WO98/24884 and WO99/45962; and WO01/14424; the contents of each of which are hereby incorporated by reference for this purpose.

In another embodiment, human antibodies can be raised using a mouse that carries human immunoglobulin sequences on transgenes and transchomosomes such as a mouse that carries a human heavy chain transgene and a human light chain transchromosome. Such mice, referred to herein as "KM mice", are described in detail in WO02/43478, the contents of which are hereby incorporated by reference for this purpose.

Still further, alternative transgenic animal systems expressing human immunoglobulin genes are available in the art and can be used to raise antibodies of the disclosure. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963, the contents of each of which are hereby incorporated by reference for this purpose.

Moreover, alternative transchromosomic animal systems expressing human immunoglobulin genes are available in the art and can be used to raise antibodies of the disclosure. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727, the contents of which are hereby incorporated by reference for this purpose. Furthermore, cows carrying human heavy and light chain transchromosomes have been described in the art (Kuroiwa et al., 2002 Nature Biotechnology 20:889-894, the contents of which are hereby incorporated by reference for this purpose) and can be used to raise antibodies of the disclosure.

Human monoclonal antibodies of the disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698; 5,427,908 and 5,580,717; 5,969,108 and 6,172,197; and 5,885,793; 6,521,404; 6,544,731; 6,555,313; 6,582,915 and 6,593,081, the contents of each of which are hereby incorporated by reference for this purpose.

Human antibodies or antigen binding fragments of the disclosure can also be prepared using SCID mice into which human immune cells have been reconstituted such that a human antibody response can be generated upon immunization. Such mice are described in, for example, U.S. Pat. Nos. 5,476,996 and 5,698,767, the contents of each of which are hereby incorporated by reference for this purpose.

Antibodies of the disclosure may be prepared by any of the methods described herein.

Generation of Hybridomas Producing Antibodies or Antigen Binding Fragments of the Disclosure To generate hybridomas producing the antibodies or antigen binding fragments of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1X HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify antibodies or antigen binding fragments thereof, selected hybridomas can be grown in two-liter spinner-flasks for antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The antibodies or antigen binding fragments can be aliquoted and stored at −80° C.

Hybridomas producing the antibodies or antigen binding fragments of the disclosure may be produced, for example, using the methods described herein.

Generation of Transfectomas Producing Antibodies or Antigen Binding Fragments of the Disclosure Antibodies or antigen binding fragments of the disclosure can also be produced in a host cell transfectoma using, for example, a combination of suitable recombinant DNA techniques and gene transfection methods (e.g., Morrison, S. (1985) Science 229:1202, the contents of which are incorporated herein by reference for this purpose).

For example, to express the antibodies, or antigen-binding fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes may be inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology; Methods in Enzymology 185, Academic Press, San Diego, CA 1990, the contents of which are incorporated herein by reference for this purpose). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472, the contents of which are incorporated herein by reference for this purpose).

In addition to the antibody chain genes and regulatory sequences, the recombinant expression vectors of the disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, the contents of each of which are incorporated herein by reference for this purpose). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is or are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the disclosure in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13, the contents of which are incorporated herein by reference for this purpose).

Mammalian host cells for expressing the antibodies of the disclosure are described elsewhere herein. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Accordingly, the disclosure provides a process for the production of an anti-NPR1 antibody of the disclosure, or antigen-binding fragment thereof, comprising culturing a host cell of the disclosure and isolating the antibody or antigen-binding fragment thereof.

Uses and Methods of Treatment

Methods of Treatment

Provided herein are methods of treating a disease associated with NPR1 loss of function by using the anti-NPR1 antibodies or antigen binding fragments thereof disclosed herein (e.g., an antibody or group of antibodies as defined in Table 2, Table 3, or Table 4). In some embodiments, the antibody or antigen binding fragment thereof may be selected from WW01_LALA, WW03_LALA, WW05_LALA, WW06_LALA, XX01_LALA, XX01_DAPA, XX01_N30S_DAPA, XX03_LALA, XX04_LALA, XX06_LALA, XX06_DAPA, XX07_LALA, XX08_LALA, XX08_DAPA, XX08_N30S_DAPA, XX08_N30Q_DAPA, XX09_LALA, XX11_LALA, XX12_LALA, XX13_LALA, XX14_LALA, XX15_LALA, XX15_DAPA, XX16_LALA, XX16_DAPA, XX17_LALA, XX17_DAPA, XX18_LALA, XX18_DAPA, XX19_LALA, XX19_DAPA, XX20_LALA, XX20_DAPA, YY01_LALA, YY02_LALA, YY03_LALA, YY04_LALA, YY05_LALA, YY06_LALA, YY07_LALA, ZZ05_LALA, ZZ12_LALA, ZZ13_LALA, ZZ14_LALA, ZZ15_LALA, ZZ16_LALA, and ZZ17_LALA.

In some embodiments, the antibody or antigen binding fragment thereof may be selected from WW01_LALA, WW03_LALA, XX01_LALA, XX01_DAPA, XX01_N30S_DAPA, XX03_LALA, XX04_LALA, XX06_LALA, XX06_DAPA, XX07_LALA, XX08_LALA, XX08_DAPA, XX08 N30S_DAPA, XX08 N30Q_DAPA, XX09_LALA, XX11_LALA, XX12_LALA, XX13_LALA, XX14_LALA, XX15_LALA, XX15_DAPA, XX16_LALA, XX16_DAPA, XX17_LALA, XX17_DAPA, XX18_LALA, XX18_DAPA, XX19_LALA, XX19_DAPA, XX20_LALA, XX20_DAPA, YY01_LALA, YY03_LALA, YY04_LALA, ZZ12_LALA, and ZZ13_LALA. In some embodiments, the antibody or antigen binding fragment thereof may be selected from WW05_LALA, WW06_LALA, YY05_LALA, YY06_LALA, YY07_LALA, ZZ05_LALA, ZZ14_LALA, and ZZ16_LALA. In some embodiments, the antibody or antigen binding fragment thereof may be XX16_DAPA. In some embodiments, the antibody or antigen binding fragment thereof may be XX16_LALA.

In some embodiments, the disease associated with NPR1 loss of function is a cardiovascular disorder. In some embodiments, the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI). In some embodiments, the disease associated with NPR1 loss of function is heart failure, hypertrophic cardiomyopathy (HCM), hypertension, preeclampsia, asthma, glaucoma, or cytokine release syndrome.

In some embodiments, the heart failure is selected from a heart failure with reduced ejection fraction (HFrEF), heart failure with preserved ejection fraction (HFpEF), heart failure after acute myocardial infarct, or acute decompensated heart failure. In some embodiments, the hypertrophic cardiomyopathy is ventricular hypertrophy. In some embodiments, the hypertension is selected from resistant hypertension, hypertensive heart disease, pulmonary hypertension, pulmonary arterial hypertension, isolated systolic hypertension, resistant hypertension, and pulmonary arterial hypertension. In some embodiments, the hypertension is selected from resistant hypertension and hypertensive heart disease.

In some embodiments, the disease associated with NPR1 loss of function is a kidney disorder. In some embodiments, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

NPR1-related disorders also include any other disorders which are directly or indirectly associated with aberrant NPR1 activity and/or expression. Provided herein are also methods of treating a NPR1 related disorder directly or indirectly associated with aberrant NPR1 activity and/or expression by using the anti-NPR1 antibodies or antigen binding fragments disclosed herein (e.g., from Table 2, Table 3, or Table 4, such as XX16_DAPA or XX16_LALA).

In some embodiments, the present disclosure provides methods of treating an undesirable condition, disease, or disorder associated with natriuretic peptide receptor activity in a subject in need thereof, the method comprising administering to the subject a therapeutically effective amount of an antibody or antigen binding fragment disclosed herein. In some embodiments, the present disclosure provides a use of an antibody or antigen binding fragment disclosed herein for treatment of an undesirable condition, disease or disorder associated with natriuretic peptide receptor activity in a subject in need thereof. In some embodiments, the present disclosure provides an antibody or antigen binding fragment disclosed herein for use in a method for treating an undesirable condition, disease or disorder associated with natriuretic peptide receptor activity. In some embodiments, the present disclosure provides an antibody or antigen binding fragment disclosed herein for use in manufacturing a medicament for treating an undesirable condition, disease or disorder associated with natriuretic peptide receptor activity. Such conditions, diseases and disorders include, but are not limited to, cardiovascular disorders (e.g., hypertension, peripheral vascular disease, heart failure (including but not limited to heart failure with reduced ejection fraction (HFrEF), heart failure with preserved ejection fraction (HFpEF), heart failure after acute myocardial infarct, or acute decompensated heart failure), coronary artery disease (CAD), ischemic heart disease (IHD), mitral stenosis and regurgitation, angina, hypertrophic cardiomyopathy (e.g., ventricular hypertrophy), diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, or myocardial infarction (MI)), hypertension (e.g., resistant hypertension, hypertensive heart disease, pulmonary hypertension, pulmonary arterial hypertension, isolated systolic hypertension, resistant hypertension, or pulmonary arterial hypertension), preeclampsia, asthma, glaucoma, cytokine release syndrome, and/or a kidney disorder (e.g., diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD)).

In some embodiments, such methods include administering to a subject in need of treatment a therapeutically effective amount of an antibody or antigen-binding fragment thereof that specifically binds to the same epitope as one of the antibodies described herein. For example, such methods include administering to a subject in need of treatment a therapeutically effective amount of an antibody or antigen-binding fragment thereof that specifically binds to the same epitope as XX16. In another embodiment, such methods include administering to a subject in need of treatment a therapeutically effective amount of an antibody or antigen-binding fragment thereof that specifically binds to the same epitope as WW03. In another embodiment, such methods include administering to a subject in need of treatment a therapeutically effective amount of an antibody or antigen-binding fragment thereof that specifically binds to the same epitope as WW06.

All the aforementioned embodiments for the methods of protection and treatment according to the present invention are equally applicable to
- the use of any one of the antibodies or antigen binding fragments as described herein for the manufacture of a medicament for use according to the present invention,
- the use of any one of the antibodies or antigen binding fragments described herein according to the present invention,
- any one of the antibodies or antigen binding fragments described herein for use according to the present invention,
- the pharmaceutical compositions comprising any one of the antibodies or antigen binding fragments described herein for the use according to the present invention,
- the use of the pharmaceutical compositions comprising any one of the antibodies or antigen binding fragments described herein according to the present invention, and
- the use of the pharmaceutical compositions comprising any one of the antibodies or antigen binding fragments described herein for the manufacture of a medicament for use according to the present invention.

Combination Therapies

The various treatments described above can be combined with other treatment partners or therapeutic agents such as the current standard of care for a disease associated with NPR1 loss of function, e.g., the current standard of care for one or more of the diseases or disorders discussed herein. For example, the NPR1 antibodies or an antigen-binding fragment thereof described herein can be combined with one or more of an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), or combinations thereof. As a non-limiting set of examples, the NPR1 antibody or antigen binding from may be combined with an additional therapeutic agent selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, and combinations thereof. Exemplary diuretics and digitalis glycosides include, but are not limited to, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof. In some embodiments, the NPR1 antibodies or an antigen-binding fragment thereof described herein may be combined with an angiotensin receptor-neprilysin inhibitor (ARNi) such as a combination of sacubitril and valsartan (e.g., Entresto®). In some embodiments, the NPR1 antibodies or an antigen-binding fragment thereof described herein can be combined with one or more of a corticosteroid (e.g., an inhaled corticosteroid such as fluticasone, budesonide, mometasone, beclomethasone, ciclesonide, or fluticasone furoate; or an oral or intravenous corticosteroid such as prednisone or methylprednisolone), a leukotriene modifier (e.g., montelukast, zafirlukast, or zileuton), a bronchodilator (e.g., a long-acting beta agonist (e.g., salmeterol or formoterol), a short-acting beta agonist (e.g., albuterol or levalbuterol), theophylline or ipratropium), or combinations thereof (e.g., a combination of fluticasone and salmeterol, a combination of budesonide and formoterol, or a combination of formoterol and mometasone). In some embodiments, the NPR1 antibodies or an antigen-binding fragment thereof described herein can be combined with one or more of a beta-adrenoceptor antagonist (e.g., timolol, levobunolol, metipranolol, carteolol, or betaxolol), a carbonic anhydrase inhibitor (e.g., acetazolamide, dorzolamide, brinzolamide, or methazolamide), an alpha 2-adrenoceptor agonist (e.g., brimonidine or apraclonidine), a parasympathomimetic (e.g., cholinomimetics like pilocarpine), a prostaglandin analog (e.g., latanoprost, latanoprostene bunod, travoprost, bimatoprost, or tafluprost), a rho kinase inhibitor (e.g., netarsudil or ripasudil), or combinations thereof (e.g., a combination of rho kinase inhibitor and latanoprost).

Accordingly, the methods of treating a disease associated with NPR1 loss of function described herein can further include administering a second agent to the subject in need of treatment.

The term "combination" refers to either a fixed combination in one dosage unit form, or a combined administration where an anti-NPR1 antibody or antigen-binding fragment thereof described herein and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration and/or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present invention and a combination partner, are both administered to a patient simultaneously in the form of a single entity or dosage. The term "non-fixed combination" means that the therapeutic agents, e.g., a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agent.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g., synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Pharmaceutical Compositions, Dosages, and Methods of Administration

Also provided herein are compositions, e.g., pharmaceutical compositions, for use in treatment of an NPR1-associated disease. Such compositions include one or more anti-NPR1 antibodies or an antigen-binding fragment thereof as described herein and may include a pharmaceutically acceptable carrier. Such compositions can further include another agent, e.g., a current standard of care for the disease to be treated.

Pharmaceutical compositions typically include a pharmaceutically acceptable carrier. As used herein the term "pharmaceutically acceptable carrier" refers to a carrier or a diluent that does not cause significant irritation to a subject and does not abrogate the biological activity and properties of the administered anti-NPR1 antibody or antigen binding fragment and/or any additional therapeutic agent in the composition. Pharmaceutically acceptable carriers may enhance or stabilize the composition or can be used to facilitate preparation of the composition. Pharmaceutically acceptable carriers may include saline, solvents, dispersion media, coatings, antibacterial and antifungal agents, isotonic and absorption delaying agents, and the like, compatible with pharmaceutical administration. An adjuvant may also be included in any of these formulations. Pharmaceutical compositions are typically formulated to be compatible with its intended route of administration. Examples of routes of administration include parenteral (e.g., intravenous, intraarterial, intraperitoneal), oral, intracranial, intrathecal, or intranasal (e.g., inhalation), intradermal, subcutaneous, or transmucosal administration. In some embodiments, the pharmaceutical compositions are formulated to deliver anti-NPR1 antibodies or antigen-binding fragments thereof to cross the blood-brain barrier. The phrases "physiologically acceptable carrier" and "pharmaceutically acceptable carrier" may be used interchangeably.

As used herein, the term "excipient" refers to an inert substance added to a pharmaceutical composition to further facilitate administration of an active ingredient. Formulations for parenteral administration can, for example, contain excipients such as sterile water or saline, polyalkylene glycols such as polyethylene glycol, vegetable oils, or hydrogenated napthalenes. Other exemplary excipients include, but are not limited to, calcium bicarbonate, calcium phosphate, various sugars and types of starch, cellulose derivatives, gelatin, ethylene-vinyl acetate co-polymer particles, and surfactants, including, for example, polysorbate 20.

A pharmaceutical composition of the present disclosure can be administered by a variety of methods known in the art. The route and/or mode of administration may vary depending upon the desired results. In some embodiments, the administration is intravitreal, intravenous, intramuscular, intraperitoneal, or subcutaneous. The pharmaceutically acceptable carrier should be suitable for intravitreal, intravenous, intramuscular, subcutaneous, parenteral, spinal, or epidermal administration (e.g., by injection or infusion). Depending on the route of administration, the active compound(s), i.e., the anti-NPR1 antibody or antigen binding fragment and optionally the additional therapeutic agent, may be coated in a material to protect the compound(s) from the action of acids and other natural conditions that may inactivate the compound(s).

Typically, a therapeutically effective dose or efficacious dose of the anti-NPR1 antibodies or antigen binding fragments is employed in the pharmaceutical compositions of the present disclosure. The anti-NPR1 antibodies or antigen binding fragments may be formulated into pharmaceutically acceptable dosage forms by conventional methods known to those of skill in the art.

Methods of formulating suitable pharmaceutical compositions are known in the art, see, e.g., Remington: The Science and Practice of Pharmacy. 21$^{st}$ ed., 2005; and the books in the series Drugs and the Pharmaceutical Sciences: a Series of Textbooks and Monographs (Dekker, NY), the contents of each of which are incorporated by reference herein for this purpose. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Dosage regimens for anti-NPR1 antibodies and antigen binding fragments with or without an additional therapeutic agent may be adjusted to provide the optimum desired response (e.g., a therapeutic response). For example, a single bolus of one or both agents may be administered at one time, several divided doses may be administered over a predetermined period of time, or the dose of one or both agents may be proportionally reduced or increased as indicated by the exigencies of the therapeutic situation. For any particular subject, specific dosage regimens may be adjusted over time according to the individual's need, and the professional judgment of the treating clinician. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The skilled artisan (such as a medical doctor) will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Dosage regimens for anti-NPR1 antibodies and antigen binding fragments alone or in combination with an additional therapeutic agent may be adjusted to provide the optimum desired response (e.g., a therapeutic response). For example, a single bolus of one or both agents may be administered at one time, several divided doses may be administered over a predetermined period of time, or the dose of one or both agents may be proportionally reduced or increased as indicated by the exigencies of the therapeutic situation. For any particular subject, specific dosage regimens may be adjusted over time according to the individual's need, and the professional judgment of the treating clinician. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Dosage values for compositions comprising an anti-NPR1 antibody or antigen binding fragment, and/or any additional therapeutic agent(s), may be selected based on the unique characteristics of the active compound(s), and the particular therapeutic effect to be achieved. A physician or veterinarian can start doses of the antibodies of the disclosure employed in the pharmaceutical composition at levels lower than that required to achieve the desired therapeutic effect and gradually increase the dosage until the desired effect is achieved. In general, effective doses of the compositions of the present disclosure, for the treatment of obesity or another disorder described herein may vary depending upon many different factors, including means of administration, target site, physiological state of the patient, whether the patient is human or an animal, other medications administered, and whether treatment is prophylactic or therapeutic. The selected dosage level may also depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors. Treatment dosages may be titrated to optimize safety and efficacy.

Kits

Also provided herein are kits including one or more of the compositions provided herein (e.g., an antibody or antigen binding fragment thereof described in Table 2, Table 3, or Table 4) and instructions for use. Instructions for use can include instructions for diagnosis or treatment of an NPR1-associated disease. Kits as provided herein may be used in accordance with any of the methods described herein. Those skilled in the art will be aware of other suitable uses for kits provided herein, and will be able to employ the kits for such uses. Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

The disclosure is further illustrated by the following examples and claims, which are illustrative and are not meant to be further limiting. One skilled in the art will recognize many methods and materials similar or equivalent to those described herein, which could be used in the practice of the described compositions and methods. Such equivalents are within the scope of the present disclosure and claims. The contents of all references, including issued patents and published patent applications, cited throughout this application are hereby incorporated by reference.

EMBODIMENTS

In more detail, the disclosure provides the following embodiments:

Embodiment 1. An isolated antibody or antigen binding fragment that (i) binds to natriuretic peptide receptor 1 (NPR1); and (ii) is capable of activating NPR1 in the absence of atrial natriuretic peptide (ANP). Embodiment 2. An isolated anti-NPR1 antibody or antigen binding fragment; or the isolated antibody or antigen-binding fragment thereof of embodiment 1, which does not bind to and/or does not activate natriuretic peptide receptor 2 (NPR2) and/or natriuretic peptide receptor 3 (NPR3).

Embodiment 3. An isolated anti-NPR1 antibody or antigen binding fragment; or the isolated antibody or antigen binding fragment of embodiment 1 or embodiment 2 which binds to (a) human NPR1; and (b) mouse NPR1 and/or rat NPR1.

Embodiment 4. An isolated anti-NPR1 antibody or antigen binding fragment; or the isolated antibody or antigen binding fragment of embodiment 1 or embodiment 2 which binds to (a) human NPR1; and (b) cyno NPR1.

Embodiment 5. An isolated anti-NPR1 antibody or antigen binding fragment; or the isolated antibody or antigen-binding fragment thereof of any one of embodiments 1-4, which is ANP non-competitive.

Embodiment 6. An isolated anti-NPR1 antibody or antigen binding fragment; or the isolated antibody or antigen-binding fragment thereof of any one of embodiments 1, 2, or 4, which is ANP competitive.

Embodiment 7. An isolated anti-NPR1 antibody or antigen binding fragment; or the isolated antibody or antigen binding fragment of any one of embodiments 1-5 which is capable of stabilizing the ANP-NPR1 complex.

Embodiment 8. An isolated anti-NPR1 antibody or antigen binding fragment; or the isolated antibody or antigen binding fragment of any one of embodiments 1-5 or 7, wherein the antibody or antigen binding fragment thereof binds to an epitope within amino acids 99-133 of SEQ ID NO: 1.

Embodiment 9. An isolated anti-NPR1 antibody or antigen binding fragment; or the isolated antibody or antigen binding fragment of any one of embodiments 1-5, 7, or 8, wherein the antibody or antigen binding fragment thereof binds to an epitope comprising at least two amino acid residues within amino acids 99-133 of SEQ ID NO: 1.

Embodiment 10. An isolated anti-NPR1 antibody or antigen binding fragment; or the isolated antibody or antigen binding fragment of any one of embodiments 1-5 or 7-9, wherein the antibody or antigen binding fragment thereof binds to an epitope comprising at least 3, 4, 5, 6, 7, or 8 amino acid residues within amino acids 99-133 of SEQ ID NO: 1.

Embodiment 11. An isolated anti-NPR1 antibody or antigen binding fragment; or the isolated antibody or antigen binding fragment of any one of embodiments 1-5 or 7-10, wherein the antibody or antigen binding fragment thereof binds to an epitope within amino acids 99-111 of SEQ ID NO: 1.

Embodiment 12. An isolated anti-NPR1 antibody or antigen binding fragment; or the isolated antibody or antigen binding fragment of any one of embodiments 1-5 or 7-11, wherein the antibody or antigen binding fragment thereof binds to an epitope within amino acids 99-103 of SEQ ID NO: 1.

Embodiment 13. An isolated anti-NPR1 antibody or antigen binding fragment; or the isolated antibody or antigen binding fragment of any one of embodiments 1-5 or 7-12, wherein the antibody or antigen binding fragment thereof binds to an epitope within amino acids 105-111 of SEQ ID NO: 1.

Embodiment 14. An isolated anti-NPR1 antibody or antigen binding fragment; or the isolated antibody or antigen binding fragment of any one of embodiments 1-5 or 7-13, wherein the antibody or antigen binding fragment thereof binds to an epitope comprising at least 2, 3, or 4 amino acid residues within amino acids 105-111 of SEQ ID NO: 1.

Embodiment 15. An isolated anti-NPR1 antibody or antigen binding fragment; or the isolated antibody or antigen binding fragment of any one of embodiments 1-5 or 7-14, wherein the antibody or antigen binding fragment thereof binds to a conformational epitope of human NPR1, and wherein the conformational epitope comprises at least one amino acid residue within each of (i) amino acids 99-103 of SEQ ID NO: 1, (ii) 105-111 of SEQ ID NO: 1, (iii) 131-134 of SEQ ID NO: 1, and additionally binds to amino acid 375 and/or 378 of SEQ ID NO: 1.

Embodiment 16. An isolated anti-NPR1 antibody or antigen binding fragment; or the isolated antibody or antigen binding fragment of any one of embodiments 8-14, wherein the epitope is a conformational epitope, and wherein the conformational epitope additionally comprises at least one amino acid residue selected from the group consisting of amino acids 33, 34, 76, 82, and 104 of SEQ ID NO: 1.

Embodiment 17. An isolated anti-NPR1 antibody or antigen binding fragment; or the isolated antibody or antigen binding fragment of embodiment 15, wherein the conformational epitope additionally comprises at least one amino acid residue selected from the group consisting of amino acids 33, 34, 76, 82, 104, 374, and 375 of SEQ ID NO: 1.

Embodiment 18. An isolated anti-NPR1 antibody or antigen binding fragment; or the isolated antibody or antigen binding fragment of any one of embodiments 1-5 or 7-17, wherein the antibody or antigen binding fragment thereof binds to at least amino acids 82, 102, 103, 105, 106, 109, 132, and 375 of SEQ ID NO: 1.

Embodiment 19. An isolated anti-NPR1 antibody or antigen binding fragment; or the isolated antibody or antigen binding fragment of any one of embodiments 1-5 or 7-18, wherein the antibody or antigen binding fragment thereof binds to at least amino acids 34, 82, 102, 103, 105, 106, 107, 109, 132, 133, 375, and 378 of SEQ ID NO: 1.

Embodiment 20. An isolated anti-NPR1 antibody or antigen binding fragment; or the isolated antibody or antigen binding fragment of any one of embodiments 1-5 or 7-18, wherein the antibody or antigen binding fragment thereof binds to at least amino acids 79, 82, 99, 102, 103, 105, 106, 109, 131, 132, and 375 of SEQ ID NO: 1.

Embodiment 21. An isolated anti-NPR1 antibody or antigen binding fragment; or the isolated antibody or antigen binding fragment of any one of embodiments 1, 2, 4, or 6, wherein the antibody or antigen binding fragment thereof binds to an epitope within amino acids 188-219 of SEQ ID NO: 1.

Embodiment 22. An isolated anti-NPR1 antibody or antigen binding fragment; or the isolated antibody or antigen binding fragment of any one of embodiments 1, 2, 4, 6, or 21, wherein the antibody or antigen binding fragment thereof binds to an epitope comprising at least 2, 3, 4, 5, 6, or 7 amino acids within amino acids 188-219 of SEQ ID NO: 1.

Embodiment 23. An isolated anti-NPR1 antibody or antigen binding fragment; or the isolated antibody or antigen binding fragment of any one of embodiments 1, 2, 4, 6, 21, or 22, wherein the antibody or antigen binding fragment thereof binds to a conformational epitope within NPR1, and wherein the conformational epitope comprises at least one amino acid residue within each of (i) amino acids 188-198 of SEQ ID NO: 1, (ii) 201-208 of SEQ ID NO: 1, (iii) 215-238 of SEQ ID NO: 1, and (iv) 294-297 of SEQ ID NO: 1.

Embodiment 24. An isolated anti-NPR1 antibody or antigen binding fragment; or the isolated antibody or antigen binding fragment of any one of embodiments 1, 2, 4, 6, or 21-23, wherein the antibody or antigen binding fragment thereof binds to at least amino acids 188, 192, 194, 197, 201, 208, and 219 of SEQ ID NO: 1.

Embodiment 25. An isolated anti-NPR1 antibody or antigen binding fragment; or the isolated antibody or antigen binding fragment of any one of embodiments 1, 2, 4, 6, or 21-24, wherein the antibody or antigen binding fragment thereof binds to at least amino acids 188, 192, 194, 197, 201, 208, 219, and 295 of SEQ ID NO: 1.

Embodiment 26. An isolated anti-NPR1 antibody or antigen binding fragment; or the antibody or antigen binding fragment of any one of embodiments 1-5 or 7-20, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein the antibody or antigen binding fragment comprises the CDRs of one of the ANP non-competitive groups described in Table 3 or Table 4.

Embodiment 27. An isolated anti-NPR1 antibody or antigen binding fragment; or the antibody or antigen binding fragment of any one of embodiments 1, 2, 4, 6, or 21-25, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein the antibody or antigen binding fragment comprises the CDRs of one of the ANP competitive groups described in Table 3 or Table 4.

Embodiment 28. An isolated anti-NPR1 antibody or antigen binding fragment; or the antibody or antigen binding fragment of any one of embodiments 1-5, 7-20, or 26, wherein the antibody or antigen binding fragment is WW01_LALA, WW03_LALA, XX01_LALA, XX01_DAPA, XX01_N30S_DAPA, XX03_LALA, XX04_LALA, XX06_LALA, XX06_DAPA, XX07_LALA, XX08_LALA, XX08_DAPA, XX08 N30S_DAPA, XX08 N30Q_DAPA, XX09_LALA, XX11_LALA, XX12_LALA, XX13_LALA, XX14_LALA, XX15_LALA, XX15_DAPA, XX16_LALA, XX16_DAPA, XX17_LALA, XX17_DAPA, XX18_LALA, XX18_DAPA, XX19_LALA, XX19_DAPA, XX20_LALA, XX20_DAPA, YY01_LALA, YY03_LALA, YY04_LALA, ZZ12_LALA, and ZZ13_LALA.

Embodiment 29. An isolated anti-NPR1 antibody or antigen binding fragment; or the antibody or antigen binding fragment of any one of embodiments 1, 2, 4, 6, 21-25, or 27, wherein the antibody or antigen binding fragment is WW05_LALA, WW06_LALA, YY05_LALA, YY06_LALA, YY07_LALA, ZZ05_LALA, ZZ14_LALA, and ZZ16_LALA.

Embodiment 30. An isolated anti-NPR1 antibody or antigen binding fragment; or the antibody or antigen binding fragment of any one of embodiments 1-5, 7-20, 26, or 28, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $Y_1QY_2Y_3Y_4Y$ 5PRT (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A;

(II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $Y_1QY_2Y_3Y_4Y$ 5PRT (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A;

(III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1Y_2Y_3Y_4PR$ (SEQ ID NO: 432); wherein $Y_1$ is S, E, T, or I, $Y_2$ is Y or W, $Y_3$ is E, V, R, A, T, or M, and $Y_4$ is K, V, R, or A; or (IV) HCDR1 comprises or consists of an amino acid sequence as set forth in SEQ ID NO: 34, HCDR2 comprises or consists of an amino acid sequence as set forth in $IX_1SX_2GX_3YX_4$ (SEQ ID NO: 433), wherein $X_1$ is S or E, $X_2$ is D or K, $X_3$ is S or N, and $X_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $Y_1QY_2Y_3Y_4Y$ 5PRT (SEQ ID NO: 430); wherein $Y_1$ is M or Q, $Y_2$ is S, E, T, or I, $Y_3$ is Y or W, $Y_4$ is E, V, R, A, T, or M, and $Y_5$ is K, V, R, or A;

(b) (I) HCDR1 comprises or consists of an amino acid sequence as set forth in SEQ ID NO: 28; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A;

(II) HCDR1 comprises or consists of an amino acid sequence as set forth in SEQ ID NO: 31; HCDR2 comprises or consists of an amino acid sequence as set forth in $X_1IX_2SX_3GX_4YX_5X_6YADSVKG$ (SEQ ID NO: 429), wherein $X_1$ is A or V, $X_2$ is S or E, $X_3$ is D or K, $X_4$ is S or N, $X_5$ is I or T, and $X_6$ is Y or F; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A;

(III) HCDR1 comprises or consists of an amino acid sequence as set forth in SEQ ID NO: 32, HCDR2 comprises or consists of an amino acid sequence as set forth in $X_1SX_2GX_3Y$ (SEQ ID NO: 431), wherein $X_1$ is S or E, $X_2$ is D or K, or $X_3$ is S or N, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in $Y_1WY_2Y_3PR$ (SEQ ID NO: 435); wherein $Y_1$ is S, E, T, or I, $Y_2$ is V, R, A, T, or M, and $Y_3$ is K, V, R, or A; or (IV) HCDR1 comprises or consists of an amino acid sequence as set forth in SEQ ID NO: 34, HCDR2 comprises or consists of an amino acid sequence as set forth in $IX_1SX_2GX_3YX_4$ (SEQ ID NO: 433), wherein $X_1$ is S or E, $X_2$ is D or K, $X_3$ is S or N, and $X_4$ is I or T, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A;

(c) (I) HCDR1 comprises or consists of an amino acid sequence as set forth in SEQ ID NO: 28; HCDR2 comprises or consists of an amino acid sequence as set forth in SEQ ID NO: 119; HCDR3 comprises or consists of an amino acid sequence as set forth in SEQ ID NO: 30; LCDR1 comprises or consists of an amino acid sequence as set forth in SEQ ID NO: 41; LCDR2 comprises or consists of an amino acid sequence as set forth in SEQ ID NO: 42; and LCDR3 comprises or consists of an amino acid sequence as set forth in $QQY_1WY_2Y_3PRT$ (SEQ ID NO: 434); wherein $Y_1$ is S, E, T, or I, $Y_2$ is V, R, A, T, or M, and $Y_3$ is K, V, R, or A;

(II) HCDR1 comprises or consists of an amino acid sequence as set forth in SEQ ID NO: 31; HCDR2 comprises or consists of an amino acid sequence as set forth in SEQ ID NO: 119; HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A;

(III) HCDR1 comprises or consists of an amino acid sequence as set forth in SEQ ID NO: 32, HCDR2 comprises or consists of an amino acid sequence as set forth in SEQ ID NO: 120, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in Y$_1$WY$_2$Y$_3$PR (SEQ ID NO: 435); wherein Y$_1$ is S, E, T, or I, Y$_2$ is V, R, A, T, or M, and Y$_3$ is K, V, R, or A; or (IV) HCDR1 comprises or consists of an amino acid sequence as set forth in SEQ ID NO: 34, HCDR2 comprises or consists of an amino acid sequence as set forth in SEQ ID NO: 121, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in QQY$_1$WY$_2$Y$_3$PRT (SEQ ID NO: 434); wherein Y$_1$ is S, E, T, or I, Y$_2$ is V, R, A, T, or M, and Y$_3$ is K, V, R, or A;

(d) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(II) HCDR1 comprises or consists of an amino acid sequence as set forth in SEQ ID NO: 7, HCDR2 comprises or consists of an amino acid sequence as set forth in SIY$_1$Y$_2$Y$_3$GY$_4$Y$_5$TY$_6$YADSVKG (SEQ ID NO: 437), wherein Y$_1$ is S or G, Y$_2$ is S or G, Y$_3$ is S or Q, Y$_4$ is S, Q, or G, Y$_5$ is S, N, or M, and Y$_6$ is Y or L, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in Y$_1$Y$_2$Y$_3$GY$_4$Y$_5$ (SEQ ID NO: 439), wherein Y$_1$ is S or G, Y$_2$ is S or G, Y$_3$ is S or Q, Y$_4$ is S, Q, or G, and Y$_5$ is S, N, or M, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in IY$_1$Y$_2$Y$_3$GY$_4$Y$_5$T (SEQ ID NO: 441), wherein Y$_1$ is S or G, Y$_2$ is S or G, Y$_3$ is S or Q, Y$_4$ is S, Q, or G, and Y$_5$ is S, N, or M, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19;

(e) (I) HCDR1 comprises or consists of an amino acid sequence as set forth in GFTFX$_1$THYIH (SEQ ID NO: 436), wherein X$_1$ is N, S, or Q, HCDR2 comprises or consists of an amino acid sequence as set forth in SISY$_1$SGY$_2$Y$_3$TYYADSVKG (SEQ ID NO: 442), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(II) HCDR1 comprises or consists of an amino acid sequence as set forth in SEQ ID NO: 7, HCDR2 comprises or consists of an amino acid sequence as set forth in SISY$_1$SGY$_2$Y$_3$TYYADSVKG (SEQ ID NO: 442), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19;

(III) HCDR1 comprises or consists of an amino acid sequence as set forth in GFTFX$_1$TH (SEQ ID NO: 438), wherein X$_1$ is N, S, or Q, HCDR2 comprises or consists of an amino acid sequence as set forth in SY$_1$SGY$_2$Y$_3$ (SEQ ID NO: 443), wherein Y$_1$ is S or G, Y$_2$ is S or Q, and Y$_3$ is S or N, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in GFTFX$_1$THY (SEQ ID NO: 440), wherein X$_1$ is N, S, or Q, HCDR2 comprises or consists of an amino acid sequence as set forth in ISY$_1$SGY$_2$Y$_3$T (SEQ ID NO: 444), wherein Y$_1$ is S or G, Y$_2$ is S or Q, and Y$_3$ is S or N, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19;

(f) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in Y$_1$QY$_2$Y$_3$Y$_4$E (SEQ ID NO: 449), wherein Y$_1$ is K or H, Y$_2$ is S, Q, or H, Y$_3$ is G or A, and Y$_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IY$_1$QY$_2$Y$_3$Y$_4$EY$_5$ (SEQ ID NO: 451), wherein Y$_1$ is K or H, Y$_2$ is S, Q, or H, Y$_3$ is G or A, Y$_4$ is S, H, or L, and Y$_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239;

(g) (I) HCDR1 comprises or consists of an amino acid sequence as set forth in GFX$_1$FSX$_2$YX$_3$X$_4$X$_5$ (SEQ ID NO: 445), wherein X$_1$ is S or T, X$_2$ is S, K, or R, X$_3$ is W or Y, X$_4$ is I or L, and X$_5$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$X$_3$X$_4$ (SEQ ID NO: 447), wherein X$_1$ is S, K, or R, X$_2$ is W or Y, X$_3$ is I or L, and X$_4$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFX$_1$FSX$_2$Y (SEQ ID NO: 448), wherein X$_1$ is S or T, and X$_2$ is S, K, or R, HCDR2 comprises or consists of an amino acid sequence as set forth in HQY$_1$Y$_2$Y$_3$E (SEQ ID NO: 456), wherein Y$_1$ is Q or H, Y$_2$ is G or A, and Y$_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFX$_1$FSX$_2$YX$_3$ (SEQ ID NO: 450), wherein X$_1$ is S or T, X$_2$ is S, K, or R, and X$_3$ is W or Y, HCDR2 comprises or consists of an amino acid sequence as set forth in IHQY$_1$Y$_2$Y$_3$EY$_4$ (SEQ ID NO: 458), wherein Y$_1$ is Q or H, Y$_2$ is G or A, Y$_3$ is H or L, and Y$_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239;

(h) (I) HCDR1 comprises or consists of an amino acid sequence as set forth in GFTFSX$_1$YX$_2$IX$_3$ (SEQ ID NO: 452), wherein X$_1$ is S or R, X$_2$ is W or Y, and X$_3$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$IX$_3$ (SEQ ID NO: 454), wherein X$_1$ is S or R, X$_2$ is W or Y, and X$_3$ is S or N, HCDR2 comprises or consists of an amino acid sequence as set forth in Y$_1$IY$_2$QY$_3$Y$_4$Y$_5$EY$_6$Y$_7$YVESVKG (SEQ ID NO: 446), wherein Y$_1$ is S or N, Y$_2$ is K or H, Y$_3$ is S, Q, or H, Y$_4$ is G or A, Y$_5$ is S, H, or L, Y$_6$ is T or K, and Y$_7$ is Y, K, or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFTFSX$_1$Y (SEQ ID NO: 455), wherein X$_1$ is S or R, HCDR2 comprises or consists of an amino acid sequence as set forth in Y$_1$QY$_2$Y$_3$Y$_4$E (SEQ ID NO: 449), wherein Y$_1$ is K or H, Y$_2$ is S, Q, or H, Y$_3$ is G or A, and Y$_4$ is S, H, or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFTFSX$_1$YX$_2$ (SEQ ID NO: 457), wherein X$_1$ is S or R, and X$_2$ is W or Y, HCDR2 comprises or consists of an amino acid sequence as set forth in IY$_1$QY$_2$Y$_3$Y$_4$EY$_5$ (SEQ ID NO: 451), wherein Y$_1$ is K or H, Y$_2$ is S, Q, or H, Y$_3$ is G or A, Y$_4$ is S, H, or L, and Y$_5$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239; or (i) (I) HCDR1 comprises or consists of an amino acid sequence as set forth in GFTFSX$_1$YX$_2$IX$_3$ (SEQ ID NO: 452), wherein X$_1$ is S or R, X$_2$ is W or Y, and X$_3$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(II) HCDR1 comprises or consists of an amino acid sequence as set forth in X$_1$YX$_2$IX$_3$ (SEQ ID NO: 454), wherein X$_1$ is S or R, X$_2$ is W or Y, and X$_3$ is S or N, HCDR2 comprises or consists of an amino acid sequence as set forth in SIHQY$_1$Y$_2$Y$_3$EY$_4$Y$_5$YVESVKG (SEQ ID NO: 453), wherein Y$_1$ is Q or H, Y$_2$ is G or A, Y$_3$ is H or L, Y$_4$ is T or K, and Y$_5$ is K or R, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239;

(III) HCDR1 comprises or consists of an amino acid sequence as set forth in GFTFSX$_1$Y (SEQ ID NO: 455), wherein X$_1$ is S or R, HCDR2 comprises or consists of an amino acid sequence as set forth in HQY$_1$Y$_2$Y$_3$E (SEQ ID NO: 456), wherein Y$_1$ is Q or H, Y$_2$ is G or A, and Y$_3$ is H or L, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in GFTFSX$_1$YX$_2$ (SEQ ID NO: 457), wherein X$_1$ is S or R, and X$_2$ is W or Y, HCDR2 comprises or consists of an amino acid sequence as set forth in IHQY$_1$Y$_2$Y$_3$EY$_4$ (SEQ ID NO: 458), wherein Y$_1$ is Q or H, Y$_2$ is G or A, Y$_3$ is H or L, and Y$_4$ is T or K, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

Embodiment 31. An isolated anti-NPR1 antibody or antigen binding fragment; or the antibody or antigen binding fragment of any one of embodiments 1, 2, 4, 6, 21-25, 27, or 29, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in GX$_1$X$_2$X$_3$GX$_4$LGFDH (SEQ ID NO: 459), wherein X$_1$ is A or S, X$_2$ is V or L, X$_3$ is A or P, and X$_4$ is Q or L, LCDR1 comprises or consists of an amino acid sequence as set forth in SEQ ID NO: 320, LCDR2 comprises or consists of an amino acid sequence as set forth in GNSNRPY$_1$ (SEQ ID NO: 460), wherein Y$_1$ is S or N, and LCDR3 comprises or consists of an amino acid sequence as set forth in QSYZ$_1$Z$_2$Z$_3$Z$_4$Z$_5$Z$_6$Z$_7$V (SEQ ID NO: 461), wherein Z$_1$ is Y, D, or G, Z$_2$ is T, S, or A, Z$_3$ is S, P, or F, Z$_4$ is S, T, or P, Z$_5$ is H, S, or R, Z$_6$ is G, S, or F, and Z$_7$ is P, S, or V;

(II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in GX$_1$X$_2$X$_3$GX$_4$LGFDH (SEQ ID NO: 459), wherein X$_1$ is A or S, X$_2$ is V or L, X$_3$ is A or P, and X$_4$ is Q or L, LCDR1 comprises or consists of an amino acid sequence as set forth in SEQ ID NO: 320, LCDR2 comprises or consists of an amino acid sequence as set forth in GNSNRPY$_1$ (SEQ ID NO: 460), wherein Y$_1$ is S or N, and LCDR3 comprises or consists of an amino acid sequence as set forth in QSYZ$_1$Z$_2$Z$_3$Z$_4$Z$_5$Z$_6$Z$_7$V (SEQ ID NO: 461), wherein Z$_1$ is Y, D, or G, Z$_2$ is T, S, or A, Z$_3$ is S, P, or F, Z$_4$ is S, T, or P, Z$_5$ is H, S, or R, Z$_6$ is G, S, or F, and Z$_7$ is P, S, or V;

(III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in GX$_1$X$_2$X$_3$GX$_4$LGFDH (SEQ ID NO: 459), wherein X$_1$ is A or S, X$_2$ is V or L, X$_3$ is A or P, and X$_4$ is Q or L, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in YZ$_1$Z$_2$Z$_3$Z$_4$Z$_5$Z$_6$Z$_7$ (SEQ ID NO: 462), wherein Z$_1$ is Y, D, or G, Z$_2$ is T, S, or A, Z$_3$ is S, P, or F, Z$_4$ is S, T, or P, Z$_5$ is H, S, or R, Z$_6$ is G, S, or F, and Z$_7$ is P, S, or V; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in ARGX$_1$X$_2$X$_3$GX$_4$LGFDH (SEQ ID NO: 463), wherein X$_1$ is A or S, X$_2$ is V or L, X$_3$ is A or P, and X$_4$ is Q or L, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in QSYZ$_1$Z$_2$Z$_3$Z$_4$Z$_5$Z$_6$Z$_7$V (SEQ ID NO: 461), wherein Z$_1$ is Y, D, or G, Z$_2$ is T, S, or A, Z$_3$ is S, P, or F, Z$_4$ is S, T, or P, Z$_5$ is H, S, or R, Z$_6$ is G, S, or F, and Z$_7$ is P, S, or V;

(b) (I) HCDR1 comprises or consists of an amino acid sequence as set forth in GFTFX$_1$X$_2$YAX$_3$X$_4$ (SEQ ID NO: 464), wherein X$_1$ is S or G, X$_2$ is S or T, X$_3$ is I or M, and X$_4$ is S or T, HCDR2 comprises or consists of an amino acid sequence as set forth in Y$_1$ISY$_2$Y$_3$GY$_4$Y$_5$Y$_6$Y$_7$YAY$_8$SVKG (SEQ ID NO: 465), wherein Y$_1$ is A or S, Y$_2$ is A, S, or G, Y$_3$ is S or H, Y$_4$ is G or Y, Y$_5$ is S or Y, Y$_6$ is T or A, Y$_7$ is Y, R, or N, and Y$_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(II) HCDR1 comprises or consists of an amino acid sequence as set forth in X$_1$YAX$_2$X$_3$ (SEQ ID NO: 466), wherein X$_1$ is S or T, X$_2$ is I or M, and X$_3$ is S or T, HCDR2 comprises or consists of an amino acid sequence as set forth in Y$_1$ISY$_2$Y$_3$GY$_4$Y$_5$Y$_6$Y$_7$YAY$_8$SVKG (SEQ ID NO: 465), wherein Y$_1$ is A or S, Y$_2$ is A, S, or G, Y$_3$ is S or H, Y$_4$ is G or Y, Y$_5$ is S or Y, Y$_6$ is T or A, Y$_7$ is Y, R, or N, and Y$_8$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(III) HCDR1 comprises or consists of an amino acid sequence as set forth in GFTFX$_1$X$_2$Y (SEQ ID NO: 467), wherein X$_1$ is S or G, and X$_2$ is S or T, HCDR2 comprises or consists of an amino acid sequence as set forth in SY$_1$Y$_2$GY$_3$Y$_4$ (SEQ ID NO: 468), wherein Y$_1$ is A, S, or G, Y$_2$ is S or H, Y$_3$ is G or Y, and Y$_4$ is S or Y, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in GFTFX$_1$X$_2$YA (SEQ ID NO: 469), wherein X$_1$ is S or G, and X$_2$ is S or T, HCDR2 comprises or consists of an amino acid sequence as set forth in ISY$_1$Y$_2$GY$_3$Y$_4$T (SEQ ID NO: 470), wherein Y$_1$ is S or G, Y$_2$ is S or H, Y$_3$ is G or Y, and Y$_4$ is S or Y, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339; or (c) (I) HCDR1 comprises or consists of an amino acid sequence as set forth in GFTFX$_1$X$_2$YAX$_3$X$_4$ (SEQ ID NO: 464), wherein X$_1$ is S or G, X$_2$ is S or T, X$_3$ is I or M, and X$_4$ is S or T, HCDR2 comprises or consists of an amino acid sequence as set forth in SISY$_1$Y$_2$GYYY$_3$Y$_4$YAY$_5$SVKG (SEQ ID NO: 471), wherein Y$_1$ is A or S, Y$_2$ is S or H, Y$_3$ is T or A, Y$_4$ is R or N, and Y$_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(II) HCDR1 comprises or consists of an amino acid sequence as set forth in X$_1$YAX$_2$X$_3$ (SEQ ID NO: 466), wherein X$_1$ is S or T, X$_2$ is I or M, and X$_3$ is S or T, HCDR2 comprises or consists of an amino acid sequence as set forth in SISY$_1$Y$_2$GYYY$_3$Y$_4$YAY5SVKG (SEQ ID NO: 471), wherein Y$_1$ is A or S, Y$_2$ is S or H, Y$_3$ is T or A, Y$_4$ is R or N, and Y$_5$ is E or G, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339;

(III) HCDR1 comprises or consists of an amino acid sequence as set forth in GFTFX$_1$X$_2$Y (SEQ ID NO: 467), wherein X$_1$ is S or G, and X$_2$ is S or T, HCDR2 comprises or consists of an amino acid sequence as set forth in SY$_1$Y$_2$GYY (SEQ ID NO: 472), wherein Y$_1$ is A or S, and Y$_2$ is S or H, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in GFTFX$_1$X$_2$YA (SEQ ID NO: 469), wherein X$_1$ is S or G, and X$_2$ is S or T, HCDR2 comprises or consists of an amino acid sequence as set forth in ISY$_1$Y$_2$G (SEQ ID NO: 473), wherein Y$_1$ is A, S, or G, and Y$_2$ is S or H, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

Embodiment 32. An isolated anti-NPR1 antibody or antigen binding fragment; or the antibody or antigen binding fragment of any one of embodiments 1-5, 7-20, 26, 28, or 30, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 28, HCDR2 comprises or consists of an amino acid sequence as set forth in any one of comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (II) HCDR1 comprises or consists of an amino acid sequence as set forth in SEQ ID NO: 31, HCDR2 comprises or consists of an amino acid sequence as set forth in any one of SEQ ID NOs: 29, 119, and 190, HCDR3 comprises or consists of an amino acid sequence as set forth in SEQ ID NO: 30, LCDR1 comprises or consists of an amino acid sequence as set forth in SEQ ID NO: 41, LCDR2 comprises or consists of an amino acid sequence as set forth in SEQ ID NO: 42, and LCDR3 comprises or consists of an amino acid sequence as set forth in any one of SEQ ID NOs: 43, 126, 134, 145, 172, 178, and 184; (III) HCDR1 comprises or consists of an amino acid sequence as set forth in SEQ ID NO: 32, HCDR2 comprises or consists of an amino acid sequence as set forth in any one of SEQ ID NOs: 33, 120, and 191, HCDR3 comprises or consists of an amino acid sequence as set forth in SEQ ID NO: 30, LCDR1 comprises or consists of an amino acid sequence as set forth in SEQ ID NO: 44, LCDR2 comprises or consists of an amino acid sequence as set forth in SEQ ID NO: 45, and LCDR3 comprises or consists of an amino acid sequence as set forth in any one of SEQ ID NOs: 46, 127, 135, 146, 173, 179, and 185; or (IV) HCDR1 comprises or consists of an amino acid sequence as set forth in SEQ ID NO: 34, HCDR2 comprises or consists of an amino acid sequence as set forth in any one of SEQ ID NOs: 35, 121, and 192, HCDR3 comprises or consists of an amino acid sequence as set forth in SEQ ID NO: 36, LCDR1 comprises or consists of an amino acid sequence as set forth in SEQ ID NO: 47, LCDR2 comprises or consists of an amino acid sequence as set forth in SEQ ID NO: 45, and LCDR3 comprises or consists of an amino acid sequence as set forth in any one of SEQ ID NOs: 43, 126, 134, 145, 172, 178, and 184;

(b) (I) HCDR1 comprises or consists of an amino acid sequence as set forth in any one of SEQ ID NOs: 4, 112, and 165, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (II) HCDR1 comprises or consists of an amino acid sequence as set forth in SEQ ID NO: 7, HCDR2 comprises or consists of an amino acid sequence as set forth in any one of SEQ ID NOs: 5, 100, and 151, HCDR3 comprises or consists of an amino acid sequence as set forth in SEQ ID NO: 6, LCDR1 comprises or consists of an amino acid sequence as set forth in SEQ ID NO: 17, LCDR2 comprises or consists of an amino acid sequence as set forth in SEQ ID NO: 18, and LCDR3 comprises or consists of an amino acid sequence as set forth in SEQ ID NO: 19; (III) HCDR1 comprises or consists of an amino acid sequence as set forth in any one of SEQ ID NOs: 8, 113, and 166, HCDR2 comprises or consists of an amino acid sequence as set forth in any one of SEQ ID NOs: 9, 101, and 152, HCDR3 comprises or consists of an amino acid sequence as set forth in SEQ ID NO: 6, LCDR1 comprises or consists of an amino acid sequence as set forth in SEQ ID NO: 20, LCDR2 comprises or consists of an amino acid sequence as set forth in SEQ ID NO: 21, and LCDR3 comprises or consists of an amino acid sequence as set forth in SEQ ID NO: 22; or (IV) HCDR1 comprises or consists of an amino acid sequence as set forth in any one of SEQ ID NOs: 10, 114, and 167, HCDR2 comprises or consists of an amino acid sequence as set forth in any one of SEQ ID NOs: 11, 102, and 153, HCDR3 comprises or consists of an amino acid sequence as set forth in SEQ ID NO: 12, LCDR1 comprises or consists of an amino acid sequence as set forth in SEQ ID NO: 23, LCDR2 comprises or consists of an amino acid sequence as set forth in SEQ ID NO: 21, and LCDR3 comprises or consists of an amino acid sequence as set forth in SEQ ID NO: 19; or (c) (I) HCDR1 comprises or consists of an amino acid sequence as set forth in any one of SEQ ID NOs: 226, 367, and 378, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (II) HCDR1 comprises or consists of an amino acid sequence as set forth in any one of SEQ ID NOs: 229, 369, and 380, HCDR2 comprises or consists of an amino acid sequence as set forth in any one of SEQ ID NOs: 227, 368, and 379, HCDR3 comprises or consists of an amino acid sequence as set forth in SEQ ID NO: 228, LCDR1 comprises or consists of an amino acid sequence as set forth in SEQ ID NO: 237, LCDR2 comprises or consists of an amino acid sequence as set forth in SEQ ID NO: 238, and LCDR3 comprises or consists of an amino acid sequence as set forth in SEQ ID NO: 239; (III) HCDR1 comprises or consists of an amino acid sequence as set forth in any one of SEQ ID NOs: 32, 370, and 381, HCDR2 comprises or consists of an amino acid sequence as set forth in any one of SEQ ID NOs: 230, 371, and 382, HCDR3 comprises or consists of an amino acid sequence as set forth in SEQ ID NO: 228, LCDR1 comprises or consists of an amino acid sequence as set forth in SEQ ID NO: 240, LCDR2 comprises or consists of an amino acid sequence as set forth in SEQ ID NO: 241, and LCDR3 comprises or consists of an amino acid sequence as set forth in SEQ ID NO: 242; or (IV) HCDR1 comprises or consists of an amino acid sequence as set forth in any one of SEQ ID NOs: 34, 372, and 383, HCDR2 comprises or consists of an amino acid sequence as set forth in any one of SEQ ID NOs: 231, 373, and 384, HCDR3 comprises or consists of an amino acid sequence as set forth in SEQ ID NO: 232, LCDR1 comprises or consists of an amino acid sequence as set forth in SEQ ID NO: 243, LCDR2 comprises or consists of an amino acid sequence as set forth in SEQ ID NO: 241, and LCDR3 comprises or consists of an amino acid sequence as set forth in SEQ ID NO: 239.

Embodiment 33. An isolated anti-NPR1 antibody or antigen binding fragment; or the antibody or antigen binding fragment of any one of embodiments 1, 2, 4, 6, 21-25, 27, 29, or 31, wherein the antibody or antigen binding fragment comprises three heavy chain complementarity determining regions (HCDR1, HCDR2, and HCDR3) and three light chain complementarity determining regions (LCDR1, LCDR2, and LCDR3), and wherein:

(a) (I) HCDR1 comprises or consists of an amino acid sequence as set forth in SEQ ID NO: 310, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (II) HCDR1 comprises or consists of an amino acid sequence as set forth in SEQ ID NO: 229, HCDR2 comprises or consists of an amino acid sequence as set forth in SEQ ID NO: 311, HCDR3 comprises or consists of an amino acid sequence as set forth in any one of SEQ ID NOs: 312 and 348, LCDR1 comprises or consists of an amino acid sequence as set forth in SEQ ID NO: 320, LCDR2 comprises or consists of an amino acid sequence as set forth in any one of SEQ ID NOs: 321 and 354, and LCDR3 comprises or consists of an amino acid sequence as set forth in any one of SEQ ID NOs: 322, 355, and 361; (III) HCDR1 comprises or consists of an amino acid sequence as set forth in SEQ ID NO: 80, HCDR2 comprises or consists of an amino acid sequence as set forth in SEQ ID NO: 313, HCDR3 comprises or consists of an amino acid sequence as set forth in any one of SEQ ID NOs: 312 and 348, LCDR1 comprises or consists of an amino acid sequence as set forth in SEQ ID NO: 323, LCDR2 comprises or consists of an amino acid sequence as set forth in SEQ ID NO: 324, and LCDR3 comprises or consists of an amino acid sequence as set forth in any one of SEQ ID NOs: 325, 356, and 362; or (IV) HCDR1 comprises or consists of an amino acid sequence as set forth in SEQ ID NO: 82, HCDR2 comprises or consists of an amino acid sequence as set forth in SEQ ID NO: 314, HCDR3 comprises or consists of an amino acid sequence as set forth in any one of SEQ ID NOs: 315 and 349, LCDR1 comprises or consists of an amino acid sequence as set forth in SEQ ID NO: 326, LCDR2 comprises or consists of an amino acid sequence as set forth in SEQ ID NO: 324, and LCDR3 comprises or consists of an amino acid sequence as set forth in any one of SEQ ID NOs: 322, 355, and 361; or (b) (I) HCDR1 comprises or consists of an amino acid sequence as set forth in any one of SEQ ID NOs: 270 and 407, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (II) HCDR1 comprises or consists of an amino acid sequence as set forth in any one of SEQ ID NOs: 273 and 409, HCDR2 comprises or consists of an amino acid sequence as set forth in any one of SEQ ID NOs: 271, 389, and 408, HCDR3 comprises or consists of an amino acid sequence as set forth in SEQ ID NO: 331, LCDR1 comprises or consists of an amino acid sequence as set forth in SEQ ID NO: 337, LCDR2 comprises or consists of an amino acid sequence as set forth in SEQ ID NO: 338, and LCDR3 comprises or consists of an amino acid sequence as set forth in SEQ ID NO: 339; (III) HCDR1 comprises or consists of an amino acid sequence as set forth in any one of SEQ ID NOs: 32 and 410, HCDR2 comprises or consists of an amino acid sequence as set forth in any one of SEQ ID NOs: 274, 390, and 411, HCDR3 comprises or consists of an amino acid sequence as set forth in SEQ ID NO: 331, LCDR1 comprises or consists of an amino acid sequence as set forth in SEQ ID NO: 340, LCDR2 comprises or consists of an amino acid sequence as set forth in SEQ ID NO: 341, and LCDR3 comprises or consists of an amino acid sequence as set forth in SEQ ID NO: 342; or (IV) HCDR1 comprises or consists of an amino acid sequence as set forth in any one of SEQ ID NOs: 275 and 412, HCDR2 comprises or consists of an amino acid sequence as set forth in any one of SEQ ID NOs: 276, 391, and 413, HCDR3 comprises or consists of an amino acid sequence as set forth in SEQ ID NO: 332, LCDR1 comprises or consists of an amino acid sequence as set forth in SEQ ID NO: 343, LCDR2 comprises or consists of an amino acid sequence as set forth in SEQ ID NO: 341, and LCDR3 comprises or consists of an amino acid sequence as set forth in SEQ ID NO: 339.

Embodiment 34. An isolated anti-NPR1 antibody or antigen binding fragment; or the antibody or antigen binding fragment of any one of embodiments 1-5, 7-20, 26, 28, 30, or 32, wherein the antibody or antigen binding fragment comprises three heavy chain complementarity determining regions (HCDR1, HCDR2, and HCDR3) and three light chain complementarity determining regions (LCDR1, LCDR2, and LCDR3) selected from:

- (a) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 134 (LCDR3);
- (b) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 126 (LCDR3);
- (c) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 145 (LCDR3);
- (d) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 172 (LCDR3);
- (e) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 178 (LCDR3);
- (f) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 184 (LCDR3);
- (g) (I) SEQ ID NO: 4 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3);
- (h) (I) SEQ ID NO: 112 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 100 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 101 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 102 (HCDR2), SEQ ID NO: 12 (HCDR3), SEQ ID NO: 23 (LCDR1), SEQ ID NO: 21 (LCDR2), and SEQ ID NO: 19 (LCDR3);
- (i) (I) SEQ ID NO: 28 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 119 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 120 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 121 (HCDR2), SEQ ID NO: 36 (HCDR3), SEQ ID NO: 47 (LCDR1), SEQ ID NO: 45 (LCDR2), and SEQ ID NO: 43 (LCDR3);

(j) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 126 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 127 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 126 (LCDR3);

(k) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 134 (LCDR3);

(l) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 145 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 146 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 145 (LCDR3);

(m) (I) SEQ ID NO: 4 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3);

(n) (I) SEQ ID NO: 112 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 113 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 114 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3);

(o) (I) SEQ ID NO: 165 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 151 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 166 (HCDR1), SEQ ID NO: 152 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 167 (HCDR1), SEQ ID NO: 153 (HCDR2), SEQ ID NO: 12 (HCDR3), SEQ ID NO: 23 (LCDR1), SEQ ID NO: 21 (LCDR2), and SEQ ID NO: 19 (LCDR3);

(p) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 172 (LCDR3);

(q) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 178 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 179 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 178 (LCDR3);

(r) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 184 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 185 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 184 (LCDR3);

(s) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 134 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 135 (LCDR3); or (IV) SEQ ID NO: 34 (HCDR1), SEQ ID NO: 192

(HCDR2), SEQ ID NO: 36 (HCDR3), SEQ ID NO: 47 (LCDR1), SEQ ID NO: 45 (LCDR2), and SEQ ID NO: 134 (LCDR3);

(t) (I) SEQ ID NO: 28 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (II) SEQ ID NO: 31 (HCDR1), SEQ ID NO: 190 (HCDR2), SEQ ID NO: 30 (HCDR3), SEQ ID NO: 41 (LCDR1), SEQ ID NO: 42 (LCDR2), and SEQ ID NO: 172 (LCDR3); (III) SEQ ID NO: 32 (HCDR1), SEQ ID NO: 191 (HCDR2), SEQ ID NO: 30 (HCDR3), SEQ ID NO: 44 (LCDR1), SEQ ID NO: 45 (LCDR2), and SEQ ID NO: 173 (LCDR3); or (IV) SEQ ID NO: 34 (HCDR1), SEQ ID NO: 192 (HCDR2), SEQ ID NO: 36 (HCDR3), SEQ ID NO: 47 (LCDR1), SEQ ID NO: 45 (LCDR2), and SEQ ID NO: 172 (LCDR3);

(u) (I) SEQ ID NO: 4 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (II) SEQ ID NO: 7 (HCDR1), SEQ ID NO: 5 (HCDR2), SEQ ID NO: 6 (HCDR3), SEQ ID NO: 17 (LCDR1), SEQ ID NO: 18 (LCDR2), and SEQ ID NO: 19 (LCDR3); (III) SEQ ID NO: 8 (HCDR1), SEQ ID NO: 9 (HCDR2), SEQ ID NO: 6 (HCDR3), SEQ ID NO: 20 (LCDR1), SEQ ID NO: 21 (LCDR2), and SEQ ID NO: 22 (LCDR3); or (IV) SEQ ID NO: 10 (HCDR1), SEQ ID NO: 11 (HCDR2), SEQ ID NO: 12 (HCDR3), SEQ ID NO: 23 (LCDR1), SEQ ID NO: 21 (LCDR2), and SEQ ID NO: 19 (LCDR3);

(v) (I) SEQ ID NO: 28 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (II) SEQ ID NO: 31 (HCDR1), SEQ ID NO: 29 (HCDR2), SEQ ID NO: 30 (HCDR3), SEQ ID NO: 41 (LCDR1), SEQ ID NO: 42 (LCDR2), and SEQ ID NO: 43 (LCDR3); (III) SEQ ID NO: 32 (HCDR1), SEQ ID NO: 33 (HCDR2), SEQ ID NO: 30 (HCDR3), SEQ ID NO: 44 (LCDR1), SEQ ID NO: 45 (LCDR2), and SEQ ID NO: 46 (LCDR3); or (IV) SEQ ID NO: 34 (HCDR1), SEQ ID NO: 35 (HCDR2), SEQ ID NO: 36 (HCDR3), SEQ ID NO: 47 (LCDR1), SEQ ID NO: 45 (LCDR2), and SEQ ID NO: 43 (LCDR3);

(w) (I) SEQ ID NO: 367 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 369 (HCDR1), SEQ ID NO: 368 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 370 (HCDR1), SEQ ID NO: 371 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 372 (HCDR1), SEQ ID NO: 373 (HCDR2), SEQ ID NO: 232 (HCDR3), SEQ ID NO: 243 (LCDR1), SEQ ID NO: 241 (LCDR2), and SEQ ID NO: 239 (LCDR3);

(x) (I) SEQ ID NO: 378 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 380 (HCDR1), SEQ ID NO: 379 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 381 (HCDR1), SEQ ID NO: 382 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 383 (HCDR1), SEQ ID NO: 384 (HCDR2), SEQ ID NO: 232 (HCDR3), SEQ ID NO: 243 (LCDR1), SEQ ID NO: 241 (LCDR2), and SEQ ID NO: 239 (LCDR3);

(y) (I) SEQ ID NO: 226 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (II) SEQ ID NO: 229 (HCDR1), SEQ ID NO: 227 (HCDR2), SEQ ID NO: 228 (HCDR3), SEQ ID NO: 237 (LCDR1), SEQ ID NO: 238 (LCDR2), and SEQ ID NO: 239 (LCDR3); (III) SEQ ID NO: 32 (HCDR1), SEQ ID NO: 230 (HCDR2), SEQ ID NO: 228 (HCDR3), SEQ ID NO: 240 (LCDR1), SEQ ID NO: 241 (LCDR2), and SEQ ID NO: 242 (LCDR3); or (IV) SEQ ID NO: 34 (HCDR1), SEQ ID NO: 231 (HCDR2), SEQ ID NO: 232 (HCDR3), SEQ ID NO: 243 (LCDR1), SEQ ID NO: 241 (LCDR2), and SEQ ID NO: 239 (LCDR3);

(z) (I) SEQ ID NO: 270 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (II) SEQ ID NO: 273 (HCDR1), SEQ ID NO: 271 (HCDR2), SEQ ID NO: 272 (HCDR3), SEQ ID NO: 282 (LCDR1), SEQ ID NO: 261 (LCDR2), and SEQ ID NO: 283 (LCDR3); (III) SEQ ID NO: 32 (HCDR1), SEQ ID NO: 274 (HCDR2), SEQ ID NO: 272 (HCDR3), SEQ ID NO: 284 (LCDR1), SEQ ID NO: 241 (LCDR2), and SEQ ID NO: 285 (LCDR3); or (IV) SEQ ID NO: 275 (HCDR1), SEQ ID NO: 276 (HCDR2), SEQ ID NO: 277 (HCDR3), SEQ ID NO: 286 (LCDR1), SEQ ID NO: 241 (LCDR2), and SEQ ID NO: 283 (LCDR3); or (aa) (I) SEQ ID NO: 291 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (II) SEQ ID NO: 294 (HCDR1), SEQ ID NO: 292 (HCDR2), SEQ ID NO: 293 (HCDR3), SEQ ID NO: 237 (LCDR1), SEQ ID NO: 238 (LCDR2), and SEQ ID NO: 304 (LCDR3); (III) SEQ ID NO: 295 (HCDR1), SEQ ID NO: 296 (HCDR2), SEQ ID NO: 293 (HCDR3), SEQ ID NO: 240 (LCDR1), SEQ ID NO: 241 (LCDR2), and SEQ ID NO: 305 (LCDR3); or (IV) SEQ ID NO: 297 (HCDR1), SEQ ID NO: 298 (HCDR2), SEQ ID NO: 299 (HCDR3), SEQ ID NO: 243 (LCDR1), SEQ ID NO: 241 (LCDR2), and SEQ ID NO: 304 (LCDR3).

Embodiment 35. An isolated anti-NPR1 antibody or antigen binding fragment; or the antibody or antigen binding fragment of any one of embodiments 1, 2, 4, 6, 21-25, 27, 29, 31, or 33, wherein the antibody or antigen binding fragment comprises three heavy chain complementarity determining regions (HCDR1, HCDR2, and HCDR3) and three light chain complementarity determining regions (LCDR1, LCDR2, and LCDR3) selected from:

(a) (I) SEQ ID NO: 52 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (II) SEQ ID NO: 55 (HCDR1), SEQ ID NO: 53 (HCDR2), SEQ ID NO: 54 (HCDR3), SEQ ID NO: 65 (LCDR1), SEQ ID NO: 66 (LCDR2), and SEQ ID NO: 67 (LCDR3); (III) SEQ ID NO: 56 (HCDR1), SEQ ID NO: 57 (HCDR2), SEQ ID NO: 54 (HCDR3), SEQ ID NO: 68 (LCDR1), SEQ ID NO: 69 (LCDR2), and SEQ ID NO: 70 (LCDR3); or (IV) SEQ ID NO: 58 (HCDR1), SEQ ID NO: 59 (HCDR2), SEQ ID NO: 60 (HCDR3), SEQ ID NO: 71 (LCDR1), SEQ ID NO: 69 (LCDR2), and SEQ ID NO: 67 (LCDR3);

(b) (I) SEQ ID NO: 76 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (II) SEQ ID NO: 79 (HCDR1), SEQ ID NO: 77 (HCDR2), SEQ ID NO: 78 (HCDR3), SEQ ID NO: 89 (LCDR1), SEQ ID NO: 90 (LCDR2), and SEQ ID NO: 91 (LCDR3); (III) SEQ ID NO: 80 (HCDR1), SEQ ID NO: 81 (HCDR2), SEQ ID NO: 78 (HCDR3), SEQ ID NO: 92 (LCDR1), SEQ ID NO: 93 (LCDR2), and SEQ ID NO: 94 (LCDR3); or (IV) SEQ ID NO: 82 (HCDR1), SEQ ID NO: 83 (HCDR2), SEQ ID NO: 84 (HCDR3), SEQ ID NO: 95 (LCDR1), SEQ ID NO: 93 (LCDR2), and SEQ ID NO: 91 (LCDR3);

(c) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 361 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 362 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 361 (LCDR3);

(d) (I) SEQ ID NO: 270 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 389 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 390 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 391 (HCDR2), SEQ ID NO: 332 (HCDR3), SEQ ID NO: 343 (LCDR1), SEQ ID NO: 341 (LCDR2), and SEQ ID NO: 339 (LCDR3);

(e) (I) SEQ ID NO: 407 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 409 (HCDR1), SEQ ID NO: 408 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 410 (HCDR1), SEQ ID NO: 411 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 412 (HCDR1), SEQ ID NO: 413 (HCDR2), SEQ ID NO: 332 (HCDR3), SEQ ID NO: 343 (LCDR1), SEQ ID NO: 341 (LCDR2), and SEQ ID NO: 339 (LCDR3);

(f) (I) SEQ ID NO: 310 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (II) SEQ ID NO: 229 (HCDR1), SEQ ID NO: 311 (HCDR2), SEQ ID NO: 312 (HCDR3), SEQ ID NO: 320 (LCDR1), SEQ ID NO: 321 (LCDR2), and SEQ ID NO: 322 (LCDR3); (III) SEQ ID NO: 80 (HCDR1), SEQ ID NO: 313 (HCDR2), SEQ ID NO: 312 (HCDR3), SEQ ID NO: 323 (LCDR1), SEQ ID NO: 324 (LCDR2), and SEQ ID NO: 325 (LCDR3); or (IV) SEQ ID NO: 82 (HCDR1), SEQ ID NO: 314 (HCDR2), SEQ ID NO: 315 (HCDR3), SEQ ID NO: 326 (LCDR1), SEQ ID NO: 324 (LCDR2), and SEQ ID NO: 322 (LCDR3);

(g) (I) SEQ ID NO: 270 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (II) SEQ ID NO: 273 (HCDR1), SEQ ID NO: 271 (HCDR2), SEQ ID NO: 331 (HCDR3), SEQ ID NO: 337 (LCDR1), SEQ ID NO: 338 (LCDR2), and SEQ ID NO: 339 (LCDR3); (III) SEQ ID NO: 32 (HCDR1), SEQ ID NO: 274 (HCDR2), SEQ ID NO: 331 (HCDR3), SEQ ID NO: 340 (LCDR1), SEQ ID NO: 341 (LCDR2), and SEQ ID NO: 342 (LCDR3); or (IV) SEQ ID NO: 275 (HCDR1), SEQ ID NO: 276 (HCDR2), SEQ ID NO: 332 (HCDR3), SEQ ID NO: 343 (LCDR1), SEQ ID NO: 341 (LCDR2), and SEQ ID NO: 339 (LCDR3); or (h) (I) SEQ ID NO: 310 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (II) SEQ ID NO: 229 (HCDR1), SEQ ID NO: 311 (HCDR2), SEQ ID NO: 348 (HCDR3), SEQ ID NO: 320 (LCDR1), SEQ ID NO: 354 (LCDR2), and SEQ ID NO: 355 (LCDR3); (III) SEQ ID NO: 80 (HCDR1), SEQ ID NO: 313 (HCDR2), SEQ ID NO: 348 (HCDR3), SEQ ID NO: 323 (LCDR1), SEQ ID NO: 324 (LCDR2), and SEQ ID NO: 356 (LCDR3); or (IV) SEQ ID NO: 82 (HCDR1), SEQ ID NO: 314 (HCDR2), SEQ ID NO: 349 (HCDR3), SEQ ID NO: 326 (LCDR1), SEQ ID NO: 324 (LCDR2), and SEQ ID NO: 355 (LCDR3).

Embodiment 36. An isolated anti-NPR1 antibody or antigen binding fragment; or the antibody or antigen binding fragment of any one of embodiments 1-5, 7-20, 26, 28, 30, 32, or 34, wherein the antibody or antigen binding fragment comprises:

(a) a heavy chain variable region comprising an amino acid sequence of SEQ ID NO: 201, and a light chain variable region comprising an amino acid sequence of SEQ ID NO: 136;

(b) a heavy chain variable region comprising an amino acid sequence of SEQ ID NO: 122, and a light chain variable region comprising an amino acid sequence of SEQ ID NO: 136;

(c) a heavy chain variable region comprising an amino acid sequence of SEQ ID NO: 201, and a light chain variable region comprising an amino acid sequence of SEQ ID NO: 128;

(d) a heavy chain variable region comprising an amino acid sequence of SEQ ID NO: 122, and a light chain variable region comprising an amino acid sequence of SEQ ID NO: 128;

(e) a heavy chain variable region comprising an amino acid sequence of SEQ ID NO: 201, and a light chain variable region comprising an amino acid sequence of SEQ ID NO: 147;

(f) a heavy chain variable region comprising an amino acid sequence of SEQ ID NO: 122, and a light chain variable region comprising an amino acid sequence of SEQ ID NO: 147;

(g) a heavy chain variable region comprising an amino acid sequence of SEQ ID NO: 201, and a light chain variable region comprising an amino acid sequence of SEQ ID NO: 174;

(h) a heavy chain variable region comprising an amino acid sequence of SEQ ID NO: 122, and a light chain variable region comprising an amino acid sequence of SEQ ID NO: 174;

(i) a heavy chain variable region comprising an amino acid sequence of SEQ ID NO: 201, and a light chain variable region comprising an amino acid sequence of SEQ ID NO: 180;

(j) a heavy chain variable region comprising an amino acid sequence of SEQ ID NO: 122, and a light chain variable region comprising an amino acid sequence of SEQ ID NO: 180;

(k) a heavy chain variable region comprising an amino acid sequence of SEQ ID NO: 201, and a light chain variable region comprising an amino acid sequence of SEQ ID NO: 186;

(l) a heavy chain variable region comprising an amino acid sequence of SEQ ID NO: 122, and a light chain variable region comprising an amino acid sequence of SEQ ID NO: 186;

(m) a heavy chain variable region comprising an amino acid sequence of SEQ ID NO: 103, and a light chain variable region comprising an amino acid sequence of SEQ ID NO: 24;

(n) a heavy chain variable region comprising an amino acid sequence of SEQ ID NO: 115, and a light chain variable region comprising an amino acid sequence of SEQ ID NO: 24;

(o) a heavy chain variable region comprising an amino acid sequence of SEQ ID NO: 122, and a light chain variable region comprising an amino acid sequence of SEQ ID NO: 48;

(p) a heavy chain variable region comprising an amino acid sequence of SEQ ID NO: 37, and a light chain variable region comprising an amino acid sequence of SEQ ID NO: 128;

(q) a heavy chain variable region comprising an amino acid sequence of SEQ ID NO: 37, and a light chain variable region comprising an amino acid sequence of SEQ ID NO: 136;

(r) a heavy chain variable region comprising an amino acid sequence of SEQ ID NO: 37, and a light chain variable region comprising an amino acid sequence of SEQ ID NO: 147;

(s) a heavy chain variable region comprising an amino acid sequence of SEQ ID NO: 154, and a light chain variable region comprising an amino acid sequence of SEQ ID NO: 24;

(t) a heavy chain variable region comprising an amino acid sequence of SEQ ID NO: 161, and a light chain variable region comprising an amino acid sequence of SEQ ID NO: 24;

(u) a heavy chain variable region comprising an amino acid sequence of SEQ ID NO: 168, and a light chain variable region comprising an amino acid sequence of SEQ ID NO: 24;

(v) a heavy chain variable region comprising an amino acid sequence of SEQ ID NO: 37, and a light chain variable region comprising an amino acid sequence of SEQ ID NO: 174;

(w) a heavy chain variable region comprising an amino acid sequence of SEQ ID NO: 37, and a light chain variable region comprising an amino acid sequence of SEQ ID NO: 180;

(x) a heavy chain variable region comprising an amino acid sequence of SEQ ID NO: 37, and a light chain variable region comprising an amino acid sequence of SEQ ID NO: 186;

(y) a heavy chain variable region comprising an amino acid sequence of SEQ ID NO: 193, and a light chain variable region comprising an amino acid sequence of SEQ ID NO: 136;

(z) a heavy chain variable region comprising an amino acid sequence of SEQ ID NO: 193, and a light chain variable region comprising an amino acid sequence of SEQ ID NO: 174;

(aa) a heavy chain variable region comprising an amino acid sequence of SEQ ID NO: 13, and a light chain variable region comprising an amino acid sequence of SEQ ID NO: 24;

(bb) a heavy chain variable region comprising an amino acid sequence of SEQ ID NO: 37, and a light chain variable region comprising an amino acid sequence of SEQ ID NO: 48;

(cc) a heavy chain variable region comprising an amino acid sequence of SEQ ID NO: 374, and a light chain variable region comprising an amino acid sequence of SEQ ID NO: 244;

(dd) a heavy chain variable region comprising an amino acid sequence of SEQ ID NO: 385, and a light chain variable region comprising an amino acid sequence of SEQ ID NO: 244;

(ee) a heavy chain variable region comprising an amino acid sequence of SEQ ID NO: 233, and a light chain variable region comprising an amino acid sequence of SEQ ID NO: 244;

(ff) a heavy chain variable region comprising an amino acid sequence of SEQ ID NO: 278, and a light chain variable region comprising an amino acid sequence of SEQ ID NO: 287; or (gg) a heavy chain variable region comprising an amino acid sequence of SEQ ID NO: 300, and a light chain variable region comprising an amino acid sequence of SEQ ID NO: 306.

Embodiment 37. An isolated anti-NPR1 antibody or antigen binding fragment; or the antibody or antigen binding fragment of any one of embodiments 1, 2, 4, 6, 21-25, 27, 29, 31, 33, or 35, wherein the antibody or antigen binding fragment comprises:

(a) a heavy chain variable region comprising an amino acid sequence of SEQ ID NO: 61, and a light chain variable region comprising an amino acid sequence of SEQ ID NO: 72;

(b) a heavy chain variable region comprising an amino acid sequence of SEQ ID NO: 85, and a light chain variable region comprising an amino acid sequence of SEQ ID NO: 96;

(c) a heavy chain variable region comprising an amino acid sequence of SEQ ID NO: 350, and a light chain variable region comprising an amino acid sequence of SEQ ID NO: 363;

(d) a heavy chain variable region comprising an amino acid sequence of SEQ ID NO: 392, and a light chain variable region comprising an amino acid sequence of SEQ ID NO: 344;

(e) a heavy chain variable region comprising an amino acid sequence of SEQ ID NO: 414, and a light chain variable region comprising an amino acid sequence of SEQ ID NO: 344;

(f) a heavy chain variable region comprising an amino acid sequence of SEQ ID NO: 316, and a light chain variable region comprising an amino acid sequence of SEQ ID NO: 327;

(g) a heavy chain variable region comprising an amino acid sequence of SEQ ID NO: 333, and a light chain variable region comprising an amino acid sequence of SEQ ID NO: 344; or
(h) a heavy chain variable region comprising an amino acid sequence of SEQ ID NO: 350, and a light chain variable region comprising an amino acid sequence of SEQ ID NO: 357.

Embodiment 38. An isolated anti-NPR1 antibody or antigen binding fragment; or the antibody or antigen binding fragment of any one of embodiments 1-5, 7-20, 26, 28, 30, 32, 34, or 36, wherein the antibody or antigen binding fragment comprises:
(a) a heavy chain comprising an amino acid sequence of SEQ ID NO: 203, and a light chain comprising an amino acid sequence of SEQ ID NO: 138;
(b) a heavy chain comprising an amino acid sequence of SEQ ID NO: 208, and a light chain comprising an amino acid sequence of SEQ ID NO: 138;
(c) a heavy chain comprising an amino acid sequence of SEQ ID NO: 203, and a light chain comprising an amino acid sequence of SEQ ID NO: 130;
(d) a heavy chain comprising an amino acid sequence of SEQ ID NO: 208, and a light chain comprising an amino acid sequence of SEQ ID NO: 130;
(e) a heavy chain comprising an amino acid sequence of SEQ ID NO: 203, and a light chain comprising an amino acid sequence of SEQ ID NO: 149;
(f) a heavy chain comprising an amino acid sequence of SEQ ID NO: 208, and a light chain comprising an amino acid sequence of SEQ ID NO: 149;
(g) a heavy chain comprising an amino acid sequence of SEQ ID NO: 203, and a light chain comprising an amino acid sequence of SEQ ID NO: 176;
(h) a heavy chain comprising an amino acid sequence of SEQ ID NO: 208, and a light chain comprising an amino acid sequence of SEQ ID NO: 176;
(i) a heavy chain comprising an amino acid sequence of SEQ ID NO: 203, and a light chain comprising an amino acid sequence of SEQ ID NO: 182;
(j) a heavy chain comprising an amino acid sequence of SEQ ID NO: 208, and a light chain comprising an amino acid sequence of SEQ ID NO: 182;
(k) a heavy chain comprising an amino acid sequence of SEQ ID NO: 203, and a light chain comprising an amino acid sequence of SEQ ID NO: 188;
(l) a heavy chain comprising an amino acid sequence of SEQ ID NO: 208, and a light chain comprising an amino acid sequence of SEQ ID NO: 188;
(m) a heavy chain comprising an amino acid sequence of SEQ ID NO: 105, and a light chain comprising an amino acid sequence of SEQ ID NO: 26;
(n) a heavy chain comprising an amino acid sequence of SEQ ID NO: 108, and a light chain comprising an amino acid sequence of SEQ ID NO: 26;
(o) a heavy chain comprising an amino acid sequence of SEQ ID NO: 117, and a light chain comprising an amino acid sequence of SEQ ID NO: 26;
(p) a heavy chain comprising an amino acid sequence of SEQ ID NO: 124, and a light chain comprising an amino acid sequence of SEQ ID NO: 50;
(q) a heavy chain comprising an amino acid sequence of SEQ ID NO: 39, and a light chain comprising an amino acid sequence of SEQ ID NO: 130;
(r) a heavy chain comprising an amino acid sequence of SEQ ID NO: 39, and a light chain comprising an amino acid sequence of SEQ ID NO: 138;
(s) a heavy chain comprising an amino acid sequence of SEQ ID NO: 141, and a light chain comprising an amino acid sequence of SEQ ID NO: 138;
(t) a heavy chain comprising an amino acid sequence of SEQ ID NO: 39, and a light chain comprising an amino acid sequence of SEQ ID NO: 149;
(u) a heavy chain comprising an amino acid sequence of SEQ ID NO: 156, and a light chain comprising an amino acid sequence of SEQ ID NO: 26;
(v) a heavy chain comprising an amino acid sequence of SEQ ID NO: 159, and a light chain comprising an amino acid sequence of SEQ ID NO: 26;
(w) a heavy chain comprising an amino acid sequence of SEQ ID NO: 163, and a light chain comprising an amino acid sequence of SEQ ID NO: 26;
(x) a heavy chain comprising an amino acid sequence of SEQ ID NO: 170, and a light chain comprising an amino acid sequence of SEQ ID NO: 26;
(y) a heavy chain comprising an amino acid sequence of SEQ ID NO: 39, and a light chain comprising an amino acid sequence of SEQ ID NO: 176;
(z) a heavy chain comprising an amino acid sequence of SEQ ID NO: 39, and a light chain comprising an amino acid sequence of SEQ ID NO: 182;
(aa) a heavy chain comprising an amino acid sequence of SEQ ID NO: 39, and a light chain comprising an amino acid sequence of SEQ ID NO: 188;
(bb) a heavy chain comprising an amino acid sequence of SEQ ID NO: 195, and a light chain comprising an amino acid sequence of SEQ ID NO: 138;
(cc) a heavy chain comprising an amino acid sequence of SEQ ID NO: 195, and a light chain comprising an amino acid sequence of SEQ ID NO: 176;
(dd) a heavy chain comprising an amino acid sequence of SEQ ID NO: 15, and a light chain comprising an amino acid sequence of SEQ ID NO: 26;
(ee) a heavy chain comprising an amino acid sequence of SEQ ID NO: 39, and a light chain comprising an amino acid sequence of SEQ ID NO: 50;
(ff) a heavy chain comprising an amino acid sequence of SEQ ID NO: 376, and a light chain comprising an amino acid sequence of SEQ ID NO: 246;
(gg) a heavy chain comprising an amino acid sequence of SEQ ID NO: 387, and a light chain comprising an amino acid sequence of SEQ ID NO: 246;
(hh) a heavy chain comprising an amino acid sequence of SEQ ID NO: 235, and a light chain comprising an amino acid sequence of SEQ ID NO: 246;
(ii) a heavy chain comprising an amino acid sequence of SEQ ID NO: 280, and a light chain comprising an amino acid sequence of SEQ ID NO: 289; or
(jj) a heavy chain comprising an amino acid sequence of SEQ ID NO: 302, and a light chain comprising an amino acid sequence of SEQ ID NO: 308.

Embodiment 39. An isolated anti-NPR1 antibody or antigen binding fragment; or the antibody or antigen binding fragment of any one of embodiments 1, 2, 4, 6, 21-25, 27, 29, 31, 33, 35, or 37, wherein the antibody or antigen binding fragment comprises:
(a) a heavy chain comprising an amino acid sequence of SEQ ID NO: 63, and a light chain comprising an amino acid sequence of SEQ ID NO: 74;
(b) a heavy chain comprising an amino acid sequence of SEQ ID NO: 87, and a light chain comprising an amino acid sequence of SEQ ID NO: 98;

(c) a heavy chain comprising an amino acid sequence of SEQ ID NO: 352, and a light chain comprising an amino acid sequence of SEQ ID NO: 365;

(d) a heavy chain comprising an amino acid sequence of SEQ ID NO: 394, and a light chain comprising an amino acid sequence of SEQ ID NO: 346;

(e) a heavy chain comprising an amino acid sequence of SEQ ID NO: 416, and a light chain comprising an amino acid sequence of SEQ ID NO: 346;

(f) a heavy chain comprising an amino acid sequence of SEQ ID NO: 318, and a light chain comprising an amino acid sequence of SEQ ID NO: 329;

(g) a heavy chain comprising an amino acid sequence of SEQ ID NO: 335, and a light chain comprising an amino acid sequence of SEQ ID NO: 346; or (h) a heavy chain comprising an amino acid sequence of SEQ ID NO: 352, and a light chain comprising an amino acid sequence of SEQ ID NO: 359.

Embodiment 40. The antibody or antigen binding fragment of any one of embodiments 1-39, which is an antigen binding fragment selected from the group consisting of a Fab, Fab', F(ab')$_2$, Fv, single domain antibody (dAb), and a single chain variable fragment (scFv), optionally wherein the antigen binding fragment is selected from the group consisting of a Fab, Fab', Fv, single domain antibody (dAb), and a single chain variable fragment (scFv).

Embodiment 41. The antibody or antigen binding fragment of any one of embodiments 1-40, which is monoclonal.

Embodiment 42. The antibody or antigen binding fragment of any one of embodiments 1-41, which is fully human.

Embodiment 43. The antibody or antigen binding fragment of any one of embodiments 1-42, which is an IgG antibody, optionally which is an IgG$_1$ antibody.

Embodiment 44. The antibody or antigen binding fragment of any one of embodiments 1-43, which is an IgG$_1$ antibody having a kappa light chain.

Embodiment 45. The antibody or antigen binding fragment of any one of embodiments 1-44, which is a fully human antibody of the IgG1 isotype and has a kappa light chain.

Embodiment 46. The antibody or antigen binding fragment of any one of embodiments 1-45, wherein the antibody or antigen binding fragment has further modifications as described herein, e.g., wherein the antibody or antigen binding fragment additionally has mutations in the Fc region according to the EU index of Kabat, wherein the mutations comprise at least D265A and P329A; or wherein the mutations comprise at least L234A and L235A.

Embodiment 47. The antibody or antigen binding fragment of any one of embodiments 1-40, wherein the antibody or antigen binding fragment is: a) monoclonal; and/or b) fully human; and/or c) an IgG antibody, optionally an IgG$_1$ antibody; and/or d) has a kappa light chain; and/or e) has mutations in the Fc region according to the EU index of Kabat, optionally wherein the mutations comprise at least D265A and P329A; and/or f) has mutations in the Fc region according to the EU index of Kabat, optionally wherein the mutations comprise at least L234A and L235A.

Embodiment 48. The antibody or antigen binding fragment of any one of embodiments 1-47, wherein the antibody or antigen binding fragment is therapeutic.

Embodiment 49. An isolated antibody or antigen binding fragment that binds to the same epitope on human NPR1 as the antibody or antigen binding fragment of any one of embodiments 1 to 48.

Embodiment 50. An isolated antibody or antigen binding fragment that competes for binding to human NPR1 with the antibody or antigen binding fragment of any one of embodiments 1 to 49.

Embodiment 51. An isolated nucleic acid or nucleic acids encoding the amino acid sequence of the antibody or antigen binding fragment of any one of embodiments 1 to 50.

Embodiment 52. A vector comprising the isolated nucleic acid(s) of embodiment 51.

Embodiment 53. A host cell comprising the isolated nucleic acid(s) of embodiment 51 or the vector of embodiment 52.

Embodiment 54. A method of producing the antibody or antigen binding fragment of any one of embodiments 1 to 50, comprising culturing the host cell of embodiment 53 under conditions suitable to produce the antibody or antigen binding fragment.

Embodiment 55. The method of embodiment 54, wherein the method additionally comprises purification of the antibody or antigen binding fragment.

Embodiment 56. A pharmaceutical composition comprising a purified antibody or antigen binding fragment produced by the method of embodiment 55 and a pharmaceutically acceptable carrier.

Embodiment 57. A pharmaceutical composition comprising an antibody or antigen binding fragment of any one of embodiments 1 to 50 and a pharmaceutically acceptable carrier.

Embodiment 58. The pharmaceutical composition of embodiment 56 or 57 or a combination comprising an antibody or antigen binding fragment of any one of embodiments 1 to 50, wherein the composition further comprises an additional therapeutic agent.

Embodiment 59. The pharmaceutical composition or combination of embodiment 58, wherein the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), and combinations thereof.

Embodiment 60. The pharmaceutical composition or combination of embodiment 58 or embodiment 59, wherein the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, and combinations thereof.

Embodiment 61. The pharmaceutical composition or combination of embodiment 58 or embodiment 59, wherein the additional therapeutic agent is selected from chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof.

Embodiment 62. The pharmaceutical composition or combination of any one of embodiments 58-61, wherein the additional therapeutic agent is an angiotensin receptor-neprilysin inhibitor (ARNi).

Embodiment 63. The pharmaceutical composition or combination of embodiment 58, wherein the additional therapeutic agent is selected from a corticosteroid, a leukotriene modifier, a bronchodilator, and combinations thereof.

Embodiment 64. The pharmaceutical composition or combination of embodiment 63, wherein the additional therapeutic agent is selected from fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline and ipratropium, and combinations thereof.

Embodiment 65. The pharmaceutical composition or combination of embodiment 63 or embodiment 64, wherein the additional therapeutic agent is selected from salmeterol, formoterol, albuterol, and levalbuterol, and combinations thereof.

Embodiment 66. The pharmaceutical composition or combination of embodiment 58, wherein the additional therapeutic agent is selected from a beta-adrenoceptor antagonist, a carbonic anhydrase inhibitor, an alpha 2-adrenoceptor agonist, a parasympathomimetic, a prostaglandin analog, a rho kinase inhibitor, and combinations thereof, and combinations thereof.

Embodiment 67. The pharmaceutical composition or combination of embodiment 66, wherein the additional therapeutic agent is selected from timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil and ripasudil, and combinations thereof.

Embodiment 68. The pharmaceutical composition of embodiment 58, wherein the additional therapeutic agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), an angiotensin receptor-neprilysin inhibitor (ARNi), a corticosteroid, a leukotriene modifier, a bronchodilator, a beta-adrenoceptor antagonist, a carbonic anhydrase inhibitor, an alpha 2-adrenoceptor agonist, a parasympathomimetic, a prostaglandin analog, a rho kinase inhibitor, and combinations thereof.

Embodiment 69. The pharmaceutical composition of embodiment 68, wherein the additional therapeutic agent is selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a digitalis glycoside, canagliflozin, dapagliflozin, empagliflozin, ertugliflozin, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, fluticasone, budesonide, mometasone, beclomethasone, ciclesonide, fluticasone furoate, prednisone, methylprednisolone, montelukast, zafirlukast, zileuton, a long-acting beta agonist, a short-acting beta agonist, theophylline, ipratropium, salmeterol, formoterol, albuterol, and levalbuterol, timolol, levobunolol, metipranolol, carteolol, betaxolol, acetazolamide, dorzolamide, brinzolamide, methazolamide, brimonidine, apraclonidine, a cholinomimetic, latanoprost, latanoprostene bunod, travoprost, bimatoprost, tafluprost, netarsudil and ripasudil, and combinations thereof.

Embodiment 70. The antibody or antigen binding fragment thereof of any of embodiments 1-50, the isolated nucleic acid or nucleic acids of embodiment 51, the vector of embodiment 52, the host cell of embodiment 53 or pharmaceutical composition of any of embodiments 56-69 for use (i) in therapy, (ii) as a medicament or (iii) in the manufacture of a medicament for the treatment of a disease.

Embodiment 71. Use of the antibody or antigen binding fragment of any of embodiments 1-50, the isolated nucleic acid or nucleic acids of embodiment 51, the vector of embodiment 52, the host cell of embodiment 53 or pharmaceutical composition of any of embodiments 56-69 for the manufacture of a medicament for the treatment of a disorder or disease associated with natriuretic peptide receptor activity in a subject in need of such treatment.

Embodiment 72. Use of the antibody or antigen binding fragment of any one of embodiments 1-50, the isolated nucleic acid or nucleic acids of embodiment 51, the vector of embodiment 52, the host cell of embodiment 53 or pharmaceutical composition of any of embodiments 56-69 for the manufacture of a medicament for the treatment of a cardiovascular disorder in a subject in need of such treatment.

Embodiment 73. The use of embodiment 72, wherein the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

Embodiment 74. Use of the antibody or antigen binding fragment of any one of embodiments 1-50, the isolated nucleic acid or nucleic acids of embodiment 51, the vector of embodiment 52, the host cell of embodiment 53 or pharmaceutical composition of any of embodiments 56-69, for the manufacture of a medicament for the treatment of heart failure, hypertrophic cardiomyopathy (HCM), hypertension, preeclampsia, asthma, glaucoma, and/or cytokine release syndrome in a subject in need of such treatment.

Embodiment 75. The use of embodiment 73 or embodiment 74, wherein the subject has heart failure, and wherein the heart failure is selected from a heart failure with reduced ejection fraction (HFrEF), heart failure with preserved ejection fraction (HFpEF), heart failure after acute myocardial infarct, or acute decompensated heart failure.

Embodiment 76. The use of embodiment 73 or embodiment 74, wherein the subject has hypertrophic cardiomyopathy, and wherein the hypertrophic cardiomyopathy is ventricular hypertrophy.

Embodiment 77. The use of embodiment 73 or embodiment 74, wherein the subject has hypertension, and wherein the hypertension is selected from resistant hypertension, hypertensive heart disease, pulmonary hypertension, pulmonary arterial hypertension, isolated systolic hypertension, resistant hypertension, and pulmonary arterial hypertension.

Embodiment 78. The use of any one of embodiments 73, 74, or 77, wherein the subject has hypertension, and wherein the hypertension is selected from resistant hypertension or hypertensive heart disease.

Embodiment 79. Use of the antibody or antigen binding fragment of any one of embodiments 1-50, the isolated nucleic acid or nucleic acids of embodiment 51, the vector of embodiment 52, the host cell of embodiment 53 or pharmaceutical composition of any of embodiments 56-69, for the manufacture of a medicament for the treatment of a kidney disorder in a subject in need of such treatment.

Embodiment 80. The use of embodiment 79, wherein the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

Embodiment 81. The antibody or antigen binding fragment of any of embodiments 1-50, the isolated nucleic acid or nucleic acids of embodiment 51, the vector of embodiment 52, the host cell of embodiment 53 or pharmaceutical composition or combination of any of embodiments 56-69 for use in the treatment of a disorder or disease associated with natriuretic peptide receptor activity in a subject in need of such treatment.

Embodiment 82. The antibody or antigen binding fragment of any one of embodiments 1-50, the isolated nucleic acid or nucleic acids of embodiment 51, the vector of embodiment 52, the host cell of embodiment 53 or pharmaceutical composition or combination of any of embodiments 56-69 for use in the treatment of a cardiovascular disorder in a subject in need of such treatment.

Embodiment 83. The antibody or antigen binding fragment, isolated nucleic acid or nucleic acids, vector, host cell, pharmaceutical composition, or combination of embodiment 82, wherein the cardiovascular disorder is selected from: hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

Embodiment 84. The antibody or antigen binding fragment of any one of embodiments 1-50, the isolated nucleic acid or nucleic acids of embodiment 51, the vector of embodiment 52, the host cell of embodiment 53 or pharmaceutical composition or combination of any of embodiments 56-69, for use in the treatment of heart failure, hypertrophic cardiomyopathy (HCM), hypertension, preeclampsia, asthma, glaucoma, and/or cytokine release syndrome in a subject in need of such treatment.

Embodiment 85. The antibody or antigen binding fragment, isolated nucleic acid or nucleic acids, vector, host cell, pharmaceutical composition, or combination of embodiment 83 or embodiment 84, wherein the subject has heart failure, and wherein the heart failure is selected from a heart failure with reduced ejection fraction (HFrEF), heart failure with preserved ejection fraction (HFpEF), heart failure after acute myocardial infarct, or acute decompensated heart failure.

Embodiment 86. The antibody or antigen binding fragment, isolated nucleic acid or nucleic acids, vector, host cell, pharmaceutical composition, or combination of embodiment 83 or embodiment 84, wherein the subject has hypertrophic cardiomyopathy, and wherein the hypertrophic cardiomyopathy is ventricular hypertrophy.

Embodiment 87. The antibody or antigen binding fragment, isolated nucleic acid or nucleic acids, vector, host cell, pharmaceutical composition, or combination of embodiment 83 or embodiment 84, wherein the subject has hypertension, and wherein the hypertension is selected from resistant hypertension, hypertensive heart disease, pulmonary hypertension, pulmonary arterial hypertension, isolated systolic hypertension, resistant hypertension, and pulmonary arterial hypertension.

Embodiment 88. The antibody or antigen binding fragment, isolated nucleic acid or nucleic acids, vector, host cell, pharmaceutical composition, or combination of embodiments 83, 84, or 87, wherein the subject has hypertension, and wherein the hypertension is selected from resistant hypertension or hypertensive heart disease.

Embodiment 89. The antibody or antigen binding fragment of any one of embodiments 1-50, the isolated nucleic acid or nucleic acids of embodiment 51, the vector of embodiment 52, the host cell of embodiment 53 or pharmaceutical composition or combination of any of embodiments 56-69, for use in the the treatment of a kidney disorder in a subject in need of such treatment.

Embodiment 90. The antibody or antigen binding fragment, isolated nucleic acid or nucleic acids, vector, host cell, pharmaceutical composition, or combination of embodiment 89, wherein the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The examples provided do not in any way limit the disclosure.

This disclosure provides anti-NPR1 antibodies that specifically bind and activate NPR1, e.g., antibodies and antigen binding fragments that (i) bind to NPR1; and (ii) activate NPR1 in the absence of ANP. Antibodies that specifically bind and activate NPR1 could have different possible modes of action: (1) the antibody induces a conformational change within the NPR1 monomers to activate the receptor; (2) the antibody directly mimics the structure and function of the natural ligand ANP and activates the receptor by binding in the ANP binding pocket of NPR1; or (3) the antibody stabilizes the preformed functionally active complex of hNPR1 and ANP (NPR1-ANP-complex).

Example 1: HuCAL® Phage Library Panning and Screening

For the selection of NPR1-specific antibodies covering the described different methods of action, 13 different panning strategies were applied (see Table 5). Ten strategies were performed exclusively on protein (strategies 1-6 and 10-13). In addition, three differential cell pannings were performed (strategies 7-9). In total, four panning strategies (strategies 3 and 11-13) aimed for the enrichment of ANP competing antibodies (elution with ANP, pre-adsorption of phage on NPR1-ANP-complexes, and anti-idiotype pannings on murine anti-ANP antibodies).

For solution panning, NPR1 was biotinylated and the retained activity of biotinylated NPR1 for ANP binding was confirmed. During solution panning, the Fab displaying

TABLE 5

Overview of HuCAL ® panning strategies

| Strategy | 1st round | 2nd round | 3rd round | comments |
|---|---|---|---|---|
| 1 | hNPR1 solution | hNPR1 solution | hNPR1 solution | Solution panning with human antigen only |
| 2 | hNPR1 capture | hNPR1 capture | hNPR1 capture | Fc capture panning with human antigen only |
| 3 | hNPR1 solution | hNPR1 solution + ANP elution | hNPR1 solution + ANP elution | Solution panning aiming for enrichment of ANP competitors |
| 4 | hNPR1 solution | hNPR1 solution + pH 5.8 elution | hNPR1 solution + pH 5.8 elution | Solution panning aiming for enrichment of pH dependent binders |
| 5 | hNPR1 solution | rNPR1 capture | hNPR1 solution | Solution/Fc capture panning aiming for rat crossreactivity |
| 6 | rNPR1 capture | hNPR1 capture | rNPR1 capture | Fc capture panning aiming for rat crossreactivity |
| 7 | hNPR1 capture | CHO-K1 NPR1 cells | rNPR1 capture | Fc capture/cell panning aiming for rat crossreactivity |
| 8 | hNPR1 solution | CHO-K1 NPR1 cells | hNPR1 solution | Solution/cell panning with human antigen only |
| 9 | CHO-K1 NPR1 cells | hNPR1 solution | CHO-K1 NPR1 cells | Solution/cell panning with human antigen only |
| 10 | hNPR1-ANP-complex solution | rNPR1-ANP-complex capture | hNPR1-ANP-complex solution | Solution panning aiming for enrichment of NPR-ANP complex stabilizers and rat crossreactivity |
| 11 | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | Solution panning aiming for enrichment of ANP competitors |
| 12 | mouse anti-ANP-mAb capture | hNPR1 solution | mouse anti-ANP-mAb capture | Fc capture/cell panning with anti-ANP mAb |
| 13 | mouse anti-ANP mix of two mAbs capture | mouse anti-ANP mix of two mAbs capture + ANP elution | mouse anti-ANP mix of two mAbs capture + ANP elution | Fc capture panning with anti-ANP mAb aiming for enrichment of ANP competitors |

For Fc capture panning, NPR1-hFc was immobilized on a 96-well plate via an appropriate capture antibody (a goat or mouse anti-human Fc antibody). The antigen was immobilized in an appropriate number of wells of a 96-well plate and wells were subsequently blocked prior to the addition of phage-antibodies. In parallel to well preparation, phage-antibodies were blocked. During blocking of phage, additional blocking reagents were added to the blocking buffer to avoid selection of antibodies against the hFc-tag or the capture antibody (goat or mouse γ globulin). Following the blocking procedure, two pre-adsorption steps on human γ globulin and on the counter-target hNPR3-hFc were performed to avoid selection of antibodies against the Fc-tag or the counter-target. The pre-blocked and pre-adsorbed phage mix was added to each well with immobilized NPR1-hFc and the phage-antibodies were allowed to bind to the antigen. Intensive washing ensured removal of non-specifically bound phage, followed by elution of specifically bound phage. The second and third round of solid phase panning was performed according to the protocol of the first panning round. Amounts of antigen were decreased and washing conditions with increased stringency were applied.

phage and the biotinylated NPR1-hFc were incubated in solution, which facilitated the accessibility of the antigen by the phage. An appropriate amount of Streptavidin beads was blocked and, in parallel, an appropriate amount of phage-antibodies was blocked. During blocking of phage, human γ globulin, the counter-target hNPR3-hFc and the Flag-TEV linker peptide were added to the blocking buffer to avoid selection of antibodies against the hFc-tag, the counter-target, or the linker peptide. For removal of Streptavidin-, Biotin-, or bead-binding phage, pre-adsorption steps of blocked phage particles were performed using blocked Streptavidin beads with and without coupled biotinylated irrelevant antigen. Subsequently, biotinylated NPR1-hFc/NPR1-hFc-ANP-complex was added to the pre-adsorbed and blocked phage particles and the phage-antibodies were allowed to bind to the antigen in solution. For enrichment of antibody phage binding to the ANP-binding site of NPR1 (ANP competitive antibodies) the pre-formed NPR1-ANP-complex was added to the phage blocking solution or the ANP peptide was used for elution of the bound phage. Thereby, the ANP peptide was used at least in 250-fold molar excess to the NPR1 antigen or the NPR1 expressing cells. The phage-antigen complexes were captured using blocked Streptavidin beads and phage particles bound to the Streptavidin beads were collected with a magnetic separator. Phage bound nonspecifically were washed off by several washing steps. Specifically bound phage were eluted from Streptavidin beads. The eluate was transferred to an *E. coli* culture for phage infection. The second and third round of bead-based solution panning was performed according to the protocol of the first panning round. Amounts of antigen were decreased and washing conditions with increased stringency were applied.

For whole cell panning, an appropriate amount of phage-antibodies was blocked. During blocking of phage, counter-target hNPR3-hFc was added to the blocking buffer to avoid selection of antibodies against the counter-target. In parallel, an appropriate amount of target cells expressing NPR1 and an appropriate amount of adsorption cells without expression of antigen (parental cells) per phage pool were blocked. The blocked target cells were spun down, resuspended in the pre-blocked phage particles and the phage-antibodies were allowed to bind to the NPR1 presented on the cell. The phage-cell complexes were washed several times. For enrichment of antibody phage binding to the ANP-binding site of NPR1 (ANP competitive antibodies) the pre-formed NPR1-ANP-complex was added to the phage blocking solution or the ANP peptide was used for elution of the bound phage. Thereby, the ANP peptide was used at least in 250-fold molar excess to the NPR1 antigen or the NPR1 expressing cells. Specifically bound phage were eluted from target cells. After centrifugation, the supernatant (eluate) was applied to adsorption cells for removal of phage binding to cell surface molecules other than the target antigen (post-adsorption). The final supernatant was transferred to an *E. coli* culture for phage infection. The second and third round of the whole cell panning were performed according to the protocol of the first panning round. Washing conditions with increased stringency were applied.

The outputs of the panning rounds were subsequently subcloned into bacterial expression vectors and bacterial lysates (BEL) were used for primary and secondary screening. The outputs were analyzed for binding to human and rat NPR1 during the primary screening (ELISA-based). Clones binding to human NPR3 were deselected. Secondary screening was performed on hNPR1 expressing CHO-K1 cells. Further screenings regarding ANP competition and binding solely in presence of ANP were performed. Approximately 1700 clones fulfilled the screening selection criteria and 760 clones were selected for sequencing. The sequencing of 760 clones resulted in 210 HCDR3 unique hits, whose binding properties are summarized in Table 6. Of these clones, 72 demonstrated significant ANP competition, while 7 clones bound only in presence of ANP.

Example 2: Antibody Reformatting, Expression, and Purification

After confirmation of binding, the VH and VL domains of the 210 HCDR3 unique clones were subcloned into a vector with a human IgG constant region. 180 of the 210 clones were selected for expression and 166 of the 180 passed the production quality control. They were characterized in regard to binding to relevant cell lines and functional activity. 40 of the 166 candidates were then selected for exploratory scale production, and 31 of these candidates were characterized in detail as shown below with respect to binding to relevant antigens and cell lines, ANP competition, and functionality in a cell based cGMP production assay.

For production of the IgG candidates, eukaryotic HKB11 cells were transfected with mammalian expression vector DNA encoding both heavy and light chains of IgG. Cell culture supernatants were harvested at appropriate times and subjected to Protein A affinity chromatography. If needed, a second purification step was performed to remove aggregates. Buffer exchange was performed to 1x Dulbecco's PBS (pH 7.2) and samples were sterile filtered (0.2 μm pore size).

Figure 2:
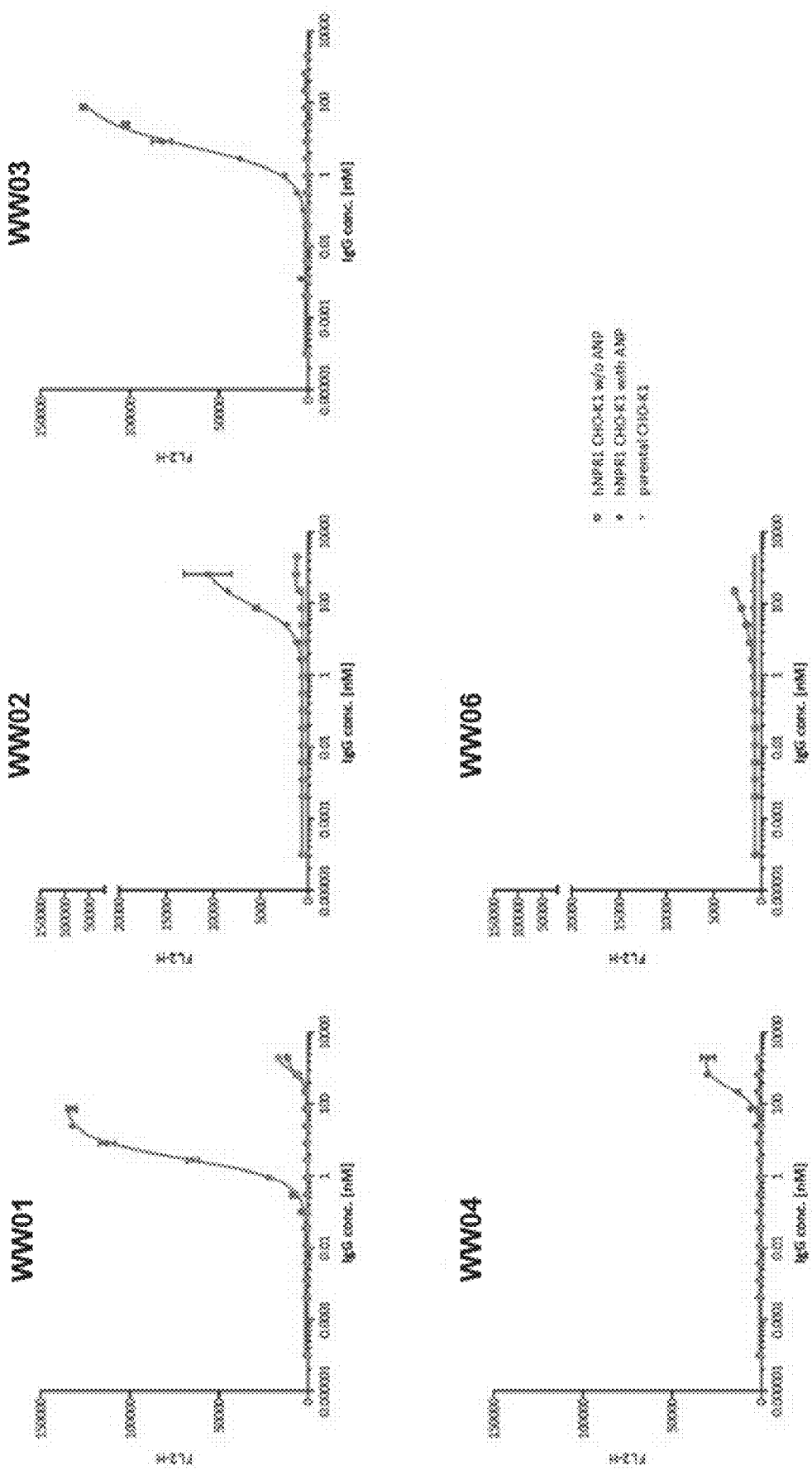
FIG. 2 is a set of graphs displaying the results of flow cytometry analysis of antibody candidates WW01, WW02, WW03, WW04, and WW06 for binding to human NPR1 expressing CHO-K1 cells in the absence and presence of a saturating concentration of ANP and on parental CHO-K1 cells.

Example 3: Antigen Binding, ANP Competition and Cellular cGMP Production-HuCAL® Candidates The 31 IgGs which passed the exploratory scale production quality control were tested via ELISA for binding to the following antigens: human NPR1, constitutively active human NPR1 mutant (W74R), rat NPR1, and human NPR3 (counter target). The clones were also tested by flow cytometry for binding to human NPR1 expressing CHO K1 cells in the absence and presence of ANP and on parental CHO K1 cells. The binding properties of the five functional candidates are shown in FIG. 1 and FIG. 2.

The same 31 IgGs were tested for ANP competition using a Fluorescence Resonance Energy Transfer (FRET)-based assay in which the NPR1-specific antibodies competed with ANP for binding to NPR1. In this FRET based assay (see FIG. 3), Eu-labeled Streptavidin (for measurement of IgGs) or Eu-labeled anti-hFc antibody (for measurement of FabCys) was used as an energy donor, while Cy5-labeled ANP was used as an acceptor (for all measurements). The resulting fluorescent signal was decreased by ANP-competitive antibodies. The assay was performed as follows: antibodies were mixed with NPR1 and incubated for 5 minutes at room temperature. After addition of the Eu-labeled donor and incubation for 30 minutes at room temperature, the Cy5-ANP solution was added. After a further 60-minute incubation, readout was performed using a TECAN Infinite M1000 Pro using an excitation wavelength of 317 nm and an

TABLE 6

Binding properties of 210 HCDR3 unique hits (HuCAL ®)

| | | | Binding to | | |
|---|---|---|---|---|---|
| Number of HCDR3 unique candidates | | | hNPR1 | rNPR1 | hNPR1 expr. cells |
| 210 of which 7 clones only bind in presence of ANP | 47 human/ rat cross reactive | 28 human/rat cross reactive cell binders | Yes | Yes | Yes |
| | | 19 human/rat cross reactive (not binding to cells) | Yes | Yes | No |
| | 156 human specific | 53 human specific cell binders | Yes | No | Yes |
| | | 103 human specific (not binding to cells) | Yes | No | No | emission wavelength of 665 nm. Percentage of ANP competition was calculated according to the following formulae:

$$Ratio^* = [(A_{665} \text{ nm}/A_{620} \text{ nm})*10^4]$$

$$Ratio = (Ratio^* - Ratio_{neg})$$

$$\text{Competition \%} = [100 - (Ratio/(Ratio_{pos}/100))]$$

$Ratio_{neg}$: mean Ratio*data values of control without NPR1

$Ratio_{pos}$: mean Ratio data values of control without agonist (reaction buffer)

Figure 4:
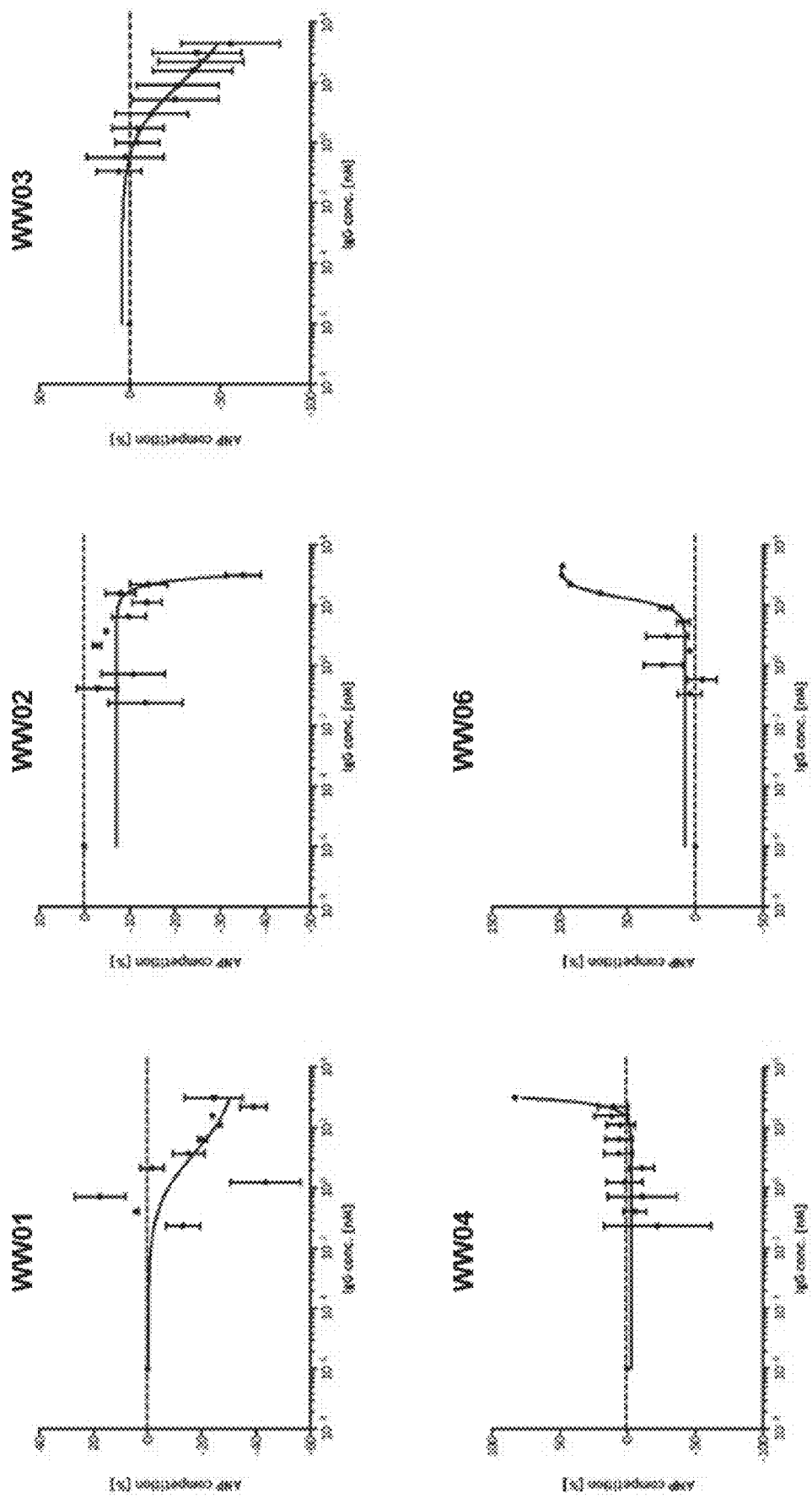
FIG. 4 is a set of graphs displaying the results of ANP competition analyses of candidates WW01, WW02, WW03, WW04, and WW06 using the FRET-based assay depicted in FIG. 3.

15 of the 31 IgGs were ANP competitive, but only two of these candidates showed functionality in the cGMP assay (WW04 and WW06). The other three functional candidates WW01, WW02 and WW03 demonstrated a "negative" ANP competition in this assay indicating the stabilization of the NPR1-ANP-complex. The FRET assay results for the five functional candidates are depicted in FIG. 4.

Additionally, as discussed above, the 31 IgGs were tested for their functional activity in a cellular cGMP production assay using human NPR1 expressing CHO-K1 cells. For the functional characterization of the selected antibodies the production of cyclic guanosine 3',5'-cyclic monophosphate (cGMP) upon binding to and stimulation of NPR1 expressed on the cell surface of CHO-K1 cells was monitored. Cellular cGMP is a major second messenger that mediates cell activities and is synthesized by activated NPR1 triggered by ANP or NPR1-specific antibodies. Therefore, a commercial assay kit was used (Cisbio Bioassays CisBio HTRF Assay Kit CisBio (Cat. #62GM2PEB)). The assay was performed according to manufacturer's instructions with minor deviations. In brief, cells were adjusted to $1\times10^5$ cells/mL, 20 μL/well were seeded in 96 well microtiter plates and were incubated overnight. After addition of 10 μL/well of the antibodies in different concentrations, the plate was incubated for 30 min at 37° C. to allow for cGMP production. In parallel, a standard curve using a calibrator (contained in the kit) was generated. The cells were lysed and a mix of cGMP-d2 and anti-cGMP-Cryptate was added and incubated for 1 h at room temperature. The readout was performed using a Tecan M1000 Pro using an excitation wavelength of 317 nm and an emission wavelength of 665 nm. cGMP concentration (Delta F [%]) was calculated according to the following formulae:

$$Ratio = [(A_{665} \text{ nm}/B_{620} \text{ nm})*10^4]$$

$$\text{Mean Ratio} = (\Sigma ratios/2)$$

$$CV = [(\text{Std deviation/Mean ratio})*100]$$

$$\text{Delta } F = [((\text{Calibrator or sample Ratio} - Ratio_{neg})/Ratio_{neg})*100]$$

$Ratio_{neg}$: negative control

Figure 5:
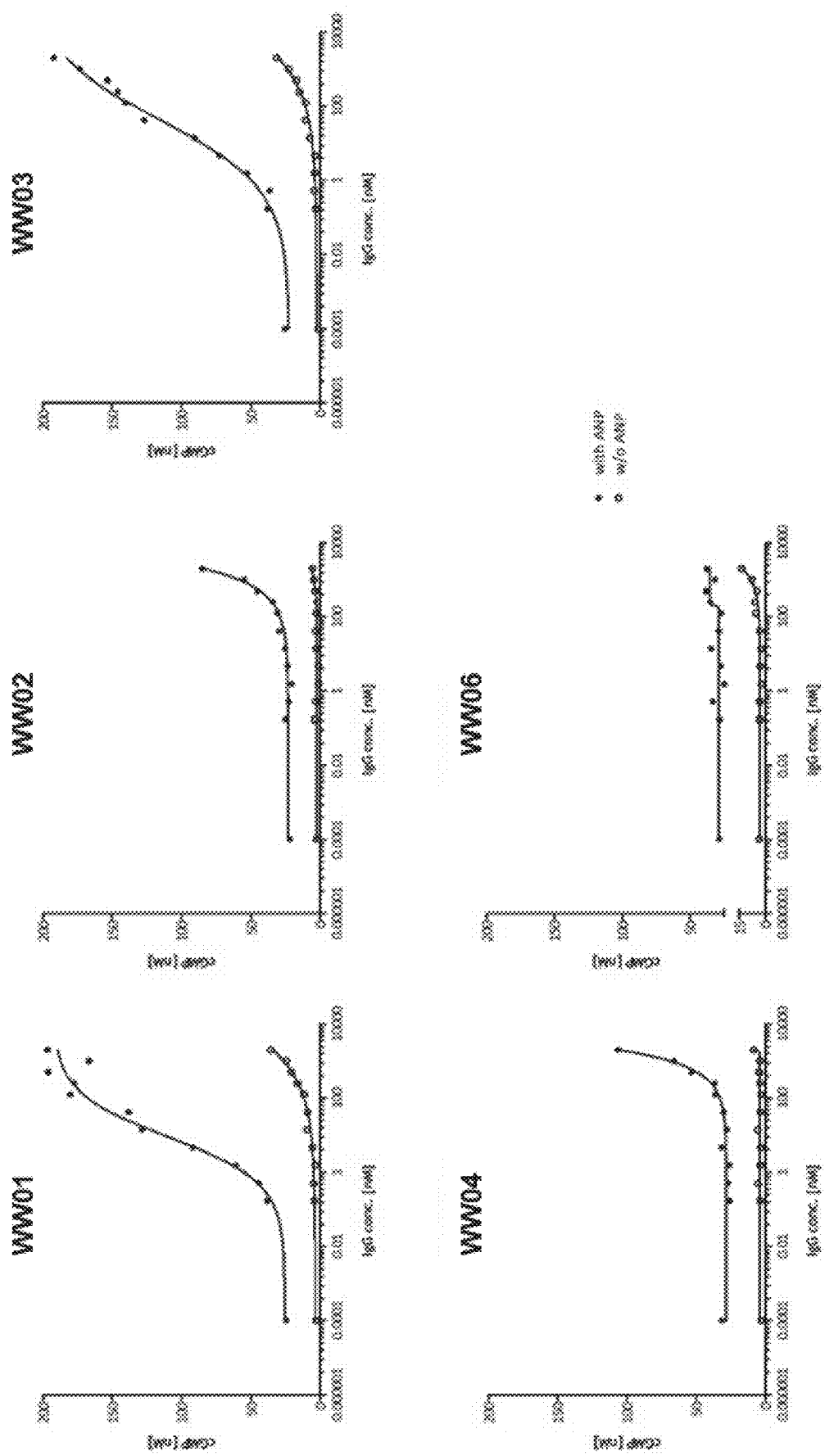
FIG. 5 is a set of graphs depicting the results of functional activity analyses of candidates WW01, WW02, WW03, WW04, and WW06 in a cellular cGMP production assay using human NPR1 expressing CHO-K1 cells. Results represent the cellular production of cGMP [nM] in the absence or presence of 0.075 nM ANP.

Five candidates with significant functional activity were identified using the cellular cGMP assay: WW01, WW02, WW03, WW04, and WW06. These five candidates were functionally active and could be assigned to different methods of action. WW01, WW02, and WW03 were able to stabilize the NPR1-ANP-complex, while WW06 was determined to be ANP competitive. These candidates were all derived from initial panning codes 10 and 11 (aiming for method of action 2 or 3). The results of the assay for the cellular production of cGMP in the absence or presence of 0.075 nM ANP induced by the five functional candidates (IgG format) are shown in FIG. 5.

Example 4: Production and Characterization of HuCAL® Candidates in FabCys Format The functional clones were also tested for functionality in FabCys format. Eukaryotic HKB11 cells were transfected with mammalian expression vector DNA encoding both heavy and light chains of disulfide-bridged FabCys. Cell culture supernatants were harvested at appropriate times and subjected to metal ion affinity chromatography using a liquid handling station. Buffer exchange was performed to 1x Dulbecco's PBS (pH 7.2) and samples were sterile filtered (0.2 μm pore size).

The five functional candidates WW01, WW02, WW03, WW04 and WW06 were additionally analyzed with regard to their monovalent affinities for human and rat NPR1 and the counter-target human NPR3 in absence and presence of ANP in monovalent FabCys format. The results of the affinity determination, epitope binning, and cGMP assay are summarized in Table 7.

TABLE 7

Summary of Affinity, Epitope, and cGMP data for WW01, WW02, WW03, WW04, and WW06 in FabCys Format

| | Characterization in monovalent FabCys format | | | | | | |
|---|---|---|---|---|---|---|---|
| | Affinity FabCys $K_D$ [nM] | | | | Epitope Bin on hNPR1 | cGMP assay cGMP conc [nM] at 2 μM FabCys | |
| | | | | | | | +0.075 |
| Antibody | hNPR1 | hNPR1 + ANP | rNPR1 | rNPR1 + ANP | (-ANP-complex) | Without ANP | nM ANP |
| WW01 | — | 1.5 | — | 2.0 | B | 30 | 121 |
| WW02 | weak | weak | weak | weak | n.a. | 4 | 20 |
| WW03 | 1000 | 0.1 | 2600 | 1.0 | B | 32 | 108 |
| WW04 | 0.8 | 0.4 | 66 | 73 | D | 4 | 0 |
| WW06 | 5.3 | 12 | weak | weak | D | 281 | 251 |

For candidates WW01 and WW03 no or very weak binding to human and rat NPR1 was observed in the absence of ANP, while the affinities in the presence of ANP were in the low nanomolar to subnanomolar range. Both shared the same epitope bin "B". The affinity of candidates WW02 was too weak for adequate determination of $K_D$ values and the epitope bin. WW04 and WW06 had affinities in the double-digit nanomolar to subnanomolar range, which were independent from the presence or absence of ANP. Both shared the same epitope bin "A". WW06 was the only candidate which did not exhibit rat cross-reactivity.

While for WW02, WW03 and WW04 no binding to the counter-target hNPR3 in the absence or presence of ANP was observed, additional binding to the counter-target was detected for WW01 as well as for WW06 at higher concentrations.

Example 5: Reformatting HuCAL® Candidates into IgG Format

Subcloning from the FabCys vector into an $IgG_1$_LALA vector for expression in mammalian cells was performed via amplification of the Fab-encoding insert using one biotinylated primer and one non-biotinylated primer. The amplified product was bound on streptavidin beads, digested using restriction enzymes, and washed, resulting in the release of the purified insert into the supernatant. The insert was cloned into the acceptor vector, the DNA was transformed and single clones were quality controlled via colony PCR and sequencing.

Figure 6:
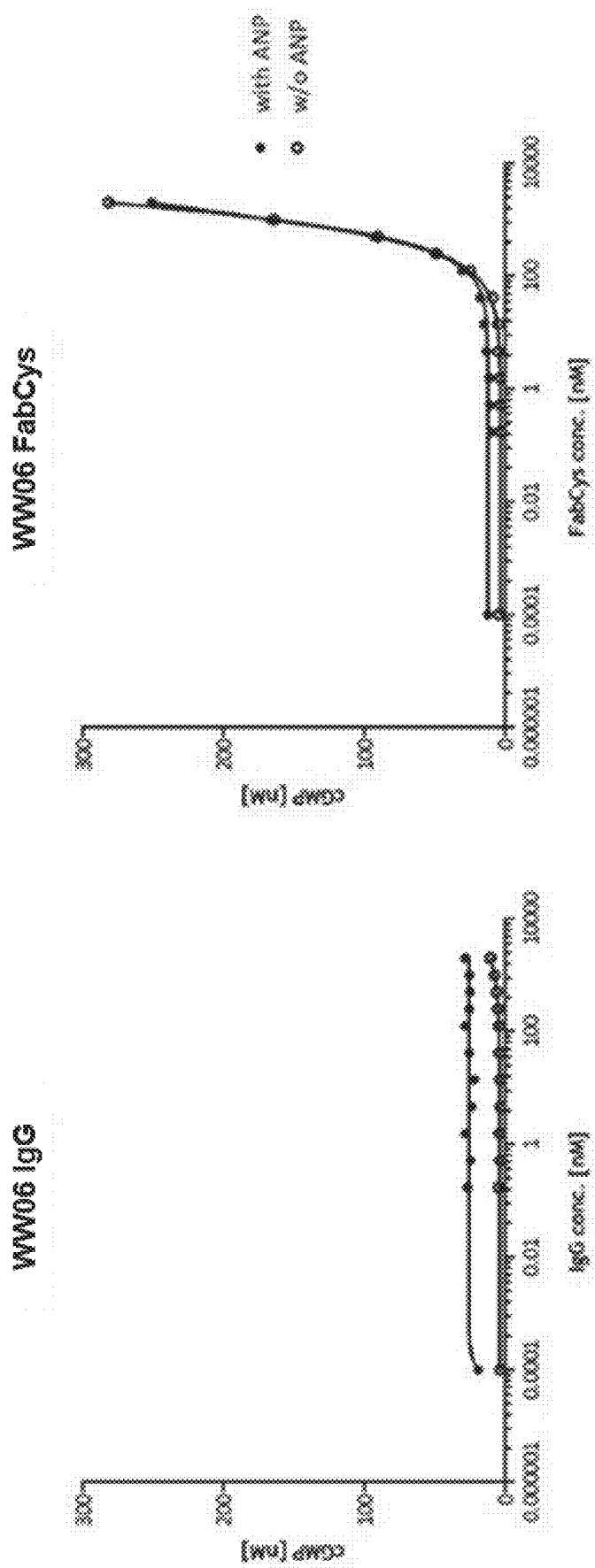
FIG. 6 is a set of graphs depicting the results of functional activity analyses of candidate WW06 in IgG or FabCys format in a cellular cGMP production assay using human NPR1 expressing CHO-K1 cells. Results represent the cellular production of cGMP [nM] in the absence or presence of 0.075 nM ANP.

The five functional candidates WW01, WW02, WW03, WW04, and WW06 in IgG format were characterized as described above. Binding data (ELISA, flow cytometry, ANP competition) and functional data (cGMP assay) as well as affinities, and epitope bins are shown in Table 8. Interestingly, WW06 had a significantly increased functional activity in FabCys format compared to IgG format as shown in FIG. 6.

Example 6: Generation of HuCAL® Maturation Libraries

To increase affinity and biological activity of the selected antibody fragments (WW01, WW02, WW03, WW04, and WW06), LCDR3 and HCDR2 regions were exchanged in parallel by diversified cassettes/modules (Prassler et al. (2009): In vitro affinity maturation of HuCAL® antibodies: complementarity determining region exchange and RapMAT technology; Immunotherapy 1 (4), pp. 571-583, the contents of which are hereby incorporated by reference for this purpose), while the framework regions were kept constant. Parental Fab fragments were transferred from the corresponding expression vector into a library cloning vector for affinity maturation.

The generation of HuCAL® maturation libraries was performed for each maturation candidate individually. For LCDR3 optimization, an approximately 400 bp DNA fragment encoding for the LCDR3, framework 4 as well as the constant region of the light chain was removed from the sequence encoding the parental antibody by restriction digest. In order to reduce the background of the parental undiversified sequence the excised fragment was replaced by an approximately 520 bp dummy sequence via ligation, before a repertoire of DNA fragments encoding for diversified LCDR3 regions together with framework 4 and the constant domain (diversified LCDR3 cassette) was inserted via restriction digest and ligation.

In a second library set the HCDR2-encoding sequence was diversified, while the connecting framework regions were kept constant. In order to reduce the background of the parental undiversified sequence an approximately 150 bp DNA fragment containing the parental HCDR2 and the framework 3 sequences was replaced by an approximately 590 bp dummy sequence via restriction digest and ligation, before the diversified HCDR2 cassette (including framework 3) was inserted also via restriction digest and ligation.

TABLE 8

Summary of Affinity, Epitope, and cGMP data for WW01, WW02, WW03, WW04, and WW06 in IgG Format Characterization in bivalent IgG format

| | Elisa +/− 100 nM ANP IgG binding/$EC_{50}$ [nM] | | | | | | | | Flow Cytometry [S/BG] at 2 µM IgG | | ANF | cGMP assay cGMP conc [nM] at 2 µM IgG |
|---|---|---|---|---|---|---|---|---|---|---|---|---|
| | hNPR1 + | | W74R + | | rNPR1 + | | hNPR3 + | | | hNPR1 CHO | competition assay | |
| Antibody | hNPR1 | 100 nM ANP | W74R | 100 nM ANP | rNPR1 | 100 nM ANP | hNPR3 | 100 nM ANP | hNPR1 CHO K1 | KI + 100 nM ANP | ANP competition by IgG | Without ANP | +0.075 nM ANP |
| WW01 | no specific binding | 1.0 | no specific binding | no specific binding | no specific binding | no specific binding | no specific binding | no specific binding | 19.9 | 222.2 | No | 36 | 197 |
| WW02 | no specific binding | 531.6 | no specific binding | no specific binding | no specific binding | no specific binding | no specific binding | no specific binding | 2.0 | 17.4 | No | 6 | 85 |
| WW03 | 42.7 | 1.4 | no specific binding | no specific binding | no specific binding | no specific binding | no specific binding | no specific binding | 2.2 | 214.3 | No | 31 | 192 |
| WW04 | 2.5 | 4.2 | 3.5 | 1.8 | no specific binding | no specific binding | no specific binding | no specific binding | 1.9 | 46.6 | Yes | 8 | 107 |
| WW06 | 2.5 | 1.1 | 0.9 | 0.8 | no specific binding | no specific binding | no specific binding | no specific binding | 4.6 | 1.1 | Yes | 13 | 38 |

The ten maturation libraries were successfully cloned and had library sizes between $9.2 \times 10^8$ and $2.2 \times 10^9$ cfu. Ligation mixtures were electroporated into *E. coli* cells yielding $>10^8$ independent colonies. Amplification of the library was performed as described previously (Rauchenberger et al. (2003): Human combinatorial Fab library yielding specific and functional antibodies against the human fibroblast growth factor receptor 3; *J Biol Chem* 278 (40), pp. 38194-38205, the contents of which are hereby incorporated by reference for this purpose). For quality control, approx. 10-20 single clones per library were picked randomly and sequenced.

For the selection of affinity improved candidates, phage derived from maturation libraries were subjected to three rounds of maturation panning as described further below. Panning stringency was increased by prolonged washing steps. In addition, off-rate selection was performed (Hawkins et al. (1992): Selection of phage antibodies by binding affinity. Mimicking affinity maturation. In *J. Mol. Biol.* 226 (3), pp. 889-896, the contents of which are hereby incorporated by reference for this purpose).

Example 7: Pannings and Screenings-HuCAL®

The maturation libraries were used for four different maturation panning strategies. Strategies #3 and #4 aimed for the enrichment of progenies with improved affinities compared to the parental clones. In addition, strategies #1 and #2 aimed for the enrichment of clones with improved affinities for NPR1 instead of NPR1-ANP-complex. The rationale behind that was the idea to generate candidates which are able to directly active NPR1 by a conformational change. During the panning process, all maturation libraries were kept separately. The panning strategies are summarized in Table 9 in detail. The outputs of the third panning rounds were subsequently sub-cloned into a bacterial expression vector and bacterial lysates (BEL) were used for SET screening.

Figure 7:
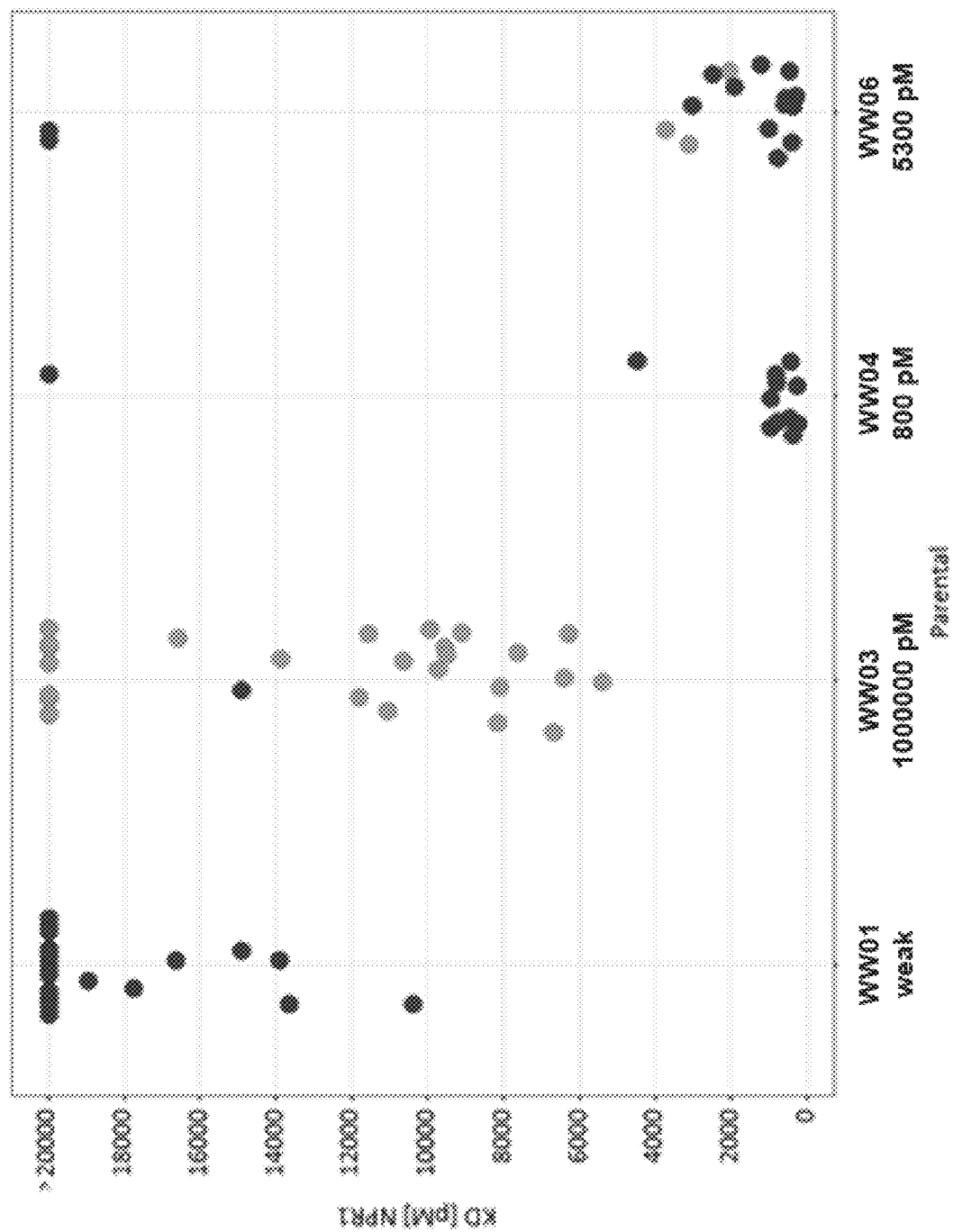
FIG. 7 demonstrates the results of SET screening (hNPR1 affinity) of 82 HCDR2 or LCDR3 unique improved HuCAL® derivatives based on the parental antibody.
Figure 8:
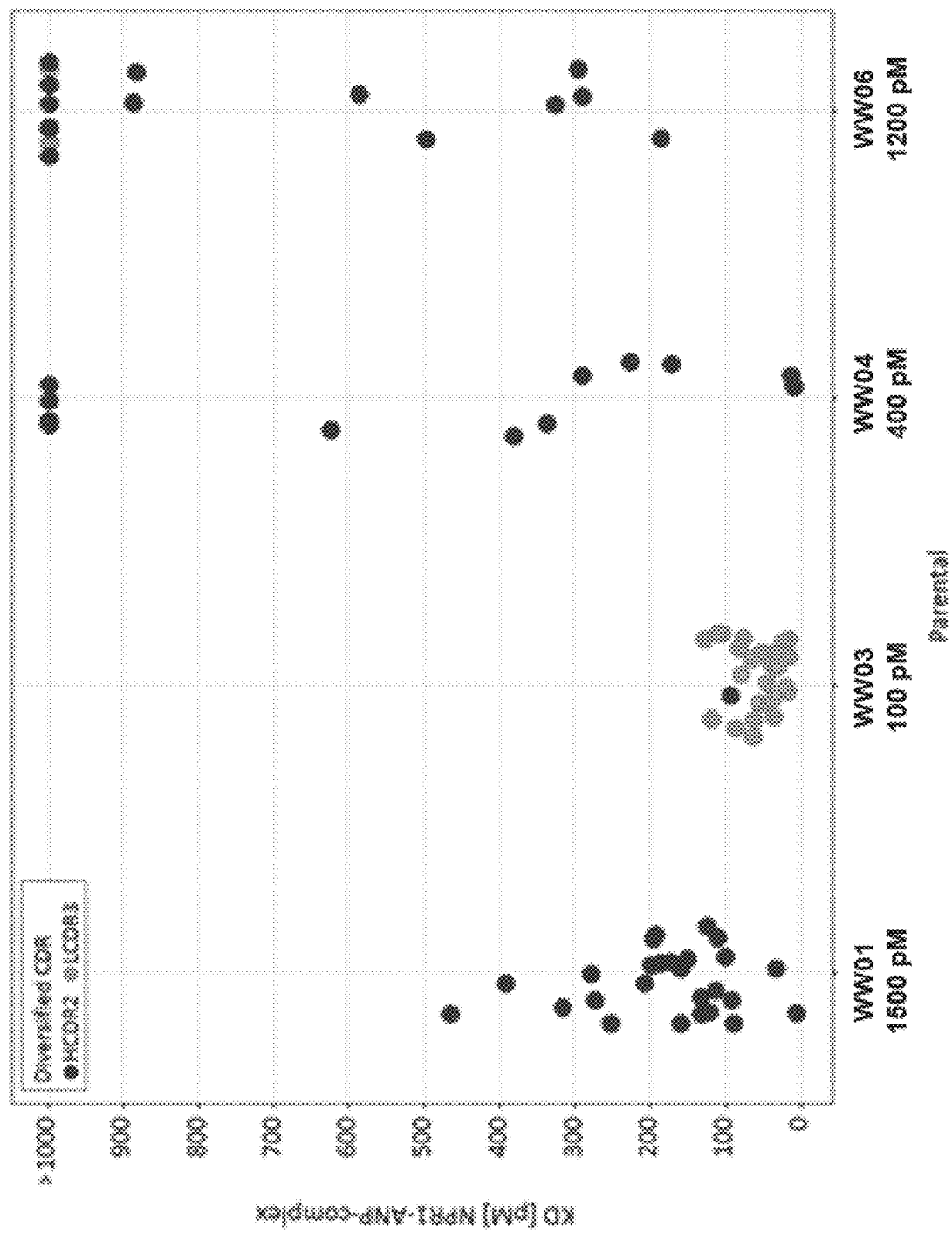
FIG. 8 demonstrates the results of SET screening (hNPR1-ANP complex affinity) of 82 HCDR2 or LCDR3 unique improved HuCAL® derivatives based on the parental antibody.

During SET screening, 82 HCDR2 or LCDR3 unique improved derivatives were identified. Compared to their parental clones, the affinities of WW01 and WW03 derivatives were improved up to 20-fold both for hNPR1 and hNPR1-ANP-complex. The affinities of the WW04 derivatives were not improved significantly, while the WW06 derivatives had up to 3-fold improved affinities compared to the parental clone. See FIG. 7 (which shows affinities for hNPR1) and FIG. 8 (which shows affinities for hNPR1-ANP complex). Affinities ($K_D$ [pM]) are indicated at the x-axis below the parental clone name for both figures.

Example 8: Characterization of Matured Candidates-HuCAL®

74 of the 82 improved candidates were successfully subcloned into FabCys format and 61 of the 74 clones passed the production quality control and were characterized in regard to binding to relevant antigens, binding to relevant cell lines, ANP competition, and functional activity in the cGMP production assay in comparison to their parental clones. All 16 derivatives of WW01 and all 27 derivatives of WW03 had up to 20-fold improved binding and functional activity. The majority of the derivatives also showed improved binding and functionality in the presence of ANP. Some derivatives showed binding to W74R (constitutively active hNPR1 mutant), which was not true for the parental FabCys. One of the four derivatives of WW04 had two-fold improved binding and functional activity, while the rest behaved like the parental FabCys. All 14 derivatives of WW06 had improved binding for NPR1 and remained competitive with ANP. The functional activities of 10 of the 14 progenies were improved up to three-fold compared to the parental FabCys. Some derivatives displayed rat cross-reactivity, which was not true for the parental FabCys.

After FabCys characterization, a further 40 of the 61 derivatives were selected for IgG conversion and further characterization. Ten potential candidates shown in Table 10

TABLE 9

Overview of HuCAL ® Maturation Panning Strategies

| Strategy | Parental antibodies | $1^{st}$ round | $2^{nd}$ round | $3^{rd}$ round | comments |
|---|---|---|---|---|---|
| 1 | WW01 WW02 WW03 WW04 WW06 | CHO-K1 NPR1 cells | hNPR1 solution | CHO-K1 NPR1 cells | Cell/solution panning aiming for improved candidates |
| 2 | WW01 WW02 WW03 WW04 | CHO-K1 NPR1 cells | hNPR1-ANP-complex solution | CHO-K1 NPR1 cells | Cell/solution panning aiming for improved candidates |
| 3 | WW01 WW02 WW03 WW04 | hNPR1-ANP-complex solution | CHO-K1 NPR1-ANP-complex Cells | hNPR1-ANP-complex solution | Solution/cell aiming for improved NPR1-ANP-complex |
| 4 | WW04 WW06 | Preadsorption on NPR1-ANP complex CHO-K1 NPR1 cells | Preadsorption on NPR1-ANP complex hNPR1 solution | Preadsorption on NPR1-ANP complex CHO-K1 NPR1 cells | Cell/solution panning aiming for improved ANP competitors |

The outputs of the 3rd panning rounds were used for Solution Equilibrium Titration (SET) screening. 88 clones per subcode (2640 clones in total) were analyzed in SET screening for improved affinity for hNPR1 and/or hNPR1-ANP-complex compared to the parental clones.

were then assayed with respect to binding to relevant antigens, binding to relevant cell lines, ANP competition, and functional activity in the cGMP production assay in comparison to their parental clones. They were further analyzed via 3P assay and their affinities for human and rat NPR1 in absence and presence of ANP were determined via SET $K_D$ measurement. WW01 and WW03 derivative antibodies were analyzed in IgG format and the WW06 derivatives in FabCys format.

For protein panel profiling (Frese et al. (2013): An automated immunoassay for early specificity profiling of antibodies; mAbs 5 (2), pp. 279-287, the contents of which are herein incorporated by reference for this purpose), 32 different proteins and controls were coated on two 384-well MSD standard plates at a concentration of 1.0 μg/mL at 4° C. overnight. The coating solution was discarded and plates were blocked with 50 μL 3% (w/v) BSA in PBS for one hour at RT on a microtiter plate shaker (~500 rpm) followed by three washing steps with 50 μL washing buffer (PBS with 0.05% (v/v) Tween 20). Antibody samples were diluted to 100 nM and 10 nM in assay buffer (PBS with 0.5% (w/v) BSA, 0.05% (v/v) Tween 20). As controls, a reference antibody (Fab or IgG, depending on the sample format) and assay buffer were used. Samples and controls were added at 30 μL/well and incubated for three hours at RT on a microtiter plate shaker. The plates were washed three times and 30 μL detection antibody (ECL-labeled anti-human Fab) were added per well and incubated for one hour on a microtiter plate shaker (~500 rpm). After washing the MSD plate and adding 35 μL/well MSD Read Buffer T with surfactant, electrochemiluminescence signals were detected using a Sector Imager 6000 (Meso Scale Discovery; Gaithersburg, MD, USA). For evaluation, signals of the antibody sample on a certain protein were divided by the respective signals of the reference mAb resulting in a binding ratio (BR). The cumulative binding ratio (CBR) of all proteins except the controls (25 in total) was then calculated: CBR up to 150 represented an antibody or fragment thereof without detectable non-specific binding. Values above represented an antibody or fragment thereof with increased non-specific binding compared to a reference mAb.

TABLE 10

Overview of Matured HuCAL ® Candidates

| Matured antibody | Parental antibody | Matured CDR |
|---|---|---|
| XX01 | WW01 | HCDR2 |
| XX02 | WW06 | HCDR2 |
| XX03 | WW03 | HCDR2 |
| XX04 | WW03 | LCDR3 |
| XX05 | WW06 | HCDR2 |
| XX06 | WW03 | LCDR3 |
| XX07 | WW03 | LCDR3 |
| XX08 | WW01 | HCDR2 |
| XX10 | WW06 | HCDR2 |
| XX12 | WW03 | LCDR3 |

Figure 9:
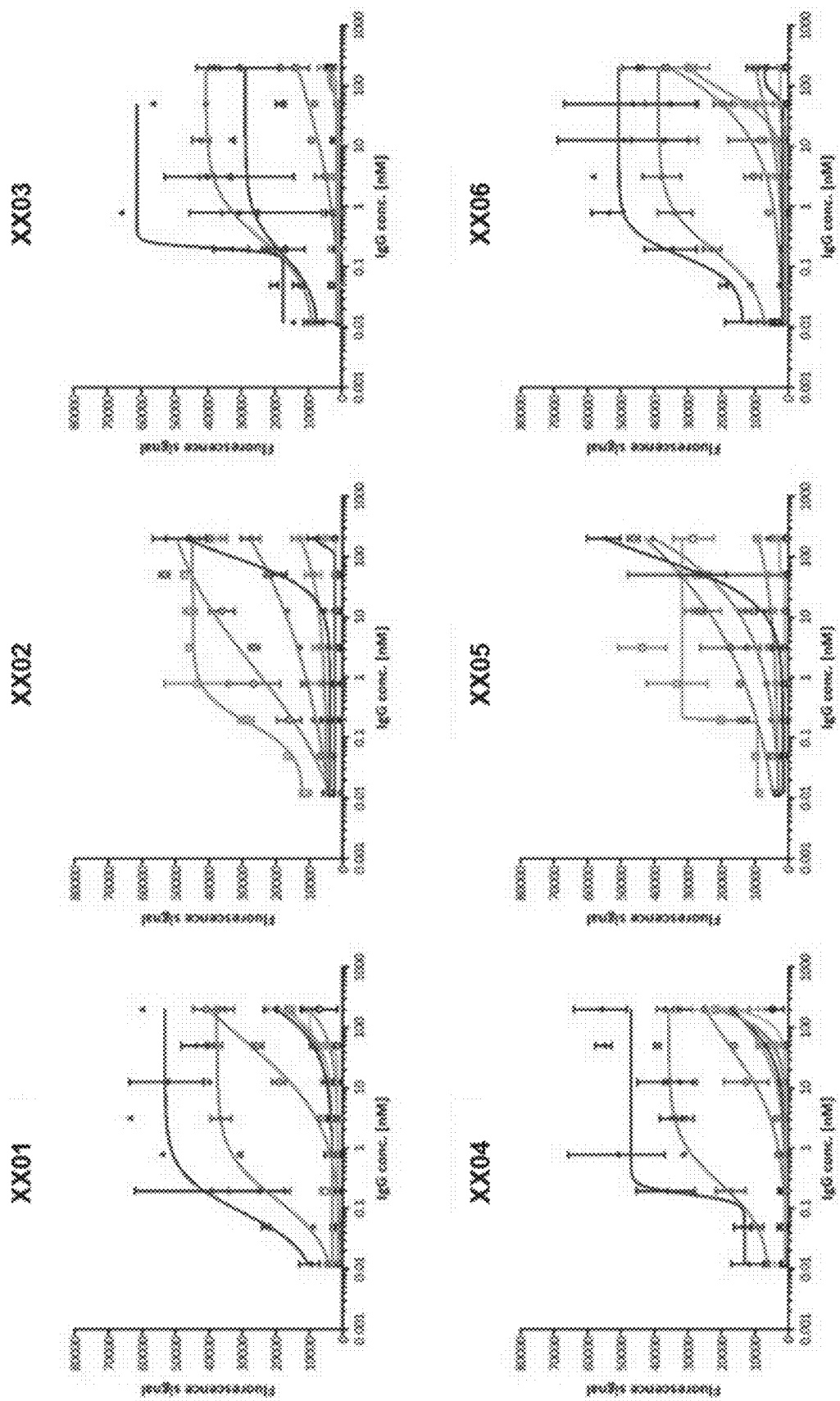
FIG. 9 is a set of graphs displaying the results of antibody candidates XX01-XX08, XX10, and XX12 binding to the following antigens (ELISA analysis): human NPR1, constitutively active human NPR1 mutant (W74R), rat NPR1, and human NPR3 (counter target) in the absence of or in the presence of a 250 fold molar excess of ANP.
Figure 9:
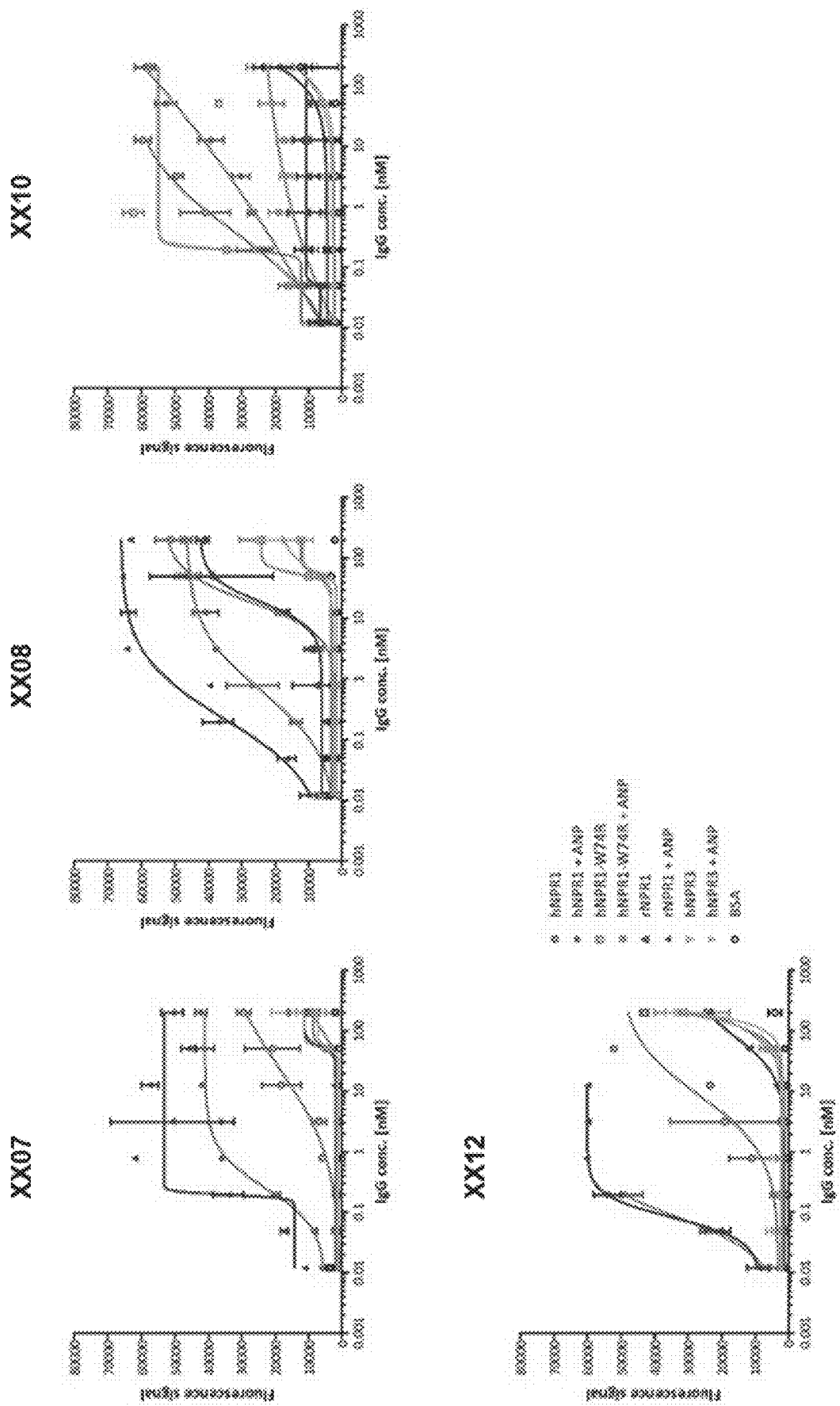
Figure 10:
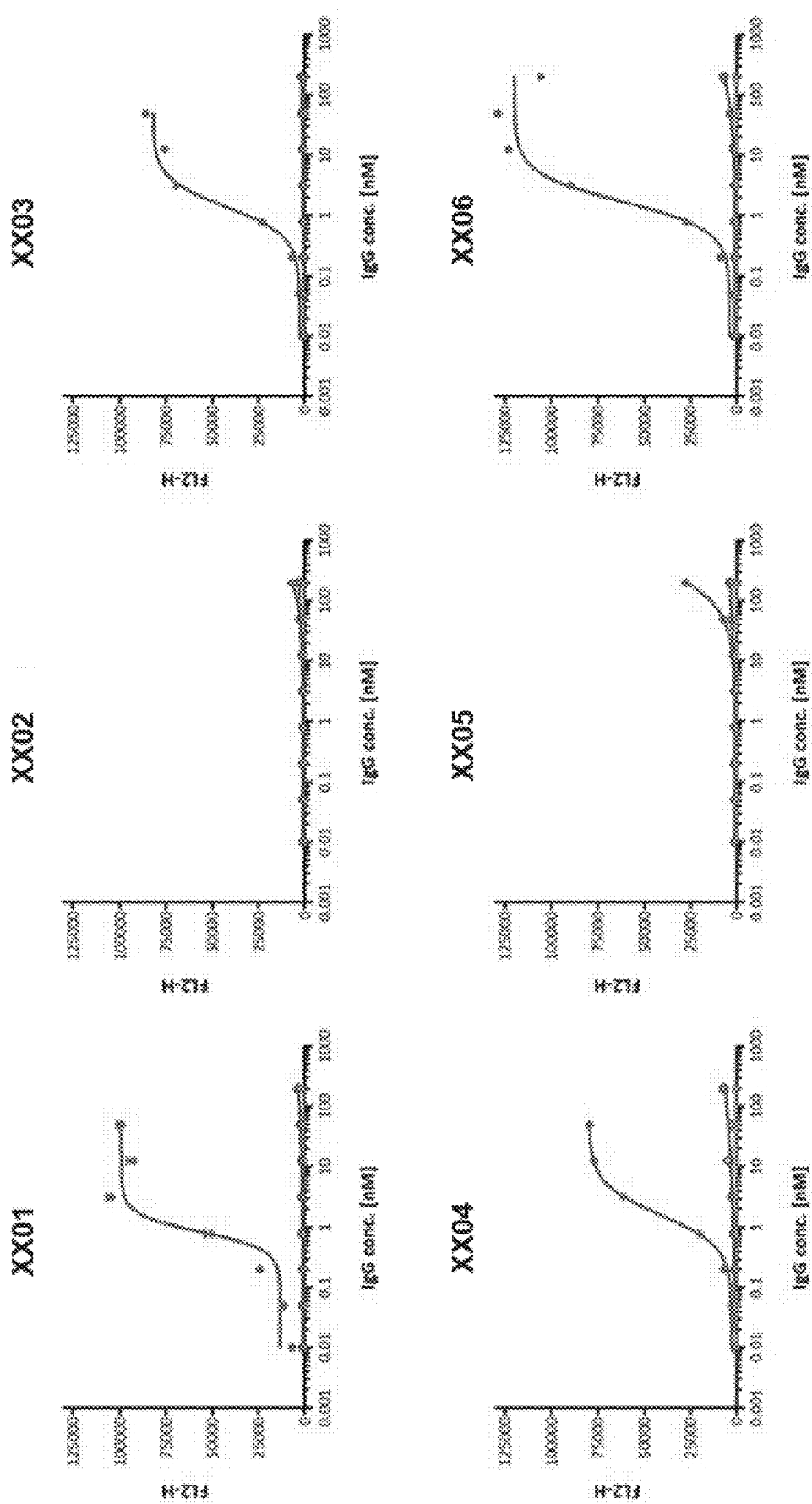
FIG. 10 is a set of graphs displaying the results of flow cytometry analysis of antibody candidates XX01-XX08, XX10, and XX12 for binding to human NPR1 expressing CHO-K1 cells in the absence or presence of a saturating concentration of ANP and on parental CHO-K1 cells.
Figure 10:
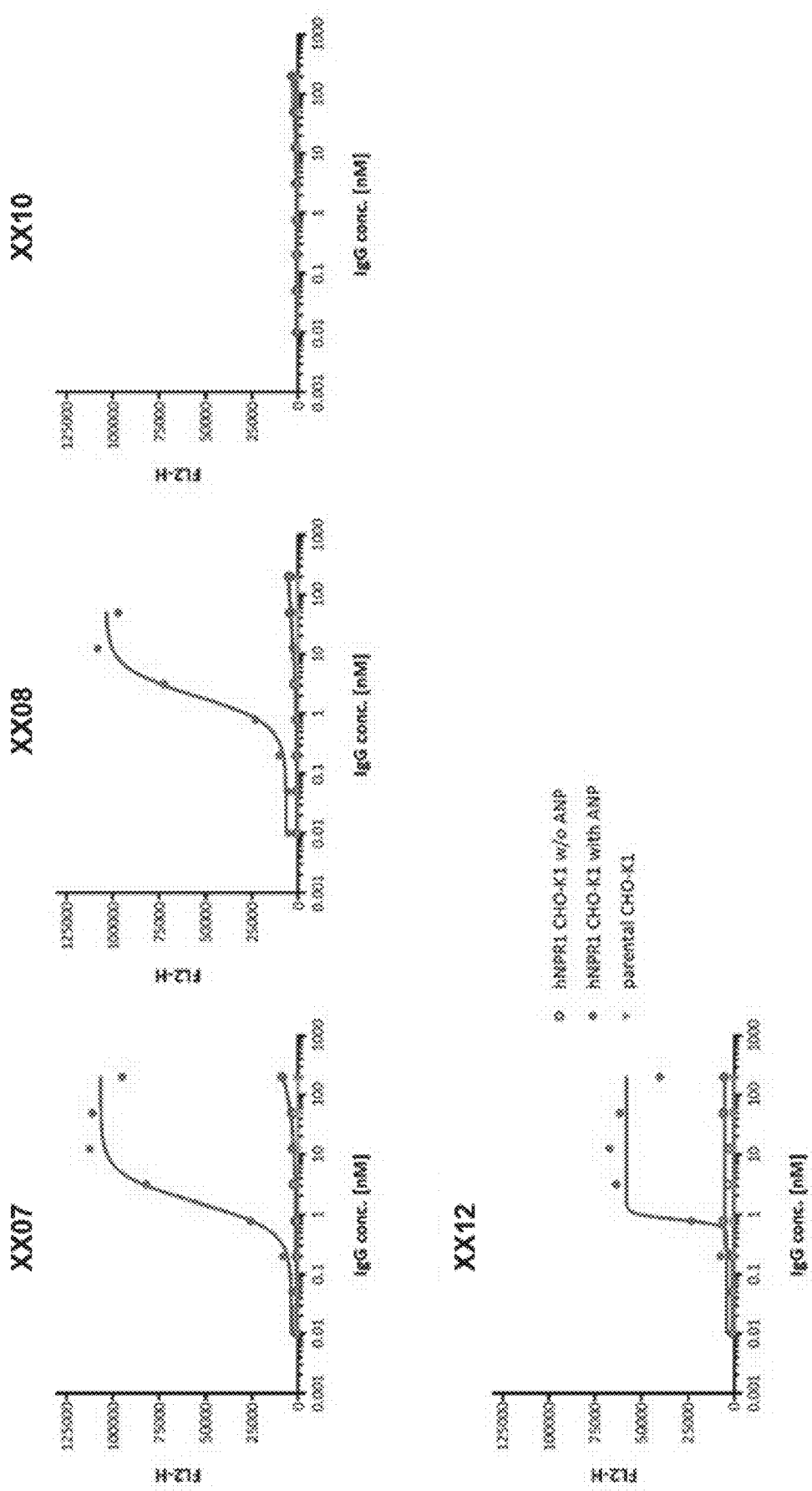
Figure 11:
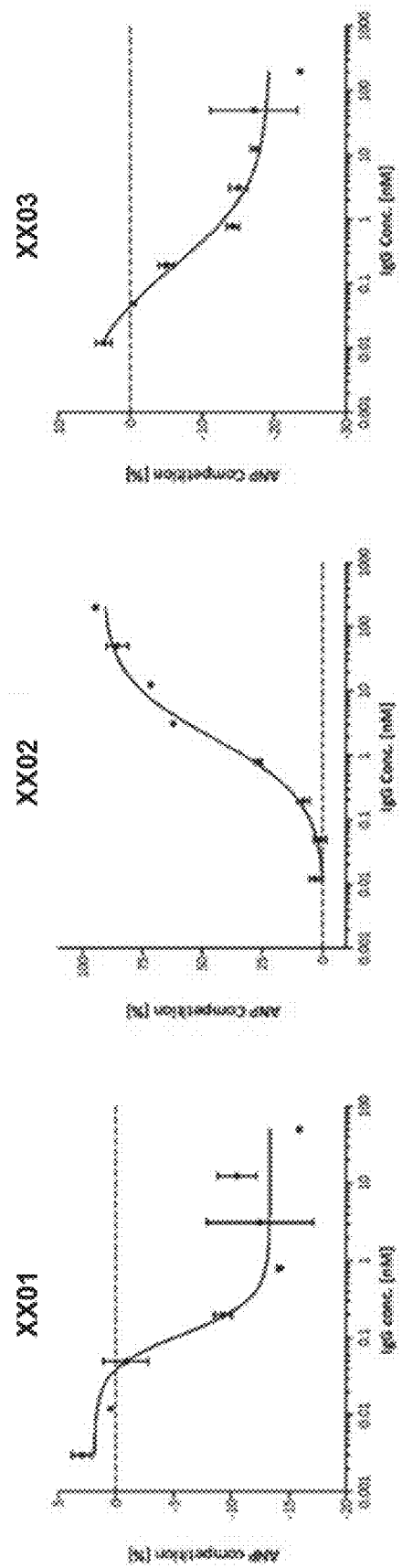
FIG. 11 is a set of graphs displaying the results of ANP competition analyses of candidates XX01-XX07, XX10, and XX12 using the FRET-based assay depicted in FIG. 3.
Figure 11:
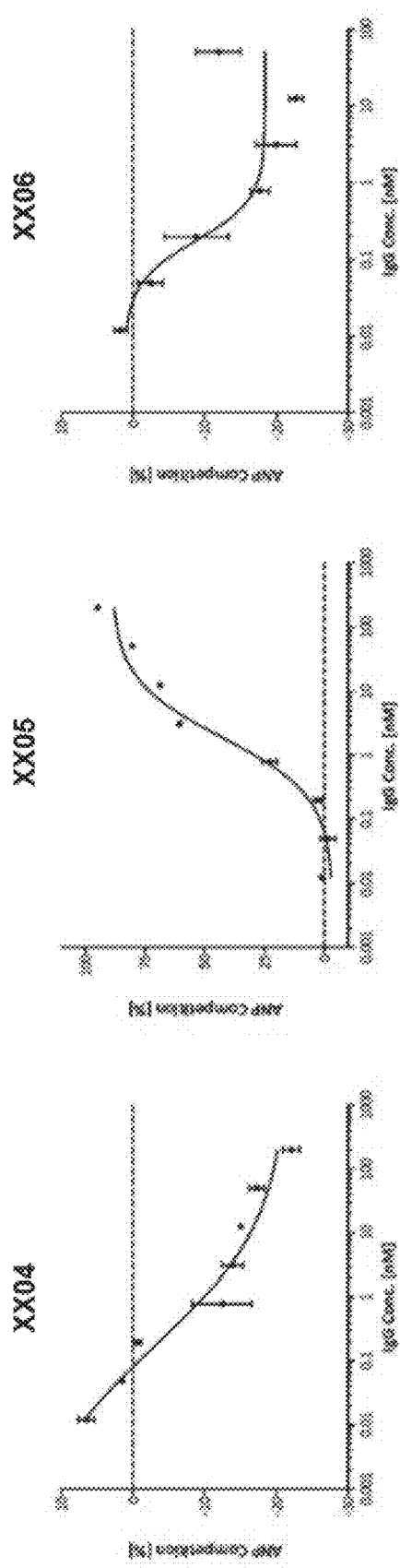
Figure 11:
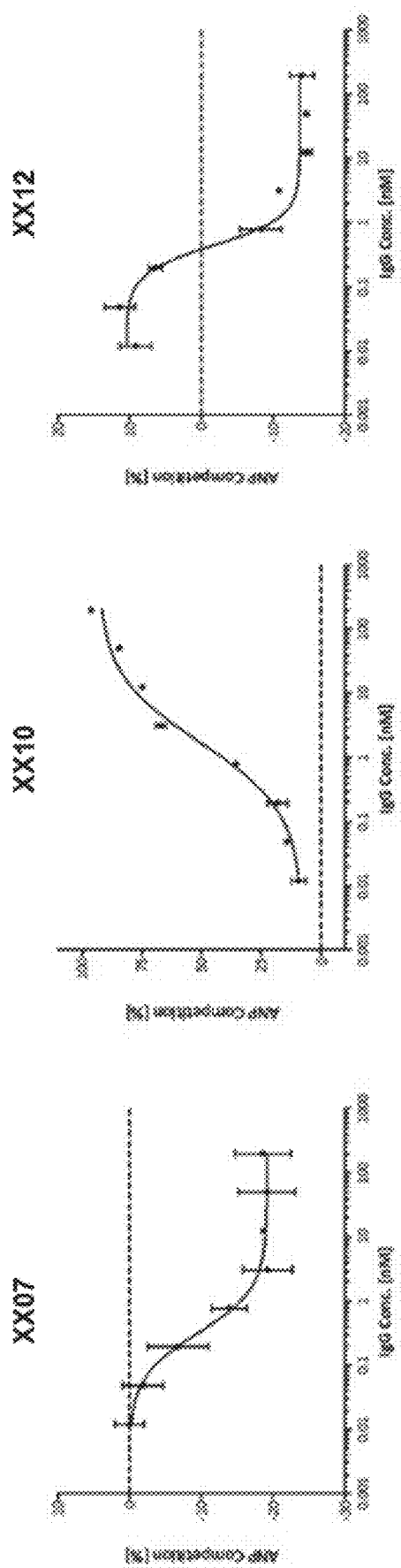

Furthermore, the clones were tested via ELISA for binding to the following antigens: human NPR1, constitutively active human NPR1 mutant (W74R), rat NPR1, human NPR3 (counter target), each in the absence and presence of ANP, and BSA. The clones were also analyzed by flow cytometry for binding to human NPR1 expressing CHO K1 cells in absence and presence of ANP (100 nM) and to parental CHO K1 cells. The binding properties of the 10 candidates are shown in FIGS. 9 and 10. The ANP competition results for nine of the candidates are shown in FIG. 11.

Figure 12:
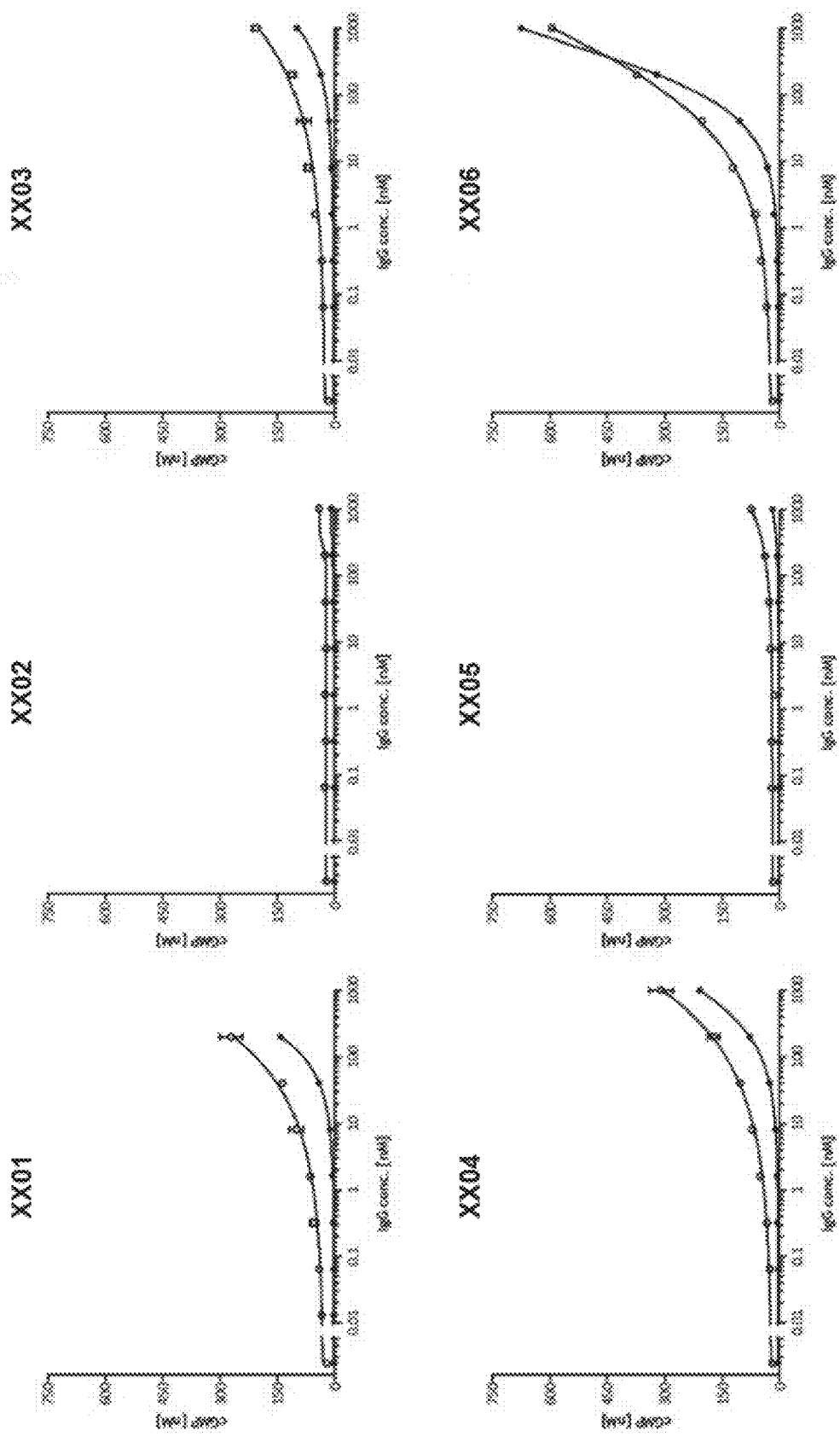
FIG. 12 is a set of graphs depicting the results of functional activity analyses of candidates XX01-XX08, XX10, and XX12 in a cellular cGMP production assay using human NPR1 expressing CHO-K1 cells. Results represent the cellular production of cGMP [nM] in the absence or presence of 0.075 nM ANP.
Figure 12:
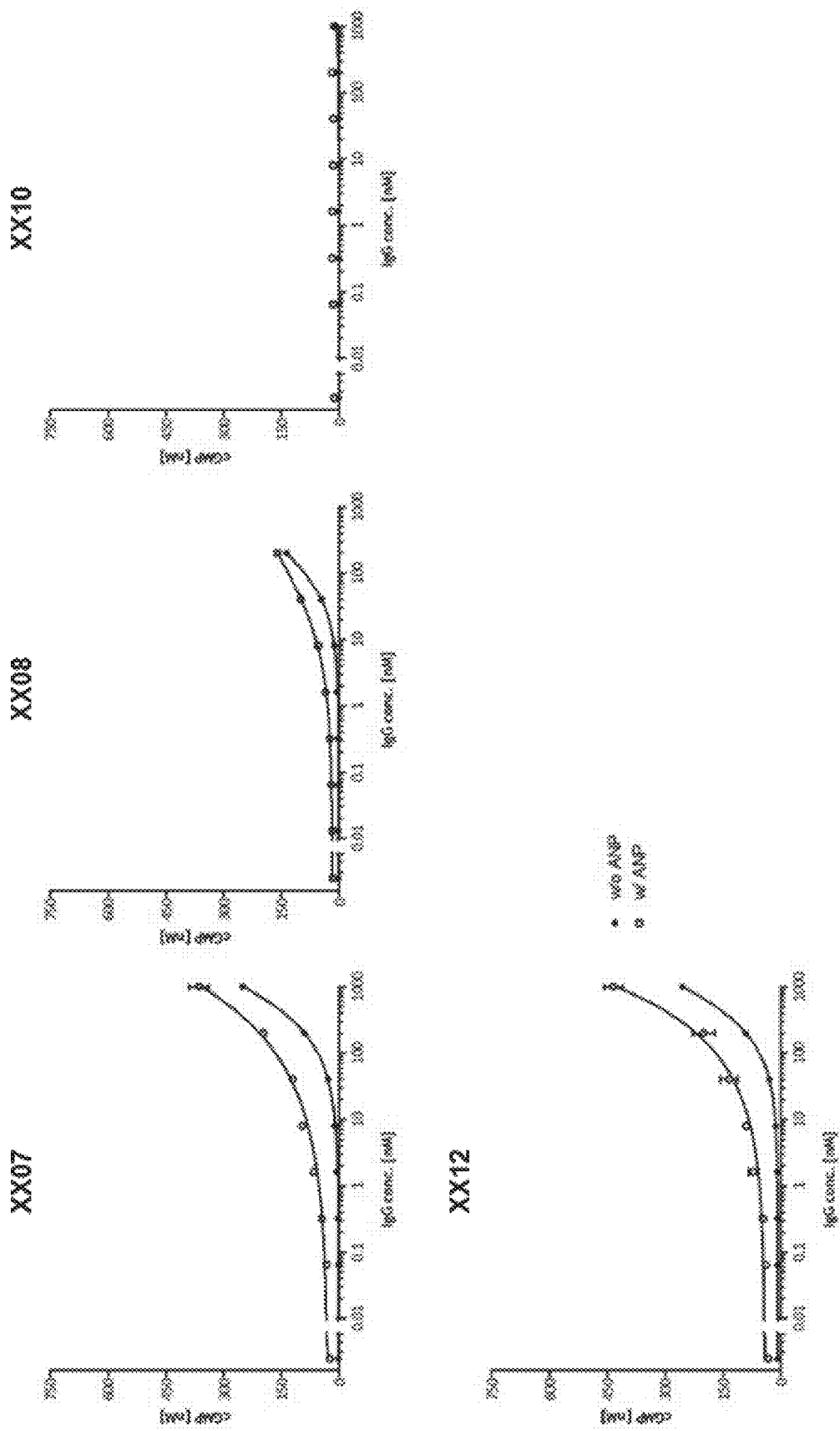

Negative values for XX01, XX03, XX04, XX06, XX07, and XX12 suggest enhancement of ANP binding by these antibodies. The functional activity of the 10 candidates was analyzed using the cellular cGMP production assay and results are shown in FIG. 12. As expected from the functional data of the parental clone WW06, its derivatives XX02, XX05, and XX10 showed weak to no functional activity in the IgG format, whereas they had very high functionality in monovalent FabCys format.

The affinities for XX01-XX08, XX10, and XX12 in monovalent FabCys format were determined via SET $K_D$ measurement. The results are summarized in Table 11 in comparison to the affinities of the parental clones (determined in another experiment via Biacore®). The affinities for human and rat NPR1 of WW01 and WW03 derivatives were improved up to 2,300-fold, while the affinities for the NPR1-ANP-complexes were only slightly improved (maximal 5-fold). They had affinities between 10 and 46 nM for hNPR1 and between 100 and 300 pM for hNPR1-ANP-complex. All WW01 and WW03 progenies displayed rat cross-reactivity with rat/human $K_D$ ratios <5. The affinities of the WW06 derivatives for human NPR1 and hNPR1-ANP-complex were improved maximally 8-fold and had $K_D$ values between 1 and 5 nM, while no binding to rat NPR1 or rat NPR1-ANP-complex could be observed.

TABLE 11

Affinities of Parental and Matured HuCAL ® Candidates

| | Affinity (SET measurement) FabCys $K_D$ [nM] | | | |
|---|---|---|---|---|
| Antibody | hNPR1 | hNPR1 + ANP | rNPR1 | rNPR1 + ANP |
| WW01 | weak | 1.5 | weak | 2.0 |
| XX01 | 43 | 0.3 | 1.4 | 0.5 |
| XX08 | 46 | 0.3 | 1.8 | 0.2 |
| WW03 | 1000 | 0.1 | 2600 | 1.0 |
| XX03 | 22 | 0.2 | 1.1 | 0.1 |
| XX04 | 32 | 0.1 | 3.3 | 0.3 |
| XX06 | 10 | 0.1 | 2.3 | 0.3 |
| XX07 | 21 | 0.2 | 2.9 | 0.5 |
| XX12 | 16 | 0.2 | 3.0 | 0.5 |
| WW06 | 5.3 | 12 | — | — |
| XX02 | 1.0 | 1.4 | — | — |
| XX05 | 3.2 | 5.1 | — | — |
| XX10 | 2.2 | 4.0 | — | — |

Example 9: Cross-Cloning and PTM Removal

Parental clone WW03 had a 'DG' site in HCDR2. The majority of the WW03 derivatives (26 out of 27) were diversified in LCDR3. Only one candidate (XX03) was diversified in HCDR2 including the mutation of 'DG' into 'DK' at amino acid position 54 in the heavy chain variable region (see, e.g., position 54 of SEQ ID NO: 122). The light chains of the functional LCDR3 diversified clones were cross-cloned with the heavy chain of XX03 to engineer these clones without loss of functionality. Furthermore, the 'DG' to 'DK' mutation was inserted in the original heavy chains of several LCDR3 diversified derivatives. An overview of exemplary cross-cloned and D54K engineered candidates is shown in Table 12.

TABLE 12

Overview of VL-VH Cross-cloned and D54K Engineered Clones (WW03 derivatives)

| Antibody | Light chain origin | Heavy chain origin |
|---|---|---|
| XX13 | XX06 | WW03 D54K |
| XX14 | XX09 | |
| XX15 | XX04 | XX03 |

TABLE 12-continued

Overview of VL-VH Cross-cloned and D54K
Engineered Clones (WW03 derivatives)

| Antibody | Light chain origin | Heavy chain origin |
|---|---|---|
| XX16 | | XX06 |
| XX17 | | XX07 |
| XX18 | | XX09 |
| XX19 | | XX11 |
| XX20 | | XX12 |

Figure 13:
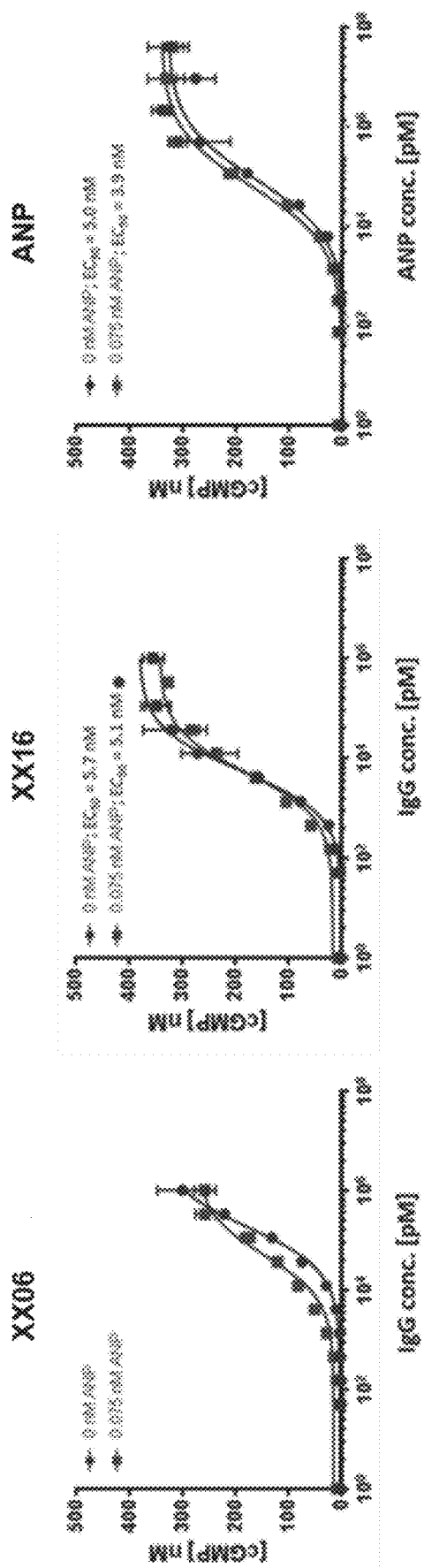
FIG. 13 is a set of graphs depicting the results of functional activity analyses of candidates XX06 and XX16 alongside natural ligand ANP in a cellular cGMP production assay using human NPR1 expressing CHO-K1 cells. Results represent the cellular production of cGMP [nM] in the absence or presence of 0.075 nM ANP.
Figure 14:
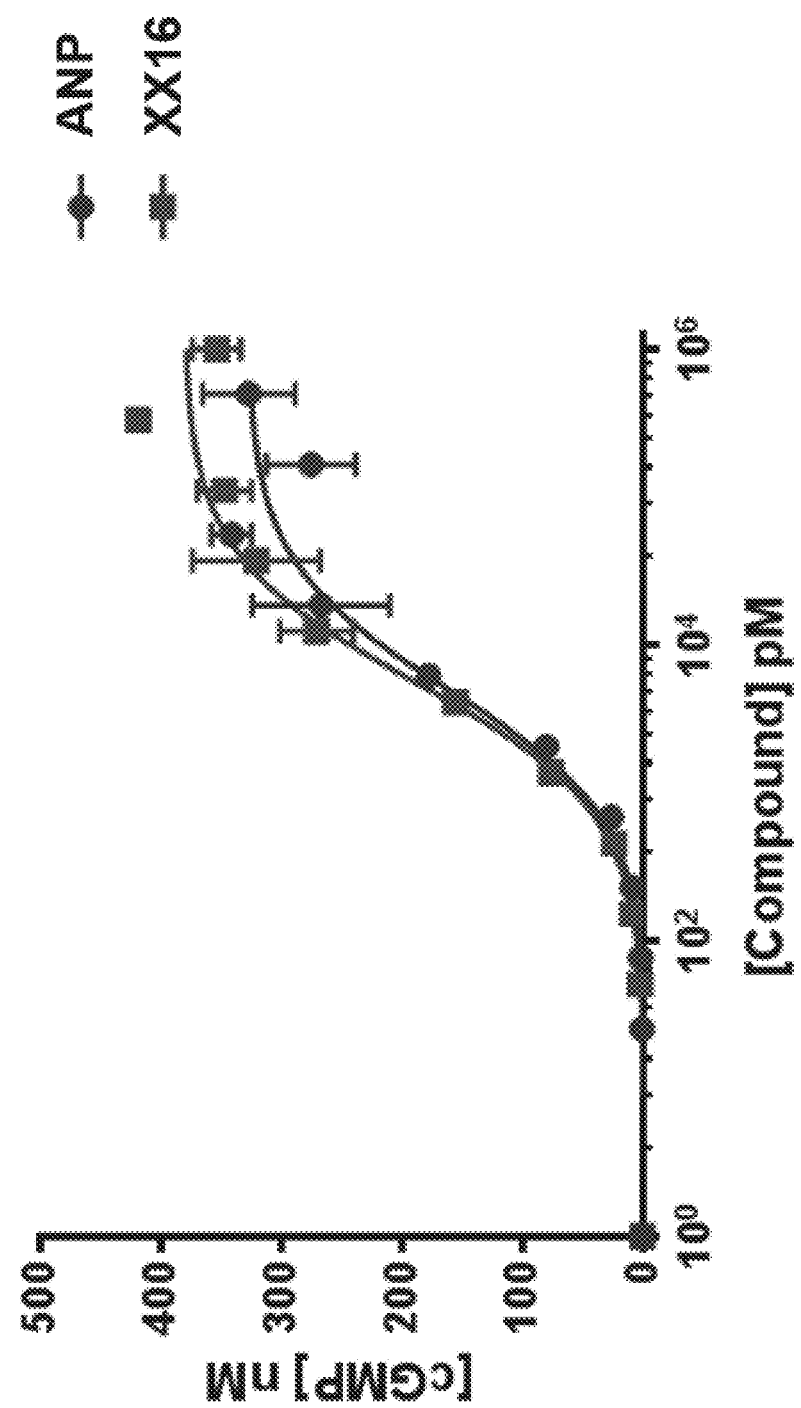
FIG. 14 is a graph depicting the results of functional activity analyses of candidate XX16 alongside natural ligand ANP in a cellular cGMP production assay using human NPR1 expressing CHO-K1 cells. Results represent the cellular production of cGMP [nM] as a function of either ANP or XX16.

Exemplary functional data of a cross-clone (XX16) compared to the original clone (XX06) and ANP are shown in FIG. 13. All cross-clones had similar or even better functional activity compared to their original clones. XX16 even had a maximal cGMP concentration comparable to the natural ligand ANP in an in vitro study analyzing their activity in hNPR1 transformed CHO cells (see FIG. 14).

Cross-cloned and PTM removed clones were tested for their specificity via 3P assay. Both D54K engineered clones XX13 and XX14 showed non-specific binding to several antigens and were deselected, while no cross-clone showed non-specific binding. Results are shown in Table 13.

TABLE 13

In vitro functional data for XX15 and XX16 cGMP Generation for human, rat, cyno NPR1 and human NPR2 expressing CHO cells

| Antibody | hNPR1 EC50 (nM) +/−STDEV | hNPR1 Y max (% of ANP) +/−STDEV | rNPR1 EC50 (nM) +/−STDEV | rNPR1 Y max (% of ANP) +/−STDEV | cNPR1 EC50 (nM) +/−STDEV | cNPR1 Y max (% of ANP) +/−STDEV | hNPR2 EC50 (nM) | hNPR2 Y max (% of ANP) |
|---|---|---|---|---|---|---|---|---|
| XX16 | 3.2 +/− 0.4 | 97 +/− 1 | 8 +/− 2 | 94 +/− 8 | 12 +/− 2 | 86 +/− 2 | >500 | <1 |
| XX15 | 9.4 +/− 0.4 | 98 +/− 7 | 23 +/− 6 | 100 +/− 10 | 30 +/− 2 | 95 +/− 3 | >500 | <1 |
| XX18 | 40 +/− 10 | 110 +/− 10 | 26 +/− 9 | 99 +/− 8 | 50 +/− 10 | 90 +/− 5 | >500 | <1 |

Example 10: Crystal Structure of Anti-NPR1 Antibodies

Crystal structures for several molecules in complex with hNPR1 were created as described below.

For Fab03-WW03, the Fab construct of WW03 was complexed to the extracellular domain of hNPR1 (C264T) with a molar ratio of 2 Fab molecules for every 1 NPR1 molecule. The complex was incubated for 1 hour in the cold room rocking and then loaded onto a Superdex 200 16/60 column in the buffer 20 mM HEPES pH7.4, 100 mM NaCl. The complexed protein was separated from a small aggregate peak and the excess Fab and then concentrated to 19.8 mg/mL. The complex crystallized in space group P212121 and diffracted to a resolution of 2.89 Å. The model was built using molecular replacement with the hNPR1 structure and a Fab molecule, iteratively built in Coot and refined with Buster to an Rfree of 21.7%.

For Fab06-WW06, the Fab construct of WW06 was complexed to the extracellular domain of hNPR1 (C264T) with a molar ratio of 2 Fab molecules for every 1 NPR1 molecule. The complex was incubated for 1 hour in the cold room rocking and then loaded onto a Superdex 200 16/60 column in the buffer 20 mM HEPES pH7.4, 100 mM NaCl. The complexed protein was separated from a small aggregate peak and the excess Fab and then concentrated to approximately 20.0 mg/mL. The complex crystallized in space group P212121 and diffracted to a resolution of 2.17 Å. The model was built using molecular replacement with the hNPR1 structure and a Fab molecule, iteratively built in Coot and refined with Buster to an Rfree of 20.9%.

For Fab16-XX16, the Fab construct of XX16 was complexed to the extracellular domain of hNPR1 (C264T) with a molar ratio of 2 Fab molecules for every 1 NPR1 molecule. The complex was incubated for 1 hour in the cold room rocking and then loaded onto a Superdex 200 16/60 column in the buffer 20 mM HEPES pH7.4, 100 mM NaCl. The complexed protein was separated from a small aggregate peak and the excess Fab and then concentrated to approximately 20.0 mg/mL. The complex crystallized in space group P212121 and diffracted to a resolution of 3.02 Å. The model was built using molecular replacement with the hNPR1 structure and a Fab molecule, iteratively built in Coot and refined with Buster to an Rfree of 24.4%.

Figure 15:
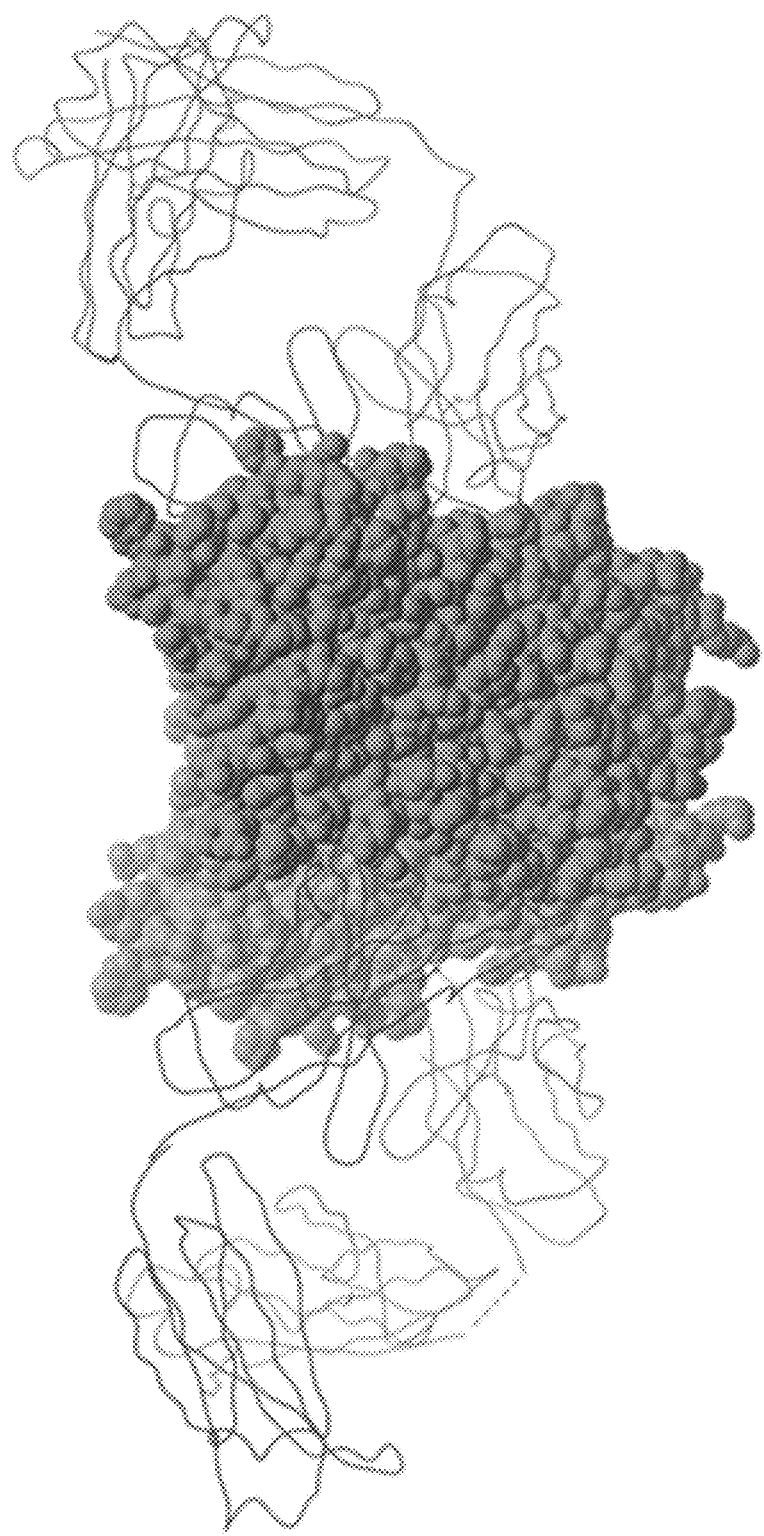
FIG. 15 is a graphical representation of the crystal structure of Fab06 (the WW06 antibody in Fab format) in complex with hNPR1 extracellular domain.
Figure 16:
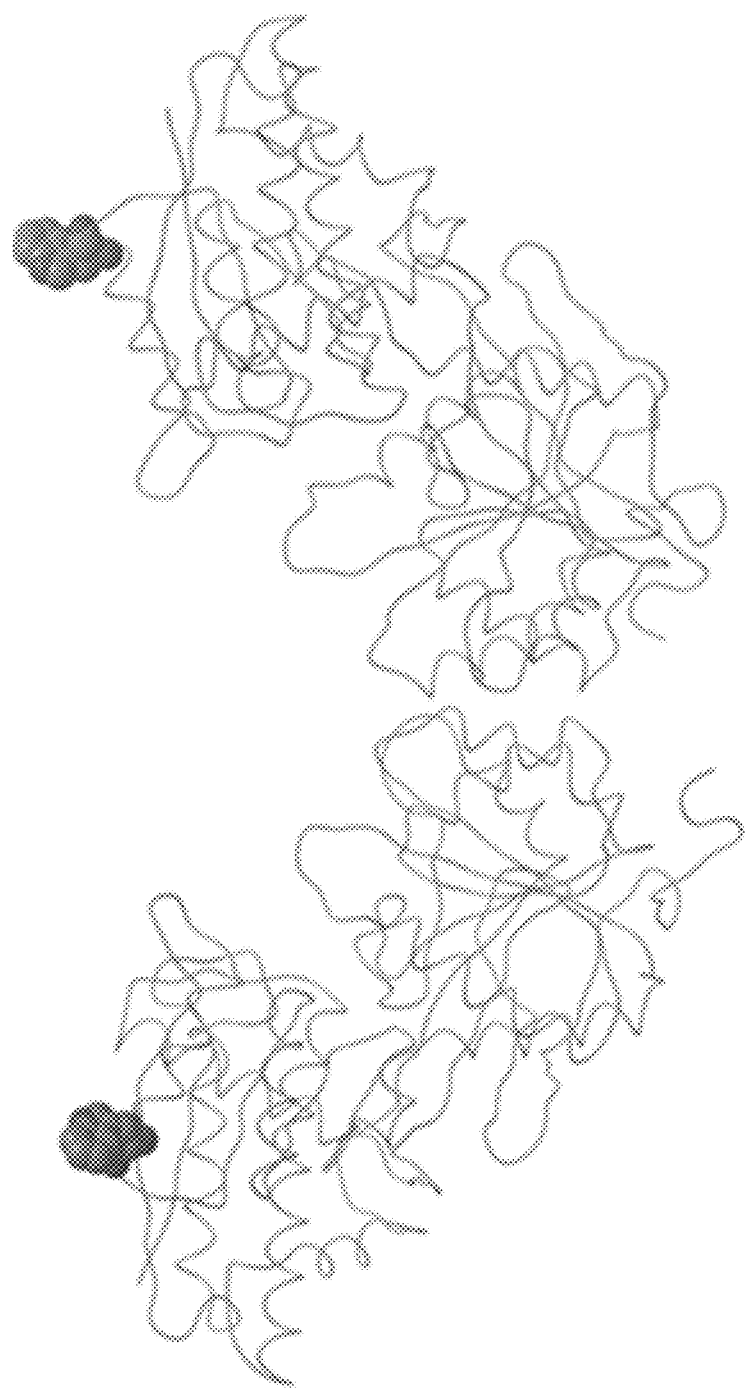
FIG. 16 is a graphical representation of the conformation of the hNPR1 extracellular domain as it would be in complex with Fab06. The Fab06 were removed from this representation to more clearly reveal the conformation of hNPR1 induced by Fab binding. W74R is shown in space filling.
Figure 17:
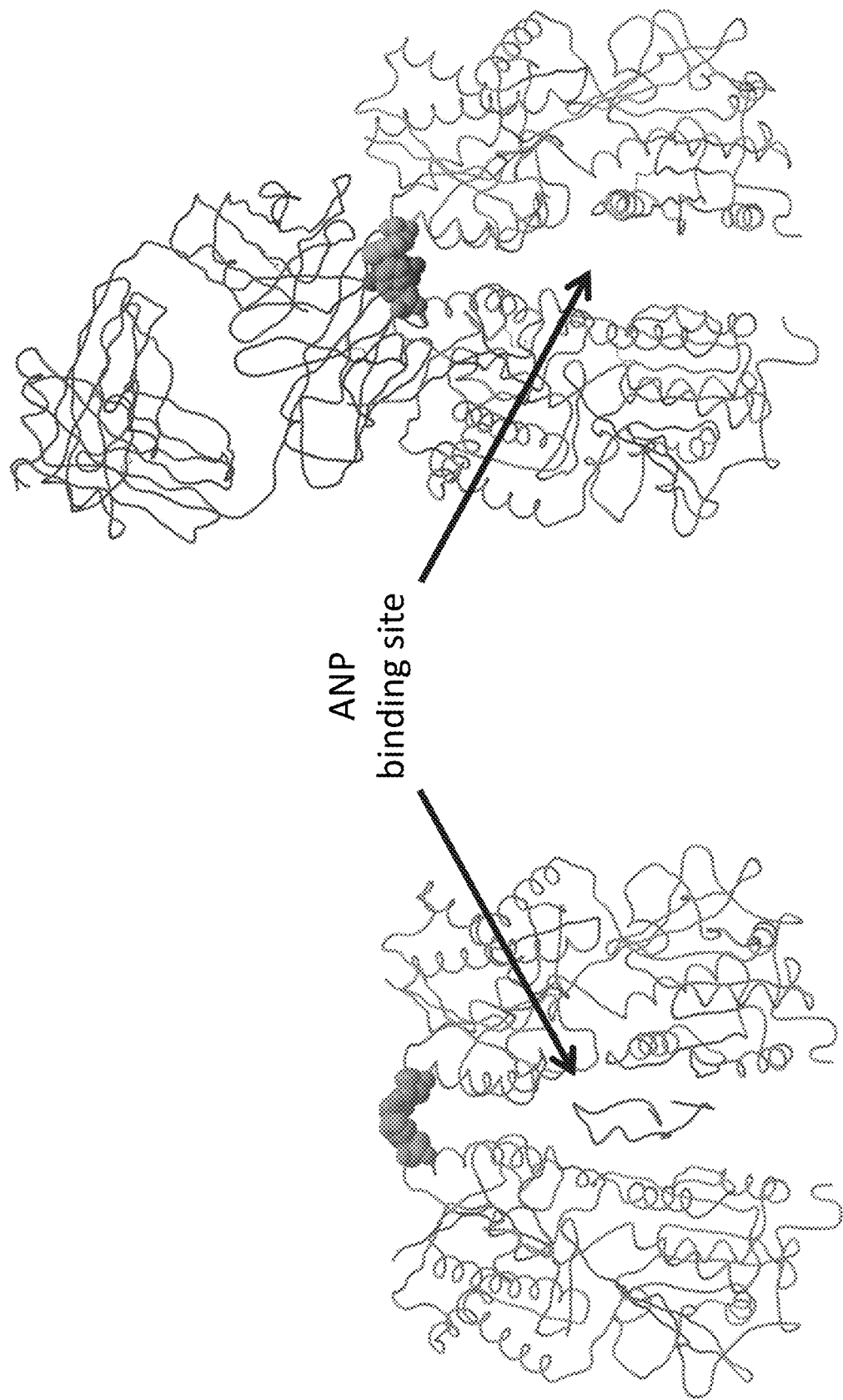
FIG. 17 is a graphical representation of the crystal structure of hNPR1 extracellular domain in complex with ANP (left) and the crystal structure of Fab16 (the XX16 antibody in Fab format) in complex with hNPR1 extracellular domain (right) with W74 shown in space filling.
Figure 18:
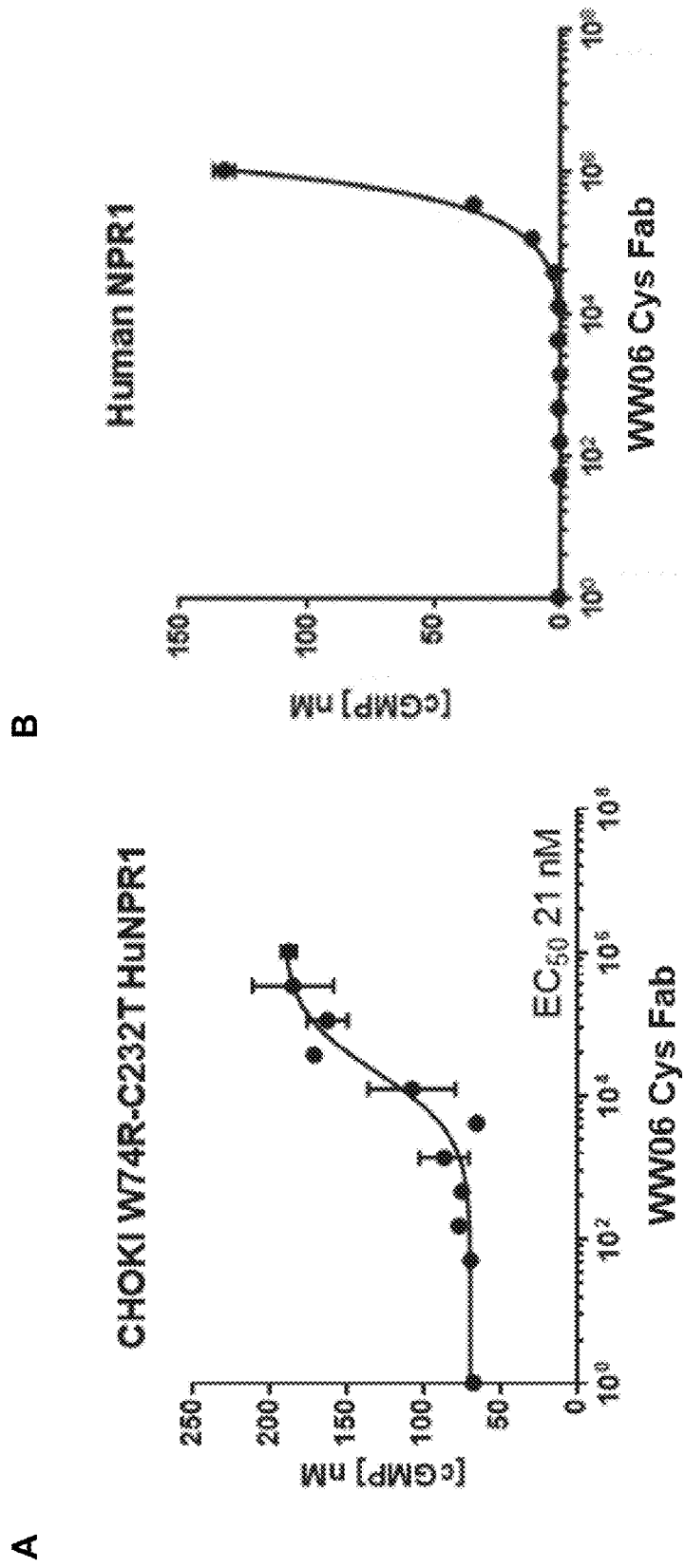
FIG. 18 is a set of graphs depicting the results of functional activity analyses of candidate WW06 in a cellular cGMP production assay using when tested on CHO-K1 cells expressing hNPR1 W74R/C232T (constitutively active mutant; panel A) compared to WT hNPR1 (panel B).

The crystal structure of Fab06 in complex with hNPR1 is shown in FIG. 15. FIG. 16 shows the conformation of the hNPR1 ECD as it would be in complex with Fab06; the Fab06 were removed from the image to more clearly reveal the conformation of hNPR1 induced by Fab binding. The structures shown in FIGS. 15 and 16 explain the discrepancy between Fab and IgG functional data shown in FIG. 6. The Fab C-termini are 180 degrees apart precluding a single IgG spanning a receptor dimer. The structure of hNPR1-ECD in complex with ANP (which was also determined as a part of this work) is shown for comparison in FIG. 17 (left), and the crystal structure of Fab16 (the XX16 antibody in Fab format) in complex with hNPR1 extracellular domain (right). The WW06 Fab was significantly more potent (cGMP production) when tested on CHO cells expressing hNPR1 W74R/C232T (constitutively active mutant) compared to WT hNPR1 (FIG. 18, panels A and B) suggesting that the mutation destabilizes the head-to-head conformation of NPR1 and facilitates antibody binding/receptor activation.

Example 11: Ylanthia® Phage Library Panning and Screening

Six panning strategies were performed, which reflected the most successful strategies from the initial pannings (HuCAL®) or modifications of these strategies aiming for specific methods of action. The panning strategies are summarized in Table 14 in detail. Strategies #2 and #5 were identical to strategies performed in the initial HuCAL® campaign and were selected because all five initial functional candidates were derived from these panning strategies. Strategies #3 and #4 were variations from initial strategies with focus on hNPR1 alternating with hNPR1 expressing cells. In addition, a constitutively active mutant of NPR1 (W74R) was used as an antigen in strategies #1 and #6. Bacterial lysates (BEL) of the outputs of the 3rd panning rounds in phage display vector pYPDis were directly used for primary and secondary screenings.

compared to IgG format, the functional screening was performed in FabCys format rather than IgG format.

The sub-cloning of 138 HCDR3 unique clones into the FabCys format was performed via YClone®. 111 out of 138 clones were successfully converted into FabCys format and

TABLE 14

Overview of panning strategies-Ylanthia ®

| Strategy | 1st round | 2nd round | 3rd round | Comments |
|---|---|---|---|---|
| 1 | W74R hNPR1 capture | W74R hNPR1 capture | W74R hNPR1 capture | Fc capture panning with active W74R mutant only |
| 2 | hNPR1-ANP-complex solution | rNPR1-ANP-complex capture | hNPR1-ANP-complex solution | Solution/Fc capture panning aiming for enrichment of NPR1-ANP-complex |
| 3 | CHO-KI NPR-ANP-complex cell | hNPR1-ANP-complex solution | CHO-K1 NPR-ANP-complex cell | Cell/solution panning aiming for enrichment of NPR1-ANP-complex stabilizers |
| 4 | hNPR1 solution | CHO-K1 NPR1 cell + ANP elution | hNPR1 solution + ANP elution | Solution/cell aiming for enrichment of ANP competitors |
| 5 | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | pre-adsorption on NPR1-ANP complex, save the unbound phage still in solution, bind to hNPR1 in solution without ANP and capture NPR1/phage complexes | Solution panning aiming for enrichment of ANP competitors |
| 6 | CHO-K1 NPR1 cell | W74R hNPR1 capture | CHO-K1 NPR1 cell | Cell/Fc capture panning with human antigen and active W74R mutant |

The outputs of the 3rd panning rounds were analyzed for binding to relevant antigens and cell lines. 368 clones per subcode (in total 4416 clones) were screened in ELISA-based primary screening on human NPR1 in absence and presence of ANP, constitutively active hNPR1 mutant (W74R) and counter-target human hNPR3. The primary screening yielded 810 hits, which were analyzed with respect to binding of relevant cell lines (human NPR1 expressing CHO-K1 cells in absence and presence of ANP, parental CHO-K1 cells) and rat NPR1 in secondary screening. In total, 380 clones from primary and secondary screening were selected for sequencing with priority for exclusive binding to NPR1-ANP-complex, good cell binding, and rat cross-reactivity. The VL and VH sequencing resulted in 138 HCDR3 unique clones with different binding properties (Table 15). Of these clones six bound only in presence of ANP.

95 clones were selected for further analysis. 92 of the 95 FabCys passed the production quality control and were analyzed in detail. Afterwards, 30 of the 92 clones with the most promising properties were selected for IgG conversion via AmplyFly®, exploratory scale expression and S-DAS. 24 of the 30 IgGs passed the production quality control and were analyzed in detail.

All 92 FabCys and 24 IgGs were tested for binding to relevant antigens via ELISA and relevant cell lines by flow cytometry. Furthermore, the clones were tested for ANP competition and functional activity in the cellular cGMP production assay. Eight functional candidates were identified and analyzed for specificity in the Protein Panel Profiling assay (3P assay) in IgG format. For comparison, one of the functional candidates from the initial campaign (WW03) was analyzed. YY02 and YY03 showed low non-specific binding; and YY01, YY04, YY05, YY06, YY07 and

TABLE 15

Binding properties of HCDR3 unique hits-Ylanthia ®

| | | | Binding to: | | |
|---|---|---|---|---|---|
| | Number of unique candidates | | hNPR1 | rNPR1 | hNPR1 expressing cells |
| 140 (of which 6 clones bound only in presence of ANP) | 53 human/rat cross-reactive | 2 human/rat cross-reactive cell binders | Yes | Yes | Yes |
| | | 51 human/rat cross-reactive (not binding to cells) | Yes | Yes | No |
| | 79 human specific | 14 human specific cell binders | Yes | No | Yes |
| | | 65 human specific (not binding to cells) | Yes | No | No |

Figure 19:
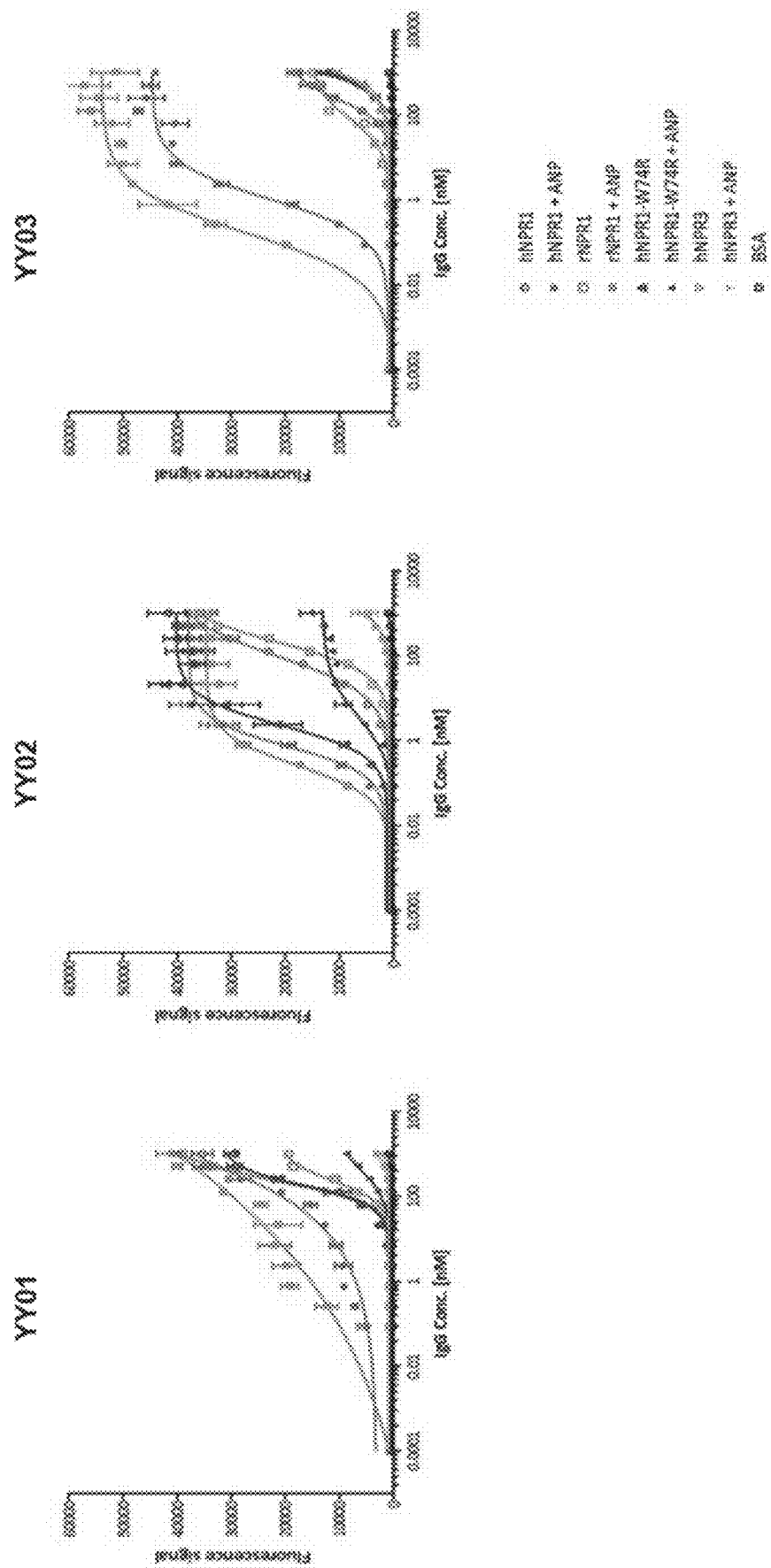
FIG. 19 is a set of graphs displaying the results of antibody candidates YY01-YY07 binding to the following antigens (ELISA analysis): human NPR1, constitutively active human NPR1 mutant (W74R), rat NPR1, and human NPR3 (counter target) in the absence of or presence of a 250 fold molar excess of ANP.
Figure 19:
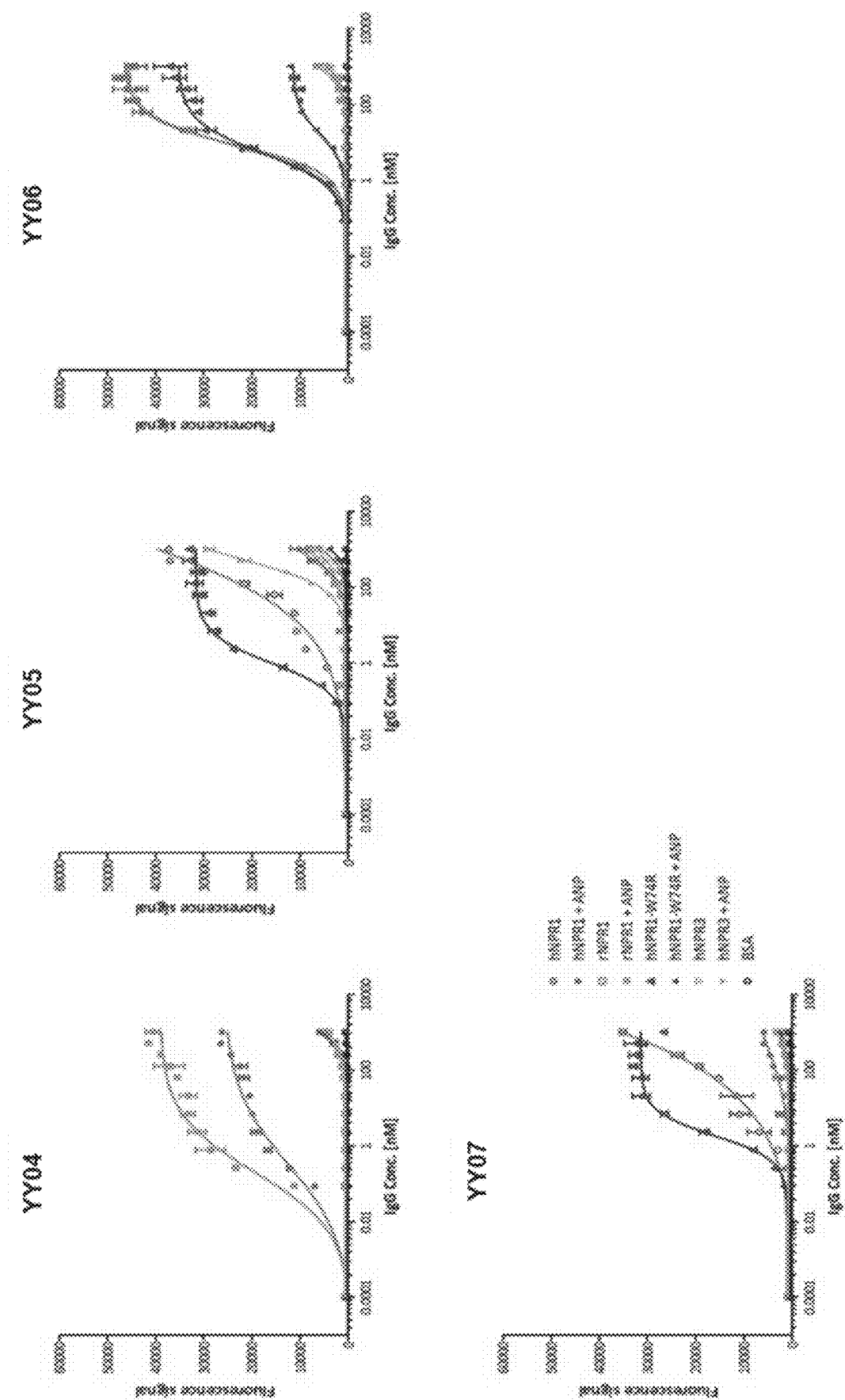
Figure 20:
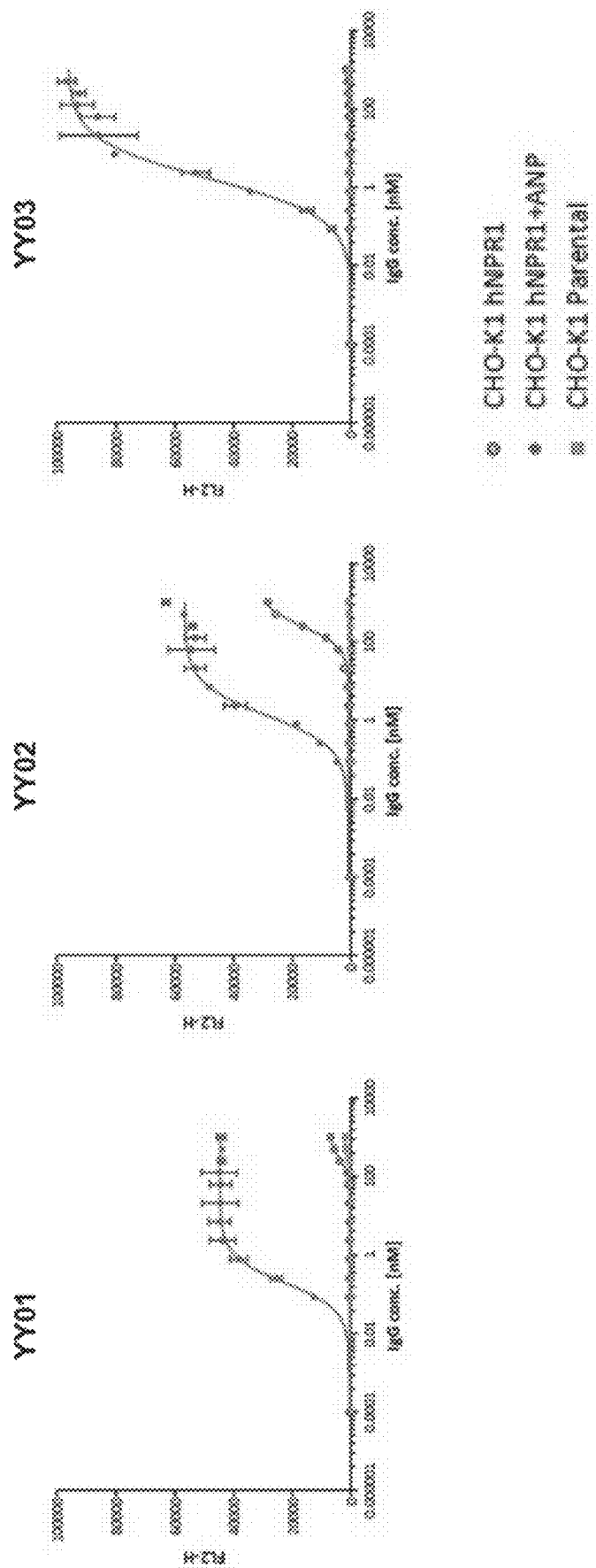
FIG. 20 is a set of graphs displaying the results of flow cytometry analysis of antibody candidates YY01-YY07 for binding to human NPR1 expressing CHO-K1 cells in the absence or presence of a saturating concentration of ANP and on parental CHO K1 cells.
Figure 20:
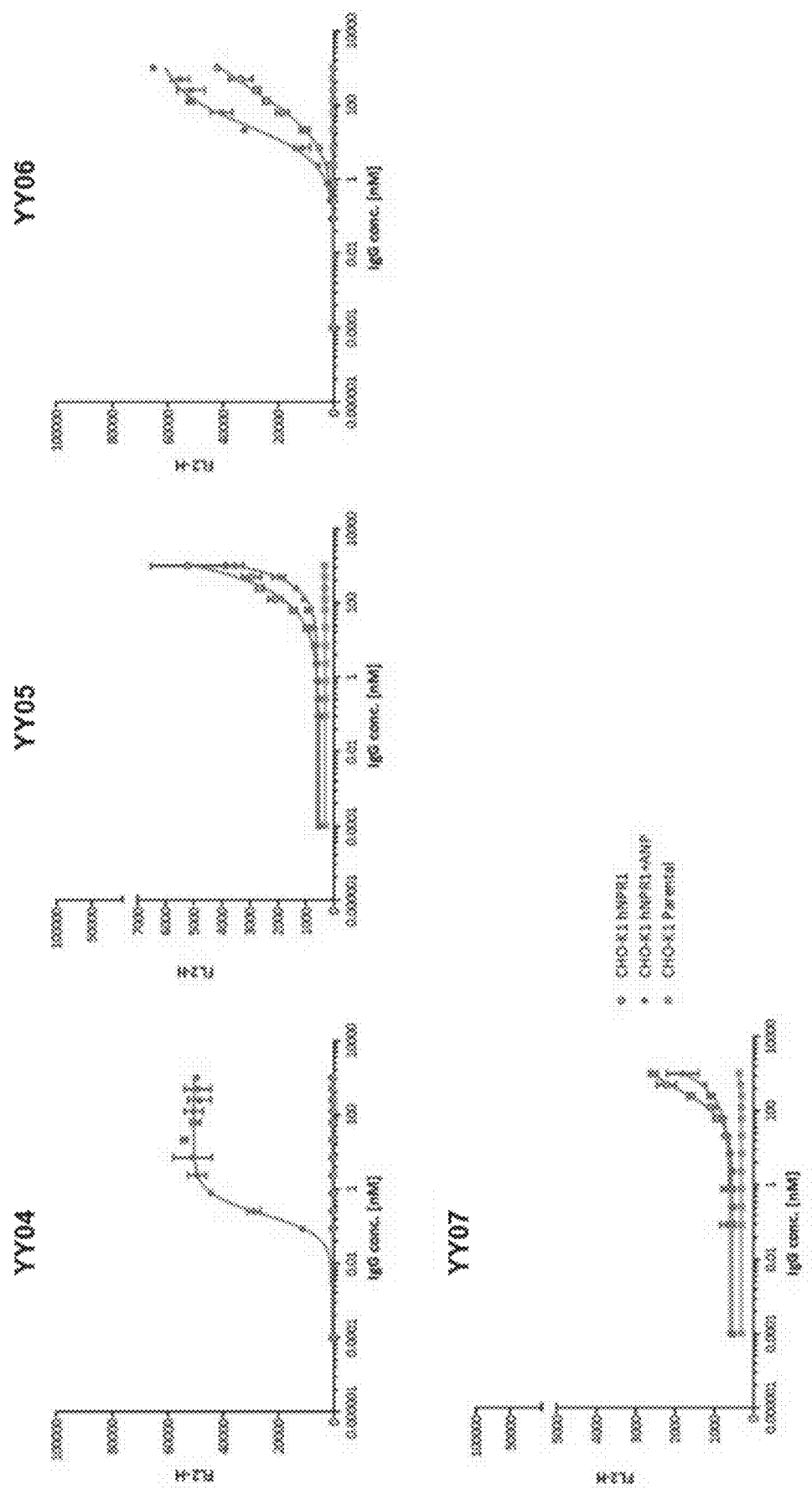
Figure 21:
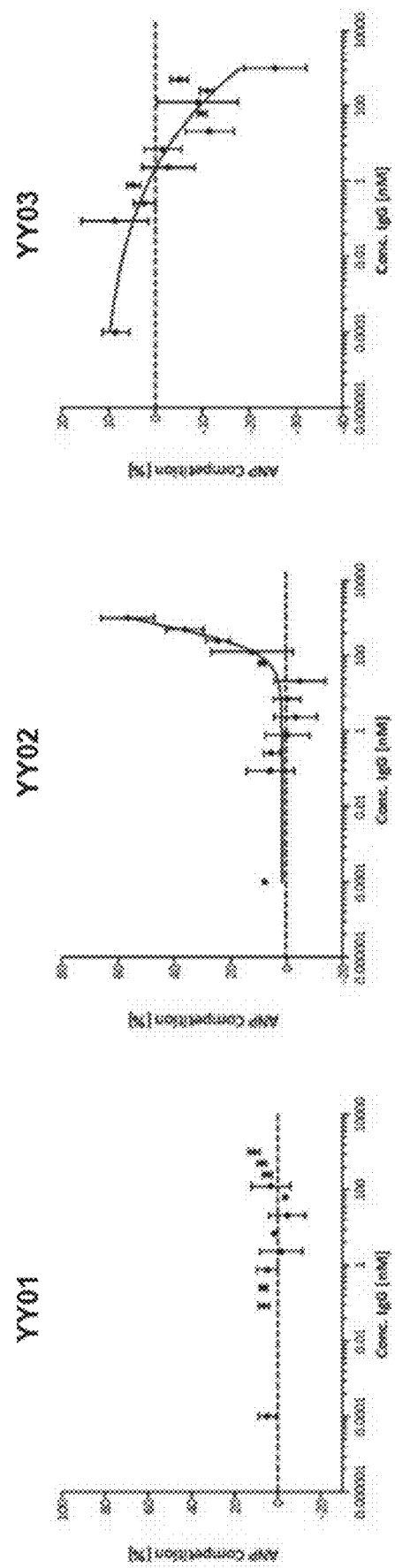
FIG. 21 is a set of graphs displaying the results of ANP competition analyses of candidates YY01-YY07 using the FRET-based assay depicted in FIG. 3.
Figure 21:
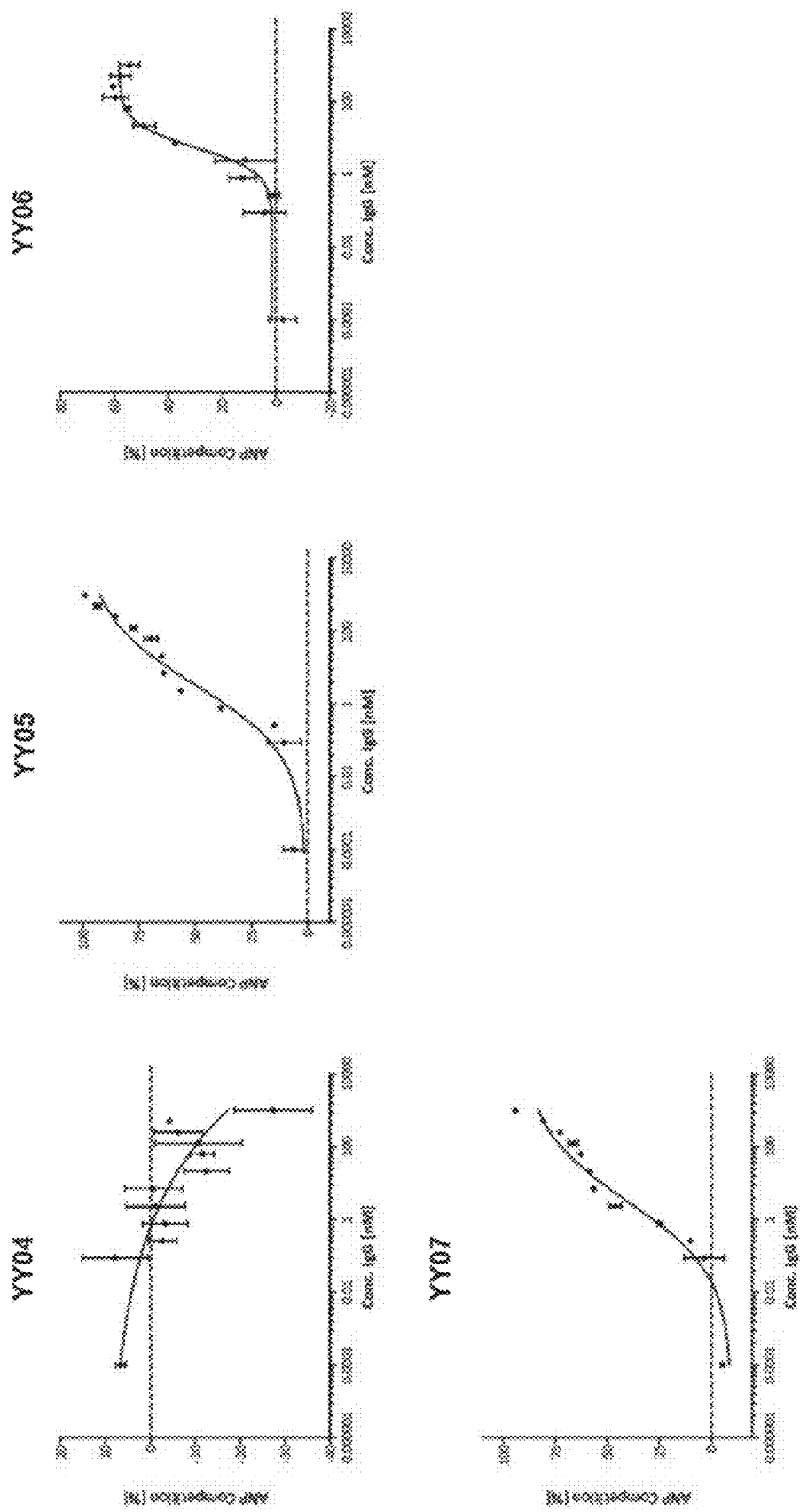

Since candidate WW06 derived from the initial HuCAL® pannings was significantly more active in FabCys format WW03 did not show non-specific binding in this assay. All 92 FabCys and 24 IgGs were tested via ELISA for binding on the following antigens: human NPR1, constitutively active human NPR1 mutant (W74R), rat NPR1, human NPR3 (counter target) in the absence or presence of ANP (100 nM) and irrelevant antigens. The clones were also tested by flow cytometry for binding on human NPR1 expressing CHO K1 cells in the absence and presence of ANP and on parental CHO K1 cells. The binding properties of the seven functional candidates in IgG format are shown in FIGS. 19 and 20. All 92 FabCys and 24 IgGs were tested for ANP competition. 22 out of 92 FabCys and 12 out of 24 IgGs showed a significant ANP competition >70% at a concentration of 1 µM FabCys/IgG. The results of the seven functional candidates in IgG format are shown in FIG. 21. YY02, YY05, YY06, and YY07 showed clear ANP competition. YY03 and YY04 showed a "negative" ANP competition in this assay indicating the stabilization of the NPR1-ANP-complex.

Figure 22:
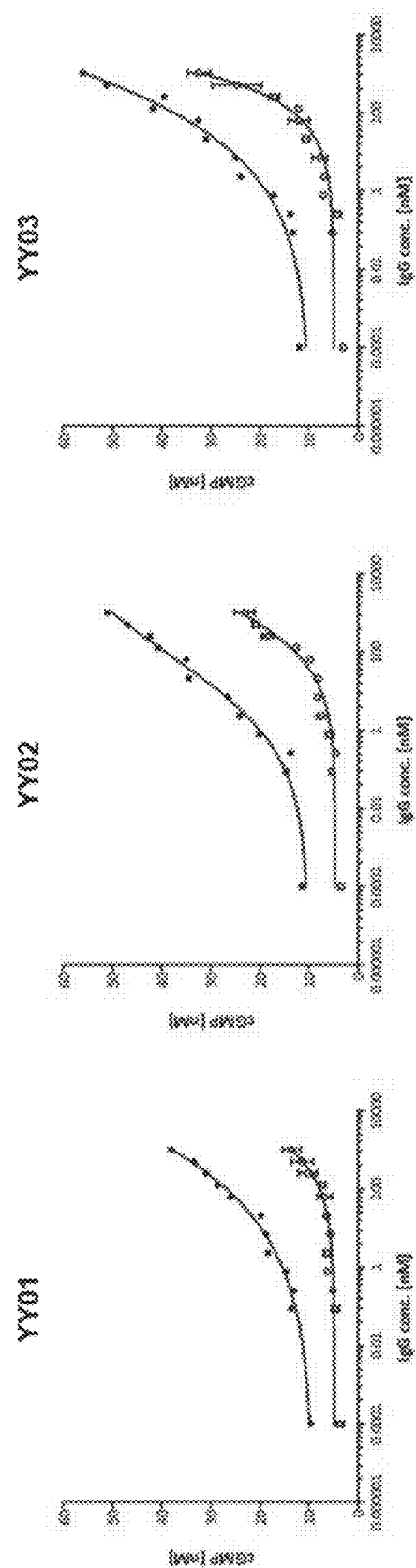
FIG. 22 is a set of graphs depicting the results of functional activity analyses of candidates YY01-YY07 in a cellular cGMP production assay using human NPR1 expressing CHO-K1 cells. Results represent the cellular production of cGMP [nM] in the absence or presence of 0.075 nM ANP.
Figure 22:
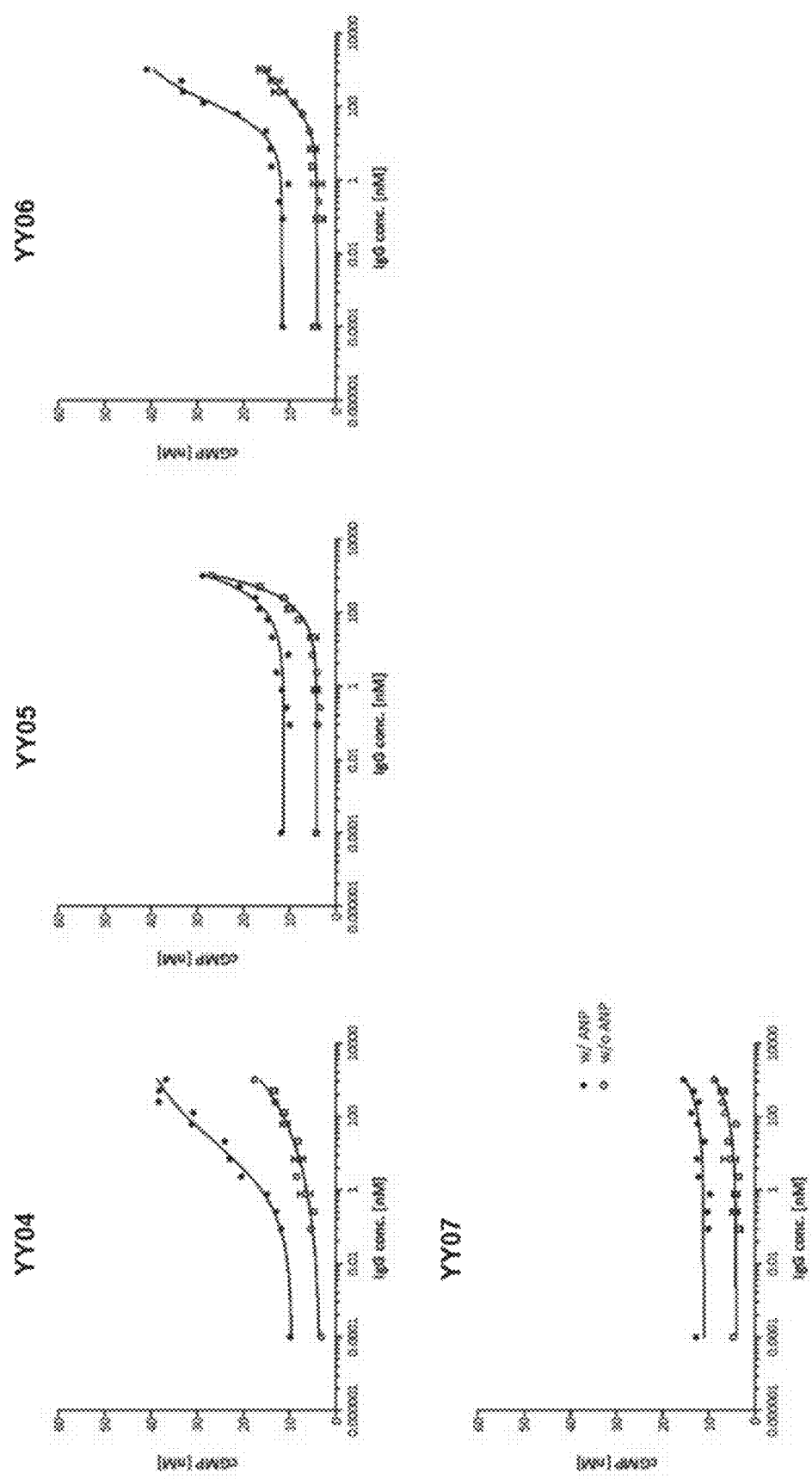
Figure 23:
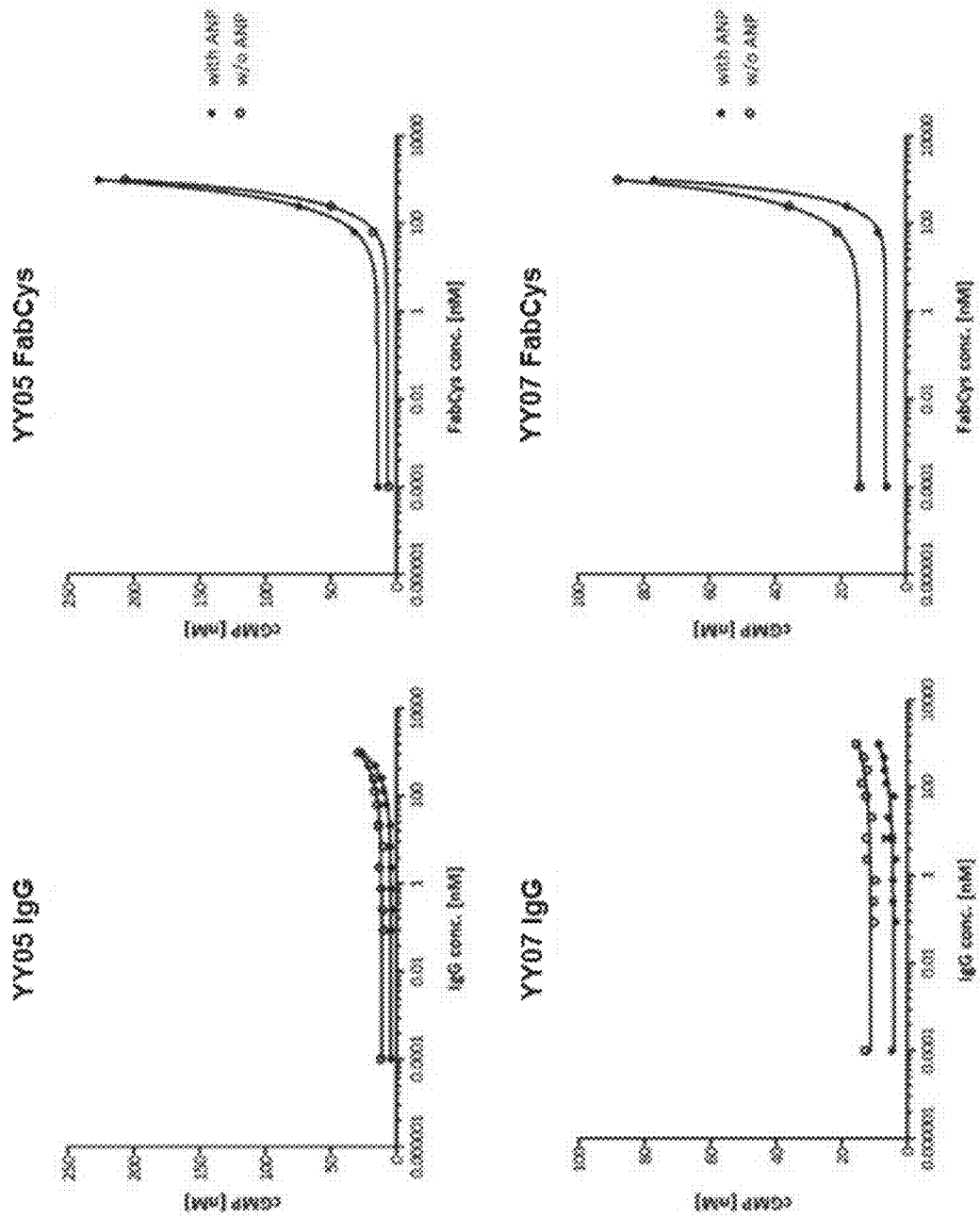
FIG. 23 is a set of graphs depicting the results of functional activity analyses of candidates YY05 and YY07 in IgG or FabCys format in a cellular cGMP production assay using human NPR1 expressing CHO-K1 cells. Results represent the cellular production of cGMP [nM] in the absence or presence of 0.075 nM ANP.

All 92 FabCys and 24 IgGs were tested for their functional activity in the cellular cGMP production assay using human NPR1 expressing CHO-K1 cells in presence and absence of ANP. 8 of the 92 FabCys and the same 8 out of 24 IgGs were functionally active and could be assigned to the different methods of action. Five out of eight clones showed much higher functional activity in presence of ANP, including YY01, YY02, YY03, and YY04. Three other clones behaved ANP independent in the functional assay, namely YY05, YY06, and YY07. All eight clones were derived from the panning strategies #2, #3 and #5, whereby #2 and #5 were exact repetitions of the initial HuCAL® panning strategies #10 and #11, which led to the identification of the five functional clones from the initial HuCAL® campaign. The results of the cGMP assay for seven functional candidates in IgG format are shown in FIG. 22. As seen before for candidate WW06 derived from the initial HuCAL® campaign, the functional activities of candidates YY05 and YY07 significantly increased in monovalent FabCys format compared to the bivalent IgG format (FIG. 23).

The seven functional candidates YY01-YY07 were analyzed with regard to their monovalent affinities for human and rat NPR1 in absence and presence of ANP in monovalent FabCys format. The results of the affinity determination and the epitope binning are summarized in Table 16.

The affinities were in the low nM to low µM range and strongly depended on the presence or absence of ANP. Four of the seven functional candidates showed significantly improved binding in presence of ANP (YY01, YY02, YY03, and YY04). YY05 and YY07 competed with ANP for binding to NPR1 and showed much higher affinities in absence of ANP. The affinities of YY06 were independent from ANP. Some candidates exhibited non-specific binding to the reference flow cell, while others had such high affinities that their $K_D$ values approach the assay limit. YY01, YY02, YY03, and YY04 share one epitope bin, which is the same as for WW03 from the initial HuCAL® campaign. YY05 and YY07 share another epitope bin, which is the same as for WW06 from the initial HuCAL® campaign. YY06 binds to a single epitope bin.

Example 12: Reformatting into IgG-Ylanthia®

Subcloning of the Ylanthia® candidates from the FabCys vector into the IgG1_LALA vector for expression in mammalian cells was performed via amplification of the Fab-encoding insert using two biotinylated primers. The amplified product was bound on streptavidin beads, digested using restriction enzymes, and washed, resulting in the release of the purified insert into the supernatant. The insert was cloned into the acceptor vector, the DNA was transformed and single clones were quality controlled via colony PCR and sequencing.

Five Ylanthia® candidates were selected for affinity maturation. YY01 and YY04 stabilize the NPR1-ANP-complex, YY06 behaves in an ANP-independent manner, and YY05 and YY07 are ANP-competitive. Binding data (ELISA, flow cytometry, ANP competition), functional data (cGMP assay), affinities, and epitope bins are shown in Table 17.

TABLE 16

Characterization in monovalent FabCys format-Ylanthia ®

Characterization in monovalent FabCys format

| Antibody | Affinity FabCys $K_D$ [nM] | | | | Epitope | cGMP assay cGMP conc [nM] at 1 µM | |
|---|---|---|---|---|---|---|---|
| | hNPR1 | hNPR1 + ANP | rNPR1 | rNPR1 + ANP | Bin on hNPR1 (−ANP-complex) | Binning FabCys Without ANP | FabCys +0.075 nM ANP |
| YY01 | — | 16 | — | 14 | B | 15 | 46 |
| YY02 | 45 | 1.1 | 280 | 4.4 | B | — | — |
| YY03 | — | 0.1 | 0.1 | 0.1 | B | — | — |
| YY04 | 4.9 | 1.1 | — | 1 | B | 18 | 67 |
| YY05 | 0.9 | 350 | 700 | 16000 | A | 207 | 227 |
| YY06 | 0.5 | 1 | 1600 | 1400 | C | 20 | 75 |
| YY07 | 1.8 | 590 | — | — | A | 77 | 88 |

TABLE 17

Summary of Affinity, Epitope, and cGMP data for YY01, YY04, YY08, YY06, and YY07 in IgG Format Characterization in bivalent IgG format

| | Elisa +/− 100 nM ANP IgG binding at 1 µM IgG | | | | | | | | Flow Cytometry [S/BG] at 1 µM IgG | | ANP | cGMP assay cGMP | |
|---|---|---|---|---|---|---|---|---|---|---|---|---|---|
| | hNPR1 | hNPR1 + 100 nM ANP | W74R | W74R + 100 nM ANP | rNPR1 | rNPR1 + 100 nM ANP | hNPR3 | hNPR3 + 100 nM ANP | hNPR1 CHO KI | hNPR1 CHOK1 + 100 nM ANP | competition assay ANP competition by IgG | conc [nM] at 1µM IgG Without ANP | +0.075 nM ANP |
| Antibody | | | | | | | | | | | | | |
| YY01 | 54 | 76 | 33 | 53 | 26 | 50 | 18 | 6 | 35 | 21 | yes | 5 | 14 |
| YY04 | 31 | 60 | 11 | 13 | 8 | 54 | 69 | 18 | 2 | 33 | no | 10 | 15 |
| YY05 | 81 | 32 | 69 | 23 | 11 | 16 | 7 | 4 | 15 | 5 | yes | 13 | 15 |
| YY06 | 91 | 102 | 83 | 86 | 3 | 4 | 6 | 6 | 26 | 18 | yes | 12 | 15 |
| YY07 | 68 | 24 | 53 | 20 | 3 | 3 | 6 | 5 | 00 | 44 | yes | 4 | 6 |

Example 13: Generation of Ylanthia® Maturation Libraries

To increase affinity and biological activity and to reduce non-specificity of selected antibody candidates, LCDR3 and HCDR1/HCDR2 regions were optimized in parallel using diversified Ylanthia® maturation modules (YMM) previously generated with Slonomics® technology (van den Brulle et al. (2008): A novel solid phase technology for high-throughput gene synthesis; Biotechniques 45 (3), pp. 340-343, the contents of which are herein incorporated by reference for this purpose).

Cloning of the maturation libraries was performed in vectors encoding the parental Fab fragments. The generation of the maturation libraries was performed for five parental antibodies (YY01, YY04, YY05, YY06, and YY07). For the library generation, all maturation candidates were treated individually. The maturation libraries were successfully cloned and had library sizes between $6.2 \times 10^8$ and $4.5 \times 10^9$ cfu.

In order to monitor the cloning efficiency, the parental HCDR1/2 and LCDR3 were replaced by MBP-stuffers prior to insertion of the diversified YMM. Digested vector fragments were ligated with a 2-fold molar excess of the insert fragments carrying the diversified HCDR1/2 or LCDR3s.

Ligation mixtures were electroporated in E. coli cells yielding in $>10^8$ independent colonies. Amplification of the library was performed as described in the literature (Tiller et al. (2013): A fully synthetic human Fab antibody library based on fixed VH/VL framework pairings with favorable biophysical properties; mAbs 5 (3), pp. 445-470, the contents of which are herein incorporated by reference for this purpose). For quality control, approx. 10-20 single clones per library were randomly picked and sequenced.

Example 14: Pannings and Screenings—Ylanthia®

The nine maturation libraries were used for four different maturation panning strategies, which aimed for the enrichment of progenies with improved affinities compared to the parental clones. Furthermore, rat material was included where appropriate and the pannings were performed with high stringencies concerning antigen concentration and washing conditions. During the panning process, the libraries of YY01 and YY04 (only LCDR3) as well as YY05 and YY07 were pooled, while the libraries of YY06 were kept separately. The panning strategies are summarized in Table 18 in detail. The bacterial lysates (BEL) of the outputs after the third panning rounds were directly used for an ELISA-based pre-screening and for SET screening.

TABLE 18

Overview of Ylanthia ® Maturation Panning Strategies

| Strategy | Parental antibodies | 1st round | 2nd round | 3rd round | comments |
|---|---|---|---|---|---|
| 1 | YY01/YY04 | hNPR1-ANP-complex solution | rNPR1-ANP-complex solution | hNPR1-ANP-complex solution | Solution panning aiming for enrichment of NPR1-ANP-complex stabilizers |
| 2 | YY06 | hNPR1-ANP-complex solution | hNPR1-ANP-complex solution | hNPR1-ANP-complex solution | Solution panning aiming for enrichment of NPR1-ANP-complex stabilizers |
| 3 | YY06 YY05/YY07 | Preadsorption on NPR1-ANP-complex hNPR1 solution | Preadsorption on NPR1-ANP-complex hNPR1 solution | Preadsorption on NPR1-ANP-complex hNPR1 solution | Solution panning aiming for enrichment of ANP competitors |
| 4 | YY05/YY07 | Preadsorption on NPR1-ANP-complex hNPR1 solution | Preadsorption on NPR1-ANP-complex hNPR1 solution | Preadsorption on NPR1-ANP-complex rNPR1 solution | Solution panning aiming for enrichment of ANP competitors |

The outputs of the third panning rounds were used for an ELISA-based pre-screening to ensure that only clones binding to NPR1 and/or NPR1-ANP-complex were selected for further Solution Equilibrium Titration (SET) screening. 880 clones in total were analyzed in SET screening for improved affinity for hNPR1 and/or hNPR1-ANP-complex compared to the parental clones.

Figure 24:
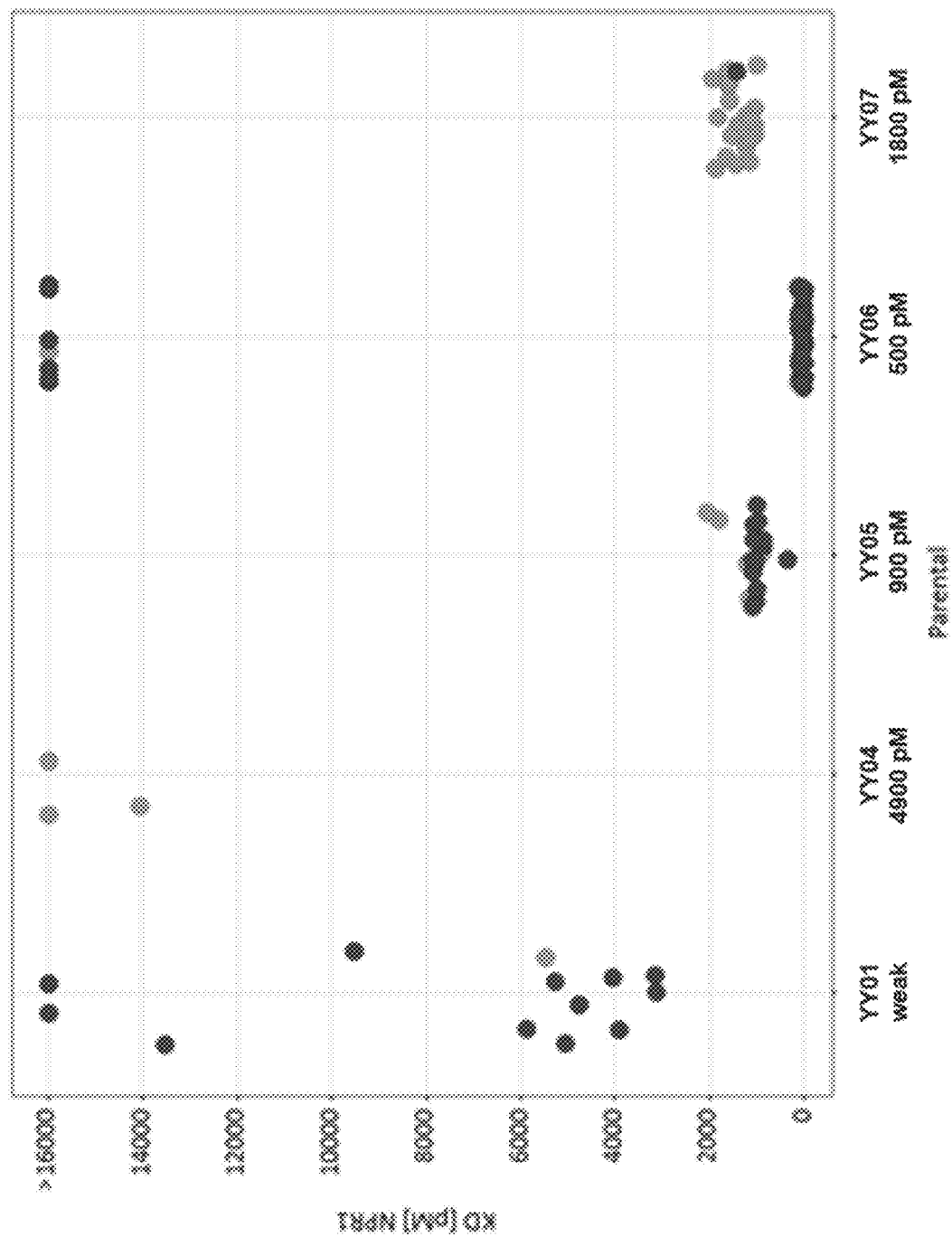
FIG. 24 demonstrates the results of SET screening (hNPR1 affinity) of 112 HCDR1/2 or LCDR3 unique improved Ylanthia® derivatives based on the parental antibody.
Figure 25:
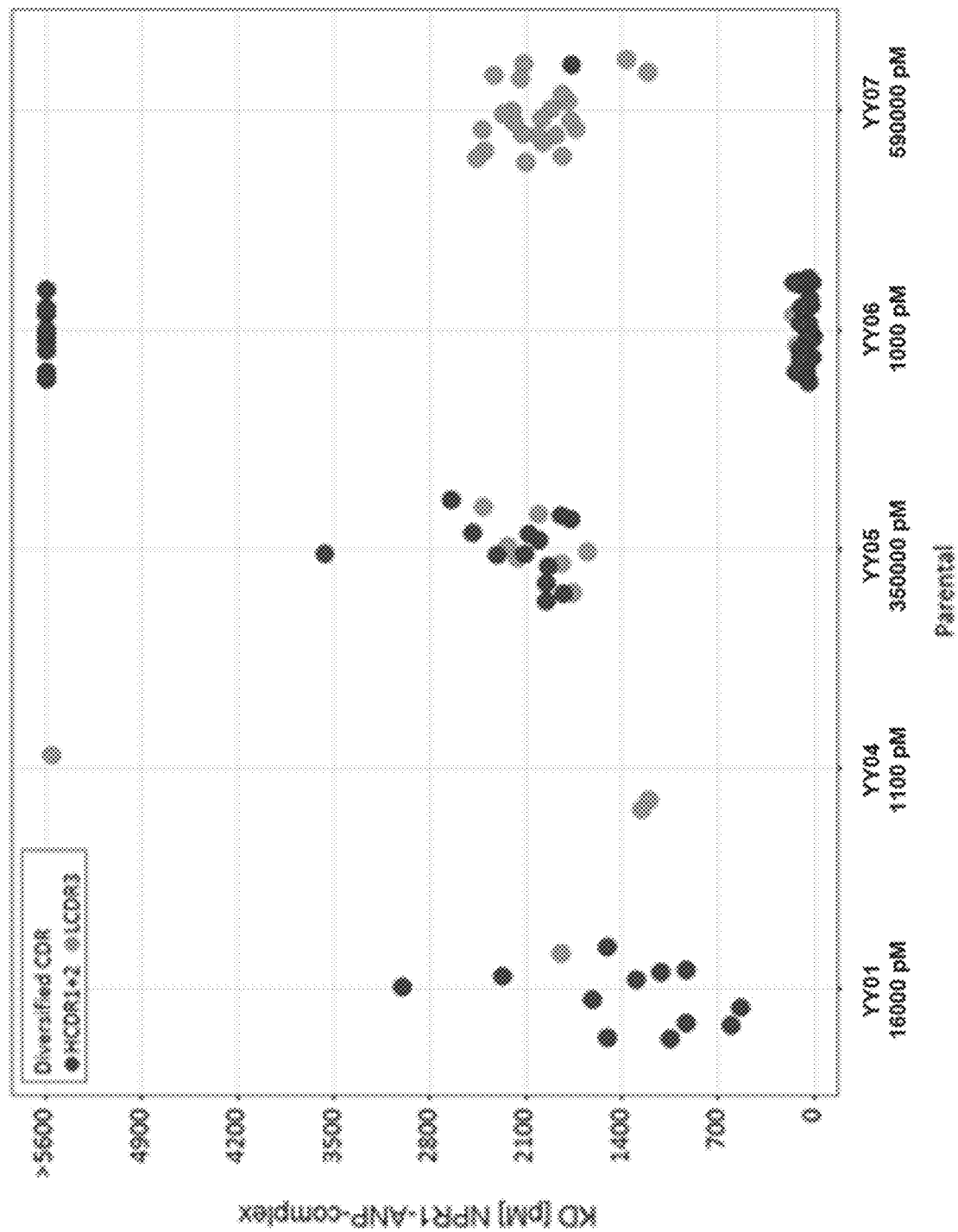
FIG. 25 demonstrates the results of SET screening (hNPR1-ANP complex affinity) of 112 HCDR1/2 or LCDR3 unique improved Ylanthia® derivatives based on the parental antibody.

During SET screening, 263 HCDR1//2 or LCDR3 unique improved derivatives were identified, which resulted in 112 unique clones after sequencing and conversion to IgG$_1$_LALA format. Compared to their parental clones, the affinities of the YY05 and YY07 derivatives were not improved for NPR1 but were improved up to 200-fold for NPR1-ANP-complex. The derivatives of YY01 had similar affinities to the parental clone YY04, whose derivatives had only slightly improved affinities. The affinities of the YY06 derivatives were improved 4- to 40-fold for NPR1 and 7- to 70-fold for NPR1-ANP-complex. See FIG. 24 (which shows affinities for hNPR1) and FIG. 25 (which shows affinities for hNPR1-ANP complex). Affinities ($K_D$ [pM]) are indicated at the x-axis below the parental clone name for both figures.

Example 15: Characterization of Matured Candidates—Ylanthia®

95 of 112 improved candidates were selected for advanced production. 77 of the 95 clones passed the production quality control and were characterized in regard to binding to relevant antigens, binding to relevant cell lines, and functional activity in the cGMP production assay in comparison to their parental clones. After detailed IgG characterization, 17 candidates (detailed in Table 19) were selected, produced in exploratory scale IgG production, and further analyzed via 3P assay. Furthermore, they were converted to FabCys format for their affinity determination on human and rat NPR1 in absence and presence of ANP via SET $K_D$ measurement.

TABLE 19

Overview of Matured Ylanthia ® Candidates

| Matured antibody | Parental antibody | Matured CDR |
|---|---|---|
| ZZ01 | YY07 | LCDR3 |
| ZZ02 | YY05 | LCDR3 |
| ZZ03 | YY07 | LCDR3 |
| ZZ04 | YY07 | LCDR3 |
| ZZ05 | YY07 | LCDR3 |
| ZZ06 | YY07 | LCDR3 |
| ZZ07 | YY07 | LCDR3 |
| ZZ08 | YY07 | LCDR3 |
| ZZ09 | YY05 | HCDR1 + 2 |
| ZZ10 | YY05 | HCDR1 + 2 |
| ZZ11 | YY04 | LCDR3 |
| ZZ12 | YY01 | HCDR1 + 2 |
| ZZ13 | YY01 | HCDR1 + 2 |
| ZZ14 | YY06 | HCDR1 + 2 |
| ZZ15 | YY06 | HCDR1 + 2 |
| ZZ16 | YY06 | HCDR1 + 2 |
| ZZ17 | YY06 | HCDR1 + 2 |

Affinities for 16 of the matured Ylanthia® candidates (in monovalent FabCys format) were determined via SET measurement and/or via Octet. The results are summarized in Tables 20 and 21 below in comparison to the affinities of the parental clones.

TABLE 20

Summary of Affinity data (SET) for YY01, YY06, ZZ12, ZZ13, ZZ15, ZZ16, and ZZ17 in FabCys Format

| | Affinity (SET measurement) FabCys $K_D$ [nM] | | | | |
|---|---|---|---|---|---|
| Antibody | hNPR1 | hNPR1 + ANP | rNPR1 | rNPR1 + ANP | comment |
| YY01 | — | 16.00 | — | 14.00 | $K_D$ determination via Octet |
| ZZ12 | 6.70 | 0.32 | 2.10 | 1.40 | |
| ZZ13 | 9.90 | 1.30 | 2.30 | 1.40 | |
| YY04 | 4.90 | 1.10 | — | 1.00 | $K_D$ determination via Octet |
| ZZ11 | 46.00 | 2.40 | 21.00 | 18.00 | |
| YY05 | 0.90 | 350.00 | 700.00 | 16000.00 | $K_D$ determination via Octet; assay limit reached |
| ZZ02 | 0.37 | 0.58 | — | — | |
| ZZ09 | 0.49 | 0.57 | — | — | |
| ZZ10 | 0.52 | 1.40 | — | — | |
| YY06 | 0.50 | 1.00 | 1600.00 | 1400.00 | $K_D$ determination via Octet |
| ZZ15 | 0.053 | 0.074 | — | — | |
| ZZ16 | 0.040 | 0.034 | 62.00 | 51.00 | |
| ZZ17 | 0.046 | 0.050 | 52.00 | 36.00 | |
| YY07 | 1.80 | 590.0 | — | — | |
| ZZ01 | 0.65 | 0.85 | — | — | |
| ZZ03 | 0.75 | 1.30 | — | — | |
| ZZ04 | 0.30 | 0.38 | — | — | |
| ZZ05 | 0.74 | 1.20 | — | — | |
| ZZ06 | 0.35 | 0.50 | — | — | |
| ZZ07 | 0.62 | 1.50 | — | — | |
| ZZ08 | 0.57 | 1.30 | — | — | |

TABLE 21

Summary of Affinity data (Octet) for YY01, YY06, ZZ12, ZZ13, ZZ15, ZZ16, and ZZ17 in FabCys Format

| | Affinity (Octet measurement) FabCys $K_D$ [nM] | | | | |
|---|---|---|---|---|---|
| Antibody | hNPR1 | hNPR1 + ANP | rNPR1 | rNPR1 + ANP | comment |
| YY01 | — | 26.00 | — | 8.80 | Heterogenous binding |
| ZZ12 | — | 0.04 | — | 0.10 | |
| ZZ13 | — | 0.14 | 66.00 | 0.10 | |
| YY06 | 0.62 | 0.80 | 100.00 | 38.00 | |
| ZZ15 | 0.26 | 0.19 | — | — | |
| ZZ16 | 0.14 | 0.11 | — | — | |
| ZZ17 | 0.16 | 0.09 | — | — | |

Example 16: Epitope Determination for ANP Competitive and ANP Non-Competitive Agonist Antibodies The crystal structure of the hNPR1 and XX16 Fab complex was used to identify the XX16 Fab epitope on hNPR1. The interaction surface on hNPR1 by XX16 Fab was formed by several continuous and discontinuous (i.e., noncontiguous) sequences as detailed in Table 22. These residues form the three-dimensional conformational epitope recognized by XX16 Fab.

Results of the epitope mapping of XX16 Fab (ANP non-competitive) are shown in Table 22. hNPR1 residues are numbered based upon SEQ ID NO: 1 (P16066). Fab residues are numbered based upon their linear amino acid sequence. hNPR1 residues shown have at least one atom within 5 Å of an atom in the XX16 Fab, to account for potential water mediated interactions.

TABLE 22

Epitope Mapping of XX16 Fab

| Antibody XX16 Fab | | | Antigen (NPR1) | | |
|---|---|---|---|---|---|
| Amino acid | Number | Chain | Amino acid | Number | Chain |
| SER | 31 | H | TRP | 106 | A |
| TYR | 32 | H | TRP | 106 | A |
| | | | TRP | 106 | B |
| TRP | 33 | H | ASN | 109 | A |
| GLU | 52 | H | HIS | 108 | A |
| | | | ASN | 109 | A |
| SER | 53 | H | GLU | 107 | A |
| | | | ASN | 109 | A |
| LYS | 54 | H | GLU | 107 | A |
| ASN | 56 | H | GLY | 33 | A |
| | | | ASN | 34 | A |
| | | | THR | 36 | A |
| | | | TRP | 76 | A |
| TYR | 57 | H | ASN | 34 | A |
| | | | TRP | 76 | A |
| | | | ASN | 109 | A |
| | | | PRO | 110 | A |
| | | | ALA | 111 | A |
| | | | VAL | 374 | A |
| | | | THR | 375 | A |
| PHE | 59 | H | THR | 375 | A |
| ARG | 100 | H | TRP | 106 | A |
| | | | ASP | 103 | B |
| | | | GLU | 107 | B |
| TYR | 101 | H | VAL | 102 | A |
| | | | TRP | 106 | A |
| | | | VAL | 102 | B |
| | | | ASP | 103 | B |
| | | | TRP | 106 | B |
| | | | GLU | 107 | B |
| SER | 102 | H | LYS | 105 | A |
| | | | TRP | 106 | A |
| MET | 103 | H | VAL | 102 | A |
| | | | LYS | 105 | A |
| | | | TRP | 106 | A |
| | | | TRP | 132 | A |
| | | | LEU | 99 | B |
| | | | VAL | 102 | B |
| | | | ASP | 103 | B |
| ILE | 104 | H | LYS | 105 | A |
| | | | HIS | 131 | A |
| | | | TRP | 132 | A |
| | | | LEU | 99 | B |
| | | | ALA | 100 | B |
| | | | ASP | 103 | B |
| TYR | 105 | H | LYS | 105 | A |
| | | | TRP | 132 | A |
| SER | 106 | H | LYS | 105 | A |
| | | | HIS | 131 | A |
| | | | TRP | 132 | A |
| | | | ARG | 133 | A |
| TYR | 107 | H | LYS | 105 | A |
| | | | ASN | 109 | A |
| | | | PRO | 110 | A |
| | | | ALA | 111 | A |
| | | | VAL | 134 | A |
| | | | THR | 375 | A |
| ASP | 113 | H | GLU | 107 | B |
| ARG | 18 | L | GLN | 336 | B |
| SER | 30 | L | GLU | 86 | B |
| | | | ASN | 87 | B |
| | | | ALA | 88 | B |
| SER | 31 | L | SER | 84 | B |
| | | | GLU | 86 | B |
| TYR | 32 | L | HIS | 131 | A |
| TYR | 49 | L | ASP | 103 | B |
| | | | LEU | 104 | B |
| | | | GLU | 107 | B |
| | | | HIS | 108 | B |
| SER | 52 | L | LEU | 43 | B |
| | | | LEU | 82 | B |
| THR | 53 | L | VAL | 81 | B |
| | | | LEU | 82 | B |
| | | | GLY | 83 | B |
| | | | LEU | 104 | B |
| | | | HIS | 108 | B |
| LEU | 54 | L | ARG | 79 | B |
| | | | VAL | 81 | B |
| | | | HIS | 108 | B |
| GLN | 55 | L | GLU | 107 | B |
| | | | HIS | 108 | B |
| SER | 56 | L | GLU | 107 | B |
| | | | HIS | 108 | B |
| VAL | 58 | L | ARG | 79 | B |
| PRO | 59 | L | ARG | 79 | B |
| SER | 60 | L | ARG | 79 | B |
| SER | 65 | L | THR | 44 | B |

TABLE 22-continued

Epitope Mapping of XX16 Fab

| Antibody XX16 Fab | | | Antigen (NPR1) | | |
|---|---|---|---|---|---|
| Amino acid | Number | Chain | Amino acid | Number | Chain |
| GLY | 66 | L | THR | 44 | B |
| SER | 67 | L | THR | 44 | B |
|  |  |  | GLU | 86 | B |
|  |  |  | ASN | 87 | B |
| SER | 76 | L | GLN | 336 | B |
| TRP | 92 | L | HIS | 131 | A |
|  |  |  | ARG | 133 | A |
|  |  |  | ALA | 88 | B |
| ARG | 93 | L | ARG | 133 | A |
|  |  |  | GLU | 378 | A |
| LYS | 94 | L | ASP | 376 | A |

Critical epitope residues for the binding of XX16 Fab and NPR1, which were determined using structural analysis and affinity maturation data, include (first tier) 99-103, 105-111, 131-133, 378; and (second tier): 33-34, 76, 82, 104, 374-375. Amino acids 99-103 of NPR1 (SEQ ID NO: 1) comprise both a E106 backbone that enabled the affinity maturation by D54K in HCDR2, and W106 from both NPR1 protomers that clamp Y101 of HCDR3. Certain critical epitope residues are shown in Table 23 below. Regions of NPR1 encompassing these critical residues include N34, W76, L82, V102-A111, H131-V134, and V374-E378.

TABLE 23

Critical Epitope Residues of XX16 Fab (ANP non-competitive)

| Critical epitope residue (amino acid) | Critical epitope residue (number) | Explanation |
|---|---|---|
| N | 34 | H-bond with N56 (backbone) of VH |
| L | 82 | H-bond (chain B) with T53 (side chain) of VL |
| V | 102 | Packing against M103 (side chain) of VH |
| D | 103 | Salt bridge (chain B) with R100 (side chain) of VH |
| K | 105 | H-bond (backbone) with M103 (backbone) and Y105 (backbone) of VH |
| W | 106 | Packing between Y32 (side chain) and Y101 (side chain) of VH |
| E | 107 | Salt bridge (chain B) with R100 (side chain) of VH |
| E | 107 | H-bond (backbone) with K54 (side chain) of VH |
| N | 109 | H-bond with E52 (side chain), S53 (side chain) and W33 (side chain) of VH |
| W | 132 | Packing against M103 (side chain) of VH |
| R | 133 | H-bond with S106 (side chain) of VH |
| T | 375 | Packing against Y57 (side chain) of VH |
| E | 378 | Salt bridge with R93 (side chain) of VL |

The crystal structure of the hNPR1 and WW03 Fab complex was used to identify the WW03 Fab epitope on hNPR1. The interaction surface on hNPR1 by WW03 Fab was formed by several continuous and discontinuous (i.e., noncontiguous) sequences as detailed in Table 24. These residues form the three-dimensional conformational epitope recognized by WW03 Fab.

Results of the epitope mapping of WW03 Fab (ANP non-competitive) are shown in Table 24. hNPR1 residues are numbered based upon SEQ ID NO: 1 (P16066). Fab residues are numbered based upon their linear amino acid sequence. hNPR1 residues shown have at least one atom within 5 Å of an atom in the WW03 Fab, to account for potential water mediated interactions.

TABLE 24

Epitope Mapping of WW03 Fab

| Antibody WW03 Fab | | | Antigen (NPR1) | | |
|---|---|---|---|---|---|
| Amino acid | Number | Chain | Amino acid | Number | Chain |
| SER | 31 | H | TRP | 106 | A |
| TYR | 32 | H | TRP | 106 | A |
|  |  |  | TRP | 106 | B |
| TRP | 33 | H | ASN | 109 | A |
| SER | 52 | H | HIS | 108 | A |
|  |  |  | ASN | 109 | A |
| SER | 53 | H | TRP | 106 | A |
|  |  |  | GLU | 107 | A |
|  |  |  | ASN | 109 | A |
| ASP | 54 | H | THR | 36 | A |
|  |  |  | ARG | 79 | A |
| SER | 56 | H | ASN | 34 | A |
| TYR | 57 | H | ASN | 109 | A |
|  |  |  | PRO | 110 | A |
|  |  |  | ALA | 111 | A |
|  |  |  | VAL | 374 | A |
|  |  |  | THR | 375 | A |
| TYR | 59 | H | THR | 375 | A |
| ARG | 100 | H | ASP | 103 | B |
|  |  |  | TRP | 106 | B |
|  |  |  | GLU | 107 | B |
| TYR | 101 | H | VAL | 102 | A |
|  |  |  | TRP | 106 | A |
|  |  |  | VAL | 102 | B |
|  |  |  | ASP | 103 | B |
|  |  |  | TRP | 106 | B |
|  |  |  | GLU | 107 | B |
| SER | 102 | H | LYS | 105 | A |
|  |  |  | TRP | 106 | A |
|  |  |  | ASN | 109 | A |
| MET | 103 | H | VAL | 102 | A |
|  |  |  | LYS | 105 | A |
|  |  |  | TRP | 106 | A |
|  |  |  | TRP | 132 | A |
|  |  |  | LEU | 99 | B |
|  |  |  | VAL | 102 | B |

TABLE 24-continued

Epitope Mapping of WW03 Fab

| Antibody WW03 Fab | | | Antigen (NPR1) | | |
|---|---|---|---|---|---|
| Amino acid | Number | Chain | Amino acid | Number | Chain |
| | | | ASP | 103 | B |
| ILE | 104 | H | HIS | 131 | A |
| | | | TRP | 132 | A |
| | | | LEU | 99 | B |
| | | | ASP | 103 | B |
| TYR | 105 | H | LYS | 105 | A |
| | | | TRP | 132 | A |
| SER | 106 | H | LYS | 105 | A |
| | | | TRP | 132 | A |
| | | | ARG | 133 | A |
| TYR | 107 | H | LYS | 105 | A |
| | | | ASN | 109 | A |
| | | | PRO | 110 | A |
| | | | ALA | 111 | A |
| | | | VAL | 134 | A |
| | | | THR | 375 | A |
| ASP | 113 | H | GLU | 107 | B |
| ARG | 18 | L | GLN | 336 | B |
| SER | 30 | L | ASN | 87 | B |
| | | | ALA | 88 | B |
| SER | 31 | L | SER | 84 | B |
| TYR | 32 | L | HIS | 131 | A |
| TYR | 49 | L | ASP | 103 | B |
| | | | GLU | 107 | B |
| | | | HIS | 108 | B |
| SER | 52 | L | LEU | 43 | B |
| | | | LEU | 82 | B |
| THR | 53 | L | VAL | 81 | B |
| | | | LEU | 82 | B |
| | | | GLY | 83 | B |
| | | | LEU | 104 | B |
| | | | HIS | 108 | B |
| LEU | 54 | L | ARG | 79 | B |
| | | | VAL | 81 | B |
| | | | HIS | 108 | B |
| GLN | 55 | L | GLU | 107 | B |
| | | | HIS | 108 | B |
| SER | 56 | L | GLU | 107 | B |
| | | | HIS | 108 | B |
| VAL | 58 | L | ARG | 79 | B |
| PRO | 59 | L | ARG | 79 | B |
| SER | 60 | L | ARG | 79 | B |
| GLY | 66 | L | THR | 44 | B |
| SER | 67 | L | THR | 44 | B |
| | | | GLU | 86 | B |
| | | | ASN | 87 | B |
| TYR | 92 | L | ARG | 133 | A |
| GLU | 93 | L | ARG | 133 | A |
| LYS | 94 | L | ASP | 376 | A |

Critical epitope residues for the binding of WW03 Fab and NPR1, which were determined using structural analysis and affinity maturation data, include the residues shown in Table 25. Regions of NPR1 encompassing these critical residues include R79, L82, L99-A111, H131-V134, and V374-T375.

TABLE 25

Critical Epitope Residues of WW03 Fab (ANP non-competitive)

| Critical epitope residue (amino acid) | Critical epitope residue (number) | Explanation |
|---|---|---|
| R | 79 | Salt bridge with D54 (side chain) of VH; H-bond (chain B) with S60 (side chain) of VL |
| L | 82 | H-bond (backbone) with T53 (side chain) of VL |
| L | 99 | Packing against M103 (side chain) and I104 (side chain) of VH |
| V | 102 | Packing against M103 (side chain) of VH |
| D | 103 | Salt bridge with R100 (side chain) of VH |
| K | 105 | H-bond with M103 (backbone) and Y105 (backbone) of VH |
| W | 106 | Packing between Y32 (side chain) and Y101 (side chain) of VH; stacking (chain B) against Y101 (side chain) of VH |
| N | 109 | H-bond with S53 (side chain) of VH |
| H | 131 | H-bond with I104 (backbone) of VH |
| W | 132 | H-bond with M103 (side chain) of VH |
| T | 375 | H-bond with Y59 (side chain) of VH; pack against Y57 (side chain) of VH |

The crystal structure of the hNPR1 and WW06 Fab complex was used to identify the WW06 Fab epitope on hNPR1. The interaction surface on hNPR1 by WW06 Fab was formed by several continuous and discontinuous (i.e., noncontiguous) sequences as detailed in Table 26. These residues form the three-dimensional conformational epitope recognized by WW06 Fab.

Results of the epitope mapping of the WW06 Fab (ANP competitive) are shown in Table 26. hNPR1 residues are numbered based upon SEQ ID NO: 1 (P16066). WW06 Fab residues are numbered based upon their linear amino acid sequence. hNPR1 residues shown have at least one atom within 5 Å of an atom in the WW06 Fab, to account for potential water mediated interactions.

TABLE 26

Epitope Mapping of WW06 Fab (ANP competitive)

| Antibody WW06 Fab | | | Antigen (NPR1) | | |
|---|---|---|---|---|---|
| Amino acid | Number | Chain | Amino acid | Number | Chain |
| Y | 27 | H | R | 294 | B |
|   |   | H | G | 295 | B |
| S | 28 | H | R | 294 | B |
|   |   | H | G | 295 | B |
|   |   | H | D | 296 | B |
| S | 31 | H | R | 230 | A |
|   |   | H | D | 296 | B |
| Y | 32 | H | G | 295 | B |
|   |   | H | D | 296 | B |
|   |   | H | G | 297 | B |
| W | 33 | H | Y | 188 | A |
|   |   | H | E | 219 | A |
| R | 50 | H | F | 197 | A |
|   |   | H | E | 219 | A |
| D | 52 | H | Y | 188 | A |
|   |   | H | A | 221 | A |
|   |   | H | H | 227 | A |
| D | 54 | H | D | 224 | A |
| N | 55 | H | Y | 188 | A |
|   |   | H | P | 190 | A |
|   |   | H | A | 221 | A |
|   |   | H | D | 223 | A |
| Y | 57 | H | Y | 188 | A |
|   |   | H | R | 189 | A |
|   |   | H | P | 190 | A |
|   |   | H | G | 191 | A |
|   |   | H | D | 192 | A |
|   |   | H | E | 193 | A |
|   |   | H | E | 194 | A |
|   |   | H | F | 197 | A |
| T | 58 | H | E | 194 | A |
| R | 59 | H | E | 194 | A |
|   |   | H | F | 197 | A |
|   |   | H | E | 201 | A |
| Q | 65 | H | D | 94 | A |
|   |   | H | E | 194 | A |
| R | 98 | H | G | 295 | B |
| W | 99 | H | E | 219 | A |
| L | 100 | H | R | 230 | A |
| S | 101 | H | H | 217 | A |
| P | 102 | H | K | 238 | A |
| G | 103 | H | D | 216 | A |
|   |   | H | H | 217 | A |
|   |   | H | T | 234 | A |
|   |   | H | K | 238 | A |
| Y | 104 | H | L | 218 | A |
|   |   | H | E | 219 | A |
|   |   | H | F | 220 | A |
|   |   | H | H | 227 | A |
|   |   | H | R | 230 | A |
|   |   | H | L | 231 | A |
|   |   | H | T | 234 | A |
|   |   | H | K | 238 | A |

TABLE 26-continued

Epitope Mapping of WW06 Fab (ANP competitive)

| Antibody WW06 Fab | | | Antigen (NPR1) | | |
|---|---|---|---|---|---|
| Amino acid | Number | Chain | Amino acid | Number | Chain |
| A | 105 | H | K | 238 | A |
| L | 106 | H | R | 233 | A |
|   |   | H | T | 234 | A |
|   |   | H | R | 237 | A |
|   |   | H | K | 238 | A |
| G | 107 | H | R | 237 | A |
| Q | 109 | H | G | 297 | B |
| Q |   | H | V | 300 | B |
| I | 29 | L | R | 208 | A |
| G | 30 | L | R | 208 | A |
| A | 31 | L | F | 204 | A |
|   |   | L | R | 208 | A |
| G | 32 | L | R | 208 | A |
| Y | 33 | L | Y | 186 | A |
|   |   | L | E | 201 | A |
|   |   | L | F | 204 | A |
|   |   | L | H | 217 | A |
| Y | 93 | L | F | 197 | A |
|   |   | L | E | 201 | A |
| L | 95 | L | L | 144 | A |
|   |   | L | E | 201 | A |
|   |   | L | F | 204 | A |
|   |   | L | M | 205 | A |
| Q | 96 | L | L | 144 | A |
|   |   | L | G | 145 | A |
|   |   | L | V | 148 | A |
|   |   | L | M | 205 | A |
| S | 98 | L | F | 197 | A |
|   |   | L | F | 198 | A |
|   |   | L | E | 201 | A |
| R | 100 | L | E | 219 | A |

Critical epitope residues for the binding of WW06 and NPR1, which were determined using structural analysis and affinity maturation data, include the residues shown in Table 27. Regions of NPR1 encompassing these critical residues include Y188-F198, E201-R208, V215-K238, and R294-G297.

TABLE 27

Critical Epitope Residues of WW06 (ANP competitive)

| Critical epitope residue (amino acid) | Critical epitope residue (number) | Explanation |
|---|---|---|
| Y | 188 | Packing against W33 (side chain) of VH |
| D | 192 | H-bond with Y57 (side chain) of VH |
| E | 194 | Salt bridge with R59 (side chain) of VH |
| F | 197 | Stacking against R59 (side chain) of VH |
| E | 201 | H-bond with S98 (side chain) of VL |
| R | 208 | H-bond with G30 (backbone) of VL |
| E | 219 | Salt bridge with R50 (side chain) of VH |
| G | 295 | H-bond (backbone, chain B) with S28 (backbone) of VH |

Example 17: Mouse In Vivo Characterization of Effect of WW06 on Plasma cGMP

WW06 FabCys was used in an in vivo study in hNPR1 transgenic mice to determine the effect of this antibody on plasma cGMP levels in vivo.

For analysis of plasma cGMP samples, the LC-MS/MS detection method using $^{15}N_2$, $^{13}C$ cGMP as an internal standard was adopted from Oeckl and Ferger, Journal of Neuroscience Methods 203 (2012) 338-343; and Zhang et al., J. Chromatogr B: Analyt Technol Biomed Life Sci 2009; 877:513-20; the contents of each of which are hereby incorporated by reference for this purpose).

Figure 26:
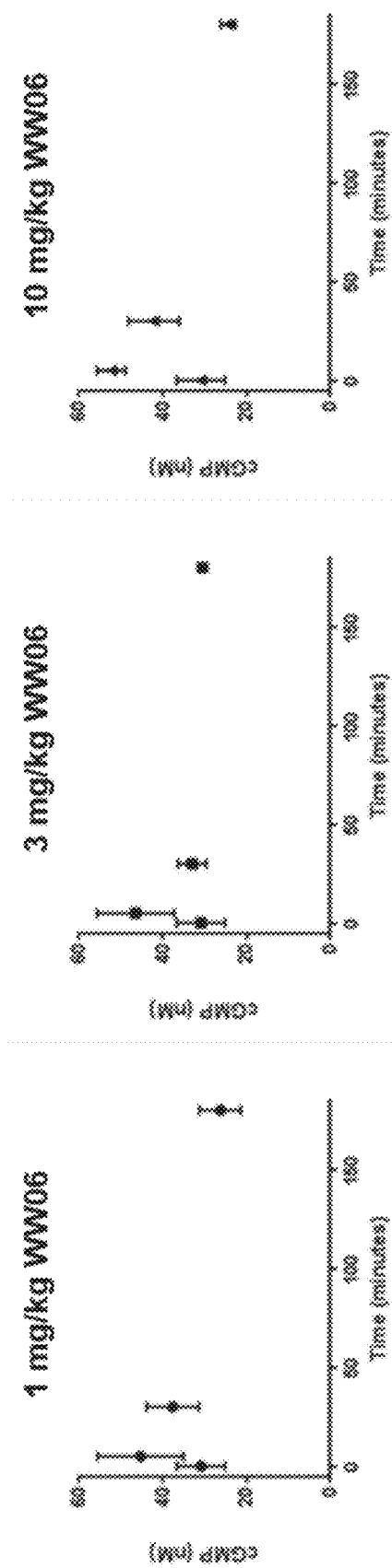
FIG. 26 is a set of graphs representing the plasma cGMP (nM) concentration over time in hNPR1 Tg mice which were intravenously administered 1 mg/kg, 3 mg/kg, or 10 mg/kg of the WW06 Fab.
Figure 27:
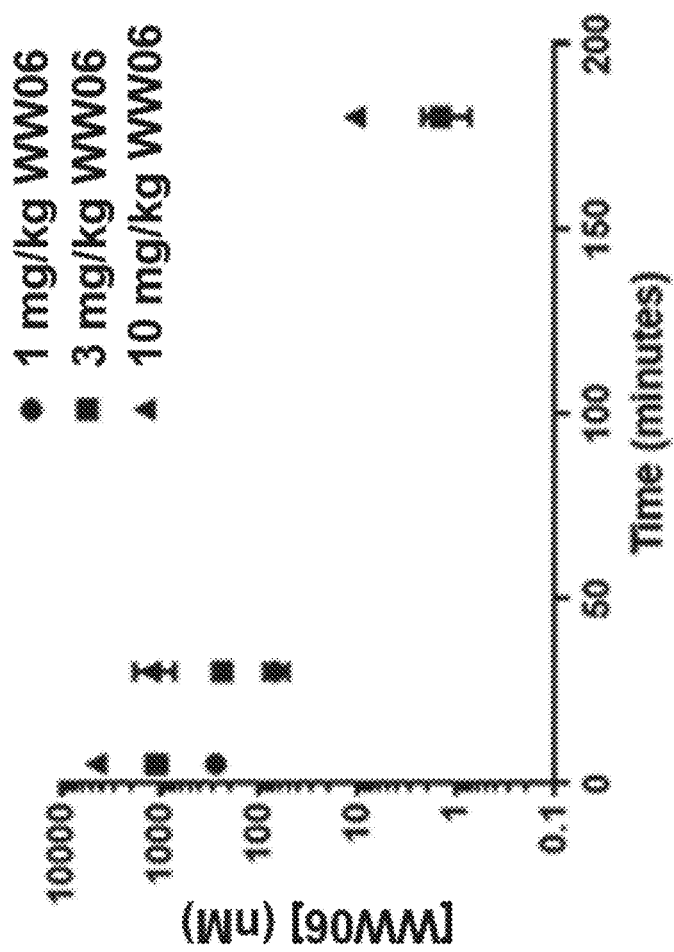
FIG. 27 is a graph representing the concentration of antibody over time in hNPR1 Tg mice which were intravenously administered 1 mg/kg, 3 mg/kg, or 10 mg/kg of the WW06 Fab.

Plasma cGMP concentration in hNPR1 Tg mice which were intravenously administered the WW06 Fab increased at the 5 minute time point and the signal returned to baseline by 3 h. As expected and consistent with the data shown in FIGS. 26 and 27, the T1/2 of the FabCys antibody was <30 min. Each value shown is the average of three points collected from three individual animals. Dose response data are shown in FIG. 26, and PK data are shown in FIG. 27.

Example 18: Effect of XX16 on Heart Weight and NT-proBNP in ANP KO and WT Mice XX16 was used in an in vivo study to determine its effect on heart weight and NT-proBNP levels in ANP knockout (KO) and wild-type (WT) mice.

ANP knockout mice are hypertensive and have cardiac hypertrophy (increased HW/BW ratio). NT-proBNP is a biomarker of cardiac dysfunction. XX16 was administered at 0.3 or 3 mg/kg subcutaneously once every two weeks for four weeks in ANP knockout and wild type mice.

Figure 28:
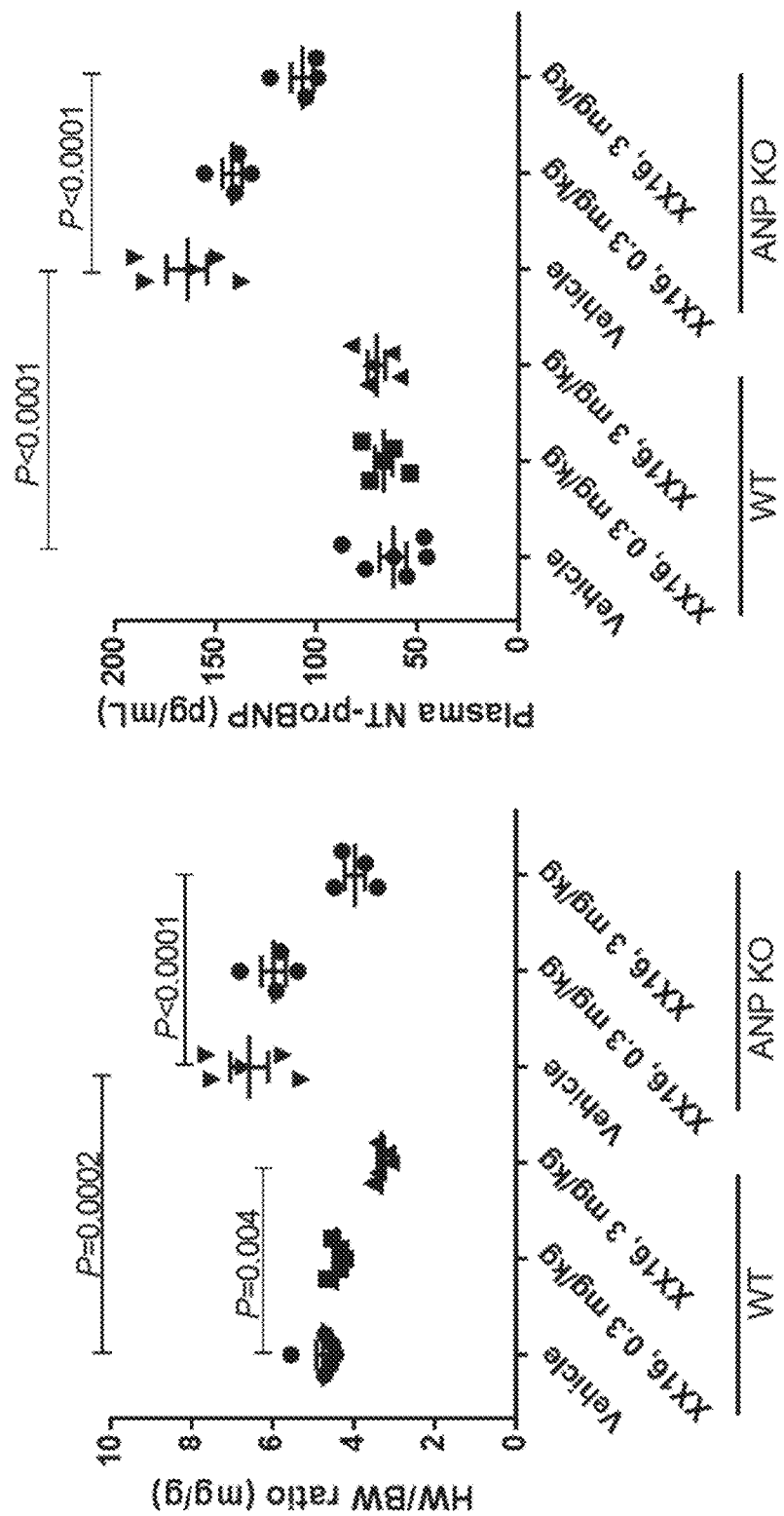
FIG. 28 is a set of graphs demonstrating the results of subcutaneous administration of vehicle, 0.3 mg/kg XX16, or 3 mg/kg XX16 once every two weeks in wild type or ANP knockout (ANP KO) mice on heart weight/body weight ratio (left) and plasma NT-proBNP levels (pg/mL; right). Measurements were taken two weeks after the second administration.

Results are shown in FIG. 28. At two weeks after the second treatment, XX16 dose-dependently reduced heart weight/body weight ratio and NT-proBNP in both wild type and ANP KO mice in comparison to vehicle treated animals.

Figure 29:
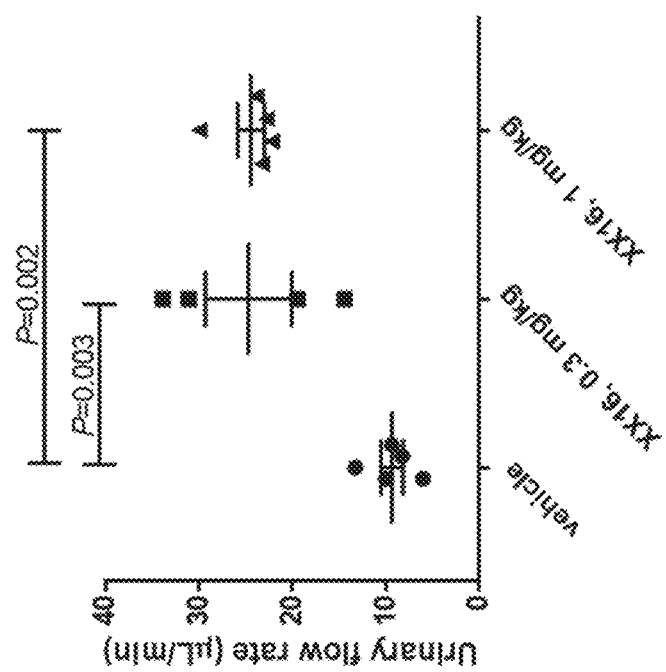
FIG. 29 is a set of graphs demonstrating the results of a single intravenous administration of vehicle, 0.3 mg/kg XX16, or 1 mg/kg XX16 on blood pressure (mean arterial pressure; left) and urinary flow rate (right) in hypertensive rats (spontaneous hypertensive rat stroke prone, SHRsp). Measurements were taken three hours after the intravenous administration.
Figure 29:
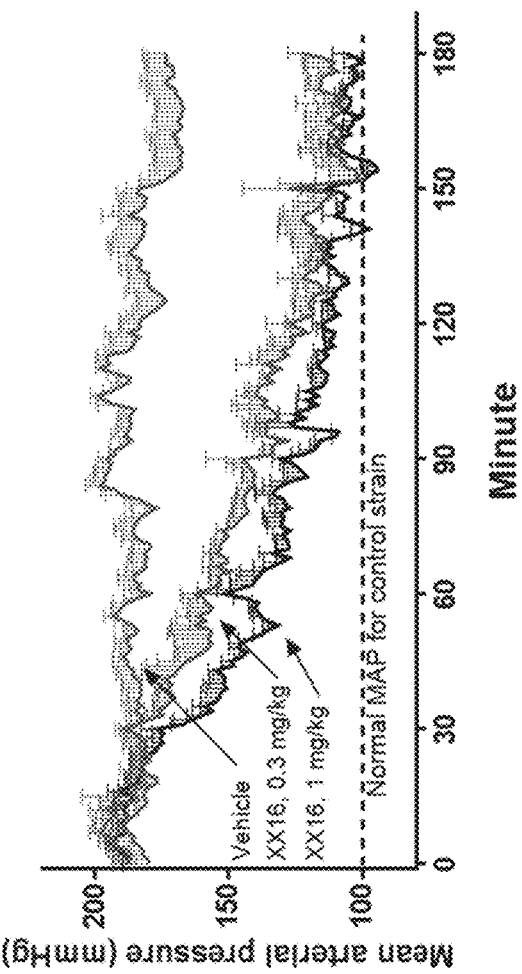

Example 19: Acute Effect of XX16 on Blood Pressure and Urinary Flow Rate in Hypertensive Rats XX16 was used to determine its effect on blood pressure and urinary flow rate in hypertensive rats (spontaneous hypertensive rat stroke prone, SHRsp). Animals were administered 0.3 mg/kg XX16, 1 mg/kg XX16, or a vehicle control intravenously (one time). Blood pressure was measured using a femoral artery catheter. Measurements were taken three hours after the intravenous administration and results are shown in FIG. 29.

Intravenous XX16 treatment normalized mean arterial pressure and increased urinary flow rate acutely in hypertensive rats (SHRsp) in comparison to vehicle treated animals.

Figure 30:
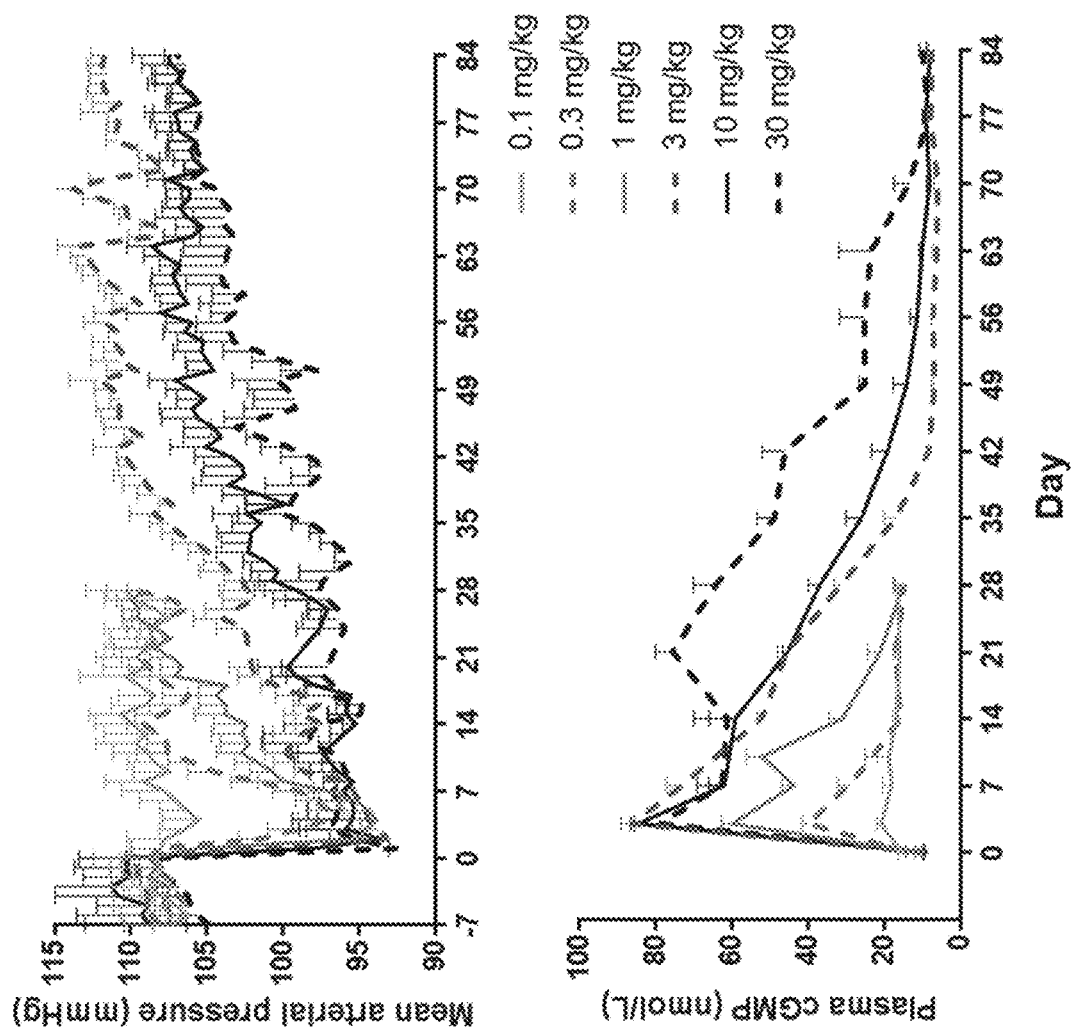
FIG. 30 is a set of graphs demonstrating the results of a single subcutaneous administration of 0.1, 0.3, 1, 3, 10, or 30 mg/kg XX16 in telemetry implanted normal rats on mean arterial pressure (MAP; top) and plasma cGMP (bottom) over time.
Figure 31:
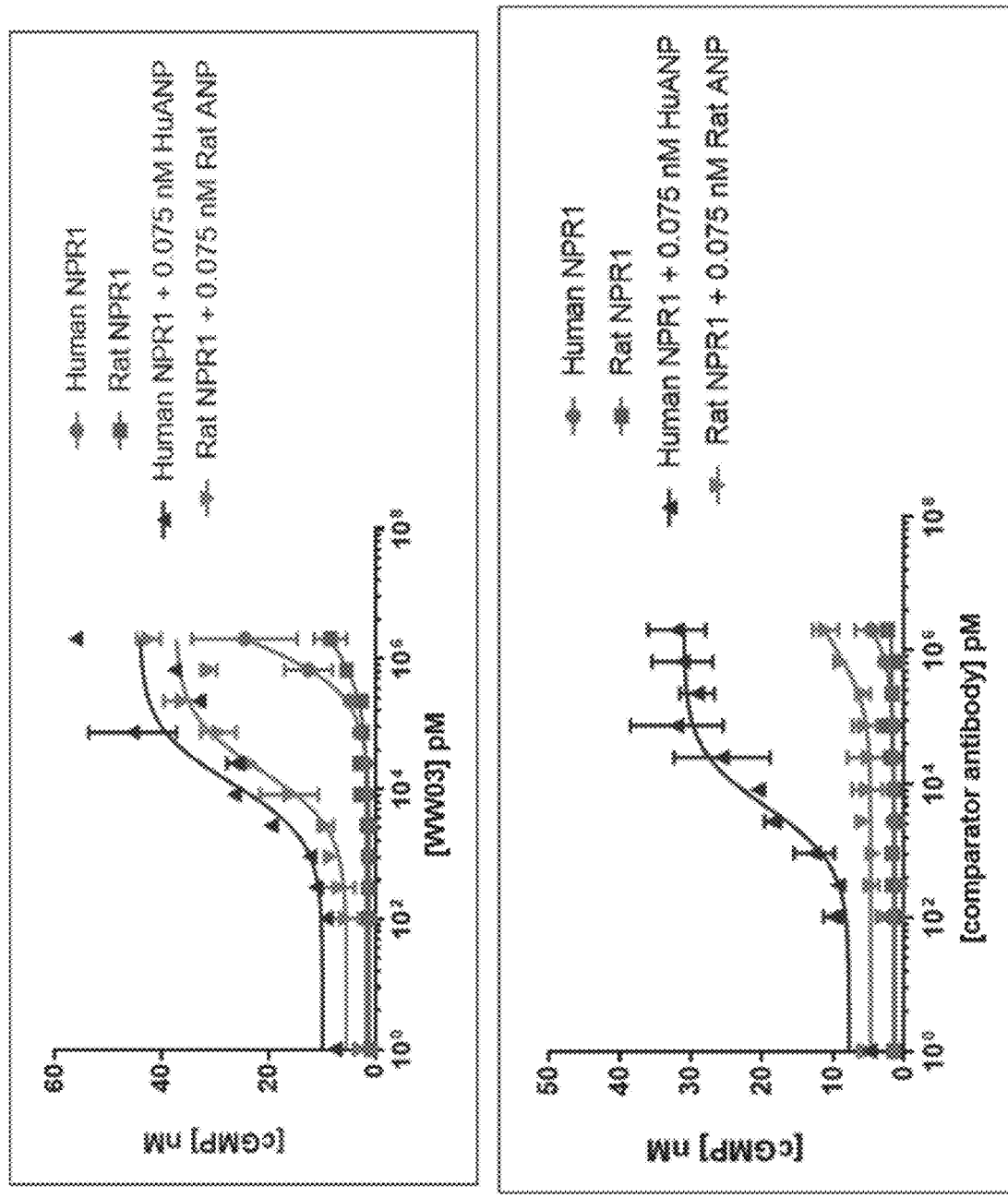
FIG. 31 is a set of graphs depicting the results of functional activity analyses of candidate WW03 and a comparator antibody (antibody 5591-IgG from PCT Application No. WO2010/065293A1) in a cellular cGMP production assay using human NPR1 expressing CHO-K1 cells or rat NPR1 expressing rat cells. Results represent the cellular production of cGMP [nM] in the absence or presence of 0.075 nM ANP (human or rat).

Example 20: Chronic Effects of XX16 on Blood Pressure and Plasma cGMP in Wistar-Han Rats Chronic hemodynamic effects of XX16 in telemetry implanted normal rats were evaluated. XX16 (at doses of 0.1, 0.3, 1, 3, 10, and 30 mg/kg) was administered subcutaneously one time. Results are shown in FIG. 30. Subcutaneous administration of XX16 decreased mean arterial pressure (MAP) in all groups except for the 0.1 mg/kg group. There was a floor (around 95 mmHg) for the MAP reduction. A dose-dependent effect for the time to return baseline MAP was observed; this effect was greater than 70 days for the 30 mg/kg treatment group. Plasma cGMP concentration also had a ceiling around 90 nmol/L, after which the plasma cGMP gradually reduced toward baseline. This effect is very similar to the blood pressure response.

Example 21: Comparison of Extant Anti-NPR1 Antibodies with Antibodies of the Application The WW03 antibody was compared with antibody 5591-IgG of PCT Application No. WO2010/065293A1 in terms of the ability of both antibodies to produce cGMP in human cells expressing hNPR1 or rat cells expressing rNPR1 (both in the presence or absence of 0.075 nM human or rat ANP, respectively). The WW03 antibody displayed superior potentiation in the absence of ANP on both cell lines. Additionally, the WW03 antibody demonstrated superior potentiation on rat cells expressing rNPR1 (both in the presence and absence of ANP).

In summary, previous antibodies (e.g., those of WO2010/065293, including 5591-IgG) demonstrate no activity in vivo (e.g., through analysis of activation using cGMP assays). In contrast, the antibodies of the instant application demonstrated in vivo activity in both mouse and rat. Further, the epitope binding of the antibodies described herein has been demonstrated to be dissimilar to the antibodies of WO2010/065293 using crystal structure data. The activity, cross-reactivity, and crystallographic data described herein demonstrate the differing and superior effects of the antibodies described in this application as compared to previous antibodies.

---

SEQUENCE LISTING

```
Sequence total quantity: 473
SEQ ID NO: 1             moltype = AA   length = 1061
FEATURE                  Location/Qualifiers
source                   1..1061
                         mol_type = protein
                         organism = Homo sapiens
SEQUENCE: 1
MPGPRRPAGS RLRLLLLLLL PPLLLLLRGS HAGNLTVAVV LPLANTSYPW SWARVGPAVE  60
LALAQVKARP DLLPGWTVRT VLGSSENALG VCSDTAAPLA AVDLKWEHNP AVFLGPGCVY 120
AAAPVGRFTA HWRVPLLTAG APALGFGVKD EYALTTRAGP SYAKLGDFVA ALHRRLGWER 180
QALMLYAYRP GDEEHCFFLV EGLFMRVRDR LNITVDHLEF AEDDLSHYTR LLRTMPRKGR 240
VIYICSSPDA FRTLMLLALE AGLCGEDYVF FHLDIFGQSL QGGQGPAPRR PWERGDGQDV 300
SARQAFQAAK IITYKDPDNP EYLEFLKQLK HLAYEQFNFT MEDGLVNTIP ASFHDGLLLY 360
IQAVTETLAH GGTVTDGENI TQRMWNRSFQ GVTGYLKIDS SGDRETDFSL WDMDPENGAF 420
RVVLNYNGTS QELVAVSGRK LNWPLGYPPP DIPKCGFDNE DPACNQDHLS TLEVLALVGS 480
LSLLGILIVS FFIYRKMQLE KELASELWRV RWEDVEPSSL ERHLRSAGSR LTLSGRGSNY 540
GSLLTTEGQF QVFAKTAYYK GNLVAVKRVN RKRIELTRKV LFELKHMRDV QNEHLTRFVG 600
ACTDPPNICI LTEYCPRGSL QDILENESIT LDWMFRYSLT NDIVKGMLFL HNGAICSHGN 660
LKSSNCVVDG RFVLKITDYG LESFRDLDPE QGHTVYAKKL WTAPELLRMA SPPVRGSQAG 720
DVYSFGIILQ EIALRSGVFH VEGLDLSPKE IIERVTRGEQ PPFRPSLALQ SHLEELGLLM 780
QRCWAEDPQE RPPFQQIRLT LRKFNRENSS NILDNLLSRM EQYANNLEEL VEERTQAYLE 840
EKRKAEALLY QILPHSVAEQ LKRGETVQAE AFDSVTIYFS DIVGFTALSA ESTPMQVVTL 900
LNDLYTCFDA VIDNFDVYKV ETIGDAYMVV SGLPVRNGRL HACEVARMAL ALLDAVRSFR 960
```

```
IRHRPQEQLR LRIGIHTGPV CAGVVGLKMP RYCLFGDTVN TASRMESNGE ALKIHLSSET    1020
KAVLEEFGGF ELELRGDVEM KGKGKVRTYW LLGERGSSTR G                       1061

SEQ ID NO: 2           moltype = AA  length = 1057
FEATURE                Location/Qualifiers
source                 1..1057
                       mol_type = protein
                       organism = Mus musculus
SEQUENCE: 2
MPGSRRVRPR LRALLLLPPL LLLRSGHASD LTVAVVLPLT NTSYPWSWAR VGPAVELALG    60
RVKARPDLLP GWTVRMVLGS SENAAGVCSD TAAPLAAVDL KWEHSPAVFL GPGCVYSAAP    120
VGRFTAHWRV PLLTAGAPAL GIGVKDEYAL TTRTGPSHVK LGDFVTALHR RLGWEHQALV    180
LYADRLGDDR PCFFIVEGLY MRVRERLNIT VNHQEFVEGD PDHYTKLLRT VQRKGRVIYI    240
CSSPDAFRNL MLLALDAGLT GEDYVFFHLD VFGQSLQGAQ GPVPRKPWER DDGQDRRARQ    300
AFQAAKIITY KEPDNPEYLE FLKQLKLLAD KKFNFTMEDG LKNIIPASFH DGLLLYVQAV    360
TETLAQGGTV TDGENITQRM WNRSFQGVTG YLKIDRNGDR DTDFSLWDMD PETGAFRVVL    420
NFNGTSQELM AVSEHRLYWP LGYPPPDIPK CGFDNEDPAC NQDHFSTLEV LALVGSLSLV    480
SFLIVSFFIY RKMQLEKELV SELWRVRWED LQPSSLERHL RSAGSRLTLS GRGSNYGSLL    540
TTEGQFQVFA KTAYYKGNLV AVKRVNRKRI ELTRKVLFEL KHMRDVQNEH LTRFVGACTD    600
PPNICILTEY CPRGSLQDIL ENESITLDWM FRYSLTNDIV KGMLFLHNGA IGSHGNLKSS    660
NCVVDGRFVL KITDYGLESF RDPEPEQGHT LFAKKLWTAP ELLRMASPPA RGSQAGDVYS    720
FGIILQEIAL RSGVFYVEGL DLSPKEIIER VTRGEQPPFR PSMDLQSHLE ELGQLMQRCW    780
AEDPQERPPF QQIRLALRKF NKENSSNILD NLLSRMEQYA NNLEELVEER TQAYLEEKRK    840
AEALLYQILP HSVAEQLKRG ETVQAEAFDS VTIYFSDIVG FTALSAESTP MQVVTLLNDL    900
YTCFDAVIDN FDVYKVETIG DAYMVVSGLP VRNGQLHARE VARMALALLD AVRSFRIRHR    960
PQEQLRLRIG IHTGPVCAGV VGLKMPRYCL FGDTVNTASR MESNGEALRI HLSSETKAVL    1020
EEFDGFELEL RGDVEMKGKG KVRTYWLLGE RGCSTRG                            1057

SEQ ID NO: 3           moltype = AA  length = 1057
FEATURE                Location/Qualifiers
source                 1..1057
                       mol_type = protein
                       organism = Rattus norvegicus
SEQUENCE: 3
MPGSRRVRPR LRALLLLPPL LLLRGGHASD LTVAVVLPLT NTSYPWSWAR VGPAVELALA    60
RVKARPDLLP GWTVRMVLGS SENAAGVCSD TAAPLAAVDL KWEHSPAVFL GPGCVYSAAP    120
VGRFTAHWRV PLLTAGAPAL GIGVKDEYAL TTRTGPSHVK LGDFVTALHR RLGWEHQALV    180
LYADRLGDDR PCFFIVEGLY MRVRERLNIT VNHQEFVEGD PDHYPKLLRA VRRKGRVIYI    240
CSSPDAFRNL MLLALNAGLT GEDYVFFHLD VFGQSLKSAQ GLVPQKPWER GDGQDRSARQ    300
AFQAAKIITY KEPDNPEYLE FLKQLKLLAD KKFNFTVEDG LKNIIPASFH DGLLLYVQAV    360
TETLAQGGTV TDGENITQRM WNRSFQGVTG YLKIDRNGDR DTDFSLWDMD PETGAFRVVL    420
NYNGTSQELM AVSEHKLYWP LGYPPPDVPK CGFDNEDPAC NQDHFSTLEV LALVGSLSLI    480
SFLIVSFFIY RKMQLEKELV SELWRVRWED LQPSSLERHL RSAGSRLTLS GRGSNYGSLL    540
TTEGQFQVFA KTAYYKGNLV AVKRVNRKRI ELTRKVLFEL KHMRDVQNEH LTRFVGACTD    600
PPNICILTEY CPRGSLQDIL ENESITLDWM FRYSLTNDIV KGMLFLHNGA ICSHGNLKSS    660
NCVVDGRFVL KITDYGLESF RDPEPEQGHT LFAKKLWTAP ELLRMASPPA RGSQAGDVYS    720
FGIILQEIAL RSGVFYVEGL DLSPKEIIER VTRGEQPPFR PSMDLQSHLE ELGQLMQRCW    780
AEDPQERPPF QQIRLALRKF NKENSSNILD NLLSRMEQYA NNLEELVEER TQAYLEEKRK    840
AEALLYQILP HSVAEQLKRG ETVQAEAFDS VTIYFSDIVG FTALSAESTP MQVVTLLNDL    900
YTCFDAVIDN FDVYKVETIG DAYMVVSGLP VRNGQLHARE VARMALALLD AVRSFRIRHR    960
PQEQLRLRIG IHTGPVCAGV VGLKMPRYCL FGDTVNTASR MESNGEALKI HLSSETKAVL    1020
EEFDGFELEL RGDVEMKGKG KVRTYWLLGE RGCSTRG                            1057

SEQ ID NO: 4           moltype = AA  length = 10
FEATURE                Location/Qualifiers
REGION                 1..10
                       note = source = /note="Description of Artificial Sequence:
                       Synthetic peptide"
source                 1..10
                       mol_type = protein
                       organism = synthetic construct
SEQUENCE: 4
GFTFNTHYIH                                                          10

SEQ ID NO: 5           moltype = AA  length = 17
FEATURE                Location/Qualifiers
REGION                 1..17
                       note = source = /note="Description of Artificial Sequence:
                       Synthetic peptide"
source                 1..17
                       mol_type = protein
                       organism = synthetic construct
SEQUENCE: 5
SISGSGSNTY YADSVKG                                                  17

SEQ ID NO: 6           moltype = AA  length = 12
FEATURE                Location/Qualifiers
REGION                 1..12
                       note = source = /note="Description of Artificial Sequence:
```

```
                        Synthetic peptide"
source                  1..12
                        mol_type = protein
                        organism = synthetic construct
SEQUENCE: 6
ERGYVYYHMF DP                                                                    12

SEQ ID NO: 7            moltype = AA  length = 5
FEATURE                 Location/Qualifiers
REGION                  1..5
                        note = source = /note="Description of Artificial Sequence:
                        Synthetic peptide"
source                  1..5
                        mol_type = protein
                        organism = synthetic construct
SEQUENCE: 7
THYIH                                                                            5

SEQ ID NO: 8            moltype = AA  length = 7
FEATURE                 Location/Qualifiers
REGION                  1..7
                        note = source = /note="Description of Artificial Sequence:
                        Synthetic peptide"
source                  1..7
                        mol_type = protein
                        organism = synthetic construct
SEQUENCE: 8
GFTFNTH                                                                          7

SEQ ID NO: 9            moltype = AA  length = 6
FEATURE                 Location/Qualifiers
REGION                  1..6
                        note = source = /note="Description of Artificial Sequence:
                        Synthetic peptide"
source                  1..6
                        mol_type = protein
                        organism = synthetic construct
SEQUENCE: 9
SGSGSN                                                                           6

SEQ ID NO: 10           moltype = AA  length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 10
GFTFNTHY                                                                         8

SEQ ID NO: 11           moltype = AA  length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 11
ISGSGSNT                                                                         8

SEQ ID NO: 12           moltype = AA  length = 14
FEATURE                 Location/Qualifiers
REGION                  1..14
                        note = source = /note="Description of Artificial Sequence:
                        Synthetic peptide"
source                  1..14
                        mol_type = protein
                        organism = synthetic construct
SEQUENCE: 12
ARERGYVYYH MFDP                                                                  14

SEQ ID NO: 13           moltype = AA  length = 121
FEATURE                 Location/Qualifiers
REGION                  1..121
                        note = source = /note="Description of Artificial Sequence:
                        Synthetic polypeptide"
source                  1..121
```

```
                              mol_type = protein
                              organism = synthetic construct
SEQUENCE: 13
QVQLLESGGG LVQPGGSLRL SCAASGFTFN THYIHWVRQA PGKGLEWVSS ISGSGSNTYY    60
ADSVKGRFTI SRDNSKNTLY LQMNSLRAED TAVYYCARER GYVYYHMFDP WGQGTLVTVS   120
S                                                                   121

SEQ ID NO: 14                 moltype = DNA  length = 363
FEATURE                       Location/Qualifiers
misc_feature                  1..363
                              note = source = /note="Description of Artificial Sequence:
                               Synthetic polynucleotide"
source                        1..363
                              mol_type = other DNA
                              organism = synthetic construct
SEQUENCE: 14
caggtgcaat tgctggaaag cggcggtggc ctggtgcagc cgggtggcag cctgcgtctg    60
agctgcgcgg cgtccggatt cacctttaac actcattaca tccattgggt gcgccaggcc   120
cccggcaaag gtctcgagtg gtttcctct atctctggtt ctggttctaa cacctactat    180
gcggatagcg tgaaaggccg ctttaccatc agccgcgata attcgaaaaa caccctgtat   240
ctgcaaatga acagcctgcg tgcggaagat acggccgtgt attattgcgc gcgtgaacgt   300
ggttacgttt actaccatat gttcgatccg tggggccaag gcaccctggt gactgttagc   360
tca                                                                 363

SEQ ID NO: 15                 moltype = AA  length = 451
FEATURE                       Location/Qualifiers
REGION                        1..451
                              note = source = /note="Description of Artificial Sequence:
                               Synthetic polypeptide"
source                        1..451
                              mol_type = protein
                              organism = synthetic construct
SEQUENCE: 15
QVQLLESGGG LVQPGGSLRL SCAASGFTFN THYIHWVRQA PGKGLEWVSS ISGSGSNTYY    60
ADSVKGRFTI SRDNSKNTLY LQMNSLRAED TAVYYCARER GYVYYHMFDP WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 16                 moltype = DNA  length = 1353
FEATURE                       Location/Qualifiers
misc_feature                  1..1353
                              note = source = /note="Description of Artificial Sequence:
                               Synthetic polynucleotide"
source                        1..1353
                              mol_type = other DNA
                              organism = synthetic construct
SEQUENCE: 16
caggtgcaat tgctggaaag cggcggtggc ctggtgcagc cgggtggcag cctgcgtctg    60
agctgcgcgg cgtccggatt cacctttaac actcattaca tccattgggt gcgccaggcc   120
cccggcaaag gtctcgagtg gtttcctct atctctggtt ctggttctaa cacctactat    180
gcggatagcg tgaaaggccg ctttaccatc agccgcgata attcgaaaaa caccctgtat   240
ctgcaaatga acagcctgcg tgcggaagat acggccgtgt attattgcgc gcgtgaacgt   300
ggttacgttt actaccatat gttcgatccg tggggccaag gcaccctggt gactgttagc   360
tcagcctcca ccaagggtcc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgacaaaac tcacacatgc ccaccgtgcc cagcacctga gcagcgggg   720
ggaccgtcag tcttcctctt ccccccaaaa cccaaggaca cctcatgat ctcccgcacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgggtggt cagcgtcctc accgtcctgc accaggactg gctgaatggc   960
aaggagtaca agtgcaaggt ctccaacaaa gccctcccag cccccatcga gaaaaccatc  1020
tccaaagcca aagggcagcc ccgagaacca caggtgtaca ccctgccccc atcccggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                               1353

SEQ ID NO: 17                 moltype = AA  length = 12
FEATURE                       Location/Qualifiers
REGION                        1..12
                              note = source = /note="Description of Artificial Sequence:
```

```
                    Synthetic peptide"
source              1..12
                    mol_type = protein
                    organism = synthetic construct
SEQUENCE: 17
RASQSITRNY LA                                                              12

SEQ ID NO: 18       moltype = AA  length = 7
FEATURE             Location/Qualifiers
REGION              1..7
                    note = source = /note="Description of Artificial Sequence:
                    Synthetic peptide"
source              1..7
                    mol_type = protein
                    organism = synthetic construct
SEQUENCE: 18
GASSRAT                                                                     7

SEQ ID NO: 19       moltype = AA  length = 9
FEATURE             Location/Qualifiers
REGION              1..9
                    note = source = /note="Description of Artificial Sequence:
                    Synthetic peptide"
source              1..9
                    mol_type = protein
                    organism = synthetic construct
SEQUENCE: 19
QQHSMYPRT                                                                   9

SEQ ID NO: 20       moltype = AA  length = 8
FEATURE             Location/Qualifiers
REGION              1..8
                    note = source = /note="Description of Artificial Sequence:
                    Synthetic peptide"
source              1..8
                    mol_type = protein
                    organism = synthetic construct
SEQUENCE: 20
SQSITRNY                                                                    8

SEQ ID NO: 21       moltype =     length =
SEQUENCE: 21
000

SEQ ID NO: 22       moltype = AA  length = 6
FEATURE             Location/Qualifiers
REGION              1..6
                    note = source = /note="Description of Artificial Sequence:
                    Synthetic peptide"
source              1..6
                    mol_type = protein
                    organism = synthetic construct
SEQUENCE: 22
HSMYPR                                                                      6

SEQ ID NO: 23       moltype = AA  length = 7
FEATURE             Location/Qualifiers
REGION              1..7
                    note = source = /note="Description of Artificial Sequence:
                    Synthetic peptide"
source              1..7
                    mol_type = protein
                    organism = synthetic construct
SEQUENCE: 23
QSITRNY                                                                     7

SEQ ID NO: 24       moltype = AA  length = 108
FEATURE             Location/Qualifiers
REGION              1..108
                    note = source = /note="Description of Artificial Sequence:
                    Synthetic polypeptide"
source              1..108
                    mol_type = protein
                    organism = synthetic construct
SEQUENCE: 24
DIVLTQSPAT LSLSPGERAT LSCRASQSIT RNYLAWYQQK PGQAPRLLIY GASSRATGIP           60
ARFSGSGSGT DFTLTISSLE PEDFAVYYCQ QHSMYPRTFG QGTKVEIK                       108

SEQ ID NO: 25       moltype = DNA  length = 324
```

```
FEATURE                 Location/Qualifiers
misc_feature            1..324
                        note = source = /note="Description of Artificial Sequence:
                        Synthetic polynucleotide"
source                  1..324
                        mol_type = other DNA
                        organism = synthetic construct
SEQUENCE: 25
gatatcgtgc tgacccagag cccggcgacc ctgagcctga gcccgggtga acgtgccacc   60
ctgagctgca gagcgagcca gtctatcact cgtaactacc tggcttggta ccagcagaaa  120
ccgggccagg ccccgcgtct attaatctac ggtgcttctt ctcgtgcgac cggcattccg  180
gcgcgtttta gcggcagcgg atccggcacc gatttcaccc tgaccattag cagcctgaa   240
ccggaagact ttgcggtgta ttattgccag cagcattcta tgtacccgcg tacctttggc  300
cagggcacga aagttgaaat taaa                                          324

SEQ ID NO: 26           moltype = AA  length = 215
FEATURE                 Location/Qualifiers
REGION                  1..215
                        note = source = /note="Description of Artificial Sequence:
                        Synthetic polypeptide"
source                  1..215
                        mol_type = protein
                        organism = synthetic construct
SEQUENCE: 26
DIVLTQSPAT LSLSPGERAT LSCRASQSIT RNYLAWYQQK PGQAPRLLIY GASSRATGIP    60
ARFSGSGSGT DFTLTISSLE PEDFAVYYCQ QHSMYPRTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 27           moltype = DNA  length = 645
FEATURE                 Location/Qualifiers
misc_feature            1..645
                        note = source = /note="Description of Artificial Sequence:
                        Synthetic polynucleotide"
source                  1..645
                        mol_type = other DNA
                        organism = synthetic construct
SEQUENCE: 27
gatatcgtgc tgacccagag cccggcgacc ctgagcctga gcccgggtga acgtgccacc   60
ctgagctgca gagcgagcca gtctatcact cgtaactacc tggcttggta ccagcagaaa  120
ccgggccagg ccccgcgtct attaatctac ggtgcttctt ctcgtgcgac cggcattccg  180
gcgcgtttta gcggcagcgg atccggcacc gatttcaccc tgaccattag cagcctgaa   240
ccggaagact ttgcggtgta ttattgccag cagcattcta tgtacccgcg tacctttggc  300
cagggcacga aagttgaaat taaacgtacg gtggccgctc ccagcgtgtt catcttcccc  360
cccagcgacg agcagctgaa gagcggcacc gccagcgtgg tgtgcctgct gaacaacttc  420
tacccccggg aggccaaggt gcagtggaag gtggacaacg ccctgcagag cggcaacagc  480
caggaaagcg tcaccgagca ggacagcaag gactccacct acagcctgag cagcaccctg  540
accctgagca aggccgacta cgagaagcac aaggtgtacg cctgcgaggt gacccaccag  600
ggcctgtcca gccccgtgac caagagcttc aaccggggcg agtgt                  645

SEQ ID NO: 28           moltype = AA  length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 28
GFTFSSYWMN                                                           10

SEQ ID NO: 29           moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 29
AISSDGSYTY YADSVKG                                                   17

SEQ ID NO: 30           moltype = AA  length = 16
FEATURE                 Location/Qualifiers
REGION                  1..16
                        note = source = /note="Description of Artificial Sequence:
                        Synthetic peptide"
source                  1..16
                        mol_type = protein
```

```
                        organism = synthetic construct
SEQUENCE: 30
DRYSMIYSYG AGAFDY                                                        16

SEQ ID NO: 31           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 31
SYWMN                                                                     5

SEQ ID NO: 32           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 32
GFTFSSY                                                                   7

SEQ ID NO: 33           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 33
SSDGSY                                                                    6

SEQ ID NO: 34           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 34
GFTFSSYW                                                                  8

SEQ ID NO: 35           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 35
ISSDGSYT                                                                  8

SEQ ID NO: 36           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 36
ARDRYSMIYS YGAGAFDY                                                      18

SEQ ID NO: 37           moltype = AA  length = 125
FEATURE                 Location/Qualifiers
REGION                  1..125
                        note = source = /note="Description of Artificial Sequence:
                         Synthetic polypeptide"
source                  1..125
                        mol_type = protein
                        organism = synthetic construct
SEQUENCE: 37
```

```
QVQLLESGGG LVQPGGSLRL SCAASGFTFS SYWMNWVRQA PGKGLEWVSA ISSDGSYTYY    60
ADSVKGRFTI SRDNSKNTLY LQMNSLRAED TAVYYCARDR YSMIYSYGAG AFDYWGQGTL   120
VTVSS                                                              125

SEQ ID NO: 38           moltype = DNA   length = 375
FEATURE                 Location/Qualifiers
misc_feature            1..375
                        note = source = /note="Description of Artificial Sequence:
                        Synthetic polynucleotide"
source                  1..375
                        mol_type = other DNA
                        organism = synthetic construct
SEQUENCE: 38
caggtgcaat tgctggaaag cggcggtggc ctggtgcagc cgggtggcag cctgcgtctg    60
agctgcgcgg cgtccggatt cacctttct tcttactgga tgaactgggt gcgccaggcc   120
ccgggcaaag gtctccgagtg gtttccgct atctcttctg acggttctta cacctactat   180
gcggatagcg tgaaaggccg ctttaccatc agccgcgata attcgaaaaa caccctgtat   240
ctgcaaatga cagcctgcg tgcggaagat acggccgtgt attattgcg cgtgaccgt    300
tactctatga tctactctta cggtgctggt gctttcgatt actggggcca aggcaccctg   360
gtgactgtta gctca                                                   375

SEQ ID NO: 39           moltype = AA   length = 455
FEATURE                 Location/Qualifiers
REGION                  1..455
                        note = source = /note="Description of Artificial Sequence:
                        Synthetic polypeptide"
source                  1..455
                        mol_type = protein
                        organism = synthetic construct
SEQUENCE: 39
QVQLLESGGG LVQPGGSLRL SCAASGFTFS SYWMNWVRQA PGKGLEWVSA ISSDGSYTYY    60
ADSVKGRFTI SRDNSKNTLY LQMNSLRAED TAVYYCARDR YSMIYSYGAG AFDYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                             455

SEQ ID NO: 40           moltype = DNA   length = 1365
FEATURE                 Location/Qualifiers
misc_feature            1..1365
                        note = source = /note="Description of Artificial Sequence:
                        Synthetic polynucleotide"
source                  1..1365
                        mol_type = other DNA
                        organism = synthetic construct
SEQUENCE: 40
caggtgcaat tgctggaaag cggcggtggc ctggtgcagc cgggtggcag cctgcgtctg    60
agctgcgcgg cgtccggatt cacctttct tcttactgga tgaactgggt gcgccaggcc   120
ccgggcaaag gtctccgagtg gtttccgct atctcttctg acggttctta cacctactat   180
gcggatagcg tgaaaggccg ctttaccatc agccgcgata attcgaaaaa caccctgtat   240
ctgcaaatga cagcctgcg tgcggaagat acggccgtgt attattgcg cgtgaccgt    300
tactctatga tctactctta cggtgctggt gctttcgatt actggggcca aggcaccctg   360
gtgactgtta gctcagcctc caccaagggt ccatcggtct tccccctggc accctcctcc   420
aagagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
aagagagttg agcccaaatc ttgtgacaaa actcacacat gcccaccgtg cccagcacct   720
gaagcagcgg ggggaccgtc agtcttcctc ttccccccaa aacccaagga caccctcatg   780
atctcccgga cccctgaggt cacatgcgtg gtggtggacg tgagccacga agaccctgag   840
gtcaagttca actggtacgt ggacggcgtg gaggtgcata atgccaagac aaagccgcgg   900
gaggagcagt acaacagcac gtaccgggtg gtcagcgtcc tcaccgtcct gcaccaggac   960
tggctgaatg gcaaggagta caagtgcaag gtctccaaca agccctccc agccccatc   1020
gagaaaacca tctccaaagc caaagggcag ccccgagaac cacaggtgta caccctgccc   1080
ccatcccggg aggagatgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
gacaagagca ggtggcagca ggggaacgtc ttctcatgct ccgtgatgca tgaggctctg   1320
cacaaccact acacgcagaa gagcctctcc ctgtctccgg gtaaa                  1365

SEQ ID NO: 41           moltype = AA   length = 11
FEATURE                 Location/Qualifiers
REGION                  1..11
                        note = source = /note="Description of Artificial Sequence:
                        Synthetic peptide"
source                  1..11
                        mol_type = protein
```

```
                         organism = synthetic construct
SEQUENCE: 41
RASQGISSYL A                                                               11

SEQ ID NO: 42           moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 42
TASTLQS                                                                    7

SEQ ID NO: 43           moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 43
MQSYEKPRT                                                                  9

SEQ ID NO: 44           moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 44
SQGISSY                                                                    7

SEQ ID NO: 45           moltype =    length =
SEQUENCE: 45
000

SEQ ID NO: 46           moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 46
SYEKPR                                                                     6

SEQ ID NO: 47           moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 47
QGISSY                                                                     6

SEQ ID NO: 48           moltype = AA   length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 48
DIQMTQSPSS LSASVGDRVT ITCRASQGIS SYLAWYQQKP GKAPKLLIYT ASTLQSGVPS           60
RFSGSGSGTD FTLTISSLQP EDFATYYCMQ SYEKPRTFGQ GTKVEIK                        107

SEQ ID NO: 49           moltype = DNA   length = 321
FEATURE                 Location/Qualifiers
misc_feature            1..321
                        note = source = /note="Description of Artificial Sequence:
```

```
                          Synthetic polynucleotide"
source                    1..321
                          mol_type = other DNA
                          organism = synthetic construct
SEQUENCE: 49
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgcatgcag tcttacgaaa aaccgcgtac ctttggccag   300
ggcacgaaag ttgaaattaa a                                             321

SEQ ID NO: 50             moltype = AA  length = 214
FEATURE                   Location/Qualifiers
REGION                    1..214
                          note = source = /note="Description of Artificial Sequence:
                          Synthetic polypeptide"
source                    1..214
                          mol_type = protein
                          organism = synthetic construct
SEQUENCE: 50
DIQMTQSPSS LSASVGDRVT ITCRASQGIS SYLAWYQQKP GKAPKLLIYT ASTLQSGVPS    60
RFSGSGSGTD FTLTISSLQP EDFATYYCMQ SYEKPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 51             moltype = DNA  length = 642
FEATURE                   Location/Qualifiers
misc_feature              1..642
                          note = source = /note="Description of Artificial Sequence:
                          Synthetic polynucleotide"
source                    1..642
                          mol_type = other DNA
                          organism = synthetic construct
SEQUENCE: 51
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgcatgcag tcttacgaaa aaccgcgtac ctttggccag   300
ggcacgaaag ttgaaattaa acgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg gacaacgccc tgcaaagcgg caacagccag   480
gaaagcgtca ccgagcagga cagcaaggac tccacctaca gcctgagcag cacccctgacc  540
ctgagcaagg ccgactacga aagcacaag gtgtacgcct gcgaggtgac ccaccagggc    600
ctgtccagcc ccgtgaccaa gagcttcaac cggggcgagt gt                      642

SEQ ID NO: 52             moltype = AA  length = 10
FEATURE                   Location/Qualifiers
REGION                    1..10
                          note = source = /note="Description of Artificial Sequence:
                          Synthetic peptide"
source                    1..10
                          mol_type = protein
                          organism = synthetic construct
SEQUENCE: 52
GYSFSNYWIG                                                           10

SEQ ID NO: 53             moltype = AA  length = 17
FEATURE                   Location/Qualifiers
REGION                    1..17
                          note = source = /note="Description of Artificial Sequence:
                          Synthetic peptide"
source                    1..17
                          mol_type = protein
                          organism = synthetic construct
SEQUENCE: 53
IIYPDVSYTR YSPSFQG                                                   17

SEQ ID NO: 54             moltype = AA  length = 10
FEATURE                   Location/Qualifiers
REGION                    1..10
                          note = source = /note="Description of Artificial Sequence:
                          Synthetic peptide"
source                    1..10
                          mol_type = protein
                          organism = synthetic construct
SEQUENCE: 54
YWSEAYTFDY                                                           10
```

```
SEQ ID NO: 55          moltype = AA   length = 5
FEATURE                Location/Qualifiers
REGION                 1..5
                       note = source = /note="Description of Artificial Sequence:
                       Synthetic peptide"
source                 1..5
                       mol_type = protein
                       organism = synthetic construct
SEQUENCE: 55
NYWIG                                                                  5

SEQ ID NO: 56          moltype = AA   length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 56
GYSFSNY                                                                7

SEQ ID NO: 57          moltype = AA   length = 6
FEATURE                Location/Qualifiers
REGION                 1..6
                       note = source = /note="Description of Artificial Sequence:
                       Synthetic peptide"
source                 1..6
                       mol_type = protein
                       organism = synthetic construct
SEQUENCE: 57
YPDVSY                                                                 6

SEQ ID NO: 58          moltype = AA   length = 8
FEATURE                Location/Qualifiers
REGION                 1..8
                       note = source = /note="Description of Artificial Sequence:
                       Synthetic peptide"
source                 1..8
                       mol_type = protein
                       organism = synthetic construct
SEQUENCE: 58
GYSFSNYW                                                               8

SEQ ID NO: 59          moltype = AA   length = 8
FEATURE                Location/Qualifiers
REGION                 1..8
                       note = source = /note="Description of Artificial Sequence:
                       Synthetic peptide"
source                 1..8
                       mol_type = protein
                       organism = synthetic construct
SEQUENCE: 59
IYPDVSYT                                                               8

SEQ ID NO: 60          moltype = AA   length = 12
FEATURE                Location/Qualifiers
REGION                 1..12
                       note = source = /note="Description of Artificial Sequence:
                       Synthetic peptide"
source                 1..12
                       mol_type = protein
                       organism = synthetic construct
SEQUENCE: 60
ARYWSEAYTF DY                                                         12

SEQ ID NO: 61          moltype = AA   length = 119
FEATURE                Location/Qualifiers
REGION                 1..119
                       note = source = /note="Description of Artificial Sequence:
                       Synthetic polypeptide"
source                 1..119
                       mol_type = protein
                       organism = synthetic construct
SEQUENCE: 61
QVQLVQSGAE VKKPGESLKI SCKGSGYSFS NYWIGWVRQM PGKGLEWMGI IYPDVSYTRY      60
SPSFQGQVTI SADKSISTAY LQWSSLKASD TAMYYCARYW SEAYTFDYWG QGTLVTVSS      119
```

```
SEQ ID NO: 62            moltype = DNA   length = 357
FEATURE                  Location/Qualifiers
misc_feature             1..357
                         note = source = /note="Description of Artificial Sequence:
                         Synthetic polynucleotide"
source                   1..357
                         mol_type = other DNA
                         organism = synthetic construct
SEQUENCE: 62
caggtgcaat tggtgcagag cggtgcggaa gtgaaaaaac cgggcgaaag cctgaaaatt    60
agctgcaaag gctccggata tagcttctct aactactgga tcggttgggt gcgccagatg   120
ccgggcaaag gtctcgagtg gatgggcatc atctacccgg acgttagcta caccgcgtat   180
agcccgagct ttcagggcca ggtgaccatt agcgcggata aaagcatcag caccgcgtat   240
ctgcaatgga gcagcctgaa agcgagcgat accgcggtgt attattgcgc gcgttactgg   300
tctgaagctt acactttcga ttactggggc caaggcaccc tggtgactgt tagctca      357

SEQ ID NO: 63            moltype = AA   length = 449
FEATURE                  Location/Qualifiers
REGION                   1..449
                         note = source = /note="Description of Artificial Sequence:
                         Synthetic polypeptide"
source                   1..449
                         mol_type = protein
                         organism = synthetic construct
SEQUENCE: 63
QVQLVQSGAE VKKPGESLKI SCKGSGYSFS NYWIGWVRQM PGKGLEWMGI IYPDVSYTRY    60
SPSFQGQVTI SADKSISTAY LQWSSLKASD TAMYYCARYW SEAYTFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 64            moltype = DNA   length = 1347
FEATURE                  Location/Qualifiers
misc_feature             1..1347
                         note = source = /note="Description of Artificial Sequence:
                         Synthetic polynucleotide"
source                   1..1347
                         mol_type = other DNA
                         organism = synthetic construct
SEQUENCE: 64
caggtgcaat tggtgcagag cggtgcggaa gtgaaaaaac cgggcgaaag cctgaaaatt    60
agctgcaaag gctccggata tagcttctct aactactgga tcggttgggt gcgccagatg   120
ccgggcaaag gtctcgagtg gatgggcatc atctacccgg acgttagcta caccgcgtat   180
agcccgagct ttcagggcca ggtgaccatt agcgcggata aaagcatcag caccgcgtat   240
ctgcaatgga gcagcctgaa agcgagcgat accgcggtgt attattgcgc gcgttactgg   300
tctgaagctt acactttcga ttactggggc caaggcaccc tggtgactgt tagctcagcc   360
tccaccaagg gtccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagagagt tgagcccaaa   660
tcttgtgaca aaactcacac atgcccaccg tgcccagcac ctgaagcagc ggggggaccg   720
tcagtcttcc tcttcccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccggg tggtcagcgt cctcaccgtc ctgcaccagg actggctgaa tggcaaggag   960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatccag cgacatcgcc   1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaa                                      1347

SEQ ID NO: 65            moltype = AA   length = 11
FEATURE                  Location/Qualifiers
REGION                   1..11
                         note = source = /note="Description of Artificial Sequence:
                         Synthetic peptide"
source                   1..11
                         mol_type = protein
                         organism = synthetic construct
SEQUENCE: 65
SGDNIRKKYV F                                                         11

SEQ ID NO: 66            moltype = AA   length = 7
```

```
FEATURE              Location/Qualifiers
REGION               1..7
                     note = source = /note="Description of Artificial Sequence:
                      Synthetic peptide"
source               1..7
                     mol_type = protein
                     organism = synthetic construct
SEQUENCE: 66
GDNDRPS                                                                         7

SEQ ID NO: 67        moltype = AA  length = 11
FEATURE              Location/Qualifiers
REGION               1..11
                     note = source = /note="Description of Artificial Sequence:
                      Synthetic peptide"
source               1..11
                     mol_type = protein
                     organism = synthetic construct
SEQUENCE: 67
GTYTLLFTSK V                                                                    11

SEQ ID NO: 68        moltype = AA  length = 7
FEATURE              Location/Qualifiers
REGION               1..7
                     note = source = /note="Description of Artificial Sequence:
                      Synthetic peptide"
source               1..7
                     mol_type = protein
                     organism = synthetic construct
SEQUENCE: 68
DNIRKKY                                                                         7

SEQ ID NO: 69        moltype =   length =
SEQUENCE: 69
000

SEQ ID NO: 70        moltype = AA  length = 8
FEATURE              Location/Qualifiers
REGION               1..8
                     note = source = /note="Description of Artificial Sequence:
                      Synthetic peptide"
source               1..8
                     mol_type = protein
                     organism = synthetic construct
SEQUENCE: 70
YTLLFTSK                                                                        8

SEQ ID NO: 71        moltype = AA  length = 6
FEATURE              Location/Qualifiers
REGION               1..6
                     note = source = /note="Description of Artificial Sequence:
                      Synthetic peptide"
source               1..6
                     mol_type = protein
                     organism = synthetic construct
SEQUENCE: 71
NIRKKY                                                                          6

SEQ ID NO: 72        moltype = AA  length = 108
FEATURE              Location/Qualifiers
REGION               1..108
                     note = source = /note="Description of Artificial Sequence:
                      Synthetic polypeptide"
source               1..108
                     mol_type = protein
                     organism = synthetic construct
SEQUENCE: 72
DIELTQPPSV SVSPGQTASI TCSGDNIRKK YVFWYQQKPG QAPVLVIYGD NDRPSGIPER   60
FSGSNSGNTA TLTISGTQAE DEADYYCGTY TLLFTSKVFG GGTKLTVL               108

SEQ ID NO: 73        moltype = DNA  length = 324
FEATURE              Location/Qualifiers
misc_feature         1..324
                     note = source = /note="Description of Artificial Sequence:
                      Synthetic polynucleotide"
source               1..324
                     mol_type = other DNA
                     organism = synthetic construct
SEQUENCE: 73
```

```
gatatcgaac tgacccagcc gccgagcgtg agcgtgagtc cgggccagac cgcgagcatt    60
acctgtagcg gcgataacat ccgtaaaaaa tacgttttct ggtaccagca gaaaccgggc   120
caggcgccgg tgctggtgat ctacggtgac aacgaccgtc cgagcggcat cccggaacgt   180
tttagcggat ccaacagcgg caacaccgcg accctgacca ttagcggcac ccaggcgaa    240
gacgaagcgg attattactg cggtacttac actctgctgt tcacttctaa agtgtttggc   300
ggcggcacga agttaaccgt ccta                                          324
```

| | | |
|---|---|---|
| SEQ ID NO: 74 | moltype = AA  length = 214 | |
| FEATURE | Location/Qualifiers | |
| REGION | 1..214 | |
| | note = source = /note="Description of Artificial Sequence: Synthetic polypeptide" | |
| source | 1..214 | |
| | mol_type = protein | |
| | organism = synthetic construct | |

```
SEQUENCE: 74
DIELTQPPSV SVSPGQTASI TCSGDNIRKK YVFWYQQKPG QAPVLVIYGD NDRPSGIPER    60
FSGSNSGNTA TLTISGTQAE DEADYYCGTY TLLFTSKVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214
```

| | | |
|---|---|---|
| SEQ ID NO: 75 | moltype = DNA  length = 642 | |
| FEATURE | Location/Qualifiers | |
| misc_feature | 1..642 | |
| | note = source = /note="Description of Artificial Sequence: Synthetic polynucleotide" | |
| source | 1..642 | |
| | mol_type = other DNA | |
| | organism = synthetic construct | |

```
SEQUENCE: 75
gatatcgaac tgacccagcc gccgagcgtg agcgtgagtc cgggccagac cgcgagcatt    60
acctgtagcg gcgataacat ccgtaaaaaa tacgttttct ggtaccagca gaaaccgggc   120
caggcgccgg tgctggtgat ctacggtgac aacgaccgtc cgagcggcat cccggaacgt   180
tttagcggat ccaacagcgg caacaccgcg accctgacca ttagcggcac ccaggcggaa   240
gacgaagcgg attattactg cggtacttac actctgctgt tcacttctaa agtgtttggc   300
ggcggcacga agttaaccgt cctaggtcag cccaaggctg cccctcggt cactctgttc    360
ccgcccctct ctgaggagct tcaagccaac aaggccacac tggtgtgtct cataagtgac   420
ttctacccgg gagccgtgac agtggcctgg aaggcagata gcagcccgt caaggcggga    480
gtggagacca ccacaccctc aaacaaagc aacaacaagt acgcggccag cagctatctg   540
agcctgacgc ctgagcagtg gaagtccac agaagctaca gctgccaggt cacgcatgaa   600
gggagcaccg tggagaagac agtggcccct acagaatgtt ca                      642
```

| | | |
|---|---|---|
| SEQ ID NO: 76 | moltype = AA  length = 10 | |
| FEATURE | Location/Qualifiers | |
| REGION | 1..10 | |
| | note = source = /note="Description of Artificial Sequence: Synthetic peptide" | |
| source | 1..10 | |
| | mol_type = protein | |
| | organism = synthetic construct | |

```
SEQUENCE: 76
GYSFTSYWIA                                                           10
```

| | | |
|---|---|---|
| SEQ ID NO: 77 | moltype = AA  length = 17 | |
| FEATURE | Location/Qualifiers | |
| REGION | 1..17 | |
| | note = source = /note="Description of Artificial Sequence: Synthetic peptide" | |
| source | 1..17 | |
| | mol_type = protein | |
| | organism = synthetic construct | |

```
SEQUENCE: 77
RIDPDNSYTR YSPSFQG                                                   17
```

| | | |
|---|---|---|
| SEQ ID NO: 78 | moltype = AA  length = 17 | |
| FEATURE | Location/Qualifiers | |
| REGION | 1..17 | |
| | note = source = /note="Description of Artificial Sequence: Synthetic peptide" | |
| source | 1..17 | |
| | mol_type = protein | |
| | organism = synthetic construct | |

```
SEQUENCE: 78
WLSPGYALGE QPAGMDH                                                   17
```

| | | |
|---|---|---|
| SEQ ID NO: 79 | moltype = AA  length = 5 | |
| FEATURE | Location/Qualifiers | |
| REGION | 1..5 | |
| | note = source = /note="Description of Artificial Sequence: | |

```
                       Synthetic peptide"
source                 1..5
                       mol_type = protein
                       organism = synthetic construct
SEQUENCE: 79
SYWIA                                                                     5

SEQ ID NO: 80          moltype = AA  length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 80
GYSFTSY                                                                   7

SEQ ID NO: 81          moltype = AA  length = 6
FEATURE                Location/Qualifiers
REGION                 1..6
                       note = source = /note="Description of Artificial Sequence:
                       Synthetic peptide"
source                 1..6
                       mol_type = protein
                       organism = synthetic construct
SEQUENCE: 81
DPDNSY                                                                    6

SEQ ID NO: 82          moltype = AA  length = 8
FEATURE                Location/Qualifiers
REGION                 1..8
                       note = source = /note="Description of Artificial Sequence:
                       Synthetic peptide"
source                 1..8
                       mol_type = protein
                       organism = synthetic construct
SEQUENCE: 82
GYSFTSYW                                                                  8

SEQ ID NO: 83          moltype = AA  length = 8
FEATURE                Location/Qualifiers
REGION                 1..8
                       note = source = /note="Description of Artificial Sequence:
                       Synthetic peptide"
source                 1..8
                       mol_type = protein
                       organism = synthetic construct
SEQUENCE: 83
IDPDNSYT                                                                  8

SEQ ID NO: 84          moltype = AA  length = 19
FEATURE                Location/Qualifiers
REGION                 1..19
                       note = source = /note="Description of Artificial Sequence:
                       Synthetic peptide"
source                 1..19
                       mol_type = protein
                       organism = synthetic construct
SEQUENCE: 84
ARWLSPGYAL GEQPAGMDH                                                     19

SEQ ID NO: 85          moltype = AA  length = 126
FEATURE                Location/Qualifiers
REGION                 1..126
                       note = source = /note="Description of Artificial Sequence:
                       Synthetic polypeptide"
source                 1..126
                       mol_type = protein
                       organism = synthetic construct
SEQUENCE: 85
QVQLVQSGAE VKKPGESLKI SCKGSGYSFT SYWIAWVRQM PGKGLEWMGR IDPDNSYTRY         60
SPSFQGQVTI SADKSISTAY LQWSSLKASD TAMYYCARWL SPGYALGEQP AGMDHWGQGT        120
LVTVSS                                                                  126

SEQ ID NO: 86          moltype = DNA  length = 378
FEATURE                Location/Qualifiers
misc_feature           1..378
                       note = source = /note="Description of Artificial Sequence:
```

```
                            Synthetic polynucleotide"
source                      1..378
                            mol_type = other DNA
                            organism = synthetic construct
SEQUENCE: 86
caggtgcaat tggtgcagag cggtgcggaa gtgaaaaaac cgggcgaaag cctgaaaatt   60
agctgcaaag gctccggata tagcttcact tcttactgga tcgcttgggt gcgccagatg  120
ccgggcaaag gtctcgagtg gatgggccgt atcgacccgg acaacagcta cacccgttat  180
agcccgagct ttcagggcca ggtgaccatt agcgcggata aaagcatcag caccgcgtat  240
ctgcaatgga gcagcctgaa agcgagcgat accgcgatgt attattgcgc gcgttggctg  300
tctccgggtt acgctctggg tgaacagccg gctggtatgg atcattgggg ccaaggcacc  360
ctggtgactg ttagctca                                                378

SEQ ID NO: 87               moltype = AA  length = 456
FEATURE                     Location/Qualifiers
REGION                      1..456
                            note = source = /note="Description of Artificial Sequence:
                            Synthetic polypeptide"
source                      1..456
                            mol_type = protein
                            organism = synthetic construct
SEQUENCE: 87
QVQLVQSGAE VKKPGESLKI SCKGSGYSFT SYWIAWVRQM PGKGLEWMGR IDPDNSYTRY   60
SPSFQGVTI  SADKSISTAY LQWSSLKASD TAMYYCARWL SPGYALGEQP AGMDHWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                            456

SEQ ID NO: 88               moltype = DNA  length = 1368
FEATURE                     Location/Qualifiers
misc_feature                1..1368
                            note = source = /note="Description of Artificial Sequence:
                            Synthetic polynucleotide"
source                      1..1368
                            mol_type = other DNA
                            organism = synthetic construct
SEQUENCE: 88
caggtgcaat tggtgcagag cggtgcggaa gtgaaaaaac cgggcgaaag cctgaaaatt   60
agctgcaaag gctccggata tagcttcact tcttactgga tcgcttgggt gcgccagatg  120
ccgggcaaag gtctcgagtg gatgggccgt atcgacccgg acaacagcta cacccgttat  180
agcccgagct ttcagggcca ggtgaccatt agcgcggata aaagcatcag caccgcgtat  240
ctgcaatgga gcagcctgaa agcgagcgat accgcgatgt attattgcgc gcgttggctg  300
tctccgggtt acgctctggg tgaacagccg gctggtatgg atcattgggg ccaaggcacc  360
ctggtgactg ttagctcagc ctccaccaag ggtccatcgg tcttccccct ggcaccctcc  420
tccaagagca cctctggggg cacagcggcc ctgggctgcc tggtcaagga ctacttcccc  480
gaaccggtga cggtgtcgtg gaactcaggc gccctgacca gcggcgtgca cacctttccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagagag ttgagcccaa atcttgtgac aaaactcaca catgcccacc gtgcccagca  720
cctgaagcag cggggggacc gtcagtcttc ctcttccccc caaaacccaa ggacaccctc  780
atgatctccc ggacccctga ggtcacatgc gtggtggtgg acgtgagcca cgaagaccct  840
gaggtcaagt tcaactggta cgtggacggc gtggaggtgc ataatgccaa gacaaagccg  900
cgggaggagc agtacaacag cacgtaccgg gtggtcagcg tcctcaccgt cctgcaccag  960
gactggctga atggcaagga gtacaagtgc aaggtctcca acaaagccct cccagccccc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctacag caagctcacc 1260
gtggacaaga gcaggtggca gcaggggaac gtcttctcat gctccgtgat gcatgaggct 1320
ctgcacaacc actacacgca gaagagcctc tccctgtctc cgggtaaa             1368

SEQ ID NO: 89               moltype = AA  length = 14
FEATURE                     Location/Qualifiers
REGION                      1..14
                            note = source = /note="Description of Artificial Sequence:
                            Synthetic peptide"
source                      1..14
                            mol_type = protein
                            organism = synthetic construct
SEQUENCE: 89
TGSSSNIGAG YAVH                                                     14

SEQ ID NO: 90               moltype = AA  length = 7
FEATURE                     Location/Qualifiers
REGION                      1..7
                            note = source = /note="Description of Artificial Sequence:
```

```
                            Synthetic peptide"
source                 1..7
                       mol_type = protein
                       organism = synthetic construct
SEQUENCE: 90
SNNKRPS                                                                     7

SEQ ID NO: 91          moltype = AA  length = 11
FEATURE                Location/Qualifiers
REGION                 1..11
                       note = source = /note="Description of Artificial Sequence:
                            Synthetic peptide"
source                 1..11
                       mol_type = protein
                       organism = synthetic construct
SEQUENCE: 91
QSYDLQKSSR V                                                               11

SEQ ID NO: 92          moltype = AA  length = 10
FEATURE                Location/Qualifiers
REGION                 1..10
                       note = source = /note="Description of Artificial Sequence:
                            Synthetic peptide"
source                 1..10
                       mol_type = protein
                       organism = synthetic construct
SEQUENCE: 92
SSSNIGAGYA                                                                 10

SEQ ID NO: 93          moltype =   length =
SEQUENCE: 93
000

SEQ ID NO: 94          moltype = AA  length = 8
FEATURE                Location/Qualifiers
REGION                 1..8
                       note = source = /note="Description of Artificial Sequence:
                            Synthetic peptide"
source                 1..8
                       mol_type = protein
                       organism = synthetic construct
SEQUENCE: 94
YDLQKSSR                                                                    8

SEQ ID NO: 95          moltype = AA  length = 9
FEATURE                Location/Qualifiers
REGION                 1..9
                       note = source = /note="Description of Artificial Sequence:
                            Synthetic peptide"
source                 1..9
                       mol_type = protein
                       organism = synthetic construct
SEQUENCE: 95
SSNIGAGYA                                                                   9

SEQ ID NO: 96          moltype = AA  length = 111
FEATURE                Location/Qualifiers
REGION                 1..111
                       note = source = /note="Description of Artificial Sequence:
                            Synthetic polypeptide"
source                 1..111
                       mol_type = protein
                       organism = synthetic construct
SEQUENCE: 96
DIVLTQPPSV SGAPGQRVTI SCTGSSSNIG AGYAVHWYQQ LPGTAPKLLI YSNNKRPSGV           60
PDRFSGSKSG TSASLAITGL QAEDEADYYC QSYDLQKSSR VFGGGTKLTV L                  111

SEQ ID NO: 97          moltype = DNA  length = 333
FEATURE                Location/Qualifiers
misc_feature           1..333
                       note = source = /note="Description of Artificial Sequence:
                            Synthetic polynucleotide"
source                 1..333
                       mol_type = other DNA
                       organism = synthetic construct
SEQUENCE: 97
gatatcgtgc tgacccagcc gccgagcgtg agcggtgcac cgggccagcg cgtgaccatt           60
agctgtaccg gcagcagcag caacattggt gctggttacg ctgtgcattg gtaccagcag         120
ctgccgggca cggcgccgaa actgctgatc tactctaaca acaaacgccc gagcggcgtg         180
```

```
ccggatcgct ttagcggatc caaaagcggc accagcgcca gcctggcgat taccggcctg    240
caagcagaag acgaagcgga ttattactgc cagtcttacg acctgcagaa atcttctcgt    300
gtgtttggcg gcggcacgaa gttaaccgtc cta                                 333
```

```
SEQ ID NO: 98              moltype = AA   length = 217
FEATURE                    Location/Qualifiers
REGION                     1..217
                           note = source = /note="Description of Artificial Sequence:
                             Synthetic polypeptide"
source                     1..217
                           mol_type = protein
                           organism = synthetic construct
SEQUENCE: 98
DIVLTQPPSV SGAPGQRVTI SCTGSSSNIG AGYAVHWYQQ LPGTAPKLLI YSNNKRPSGV    60
PDRFSGSKSG TSASLAITGL QAEDEADYYC QSYDLQKSSR VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 99              moltype = DNA   length = 651
FEATURE                    Location/Qualifiers
misc_feature               1..651
                           note = source = /note="Description of Artificial Sequence:
                             Synthetic polynucleotide"
source                     1..651
                           mol_type = other DNA
                           organism = synthetic construct
SEQUENCE: 99
gatatcgtgc tgacccagcc gccgagcgtg agcggtgcac cgggccagcg cgtgaccatt    60
agctgtaccg gcagcagcag caacattggt gctggttacg ctgtgcattg gtaccagcag    120
ctgccgggca cggcgccgaa actgctgatc tactctaaca acaaacgccc gagcggcgtg    180
ccggatcgct ttagcggatc caaaagcggc accagcgcca gcctggcgat taccggcctg    240
caagcagaag acgaagcgga ttattactgc cagtcttacg acctgcagaa atcttctcgt    300
gtgtttggcg gcggcacgaa gttaaccgtc ctaggtcagc ccaaggctgc ccctcggtc     360
actctgttcc cgccctcctc tgaggagctt caagccacaa aggccacact ggtgtgtctc    420
ataagtgact tctacccggg agccgtgaca gtggcctgga aggcagatag cagcccggtc    480
aaggcgggag tggagaccac cacacccctc aaacaaagca caacaagta cgcggccagc    540
agctatctga gctgacgcc tgagcagtgg aagtcccaca gaagctacag ctgccaggtc    600
acgcatgaag ggagcaccgt ggagaagaca gtggccccta cagaatgttc a             651

SEQ ID NO: 100             moltype = AA   length = 17
FEATURE                    Location/Qualifiers
REGION                     1..17
                           note = source = /note="Description of Artificial Sequence:
                             Synthetic peptide"
source                     1..17
                           mol_type = protein
                           organism = synthetic construct
SEQUENCE: 100
SISSSGQSTY YADSVKG                                                   17

SEQ ID NO: 101             moltype = AA   length = 6
FEATURE                    Location/Qualifiers
REGION                     1..6
                           note = source = /note="Description of Artificial Sequence:
                             Synthetic peptide"
source                     1..6
                           mol_type = protein
                           organism = synthetic construct
SEQUENCE: 101
SSSGQS                                                                6

SEQ ID NO: 102             moltype = AA   length = 8
FEATURE                    Location/Qualifiers
REGION                     1..8
                           note = source = /note="Description of Artificial Sequence:
                             Synthetic peptide"
source                     1..8
                           mol_type = protein
                           organism = synthetic construct
SEQUENCE: 102
ISSSGQST                                                              8

SEQ ID NO: 103             moltype = AA   length = 121
FEATURE                    Location/Qualifiers
REGION                     1..121
                           note = source = /note="Description of Artificial Sequence:
                             Synthetic polypeptide"
source                     1..121
                           mol_type = protein
```

```
                         organism = synthetic construct
SEQUENCE: 103
EVQLLESGGG LVQPGGSLRL SCAASGFTFN THYIHWVRQA PGKGLEWVSS ISSSGQSTYY    60
ADSVKGRFTI SRDNSKNTLY LQMNSLRAED TAVYYCARER GYVYYHMFDP WGQGTLVTVS   120
S                                                                  121

SEQ ID NO: 104           moltype = DNA  length = 363
FEATURE                  Location/Qualifiers
misc_feature             1..363
                         note = source = /note="Description of Artificial Sequence:
                         Synthetic polynucleotide"
source                   1..363
                         mol_type = other DNA
                         organism = synthetic construct
SEQUENCE: 104
gaggtgcaat tgctggaaag cggcggtggc ctggtgcagc cgggtggcag cctgcgtctg    60
agctgcgcgg cgtccggatt cacctttaac actcattaca tccattgggt gcgccaggcc   120
cccggcaaag gtctcgagtg ggtttcctct atctcttctt ctggccagtc tacttactat   180
gcggatagcg tgaaaggccg ctttaccatc agccgcgata attcgaaaaa caccctgtat   240
ctgcaaatga acagcctgcg tgcggaagat acggccgtgt attattgcgc gcgtgaacgt   300
ggttacgttt actaccatat gttcgatccg tggggccaag caccctggt gactgttagc    360
tca                                                                363

SEQ ID NO: 105           moltype = AA  length = 451
FEATURE                  Location/Qualifiers
REGION                   1..451
                         note = source = /note="Description of Artificial Sequence:
                         Synthetic polypeptide"
source                   1..451
                         mol_type = protein
                         organism = synthetic construct
SEQUENCE: 105
EVQLLESGGG LVQPGGSLRL SCAASGFTFN THYIHWVRQA PGKGLEWVSS ISSSGQSTYY    60
ADSVKGRFTI SRDNSKNTLY LQMNSLRAED TAVYYCARER GYVYYHMFDP WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 106           moltype = DNA  length = 1353
FEATURE                  Location/Qualifiers
misc_feature             1..1353
                         note = source = /note="Description of Artificial Sequence:
                         Synthetic polynucleotide"
source                   1..1353
                         mol_type = other DNA
                         organism = synthetic construct
SEQUENCE: 106
gaggtgcaat tgctggaaag cggcggtggc ctggtgcagc cgggtggcag cctgcgtctg    60
agctgcgcgg cgtccggatt cacctttaac actcattaca tccattgggt gcgccaggcc   120
cccggcaaag gtctcgagtg ggtttcctct atctcttctt ctggccagtc tacttactat   180
gcggatagcg tgaaaggccg ctttaccatc agccgcgata attcgaaaaa caccctgtat   240
ctgcaaatga acagcctgcg tgcggaagat acggccgtgt attattgcgc gcgtgaacgt   300
ggttacgttt actaccatat gttcgatccg tggggccaag caccctggt gactgttagc    360
tcagcctcca ccaagggtcc atcggtcttc cccctggcac cctcctccaa gagcacctct   420
gggggcacag cggccctggg ctgcctggtc aaggactact ccccgaacc ggtgacggtg    480
tcgtggaact caggcgccct gaccagcggc gtgcacacct tcccggctgt cctacagtcc   540
tcaggactct actccctcag cagcgtggtg accgtgcctc cagcagctt gggcacccag    600
acctacatct gcaacgtgaa tcacaagccc agcaacacca aggtggacaa gagagttgag   660
cccaaatctt gtgacaaaac tcacacatgc ccaccgtgcc cagcacctga gcagcgggg    720
ggaccgtcag tcttcctctt ccccccaaaa cccaaggaca cctcatgat ctcccggacc    780
cctgaggtca catgcgtggt ggtggacgtg agccacgaag acctgaggt caagttcaac    840
tggtacgtgg acggcgtgga ggtgcataat gccaagacaa agccgcggga ggagcagtac   900
aacagcacgt accgggtggt cagcgtcctc accgtcctgc accaggactg gctgaatggc   960
aaggagtaca agtgcaaggt ctccaacaaa gcccctccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                              1353

SEQ ID NO: 107           moltype = DNA  length = 363
FEATURE                  Location/Qualifiers
misc_feature             1..363
                         note = source = /note="Description of Artificial Sequence:
                         Synthetic polynucleotide"
```

```
source                  1..363
                        mol_type = other DNA
                        organism = synthetic construct
SEQUENCE: 107
gaagtgcagc tgcttgagtc cggggggtgga ctggtgcagc cggaggatc cctgcgcctg    60
agctgcgctg catccggctt caccttcaac acgcactaca tccattgggt cagacaggcc   120
ccaggaaaag gcctgaatg ggtgtcctcc atctcctcgt cggggcagtc aacctactac    180
gcggactccg tcaagggccg gtttaccatt agccgggaca cagcaagaa tacccctgtac  240
ctccaaatga actcgctgag ggccgaagat accgccgtgt attactgtgc ccgcgagaga   300
ggctacgtgt actaccacat gttcgacccg tggggacagg gtactctcgt gactgtgtct   360
tct                                                                  363

SEQ ID NO: 108          moltype = AA  length = 451
FEATURE                 Location/Qualifiers
REGION                  1..451
                        note = source = /note="Description of Artificial Sequence:
                        Synthetic polypeptide"
source                  1..451
                        mol_type = protein
                        organism = synthetic construct
SEQUENCE: 108
EVQLLESGGG LVQPGGSLRL SCAASGFTFN THYIHWVRQA PGKGLEWVSS ISSSGQSTYY    60
ADSVKGRFTI SRDNSKNTLY LQMNSLRAED TAVYYCARER GYVYYHMFDP WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVAV SHEDPEVKFN WYVDGVEVHN AKTKPREEQY   300
NSTYRVVSVL TVLHQDWLNG KEYKCKVSNK ALAAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                   451

SEQ ID NO: 109          moltype = DNA  length = 1353
FEATURE                 Location/Qualifiers
misc_feature            1..1353
                        note = source = /note="Description of Artificial Sequence:
                        Synthetic polynucleotide"
source                  1..1353
                        mol_type = other DNA
                        organism = synthetic construct
SEQUENCE: 109
gaagtgcagc tgcttgagtc cggggggtgga ctggtgcagc cggaggatc cctgcgcctg    60
agctgcgctg catccggctt caccttcaac acgcactaca tccattgggt cagacaggcc   120
ccaggaaaag gcctggaatg ggtgtcctcc atctcctcgt cggggcagtc aacctactac   180
gcggactccg tcaagggccg gtttaccatt agccgggaca cagcaagaa tacccctgtac  240
ctccaaatga actcgctgag ggccgaagat accgccgtgt attactgtgc ccgcgagaga   300
ggctacgtgt actaccacat gttcgacccg tggggacagg gtactctcgt gactgtgtct   360
tctgcgagca ctaagggccc gtcagtgttc ccgctggctc catcgtcgaa gtccacctcc   420
ggaggaaccg cagcactcgg ttgcctggtc aaggactact ccctgagcc agtgaccgtg   480
tcgtggaaca gcggagccct gacttccggc gtgcacactt ttcccgcggt gctgcagtcc   540
tccggtctgt actccctttc gtccgtggtc accgtgccgt cgtctagcct gggcacccag   600
acctacatct gcaacgtgaa ccacaagccg tccaacacca agtgggataa gcgggtgggag  660
ccgaagtcct gcgataagac acacacgtgc ccgccatgtc cagcgcctga attgcttggc   720
ggaccttccg tgttcctgtt cccgcctaag cccaaggaca ccttgatgat tagccggact   780
cccgaagtca cctgtgtggt ggtggcagtg tcccacgagg accccgaggt caagtttaat   840
tggtacgtgg acggcgtcga agtgcacaac gccaagacta gccccgggga ggaacagtac   900
aacagcacct accgggtcgt gtccgtgctg accgtgctgc accaggactg gctgaatggg   960
aaagagtaca gtgcaaagt gtccaacaag gccttggccg ctcctatcga aaaaactatc   1020
agcaaggcta agggacagcc gagggaaccc aagtctaca ccctgccccc ttcacgcgaa   1080
gagatgacca agaatcaagt gtcgctgacc tgcctcgtca agggattcta cccctccgac  1140
attgcggtgg agtgggagtc caacggccag ccggagaaca actacaagac tactccgccc  1200
gtgctggact ccgacggcag cttcttcctg tattccaagc tgaccgtgga caagtccgg   1260
tggcagcaag gaaacgtgtt ctcctgctcg gtcatgcacg aagccctgca caaccactat   1320
acgcagaagt ccctgtcctt gagcccgggg aaa                                 1353

SEQ ID NO: 110          moltype = DNA  length = 324
FEATURE                 Location/Qualifiers
misc_feature            1..324
                        note = source = /note="Description of Artificial Sequence:
                        Synthetic polynucleotide"
source                  1..324
                        mol_type = other DNA
                        organism = synthetic construct
SEQUENCE: 110
gacatcgtgc tgactcagtc ccctgcgact ctgagcctgt caccgggaga acgggccacc    60
ctctcttgcc gcgcctccca atccattact cggaactacc tggcctggta tcagcagaag   120
ccaggacagg cccctaggct tctgatctac ggggccagct caagagcaac tggcatcccg   180
gctcgcttct ccggttcggg aagcggcacc gacttcaccc tgacaatttc gtccctcgaa   240
cccgaggatt tcgccgtgta ctactgccaa cagcactcca gtaccccccg gacctttggg   300
cagggaacca aagtcgagat caag                                            324
```

```
SEQ ID NO: 111          moltype = DNA   length = 645
FEATURE                 Location/Qualifiers
misc_feature            1..645
                        note = source = /note="Description of Artificial Sequence:
                        Synthetic polynucleotide"
source                  1..645
                        mol_type = other DNA
                        organism = synthetic construct
SEQUENCE: 111
gacatcgtgc tgactcagtc ccctgcgact ctgagcctgt caccgggaga acgggccacc   60
ctctcttgcc gcgcctccca atccattact cggaactacc tggcctggta tcagcagaag  120
ccaggacagg cccctaggct tctgatctac ggggccagct caagagcaac tggcatcccg  180
gctcgcttct ccggttcggg aagcggcacc gacttcaccc tgacaatttc gtccctcgaa  240
cccgaggatt tcgccgtgta ctactgccaa cagcactcca tgtaccccog gacctttggg  300
cagggaacca aagtcgagat caagcgtacg gtggccgctc ccagcgtgtt catcttcccc  360
cccagcgacg agcagctgaa gagcggcacc gccagcgtgg tgtgcctgct gaacaacttc  420
taccccoggg aggccaaggt gcagtggaag gtggacaacg ccctgcagag cggcaacagc  480
caggagagcg tcaccgagca ggacagcaag gactccacct acagcctgag cagcaccctg  540
accctgagca aggccgacta cgagaagcat aaggtgtacg cctgcgaggt gacccaccag  600
ggcctgtcca gccccgtgac caagagcttc aacaggggcg agtgc            645

SEQ ID NO: 112          moltype = AA   length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 112
GFTFSTHYIH                                                          10

SEQ ID NO: 113          moltype = AA   length = 7
FEATURE                 Location/Qualifiers
REGION                  1..7
                        note = source = /note="Description of Artificial Sequence:
                        Synthetic peptide"
source                  1..7
                        mol_type = protein
                        organism = synthetic construct
SEQUENCE: 113
GFTFSTH                                                             7

SEQ ID NO: 114          moltype = AA   length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 114
GFTFSTHY                                                            8

SEQ ID NO: 115          moltype = AA   length = 121
FEATURE                 Location/Qualifiers
REGION                  1..121
                        note = source = /note="Description of Artificial Sequence:
                        Synthetic polypeptide"
source                  1..121
                        mol_type = protein
                        organism = synthetic construct
SEQUENCE: 115
EVQLLESGGG LVQPGGSLRL SCAASGFTFS THYIHWVRQA PGKGLEWVSS ISSSGQSTYY   60
ADSVKGRFTI SRDNSKNTLY LQMNSLRAED TAVYYCARER GYVYYHMFDP WGQGTLVTVS  120
S                                                                  121

SEQ ID NO: 116          moltype = DNA   length = 363
FEATURE                 Location/Qualifiers
misc_feature            1..363
                        note = source = /note="Description of Artificial Sequence:
                        Synthetic polynucleotide"
source                  1..363
                        mol_type = other DNA
                        organism = synthetic construct
SEQUENCE: 116
gaagtgcagc tgcttgagtc cggggggtgga ctggtgcagc ccggaggatc cctgcgcctg   60
agctgcgctg catccggctt caccttcagc acgcactaca tccattgggt cagacaggcc  120
ccaggaaaag gcctggaatg ggtgtcctcc atctcctcgt cggggcagtc aacctactac  180
```

```
gcggactccg tcaagggccg gtttaccatt agccgggaca acagcaagaa taccctgtac    240
ctccaaatga actcgctgag ggccgaagat accgccgtgt attactgtgc ccgcgagaga    300
ggctacgtgt actaccacat gttcgacccg tggggacagg gtactctcgt gactgtgtct    360
tct                                                                 363
```

| | |
|---|---|
| SEQ ID NO: 117 | moltype = AA   length = 451 |
| FEATURE | Location/Qualifiers |
| REGION | 1..451 |
| | note = source = /note="Description of Artificial Sequence: Synthetic polypeptide" |
| source | 1..451 |
| | mol_type = protein |
| | organism = synthetic construct |

```
SEQUENCE: 117
EVQLLESGGG LVQPGGSLRL SCAASGFTFS THYIHWVRQA PGKGLEWVSS ISSSGQSTYY    60
ADSVKGRFTI SRDNSKNTLY LQMNSLRAED TAVYYCARER GYVYYHMFDP WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVAV SHEDPEVKFN WYVDGVEVHN AKTKPREEQY   300
NSTYRVVSVL TVLHQDWLNG KEYKCKVSNK ALAAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451
```

| | |
|---|---|
| SEQ ID NO: 118 | moltype = DNA   length = 1353 |
| FEATURE | Location/Qualifiers |
| misc_feature | 1..1353 |
| | note = source = /note="Description of Artificial Sequence: Synthetic polynucleotide" |
| source | 1..1353 |
| | mol_type = other DNA |
| | organism = synthetic construct |

```
SEQUENCE: 118
gaagtgcagc tgcttgagtc cggggggtgga ctggtgcagc ccggaggatc cctgcgcctg    60
agctgcgctg catccggctt caccttcagc acgcactaca tccattgggt cagacaggcc   120
ccaggaaaag gcctggaatg ggtgtcctcc atctcctcgt cggggcagtc aacctactac   180
gcggactccg tcaagggccg gtttaccatt agccgggaca acagcaagaa taccctgtac   240
ctccaaatga actcgctgag ggccgaagat accgccgtgt attactgtgc ccgcgagaga   300
ggctacgtgt actaccacat gttcgacccg tggggacagg gtactctcgt gactgtgtct   360
tctgcgagca ctaagggccc gtcagtgttc cgcctgcctc catcgtcgaa gtccacctcc   420
ggaggaaccg cagcactcgg ttgcctggtc aaggactact ccctgagcc agtgaccgtg   480
tcgtggaaca gcggagccct gacttccggc gtgcacactt ttcccgcggt gctgcagtcc   540
tccggtctgt actcccttc gtccgtggtc accgtgccgt cgtctagcct gggcacccag   600
acctacatct gcaacgtgaa ccacaagccg tccaacacca aagtggataa gcgggtggag   660
ccgaagtcct gcgataagac acacgtgc ccgccatgtc cagcgcctga attgcttggc   720
ggaccttccg tgttcctgtt cccgcctaag cccaaggaca ccttgatgat tagccggact   780
cccgaagtca cctgtgtggt ggtggcagtg tcccacgagg accccgaggt caagttaat   840
tggtacgtgg acggcgtcga agtgcacaac gccaagacta aggccccgga ggaacagtac   900
aacagcacct accgggtcgt gtccgtgctg accgtgctgc accaggactg gctgaatggg   960
aaagagtaca agtgcaaagt gtccaacaag gccttggccg ctcctatcga aaaaactatc  1020
agcaaggcta agggacagcc gagggaaccc caagtctaca ccctgccccc ttcacgcgaa  1080
gagatgacca agaatcaagt gtcgctgacc tgcctcgtca agggattcta ccctccgac  1140
attgcggtgg agtgggagtc caacggccag cccgagaaca actacaagac tactccgccc  1200
gtgctggact ccgacggcag cttcttcctg tattccaagc tgaccgtgga caagtcccgg  1260
tggcagcaag gaaacgtgtt ctcctgctcg gtcatgcacg aagccctgca caaccactat  1320
acgcagaagt ccctgtcctt gagcccgggg aaa                               1353
```

| | |
|---|---|
| SEQ ID NO: 119 | moltype = AA   length = 17 |
| FEATURE | Location/Qualifiers |
| REGION | 1..17 |
| | note = source = /note="Description of Artificial Sequence: Synthetic peptide" |
| source | 1..17 |
| | mol_type = protein |
| | organism = synthetic construct |

```
SEQUENCE: 119
VIESKGNYIF YADSVKG                                                   17
```

| | |
|---|---|
| SEQ ID NO: 120 | moltype = AA   length = 6 |
| FEATURE | Location/Qualifiers |
| REGION | 1..6 |
| | note = source = /note="Description of Artificial Sequence: Synthetic peptide" |
| source | 1..6 |
| | mol_type = protein |
| | organism = synthetic construct |

```
SEQUENCE: 120
ESKGNY                                                                6
```

| | |
|---|---|
| SEQ ID NO: 121 | moltype = AA   length = 8 |

```
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 121
IESKGNYI                                                                           8

SEQ ID NO: 122          moltype = AA  length = 125
FEATURE                 Location/Qualifiers
REGION                  1..125
                        note = source = /note="Description of Artificial Sequence:
                        Synthetic polypeptide"
source                  1..125
                        mol_type = protein
                        organism = synthetic construct
SEQUENCE: 122
EVQLLESGGG LVQPGGSLRL SCAASGFTFS SYWMNWVRQA PGKGLEWVSV IESKGNYIFY        60
ADSVKGRFTI SRDNSKNTLY LQMNSLRAED TAVYYCARDR YSMIYSYGAG AFDYWGQGTL       120
VTVSS                                                                  125

SEQ ID NO: 123          moltype = DNA  length = 375
FEATURE                 Location/Qualifiers
misc_feature            1..375
                        note = source = /note="Description of Artificial Sequence:
                        Synthetic polynucleotide"
source                  1..375
                        mol_type = other DNA
                        organism = synthetic construct
SEQUENCE: 123
gaggtgcaat tgctggaaag cggcggtggc ctggtgcagc cgggtggcag cctgcgtctg        60
agctgcgcgg cgtccggatt cacctttttct tcttactgga tgaactgggt gcgccaggcc     120
ccgggcaaag gtctcgagtg ggtttccgtt atcgaatcta aaggcaacta catcttctat      180
gcggatagcg tgaaaggccg ctttaccatc agccgcgata attcgaaaaa cacccctgtat    240
ctgcaaatga acagcctgcg tgcggaagat acggccgtgt attattgcgc gcgtgaccgt     300
tactctatga tctactctta cggtgctggt gctttcgatt actggggcca aggcaccctg     360
gtgactgtta gctca                                                      375

SEQ ID NO: 124          moltype = AA  length = 455
FEATURE                 Location/Qualifiers
REGION                  1..455
                        note = source = /note="Description of Artificial Sequence:
                        Synthetic polypeptide"
source                  1..455
                        mol_type = protein
                        organism = synthetic construct
SEQUENCE: 124
EVQLLESGGG LVQPGGSLRL SCAASGFTFS SYWMNWVRQA PGKGLEWVSV IESKGNYIFY        60
ADSVKGRFTI SRDNSKNTLY LQMNSLRAED TAVYYCARDR YSMIYSYGAG AFDYWGQGTL       120
VTVSSASTKG PSVFPLAPSS KSTSGGTAAL GCLVKDYFPE PVTVSWNSGA LTSGVHTFPA       180
VLQSSGLYSL SSVVTVPSSS LGTQTYICNV NHKPSNTKVD KRVEPKSCDK THTCPPCPAP       240
EAAGGPSVFL FPPKPKDTLM ISRTPEVTCV VVDVSHEDPE VKFNWYVDGV EVHNAKTKPR       300
EEQYNSTYRV VSVLTVLHQD WLNGKEYKCK VSNKALPAPI EKTISKAKGQ PREPQVYTLP       360
PSREEMTKNQ VSLTCLVKGF YPSDIAVEWE SNGQPENNYK TTPPVLDSDG SFFLYSKLTV       420
DKSRWQQGNV FSCSVMHEAL HNHYTQKSLS LSPGK                                 455

SEQ ID NO: 125          moltype = DNA  length = 1365
FEATURE                 Location/Qualifiers
misc_feature            1..1365
                        note = source = /note="Description of Artificial Sequence:
                        Synthetic polynucleotide"
source                  1..1365
                        mol_type = other DNA
                        organism = synthetic construct
SEQUENCE: 125
gaggtgcaat tgctggaaag cggcggtggc ctggtgcagc cgggtggcag cctgcgtctg        60
agctgcgcgg cgtccggatt cacctttttct tcttactgga tgaactgggt gcgccaggcc     120
ccgggcaaag gtctcgagtg ggtttccgtt atcgaatcta aaggcaacta catcttctat      180
gcggatagcg tgaaaggccg ctttaccatc agccgcgata attcgaaaaa cacccctgtat    240
ctgcaaatga acagcctgcg tgcggaagat acggccgtgt attattgcgc gcgtgaccgt     300
tactctatga tctactctta cggtgctggt gctttcgatt actggggcca aggcaccctg     360
gtgactgtta gctcagcctc caccaagggt ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagagagttg agcccaaatc ttgtgacaaa actcacacat gcccaccgtg cccagcacct     720
```

```
gaagcagcgg ggggaccgtc agtcttcctc ttccccccaa acccaagga cacccctcatg   780
atctcccgga cccctgaggt cacatgcgtg gtggtggacg tgagccacga agaccctgag   840
gtcaagttca actggtacgt ggacggcgtg gaggtgcata atgccaagac aaagccgcgg   900
gaggagcagt acaacagcac gtaccgggtg gtcagcgtcc tcaccgtcct gcaccaggac   960
tggctgaatg gcaaggagta caagtgcaag gtctccaaca aagcccctcc cagcccccatc  1020
gagaaaacca tctccaaagc caaagggcag ccccgagaac cacaggtgta caccctgccc  1080
ccatcccggg aggagatgac caagaaccag gtcagcctga cctgcctggt caaaggcttc  1140
tatcccagcg acatcgccgt ggagtgggag agcaatgggc agccggagaa caactacaag  1200
accacgcctc ccgtgctgga ctccgacggc tccttcttcc tctacagcaa gctcaccgtg  1260
gacaagagca ggtggcagca ggggaacgtc ttctcatgct ccgtgatgca tgaggctctg  1320
cacaaccact acacgcagaa gagcctctcc ctgtctccgg gtaaa                  1365

SEQ ID NO: 126           moltype = AA   length = 9
FEATURE                  Location/Qualifiers
REGION                   1..9
                         note = source = /note="Description of Artificial Sequence:
                         Synthetic peptide"
source                   1..9
                         mol_type = protein
                         organism = synthetic construct
SEQUENCE: 126
QQEWVKPRT                                                             9

SEQ ID NO: 127           moltype = AA   length = 6
FEATURE                  Location/Qualifiers
REGION                   1..6
                         note = source = /note="Description of Artificial Sequence:
                         Synthetic peptide"
source                   1..6
                         mol_type = protein
                         organism = synthetic construct
SEQUENCE: 127
EWVKPR                                                                6

SEQ ID NO: 128           moltype = AA   length = 107
FEATURE                  Location/Qualifiers
REGION                   1..107
                         note = source = /note="Description of Artificial Sequence:
                         Synthetic polypeptide"
source                   1..107
                         mol_type = protein
                         organism = synthetic construct
SEQUENCE: 128
DIQMTQSPSS LSASVGDRVT ITCRASQGIS SYLAWYQQKP GKAPKLLIYT ASTLQSGVPS    60
RFSGSGSGTD FTLTISSLQP EDFATYYCQQ EWVKPRTFGQ GTKVEIK                 107

SEQ ID NO: 129           moltype = DNA   length = 321
FEATURE                  Location/Qualifiers
misc_feature             1..321
                         note = source = /note="Description of Artificial Sequence:
                         Synthetic polynucleotide"
source                   1..321
                         mol_type = other DNA
                         organism = synthetic construct
SEQUENCE: 129
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcacctga ccattagctc tctgcaaccg   240
gaagactttg cgacctatta ttgccagcag gaatgggtta accgcgtac ctttggccag   300
ggcacgaaag ttgaaattaa a                                             321

SEQ ID NO: 130           moltype = AA   length = 214
FEATURE                  Location/Qualifiers
REGION                   1..214
                         note = source = /note="Description of Artificial Sequence:
                         Synthetic polypeptide"
source                   1..214
                         mol_type = protein
                         organism = synthetic construct
SEQUENCE: 130
DIQMTQSPSS LSASVGDRVT ITCRASQGIS SYLAWYQQKP GKAPKLLIYT ASTLQSGVPS    60
RFSGSGSGTD FTLTISSLQP EDFATYYCQQ EWVKPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 131           moltype = DNA   length = 642
FEATURE                  Location/Qualifiers
misc_feature             1..642
```

|  |  |
|---|---|
|  | note = source = /note="Description of Artificial Sequence: Synthetic polynucleotide" |
| source | 1..642 |
|  | mol_type = other DNA |
|  | organism = synthetic construct |

SEQUENCE: 131

```
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag gaatgggtta aaccgcgtac ctttggccag   300
ggcacgaaaa ttgaaattaa acgtacggtg gccgctccca gcgtgttcat cttcccccca   360
agcgacgagc agctgaagag cggcaccgcc agcgtggtgt gcctgctgaa caacttctac   420
cccccgggag ccaaggtgca gtggaaggtg gacaacgccc tgcagagcgg caacagccag   480
gaaagcgtca ccgagcagga cagcaaggac tccacctaca gcctgagcag cacccctgac   540
ctgagcaagg ccgactacga aagcacaag gtgtacgcct gcgaggtgac ccaccagggc   600
ctgtccagcc ccgtgaccaa gagcttcaac cggggcgagt gt                      642
```

|  |  |
|---|---|
| SEQ ID NO: 132 | moltype = DNA length = 375 |
| FEATURE | Location/Qualifiers |
| misc_feature | 1..375 |
|  | note = source = /note="Description of Artificial Sequence: Synthetic polynucleotide" |
| source | 1..375 |
|  | mol_type = other DNA |
|  | organism = synthetic construct |

SEQUENCE: 132

```
caggtgcaat tgctggaaag cggcggtggc ctggtgcagc cgggtggcag cctgcgtctg    60
agctgcgcgg cgtccggatt caccttttct tcttactgga tgaactgggt gcgccaggcc   120
ccaggcaaag gtctcgagtg ggtttccgct atctcttctg acggttctta cacctactat   180
gcggatagcg tgaaaggccg ctttaccatc agccgcgata ttcgaaaaa caccctgtat   240
ctgcaaatga acagcctgcg tgcggaagat acggccgtgt attattgcgc gcgtgaccgt   300
tactctatga tctactctta cggtgctggt gcttcgatt actggggcca aggcaccctg   360
gtgactgtta gctca                                                     375
```

|  |  |
|---|---|
| SEQ ID NO: 133 | moltype = DNA length = 1365 |
| FEATURE | Location/Qualifiers |
| misc_feature | 1..1365 |
|  | note = source = /note="Description of Artificial Sequence: Synthetic polynucleotide" |
| source | 1..1365 |
|  | mol_type = other DNA |
|  | organism = synthetic construct |

SEQUENCE: 133

```
caggtgcaat tgctggaaag cggcggtggc ctggtgcagc cgggtggcag cctgcgtctg    60
agctgcgcgg cgtccggatt caccttttct tcttactgga tgaactgggt gcgccaggcc   120
ccaggcaaag gtctcgagtg ggtttccgct atctcttctg acggttctta cacctactat   180
gcggatagcg tgaaaggccg ctttaccatc agccgcgata ttcgaaaaa caccctgtat   240
ctgcaaatga acagcctgcg tgcggaagat acggccgtgt attattgcgc gcgtgaccgt   300
tactctatga tctactctta cggtgctggt gcttcgatt actggggcca aggcaccctg   360
gtgactgtta gctcagcctc caccaagggt ccatcggtct tccccctggc accctcctcc   420
aagagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
aagagagttg agcccaaatc ttgtgacaaa actcacacat gcccaccgtg cccagcacct   720
gaagcagcgg ggggaccgtc agtcttcctc ttccccccaa aacccaagga caccctcatg   780
atctcccgga cccctgaggt cacatgcgtg gtggtggacg tgagccacga agaccctgag   840
gtcaagttca actggtacgt ggacggcgtg gaggtgcata atgccaagac aaagccgcgg   900
gaggagcagt acaacagcac gtaccgggtg gtcagcgtcc tcaccgtcct gcaccaggac   960
tggctgaatg gcaaggagta caagtgcaag gtctccaaca aagccctccc agcccccatc  1020
gagaaaacca tctccaaagc caaagggcag ccccgagaac cacaggtgta caccctgccc  1080
ccatcccggg aggagatgac caagaaccag gtcagcctga cctgcctggt caaaggcttc  1140
tatcccagcg acatcgccgt ggagtgggag agcaatgggc agccggagaa caactacaag  1200
accacgcctc ccgtgctgga ctccgacggc tccttcttcc tctacagcaa gctcaccgtg  1260
gacaagagca ggtggcagca ggggaacgtc ttctcatgct ccgtgatgca tgaggctctg  1320
cacaaccact acacgcagaa gagcctctcc ctgtctccgg gtaaa                  1365
```

|  |  |
|---|---|
| SEQ ID NO: 134 | moltype = AA length = 9 |
| FEATURE | Location/Qualifiers |
| REGION | 1..9 |
|  | note = source = /note="Description of Artificial Sequence: Synthetic peptide" |
| source | 1..9 |
|  | mol_type = protein |
|  | organism = synthetic construct |

SEQUENCE: 134
QQTWRKPRT                                                            9

```
SEQ ID NO: 135            moltype = AA   length = 6
FEATURE                   Location/Qualifiers
REGION                    1..6
                          note = source = /note="Description of Artificial Sequence:
                          Synthetic peptide"
source                    1..6
                          mol_type = protein
                          organism = synthetic construct
SEQUENCE: 135
TWRKPR                                                                        6

SEQ ID NO: 136            moltype = AA   length = 107
FEATURE                   Location/Qualifiers
REGION                    1..107
                          note = source = /note="Description of Artificial Sequence:
                          Synthetic polypeptide"
source                    1..107
                          mol_type = protein
                          organism = synthetic construct
SEQUENCE: 136
DIQMTQSPSS LSASVGDRVT ITCRASQGIS SYLAWYQQKP GKAPKLLIYT ASTLQSGVPS              60
RFSGSGSGTD FTLTISSLQP EDFATYYCQQ TWRKPRTFGQ GTKVEIK                            107

SEQ ID NO: 137            moltype = DNA   length = 321
FEATURE                   Location/Qualifiers
misc_feature              1..321
                          note = source = /note="Description of Artificial Sequence:
                          Synthetic polynucleotide"
source                    1..321
                          mol_type = other DNA
                          organism = synthetic construct
SEQUENCE: 137
gatatccaga tgacccagag cccgagcagc ctgagcgcca gcgtgggcga tcgcgtgacc              60
attacctgca gagccagcca gggtatttct tcttacctgg cttggtacca gcagaaaccg              120
ggcaaagcgc cgaaactatt aatctacact gcttctactc tgcaaagcgg cgtgccgagc              180
cgctttagcg gcagcggatc cggcaccgat ttcaccctga ccattagctc tctgcaaccg              240
gaagactttg cgacctatta ttgccagcag acttggcgta aaccgcgtac ctttggccag              300
ggcacgaaag ttgaaattaa a                                                       321

SEQ ID NO: 138            moltype = AA   length = 214
FEATURE                   Location/Qualifiers
REGION                    1..214
                          note = source = /note="Description of Artificial Sequence:
                          Synthetic polypeptide"
source                    1..214
                          mol_type = protein
                          organism = synthetic construct
SEQUENCE: 138
DIQMTQSPSS LSASVGDRVT ITCRASQGIS SYLAWYQQKP GKAPKLLIYT ASTLQSGVPS              60
RFSGSGSGTD FTLTISSLQP EDFATYYCQQ TWRKPRTFGQ GTKVEIKRTV AAPSVFIFPP              120
SDEQLKSGTA SVVCLLNNFY PREAKVQWKV DNALQSGNSQ ESVTEQDSKD STYSLSSTLT              180
LSKADYEKHK VYACEVTHQG LSSPVTKSFN RGEC                                          214

SEQ ID NO: 139            moltype = DNA   length = 642
FEATURE                   Location/Qualifiers
misc_feature              1..642
                          note = source = /note="Description of Artificial Sequence:
                          Synthetic polynucleotide"
source                    1..642
                          mol_type = other DNA
                          organism = synthetic construct
SEQUENCE: 139
gatatccaga tgacccagag cccgagcagc ctgagcgcca gcgtgggcga tcgcgtgacc              60
attacctgca gagccagcca gggtatttct tcttacctgg cttggtacca gcagaaaccg              120
ggcaaagcgc cgaaactatt aatctacact gcttctactc tgcaaagcgg cgtgccgagc              180
cgctttagcg gcagcggatc cggcaccgat ttcaccctga ccattagctc tctgcaaccg              240
gaagactttg cgacctatta ttgccagcag acttggcgta aaccgcgtac ctttggccag              300
ggcacgaaag ttgaaattaa acgtacggtg gccgctccca gcgtgttcat cttccccccc              360
agcgacgagc agctgaagag cggcaccgcc agcgtggtgt gcctgctgaa caacttctac              420
ccccgggagg ccaaggtgca gtggaaggtg gacaacgccc tgcagagcgg caacagccag              480
gaaagcgtca ccgagcagga cagcaaggac tccacctaca gcctgagcag cacccctgacc             540
ctgagcaagg ccgactacga aaagcacaag gtgtacgcct gcgaggtgac ccaccagggc              600
ctgtccagcc ccgtgaccaa gagcttcaac cggggcgagt gt                                642

SEQ ID NO: 140            moltype = DNA   length = 375
FEATURE                   Location/Qualifiers
misc_feature              1..375
                          note = source = /note="Description of Artificial Sequence:
                          Synthetic polynucleotide"
```

```
source                  1..375
                        mol_type = other DNA
                        organism = synthetic construct
SEQUENCE: 140
caagtgcagc tgcttgagag cggtggcgga ctggtgcagc caggggatc cttgcgcctg    60
tcatgcgctg cgtcggggtt caccttctcg tcctactgga tgaactgggt cagacaggct   120
ccggggaagg gactcgaatg ggtgtccgcc atttcctccg acggctccta cacttactac   180
gccgatagcg tcaagggccg gttcaccatc tcccgggaca attcgaagaa caccctgtac   240
ctccaaatga actcactgcg cgccgaggac actgcggtgt attactgtgc ccgggatagg   300
tacagcatga tctactccta cggtgccgga gcctttgact actggggaca gggaacccctt  360
gtgaccgtgt ctagc                                                    375

SEQ ID NO: 141          moltype = AA  length = 455
FEATURE                 Location/Qualifiers
REGION                  1..455
                        note = source = /note="Description of Artificial Sequence:
                        Synthetic polypeptide"
source                  1..455
                        mol_type = protein
                        organism = synthetic construct
SEQUENCE: 141
QVQLLESGGG LVQPGGSLRL SCAASGFTFS SYWMNWVRQA PGKGLEWVSA ISSDGSYTYY    60
ADSVKGRFTI SRDNSKNTLY LQMNSLRAED TAVYYCARDR YSMIYSYGAG AFDYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLGGPSVFL FPPKPKDTLM ISRTPEVTCV VVAVSHEDPE VKFNWYVDGV EVHNAKTKPR   300
EEQYNSTYRV VSVLTVLHQD WLNGKEYKCK VSNKALAAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 142          moltype = DNA  length = 1365
FEATURE                 Location/Qualifiers
misc_feature            1..1365
                        note = source = /note="Description of Artificial Sequence:
                        Synthetic polynucleotide"
source                  1..1365
                        mol_type = other DNA
                        organism = synthetic construct
SEQUENCE: 142
caagtgcagc tgcttgagag cggtggcgga ctggtgcagc caggggatc cttgcgcctg    60
tcatgcgctg cgtcggggtt caccttctcg tcctactgga tgaactgggt cagacaggct   120
ccggggaagg gactcgaatg ggtgtccgcc atttcctccg acggctccta cacttactac   180
gccgatagcg tcaagggccg gttcaccatc tcccgggaca attcgaagaa caccctgtac   240
ctccaaatga actcactgcg cgccgaggac actgcggtgt attactgtgc ccgggatagg   300
tacagcatga tctactccta cggtgccgga gcctttgact actggggaca gggaacccctt  360
gtgaccgtgt ctagcgcgtc cactaagggc ccgtcagtgt tcccgctggc tccatcgtcg   420
aagtccacct ccggaggaac cgcagcactc ggttgcctga tcaaggacta cttccctgag   480
ccagtgaccg tgtcgtggaa cagcggagcc ctgacttccg gcgtgcacac tttttcccgcg  540
gtgctgcagt cctccggtct gtactccctt tcgtccgtgg tcaccgtgcc gtcgtctagc   600
ctgggcaccc agacctacat ctgcaacgtg aaccacaagc cgtccaacac caaagtggat   660
aagcgtgtgg agccgaagtc ctgcgataag acacacactgc gcccgccatg tccagcgcct  720
gaattgcttg gcggaccttc cgtgttcctg ttcccgccta gcccaagga ccttgatg     780
attagccgga ctcccgaagt cacctgtgtg gtggtggcag tgtcccacga ggaccccgag   840
gtcaagtttta attggtacgt ggacggcgtc gaagtgcaca cgccaagac taagcccgg    900
gaggaacagt acaacagcac ctaccgggtc gtgtccgtgc tgaccgtgct gcaccaggac   960
tggctgaatg ggaaagagta caagtgcaaa gtgtccaaca aggccttggc cgctcctatc  1020
gaaaaaacta tcagcaaggc taagggacag ccgagggaac ccaagtcta caccctgccc   1080
ccttcacgcg aagagatgac caagaatcaa gtgtcgctga cctgcctcgt caagggattc   1140
tacccctccg acattgcggt ggagtgggag tccaacggct agcccgagaa caactacaag   1200
actactccgc ccgtgctgga ctccgacggc agcttcttcc tgtattccaa gctgaccgtg   1260
gacaagtccc ggtggcagca aggaaacgtg ttctcctgct cggtcatgca cgaagccctg   1320
cacaaccact atacgcagaa gtccctgtcc ttgagcccgg ggaaa                   1365

SEQ ID NO: 143          moltype = DNA  length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 143
gacatccaga tgacccagtc tccgtcctcc ctgtccgcat cagtggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa acctggcgga agcccaggac atttggccag   300
ggcactaagg tcgagattaa g                                             321
```

```
SEQ ID NO: 144          moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 144
gacatccaga tgacccagtc tccgtcctcc ctgtccgcat cagtggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa acctggcgga agcccaggac atttggccag   300
ggcactaagg tcgagattaa gcgtacggtg gccgctccca gcgtgttcat cttcccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                       642

SEQ ID NO: 145          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 145
QQIWTVPRT                                                              9

SEQ ID NO: 146          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 146
IWTVPR                                                                 6

SEQ ID NO: 147          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 147
DIQMTQSPSS LSASVGDRVT ITCRASQGIS SYLAWYQQKP GKAPKLLIYT ASTLQSGVPS      60
RFSGSGSGTD FTLTISSLQP EDFATYYCQQ IWTVPRTFGQ GTKVEIK                   107

SEQ ID NO: 148          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 148
gatatccaga tgacccagag cccgagcagc ctgagcgcca gcgtgggcga tcgcgtgacc     60
attacctgca gagccagcca gggtatttct tcttacctgg cttggtacca gcagaaaccg    120
ggcaaagcgc cgaaactatt aatctacact gcttctactc tgcaaagcgg cgtgccgagc    180
cgctttagcg gcagcggatc cggcaccgat ttcaccctga ccattagctc tctgcaaccg    240
gaagactttg cgacctatta ttgccagcag atctggactg ttccgcgtac ctttggccag    300
ggcacgaaag ttgaaattaa a                                               321

SEQ ID NO: 149          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
```

```
SEQUENCE: 149
DIQMTQSPSS LSASVGDRVT ITCRASQGIS SYLAWYQQKP GKAPKLLIYT ASTLQSGVPS     60
RFSGSGSGTD FTLTISSLQP EDFATYYCQQ IWTVPRTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 150          moltype = DNA  length = 642
FEATURE                 Location/Qualifiers
misc_feature            1..642
                        note = source = /note="Description of Artificial Sequence:
                          Synthetic polynucleotide"
source                  1..642
                        mol_type = other DNA
                        organism = synthetic construct
SEQUENCE: 150
gatatccaga tgacccagag cccgagcagc ctgagcgcca gcgtgggcga tcgcgtgacc     60
attacctgca gagccagcca gggtatttct tcttacctgg cttggtacca gcagaaaccg    120
ggcaaagcgc cgaaactatt aatctacact gcttctactc tgcaaagcgg cgtgccgagc    180
cgctttagcg gcagcggatc cggcaccgat ttcaccctga ccattagctc tctgcaaccg    240
gaagactttg cgacctatta ttgccagcag atctggactg ttccgcgtac ctttggccag    300
ggcacgaaag ttgaaattaa acgtacggtg gccgctccca gcgtgttcat cttcccccca    360
agcggcgagg agctgaagag cggcaccgcc agcgtggtgt gcctgctgaa caacttctac    420
ccccgggagg ccaaggtgca gtggaaggtg gacaacgccc tgcagagcgg caacagccag    480
gaaagcgtca ccgagcagga cagcaaggac tccacctaca gcctgagcag caccctgacc    540
ctgagcaagg ccgactacga aaagcacaag gtgtacgcct gcgaggtgac ccaccagggc    600
ctgtccagcc ccgtgaccaa gagcttcaac cggggcgagt gt                       642

SEQ ID NO: 151          moltype = AA  length = 17
FEATURE                 Location/Qualifiers
REGION                  1..17
                        note = source = /note="Description of Artificial Sequence:
                          Synthetic peptide"
source                  1..17
                        mol_type = protein
                        organism = synthetic construct
SEQUENCE: 151
SIGGQGGMTL YADSVKG                                                    17

SEQ ID NO: 152          moltype = AA  length = 6
FEATURE                 Location/Qualifiers
REGION                  1..6
                        note = source = /note="Description of Artificial Sequence:
                          Synthetic peptide"
source                  1..6
                        mol_type = protein
                        organism = synthetic construct
SEQUENCE: 152
GGQGGM                                                                6

SEQ ID NO: 153          moltype = AA  length = 8
FEATURE                 Location/Qualifiers
REGION                  1..8
                        note = source = /note="Description of Artificial Sequence:
                          Synthetic peptide"
source                  1..8
                        mol_type = protein
                        organism = synthetic construct
SEQUENCE: 153
IGGQGGMT                                                              8

SEQ ID NO: 154          moltype = AA  length = 121
FEATURE                 Location/Qualifiers
REGION                  1..121
                        note = source = /note="Description of Artificial Sequence:
                          Synthetic polypeptide"
source                  1..121
                        mol_type = protein
                        organism = synthetic construct
SEQUENCE: 154
EVQLLESGGG LVQPGGSLRL SCAASGFTFN THYIHWVRQA PGKGLEWVSS IGGQGGMTLY     60
ADSVKGRFTI SRDNSKNTLY LQMNSLRAED TAVYYCARER GYVYYHMFDP WGQGTLVTVS    120
S                                                                    121

SEQ ID NO: 155          moltype = DNA  length = 363
FEATURE                 Location/Qualifiers
misc_feature            1..363
                        note = source = /note="Description of Artificial Sequence:
                          Synthetic polynucleotide"
source                  1..363
```

```
                        mol_type = other DNA
                        organism = synthetic construct
SEQUENCE: 155
gaggtgcaat tgctggaaag cggcggtggc ctggtgcagc cgggtggcag cctgcgtctg    60
agctgcgcgg cgtccggatt caccctttaac actcattaca tccattgggt gcgccaggcc   120
cccggcaaag gtctcgagtg gtttcctct atcggtggtc agggcggtat gactctgtat    180
gcggatagcg tgaaaggccg ctttaccatc agccgcgata attcgaaaaa caccctgtat    240
ctgcaaatga acagcctgcg tgcggaagat acggccgtgt attattgcgc gcgtgaacgt    300
ggttacgttt actaccatat gttcgatccg tggggccaag caccctggt gactgttagc    360
tca                                                                  363

SEQ ID NO: 156          moltype = AA  length = 451
FEATURE                 Location/Qualifiers
REGION                  1..451
                        note = source = /note="Description of Artificial Sequence:
                        Synthetic polypeptide"
source                  1..451
                        mol_type = protein
                        organism = synthetic construct
SEQUENCE: 156
EVQLLESGGG LVQPGGSLRL SCAASGFTFN THYIHWVRQA PGKGLEWVSS IGGQGGMTLY     60
ADSVKGRFTI SRDNSKNTLY LQMNSLRAED TAVYYCARER GYVYYHMFDP WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKRVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 157          moltype = DNA  length = 1353
FEATURE                 Location/Qualifiers
misc_feature            1..1353
                        note = source = /note="Description of Artificial Sequence:
                        Synthetic polynucleotide"
source                  1..1353
                        mol_type = other DNA
                        organism = synthetic construct
SEQUENCE: 157
gaggtgcaat tgctggaaag cggcggtggc ctggtgcagc cgggtggcag cctgcgtctg    60
agctgcgcgg cgtccggatt caccctttaac actcattaca tccattgggt gcgccaggcc   120
cccggcaaag gtctcgagtg gtttcctct atcggtggtc agggcggtat gactctgtat    180
gcggatagcg tgaaaggccg ctttaccatc agccgcgata attcgaaaaa caccctgtat    240
ctgcaaatga acagcctgcg tgcggaagat acggccgtgt attattgcgc gcgtgaacgt    300
ggttacgttt actaccatat gttcgatccg tggggccaag caccctggt gactgttagc    360
tcagcctcca caagggtcc atcggtcttc ccctggcac cctcctccaa gagcacctct     420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga gcagcgggg    720
ggaccgtcag tcttcctctt ccccccaaaa cccaaggaca cctcatgat ctcccggacc     780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgggtggt cagcgtcctc accgtcctgc accaggactg gctgaatggc    960
aaggagtaca agtgcaaggt ctccaacaaa gccctcccag cccccatcga gaaaaccat   1020
tccaaagcca agggcagccc cgagaaccca ggtgtaca ccctgccccc atccggga      1080
gagatgacca gaaccaggt cagcctgacc tgcctggtca aaggcttcta tcccagcgac   1140
atcgccgtgg agtgggagag caatgggcag ccggagaaca actacaagac cacgcctcc    1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                               1353

SEQ ID NO: 158          moltype = DNA  length = 363
FEATURE                 Location/Qualifiers
misc_feature            1..363
                        note = source = /note="Description of Artificial Sequence:
                        Synthetic polynucleotide"
source                  1..363
                        mol_type = other DNA
                        organism = synthetic construct
SEQUENCE: 158
gaagtgcagc tcctggagtc gggtggcgga ctggtgcagc ctggcggatc actgcggctg     60
tcatgtgccg cgagcgggtt tacttcaac acccactaca tccactgggt ccgcaaagct    120
cccggaaagg gactcgaatg ggtgtcctcc attggtggac agggcggcat gaccctttac    180
gcggatagcg tgaaggggag gttcaccatc tcccgcgaca acagcaagaa cacctctgac   240
ctccaaatga actcgcttcg ggccgaggac actgccgtgt actattgcgc aagagagcgg    300
ggctacgtgt actaccacat gttcgaccca tggggacagg gaacgctggt caccgtgtcc    360
tcc                                                                  363
```

```
SEQ ID NO: 159            moltype = AA   length = 451
FEATURE                   Location/Qualifiers
REGION                    1..451
                          note = source = /note="Description of Artificial Sequence:
                          Synthetic polypeptide"
source                    1..451
                          mol_type = protein
                          organism = synthetic construct
SEQUENCE: 159
EVQLLESGGG LVQPGGSLRL SCAASGFTFN THYIHWVRQA PGKGLEWVSS IGGQGGMTLY    60
ADSVKGRFTI SRDNSKNTLY LQMNSLRAED TAVYYCARER GYVYYHMFDP WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVAV SHEDPEVKFN WYVDGVEVHN AKTKPREEQY   300
NSTYRVVSVL TVLHQDWLNG KEYKCKVSNK ALAAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 160            moltype = DNA   length = 1353
FEATURE                   Location/Qualifiers
misc_feature              1..1353
                          note = source = /note="Description of Artificial Sequence:
                          Synthetic polynucleotide"
source                    1..1353
                          mol_type = other DNA
                          organism = synthetic construct
SEQUENCE: 160
gaagtgcagc tcctggagtc gggtggcgga ctggtgcagc ctggcggatc actgcggctg    60
tcatgtgccg cgagcgggtt tactttcaac acccactaca tccactgggt ccgccaagct   120
cccggaaagg gactcgaatg ggtgtcctcc attggtggca agggcggcat gaccctttac   180
gcggatagcg tgaaggggag gttcaccatc tcccgcgaca acagcaagaa caccctgtac   240
ctccaaatga actcgcttcg ggccgaggac actgccgtgt actattgcgc aagagagcgg   300
ggctacgtgt actaccacat gttcgaccca tggggacagg gaacgctggt caccgtgtcc   360
tccgcctcca ctaagggccc gtcagtgttc ccgctggctc catcgtcgaa gtccacctcc   420
ggaggaaccg cagcactcgg ttgcctggtc aaggactact cccctgagcc agtgaccgtg   480
tcgtggaaca cgcgagccct gacttccggc gtgcacactt ttcccgcggt gctgcagtcc   540
tccggtctgt actccctttc gtccgtggtc accgtgccgt cgtctagcct gggcacccag   600
acctacatct gcaacgtgaa ccacaagccg tccaacacca agtgtgataa gcgggtggag   660
ccgaagtcct gcgataagac acacacgtgc ccgccatgtc cagcgcctga attgcttggc   720
ggaccttccg tgttcctgtt cccgcctaag cccaaggaca ccttgatgat tagccggact   780
cccgaagtca cctgtgtggt ggtggcagtg tcccacgagg accccgaggt caagtttaat   840
tggtacgtgg acggcgtcga agtgcacaac gccaagacta gccccgggga ggaacagtac   900
aacagcacct accgggtcgt gtccgtgctg accgtgctgc accaggactg gctgaatggg   960
aaagagtaca agtgcaaagt gtccaacaag gccttggccg ctcctatcga aaaaactatc  1020
agcaaggcta agggacagcc gagggaaccc caagtctaca ccctgccccc ttcacgcgaa  1080
gagatgacca agaatcaagt gtcgctgacc tgcctcgtca aggattctac ccctccgac  1140
attggtgtgg agtgggagtc caacggccag cccgagaaca actacaagac tactccgcca  1200
gtgctggact ccgacggcag cttcttcctg tattccaagc tgaccgtgga caagtcccgg  1260
tggcagcaag gaaacgtgtt ctcctgctcg gtcatgcacg aagccctgca caaccactat  1320
acgcagaagt ccctgtcctt gagcccgggg aaa                               1353

SEQ ID NO: 161            moltype = AA   length = 121
FEATURE                   Location/Qualifiers
REGION                    1..121
                          note = source = /note="Description of Artificial Sequence:
                          Synthetic polypeptide"
source                    1..121
                          mol_type = protein
                          organism = synthetic construct
SEQUENCE: 161
EVQLLESGGG LVQPGGSLRL SCAASGFTFS THYIHWVRQA PGKGLEWVSS IGGQGGMTLY    60
ADSVKGRFTI SRDNSKNTLY LQMNSLRAED TAVYYCARER GYVYYHMFDP WGQGTLVTVS   120
S                                                                   121

SEQ ID NO: 162            moltype = DNA   length = 363
FEATURE                   Location/Qualifiers
misc_feature              1..363
                          note = source = /note="Description of Artificial Sequence:
                          Synthetic polynucleotide"
source                    1..363
                          mol_type = other DNA
                          organism = synthetic construct
SEQUENCE: 162
gaagtgcagc tcctggagtc gggtggcgga ctggtgcagc ctggcggatc actgcggctg    60
tcatgtgccg cgagcgggtt tactttctcc acccactaca tccactgggt ccgccaagct   120
cccggaaagg gactcgaatg ggtgtcctcc attggtggac agggcggcat gaccctttac   180
gcggatagcg tgaaggggag gttcaccatc tcccgcgaca acagcaagaa caccctgtac   240
ctccaaatga actcgcttcg ggccgaggac actgccgtgt actattgcgc aagagagcgg   300
ggctacgtgt actaccacat gttcgaccca tggggacagg gaacgctggt caccgtgtcc   360
```

```
tcc                                                                                 363

SEQ ID NO: 163            moltype = AA  length = 451
FEATURE                   Location/Qualifiers
REGION                    1..451
                          note = source = /note="Description of Artificial Sequence:
                          Synthetic polypeptide"
source                    1..451
                          mol_type = protein
                          organism = synthetic construct
SEQUENCE: 163
EVQLLESGGG LVQPGGSLRL SCAASGFTFS THYIHWVRQA PGKGLEWVSS IGGQGGMTLY   60
ADSVKGRFTI SRDNSKNTLY LQMNSLRAED TAVYYCARER GYVYYHMFDP WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVAV SHEDPEVKFN WYVDGVEVHN AKTKPREEQY  300
NSTYRVVSVL TVLHQDWLNG KEYKCKVSNK ALAAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 164            moltype = DNA  length = 1353
FEATURE                   Location/Qualifiers
misc_feature              1..1353
                          note = source = /note="Description of Artificial Sequence:
                          Synthetic polynucleotide"
source                    1..1353
                          mol_type = other DNA
                          organism = synthetic construct
SEQUENCE: 164
gaagtgcagc tcctggagtc gggtggcgga ctggtgcagc ctggcggatc actgcggctg   60
tcatgtgccg cgagcgggtt tactttctcc acccactaca tccactgggt ccgccaagct  120
cccggaaagg gactcgaatg ggtgtcctcc attggtggac agggcggcat gacccttac   180
gcggatagcg tgaaggggag gttcaccatc tcccgcgaca cagcaagaa caccctgtac   240
ctccaaatga actcgcttcg ggccgaggac actgccgtgt actattgcgc aagagagcgg  300
ggctacgtgt actaccacat gttcgaccca tggggacagg gaacgctggt caccgtgtcc  360
tccgcctcca ctaagggccc gtcagtgttc ccgctggctc catcgtcgaa gtccacctcc  420
ggaggaaccg cagcactcgg ttgcctggtc aaggactact ccctgagcc agtgaccgtg   480
tcgtggaaca gcggagccct gacttccggc gtgcacactt ttcccgcggt gctgcagtcc  540
tccggtctgt actcccttc gtccgtggtc accgtgcct cgtctagcct gggcacccag   600
acctacatct gcaacgtgaa ccacaagccg tccaacacca aagtggataa gcgggtggag  660
ccgaagtcct gcgataagac acacgtgcc cgccatgtc cagcgcctga attgcttggc   720
ggaccttccg tgttcctgtt cccgcctaag cccaaggaca ccttgatgat tagccggact  780
cccgaagtca cctgtgtggt ggtggcagtg tcccacgagg accccgaggt caagtttaat  840
tggtacgtgg acggcgtcga agtgcacaac gccaagacta gccccgggga ggaacagtac  900
aacagcacct accgggtcgt gtccgtgctg accgtgctgc accaggactg gctgaatggg  960
aaagagtaca agtgcaaagt gtccaacaag gccttggccg ctcctatcga aaaaactatc 1020
agcaaggcta agggacagcc gagggaaccc caagtctaca cctgccccc ttcacgcgaa  1080
gagatgacca gaatcaagt gtcgctgacc tgcctcgtca agggattcta ccctcccgac  1140
attgcggtgg agtgggagtc caacggccag cccgagaaca actacaagac tactccgccc 1200
gtgctggact ccgacggcag cttcttcctg tattccaagc tgaccgtgga caagtcccgg  1260
tggcagcaag gaaacgtgtt ctcctgctcg gtcatgcacg aagccctgca caaccactat 1320
acgcagaagt ccctgtcctt gagcccgggg aaa                               1353

SEQ ID NO: 165            moltype = AA  length = 10
FEATURE                   Location/Qualifiers
REGION                    1..10
                          note = source = /note="Description of Artificial Sequence:
                          Synthetic peptide"
source                    1..10
                          mol_type = protein
                          organism = synthetic construct
SEQUENCE: 165
GFTFQTHYIH                                                                           10

SEQ ID NO: 166            moltype = AA  length = 7
FEATURE                   Location/Qualifiers
REGION                    1..7
                          note = source = /note="Description of Artificial Sequence:
                          Synthetic peptide"
source                    1..7
                          mol_type = protein
                          organism = synthetic construct
SEQUENCE: 166
GFTFQTH                                                                              7

SEQ ID NO: 167            moltype = AA  length = 8
FEATURE                   Location/Qualifiers
REGION                    1..8
                          note = source = /note="Description of Artificial Sequence:
```

```
                        Synthetic peptide"
source                  1..8
                        mol_type = protein
                        organism = synthetic construct
SEQUENCE: 167
GFTFQTHY                                                                   8

SEQ ID NO: 168          moltype = AA   length = 121
FEATURE                 Location/Qualifiers
REGION                  1..121
                        note = source = /note="Description of Artificial Sequence:
                        Synthetic polypeptide"
source                  1..121
                        mol_type = protein
                        organism = synthetic construct
SEQUENCE: 168
EVQLLESGGG LVQPGGSLRL SCAASGFTFQ THYIHWVRQA PGKGLEWVSS IGGQGGMTLY          60
ADSVKGRFTI SRDNSKNTLY LQMNSLRAED TAVYYCARER GYVYYHMFDP WGQGTLVTVS         120
S                                                                        121

SEQ ID NO: 169          moltype = DNA   length = 363
FEATURE                 Location/Qualifiers
misc_feature            1..363
                        note = source = /note="Description of Artificial Sequence:
                        Synthetic polynucleotide"
source                  1..363
                        mol_type = other DNA
                        organism = synthetic construct
SEQUENCE: 169
gaagtgcagc tcctggagtc gggtggcgga ctggtgcagc ctggcggatc actgcggctg          60
tcatgtgccg cgagcgggtt tactttccag acccactaca tccactgggt ccgccaagct        120
cccggaaagg gactcgaatg ggtgtcctcc attggtggac agggcggcat gacccttac         180
gcggatagcg tgaaggggag gttcaccatc tcccgcgaca cagcaagaa cacccctgtac        240
ctccaaatga actcgcttcg ggccgaggac actgccgtgt actattgcgc aagagagcgg        300
ggctacgtgt actaccacat gttcgaccca tggggacagg gaacgctggt caccgtgtcc        360
tcc                                                                      363

SEQ ID NO: 170          moltype = AA   length = 451
FEATURE                 Location/Qualifiers
REGION                  1..451
                        note = source = /note="Description of Artificial Sequence:
                        Synthetic polypeptide"
source                  1..451
                        mol_type = protein
                        organism = synthetic construct
SEQUENCE: 170
EVQLLESGGG LVQPGGSLRL SCAASGFTFQ THYIHWVRQA PGKGLEWVSS IGGQGGMTLY          60
ADSVKGRFTI SRDNSKNTLY LQMNSLRAED TAVYYCARER GYVYYHMFDP WGQGTLVTVS         120
SASTKGPSVF PLAPSSKSTS GGTAALGCLV KDYFPEPVTV SWNSGALTSG VHTFPAVLQS         180
SGLYSLSSVV TVPSSSLGTQ TYICNVNHKP SNTKVDKRVE PKSCDKTHTC PPCPAPELLG         240
GPSVFLFPPK PKDTLMISRT PEVTCVVVAV SHEDPEVKFN WYVDGVEVHN AKTKPREEQY         300
NSTYRVVSVL TVLHQDWLNG KEYKCKVSNK ALAAPIEKTI SKAKGQPREP QVYTLPPSRE         360
EMTKNQVSLT CLVKGFYPSD IAVEWESNGQ PENNYKTTPP VLDSDGSFFL YSKLTVDKSR         420
WQQGNVFSCS VMHEALHNHY TQKSLSLSPG K                                       451

SEQ ID NO: 171          moltype = DNA   length = 1353
FEATURE                 Location/Qualifiers
misc_feature            1..1353
                        note = source = /note="Description of Artificial Sequence:
                        Synthetic polynucleotide"
source                  1..1353
                        mol_type = other DNA
                        organism = synthetic construct
SEQUENCE: 171
gaagtgcagc tcctggagtc gggtggcgga ctggtgcagc ctggcggatc actgcggctg          60
tcatgtgccg cgagcgggtt tactttccag acccactaca tccactgggt ccgccaagct        120
cccggaaagg gactcgaatg ggtgtcctcc attggtggac agggcggcat gacccttac         180
gcggatagcg tgaaggggag gttcaccatc tcccgcgaca cagcaagaa cacccctgtac        240
ctccaaatga actcgcttcg ggccgaggac actgccgtgt actattgcgc aagagagcgg        300
ggctacgtgt actaccacat gttcgaccca tggggacagg gaacgctggt caccgtgtcc        360
tccgcctcca ctaagggccc gtcagtgttc ccgctggctc atcgtcgaa gtccacctcc         420
ggaggaaccg cagcactcgg ttgcctggtc aaggactact ccctgagcc agtgaccgtg         480
tcgtggaaca gcggagccct gacttccggc gtgcacactt tccccgcggt gctgcagtcc        540
tccggtctgt actcccttc gtccgtggtc accgtgccgt cgtctagcct gggcacccaa         600
acctacatct gcaacgtgaa ccacaagccc tccaacacca agtggataa gcgggtggag         660
ccgaagtcct gcgataagac acacgtgtgc ccgccatgtc cagcgcctga attgcttggc        720
ggaccttccg tgttcctgtt cccgcctaag cccaaggaca ccttgatgat tagccggact        780
cccgaagtca cctgtgtggt ggtggcagtg tcccacgagg accccgaggt caagtttaat        840
tggtacgtgg acggcgtcga agtgcacaac gccaagacta gccccggga ggaacagtac        900
```

```
aacagcacct accgggtcgt gtccgtgctg accgtgctgc caccaggactg gctgaatggg  960
aaagagtaca agtgcaaagt gtccaacaag gccttggccg ctcctatcga aaaaactatc 1020
agcaaggcta agggacagcc gagggaaccc caagtctaca ccctgccccc ttcacgcgaa 1080
gagatgacca agaatcaagt gtcgctgacc tgcctcgtca agggattcta cccctccgac 1140
attgcggtgg agtgggagtc caacggccag cccgagaaca actacaagac tactccgccc 1200
gtgctggact ccgacggcag cttcttcctg tattccaagc tgaccgtgga caagtcccgg 1260
tggcagcaag gaaacgtgtt ctcctgctcg gtcatgcacg aagccctgca caaccactat 1320
acgcagaagt ccctgtcctt gagcccgggg aaa                              1353

SEQ ID NO: 172          moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 172
QQEWAKPRT                                                            9

SEQ ID NO: 173          moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 173
EWAKPR                                                               6

SEQ ID NO: 174          moltype = AA   length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 174
DIQMTQSPSS LSASVGDRVT ITCRASQGIS SYLAWYQQKP GKAPKLLIYT ASTLQSGVPS   60
RFSGSGSGTD FTLTISSLQP EDFATYYCQQ EWAKPRTFGQ GTKVEIK                107

SEQ ID NO: 175          moltype = DNA   length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 175
gatatccaga tgacccagag cccgagcagc ctgagcgcca gcgtgggcga tcgcgtgacc  60
attacctgca gagccagcca gggtatttct tcttacctgg cttggtacca gcagaaaccg 120
ggcaaagcgc cgaaactatt aatctacact gcttctactc tgcaaagcgg cgtgccgagc 180
cgctttagcg gcagcggatc cggcaccgat ttcacccctg ccattagctc tctgcaaccg 240
gaagactttg cgacctatta ttgccagcag gaatgggcta aaccgcgtac ctttggccag 300
ggcacgaaag ttgaaattaa a                                            321

SEQ ID NO: 176          moltype = AA   length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 176
DIQMTQSPSS LSASVGDRVT ITCRASQGIS SYLAWYQQKP GKAPKLLIYT ASTLQSGVPS   60
RFSGSGSGTD FTLTISSLQP EDFATYYCQQ EWAKPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 177          moltype = DNA   length = 642
FEATURE                 Location/Qualifiers
misc_feature            1..642
                        note = source = /note="Description of Artificial Sequence:
                         Synthetic polynucleotide"
source                  1..642
```

```
                            mol_type = other DNA
                            organism = synthetic construct
SEQUENCE: 177
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag gaatgggcta aaccgcgtac ctttggccag   300
ggcacgaaag ttgaaattaa acgtacggtg gccgctccca gcgtgttcat cttccccccc   360
agcgatgagc agctgaagag cggcaccgcc agcgtggtgt gcctgctgaa caacttctac   420
ccccgggagg ccaaggtgca gtggaaggtg gacaacgccc tgcagagcgg caacagccag   480
gaaagcgtca ccgagcagga cagcaaggac tccacctaca gcctgagcag caccctgacc   540
ctgagcaagg ccgactacga aagcacaag gtgtacgcct gcgaggtgac ccaccagggc   600
ctgtccagcc ccgtgaccaa gagcttcaac cggggcgagt gt                      642

SEQ ID NO: 178           moltype = AA  length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 178
QQSWTRPRT                                                             9

SEQ ID NO: 179           moltype = AA  length = 6
FEATURE                  Location/Qualifiers
REGION                   1..6
                         note = source = /note="Description of Artificial Sequence:
                          Synthetic peptide"
source                   1..6
                         mol_type = protein
                         organism = synthetic construct
SEQUENCE: 179
SWTRPR                                                                6

SEQ ID NO: 180           moltype = AA  length = 107
FEATURE                  Location/Qualifiers
REGION                   1..107
                         note = source = /note="Description of Artificial Sequence:
                          Synthetic polypeptide"
source                   1..107
                         mol_type = protein
                         organism = synthetic construct
SEQUENCE: 180
DIQMTQSPSS LSASVGDRVT ITCRASQGIS SYLAWYQQKP GKAPKLLIYT ASTLQSGVPS    60
RFSGSGSGTD FTLTISSLQP EDFATYYCQQ SWTRPRTFGQ GTKVEIK                 107

SEQ ID NO: 181           moltype = DNA  length = 321
FEATURE                  Location/Qualifiers
misc_feature             1..321
                         note = source = /note="Description of Artificial Sequence:
                          Synthetic polynucleotide"
source                   1..321
                         mol_type = other DNA
                         organism = synthetic construct
SEQUENCE: 181
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag tcttggactg tccgcgtac ctttggccag    300
ggcacgaaag ttgaaattaa a                                             321

SEQ ID NO: 182           moltype = AA  length = 214
FEATURE                  Location/Qualifiers
REGION                   1..214
                         note = source = /note="Description of Artificial Sequence:
                          Synthetic polypeptide"
source                   1..214
                         mol_type = protein
                         organism = synthetic construct
SEQUENCE: 182
DIQMTQSPSS LSASVGDRVT ITCRASQGIS SYLAWYQQKP GKAPKLLIYT ASTLQSGVPS    60
RFSGSGSGTD FTLTISSLQP EDFATYYCQQ SWTRPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

```
SEQ ID NO: 183          moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 183
gatatccaga tgacccagag cccgagcagc ctgagcgcca gcgtgggcga tcgcgtgacc   60
attacctgca gagccagcca gggtatttct tcttacctgg cttggtacca gcagaaaccg  120
ggcaaagcgc cgaaactatt aatctacact gcttctactc tgcaaagcgg cgtgccgagc  180
cgctttagcg gcagcggatc cggcaccgat ttcaccctga ccattagctc tctgcaaccg  240
gaagactttg cgacctatta ttgccagcag tcttggactc gtccgcgtac ctttggccag  300
ggcacgaaag ttgaaattaa acgtacggtg gccgctccca gcgtgttcat cttcccccc   360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gaaagcgtca ccgagcagga cagcaaggac tccacctaca gcctgagcag caccctgacc  540
ctgagcaagg ccgactacga aagcacaag gtgtacgcct gcgaggtgac ccaccagggc  600
ctgtccagcc ccgtgaccaa gagcttcaac cggggcgagt gt                    642

SEQ ID NO: 184          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 184
QQIWMAPRT                                                            9

SEQ ID NO: 185          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 185
IWMAPR                                                               6

SEQ ID NO: 186          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 186
DIQMTQSPSS LSASVGDRVT ITCRASQGIS SYLAWYQQKP GKAPKLLIYT ASTLQSGVPS    60
RFSGSGSGTD FTLTISSLQP EDFATYYCQQ IWMAPRTFGQ GTKVEIK                 107

SEQ ID NO: 187          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 187
gatatccaga tgacccagag cccgagcagc ctgagcgcca gcgtgggcga tcgcgtgacc   60
attacctgca gagccagcca gggtatttct tcttacctgg cttggtacca gcagaaaccg  120
ggcaaagcgc cgaaactatt aatctacact gcttctactc tgcaaagcgg cgtgccgagc  180
cgctttagcg gcagcggatc cggcaccgat ttcaccctga ccattagctc tctgcaaccg  240
gaagactttg cgacctatta ttgccagcag atctggatgc tccgcgtac ctttggccag   300
ggcacgaaag ttgaaattaa a                                            321

SEQ ID NO: 188          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
```

```
SEQUENCE: 188
DIQMTQSPSS LSASVGDRVT ITCRASQGIS SYLAWYQQKP GKAPKLLIYT ASTLQSGVPS    60
RFSGSGSGTD FTLTISSLQP EDFATYYCQQ IWMAPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 189          moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 189
gatatccaga tgacccagag cccgagcagc ctgagcgcca gcgtgggcga tcgcgtgacc    60
attacctgca gagccagcca gggtatttct tcttacctgg cttggtacca gcagaaaccg   120
ggcaaagcgc cgaaactatt aatctacact gcttctactc tgcaaagcgg cgtgccgagc   180
cgctttagcg gcagcggatc cggcaccgat ttcaccctga ccattagctc tctgcaaccg   240
gaagactttg cgacctatta ttgccagcag atctggatgg ctccgcgtac ctttggccag   300
ggcacgaaag ttgaaattaa acgtacggtg gccgctccca gcgtgttcat cttcccccca   360
agcgggagg agctgaagag cggcaccgcc agcgtggtgt gcctgctgaa caacttctac   420
ccccgggagg ccaaggtgca gtggaaggtg gacaacgccc tgcagagcgg caacagccag   480
gaaagcgtca ccgagcagga cagcaaggac tccacctaca gcctgagcag cacccctgacc   540
ctgagcaagg ccgactacga aagcacaag gtgtacgcct gcgaggtgac ccaccagggc   600
ctgtccagcc ccgtgaccaa gagcttcaac cggggcgagt gt                     642

SEQ ID NO: 190          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 190
AISSKGSYTY YADSVKG                                                  17

SEQ ID NO: 191          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 191
SSKGSY                                                              6

SEQ ID NO: 192          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 192
ISSKGSYT                                                            8

SEQ ID NO: 193          moltype = AA  length = 125
FEATURE                 Location/Qualifiers
REGION                  1..125
                        note = source = /note="Description of Artificial Sequence:
                         Synthetic polypeptide"
source                  1..125
                        mol_type = protein
                        organism = synthetic construct
SEQUENCE: 193
QVQLLESGGG LVQPGGSLRL SCAASGFTFS SYWMNWVRQA PGKGLEWVSA ISSKGSYTYY    60
ADSVKGRFTI SRDNSKNTLY LQMNSLRAED TAVYYCARDR YSMIYSYGAG AFDYWGQGTL   120
VTVSS                                                               125

SEQ ID NO: 194          moltype = DNA  length = 375
FEATURE                 Location/Qualifiers
misc_feature            1..375
                        note = source = /note="Description of Artificial Sequence:
                         Synthetic polynucleotide"
source                  1..375
```

```
                        mol_type = other DNA
                        organism = synthetic construct
SEQUENCE: 194
caagttcagc tccttgagtc tggggggggc ctggtgcaac ctgggggctc tctgcggctt    60
tcatgtgcgg cctcagggtt cactttcagc tcatactgga tgaattgggt acgccaagct   120
ccaggcaaag gactcgaatg ggtaagcgct atatccagca aagggagcta tacctattac   180
gcggattccg ttaagggcag gttcactata tcccgcgaca actccaaaaa tactttgtat   240
ctgcaaatga attccctccg agccgaagat accgcagtat attactgtgc gagggacagg   300
tactccatga tttacagcta cggtgccggt gctttcgatt attggggaca ggggacactt   360
gtgaccgtca gttct                                                    375

SEQ ID NO: 195         moltype = AA   length = 455
FEATURE                Location/Qualifiers
REGION                 1..455
                        note = source = /note="Description of Artificial Sequence:
                        Synthetic polypeptide"
source                 1..455
                        mol_type = protein
                        organism = synthetic construct
SEQUENCE: 195
QVQLLESGGG LVQPGGSLRL SCAASGFTFS SYWMNWVRQA PGKGLEWVSA ISSKGSYTYY    60
ADSVKGRFTI SRDNSKNTLY LQMNSLRAED TAVYYCARDR YSMIYSYGAG AFDYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 196         moltype = DNA   length = 1365
FEATURE                Location/Qualifiers
misc_feature           1..1365
                        note = source = /note="Description of Artificial Sequence:
                        Synthetic polynucleotide"
source                 1..1365
                        mol_type = other DNA
                        organism = synthetic construct
SEQUENCE: 196
caagttcagc tccttgagtc tggggggggc ctggtgcaac ctgggggctc tctgcggctt    60
tcatgtgcgg cctcagggtt cactttcagc tcatactgga tgaattgggt acgccaagct   120
ccaggcaaag gactcgaatg ggtaagcgct atatccagca aagggagcta tacctattac   180
gcggattccg ttaagggcag gttcactata tcccgcgaca actccaaaaa tactttgtat   240
ctgcaaatga attccctccg agccgaagat accgcagtat attactgtgc gagggacagg   300
tactccatga tttacagcta cggtgccggt gctttcgatt attggggaca ggggacactt   360
gtgaccgtca gttctgcaag taccaaaggg ccgtctgttt tcccattggc ccctcatcc   420
aagagcacga gtggaggcac cgccgcgctg ggatgccttg tgaaagacta tttccccgag   480
cccgtgaccg ttagctggaa cagcggcgct cttaccagtg gcgttcacac attcccagct   540
gttttgcagt catccgggct ctactctctc tcatccgtgg tcaccgtgcc gtctagttct   600
ttgggcaccc agacctacat ctgtaacgta aatcacaaac ctagtaatac taaggtggac   660
aagcgagttg aaccgaagag ctgtgataag acacatactt gtccaccatg tccggcaccc   720
gaggcaggcg gggcccagt gtttttctc ttcccaccca agcccaaaga cacattgatg   780
atctcacgaa ccccagaggt aacttgtgtc gtggtagatg taagccatga ggaccccgaa   840
gttaagttca attggtatgt tgacggtgta gaggtgcaca atgccaaaac taaacccgg    900
gaggagcaat acaactcaac ttacagagtc gtatccgtgc tgaccgtttt gcaccaggat   960
tggttgaatg gtaaggaata caaatgtaaa gtgagcaata aagctctccc agcgcccatc  1020
gagaagacca ttagcaaagc caagggtcaa cccagggaac cccagtata tacgctgcca  1080
ccctcaaggg aagagatgac aaagaatcaa gtgtcactga cgtgtcttgt caagggtttc  1140
tatcctagcg acattgcggt ggaatgggag tcaaatgggc aacccgagaa caactacaag  1200
actactcctc ccgtcctgga cagcgacggc tccttcttcc tgtatagtaa actgaccgtc  1260
gataaaagta ggtggcagca gggaatgtc tttagttgc ctgtcatgca tgaggcgctc  1320
cataaccact acacccaaaa atctttgagc ttgagccctg ggaaa                 1365

SEQ ID NO: 197         moltype = DNA   length = 321
FEATURE                Location/Qualifiers
misc_feature           1..321
                        note = source = /note="Description of Artificial Sequence:
                        Synthetic polynucleotide"
source                 1..321
                        mol_type = other DNA
                        organism = synthetic construct
SEQUENCE: 197
gacattcaaa tgacacaaag tccgtccagt cttagtgctt ctgtgggcga tagggtcacc    60
atcacttgtc gggcgtctca gggatcagc tcttacttgg catggtatca acaaaagcca   120
ggaaaagcac ctaaattgct tatttataca gcgtccagc tccagtcagg agtgcctagt   180
aggttctcag gctctgggtc cggtactgac ttcacgctga ctatatcaag cttgcaaccc   240
gaagatttg caacatacta ctgccaacag acatggagga agccaagaac tttcggtcag   300
ggaacgaaag ttgagataaa g                                             321

SEQ ID NO: 198         moltype = DNA   length = 642
```

```
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 198
gacattcaaa tgacacaaag tccgtccagt cttagtgctt ctgtgggcga tagggtcacc   60
atcacttgtc gggcgtctca ggggatcagc tcttacttgg catggtatca acaaaagcca  120
ggaaaagcac ctaaattgct tatttataca gcgtccaccc tccagtcagg agtgcctagt  180
aggttctcag gctctgggtc cggtactgac ttcacgctga ctatatcaag cttgcaaccc  240
gaagattttg caacatacta ctgccaacag acatggagga agccaagaac tttcggtcag  300
ggaacgaaag ttgagataaa gcgcactgtc gcagcacctt ccgtgttcat tttcccgcct  360
tccgacgagc agcttaaatc agggaccgcg agtgttgttt gcttgcttaa taacttttac  420
ccacgggaag ccaaagttca gtggaaggtg gacaatgcac tccaaagcgg gaatagtcag  480
gagtcagtta ctgagcaaga tagtaaagac tctacttact ctttgagttc aaccttgacc  540
ctctcaaaag cggactacga gaagcataaa gtgtacgcct gcgaggtgac gcatcaaggt  600
ttgtcttccc cggttacgaa gtcctttaat aggggggaat gt                    642

SEQ ID NO: 199          moltype = DNA  length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 199
gatatacaga tgacgcaaag tccctctagt ctttctgcaa gtgtcgggga cagagttacc   60
attacctgca gagcgtcaca aggcatctct agttatctcg cgtggtacca acagaagcca  120
ggtaaagcac ctaaactgtt gatttacacg gcatcaacat gcagtcagg tgtcccctcc  180
cgatttagtg gcagtggtag cggtacagat tttactctta ccatttcatc tcttcagcca  240
gaagattttg ctacgtacta ctgtcaacaa gaatgggcta aaccacgaac ctttggacag  300
ggtacgaagg tcgaaataaa a                                            321

SEQ ID NO: 200          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 200
gatatacaga tgacgcaaag tccctctagt ctttctgcaa gtgtcgggga cagagttacc   60
attacctgca gagcgtcaca aggcatctct agttatctcg cgtggtacca acagaagcca  120
ggtaaagcac ctaaactgtt gatttacacg gcatcaacat gcagtcagg tgtcccctcc  180
cgatttagtg gcagtggtag cggtacagat tttactctta ccatttcatc tcttcagcca  240
gaagattttg ctacgtacta ctgtcaacaa gaatgggcta aaccacgaac ctttggacag  300
ggtacgaagg tcgaaataaa acggaccgtt gccgcccctc ccgtcttcat cttccccgca  360
tctgacgagc agcttcaaatc cggcacagct tctgtagtct gcttgctgaa taacttctac  420
ccaagagaag ccaaagttca gtggaaggtc gataatgcat gcaatctgg taatagtcag  480
gaatctgtga ctgagcagga tagcaaagac tcaacttaca gcctctcttc aaccttgacg  540
ttgtccaaag cggattatga gaaacacaag gtgtacgctt gcgaggtgac gcatcaaggg  600
cttagttccc cggtaaccaa atctttcaac cgaggtgaat gc                    642

SEQ ID NO: 201          moltype = AA  length = 125
FEATURE                 Location/Qualifiers
REGION                  1..125
                        note = source = /note="Description of Artificial Sequence:
                        Synthetic polypeptide"
source                  1..125
                        mol_type = protein
                        organism = synthetic construct
SEQUENCE: 201
QVQLLESGGG LVQPGGSLRL SCAASGFTFS SYWMNWVRQA PGKGLEWVSV IESKGNYIFY   60
ADSVKGRFTI SRDNSKNTLY LQMNSLRAED TAVYYCARDR YSMIYSYGAG AFDYWGQGTL  120
VTVSS                                                              125

SEQ ID NO: 202          moltype = DNA  length = 375
FEATURE                 Location/Qualifiers
misc_feature            1..375
                        note = source = /note="Description of Artificial Sequence:
                        Synthetic polynucleotide"
source                  1..375
                        mol_type = other DNA
                        organism = synthetic construct
SEQUENCE: 202
```

```
caagttcaat tgctggaaag cggaggtgga cttgtccaac ctggagggtc actccgactg    60
tcttgcgctg catcaggatt cacctttagt agctattgga tgaactgggt ccggcaggct   120
cctgggaaag ggcttgagtg ggtaagtgtc attgaatcaa agggcaacta catcttttat   180
gctgattctg taaagggtag gttcaccatc tccagggaca attcaaaaaa tactttgtat   240
ctgcagatga actctctcag ggcagaagac acggccgttt attactgcgc ccgcgatcga   300
tacagcatga tatactccta cggcgcagga gcttttgact actggggtca aggcacactt   360
gttactgtca gtagc                                                    375

SEQ ID NO: 203         moltype = AA  length = 455
FEATURE                Location/Qualifiers
REGION                 1..455
                       note = source = /note="Description of Artificial Sequence:
                       Synthetic polypeptide"
source                 1..455
                       mol_type = protein
                       organism = synthetic construct
SEQUENCE: 203
QVQLLESGGG LVQPGGSLRL SCAASGFTFS SYWMNWVRQA PGKGLEWVSV IESKGNYIFY    60
ADSVKGRFTI SRDNSKNTLY LQMNSLRAED TAVYYCARDR YSMIYSYGAG APDYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 204         moltype = DNA  length = 1365
FEATURE                Location/Qualifiers
misc_feature           1..1365
                       note = source = /note="Description of Artificial Sequence:
                       Synthetic polynucleotide"
source                 1..1365
                       mol_type = other DNA
                       organism = synthetic construct
SEQUENCE: 204
caagttcaat tgctggaaag cggaggtgga cttgtccaac ctggagggtc actccgactg    60
tcttgcgctg catcaggatt cacctttagt agctattgga tgaactgggt ccggcaggct   120
cctgggaaag ggcttgagtg ggtaagtgtc attgaatcaa agggcaacta catcttttat   180
gctgattctg taaagggtag gttcaccatc tccagggaca attcaaaaaa tactttgtat   240
ctgcagatga actctctcag ggcagaagac acggccgttt attactgcgc ccgcgatcga   300
tacagcatga tatactccta cggcgcagga gcttttgact actggggtca aggcacactt   360
gttactgtca gtagcgcctc aacgaaagga ccgtccgtgt ttcctcttgc tcctagctcc   420
aaatccacct caggtggaac ggccgccctg gggtgcctgg taaaggacta tttcccagag   480
ccagttacta tgtcttggaa ttctggtgca ttgacaagtg gcgtacacac tttcccgcg    540
gtcctccaat ctagtggtct gtactcactg tcctccgttg tgactgtccc aagtagctca   600
cttggcacac agacttacat ctgtaatgtt aatcataagc cgtcaaacac gaaggtggat   660
aagagggtag aacctaagtc atgtgacaaa acgcatactt gccccccctg ccctgcgccg   720
gaagccgctg gcggaccctc cgtattcttg ttccctccaa agccaaagga cactctgatg   780
attagccgga caccggaggt cacttgtgtt gtagttgacg tcagccatga ggatcctgag   840
gtgaaattta attggtacgt ggacgggggtt gaagtccaca atgctaaaac taaacctagg   900
gaagagcaat ataatagtac atacagggtt gtcagtgtgc tgaccgttct ccatcaggac   960
tggctgaacg gcaaggaata caagtgcaag gtcagcaaca aggccttgcc ggcccccatc  1020
gagaagcgca tctccaaagc caaggggcaa ccccgagaac cgcaggtata cacgctcccc  1080
cctagtagag aagagatgac aaagaatcaa gtttccttga cgtgccttgt gaaaggcttc  1140
taccctagtg acatcgcagt cgaatgggag agcaacgggc agccggagaa taactataaa  1200
acaaccccc cgtgcttga ctcagacggg tcattttttc tgtatagcaa attgactgtt  1260
gataaatcac ggtggcaaca aggaaacgtg tttagttgca gcgtaatgca cgaagctctc  1320
cacaatcact atactcaaaa gtcactgtca ctctcccctg gcaag                  1365

SEQ ID NO: 205         moltype = DNA  length = 321
FEATURE                Location/Qualifiers
misc_feature           1..321
                       note = source = /note="Description of Artificial Sequence:
                       Synthetic polynucleotide"
source                 1..321
                       mol_type = other DNA
                       organism = synthetic construct
SEQUENCE: 205
gacatacaaa tgacgcaatc tccgagtagc ttgtcagcgt ccgtaggcga ccgagtaacg    60
attacgtgta gagcgagcca gggaatttca tcttatttgg cttggtatca gcaaaagccg   120
ggaaagcac ccaaactcct catttatact gccagcacgt tgcaaagcgg cgttccgagt   180
cggttctctg gatcagggtc cgggacggac ttcaccttga cgatttcatc tttgcaacct   240
gaagattttg caacatacta ctgtcaacag gagtgggtga agccaaggac cttcggacaa   300
ggcacgaagg tcgaaatcaa g                                             321

SEQ ID NO: 206         moltype = DNA  length = 642
FEATURE                Location/Qualifiers
misc_feature           1..642
                       note = source = /note="Description of Artificial Sequence:
```

```
                          Synthetic polynucleotide"
source                    1..642
                          mol_type = other DNA
                          organism = synthetic construct
SEQUENCE: 206
gacatacaaa tgacgcaatc tccgagtagc ttgtcagcgt ccgtaggcga ccgagtaacg    60
attacgtgta gagcgagcca gggaatttca tcttatttgg cttggtatca gcaaaagccg   120
ggaaaagcac ccaaactcct catttatact gccagcacgt tgcaaagcgg cgttccgagt   180
cggttctctg gatcagggtc cgggacggac ttcaccttga cgatttcatc tttgcaacct   240
gaagattttg caacatacta ctgtcaacag gagtgggtga agccaaggac cttcggacaa   300
ggcacgaagg tcgaaatcaa gcgaaccgtg cagctccgt ccgtgtttat ttttccgcct    360
tccgacgaac aacttaaaag tggaacagcc tctgtcgtct gtctccttaa caacttctac   420
cccagggaag ctaaagtaca gtggaaggta gataacgctc tgcaaagtgg taattctcag   480
gagagcgtca cggaacagga ctccaaagac tccacctatt ctctgagctc tacactgacg   540
ctcagcaagg cagactacga aaagcacaaa gtatatgcgt gtgaggtgac gcatcaaggc   600
cttagcagtc cagttacaaa aagttttaac aggggagaat gc                     642

SEQ ID NO: 207            moltype = DNA   length = 375
FEATURE                   Location/Qualifiers
misc_feature              1..375
                          note = source = /note="Description of Artificial Sequence:
                          Synthetic polynucleotide"
source                    1..375
                          mol_type = other DNA
                          organism = synthetic construct
SEQUENCE: 207
gaagtgcagc tgctggaatc cggcggaggt ctggtccagc ctggaggttc cctgcgcctg    60
tcatgcgcag cctccggatt caccttttcg tcgtactgga tgaactgggt cagacaggct   120
cctggaaagg gcctggaatg ggtgtctgtg attgaatcca aggggaacta catcttctac   180
gcggacagcg tgaagggccg gttcactatc agcagagaca acagcaagaa cacccctgtac  240
ctccaaatga actcgctgag ggccgaagat actgccgtgt actactgtgc ccgcgatcgc   300
tactcgatga tctacagcta tggtgccgga gcgttcgatt actggggaca gggaaccctc   360
gtgaccgtca gctcc                                                    375

SEQ ID NO: 208            moltype = AA    length = 455
FEATURE                   Location/Qualifiers
REGION                    1..455
                          note = source = /note="Description of Artificial Sequence:
                          Synthetic polypeptide"
source                    1..455
                          mol_type = protein
                          organism = synthetic construct
SEQUENCE: 208
EVQLLESGGG LVQPGGSLRL SCAASGFTFS SYWMNWVRQA PGKGLEWVSV IESKGNYIFY    60
ADSVKGRFTI SRDNSKNTLY LQMNSLRAED TAVYYCARDR YSMIYSYGAG AFDYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLGGPSVFL FPPKPKDTLM ISRTPEVTCV VVAVSHEDPE VKFNWYVDGV EVHNAKTKPR   300
EEQYNSTYRV VSVLTVLHQD WLNGKEYKCK VSNKALAAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 209            moltype = DNA   length = 1365
FEATURE                   Location/Qualifiers
misc_feature              1..1365
                          note = source = /note="Description of Artificial Sequence:
                          Synthetic polynucleotide"
source                    1..1365
                          mol_type = other DNA
                          organism = synthetic construct
SEQUENCE: 209
gaagtgcagc tgctggaatc cggcggaggt ctggtccagc ctggaggttc cctgcgcctg    60
tcatgcgcag cctccggatt caccttttcg tcgtactgga tgaactgggt cagacaggct   120
cctggaaagg gcctggaatg ggtgtctgtg attgaatcca aggggaacta catcttctac   180
gcggacagcg tgaagggccg gttcactatc agcagagaca acagcaagaa cacccctgtac  240
ctccaaatga actcgctgag ggccgaagat actgccgtgt actactgtgc ccgcgatcgc   300
tactcgatga tctacagcta tggtgccgga gcgttcgatt actggggaca gggaaccctc   360
gtgaccgtca gctccgcctc aaccaagggc ccgtcagtgt tcccgctggc tccatcgtcg   420
aagtccacct ccggaggaac cgcagcactc ggttgcctgg tcaaggacta cttccctgag   480
ccagtgaccg tgtcgtggaa cagcggagcc ctgacttccg gcgtgcacac tttccccgcg   540
gtgctgcagt cctccggtct gtactccctt tcgtccgtgg tcaccgtgcc gtcgtctagc   600
ctgggcaccc agacctacat ctgcaacgtg aaccacaagc cgtccaacac caaagtggat   660
aagcgggtgg agccgaagtc ctgcgataag acacacacgt gccgccatg tccagcgcct    720
gaattgctgg gcggaccttc cgtgttcctg ttccgccatg agccaaggca ccttgatg     780
attagccgga ctcccgaagt cacctgtgtg gtggtggcag tgtcccacga ggaccccgag   840
gtcaagttta attggtacgt ggacggcgtg gaagtgcaca acgccaagac taagcccgg    900
gaggaacagt acaacagcac ctaccgggtc gtgtccgtgc tgaccgtgct gcaccaggac   960
tggctgaatg ggaaagagta caagtgcaaa gtgtccaaca aggccttggc cgctcctatc   1020
gaaaaaacta tcagcaaggc taaggacag ccgagggaac cccaagtcta cacctgccc   1080
```

```
ccttcacgcg aagagatgac caagaatcaa gtgtcgctga cctgcctcgt caagggattc   1140
tacccctccg acattgcggt gggagtggga tccaacggcc agcccgagaa caactacaag   1200
actactccgc ccgtgctgga ctccgacggc agcttcttcc tgtattccaa gctgaccgtg   1260
gacaagtccc ggtggcagca aggaaacgtg ttctcctgct cggtcatgca cgaagccctg   1320
cacaaccact atacgcagaa gtccctgtcc ttgagcccgg ggaaa                   1365
```

SEQ ID NO: 210          moltype = DNA   length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 210
```
gacatccaga tgacccagtc tccgtcctcc ctgtccgcat cagtggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa gaatgggtga agcccaggac atttggccag   300
ggcactaagg tcgagattaa g                                             321
```

SEQ ID NO: 211          moltype = DNA   length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 211
```
gacatccaga tgacccagtc tccgtcctcc ctgtccgcat cagtggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa gaatgggtga agcccaggac atttggccag   300
ggcactaagg tcgagattaa gcgtacggtg gccgctccca gcgtgttcat cttcccccct   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag cacccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

SEQ ID NO: 212          moltype = DNA   length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 212
```
gacatacaga tgactcagag tccttcctcc ctcagtgctt cagtgggtga tcgcgtgacg    60
atcacgtgca gagcctcaca aaggatctcc agttacctgg cctggtatca acaaaaacca   120
ggcaaggcgc ctaagctgtt gatatatacg gcatctacat tgcagtctgg ggtaccaagt   180
cgattcagtg gttctggctc aggcactgac tttacccctta caatatcaag tcttcagccg   240
gaggatttcg caacttacta ttgccagcag atttggacgg tgccgcgcac tttcggtcag   300
ggaacaaagg tggaaataaa a                                             321
```

SEQ ID NO: 213          moltype = DNA   length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 213
```
gacatacaga tgactcagag tccttcctcc ctcagtgctt cagtgggtga tcgcgtgacg    60
atcacgtgca gagcctcaca aaggatctcc agttacctgg cctggtatca acaaaaacca   120
ggcaaggcgc ctaagctgtt gatatatacg gcatctacat tgcagtctgg ggtaccaagt   180
cgattcagtg gttctggctc aggcactgac tttacccctta caatatcaag tcttcagccg   240
gaggatttcg caacttacta ttgccagcag atttggacgg tgccgcgcac tttcggtcag   300
ggaacaaagg tggaaataaa aagaacggtc gcagcaccga gtgttttcat cttccctccc   360
tccgacgagc agcttaaaag cggtacagcc agcgtagtgt gtttgttgaa taattttat    420
ccacgcgaag caaagttca gtggaaggta gacaacgcat tgcaaagcgg aaattcccaa    480
gaaagtgtta cggagcaaga cagtaaggac tctacatatt ccttgtcatc aacactcacc   540
cttagtaaag cagattacga gaaacacaag gtctatgcat gtgaggtaac gcatcagggc   600
ctctccagtc ccgtgaccaa gtccttcaac aggggtgagt gc                      642
```

SEQ ID NO: 214          moltype = DNA   length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 214
gacatccaga tgacccagtc tccgtcctcc ctgtccgcat cagtggggga cagagtgacc   60
atcacttgtc gggcctccca aggcatctcg tcatacctgg cctggtatca gcagaaaccc  120
ggaaaggctc caaagctgct catctacacc gcctcgactc tgcaatccgg agtgccttcc  180
cgcttctccg gatccggttc gggaaccgac ttcaccctca ccattagcag ccttcagccg  240
gaagatttcg cgacctacta ctgccagcaa atctggaccg tgcccaggac atttggccag  300
ggcactaagg tcgagattaa g                                            321

SEQ ID NO: 215          moltype = DNA   length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 215
gacatccaga tgacccagtc tccgtcctcc ctgtccgcat cagtggggga cagagtgacc   60
atcacttgtc gggcctccca aggcatctcg tcatacctgg cctggtatca gcagaaaccc  120
ggaaaggctc caaagctgct catctacacc gcctcgactc tgcaatccgg agtgccttcc  180
cgcttctccg gatccggttc gggaaccgac ttcaccctca ccattagcag ccttcagccg  240
gaagatttcg cgacctacta ctgccagcaa atctggaccg tgcccaggac atttggccag  300
ggcactaagg tcgagattaa gcgtacggtg gccgctccca gcgtgttcat cttcccccc   360
agcgacgagc agctgaagag cggcaccgcc agcgtggtgt gcctgctgaa caacttctac  420
ccccggggag ccaaggtgca gtggaaggtg gacaacgccc tgcagagcgg caacagccag  480
gagagcgtca ccgagcagga cagcaaggac tccacctaca gcctgagcag cacccctgacc  540
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 216          moltype = DNA   length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 216
gacatccaga tgacccagtc tccgtcctcc ctgtccgcat cagtggggga cagagtgacc   60
atcacttgtc gggcctccca aggcatctcg tcatacctgg cctggtatca gcagaaaccc  120
ggaaaggctc caaagctgct catctacacc gcctcgactc tgcaatccgg agtgccttcc  180
cgcttctccg gatccggttc gggaaccgac ttcaccctca ccattagcag ccttcagccg  240
gaagatttcg cgacctacta ctgccagcaa gaatgggcca agcccaggac atttggccag  300
ggcactaagg tcgagattaa g                                            321

SEQ ID NO: 217          moltype = DNA   length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 217
gacatccaga tgacccagtc tccgtcctcc ctgtccgcat cagtggggga cagagtgacc   60
atcacttgtc gggcctccca aggcatctcg tcatacctgg cctggtatca gcagaaaccc  120
ggaaaggctc caaagctgct catctacacc gcctcgactc tgcaatccgg agtgccttcc  180
cgcttctccg gatccggttc gggaaccgac ttcaccctca ccattagcag ccttcagccg  240
gaagatttcg cgacctacta ctgccagcaa gaatgggcca agcccaggac atttggccag  300
ggcactaagg tcgagattaa gcgtacggtg gccgctccca gcgtgttcat cttcccccc   360
agcgacgagc agctgaagag cggcaccgcc agcgtggtgt gcctgctgaa caacttctac  420
ccccggggag ccaaggtgca gtggaaggtg gacaacgccc tgcagagcgg caacagccag  480
gagagcgtca ccgagcagga cagcaaggac tccacctaca gcctgagcag cacccctgacc  540
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 218          moltype = DNA   length = 321
FEATURE                 Location/Qualifiers
misc_feature            1..321
                        note = source = /note="Description of Artificial Sequence:

```
                         Synthetic polynucleotide"
source                   1..321
                         mol_type = other DNA
                         organism = synthetic construct
SEQUENCE: 218
gatattcaga tgacgcaatc tccgtcttcc ttgtcagcta gtgtaggaga ccgcgtcaca   60
attacctgta gagccagcca ggggatttcc tcataccttg catggtacca gcaaaagcca  120
ggcaaagccc ccaaactgct gatctacacc gcgtctacct tgcaatctgg tgtgccgtca  180
cgcttttccg gctctggctc aggtactgat ttcacattga cgatctcaag tctccagccg  240
gaagacttcg caacttacta ctgccaacaa tcctggacga ggccgaggac tttcgggcag  300
ggaacaaagg ttgaaattaa a                                             321

SEQ ID NO: 219           moltype = DNA  length = 642
FEATURE                  Location/Qualifiers
misc_feature             1..642
                         note = source = /note="Description of Artificial Sequence:
                         Synthetic polynucleotide"
source                   1..642
                         mol_type = other DNA
                         organism = synthetic construct
SEQUENCE: 219
gatattcaga tgacgcaatc tccgtcttcc ttgtcagcta gtgtaggaga ccgcgtcaca   60
attacctgta gagccagcca ggggatttcc tcataccttg catggtacca gcaaaagcca  120
ggcaaagccc ccaaactgct gatctacacc gcgtctacct tgcaatctgg tgtgccgtca  180
cgcttttccg gctctggctc aggtactgat ttcacattga cgatctcaag tctccagccg  240
gaagacttcg caacttacta ctgccaacaa tcctggacga ggccgaggac tttcgggcag  300
ggaacaaagg ttgaaattaa aagaacagtc gcagcaccaa gtgtttttat ttttccaccc  360
tcagacgagc agctcaagtc tggcaccgcg agcgtagtat gtttgttgaa taatttttac  420
cctagggaag ctaaggtaca gtggaaagtg gataatgctc tccaaagtgg caactcccag  480
gaatcagtga ctgagcaaga ttcaaaggac agcacgtatt ctcttttctt cacgcttact  540
ctctctaagg ccgactacga aaaacacaaa gtttacgctt gcgaggttac ccaccagggg  600
ctgtcctcac cagtaacgaa aagttttaac cggggcgagt gt                      642

SEQ ID NO: 220           moltype = DNA  length = 321
FEATURE                  Location/Qualifiers
misc_feature             1..321
                         note = source = /note="Description of Artificial Sequence:
                         Synthetic polynucleotide"
source                   1..321
                         mol_type = other DNA
                         organism = synthetic construct
SEQUENCE: 220
gacatccaga tgacccagtc tccgtcctcc ctgtccgcat cagtggggga cagagtgacc   60
atcacttgtc gggcctccca aggcatctcg tcataccttgg cctggtatca gcagaaaccc  120
ggaaaggctc caaagctgct catctacacc gcctcgactc tgcaatccgg agtgccttcc  180
cgcttctccg gatccggttc gggaaccgac ttcaccctca ccattagcag ccttcagccg  240
gaagatttcg cgacctacta ctgccagcaa agctggacca ggcccaggac atttggccag  300
ggcactaagg tcgagattaa g                                             321

SEQ ID NO: 221           moltype = DNA  length = 642
FEATURE                  Location/Qualifiers
misc_feature             1..642
                         note = source = /note="Description of Artificial Sequence:
                         Synthetic polynucleotide"
source                   1..642
                         mol_type = other DNA
                         organism = synthetic construct
SEQUENCE: 221
gacatccaga tgacccagtc tccgtcctcc ctgtccgcat cagtggggga cagagtgacc   60
atcacttgtc gggcctccca aggcatctcg tcataccttgg cctggtatca gcagaaaccc  120
ggaaaggctc caaagctgct catctacacc gcctcgactc tgcaatccgg agtgccttcc  180
cgcttctccg gatccggttc gggaaccgac ttcaccctca ccattagcag ccttcagccg  240
gaagatttcg cgacctacta ctgccagcaa agctggacca ggcccaggac atttggccag  300
ggcactaagg tcgagattaa gcgtacggtg gccgctccca gtgttcatct cttcccccaa  360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gagagcgtca ccgagcagga cagcaaggac tccacctaca gcctgagcag cacccctgacc  540
ctgagcaagg ccgactacga aagcataag gtgtacgcct gcgaggtgac ccaccagggc  600
ctgtccagcc ccgtgaccaa gagcttcaac aggggcgagt gc                      642

SEQ ID NO: 222           moltype = DNA  length = 321
FEATURE                  Location/Qualifiers
misc_feature             1..321
                         note = source = /note="Description of Artificial Sequence:
                         Synthetic polynucleotide"
source                   1..321
                         mol_type = other DNA
                         organism = synthetic construct
SEQUENCE: 222
```

```
gacattcaaa tgactcagtc tccctcatct tgtcagcat cagttgggga cagggtgaca    60
atcacatgcc gagcctcaca ggggatttct agctatcttg catggtacca acagaagccc   120
ggcaaagccc ccaagctttt gatatatacg gcatccactc ttcagagcgg agtacccagt   180
aggtttagtg gctccgggag tggtacggac tttactctga cgatttcctc ccttcaacct   240
gaagactttg caacgtatta ctgtcagcaa atatggatgg ctcccagaac gtttggtcaa   300
ggtactaaag ttgaaataaa g                                             321
```

| SEQ ID NO: 223 | moltype = DNA length = 642 |
|---|---|
| FEATURE | Location/Qualifiers |
| misc_feature | 1..642 |
| | note = source = /note="Description of Artificial Sequence: Synthetic polynucleotide" |
| source | 1..642 |
| | mol_type = other DNA |
| | organism = synthetic construct |

SEQUENCE: 223
```
gacattcaaa tgactcagtc tccctcatct tgtcagcat cagttgggga cagggtgaca    60
atcacatgcc gagcctcaca ggggatttct agctatcttg catggtacca acagaagccc   120
ggcaaagccc ccaagctttt gatatatacg gcatccactc ttcagagcgg agtacccagt   180
aggtttagtg gctccgggag tggtacggac tttactctga cgatttcctc ccttcaacct   240
gaagactttg caacgtatta ctgtcagcaa atatggatgg ctcccagaac gtttggtcaa   300
ggtactaaag ttgaaataaa gcgaactgta gcagcaccta gtgtatttat cttcccccct   360
tctgatgaac agttgaagtc cgggacggct tccgtcgtat gtctcctgaa caactttac    420
ccaagggagg caaggtgca atggaaggtg gataatgcac tccagagtgg caatagccaa    480
gaatcagtaa ccgaacagga ttccaaggat tctacctaca gcctttcctc tacgcttaca   540
ttgagcaagg cggactatga aaagcataag gtgtatgcgt gcgaagtaac acaccagggt   600
ctcagcagtc cagttacgaa gtctttcaat cggggagaat gt                      642
```

| SEQ ID NO: 224 | moltype = DNA length = 321 |
|---|---|
| FEATURE | Location/Qualifiers |
| misc_feature | 1..321 |
| | note = source = /note="Description of Artificial Sequence: Synthetic polynucleotide" |
| source | 1..321 |
| | mol_type = other DNA |
| | organism = synthetic construct |

SEQUENCE: 224
```
gacatccaga tgacccagtc tccgtcctcc ctgtccgcat cagtggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa atctggatgg ccccaggac atttggccag    300
ggcactaagg tcgagattaa g                                             321
```

| SEQ ID NO: 225 | moltype = DNA length = 642 |
|---|---|
| FEATURE | Location/Qualifiers |
| misc_feature | 1..642 |
| | note = source = /note="Description of Artificial Sequence: Synthetic polynucleotide" |
| source | 1..642 |
| | mol_type = other DNA |
| | organism = synthetic construct |

SEQUENCE: 225
```
gacatccaga tgacccagtc tccgtcctcc ctgtccgcat cagtggggga cagagtgacc    60
atcacttgtc gggcctccca aggcatctcg tcatacctgg cctggtatca gcagaaaccc   120
ggaaaggctc caaagctgct catctacacc gcctcgactc tgcaatccgg agtgccttcc   180
cgcttctccg gatccggttc gggaaccgac ttcaccctca ccattagcag ccttcagccg   240
gaagatttcg cgacctacta ctgccagcaa atctggatgg ccccaggac atttggccag    300
ggcactaagg tcgagattaa gcgtacggtg gccgctccca gcgtgttcat cttcccccca   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

| SEQ ID NO: 226 | moltype = AA length = 10 |
|---|---|
| FEATURE | Location/Qualifiers |
| REGION | 1..10 |
| | note = source = /note="Description of Artificial Sequence: Synthetic peptide" |
| source | 1..10 |
| | mol_type = protein |
| | organism = synthetic construct |

SEQUENCE: 226
GFTFSSYWIS                                                           10

| SEQ ID NO: 227 | moltype = AA length = 17 |
|---|---|
| FEATURE | Location/Qualifiers |
| REGION | 1..17 |

```
                            note = source = /note="Description of Artificial Sequence:
                             Synthetic peptide"
source                      1..17
                            mol_type = protein
                            organism = synthetic construct
SEQUENCE: 227
NIKQSGSETY YVESVKG                                                           17

SEQ ID NO: 228              moltype = AA  length = 14
FEATURE                     Location/Qualifiers
REGION                      1..14
                            note = source = /note="Description of Artificial Sequence:
                             Synthetic peptide"
source                      1..14
                            mol_type = protein
                            organism = synthetic construct
SEQUENCE: 228
SLRRRSTEHA GFDV                                                              14

SEQ ID NO: 229              moltype = AA  length = 5
FEATURE                     Location/Qualifiers
REGION                      1..5
                            note = source = /note="Description of Artificial Sequence:
                             Synthetic peptide"
source                      1..5
                            mol_type = protein
                            organism = synthetic construct
SEQUENCE: 229
SYWIS                                                                        5

SEQ ID NO: 230              moltype = AA  length = 6
FEATURE                     Location/Qualifiers
REGION                      1..6
                            note = source = /note="Description of Artificial Sequence:
                             Synthetic peptide"
source                      1..6
                            mol_type = protein
                            organism = synthetic construct
SEQUENCE: 230
KQSGSE                                                                       6

SEQ ID NO: 231              moltype = AA  length = 8
FEATURE                     Location/Qualifiers
REGION                      1..8
                            note = source = /note="Description of Artificial Sequence:
                             Synthetic peptide"
source                      1..8
                            mol_type = protein
                            organism = synthetic construct
SEQUENCE: 231
IKQSGSET                                                                     8

SEQ ID NO: 232              moltype = AA  length = 16
FEATURE                     Location/Qualifiers
REGION                      1..16
                            note = source = /note="Description of Artificial Sequence:
                             Synthetic peptide"
source                      1..16
                            mol_type = protein
                            organism = synthetic construct
SEQUENCE: 232
ARSLRRRSTE HAGFDV                                                            16

SEQ ID NO: 233              moltype = AA  length = 123
FEATURE                     Location/Qualifiers
REGION                      1..123
                            note = source = /note="Description of Artificial Sequence:
                             Synthetic polypeptide"
source                      1..123
                            mol_type = protein
                            organism = synthetic construct
SEQUENCE: 233
EVQLVESGGG LVQPGGSLRL SCAASGFTFS SYWISWVRQA PGKGLEWVAN IKQSGSETYY             60
VESVKGRFTI SRDNAKNSLY LQMNSLRAED TAVYYCARSL RRRSTEHAGF DVWGQGTLVT            120
VSS                                                                         123

SEQ ID NO: 234              moltype = DNA  length = 369
FEATURE                     Location/Qualifiers
misc_feature                1..369
```

```
                            note = source = /note="Description of Artificial Sequence:
                            Synthetic polynucleotide"
source                      1..369
                            mol_type = other DNA
                            organism = synthetic construct
SEQUENCE: 234
gaagtgcagc tggtggaaag cggcggtggc ctggtgcagc aggtggtag cctgcgcctg    60
agctgcgccg ccagcggctt tacctttagc agctattgga ttagctgggt tcgccaggcc   120
ccaggcaaag gcctggaatg gtggcgaac atcaaacaga gcggcagcga gacctactat    180
gtggagagcg tgaaaggccg ctttaccatt agccgcgata cgccaaaaa cagcctgtat    240
ctgcaaatga acagcctgcg ggccgaagat accgccgtgt attattgcgc gcgtagcctg   300
cgtcgtcgta gcactgagca cgcaggattc gacgtttggg gccagggcac cctggttact   360
gtctcgagc                                                           369

SEQ ID NO: 235              moltype = AA   length = 453
FEATURE                     Location/Qualifiers
REGION                      1..453
                            note = source = /note="Description of Artificial Sequence:
                            Synthetic polypeptide"
source                      1..453
                            mol_type = protein
                            organism = synthetic construct
SEQUENCE: 235
EVQLVESGGG LVQPGGSLRL SCAASGFTFS SYWISWVRQA PGKGLEWVAN IKQSGSETYY    60
VESVKGRFTI SRDNAKNSLY LQMNSLRAED TAVYYCARSL RRRSTEHAGF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKR VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 236              moltype = DNA   length = 1359
FEATURE                     Location/Qualifiers
misc_feature                1..1359
                            note = source = /note="Description of Artificial Sequence:
                            Synthetic polynucleotide"
source                      1..1359
                            mol_type = other DNA
                            organism = synthetic construct
SEQUENCE: 236
gaagtgcagc tggtggaaag cggcggtggc ctggtgcagc aggtggtag cctgcgcctg    60
agctgcgccg ccagcggctt tacctttagc agctattgga ttagctgggt tcgccaggcc   120
ccaggcaaag gcctggaatg gtggcgaac atcaaacaga gcggcagcga gacctactat    180
gtggagagcg tgaaaggccg ctttaccatt agccgcgata cgccaaaaa cagcctgtat    240
ctgcaaatga acagcctgcg ggccgaagat accgccgtgt attattgcgc gcgtagcctg   300
cgtcgtcgta gcactgagca cgcaggattc gacgtttggg gccagggcac cctggttact   360
gtctcgagcg cgtcgaccaa aggcccagc gtgttccctc tggcccccag cagcaagagc    420
acctctggcg gaacagccgc cctgggctgc ctggtcaagg actacttccc cgagcccgtg   480
accgtgtcct ggaactctgg cgccctgacc agcggcgtgc acacctttcc agccgtgctc   540
cagagcagcg gcctgtacag cctgagcagc gtcgtgaccg tgcccagcag cagcctgggc   600
acccagacct acatctgcaa cgtgaaccac aagcccagca cacaaaaggt ggacaagcgt   660
gtggaaccca gagctgcgga caagacccac acctgtcccc cctgccctgc ccctgaagcg   720
gcgggaggcc cctccgtgtt cctgttcccc caaagcta aggacaccct gatgatcagc     780
cggacccccg aagtgacctg cgtggtggtg gacgtgtcc acgaggaccc tgaagtgaag   840
tttaattggt acgtggacgg cgtggaagtg cacaacgcca agaccaagcc cagagaggaa   900
cagtacaaca gcacctaccg ggtggtgtcc gtgctgaccg tgctgcacca ggactggctg   960
aacggcaaag agtacaagtg caaggtgtcc aacaaggccc tgcctgcccc catcgagaaa  1020
accatcagca aggccaaagg ccagccccgc gagccccagg tgtacacact gccccctagc  1080
cgggaagaga tgaccaagaa ccaggtgtcc ctgacctgcc tcgtgaaggg cttctacccc  1140
agcgacattg ccgtggaatg ggagagcaac ggccagcccg agaacaacta caagaccacc  1200
cccccctgtgc tggacagcga cggctcattc ttcctgtaca gcaagctgac cgtggacaag  1260
agccggtggc agcagggcaa cgtgttcagc tgctccgtga tgcacgaggc cctgcacaac  1320
cactacaccc agaagtccct gagcctgagc ccggcaag                          1359

SEQ ID NO: 237              moltype = AA   length = 11
FEATURE                     Location/Qualifiers
REGION                      1..11
                            note = source = /note="Description of Artificial Sequence:
                            Synthetic peptide"
source                      1..11
                            mol_type = protein
                            organism = synthetic construct
SEQUENCE: 237
RASQGISNYL A                                                         11

SEQ ID NO: 238              moltype = AA   length = 7
FEATURE                     Location/Qualifiers
REGION                      1..7
```

```
                        note = source = /note="Description of Artificial Sequence:
                            Synthetic peptide"
source                  1..7
                        mol_type = protein
                        organism = synthetic construct
SEQUENCE: 238
AASTLQS                                                                      7

SEQ ID NO: 239          moltype = AA  length = 9
FEATURE                 Location/Qualifiers
REGION                  1..9
                        note = source = /note="Description of Artificial Sequence:
                            Synthetic peptide"
source                  1..9
                        mol_type = protein
                        organism = synthetic construct
SEQUENCE: 239
QQADKFPYT                                                                    9

SEQ ID NO: 240          moltype = AA  length = 7
FEATURE                 Location/Qualifiers
REGION                  1..7
                        note = source = /note="Description of Artificial Sequence:
                            Synthetic peptide"
source                  1..7
                        mol_type = protein
                        organism = synthetic construct
SEQUENCE: 240
SQGISNY                                                                      7

SEQ ID NO: 241          moltype =   length =
SEQUENCE: 241
000

SEQ ID NO: 242          moltype = AA  length = 6
FEATURE                 Location/Qualifiers
REGION                  1..6
                        note = source = /note="Description of Artificial Sequence:
                            Synthetic peptide"
source                  1..6
                        mol_type = protein
                        organism = synthetic construct
SEQUENCE: 242
ADKFPY                                                                       6

SEQ ID NO: 243          moltype = AA  length = 6
FEATURE                 Location/Qualifiers
REGION                  1..6
                        note = source = /note="Description of Artificial Sequence:
                            Synthetic peptide"
source                  1..6
                        mol_type = protein
                        organism = synthetic construct
SEQUENCE: 243
QGISNY                                                                       6

SEQ ID NO: 244          moltype = AA  length = 107
FEATURE                 Location/Qualifiers
REGION                  1..107
                        note = source = /note="Description of Artificial Sequence:
                            Synthetic polypeptide"
source                  1..107
                        mol_type = protein
                        organism = synthetic construct
SEQUENCE: 244
DIQMTQSPSS LSASVGDRVT ITCRASQGIS NYLAWYQQKP GKVPKLLIYA ASTLQSGVPS         60
RFSGSGSGTD FTLTISSLQP EDVATYYCQQ ADKFPYTFGQ GTKVEIK                     107

SEQ ID NO: 245          moltype = DNA  length = 321
FEATURE                 Location/Qualifiers
misc_feature            1..321
                        note = source = /note="Description of Artificial Sequence:
                            Synthetic polynucleotide"
source                  1..321
                        mol_type = other DNA
                        organism = synthetic construct
SEQUENCE: 245
gatattcaga tgacccagag cccgagcagc ctgagcgcaa gcgtgggcga tcgcgtgacc         60
attacctgcc gcgccagcca gggcattagc aactatctgg cctggtatca gcagaaaccg        120
```

```
ggcaaagtgc cgaaactgct gatctatgcc gccagcaccc tgcaaagcgg cgtgccaagt    180
cgctttagcg gcagcggtag cggcaccgat ttcaccctga ccattagcag cctgcaaccg    240
gaagacgtgg cgacctatta ttgccagcag gctgacaaat cccgtacac cttcggccag    300
ggtaccaaag tggaaatcaa g                                              321

SEQ ID NO: 246          moltype = AA   length = 214
FEATURE                 Location/Qualifiers
REGION                  1..214
                        note = source = /note="Description of Artificial Sequence:
                          Synthetic polypeptide"
source                  1..214
                        mol_type = protein
                        organism = synthetic construct
SEQUENCE: 246
DIQMTQSPSS LSASVGDRVT ITCRASQGIS NYLAWYQQKP GKVPKLLIYA ASTLQSGVPS    60
RFSGSGSGTD FTLTISSLQP EDVATYYCQQ ADKFPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 247          moltype = DNA   length = 642
FEATURE                 Location/Qualifiers
misc_feature            1..642
                        note = source = /note="Description of Artificial Sequence:
                          Synthetic polynucleotide"
source                  1..642
                        mol_type = other DNA
                        organism = synthetic construct
SEQUENCE: 247
gatattcaga tgacccagag cccgagcagc ctgagcgcaa gcgtgggcga tcgcgtgacc     60
attacctgcc gcgccagcca gggcattagc aactatctgg cctggtatca gcagaaaccg    120
ggcaaagtgc cgaaactgct gatctatgcc gccagcaccc tgcaaagcgg cgtgccaagt    180
cgctttagcg gcagcggtag cggcaccgat ttcaccctga ccattagcag cctgcaaccg    240
gaagacgtgg cgacctatta ttgccagcag gctgacaaat cccgtacac cttcggccag    300
ggtaccaaag tggaaatcaa gcggaccgtg gccgctccc ccgtgttcat cttcccaccc    360
agcgacgagc agctgaagtc cggacagcc agcgtcgtgt gcctgctgaa caacttctac    420
ccccgcgagg ccaaagtgca gtggaaggtg gacaacgccc tccagagcgg caacagccag    480
gaaagcgtca ccgagcagga cagcaaggac tccacctaca gcctgagcag cacccctgacc    540
ctgagcaagg ccgactacga gaagcacaag gtgtacgcct gcgaagtgac ccaccagggc    600
ctgtccagcc ccgtgaccaa gagcttcaac cggggcgagt gt                      642

SEQ ID NO: 248          moltype = AA   length = 10
FEATURE                 Location/Qualifiers
REGION                  1..10
                        note = source = /note="Description of Artificial Sequence:
                          Synthetic peptide"
source                  1..10
                        mol_type = protein
                        organism = synthetic construct
SEQUENCE: 248
GFTFSSYSMN                                                            10

SEQ ID NO: 249          moltype = AA   length = 17
FEATURE                 Location/Qualifiers
REGION                  1..17
                        note = source = /note="Description of Artificial Sequence:
                          Synthetic peptide"
source                  1..17
                        mol_type = protein
                        organism = synthetic construct
SEQUENCE: 249
SISSSSSYIY YADSVKG                                                    17

SEQ ID NO: 250          moltype = AA   length = 11
FEATURE                 Location/Qualifiers
REGION                  1..11
                        note = source = /note="Description of Artificial Sequence:
                          Synthetic peptide"
source                  1..11
                        mol_type = protein
                        organism = synthetic construct
SEQUENCE: 250
SGYRGVYGFD Y                                                          11

SEQ ID NO: 251          moltype = AA   length = 5
FEATURE                 Location/Qualifiers
REGION                  1..5
                        note = source = /note="Description of Artificial Sequence:
                          Synthetic peptide"
source                  1..5
```

```
                        mol_type = protein
                        organism = synthetic construct
SEQUENCE: 251
SYSMN                                                                  5

SEQ ID NO: 252          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 252
SSSSSY                                                                 6

SEQ ID NO: 253          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 253
GFTFSSYS                                                               8

SEQ ID NO: 254          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 254
ISSSSSYI                                                               8

SEQ ID NO: 255          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 255
ARSGYRGVYG FDY                                                        13

SEQ ID NO: 256          moltype = AA  length = 120
FEATURE                 Location/Qualifiers
REGION                  1..120
                        note = source = /note="Description of Artificial Sequence:
                         Synthetic polypeptide"
source                  1..120
                        mol_type = protein
                        organism = synthetic construct
SEQUENCE: 256
EVQLVESGGG LVKPGGSLRL SCAASGFTFS SYSMNWVRQA PGKGLEWVSS ISSSSSYIYY     60
ADSVKGRFTI SRDNAKNSLY LQMNSLRAED TAVYYCARSG YRGVYGFDYW GQGTLVTVSS    120

SEQ ID NO: 257          moltype = DNA  length = 360
FEATURE                 Location/Qualifiers
misc_feature            1..360
                        note = source = /note="Description of Artificial Sequence:
                         Synthetic polynucleotide"
source                  1..360
                        mol_type = other DNA
                        organism = synthetic construct
SEQUENCE: 257
gaagtgcagc tggtggaaag cggcggtggc ctggtgaaac caggcggtag cctgcgcctg     60
agctgcgccg ccagcggctt tacctttagc agctatagca tgaactgggt tcgccaggcc    120
ccaggcaaag gcctggaatg ggttagcagc atcagcagca gtagcagcta tatctattac    180
gccgatagcg tgaaaggccg ctttaccatt agccgcgata acgccaaaaa cagcctgtat    240
ctgcaaatga acagcctgcg ggccgaagat accgccgtgt attattgcgc gcgaagcgga    300
tatcgtggag tttacggatt tgattattgg ggccagggca ccctggttac tgtctcgagc    360

SEQ ID NO: 258          moltype = AA  length = 450
FEATURE                 Location/Qualifiers
```

```
REGION                      1..450
                            note = source = /note="Description of Artificial Sequence:
                            Synthetic polypeptide"
source                      1..450
                            mol_type = protein
                            organism = synthetic construct
SEQUENCE: 258
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCARSG YRGVYGFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 259              moltype = DNA  length = 1350
FEATURE                     Location/Qualifiers
misc_feature                1..1350
                            note = source = /note="Description of Artificial Sequence:
                            Synthetic polynucleotide"
source                      1..1350
                            mol_type = other DNA
                            organism = synthetic construct
SEQUENCE: 259
gaagtgcagc tggtggaaag cggcggtggc ctggtgaaac caggcggtag cctgcgcctg     60
agctgcgccg ccagcggctt tacctttagc agctatagca tgaactgggt tcgccaggcc    120
ccaggcaaag gctggaatgg ggttagcagc atcagcagca gtagcagcta tatctattac    180
gccgatagcg tgaaaggccg ctttaccatt agccgcgata cgccaaaaaa cagcctgtat    240
ctgcaaatga acagcctgcg ggccgaagat accgccgtgt attattgcgc gcgaagcgga    300
tatcgtggag tttacggatt tgattattgg ggccagggca ccctggttac tgtctcgagc    360
gcgtcgacca aaggccccag cgtgttccct ctggccccca gcagcaagag cacctctggc    420
ggaacagccg ccctgggctg cctggtcaag gactacttcc ccgagccgt gaccgtgtcc    480
tggaactctg gcgccctgac cagcggcgtg cacacctttc cagccgtgct ccagagcagc    540
ggcctgtaca gcctgagcag cgtcgtgacc gtgccccaga gcagcctggg cacccagacc    600
tacatctgca acgtgaacca caagcccagc aacacaaagg tggacaagcg ggtggaaccc    660
aagagctgcg acaagaccca cacctgtccc cctgccctg ccctgaagc gggcgggaggc    720
ccctccgtgt tcctgttccc cccaaagcct aaggacaccc tgatgatcag ccggaccccc    780
gaagtgacct gcgtggtggt ggacgtgtcc cacgaggacc ctgaagtgaa gtttaattgg    840
tacgtggacg gcgtggaagt gcacaacgcc aagaccaagc cagagagga acagtacaac    900
agcacctacc gggtggtgtc cgtgctgacc gtgctgcacc aggactggct gaacggcaaa    960
gagtacaagt gcaaggtgtc caacaaggcc ctgcctgccc ccatcgagaa aaccatcagc   1020
aaggccaaag gccagccccg cgagccccag gtgtacaccc tgccccctag ccgggaagag   1080
atgaccaaga accaggtgtc cctgacctgc ctcgtgaagg gcttctaccc cagcgacatt   1140
gccgtggaat gggagagcaa cggccagccc gagaacaact acaagaccac ccccctgtg   1200
ctggacagcg acggctcatt cttcctgtac agcaagctga ccgtggacaa gagccggtgg   1260
cagcagggca acgtgttcag ctgctccgtg atgcacgagg ccctgcacaa ccactacacc   1320
cagaagtccc tgagcctgag ccccggcaag                                  1350

SEQ ID NO: 260              moltype = AA  length = 11
FEATURE                     Location/Qualifiers
REGION                      1..11
                            note = source = /note="Description of Artificial Sequence:
                            Synthetic peptide"
source                      1..11
                            mol_type = protein
                            organism = synthetic construct
SEQUENCE: 260
RASQGISSWL A                                                         11

SEQ ID NO: 261              moltype = AA  length = 7
FEATURE                     Location/Qualifiers
REGION                      1..7
                            note = source = /note="Description of Artificial Sequence:
                            Synthetic peptide"
source                      1..7
                            mol_type = protein
                            organism = synthetic construct
SEQUENCE: 261
AASSLQS                                                               7

SEQ ID NO: 262              moltype = AA  length = 9
FEATURE                     Location/Qualifiers
REGION                      1..9
                            note = source = /note="Description of Artificial Sequence:
                            Synthetic peptide"
source                      1..9
                            mol_type = protein
                            organism = synthetic construct
```

```
SEQUENCE: 262
QQYYHSPLT                                                                                    9

SEQ ID NO: 263          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 263
SQGISSW                                                                                      7

SEQ ID NO: 264          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 264
YYHSPL                                                                                       6

SEQ ID NO: 265          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 265
QGISSW                                                                                       6

SEQ ID NO: 266          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 266
DIQMTQSPSS VSASVGDRVT ITCRASQGIS SWLAWYQQKP GKAPKLLIYA ASSLQSGVPS    60
RFSGSGSGTD FTLTISSLQP EDFATYYCQQ YYHSPLTFGQ GTKVEIK                 107

SEQ ID NO: 267          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 267
gatattcaga tgacccagag cccgagcagc gttagcgcca gcgtgggcga tcgcgtgacc    60
attacctgcc gcgccagtca gggcattagc agctggctgg cctggtatca gcagaaaccg   120
ggcaaagccc cgaaactgct gatctatgcc gccagcagcc tgcaaagcgg cgtgccaagt   180
cgctttagcg gcagcggtag cggcaccgat ttcacccctg ccattagcag tctgcaaccg   240
gaagactttg ccacctatta ttgccagcag tactaccatt ctccgctgac cttcggccag   300
ggtaccaaag tggaaatcaa g                                            321

SEQ ID NO: 268          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 268
DIQMTQSPSS VSASVGDRVT ITCRASQGIS SWLAWYQQKP GKAPKLLIYA ASSLQSGVPS    60
RFSGSGSGTD FTLTISSLQP EDFATYYCQQ YYHSPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 269          moltype = DNA  length = 642
```

```
FEATURE              Location/Qualifiers
misc_feature         1..642
                     note = source = /note="Description of Artificial Sequence:
                     Synthetic polynucleotide"
source               1..642
                     mol_type = other DNA
                     organism = synthetic construct
SEQUENCE: 269
gatattcaga tgacccagag cccgagcagc gttagcgcca gcgtgggcga tcgcgtgacc    60
attacctgcc gcgccagtca gggcattagc agctggctgg cctggtatca gcagaaaccg   120
ggcaaagccc cgaaactgct gatctatgcc gccagcagcc tgcaaagcgg cgtgccaagt   180
cgctttagcg gcagcggtag cggcaccgat ttcaccctga ccattagcag tctgcaaccg   240
gaagactttg ccacctatta ttgccagcag tactaccatt ctccgctgac cttcggccag   300
ggtaccaaag tggaaatcaa gcggaccgtg gccgctccct ccgtgttcat cttcccaccc   360
agcgacgagc agctgaagtc cggcacagcc agcgtcgtgt gcctgctgaa caacttctac   420
ccccgcgagg ccaaagtgca gtggaaggtg gacaacgccc tccagagcgg caacagccag   480
gaaagcgtca ccgagcagga cagcaaggac tccacctaca gcctgagcag caccctgacc   540
ctgagcaagg ccgactacga aagcacaag tgtacgcct gcgaagtgac caccagggc    600
ctgtccagcc ccgtgaccaa gagcttcaac cggggcgagt gt                     642

SEQ ID NO: 270       moltype = AA   length = 10
FEATURE              Location/Qualifiers
REGION               1..10
                     note = source = /note="Description of Artificial Sequence:
                     Synthetic peptide"
source               1..10
                     mol_type = protein
                     organism = synthetic construct
SEQUENCE: 270
GFTFSSYAIS                                                           10

SEQ ID NO: 271       moltype = AA   length = 17
FEATURE              Location/Qualifiers
REGION               1..17
                     note = source = /note="Description of Artificial Sequence:
                     Synthetic peptide"
source               1..17
                     mol_type = protein
                     organism = synthetic construct
SEQUENCE: 271
AISGSGGSTY YAESVKG                                                   17

SEQ ID NO: 272       moltype = AA   length = 12
FEATURE              Location/Qualifiers
REGION               1..12
                     note = source = /note="Description of Artificial Sequence:
                     Synthetic peptide"
source               1..12
                     mol_type = protein
                     organism = synthetic construct
SEQUENCE: 272
ESGYVYYLKF DY                                                        12

SEQ ID NO: 273       moltype = AA   length = 5
FEATURE              Location/Qualifiers
REGION               1..5
                     note = source = /note="Description of Artificial Sequence:
                     Synthetic peptide"
source               1..5
                     mol_type = protein
                     organism = synthetic construct
SEQUENCE: 273
SYAIS                                                                 5

SEQ ID NO: 274       moltype = AA   length = 6
FEATURE              Location/Qualifiers
REGION               1..6
                     note = source = /note="Description of Artificial Sequence:
                     Synthetic peptide"
source               1..6
                     mol_type = protein
                     organism = synthetic construct
SEQUENCE: 274
SGSGGS                                                                6

SEQ ID NO: 275       moltype = AA   length = 8
FEATURE              Location/Qualifiers
REGION               1..8
                     note = source = /note="Description of Artificial Sequence:
```

```
                        Synthetic peptide"
source                  1..8
                        mol_type = protein
                        organism = synthetic construct
SEQUENCE: 275
GFTFSSYA                                                                   8

SEQ ID NO: 276          moltype = AA  length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 276
ISGSGGST                                                                   8

SEQ ID NO: 277          moltype = AA  length = 14
FEATURE                 Location/Qualifiers
REGION                  1..14
                        note = source = /note="Description of Artificial Sequence:
                        Synthetic peptide"
source                  1..14
                        mol_type = protein
                        organism = synthetic construct
SEQUENCE: 277
ARESGYVYYL KFDY                                                           14

SEQ ID NO: 278          moltype = AA  length = 121
FEATURE                 Location/Qualifiers
REGION                  1..121
                        note = source = /note="Description of Artificial Sequence:
                        Synthetic polypeptide"
source                  1..121
                        mol_type = protein
                        organism = synthetic construct
SEQUENCE: 278
EVQLLESGGG LVQPGGSLRL SCAASGFTFS SYAISWVRQA PGKGLEWVSA ISGSGGSTYY          60
AESVKGRFTI SRDNSKNTLY LQMNSLRAED TAVYYCARES GYVYYLKFDY WGQGTLVTVS         120
S                                                                        121

SEQ ID NO: 279          moltype = DNA  length = 363
FEATURE                 Location/Qualifiers
misc_feature            1..363
                        note = source = /note="Description of Artificial Sequence:
                        Synthetic polynucleotide"
source                  1..363
                        mol_type = other DNA
                        organism = synthetic construct
SEQUENCE: 279
gaagtgcagc tgctggaaag cggtggcggt ctggtgcagc caggtggtag cctgcgcctg          60
agctgtgccg caagcggctt tacctttagc agctatgcca ttagctgggt gcgccaagca         120
ccaggcaaag gcctggaatg ggtgagcgcc attagcggca gcggtggcag cacctattat         180
gccgagagcg tgaaaggtcg ctttaccatt agtcgcgata acagcaaaaa caccctgtat         240
ctgcaaatga acagcctgcg ggcagaagat accgcagttt attattgcgc gcgtgagagc         300
ggatacgttt actatctgaa attcgattat tggggccagg gcaccctggt tactgtctcg         360
agc                                                                      363

SEQ ID NO: 280          moltype = AA  length = 451
FEATURE                 Location/Qualifiers
REGION                  1..451
                        note = source = /note="Description of Artificial Sequence:
                        Synthetic polypeptide"
source                  1..451
                        mol_type = protein
                        organism = synthetic construct
SEQUENCE: 280
EVQLLESGGG LVQPGGSLRL SCAASGFTFS SYAISWVRQA PGKGLEWVSA ISGSGGSTYY          60
AESVKGRFTI SRDNSKNTLY LQMNSLRAED TAVYYCARES GYVYYLKFDY WGQGTLVTVS         120
SASTKGPSVF PLAPSSKSTS GGTAALGCLV KDYFPEPVTV SWNSGALTSG VHTFPAVLQS         180
SGLYSLSSVV TVPSSSLGTQ TYICNVNHKP SNTKVDKRVE PKSCDKTHTC PPCPAPEAAG         240
GPSVFLFPPK PKDTLMISRT PEVTCVVVDV SHEDPEVKFN WYVDGVEVHN AKTKPREEQY         300
NSTYRVVSVL TVLHQDWLNG KEYKCKVSNK ALPAPIEKTI SKAKGQPREP QVYTLPPSRE         360
EMTKNQVSLT CLVKGFYPSD IAVEWESNGQ PENNYKTTPP VLDSDGSFFL YSKLTVDKSR         420
WQQGNVFSCS VMHEALHNHY TQKSLSLSPG K                                        451

SEQ ID NO: 281          moltype = DNA  length = 1353
FEATURE                 Location/Qualifiers
```

| | | |
|---|---|---|
| misc_feature | 1..1353 | |
| | note = source = /note="Description of Artificial Sequence: Synthetic polynucleotide" | |
| source | 1..1353 | |
| | mol_type = other DNA | |
| | organism = synthetic construct | |

SEQUENCE: 281

```
gaagtgcagc tgctggaaag cggtggcggt ctggtgcagc caggtggtag cctgcgcctg    60
agctgtgcag caagcggctt tacctttagc agctatgcca ttagctgggt gcgccaagca   120
ccaggcaaag gcctggaatg ggtgagcgcc attagcggca gcggtggcag cacctattat   180
gccgagagcg tgaaaggtcg ctttaccatt agtcgcgata acagcaaaaa cacccctgtat  240
ctgcaaatga acagcctgcg ggcagaagat accgcagttt attattgcgc gcgtgagagc   300
ggatacgttt actatctgaa attcgattat tggggccagg gcaccctggt tactgtctcg   360
agcgcgtcga ccaaaggccc cagcgtgttc cctctggccc ccagcagcaa gagcacctct   420
ggcggaacag ccgccctggg ctgcctggtc aaggactact ccccgagcc cgtgaccgtg    480
tcctggaact ctggcgccct gaccagcggc gtgcacacct tccagccgt gctccagagc   540
agcggcctgt acagcctgag cagcgtcgtg accgtgccca gcagcagcct gggcacccag   600
acctacatct gcaacgtgaa ccacaagccc agcaacacaa aggtggacaa gcgggtggaa   660
cccaagagct gcgacaagac ccacacctgt cccccctgcc ctgcccctga gcggcggga    720
ggcccctccg tgttcctgtt cccccaaag cctaaggaca ccctgatgat cagccggacc    780
cccgaagtga cctgcgtggt ggtggacgtg tcccacgagg accctgaagt gaagtttaat   840
tggtacgtgg acggcgtgga agtgcacaac gccaagacca agcccagaga ggaacagtac    900
aacagcacct accgggtggt gtccgtgctg accgtgctgc accaggactg gctgaacggc    960
aaagagtaca gtgcaaggt gtccaacaag gccctgcctg cccccatcga gaaaaccatc   1020
agcaaggcca aggccagcc ccgcgagccc caggtgtaca cactgccccc tagccgggaa   1080
gagatgacca agaaccaggt gtccctgacc tgcctcgtga agggcttcta cccagcgac   1140
attgccgtgg aatgggagag caacggccag cccgagaaca actacaagac cacccccct    1200
gtgctggaca cgcgacggctc attcttcctg tacagcaagc tgaccgtgga caagagccgg  1260
tggcagcagg gcaacgtgtt cagctgctcc gtgatgcacg aggccctgca caaccactac  1320
acccagaagt ccctgagcct gagccccggc aag                                1353
```

| | | |
|---|---|---|
| SEQ ID NO: 282 | moltype = AA length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 282
RASQSISSYL N     11

| | | |
|---|---|---|
| SEQ ID NO: 283 | moltype = AA length = 9 | |
| FEATURE | Location/Qualifiers | |
| REGION | 1..9 | |
| | note = source = /note="Description of Artificial Sequence: Synthetic peptide" | |
| source | 1..9 | |
| | mol_type = protein | |
| | organism = synthetic construct | |

SEQUENCE: 283
QQHVRVPIT     9

| | | |
|---|---|---|
| SEQ ID NO: 284 | moltype = AA length = 7 | |
| FEATURE | Location/Qualifiers | |
| REGION | 1..7 | |
| | note = source = /note="Description of Artificial Sequence: Synthetic peptide" | |
| source | 1..7 | |
| | mol_type = protein | |
| | organism = synthetic construct | |

SEQUENCE: 284
SQSISSY     7

| | | |
|---|---|---|
| SEQ ID NO: 285 | moltype = AA length = 6 | |
| FEATURE | Location/Qualifiers | |
| REGION | 1..6 | |
| | note = source = /note="Description of Artificial Sequence: Synthetic peptide" | |
| source | 1..6 | |
| | mol_type = protein | |
| | organism = synthetic construct | |

SEQUENCE: 285
HVRVPI     6

| | | |
|---|---|---|
| SEQ ID NO: 286 | moltype = AA length = 6 | |
| FEATURE | Location/Qualifiers | |
| REGION | 1..6 | |
| | note = source = /note="Description of Artificial Sequence: | |

```
                              Synthetic peptide"
source                        1..6
                              mol_type = protein
                              organism = synthetic construct
SEQUENCE: 286
QSISSY                                                                      6

SEQ ID NO: 287                moltype = AA  length = 107
FEATURE                       Location/Qualifiers
REGION                        1..107
                              note = source = /note="Description of Artificial Sequence:
                              Synthetic polypeptide"
source                        1..107
                              mol_type = protein
                              organism = synthetic construct
SEQUENCE: 287
DIQMTQSPSS LSASVGDRVT ITCRASQSIS SYLNWYQQKP GKAPKLLIYA ASSLQSGVPS           60
RFSGSGSGTD FTLTISSLQP EDFATYYCQQ HVRVPITFGQ GTKVEIK                        107

SEQ ID NO: 288                moltype = DNA  length = 321
FEATURE                       Location/Qualifiers
misc_feature                  1..321
                              note = source = /note="Description of Artificial Sequence:
                              Synthetic polynucleotide"
source                        1..321
                              mol_type = other DNA
                              organism = synthetic construct
SEQUENCE: 288
gatattcaga tgacccagag cccgagcagc ctgagcgcca gcgtgggtga tcgcgtgacc           60
attacctgtc gcgcaagcca gagcattagc agctatctga actggtatca gcagaaacca          120
ggcaaagccc caaaactgct gatttatgcc gcaagcagcc tgcaaagcgg tgtgccgagc          180
cgctttagcg gcagcggtag cggcaccgat tttaccctga ccattagtag cctgcaaccg          240
gaagactttg ccacctatta ttgccagcag catgttcgtg ttccgatcac cttcggccag          300
ggtaccaaag tggaaatcaa g                                                    321

SEQ ID NO: 289                moltype = AA  length = 214
FEATURE                       Location/Qualifiers
REGION                        1..214
                              note = source = /note="Description of Artificial Sequence:
                              Synthetic polypeptide"
source                        1..214
                              mol_type = protein
                              organism = synthetic construct
SEQUENCE: 289
DIQMTQSPSS LSASVGDRVT ITCRASQSIS SYLNWYQQKP GKAPKLLIYA ASSLQSGVPS           60
RFSGSGSGTD FTLTISSLQP EDFATYYCQQ HVRVPITFGQ GTKVEIKRTV AAPSVFIFPP          120
SDEQLKSGTA SVVCLLNNFY PREAKVQWKV DNALQSGNSQ ESVTEQDSKD STYSLSSTLT          180
LSKADYEKHK VYACEVTHQG LSSPVTKSFN RGEC                                      214

SEQ ID NO: 290                moltype = DNA  length = 642
FEATURE                       Location/Qualifiers
misc_feature                  1..642
                              note = source = /note="Description of Artificial Sequence:
                              Synthetic polynucleotide"
source                        1..642
                              mol_type = other DNA
                              organism = synthetic construct
SEQUENCE: 290
gatattcaga tgacccagag cccgagcagc ctgagcgcca gcgtgggtga tcgcgtgacc           60
attacctgtc gcgcaagcca gagcattagc agctatctga actggtatca gcagaaacca          120
ggcaaagccc caaaactgct gatttatgcc gcaagcagcc tgcaaagcgg tgtgccgagc          180
cgctttagcg gcagcggtag cggcaccgat tttaccctga ccattagtag cctgcaaccg          240
gaagactttg ccacctatta ttgccagcag catgttcgtg ttccgatcac cttcggccag          300
ggtaccaaag tggaaatcaa gcggaccgtg gccgctcccc ccgtgttcat cttcccaccc          360
agcgacgagc agctgaagtc cggcacagcc agcgtcgtgt gcctgctgaa caacttctac          420
ccccgcgagg ccaaagtgca gtggaaggtg gacaacgccc tccagagcgg caacagccag          480
gaaagcgtca ccgagcagga cagcaaggac tccacctaca gcctgagcag cacccctgacc         540
ctgagcaagg ccgactacga aaagcacaag gtgtacgcct gcgaagtgac ccaccagggc          600
ctgtccagcc ccgtgaccaa gagcttcaac cggggcgagt gt                             642

SEQ ID NO: 291                moltype = AA  length = 10
FEATURE                       Location/Qualifiers
REGION                        1..10
                              note = source = /note="Description of Artificial Sequence:
                              Synthetic peptide"
source                        1..10
                              mol_type = protein
                              organism = synthetic construct
SEQUENCE: 291
```

```
GFTFSNYWIS                                                              10

SEQ ID NO: 292          moltype = AA  length = 19
FEATURE                 Location/Qualifiers
REGION                  1..19
                        note = source = /note="Description of Artificial Sequence:
                         Synthetic peptide"
source                  1..19
                        mol_type = protein
                        organism = synthetic construct
SEQUENCE: 292
RIKSKTYGGT TDYAEPVKG                                                    19

SEQ ID NO: 293          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 293
EKYSIRARGH GDYGFDV                                                      17

SEQ ID NO: 294          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 294
NYWIS                                                                    5

SEQ ID NO: 295          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 295
GFTFSNY                                                                  7

SEQ ID NO: 296          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 296
KSKTYGGT                                                                 8

SEQ ID NO: 297          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 297
GFTFSNYW                                                                 8

SEQ ID NO: 298          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 298
IKSKTYGGTT                                                              10
```

```
SEQ ID NO: 299               moltype = AA  length = 19
FEATURE                      Location/Qualifiers
REGION                       1..19
                             note = source = /note="Description of Artificial Sequence:
                             Synthetic peptide"
source                       1..19
                             mol_type = protein
                             organism = synthetic construct
SEQUENCE: 299
AREKYSIRAR GHGDYGFDV                                                  19

SEQ ID NO: 300               moltype = AA  length = 128
FEATURE                      Location/Qualifiers
REGION                       1..128
                             note = source = /note="Description of Artificial Sequence:
                             Synthetic polypeptide"
source                       1..128
                             mol_type = protein
                             organism = synthetic construct
SEQUENCE: 300
EVQLVESGGG LVKPGGSLRL SCAASGFTFS NYWISWVRQA PGKGLEWVGR IKSKTYGGTT      60
DYAEPVKGRF TISRDDSKNT LYLQMNSLKT EDTAVYYCAR EKYSIRARGH GDYGFDVWGQ     120
GTLVTVSS                                                             128

SEQ ID NO: 301               moltype = DNA  length = 384
FEATURE                      Location/Qualifiers
misc_feature                 1..384
                             note = source = /note="Description of Artificial Sequence:
                             Synthetic polynucleotide"
source                       1..384
                             mol_type = other DNA
                             organism = synthetic construct
SEQUENCE: 301
gaagtgcagc tggtggaaag cggcggtggc ctggtgaaac caggcggtag cctgcgcctg      60
agctgcgccg ccagcggctt tacctttagc aactattgga ttagctgggt tcgccaggcc     120
ccaggcaaag cctgaatg ggttggccgc atcaaaagca aaacctatgg cggcaccacc       180
gattatgccg agccagtgaa aggccgcttt accattagcc gcgacgatag caaaaacacc     240
ctgtacctgc aaatgaacag cctgaaaacc gaagatacc ccgtgtatta ttgcgcgcgt      300
gagaaatatt ccatccgtgc acgtggtcac ggagactacg gatttgatgt gtggggccag     360
ggcaccctgg ttactgtctc gagc                                            384

SEQ ID NO: 302               moltype = AA  length = 458
FEATURE                      Location/Qualifiers
REGION                       1..458
                             note = source = /note="Description of Artificial Sequence:
                             Synthetic polypeptide"
source                       1..458
                             mol_type = protein
                             organism = synthetic construct
SEQUENCE: 302
EVQLVESGGG LVKPGGSLRL SCAASGFTFS NYWISWVRQA PGKGLEWVGR IKSKTYGGTT      60
DYAEPVKGRF TISRDDSKNT LYLQMNSLKT EDTAVYYCAR EKYSIRARGH GDYGFDVWGQ     120
GTLVTVSSAS TKGPSVFPLA PSSKSTSGGT AALGCLVKDY FPEPVTVSWN SGALTSGVHT     180
FPAVLQSSGL YSLSSVVTVP SSSLGTQTYI CNVNHKPSNT KVDKRVEPKS CDKTHTCPPC     240
PAPEAAGGPS VFLFPPKPKD TLMISRTPEV TCVVVDVSHE DPEVKFNWYV DGVEVHNAKT     300
KPREEQYNST YRVVSVLTVL HQDWLNGKEY KCKVSNKALP APIEKTISKA KGQPREPQVY     360
TLPPSREEMT KNQVSLTCLV KGFYPSDIAV EWESNGQPEN NYKTTPPVLD SDGSFFLYSK     420
LTVDKSRWQQ GNVFSCSVMH EALHNHYTQK SLSLSPGK                            458

SEQ ID NO: 303               moltype = DNA  length = 1374
FEATURE                      Location/Qualifiers
misc_feature                 1..1374
                             note = source = /note="Description of Artificial Sequence:
                             Synthetic polynucleotide"
source                       1..1374
                             mol_type = other DNA
                             organism = synthetic construct
SEQUENCE: 303
gaagtgcagc tggtggaaag cggcggtggc ctggtgaaac caggcggtag cctgcgcctg      60
agctgcgccg ccagcggctt tacctttagc aactattgga ttagctgggt tcgccaggcc     120
ccaggcaaag cctgaatg ggttggccgc atcaaaagca aaacctatgg cggcaccacc       180
gattatgccg agccagtgaa aggccgcttt accattagcc gcgacgatag caaaaacacc     240
ctgtacctgc aaatgaacag cctgaaaacc gaagatacc ccgtgtatta ttgcgcgcgt      300
gagaaatatt ccatccgtgc acgtggtcac ggagactacg gatttgatgt gtggggccag     360
ggcaccctgg ttactgtctc gagcgcgtcg accaaaggcc ccagcgtgtt ccctctggcc     420
cccagcagca gagcaccctc tggcggaaca gccgcccctgg gctgcctggt caaggactac     480
ttccccgagc ccgtgaccgt gtcctggaac tctggcgccc tgaccagcgg cgtgcacacc     540
tttccagccg tgctccagag cagcggcctg tacagcctga gcgcgtcgt gaccgtgccc     600
agcagcagcc tgggcaccca gacctacatc tgcaacgtga accacaagcc cagcaacaca     660
```

```
aaggtggaca agcgggtgga acccaagagc tgcgacaaga cccacacctg tccccctgc    720
cctgccctg aagcggcggg aggcccctcc gtgttcctgt tccccccaaa gcctaaggac    780
accctgatga tcagccggac ccccgaagtg acctgcgtgg tggtggacgt gtcccacgag   840
gaccctgaag tgaagtttaa ttggtacgtg acggcgtgg aagtgcacaa cgccaagacc    900
aagcccagag aggaacagta caacagcacc taccgggtgg tgtccgtgct gaccgtgctg   960
caccaggact ggctgaacgg caaagagtac aagtgcaagg tgtccaacaa ggccctgcct   1020
gcccccatcg agaaaaccat cagcaaggcc aaaggccagc cccgcgagcc ccaggtgtac   1080
acactgcccc ctagccggga agagatgacc aagaaccagg tgtccctgac ctgcctcgtg   1140
aagggcttct accccagcga cattgccgtg gaatgggaga gcaacggcca gcccgagaac   1200
aactacaaga ccaccccccc tgtgctggac agcgacggct cattcttcct gtacagcaag   1260
ctgaccgtgg acaagagccg gtggcagcag ggcaacgtgt tcagctgctc cgtgatgcac   1320
gaggccctgc acaaccacta cacccagaag tccctgagcc tgagcccggg caag         1374

SEQ ID NO: 304              moltype = AA   length = 9
FEATURE                     Location/Qualifiers
REGION                      1..9
                            note = source = /note="Description of Artificial Sequence:
                             Synthetic peptide"
source                      1..9
                            mol_type = protein
                            organism = synthetic construct
SEQUENCE: 304
QQGYHAPFT                                                             9

SEQ ID NO: 305              moltype = AA   length = 6
FEATURE                     Location/Qualifiers
REGION                      1..6
                            note = source = /note="Description of Artificial Sequence:
                             Synthetic peptide"
source                      1..6
                            mol_type = protein
                            organism = synthetic construct
SEQUENCE: 305
GYHAPF                                                                6

SEQ ID NO: 306              moltype = AA   length = 107
FEATURE                     Location/Qualifiers
REGION                      1..107
                            note = source = /note="Description of Artificial Sequence:
                             Synthetic polypeptide"
source                      1..107
                            mol_type = protein
                            organism = synthetic construct
SEQUENCE: 306
DIQMTQSPSS LSASVGDRVT ITCRASQGIS NYLAWYQQKP GKVPKLLIYA ASTLQSGVPS    60
RFSGSGSGTD FTLTISSLQP EDVATYYCQQ GYHAPFTFGQ GTKVEIK                  107

SEQ ID NO: 307              moltype = DNA   length = 321
FEATURE                     Location/Qualifiers
misc_feature                1..321
                            note = source = /note="Description of Artificial Sequence:
                             Synthetic polynucleotide"
source                      1..321
                            mol_type = other DNA
                            organism = synthetic construct
SEQUENCE: 307
gatattcaga tgacccagag cccgagcagc ctgagcgcaa gcgtgggcga tcgcgtgacc    60
attacctgcc gcgccagcca gggcattagc aactatctgg cctggtatca gcagaaaccg   120
ggcaaagtgc cgaaactgct gatctatgcc gccagcaccc tgcaaagcgg cgtgccaagt   180
cgctttagcg gcagcggtag cggcaccgat ttcaccctga ccattagcag cctgcaaccg   240
gaagacgtgg cgacctatta ttgccagcag ggttaccatg ctccgttcac cttcggccag   300
ggtaccaaag tggaaatcaa g                                              321

SEQ ID NO: 308              moltype = AA   length = 214
FEATURE                     Location/Qualifiers
REGION                      1..214
                            note = source = /note="Description of Artificial Sequence:
                             Synthetic polypeptide"
source                      1..214
                            mol_type = protein
                            organism = synthetic construct
SEQUENCE: 308
DIQMTQSPSS LSASVGDRVT ITCRASQGIS NYLAWYQQKP GKVPKLLIYA ASTLQSGVPS    60
RFSGSGSGTD FTLTISSLQP EDVATYYCQQ GYHAPFTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 309              moltype = DNA   length = 642
FEATURE                     Location/Qualifiers
```

```
misc_feature          1..642
                      note = source = /note="Description of Artificial Sequence:
                      Synthetic polynucleotide"
source                1..642
                      mol_type = other DNA
                      organism = synthetic construct
SEQUENCE: 309
gatattcaga tgacccagag cccgagcagc ctgagcgcaa gcgtgggcga tcgcgtgacc    60
attacctgcc gcgccagcca gggcattagc aactatatgc cctggtatca gcagaaaccg   120
ggcaaagtgc cgaaactgct gatctatgcc gccagcaccc tgcaaagcgg cgtgccaagt   180
cgctttagcg gcagcggtag cggcaccgat ttcaccctga ccattagcag cctgcaaccg   240
gaagacgtgg cgacctatta ttgccagcag ggttaccatg ctccgttcac cttcggccag   300
ggtaccaaag tggaaatcaa gcggaccgtg gccgctccct ccgtgttcat cttcccaccc   360
agcgacgagc agctgaagtc cggcacagcc agcgtcgtgt gcctgctgaa caacttctac   420
ccccgcgagg ccaaagtgca gtggaaggtg gacaacgccc tccagagcgg caacagccag   480
gaaagcgtca ccgagcagga cagcaaggac tccacctaca gcctgagcag cacccctgacc  540
ctgagcaagg ccgactacga gaagcacaag gtgtacgcct gcgaagtgac ccaccagggc   600
ctgtccagcc ccgtgaccaa gagcttcaac cggggcgagt gt                      642

SEQ ID NO: 310        moltype = AA  length = 10
FEATURE               Location/Qualifiers
REGION                1..10
                      note = source = /note="Description of Artificial Sequence:
                      Synthetic peptide"
source                1..10
                      mol_type = protein
                      organism = synthetic construct
SEQUENCE: 310
GYSFTSYWIS                                                           10

SEQ ID NO: 311        moltype = AA  length = 17
FEATURE               Location/Qualifiers
REGION                1..17
                      note = source = /note="Description of Artificial Sequence:
                      Synthetic peptide"
source                1..17
                      mol_type = protein
                      organism = synthetic construct
SEQUENCE: 311
IIYPGTSYTR YSPSFQG                                                   17

SEQ ID NO: 312        moltype = AA  length = 11
FEATURE               Location/Qualifiers
REGION                1..11
                      note = source = /note="Description of Artificial Sequence:
                      Synthetic peptide"
source                1..11
                      mol_type = protein
                      organism = synthetic construct
SEQUENCE: 312
GAVAGQLGFD H                                                         11

SEQ ID NO: 313        moltype = AA  length = 6
FEATURE               Location/Qualifiers
REGION                1..6
                      note = source = /note="Description of Artificial Sequence:
                      Synthetic peptide"
source                1..6
                      mol_type = protein
                      organism = synthetic construct
SEQUENCE: 313
YPGTSY                                                                6

SEQ ID NO: 314        moltype = AA  length = 8
FEATURE               Location/Qualifiers
REGION                1..8
                      note = source = /note="Description of Artificial Sequence:
                      Synthetic peptide"
source                1..8
                      mol_type = protein
                      organism = synthetic construct
SEQUENCE: 314
IYPGTSYT                                                              8

SEQ ID NO: 315        moltype = AA  length = 13
FEATURE               Location/Qualifiers
REGION                1..13
                      note = source = /note="Description of Artificial Sequence:
                      Synthetic peptide"
```

```
source                  1..13
                        mol_type = protein
                        organism = synthetic construct
SEQUENCE: 315
ARGAVAGQLG FDH                                                         13

SEQ ID NO: 316          moltype = AA  length = 120
FEATURE                 Location/Qualifiers
REGION                  1..120
                        note = source = /note="Description of Artificial Sequence:
                         Synthetic polypeptide"
source                  1..120
                        mol_type = protein
                        organism = synthetic construct
SEQUENCE: 316
EVQLVQSGAE VKKPGESLKI SCKGSGYSFT SYWISWVRQM PGKGLEWMGI IYPGTSYTRY       60
SPSFQGQVTI SADKSISTAY LQWSSLKASD TAMYYCARGA VAGQLGFDHW GQGTLVTVSS      120

SEQ ID NO: 317          moltype = DNA  length = 360
FEATURE                 Location/Qualifiers
misc_feature            1..360
                        note = source = /note="Description of Artificial Sequence:
                         Synthetic polynucleotide"
source                  1..360
                        mol_type = other DNA
                        organism = synthetic construct
SEQUENCE: 317
gaagtgcagc tggtgcagag cggtgccgaa gtgaaaaaac cgggcgaaag cctgaaaatc       60
agctgcaaag gcagcggcta tagctttacc agctattgga ttagctgggt tcgccagatg      120
ccgggcaaag gcctggaatg gatgggcatt atctatccgg gcaccagcta tacccgctat      180
agcccgagct ttcagggcca ggttacaatt agcgccgaca aaagcatcag caccgcctat      240
ctgcaatgga gcagcctgaa agccagcgat accgccatgt attattgcgc gcgtggtgca      300
gttgcaggac aactgggatt tgatcactgg ggccagggca ccctggttac tgtctcgagc      360

SEQ ID NO: 318          moltype = AA  length = 450
FEATURE                 Location/Qualifiers
REGION                  1..450
                        note = source = /note="Description of Artificial Sequence:
                         Synthetic polypeptide"
source                  1..450
                        mol_type = protein
                        organism = synthetic construct
SEQUENCE: 318
EVQLVQSGAE VKKPGESLKI SCKGSGYSFT SYWISWVRQM PGKGLEWMGI IYPGTSYTRY       60
SPSFQGQVTI SADKSISTAY LQWSSLKASD TAMYYCARGA VAGQLGFDHW GQGTLVTVSS      120
ASTKGPSVFP LAPSSKSTSG GTAALGCLVK DYFPEPVTVS WNSGALTSGV HTFPAVLQSS      180
GLYSLSSVVT VPSSSLGTQT YICNVNHKPS NTKVDKRVEP KSCDKTHTCP PCPAPEAAGG      240
PSVFLFPPKP KDTLMISRTP EVTCVVVDVS HEDPEVKFNW YVDGVEVHNA KTKPREEQYN      300
STYRVVSVLT VLHQDWLNGK EYKCKVSNKA LPAPIEKTIS KAKGQPREPQ VYTLPPSREE      360
MTKNQVSLTC LVKGFYPSDI AVEWESNGQP ENNYKTTPPV LDSDGSFFLY SKLTVDKSRW      420
QQGNVFSCSV MHEALHNHYT QKSLSLSPGK                                      450

SEQ ID NO: 319          moltype = DNA  length = 1350
FEATURE                 Location/Qualifiers
misc_feature            1..1350
                        note = source = /note="Description of Artificial Sequence:
                         Synthetic polynucleotide"
source                  1..1350
                        mol_type = other DNA
                        organism = synthetic construct
SEQUENCE: 319
gaagtgcagc tggtgcagag cggtgccgaa gtgaaaaaac cgggcgaaag cctgaaaatc       60
agctgcaaag gcagcggcta tagctttacc agctattgga ttagctgggt tcgccagatg      120
ccgggcaaag gcctggaatg gatgggcatt atctatccgg gcaccagcta tacccgctat      180
agcccgagct ttcagggcca ggttacaatt agcgccgaca aaagcatcag caccgcctat      240
ctgcaatgga gcagcctgaa agccagcgat accgccatgt attattgcgc gcgtggtgca      300
gttgcaggac aactgggatt tgatcactgg ggccagggca ccctggttac tgtctcgagc      360
gcgtcgacca aaggcccag cgtgttcct ctggccccca gcagcaagag cacctctggc       420
ggaacagccg ccctgggctg cctggtcaag gactacttcc ccgagcccgt gaccgtgtcc      480
tggaactctg gcgccctgac cagcggcgtg cacaccttcc cagccgtgct ccagagcagc      540
ggcctgtaca gcctgagcag cgtcgtgacc gtgcccagca gcagcctggg cacccagacc      600
tacatctgca acgtgaacca caagcccagc aacacaaagg tggacaagcg ggtggaaccc      660
aagagctgcg acaagaccca cacctgtccc cctgccctg ccctgaagc ggcggaggc        720
cctccgtgt tcctgttccc cccaaagcct aaggacaccc tgatgatcag ccggacccc       780
gaagtgacct gcgtggtggt ggacgtgtcc cacgaggacc ctgaagtgaa gtttaattgg      840
tacgtggacg gcgtggaagt gcacaacgcc aagaccaagc cagagagga acagtacaac      900
agcacctacc gggtggtgtc cgtgctgacc gtgctgcacc aggactggct gaacggcaaa      960
gagtacaagt gcaaggtgtc caacaaggcc ctgcctgccc catcgagaa aaccatcagc      1020
aaggccaaag gccagcccgc gagcccag gtgtacacac tgcccctag ccgggaagag       1080
```

```
atgaccaaga accaggtgtc cctgacctgc ctcgtgaagg gcttctaccc cagcgacatt  1140
gccgtggaat gggagagcaa cggccagccc gagaacaact acaagaccac cccccctgtg  1200
ctggacagcg acggctcatt cttcctgtac agcaagctga ccgtggacaa gagccggtgg  1260
cagcagggca acgtgttcag ctgctccgtg atgcacgagg ccctgcacaa ccactacacc  1320
cagaagtccc tgagcctgag ccccggcaag                                    1350
```

| | | |
|---|---|---|
| SEQ ID NO: 320 | moltype = AA length = 14 | |
| FEATURE | Location/Qualifiers | |
| REGION | 1..14 | |
| | note = source = /note="Description of Artificial Sequence: Synthetic peptide" | |
| source | 1..14 | |
| | mol_type = protein | |
| | organism = synthetic construct | |
| SEQUENCE: 320 | | |
| TGSSSNIGAG YDVH | | 14 |

| | | |
|---|---|---|
| SEQ ID NO: 321 | moltype = AA length = 7 | |
| FEATURE | Location/Qualifiers | |
| REGION | 1..7 | |
| | note = source = /note="Description of Artificial Sequence: Synthetic peptide" | |
| source | 1..7 | |
| | mol_type = protein | |
| | organism = synthetic construct | |
| SEQUENCE: 321 | | |
| GNSNRPS | | 7 |

| | | |
|---|---|---|
| SEQ ID NO: 322 | moltype = AA length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |
| SEQUENCE: 322 | | |
| QSYYTSSHGP V | | 11 |

| | | |
|---|---|---|
| SEQ ID NO: 323 | moltype = AA length = 10 | |
| FEATURE | Location/Qualifiers | |
| REGION | 1..10 | |
| | note = source = /note="Description of Artificial Sequence: Synthetic peptide" | |
| source | 1..10 | |
| | mol_type = protein | |
| | organism = synthetic construct | |
| SEQUENCE: 323 | | |
| SSSNIGAGYD | | 10 |

| | |
|---|---|
| SEQ ID NO: 324 | moltype = length = |
| SEQUENCE: 324 | |
| 000 | |

| | | |
|---|---|---|
| SEQ ID NO: 325 | moltype = AA length = 8 | |
| FEATURE | Location/Qualifiers | |
| REGION | 1..8 | |
| | note = source = /note="Description of Artificial Sequence: Synthetic peptide" | |
| source | 1..8 | |
| | mol_type = protein | |
| | organism = synthetic construct | |
| SEQUENCE: 325 | | |
| YYTSSHGP | | 8 |

| | | |
|---|---|---|
| SEQ ID NO: 326 | moltype = AA length = 9 | |
| FEATURE | Location/Qualifiers | |
| REGION | 1..9 | |
| | note = source = /note="Description of Artificial Sequence: Synthetic peptide" | |
| source | 1..9 | |
| | mol_type = protein | |
| | organism = synthetic construct | |
| SEQUENCE: 326 | | |
| SSNIGAGYD | | 9 |

| | |
|---|---|
| SEQ ID NO: 327 | moltype = AA length = 111 |
| FEATURE | Location/Qualifiers |
| REGION | 1..111 |

```
                        note = source = /note="Description of Artificial Sequence:
                            Synthetic polypeptide"
source                  1..111
                        mol_type = protein
                        organism = synthetic construct
SEQUENCE: 327
QSVLTQPPSV SGAPGQRVTI SCTGSSSNIG AGYDVHWYQQ LPGTAPKLLI YGNSNRPSGV   60
PDRFSGSKSG TSASLAITGL QAEDEADYYC QSYYTSSHGP VFGGGTKLTV L           111

SEQ ID NO: 328          moltype = DNA   length = 333
FEATURE                 Location/Qualifiers
misc_feature            1..333
                        note = source = /note="Description of Artificial Sequence:
                            Synthetic polynucleotide"
source                  1..333
                        mol_type = other DNA
                        organism = synthetic construct
SEQUENCE: 328
cagagcgtgc tgacccagcc accaagcgtg agcggtgcac caggtcagcg cgtgaccatt    60
agctgcaccg gcagcagcag caacattggc gcaggctatg atgtgcattg gtatcagcag   120
ctgccaggca ccgcaccgaa actgctgatt tatggcaaca gcaatcgccc aagcggtgtg   180
ccggatcgct ttagcggcag caaaagcggc accagcgcca gcctggcgat taccggtctg   240
caagccgaag acgaagccga ttattactgc cagtcttact acacttcttc tcatggtccg   300
gtgtttggcg gcggtaccaa gctgaccgtg ctg                                333

SEQ ID NO: 329          moltype = AA    length = 217
FEATURE                 Location/Qualifiers
REGION                  1..217
                        note = source = /note="Description of Artificial Sequence:
                            Synthetic polypeptide"
source                  1..217
                        mol_type = protein
                        organism = synthetic construct
SEQUENCE: 329
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC QSYYTSSHGP VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 330          moltype = DNA   length = 651
FEATURE                 Location/Qualifiers
misc_feature            1..651
                        note = source = /note="Description of Artificial Sequence:
                            Synthetic polynucleotide"
source                  1..651
                        mol_type = other DNA
                        organism = synthetic construct
SEQUENCE: 330
cagagcgtgc tgacccagcc accaagcgtg agcggtgcac caggtcagcg cgtgaccatt    60
agctgcaccg gcagcagcag caacattggc gcaggctatg atgtgcattg gtatcagcag   120
ctgccaggca ccgcaccgaa actgctgatt tatggcaaca gcaatcgccc aagcggtgtg   180
ccggatcgct ttagcggcag caaaagcggc accagcgcca gcctggcgat taccggtctg   240
caagccgaag acgaagccga ttattactgc cagtcttact acacttcttc tcatggtccg   300
gtgtttggcg gcggtaccaa gctgaccgtg ctgggccagc ccaaagccgc ccctagcgtg   360
accctgttcc cccaaagcag cgaggaactc caggccaaca aggccaccct cgtgtgcctg   420
atcagcgact tctacccctgg cgccgtgacc gtggcctgga aggccgatag cagccctgtg   480
aaggccggct ggaaaccac cacccccagc aagcagagca caacaaata cgccgccagc    540
agctacctga gcctgacccc cgagcagtgg aagtcccaca gatcctacag ctgccaggtc   600
acacacgagg gcagcaccgt ggaaaagacc gtggccccca ccgagtgcag c            651

SEQ ID NO: 331          moltype = AA    length = 13
FEATURE                 Location/Qualifiers
REGION                  1..13
                        note = source = /note="Description of Artificial Sequence:
                            Synthetic peptide"
source                  1..13
                        mol_type = protein
                        organism = synthetic construct
SEQUENCE: 331
PYLGDRRSYG FDH                                                       13

SEQ ID NO: 332          moltype = AA    length = 15
FEATURE                 Location/Qualifiers
REGION                  1..15
                        note = source = /note="Description of Artificial Sequence:
                            Synthetic peptide"
source                  1..15
                        mol_type = protein
                        organism = synthetic construct
```

```
SEQUENCE: 332
ARPYLGDRRS YGFDH                                                   15

SEQ ID NO: 333          moltype = AA   length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 333
EVQLLESGGG LVQPGGSLRL SCAASGFTFS SYAISWVRQA PGKGLEWVSA ISGSGGSTYY   60
AESVKGRFTI SRDNSKNTLY LQMNSLRAED TAVYYCARPY LGDRRSYGFD HWGQGTLVTV  120
SS                                                                 122

SEQ ID NO: 334          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
SEQUENCE: 334
gaagtgcagc tgctggaaag cggtggcggt ctggtgcagc caggtggtag cctgcgcctg   60
agctgtgccg caagcggctt tacctttagc agctatgcca ttagctgggt gcgccaagca  120
ccaggcaaag gcctggaatg ggtgagcgcc attagcggca gcggtggcag cacctattat  180
gccgagagcg tgaaaggtcg ctttaccatt agtcgcgata cagcaaaaa cacccctgtat 240
ctgcaaatga acagcctgcg ggcagaagat accgcagttt attattgcgc gcgacctat  300
ctgggtgacc gtcgtagcta tggtttcgac cactggggcc agggcaccct ggttactgtc  360
tcgagc                                                             366

SEQ ID NO: 335          moltype = AA   length = 452
FEATURE                 Location/Qualifiers
REGION                  1..452
                        note = source = /note="Description of Artificial Sequence:
                         Synthetic polypeptide"
source                  1..452
                        mol_type = protein
                        organism = synthetic construct
SEQUENCE: 335
EVQLLESGGG LVQPGGSLRL SCAASGFTFS SYAISWVRQA PGKGLEWVSA ISGSGGSTYY   60
AESVKGRFTI SRDNSKNTLY LQMNSLRAED TAVYYCARPY LGDRRSYGFD HWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 336          moltype = DNA  length = 1356
FEATURE                 Location/Qualifiers
misc_feature            1..1356
                        note = source = /note="Description of Artificial Sequence:
                         Synthetic polynucleotide"
source                  1..1356
                        mol_type = other DNA
                        organism = synthetic construct
SEQUENCE: 336
gaagtgcagc tgctggaaag cggtggcggt ctggtgcagc caggtggtag cctgcgcctg   60
agctgtgccg caagcggctt tacctttagc agctatgcca ttagctgggt gcgccaagca  120
ccaggcaaag gcctggaatg ggtgagcgcc attagcggca gcggtggcag cacctattat  180
gccgagagcg tgaaaggtcg ctttaccatt agtcgcgata cagcaaaaa cacccctgtat 240
ctgcaaatga acagcctgcg ggcagaagat accgcagttt attattgcgc gcgacctat  300
ctgggtgacc gtcgtagcta tggtttcgac cactggggcc agggcaccct ggttactgtc  360
tcgagcgcgt cgaccaaagg ccccagcgtg ttccctctgg cccccagcag caagagcacc  420
tctgcggaa cagccgccct gggctgcctg gtcaaggact acttcccga gcccgtgacc  480
gtgtcctgga actctggcgc cctgaccagc ggcgtgcaca cctttccagc cgtgctccag  540
agcagcggcc tgtacagcct gagcagcgtc gtgaccgtgc ccagcagcag cctgggcacc  600
cagacctaca tctgcaacgt gaaccacaag cccagcaaca caaaggtgga caagcgggtg  660
gaacccaaga gctgcgacaa gacccacacc tgtccccct gccctgcccc tgaagcggcg  720
ggaggcccct ccgtgttcct gttccccca aagcctaagg acaccctgat gatcagccgg  780
acccccgaag tgacctgcgt ggtggtggac gtgtcccacg aggaccctga agtgaagttt  840
aattggtacg tggacggcgt ggaagtgcac aacgccaaga ccaagcccag agaggaacag  900
tacaacagca cctaccgggt ggtgtccgtg ctgaccgtgc tgcaccagga ctggctgaac  960
ggcaaagagt acaagtgcaa ggtgtccaac aaggcccctg ctgcccccat cgagaaaacc 1020
atcagcaagg ccaaagggca gccccgcgag ccccaggtgt acacactgcc cctagccgg 1080
gaagagatga ccaagaacca ggtgtccctg acctgcctcg tgaaggcctt ctaccccagc 1140
```

```
gacattgccg tggaatggga gagcaacggc cagcccgaga acaactacaa gaccaccccc  1200
cctgtgctgg acagcgacgg ctcattcttc ctgtacagca agctgaccgt ggacaagagc  1260
cggtggcagc agggcaacgt gttcagctgc tccgtgatgc acgaggccct gcacaaccac  1320
tacacccaga agtccctgag cctgagcccc ggcaag                            1356
```

```
SEQ ID NO: 337           moltype = AA   length = 14
FEATURE                  Location/Qualifiers
REGION                   1..14
                         note = source = /note="Description of Artificial Sequence:
                          Synthetic peptide"
source                   1..14
                         mol_type = protein
                         organism = synthetic construct
SEQUENCE: 337
TGTSSDVGSY NLVS                                                    14

SEQ ID NO: 338           moltype = AA   length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 338
EGSKRPS                                                            7

SEQ ID NO: 339           moltype = AA   length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 339
SSYGFHIVVV V                                                       11

SEQ ID NO: 340           moltype = AA   length = 10
FEATURE                  Location/Qualifiers
REGION                   1..10
                         note = source = /note="Description of Artificial Sequence:
                          Synthetic peptide"
source                   1..10
                         mol_type = protein
                         organism = synthetic construct
SEQUENCE: 340
TSSDVGSYNL                                                         10

SEQ ID NO: 341           moltype =     length =
SEQUENCE: 341
000

SEQ ID NO: 342           moltype = AA   length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 342
YGFHIVVV                                                           8

SEQ ID NO: 343           moltype = AA   length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 343
SSDVGSYNL                                                          9

SEQ ID NO: 344           moltype = AA   length = 111
FEATURE                  Location/Qualifiers
REGION                   1..111
                         note = source = /note="Description of Artificial Sequence:
```

```
                        Synthetic polypeptide"
source                  1..111
                        mol_type = protein
                        organism = synthetic construct
SEQUENCE: 344
QSALTQPASV SGSPGQSITI SCTGTSSDVG SYNLVSWYQQ HPGKAPKLMI YEGSKRPSGV   60
SNRFSGSKSG NTASLTISGL QAEDEADYYC SSYGFHIVVV VFGGGTKLTV L           111

SEQ ID NO: 345          moltype = DNA  length = 333
FEATURE                 Location/Qualifiers
misc_feature            1..333
                        note = source = /note="Description of Artificial Sequence:
                        Synthetic polynucleotide"
source                  1..333
                        mol_type = other DNA
                        organism = synthetic construct
SEQUENCE: 345
cagagcgccc tgacccagcc agccagcgtt agcggtagcc caggccagag cattaccatt   60
agctgcaccg gcaccagcag cgacgtgggc agctataacc tggttagctg gtatcagcag  120
catccgggca aagccccgaa actgatgatc tatgaaggca gcaaacgccc gagcggcgtt  180
agcaaccgct ttagtggcag caaaagcggc aacaccgcca gcctgaccat tagcggcctg  240
caagccgaag acgaagccga ttattactgc tcctcttacg gtttccatat cgttgttgtt  300
gtgtttggcg gcggtaccaa gctgaccgtg ctg                               333

SEQ ID NO: 346          moltype = AA  length = 217
FEATURE                 Location/Qualifiers
REGION                  1..217
                        note = source = /note="Description of Artificial Sequence:
                        Synthetic polypeptide"
source                  1..217
                        mol_type = protein
                        organism = synthetic construct
SEQUENCE: 346
QSALTQPASV SGSPGQSITI SCTGTSSDVG SYNLVSWYQQ HPGKAPKLMI YEGSKRPSGV   60
SNRFSGSKSG NTASLTISGL QAEDEADYYC SSYGFHIVVV VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 347          moltype = DNA  length = 651
FEATURE                 Location/Qualifiers
misc_feature            1..651
                        note = source = /note="Description of Artificial Sequence:
                        Synthetic polynucleotide"
source                  1..651
                        mol_type = other DNA
                        organism = synthetic construct
SEQUENCE: 347
cagagcgccc tgacccagcc agccagcgtt agcggtagcc caggccagag cattaccatt   60
agctgcaccg gcaccagcag cgacgtgggc agctataacc tggttagctg gtatcagcag  120
catccgggca aagccccgaa actgatgatc tatgaaggca gcaaacgccc gagcggcgtt  180
agcaaccgct ttagtggcag caaaagcggc aacaccgcca gcctgaccat tagcggcctg  240
caagccgaag acgaagccga ttattactgc tcctcttacg gtttccatat cgttgttgtt  300
gtgtttggcg gcggtaccaa gctgaccgtg ctggggcagc ccaaagccgc ccctagcgtg  360
accctgttcc ccccaagcag cgaggaactc caggccaaca aggccaccct cgtgtgcctg  420
atcagcgact ctacccctgg cgccgtgacc gtggcctgga aggccgatag cagccctgtg  480
aaggccggcg tggaaaccac caccccccagc aagcagagca acaacaaata cgccgccagc  540
agctacctga gcctgacccc cgagcagtgg aagtcccaca gatcctacag ctgccaggtc  600
acacacgagg gcagcaccgt ggaaaagacc gtggccccca ccgagtgcag c            651

SEQ ID NO: 348          moltype = AA  length = 11
FEATURE                 Location/Qualifiers
REGION                  1..11
                        note = source = /note="Description of Artificial Sequence:
                        Synthetic peptide"
source                  1..11
                        mol_type = protein
                        organism = synthetic construct
SEQUENCE: 348
GSLPGLLGFD H                                                        11

SEQ ID NO: 349          moltype = AA  length = 13
FEATURE                 Location/Qualifiers
REGION                  1..13
                        note = source = /note="Description of Artificial Sequence:
                        Synthetic peptide"
source                  1..13
                        mol_type = protein
                        organism = synthetic construct
SEQUENCE: 349
```

ARGSLPGLLG FDH                                                                      13

SEQ ID NO: 350          moltype = AA  length = 120
FEATURE                 Location/Qualifiers
REGION                  1..120
                        note = source = /note="Description of Artificial Sequence:
                        Synthetic polypeptide"
source                  1..120
                        mol_type = protein
                        organism = synthetic construct
SEQUENCE: 350
EVQLVQSGAE VKKPGESLKI SCKGSGYSFT SYWISWVRQM PGKGLEWMGI IYPGTSYTRY   60
SPSFQGQVTI SADKSISTAY LQWSSLKASD TAMYYCARGS LPGLLGFDHW GQGTLVTVSS  120

SEQ ID NO: 351          moltype = DNA  length = 360
FEATURE                 Location/Qualifiers
misc_feature            1..360
                        note = source = /note="Description of Artificial Sequence:
                        Synthetic polynucleotide"
source                  1..360
                        mol_type = other DNA
                        organism = synthetic construct
SEQUENCE: 351
gaagtgcagc tggtgcagag cggtgccgaa gtgaaaaaac cgggcgaaag cctgaaaatc    60
agctgcaaag gcagcggcta tagctttacc agctattgga ttagctgggt tcgccagatg   120
ccgggcaaag gcctggaatg gatgggcatt atctatccgg gcaccagcta taccgctat   180
agcccgagct ttcagggcca ggttacaatt agcgccgaca aaagcatcag caccgctat   240
ctgcaatgga gcagcctgaa agccagcgat accgccatgt attattgcgc gcgtggaagc   300
ctgcctggtc tgctgggttt tgatcactgg ggccagggca ccctggttac tgtctcgagc   360

SEQ ID NO: 352          moltype = AA  length = 450
FEATURE                 Location/Qualifiers
REGION                  1..450
                        note = source = /note="Description of Artificial Sequence:
                        Synthetic polypeptide"
source                  1..450
                        mol_type = protein
                        organism = synthetic construct
SEQUENCE: 352
EVQLVQSGAE VKKPGESLKI SCKGSGYSFT SYWISWVRQM PGKGLEWMGI IYPGTSYTRY   60
SPSFQGQVTI SADKSISTAY LQWSSLKASD TAMYYCARGS LPGLLGFDHW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 353          moltype = DNA  length = 1350
FEATURE                 Location/Qualifiers
misc_feature            1..1350
                        note = source = /note="Description of Artificial Sequence:
                        Synthetic polynucleotide"
source                  1..1350
                        mol_type = other DNA
                        organism = synthetic construct
SEQUENCE: 353
gaagtgcagc tggtgcagag cggtgccgaa gtgaaaaaac cgggcgaaag cctgaaaatc    60
agctgcaaag gcagcggcta tagctttacc agctattgga ttagctgggt tcgccagatg   120
ccgggcaaag gcctggaatg gatgggcatt atctatccgg gcaccagcta taccgctat   180
agcccgagct ttcagggcca ggttacaatt agcgccgaca aaagcatcag caccgctat   240
ctgcaatgga gcagcctgaa agccagcgat accgccatgt attattgcgc gcgtggaagc   300
ctgcctggtc tgctgggttt tgatcactgg ggccagggca ccctggttac tgtctcgagc   360
gcgtcgacca aaggcccag cgtgttccct ctggcctcca cctctgtgc                420
ggaacagccg ccctgggctg cctggtcaag gactacttcc ccgagccgt gaccgtgtcc    480
tggaactctg gcgccctgac cagcggcgtg cacacctttc agccgtgct ccagagcagc   540
ggcctgtaca gcctgagcag cgtcgtgacc gtgcccagca gcagcctggg cacccagacc   600
tacatctgca acgtgaacca caagcccagc aacacaaagg tggacaagcg ggtggaaccc   660
aagagctgcg acaagaccca cacctgtccc ccctgccctg ccccgaagc ggcggaggc     720
ccctccgtgt tcctgttccc cccaaagcct aaggacaccc tgatgatcag ccggacccc    780
gaagtgacct gcgtggtggt ggacgtgtcc cacgaggacc ctgaagtgaa gtttaattgg   840
tacgtggacg gcgtggaagt gcacaacgcc aagaccaagc cagagagga acagtacaac   900
agcacctacc gggtggtgtc cgtgctgacc gtgctgcacc aggactggct gaacggcaaa   960
gagtacaagt gcaaggtgtc caacaaggcc ctgcctgcc catcgagaa aaccatcagc   1020
aaggccaaag gccagcccg cgagcccag gtgtacacac tgcccccag ccggaagag      1080
atgaccaaga accaggtgtc cctgacctgc ctcgtgaagg gcttctaccc cagcgacatt   1140
gccgtggaat gggagagcaa cggccagccc gagaacaact acaagaccac ccccctgtg   1200
ctggacagcg acggctcatt cttcctgtac agcaagctga ccgtggacaa gagccggtgg   1260
cagcagggca acgtgttcag ctgctccgtg atgcacgagg ccctgcacaa ccactacacc   1320

```
cagaagtccc tgagcctgag ccccggcaag                                    1350

SEQ ID NO: 354          moltype = AA   length = 7
FEATURE                 Location/Qualifiers
REGION                  1..7
                        note = source = /note="Description of Artificial Sequence:
                        Synthetic peptide"
source                  1..7
                        mol_type = protein
                        organism = synthetic construct
SEQUENCE: 354
GNSNRPN                                                             7

SEQ ID NO: 355          moltype = AA   length = 11
FEATURE                 Location/Qualifiers
REGION                  1..11
                        note = source = /note="Description of Artificial Sequence:
                        Synthetic peptide"
source                  1..11
                        mol_type = protein
                        organism = synthetic construct
SEQUENCE: 355
QSYDSPTSSS V                                                        11

SEQ ID NO: 356          moltype = AA   length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 356
YDSPTSSS                                                            8

SEQ ID NO: 357          moltype = AA   length = 111
FEATURE                 Location/Qualifiers
REGION                  1..111
                        note = source = /note="Description of Artificial Sequence:
                        Synthetic polypeptide"
source                  1..111
                        mol_type = protein
                        organism = synthetic construct
SEQUENCE: 357
QSVLTQPPSV SGAPGQRVTI SCTGSSSNIG AGYDVHWYQQ LPGTAPKLLI YGNSNRPNGV    60
PDRFSGSKSG TSASLAITGL QAEDEADYYC QSYDSPTSSS VFGGGTKLTV L             111

SEQ ID NO: 358          moltype = DNA   length = 333
FEATURE                 Location/Qualifiers
misc_feature            1..333
                        note = source = /note="Description of Artificial Sequence:
                        Synthetic polynucleotide"
source                  1..333
                        mol_type = other DNA
                        organism = synthetic construct
SEQUENCE: 358
cagagcgtgc tgacccagcc accaagcgtg agcggtgcac caggtcagcg cgtgaccatt    60
agctgcaccg gcagcagcag caacattggc gcaggctatg atgtgcattg gtatcagcag    120
ctgccaggca ccgcaccgaa actgctgatt tatggcaaca gcaatcgccc aaacggtgtg    180
ccggatcgct ttagcggcag caaaagcggc accagcgcca gcctggcgat taccggtctg    240
caagccgaag acgaagccga ttattactgc cagtcttacg actctccgac ttcttcttct    300
gtgtttggcg gcggtaccaa gctgaccgtg ctg                                333

SEQ ID NO: 359          moltype = AA   length = 217
FEATURE                 Location/Qualifiers
REGION                  1..217
                        note = source = /note="Description of Artificial Sequence:
                        Synthetic polypeptide"
source                  1..217
                        mol_type = protein
                        organism = synthetic construct
SEQUENCE: 359
QSVLTQPPSV SGAPGQRVTI SCTGSSSNIG AGYDVHWYQQ LPGTAPKLLI YGNSNRPNGV    60
PDRFSGSKSG TSASLAITGL QAEDEADYYC QSYDSPTSSS VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 360          moltype = DNA   length = 651
FEATURE                 Location/Qualifiers
```

```
misc_feature          1..651
                      note = source = /note="Description of Artificial Sequence:
                        Synthetic polynucleotide"
source                1..651
                      mol_type = other DNA
                      organism = synthetic construct
SEQUENCE: 360
cagagcgtgc tgacccagcc accaagcgtg agcggtgcac caggtcagcg cgtgaccatt    60
agctgcaccg gcagcagcag caacattggc gcaggctatg atgtgcattg gtatcagcag   120
ctgccaggca ccgcaccgaa actgctgatt tatggcaaca gcaatcgccc aaacggtgtg   180
ccggatcgct ttagcggcag caaaagcggc accagcgcca gcctggcgat taccggtctg   240
caagccgaag acgaagccga ttattactgc cagtcttacg actctccgac ttcttcttct   300
gtgtttggcg gcggtaccaa gctgaccgtg ctgggccagc ccaaagccgc ccctagcgtg   360
accctgttcc cccccaagcag cgaggaactc caggccaaca aggcaccct cgtgtgcctg   420
atcagcgact tctaccctgg cgccgtgacc gtggcctgga aggccgatag cagccctgtg   480
aaggccggcg tggaaaccac cacccccagc aagcagagca caacaaata cgccgccagc   540
agctacctga gcctgacccc cgagcagtgg aagtcccaca tcctacag ctgccaggtc    600
acacacgagg gcagcaccgt ggaaaagacc gtggccccca ccgagtgcag c            651

SEQ ID NO: 361         moltype = AA  length = 11
FEATURE                Location/Qualifiers
REGION                 1..11
                       note = source = /note="Description of Artificial Sequence:
                         Synthetic peptide"
source                 1..11
                       mol_type = protein
                       organism = synthetic construct
SEQUENCE: 361
QSYGAFPRFV V                                                         11

SEQ ID NO: 362         moltype = AA  length = 8
FEATURE                Location/Qualifiers
REGION                 1..8
                       note = source = /note="Description of Artificial Sequence:
                         Synthetic peptide"
source                 1..8
                       mol_type = protein
                       organism = synthetic construct
SEQUENCE: 362
YGAFPRFV                                                             8

SEQ ID NO: 363         moltype = AA  length = 111
FEATURE                Location/Qualifiers
REGION                 1..111
                       note = source = /note="Description of Artificial Sequence:
                         Synthetic polypeptide"
source                 1..111
                       mol_type = protein
                       organism = synthetic construct
SEQUENCE: 363
QSVLTQPPSV SGAPGQRVTI SCTGSSSNIG AGYDVHWYQQ LPGTAPKLLI YGNSNRPNGV    60
PDRFSGSKSG TSASLAITGL QAEDEADYYC QSYGAFPRFV VFGGGTKLTV L             111

SEQ ID NO: 364         moltype = DNA  length = 333
FEATURE                Location/Qualifiers
misc_feature           1..333
                       note = source = /note="Description of Artificial Sequence:
                         Synthetic polynucleotide"
source                 1..333
                       mol_type = other DNA
                       organism = synthetic construct
SEQUENCE: 364
cagagcgtgc tgacccagcc accaagcgtg agcggtgcac caggtcagcg cgtgaccatt    60
agctgcaccg gcagcagcag caacattggc gcaggctatg atgtgcattg gtatcagcag   120
ctgccaggca ccgcaccgaa actgctgatt tatggcaaca gcaatcgccc aaacggtgtg   180
ccggatcgct ttagcggcag caaaagcggc accagcgcca gcctggcgat taccggtctg   240
caagccgaag acgaagccga ttattactgc caatcctatg gtgccttccc tcgtttcgtt   300
gtttttggcg gcggtaccaa gctgaccgtg ctg                                333

SEQ ID NO: 365         moltype = AA  length = 217
FEATURE                Location/Qualifiers
REGION                 1..217
                       note = source = /note="Description of Artificial Sequence:
                         Synthetic polypeptide"
source                 1..217
                       mol_type = protein
                       organism = synthetic construct
SEQUENCE: 365
QSVLTQPPSV SGAPGQRVTI SCTGSSSNIG AGYDVHWYQQ LPGTAPKLLI YGNSNRPNGV    60
```

```
PDRFSGSKSG TSASLAITGL QAEDEADYYC QSYGAFPRFV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217
```

```
SEQ ID NO: 366              moltype = DNA   length = 651
FEATURE                     Location/Qualifiers
misc_feature                1..651
                            note = source = /note="Description of Artificial Sequence:
                             Synthetic polynucleotide"
source                      1..651
                            mol_type = other DNA
                            organism = synthetic construct
SEQUENCE: 366
cagagcgtgc tgacccagcc accaagcgtg agcggtgcac caggtcagcg cgtgaccatt     60
agctgcaccg gcagcagcag caacattggc gcaggctatg atgtgcattg gtatcagcag    120
ctgccaggca ccgcaccgaa actgctgatt tatggcaaca gcaatcgccc aaacggtgtg    180
ccggatcgct tagcggcag caaaagcggc accagcgcca gctggcgat taccggtctg     240
caagccgaag acgaagccga ttattactgc caatcctatg gtgccttccc tcgtttcgtt    300
gttttttggcg gcggtaccaa gctgaccgtg ctgggccagc ccaaagccgc ccctagcgtg    360
accctgttcc ccccaagcag cgaggaactc caggccaaca aggccaccct cgtgtgcctg    420
atcagcgact tctaccctgg cgccgtgacc gtggcctgga aggccgatag cagccctgtg    480
aaggccggcg tggaaaccac caccccccagc aagcagagca acaacaaata cgccgccagc    540
agctacctga gcctgacccc cgagcagtgg aagtcccaca gatcctacag ctgccaggtc    600
acacacgagg gcagcaccgt ggaaaagacc gtggccccca ccgagtgcag c             651
```

```
SEQ ID NO: 367              moltype = AA   length = 10
FEATURE                     Location/Qualifiers
REGION                      1..10
                            note = source = /note="Description of Artificial Sequence:
                             Synthetic peptide"
source                      1..10
                            mol_type = protein
                            organism = synthetic construct
SEQUENCE: 367
GFSFSKYYLN                                                            10
```

```
SEQ ID NO: 368              moltype = AA   length = 17
FEATURE                     Location/Qualifiers
REGION                      1..17
                            note = source = /note="Description of Artificial Sequence:
                             Synthetic peptide"
source                      1..17
                            mol_type = protein
                            organism = synthetic construct
SEQUENCE: 368
SIHQQAHEKK YVESVKG                                                    17
```

```
SEQ ID NO: 369              moltype = AA   length = 5
FEATURE                     Location/Qualifiers
REGION                      1..5
                            note = source = /note="Description of Artificial Sequence:
                             Synthetic peptide"
source                      1..5
                            mol_type = protein
                            organism = synthetic construct
SEQUENCE: 369
KYYLN                                                                 5
```

```
SEQ ID NO: 370              moltype = AA   length = 7
FEATURE                     Location/Qualifiers
REGION                      1..7
                            note = source = /note="Description of Artificial Sequence:
                             Synthetic peptide"
source                      1..7
                            mol_type = protein
                            organism = synthetic construct
SEQUENCE: 370
GFSFSKY                                                               7
```

```
SEQ ID NO: 371              moltype = AA   length = 6
FEATURE                     Location/Qualifiers
REGION                      1..6
                            note = source = /note="Description of Artificial Sequence:
                             Synthetic peptide"
source                      1..6
                            mol_type = protein
                            organism = synthetic construct
SEQUENCE: 371
HQQAHE                                                                6
```

```
SEQ ID NO: 372           moltype = AA   length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 372
GFSFSKYY                                                                  8

SEQ ID NO: 373           moltype = AA   length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 373
IHQQAHEK                                                                  8

SEQ ID NO: 374           moltype = AA   length = 123
FEATURE                  Location/Qualifiers
REGION                   1..123
                         note = source = /note="Description of Artificial Sequence:
                          Synthetic polypeptide"
source                   1..123
                         mol_type = protein
                         organism = synthetic construct
SEQUENCE: 374
EVQLVESGGG LVQPGGSLRL SCAASGFSFS KYYLNWVRQA PGKGLEWVAS IHQQAHEKKY   60
VESVKGRFTI SRDNAKNSLY LQMNSLRAED TAVYYCARSL RRRSTEHAGF DVWGQGTLVT  120
VSS                                                                123

SEQ ID NO: 375           moltype = DNA   length = 369
FEATURE                  Location/Qualifiers
misc_feature             1..369
                         note = source = /note="Description of Artificial Sequence:
                          Synthetic polynucleotide"
source                   1..369
                         mol_type = other DNA
                         organism = synthetic construct
SEQUENCE: 375
gaagtgcagc tggtggaaag cggcggtggc ctggtgcagc caggtggtag cctgcgcctg   60
agctgcgccg ccagcggctt tagcttcagc aaatattact tgaactgggt tcgccaggcc  120
ccaggcaaag gcctggaatg ggtggccagc attaccagc aagcacacga gaaaaaatac   180
gtggagtccg tgaaaggccg ctttaccatt agcgcgata acgccaaaaa cagcctgtat    240
ctgcaaatga acagcctgcg ggccgaagat accgccgtgt attattgcgc gcgtagcctg   300
cgtcgtcgta gcactgagca cgcaggattc gacgtttggg gccagggcac cctggttact   360
gtctcgagc                                                          369

SEQ ID NO: 376           moltype = AA   length = 453
FEATURE                  Location/Qualifiers
REGION                   1..453
                         note = source = /note="Description of Artificial Sequence:
                          Synthetic polypeptide"
source                   1..453
                         mol_type = protein
                         organism = synthetic construct
SEQUENCE: 376
EVQLVESGGG LVQPGGSLRL SCAASGFSFS KYYLNWVRQA PGKGLEWVAS IHQQAHEKKY   60
VESVKGRFTI SRDNAKNSLY LQMNSLRAED TAVYYCARSL RRRSTEHAGF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 377           moltype = DNA   length = 1359
FEATURE                  Location/Qualifiers
misc_feature             1..1359
                         note = source = /note="Description of Artificial Sequence:
                          Synthetic polynucleotide"
source                   1..1359
                         mol_type = other DNA
                         organism = synthetic construct
```

```
SEQUENCE: 377
gaagtgcagc tggtggaaag cggcggtggc ctggtgcagc caggtggtag cctgcgcctg    60
agctgcgccg ccagcggctt tagcttcagc aaatattact tgaactgggt tcgccaggcc   120
ccaggcaaag gcctggaatg ggtggccagc attcaccagc aagcacacga gaaaaaatac   180
gtggagtccg tgaaaggccg ctttaccatt agccgcgata acgccaaaaa cagcctgtat   240
ctgcaaatga acagcctgcg ggccgaagat accgccgtgt attattgcgc gcgtagcctg   300
cgtcgtcgta gcactgagca cgcaggattc gactttgggg ccagggcac cctggttact   360
gtctcgagcg cgtcgaccaa aggccccagc gtgttccctc tggcccccag cagcaagagc   420
acctctggcg gaacagccgc cctgggctgc ctggtcaagg actacttccc cgagcccgtg   480
accgtgtcct ggaactctgg cgccctgacc agcggcgtgc acaccttcc agccgtgctc   540
cagagcagcg gcctgtacag cctgagcagc gtcgtgaccg tgcccagcag cagcctgggc   600
acccagacct acatctgcaa cgtgaaccac aagcccagca cacaaaggt ggacaagcgg   660
gtggaaccca gagctgcga caagacccac acctgtcccc cctgccctgc ccctgaagcg   720
gcgggaggcc cctccgtgtt cctgttcccc ccaaagccta aggacaccct gatgatcagc   780
cggaccccg aagtgacctg cgtggtggtg gacgtgtccc acgaggaccc tgaagtgaag   840
tttaattggt acgtggacgg cgtggaagtg cacaacgcca agaccaagcc cagagaggaa   900
cagtacaaca gcacctaccg ggtggtgtcc gtgctgaccg tgctgcacca ggactggctg   960
aacggcaaag agtacaagtg caaggtgtcc aacaaggccc tgcctgccccc catcgagaaa  1020
accatcagca aggccaaagg ccagccccgc gagcccagg tgtacacact gcccccctagc  1080
cgggaagaga tgaccaagaa ccaggtgtcc ctgacctgcc tcgtgaaggg cttctacccc  1140
agcgacattg ccgtggaatg ggagagcaac ggccagcccg agaacaacta caagaccacc  1200
ccccctgtgc tggacagcga cggctcattc ttcctgtaca gcaagctgac cgtggacaag  1260
agccggtggc agcagggcaa cgtgttcagc tgctccgtga tgcacgaggc cctgcacaac  1320
cactacaccc agaagtccct gagcctgagc cccggcaag                         1359

SEQ ID NO: 378         moltype = AA   length = 10
FEATURE                Location/Qualifiers
REGION                 1..10
                       note = source = /note="Description of Artificial Sequence:
                       Synthetic peptide"
source                 1..10
                       mol_type = protein
                       organism = synthetic construct
SEQUENCE: 378
GFTFSRYYIN                                                            10

SEQ ID NO: 379         moltype = AA   length = 17
FEATURE                Location/Qualifiers
REGION                 1..17
                       note = source = /note="Description of Artificial Sequence:
                       Synthetic peptide"
source                 1..17
                       mol_type = protein
                       organism = synthetic construct
SEQUENCE: 379
SIHQHGLETR YVESVKG                                                    17

SEQ ID NO: 380         moltype = AA   length = 5
FEATURE                Location/Qualifiers
REGION                 1..5
                       note = source = /note="Description of Artificial Sequence:
                       Synthetic peptide"
source                 1..5
                       mol_type = protein
                       organism = synthetic construct
SEQUENCE: 380
RYYIN                                                                  5

SEQ ID NO: 381         moltype = AA   length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 381
GFTFSRY                                                                7

SEQ ID NO: 382         moltype = AA   length = 6
FEATURE                Location/Qualifiers
REGION                 1..6
                       note = source = /note="Description of Artificial Sequence:
                       Synthetic peptide"
source                 1..6
                       mol_type = protein
                       organism = synthetic construct
SEQUENCE: 382
HQHGLE                                                                 6
```

```
SEQ ID NO: 383          moltype = AA  length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 383
GFTFSRYY                                                                  8

SEQ ID NO: 384          moltype = AA  length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 384
IHQHGLET                                                                  8

SEQ ID NO: 385          moltype = AA  length = 123
FEATURE                 Location/Qualifiers
REGION                  1..123
                        note = source = /note="Description of Artificial Sequence:
                        Synthetic polypeptide"
source                  1..123
                        mol_type = protein
                        organism = synthetic construct
SEQUENCE: 385
EVQLVESGGG LVQPGGSLRL SCAASGFTFS RYYINWVRQA PGKGLEWVAS IHQHGLETRY   60
VESVKGRFTI SRDNAKNSLY LQMNSLRAED TAVYYCARSL RRRSTEHAGF DVWGQGTLVT  120
VSS                                                                123

SEQ ID NO: 386          moltype = DNA  length = 369
FEATURE                 Location/Qualifiers
misc_feature            1..369
                        note = source = /note="Description of Artificial Sequence:
                        Synthetic polynucleotide"
source                  1..369
                        mol_type = other DNA
                        organism = synthetic construct
SEQUENCE: 386
gaagtgcagc tggtggaaag cggcggtggc ctggtgcagc caggtggtag cctgcgcctg   60
agctgcgccg ccagcgggtt tacttttttcc agatattaca ttaattgggt tcgccaggcc  120
ccaggcaaag ccctggaatg ggtggcgagc atccaccagc acggcctgga gaccagatat  180
gtggaatctg tcaaagggcg ctttaccatt agccgcgata cgccaaaaaa cagcctgtat  240
ctgcaaatga acagcctgcg ggccgaagat accgccgtgt attattgcgc gcgtagcctg  300
cgtcgtcgta gcactgagca cgcaggattc gacgtttggg gccagggcac cctggttact  360
gtctcgagc                                                          369

SEQ ID NO: 387          moltype = AA  length = 453
FEATURE                 Location/Qualifiers
REGION                  1..453
                        note = source = /note="Description of Artificial Sequence:
                        Synthetic polypeptide"
source                  1..453
                        mol_type = protein
                        organism = synthetic construct
SEQUENCE: 387
EVQLVESGGG LVQPGGSLRL SCAASGFTFS RYYINWVRQA PGKGLEWVAS IHQHGLETRY   60
VESVKGRFTI SRDNAKNSLY LQMNSLRAED TAVYYCARSL RRRSTEHAGF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 388          moltype = DNA  length = 1359
FEATURE                 Location/Qualifiers
misc_feature            1..1359
                        note = source = /note="Description of Artificial Sequence:
                        Synthetic polynucleotide"
source                  1..1359
                        mol_type = other DNA
                        organism = synthetic construct
```

```
SEQUENCE: 388
gaagtgcagc tggtggaaag cggcggtggc ctggtgcagc caggtggtag cctgcgcctg   60
agctgcgccg ccagcgggtt tactttttcc agatattaca ttaattgggt tcgccaggcc  120
ccaggcaaag gcctggaatg ggtggcgagc atccaccagc acggcctgga gaccagatat  180
gtggaatctg tcaaagggcg ctttaccatt agccgcgata acgccaaaaa cagcctgtat  240
ctgcaaatga acagcctgcg ggccgaagat accgccgtgt attattgcgc gcgtagcctg  300
cgtcgtcgta gcactgagca cgcaggattc gacgtttggg gccagggcac cctggttact  360
gtctcgagcg cgtcgaccaa aggccccagc gtgttcctc tggcccccag cagcaagagc  420
acctctggcg gaacagccgc cctgggctgc ctggtcaagg actacttccc cgagcccgtg  480
accgtgtcct ggaactctgg cgccctgacc agcggcgtgc acaccttcc agccgtgctc  540
cagagcagcg gcctgtacag cctgagcagc gtcgtgaccg tgcccagcag cagcctgggc  600
acccagacct acatctgcaa cgtgaaccac aagcccagca cacaaaggt ggacaagcgg  660
gtggaaccca gagctgcga caagacccac acctgtcccc cctgccctgc ccctgaagcg  720
gcgggaggcc cctccgtgtt cctgttcccc ccaaagccta aggacaccct gatgatcagc  780
cggacccccg aagtgacctg cgtggtggtg gacgtgtccc acgaggaccc tgaagtgaag  840
tttaattggt acgtggacgg cgtggaagtg cacaacgcca agaccaagcc cagagaggaa  900
cagtacaaca gcacctaccg ggtggtgtcc gtgctgaccg tgctgcacca ggactggctg  960
aacggcaaag agtacaagtg caaggtgtcc aacaaggccc tgcctgccc catcgagaaa 1020
accatcagca aggccaaagg ccagccccgc gagccccagg tgtacacact gcccctagc 1080
cgggaagaga tgaccaagaa ccaggtgtcc ctgacctgcc tcgtgaaggg cttctacccc 1140
agcgacattg ccgtggaatg ggagagcaac ggccagcccg agaacaacta caagaccacc 1200
cccctgtgc tggacagcga cggctcattc ttcctgtaca gcaagctgac cgtggacaag 1260
agccggtggc agcagggcaa cgtgttcagc tgctccgtga tgcacgaggc cctgcacaac 1320
cactacaccc agaagtccct gagcctgagc cccggcaag                        1359

SEQ ID NO: 389      moltype = AA   length = 17
FEATURE             Location/Qualifiers
REGION              1..17
                    note = source = /note="Description of Artificial Sequence:
                    Synthetic peptide"
source              1..17
                    mol_type = protein
                    organism = synthetic construct
SEQUENCE: 389
SISSHGYYTR YAESVKG                                                  17

SEQ ID NO: 390      moltype = AA   length = 6
FEATURE             Location/Qualifiers
REGION              1..6
                    note = source = /note="Description of Artificial Sequence:
                    Synthetic peptide"
source              1..6
                    mol_type = protein
                    organism = synthetic construct
SEQUENCE: 390
SSHGYY                                                              6

SEQ ID NO: 391      moltype = AA   length = 8
FEATURE             Location/Qualifiers
REGION              1..8
                    note = source = /note="Description of Artificial Sequence:
                    Synthetic peptide"
source              1..8
                    mol_type = protein
                    organism = synthetic construct
SEQUENCE: 391
ISSHGYYT                                                            8

SEQ ID NO: 392      moltype = AA   length = 122
FEATURE             Location/Qualifiers
REGION              1..122
                    note = source = /note="Description of Artificial Sequence:
                    Synthetic polypeptide"
source              1..122
                    mol_type = protein
                    organism = synthetic construct
SEQUENCE: 392
EVQLLESGGG LVQPGGSLRL SCAASGFTFS SYAISWVRQA PGKGLEWVSS ISSHGYYTRY   60
AESVKGRFTI SRDNSKNTLY LQMNSLRAED TAVYYCARPY LGDRRSYGFD HWGQGTLVTV  120
SS                                                                 122

SEQ ID NO: 393      moltype = DNA  length = 366
FEATURE             Location/Qualifiers
misc_feature        1..366
                    note = source = /note="Description of Artificial Sequence:
                    Synthetic polynucleotide"
source              1..366
                    mol_type = other DNA
                    organism = synthetic construct
```

```
SEQUENCE: 393
gaagtgcagc tgctggaaag cggtggcggt ctggtgcagc caggtggtag cctgcgcctg   60
agctgtgccg caagcgggtt tacatttttcc agctatgcta tcagctgggt gcgccaagca  120
ccaggcaaag gcctggaatg ggtgagcagc attagctcac atggatatta cacccggtat  180
gccgagtccg tgaaaggtcg ctttaccatt agtcgcgata acagcaaaaa cacccctgtat 240
ctgcaaatga acagcctgcg ggcagaagat accgcagttt attattgcgc gcgacccttat 300
ctgggtgacc gtcgtagcta tggtttcgac cactggggcc agggcaccct ggttactgtc  360
tcgagc                                                              366

SEQ ID NO: 394           moltype = AA   length = 452
FEATURE                  Location/Qualifiers
REGION                   1..452
                         note = source = /note="Description of Artificial Sequence:
                         Synthetic polypeptide"
source                   1..452
                         mol_type = protein
                         organism = synthetic construct
SEQUENCE: 394
EVQLLESGGG LVQPGGSLRL SCAASGFTFS SYAISWVRQA PGKGLEWVSS ISSHGYYTRY    60
AESVKGRFTI SRDNSKNTLY LQMNSLRAED TAVYYCARPY LGDRRSYGFD HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 395           moltype = DNA   length = 1356
FEATURE                  Location/Qualifiers
misc_feature             1..1356
                         note = source = /note="Description of Artificial Sequence:
                         Synthetic polynucleotide"
source                   1..1356
                         mol_type = other DNA
                         organism = synthetic construct
SEQUENCE: 395
gaagtgcagc tgctggaaag cggtggcggt ctggtgcagc caggtggtag cctgcgcctg   60
agctgtgccg caagcgggtt tacatttttcc agctatgcta tcagctgggt gcgccaagca  120
ccaggcaaag gcctggaatg ggtgagcagc attagctcac atggatatta cacccggtat  180
gccgagtccg tgaaaggtcg ctttaccatt agtcgcgata acagcaaaaa cacccctgtat 240
ctgcaaatga acagcctgcg ggcagaagat accgcagttt attattgcgc gcgacccttat 300
ctgggtgacc gtcgtagcta tggtttcgac cactggggcc agggcaccct ggttactgtc  360
tcgagcgcgt cgaccaaagg ccccagcgtg ttccctctgg ccccagcctc aagagcacc   420
tctggcggaa cagccgccct gggctgcctg gtcaaggact acttcccga gcccgtgacc  480
gtgtcctgga actctggcgc cctgaccagc ggcgtgcaca cctttccagc cgtgctccag   540
agcagcggcc tgtacagcct gagcagcgtc gtgaccgtgc ccagcagcag cctgggcacc   600
cagacctaca tctgcaacgt gaaccacaag cccagcacca caaggtgga caagcgggtg  660
gaacccaaga gctgcgacaa gacccacacc tgtccccct gccctgcccc tgaagcggcg   720
ggaggcccct ccgtgttcct gttccccca aagcctaagg acaccctgat gatcagccgg   780
accccccgaag tgacctgcgt ggtggtggac gtgtcccacg aggaccctga agtgaagttt   840
aattgtacg tggacgcgt ggaagtgcac aacgccaaga ccaagcccag agaggaacag   900
tacaacagca cctaccgggt ggtgtccgtg ctgaccgtgc tgcaccagga ctggctgaac   960
ggcaaagagt acaagtgcaa ggtgtccaac aaggccctgc ctgccccat cgagaaaacc  1020
atcagcaagg ccaaaggcca gccccgcgag ccccaggtgt acacactgcc cctagccgg  1080
gaagagatga ccaagaacca ggtgtccctg acctgctgc tgaagggctt ctaccccagc  1140
gacattgccg tggaatggga gagcaacggc cagcccgaga caactacaa gaccaccccc  1200
cctgtgctgg acagcgacgg ctcattcttc ctgtacagca agctgaccgt ggacaagagc  1260
cggtggcagc agggcaacgt gttcagctgc tccgtgatgc acgaggccct gcacaaccac  1320
tacacccaga gtccctgag cctgagcccc ggcaag                             1356

SEQ ID NO: 396           moltype = AA   length = 10
FEATURE                  Location/Qualifiers
REGION                   1..10
                         note = source = /note="Description of Artificial Sequence:
                         Synthetic peptide"
source                   1..10
                         mol_type = protein
                         organism = synthetic construct
SEQUENCE: 396
GFTFASYAIT                                                           10

SEQ ID NO: 397           moltype = AA   length = 17
FEATURE                  Location/Qualifiers
REGION                   1..17
                         note = source = /note="Description of Artificial Sequence:
                         Synthetic peptide"
source                   1..17
                         mol_type = protein
                         organism = synthetic construct
```

```
SEQUENCE: 397
TISGSGVYTY YAESVKG                                                           17

SEQ ID NO: 398          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 398
SYAIT                                                                         5

SEQ ID NO: 399          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 399
GFTFASY                                                                       7

SEQ ID NO: 400          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 400
SGSGVY                                                                        6

SEQ ID NO: 401          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 401
GFTFASYA                                                                      8

SEQ ID NO: 402          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 402
ISGSGVYT                                                                      8

SEQ ID NO: 403          moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 403
EVQLLESGGG LVQPGGSLRL SCAASGFTFA SYAITWVRQA PGKGLEWVST ISGSGVYTYY              60
AESVKGRFTI SRDNSKNTLY LQMNSLRAED TAVYYCARPY LGDRRSYGFD HWGQGTLVTV             120
SS                                                                          122

SEQ ID NO: 404          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
```

```
SEQUENCE: 404
gaagtgcagc tgctggaaag cggtggcggt ctggtgcagc caggtggtag cctgcgcctg    60
agctgtgccg caagcgggtt cacattcgca tcctatgcaa ttacttgggt gcgccaagca   120
ccaggcaaag gcctggaatg ggtgagcacc atttccgggt ccggtgtgta cacctattac   180
gccgagtccg tcaaaggccg ctttaccatt agtcgcgata cagcaaaaa caccctgtat   240
ctgcaaatga acagcctgcg ggcagaagat accgcagttt attattgcgc gcgacccttat  300
ctgggtgacc gtcgtagcta tggtttcgac cactggggcc agggcaccct ggttactgtc   360
tcgagc                                                              366
```

| SEQ ID NO: 405 | moltype = AA  length = 452 |
|---|---|
| FEATURE | Location/Qualifiers |
| REGION | 1..452 |
| | note = source = /note="Description of Artificial Sequence: Synthetic polypeptide" |
| source | 1..452 |
| | mol_type = protein |
| | organism = synthetic construct |

```
SEQUENCE: 405
EVQLLESGGG LVQPGGSLRL SCAASGFTFA SYAITWVRQA PGKGLEWVST ISGSGVYTYY    60
AESVKGRFTI SRDNSKNTLY LQMNSLRAED TAVYYCARPY LGDRRSYGFD HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452
```

| SEQ ID NO: 406 | moltype = DNA  length = 1356 |
|---|---|
| FEATURE | Location/Qualifiers |
| misc_feature | 1..1356 |
| | note = source = /note="Description of Artificial Sequence: Synthetic polynucleotide" |
| source | 1..1356 |
| | mol_type = other DNA |
| | organism = synthetic construct |

```
SEQUENCE: 406
gaagtgcagc tgctggaaag cggtggcggt ctggtgcagc caggtggtag cctgcgcctg    60
agctgtgccg caagcgggtt cacattcgca tcctatgcaa ttacttgggt gcgccaagca   120
ccaggcaaag gcctggaatg ggtgagcacc atttccgggt ccggtgtgta cacctattac   180
gccgagtccg tcaaaggccg ctttaccatt agtcgcgata cagcaaaaa caccctgtat   240
ctgcaaatga acagcctgcg ggcagaagat accgcagttt attattgcgc gcgacccttat  300
ctgggtgacc gtcgtagcta tggtttcgac cactggggcc agggcaccct ggttactgtc   360
tcgagccgt cgaccaaagg cccatcagtg ttccctctgg ccccagcagc aagagcacc    420
tctggcggaa cagccgccct gggctgcctg gtcaaggact acttccccga gcccgtgacc   480
gtgtcctgga actctggcgc cctgaccagc ggcgtgcaca cctttccagc cgtgctccag   540
agcagcggcc tgtacagcct gagcagcgtc gtgaccgtgc ccagcagcag cctgggcacc   600
cagacctaca tctgcaacgt gaaccacaag cccagcaaca caaaggtgga caagcgggtg  660
gaacccaaga gctgcgacaa gacccacacc tgtccccccct gccctgcccc tgaagcggcg  720
gaggcccct ccgtgttcct gttccccccca aagcctaagg acaccctgat gatcagccgg    780
accccagaag tgacctgcgt ggtggtggac gtgtcccacg aggaccctga agtgaagttt   840
aattgtacg tggacggcgt ggaagtgcac aacgccaaga ccaagcccag agaggaacag   900
tacaacagca cctaccgggt ggtgtccgtg ctgaccgtgc tgcaccagga ctggctgaac   960
ggcaaagagt acaagtgcaa ggtgtccaac aaggccctgc ctgcccccat cgagaaaacc  1020
atcagcaagg ccaaaggcca gccccgcgag ccccaggtgt acacactgcc cctagccgg  1080
gaagagatga ccaagaacca ggtgtccctg acctgcctgg tgaagggctt ctacccage  1140
gacattgccg tggaatggga gagcaacggc cagcccgaga caactacaa gaccaccccc   1200
cctgtgctgg acagcgacgg ctcattcttc ctgtacagca agctgaccgt ggacaagagc  1260
cggtggcagc agggcaacgt gttcagctgc tccgtgatgc acgaggccct gcacaaccac  1320
tacacccaga gtccctgag cctgagcccc ggcaag                             1356
```

| SEQ ID NO: 407 | moltype = AA  length = 10 |
|---|---|
| FEATURE | Location/Qualifiers |
| REGION | 1..10 |
| | note = source = /note="Description of Artificial Sequence: Synthetic peptide" |
| source | 1..10 |
| | mol_type = protein |
| | organism = synthetic construct |

```
SEQUENCE: 407
GFTFGTYAMT                                                           10
```

| SEQ ID NO: 408 | moltype = AA  length = 17 |
|---|---|
| FEATURE | Location/Qualifiers |
| REGION | 1..17 |
| | note = source = /note="Description of Artificial Sequence: Synthetic peptide" |
| source | 1..17 |
| | mol_type = protein |
| | organism = synthetic construct |

```
SEQUENCE: 408
SISASGYYAN YAGSVKG                                                    17

SEQ ID NO: 409          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 409
TYAMT                                                                 5

SEQ ID NO: 410          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 410
GFTFGTY                                                               7

SEQ ID NO: 411          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 411
SASGYY                                                                6

SEQ ID NO: 412          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 412
GFTFGTYA                                                              8

SEQ ID NO: 413          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 413
ISASG                                                                 5

SEQ ID NO: 414          moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 414
EVQLLESGGG LVQPGGSLRL SCAASGFTFG TYAMTWVRQA PGKGLEWVSS ISASGYYANY      60
AGSVKGRFTI SRDNSKNTLY LQMNSLRAED TAVYYCARPY LGDRRSYGFD HWGQGTLVTV     120
SS                                                                   122

SEQ ID NO: 415          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
```

```
SEQUENCE: 415
gaagtgcagc tgctggaaag cggtggcggt ctggtgcagc caggtggtag cctgcgcctg   60
agctgtgccg caagcgggtt tacattcggc acctatgcaa tgacttgggt gcgccaagca  120
ccaggcaaag gcctggaatg ggtgagtagc attagcgcat ccggatatta cgctaactac  180
gcaggcagcg tcaaaggccg ctttaccatt agtcgcgata acagcaaaaa caccctgtat  240
ctgcaaatga acagcctgcg ggcagaagat accgcagttt attattgcgc gcgacccttat  300
ctgggtgacc gtcgtagcta tggtttcgac cactggggcc agggcaccct ggttactgtc  360
tcgagc                                                              366

SEQ ID NO: 416            moltype = AA  length = 452
FEATURE                   Location/Qualifiers
REGION                    1..452
                          note = source = /note="Description of Artificial Sequence:
                           Synthetic polypeptide"
source                    1..452
                          mol_type = protein
                          organism = synthetic construct
SEQUENCE: 416
EVQLLESGGG LVQPGGSLRL SCAASGFTFG TYAMTWVRQA PGKGLEWVSS ISASGYYANY   60
AGSVKGRFTI SRDNSKNTLY LQMNSLRAED TAVYYCARPY LGDRRSYGFD HWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 417            moltype = DNA  length = 1356
FEATURE                   Location/Qualifiers
misc_feature              1..1356
                          note = source = /note="Description of Artificial Sequence:
                           Synthetic polynucleotide"
source                    1..1356
                          mol_type = other DNA
                          organism = synthetic construct
SEQUENCE: 417
gaagtgcagc tgctggaaag cggtggcggt ctggtgcagc caggtggtag cctgcgcctg   60
agctgtgccg caagcgggtt tacattcggc acctatgcaa tgacttgggt gcgccaagca  120
ccaggcaaag gcctggaatg ggtgagtagc attagcgcat ccggatatta cgctaactac  180
gcaggcagcg tcaaaggccg ctttaccatt agtcgcgata acagcaaaaa caccctgtat  240
ctgcaaatga acagcctgcg ggcagaagat accgcagttt attattgcgc gcgacccttat  300
ctgggtgacc gtcgtagcta tggtttcgac cactggggcc agggcaccct ggttactgtc  360
tcgagcgcgt cgaccaaagg ccccagcgtg ttccctctgg cccccagcag caagagcacc  420
tctggcggaa cagccgccct gggctgcctg gtcaaggact acttcccga gcccgtgacc  480
gtgtcctgga actctggcgc cctgaccagc ggcgtgcaca cctttccagc cgtgctccag  540
agcagcggcc tgtacagcct gagcagcgtc gtgaccgtgc ccagcagcag cctgggcacc  600
cagacctaca tctgcaacgt gaaccacaag cccagcaaca aaggtggac aagcgggtg   660
gaacccaaga gctgcgacaa gacccacacc tgtcccccct gccctgcccc tgaagcggcg  720
ggaggcccct ccgtgttcct gttcccccca aagcctaagg acaccctgat gatcagccgg  780
acccccgaag tgacctgcgt ggtggtggac gtgtcccacg aggaccctga agtgaagttt  840
aattgtacg tggacggcgt ggaagtgcac aacgccaaga ccaagccccgag agaggaacag  900
tacaacagca cctaccgggt ggtgtccgtg ctgaccgtgc tgcaccagga ctggctgaac  960
ggcaaagagt acaagtgcaa ggtgtccaac aaggcccctgc ctgccccat cgagaaaacc 1020
atcagcaagg ccaaaggcca gccccgcgag ccccaggtgt acacactgcc cctagccgg  1080
gaagagatga ccaagaacca ggtgtccctg acctgcctgc tgaagggctt ctacccagc  1140
gacattgccg tggaatggga gagcaacggc cagcccgaga acaactacaa gaccaccccc 1200
cctgtgctgg acagcgacgg ctcattcttc ctgtacagca agctgaccgt ggacaagagc 1260
cggtggcagc agggcaacgt gttcagctgc tccgtgatgc acgaggccct gcacaaccac 1320
tacacccaga gtccctgag cctgagcccc ggcaag                             1356

SEQ ID NO: 418            moltype = AA  length = 10
FEATURE                   Location/Qualifiers
REGION                    1..10
                          note = source = /note="Description of Artificial Sequence:
                           Synthetic peptide"
source                    1..10
                          mol_type = protein
                          organism = synthetic construct
SEQUENCE: 418
GFTFSDYAIS                                                          10

SEQ ID NO: 419            moltype = AA  length = 17
FEATURE                   Location/Qualifiers
REGION                    1..17
                          note = source = /note="Description of Artificial Sequence:
                           Synthetic peptide"
source                    1..17
                          mol_type = protein
                          organism = synthetic construct
```

```
SEQUENCE: 419
SISGGGYHTQ YAGSVKG                                                          17

SEQ ID NO: 420          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 420
DYAIS                                                                        5

SEQ ID NO: 421          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 421
GFTFSDY                                                                      7

SEQ ID NO: 422          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 422
SGGGYH                                                                       6

SEQ ID NO: 423          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 423
GFTFSDYA                                                                     8

SEQ ID NO: 424          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 424
ISGGGYHT                                                                     8

SEQ ID NO: 425          moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 425
EVQLLESGGG LVQPGGSLRL SCAASGFTFS DYAISWVRQA PGKGLEWVSS ISGGGYHTQY            60
AGSVKGRFTI SRDNSKNTLY LQMNSLRAED TAVYYCARPY LGDRRSYGFD HWGQGTLVTV           120
SS                                                                         122

SEQ ID NO: 426          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
```

```
SEQUENCE: 426
gaagtgcagc tgctggaaag cggtggcggt ctggtgcagc caggtggtag cctgcgcctg    60
agctgtgccg caagcggctt tacctttcc gactatgcaa tcagctgggt gcgccaagca   120
ccaggcaaag gcctggaatg ggtgagcagc atttccgggg ggggtatca tacacaatat   180
gcaggatccg tgaaaggccg ctttaccatt agtcgcgata acagcaaaaa caccctgtat   240
ctgcaaatga acagcctgcg ggcagaagat accgcagttt attattgcgc gcgaccttat   300
ctgggtgacc gtcgtagcta tggtttcgac cactggggcc agggcaccct ggttactgtc   360
tcgagc                                                              366

SEQ ID NO: 427        moltype = AA  length = 452
FEATURE               Location/Qualifiers
REGION                1..452
                      note = source = /note="Description of Artificial Sequence:
                       Synthetic polypeptide"
source                1..452
                      mol_type = protein
                      organism = synthetic construct
SEQUENCE: 427
EVQLLESGGG LVQPGGSLRL SCAASGFTFS DYAISWVRQA PGKGLEWVSS ISGGGYHTQY    60
AGSVKGRFTI SRDNSKNTLY LQMNSLRAED TAVYYCARPY LGDRRSYGFD HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 428        moltype = DNA  length = 1356
FEATURE               Location/Qualifiers
misc_feature          1..1356
                      note = source = /note="Description of Artificial Sequence:
                       Synthetic polynucleotide"
source                1..1356
                      mol_type = other DNA
                      organism = synthetic construct
SEQUENCE: 428
gaagtgcagc tgctggaaag cggtggcggt ctggtgcagc caggtggtag cctgcgcctg    60
agctgtgccg caagcggctt tacctttcc gactatgcaa tcagctgggt gcgccaagca   120
ccaggcaaag gcctgggaatg ggtgagcagc atttccgggg ggggtatca tacacaatat   180
gcaggatccg tgaaaggccg ctttaccatt agtcgcgata acagcaaaaa caccctgtat   240
ctgcaaatga acagcctgcg ggcagaagat accgcagttt attattgcgc gcgaccttat   300
ctgggtgacc gtcgtagcta tggtttcgac cactggggcc agggcaccct ggttactgtc   360
tcgagcgcgt cgaccaaagg ccccagcgtg ttccctctgg ccccagcgag cagcaccacc   420
tctggcggaa cagccgccct gggctgcctg gtcaaggact acttcccga gcccgtgacc   480
gtgtcctgga actctggcgc cctgaccagc ggcgtgcaca cctttccagc cgtgctccag   540
agcagcggcc tgtacagcct gagcagcgtc gtgaccgtgc ccagcagcag cctgggcacc   600
cagacctaca tctgcaacgt gaaccacaag cccagcaaca caaaggtgga caagcgggtg   660
gaacccaaga gctgcgacaa gacccacacc tgtccccct gccctgcccc tgaagcggcc   720
ggaggcccct ccgtgttcct gttccccca aagcctaagg acaccctgat gatcagccgg   780
acccccgaag tgacctgcgt ggtggtggac gtgtcccacg aggaccctga agtgaagttt   840
aattgtacg tggacggcgt ggaagtgcac aacgccaaga ccaagcccag agaggaacag   900
tacaacagca cctaccgggt ggtgtccgtg ctgaccgtgc tgcaccagga ctggctgaac   960
ggcaaagagt acaagtgcaa ggtgtccaac aaggccctgc ctgccccat cgagaaaacc  1020
atcagcaagg ccaaaggcca gccccgcgag ccccaggtgt acacactgcc cctagccgg  1080
gaagagatga ccaagaacca ggtgtccctg acctgcctgg tgaagggctt ctacccagg  1140
gacattgccg tggaatggga gagcaacggc cagcccgaga caactacaa gaccaccccc  1200
cctgtgctgg acagcgacgg ctcattcttc ctgtacagca agctgaccgt ggacaagagc  1260
cggtggcagc agggcaacgt gttcagctgc tccgtgatgc acgaggccct gcacaaccac  1320
tacacccaga gtccctgag cctgagcccc ggcaag                             1356

SEQ ID NO: 429        moltype = AA  length = 17
FEATURE               Location/Qualifiers
VARIANT               1
                      note = /replace="V"
VARIANT               3
                      note = /replace="E"
VARIANT               5
                      note = /replace="K"
VARIANT               7
                      note = /replace="N"
VARIANT               9
                      note = /replace="T"
VARIANT               10
                      note = /replace="F"
SITE                  1..17
                      note = /note="Variant residues given in the sequence have
                       no preference with respect to those in the annotations for
                       variant positions"
REGION                1..17
```

```
                        note = source = /note="Description of Artificial Sequence:
                         Synthetic peptide"
source                  1..17
                        mol_type = protein
                        organism = synthetic construct
SEQUENCE: 429
AISSDGSYIY YADSVKG                                                        17

SEQ ID NO: 430          moltype = AA  length = 9
FEATURE                 Location/Qualifiers
VARIANT                 1
                        note = /replace="Q"
VARIANT                 3
                        note = /replace="E" or "T" or "I"
VARIANT                 4
                        note = /replace="W"
VARIANT                 5
                        note = /replace="V" or "R" or "A" or "T" or "M"
VARIANT                 6
                        note = /replace="V" or "R" or "A"
SITE                    1..9
                        note = /note="Variant residues given in the sequence have
                         no preference with respect to those in the annotations for
                         variant positions"
REGION                  1..9
                        note = source = /note="Description of Artificial Sequence:
                         Synthetic peptide"
source                  1..9
                        mol_type = protein
                        organism = synthetic construct
SEQUENCE: 430
MQSYEKPRT                                                                  9

SEQ ID NO: 431          moltype = AA  length = 6
FEATURE                 Location/Qualifiers
VARIANT                 1
                        note = /replace="E"
VARIANT                 3
                        note = /replace="K"
VARIANT                 5
                        note = /replace="N"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 431
SSDGSY                                                                     6

SEQ ID NO: 432          moltype = AA  length = 6
FEATURE                 Location/Qualifiers
VARIANT                 1
                        note = /replace="E" or "T" or "I"
VARIANT                 2
                        note = /replace="W"
VARIANT                 3
                        note = /replace="V" or "R" or "A" or "T" or "M"
VARIANT                 4
                        note = /replace="V" or "R" or "A"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 432
SYEKPR                                                                     6

SEQ ID NO: 433          moltype = AA  length = 8
FEATURE                 Location/Qualifiers
```

```
                        -continued

VARIANT                 2
                        note = /replace="E"
VARIANT                 4
                        note = /replace="K"
VARIANT                 6
                        note = /replace="N"
VARIANT                 8
                        note = /replace="T"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 433
ISSDGSYI                                                                        8

SEQ ID NO: 434          moltype = AA  length = 9
FEATURE                 Location/Qualifiers
VARIANT                 3
                        note = /replace="E" or "T" or "I"
VARIANT                 5
                        note = /replace="R" or "A" or "T" or "M"
VARIANT                 6
                        note = /replace="V" or "R" or "A"
SITE                    1..9
                        note = /note="Variant residues given in the sequence have
                         no preference with respect to those in the annotations for
                         variant positions"
REGION                  1..9
                        note = source = /note="Description of Artificial Sequence:
                         Synthetic peptide"
source                  1..9
                        mol_type = protein
                        organism = synthetic construct
SEQUENCE: 434
QQSWVKPRT                                                                       9

SEQ ID NO: 435          moltype = AA  length = 6
FEATURE                 Location/Qualifiers
VARIANT                 1
                        note = /replace="E" or "T" or "I"
VARIANT                 3
                        note = /replace="R" or "A" or "T" or "M"
VARIANT                 4
                        note = /replace="V" or "R" or "A"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 435
SWVKPR                                                                          6

SEQ ID NO: 436          moltype = AA  length = 10
FEATURE                 Location/Qualifiers
VARIANT                 5
                        note = /replace="S" or "Q"
SITE                    1..10
                        note = /note="Variant residues given in the sequence have
                         no preference with respect to those in the annotations for
                         variant positions"
REGION                  1..10
                        note = source = /note="Description of Artificial Sequence:
                         Synthetic peptide"
source                  1..10
                        mol_type = protein
                        organism = synthetic construct
SEQUENCE: 436
GFTFNTHYIH                                                                     10
```

```
SEQ ID NO: 437          moltype = AA  length = 17
FEATURE                 Location/Qualifiers
VARIANT                 3
                        note = /replace="G"
VARIANT                 4
                        note = /replace="G"
VARIANT                 5
                        note = /replace="Q"
VARIANT                 7
                        note = /replace="Q" or "G"
VARIANT                 8
                        note = /replace="N" or "M"
VARIANT                 10
                        note = /replace="L"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 437
SISSSGSSTY YADSVKG                                                           17

SEQ ID NO: 438          moltype = AA  length = 7
FEATURE                 Location/Qualifiers
VARIANT                 5
                        note = /replace="S" or "Q"
SITE                    1..7
                        note = /note="Variant residues given in the sequence have
                         no preference with respect to those in the annotations for
                         variant positions"
REGION                  1..7
                        note = source = /note="Description of Artificial Sequence:
                         Synthetic peptide"
source                  1..7
                        mol_type = protein
                        organism = synthetic construct
SEQUENCE: 438
GFTFNTH                                                                       7

SEQ ID NO: 439          moltype = AA  length = 6
FEATURE                 Location/Qualifiers
VARIANT                 1
                        note = /replace="G"
VARIANT                 2
                        note = /replace="G"
VARIANT                 3
                        note = /replace="Q"
VARIANT                 5
                        note = /replace="Q" or "G"
VARIANT                 6
                        note = /replace="N" or "M"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 439
SSSGSS                                                                        6

SEQ ID NO: 440          moltype = AA  length = 8
FEATURE                 Location/Qualifiers
VARIANT                 5
                        note = /replace="S" or "Q"
SITE                    1..8
                        note = /note="Variant residues given in the sequence have
                         no preference with respect to those in the annotations for
                         variant positions"
REGION                  1..8
```

```
                        note = source = /note="Description of Artificial Sequence:
                         Synthetic peptide"
source                  1..8
                        mol_type = protein
                        organism = synthetic construct
SEQUENCE: 440
GFTFNTHY                                                                        8

SEQ ID NO: 441          moltype = AA  length = 8
FEATURE                 Location/Qualifiers
VARIANT                 2
                        note = /replace="G"
VARIANT                 3
                        note = /replace="G"
VARIANT                 4
                        note = /replace="Q"
VARIANT                 6
                        note = /replace="Q" or "G"
VARIANT                 7
                        note = /replace="N" or "M"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 441
ISSSGSST                                                                        8

SEQ ID NO: 442          moltype = AA  length = 17
FEATURE                 Location/Qualifiers
VARIANT                 4
                        note = /replace="G"
VARIANT                 7
                        note = /replace="Q"
VARIANT                 8
                        note = /replace="N"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 442
SISSSGSSTY YADSVKG                                                              17

SEQ ID NO: 443          moltype = AA  length = 6
FEATURE                 Location/Qualifiers
VARIANT                 2
                        note = /replace="G"
VARIANT                 5
                        note = /replace="Q"
VARIANT                 6
                        note = /replace="N"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 443
SSSGSS                                                                          6

SEQ ID NO: 444          moltype = AA  length = 8
FEATURE                 Location/Qualifiers
VARIANT                 3
                        note = /replace="G"
```

-continued

```
VARIANT                 6
                        note = /replace="Q"
VARIANT                 7
                        note = /replace="N"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 444
ISSSGSST                                                                          8

SEQ ID NO: 445          moltype = AA  length = 10
FEATURE                 Location/Qualifiers
VARIANT                 3
                        note = /replace="T"
VARIANT                 6
                        note = /replace="K" or "R"
VARIANT                 8
                        note = /replace="Y"
VARIANT                 9
                        note = /replace="L"
VARIANT                 10
                        note = /replace="N"
SITE                    1..10
                        note = /note="Variant residues given in the sequence have
                         no preference with respect to those in the annotations for
                         variant positions"
REGION                  1..10
                        note = source = /note="Description of Artificial Sequence:
                         Synthetic peptide"
source                  1..10
                        mol_type = protein
                        organism = synthetic construct
SEQUENCE: 445
GFSFSSYWIS                                                                       10

SEQ ID NO: 446          moltype = AA  length = 17
FEATURE                 Location/Qualifiers
VARIANT                 1
                        note = /replace="N"
VARIANT                 3
                        note = /replace="H"
VARIANT                 5
                        note = /replace="Q" or "H"
VARIANT                 6
                        note = /replace="A"
VARIANT                 7
                        note = /replace="H" or "L"
VARIANT                 9
                        note = /replace="K"
VARIANT                 10
                        note = /replace="K" or "R"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 446
SIKQSGSETY YVESVKG                                                               17

SEQ ID NO: 447          moltype = AA  length = 5
FEATURE                 Location/Qualifiers
VARIANT                 1
                        note = /replace="K" or "R"
VARIANT                 3
                        note = /replace="Y"
VARIANT                 4
                        note = /replace="L"
```

| | |
|---|---|
| VARIANT | 5 |
| | note = /replace="N" |
| SITE | 1..5 |
| | note = /note="Variant residues given in the sequence have no preference with respect to those in the annotations for variant positions" |
| REGION | 1..5 |
| | note = source = /note="Description of Artificial Sequence: Synthetic peptide" |
| source | 1..5 |
| | mol_type = protein |
| | organism = synthetic construct |
| SEQUENCE: 447 | |
| SYWIS | 5 |
| | |
| SEQ ID NO: 448 | moltype = AA  length = 7 |
| FEATURE | Location/Qualifiers |
| VARIANT | 3 |
| | note = /replace="T" |
| VARIANT | 6 |
| | note = /replace="K" or "R" |
| SITE | 1..7 |
| | note = /note="Variant residues given in the sequence have no preference with respect to those in the annotations for variant positions" |
| REGION | 1..7 |
| | note = source = /note="Description of Artificial Sequence: Synthetic peptide" |
| source | 1..7 |
| | mol_type = protein |
| | organism = synthetic construct |
| SEQUENCE: 448 | |
| GFSFSSY | 7 |
| | |
| SEQ ID NO: 449 | moltype = AA  length = 6 |
| FEATURE | Location/Qualifiers |
| VARIANT | 1 |
| | note = /replace="H" |
| VARIANT | 3 |
| | note = /replace="Q" or "H" |
| VARIANT | 4 |
| | note = /replace="A" |
| VARIANT | 5 |
| | note = /replace="H" or "L" |
| SITE | 1..6 |
| | note = /note="Variant residues given in the sequence have no preference with respect to those in the annotations for variant positions" |
| REGION | 1..6 |
| | note = source = /note="Description of Artificial Sequence: Synthetic peptide" |
| source | 1..6 |
| | mol_type = protein |
| | organism = synthetic construct |
| SEQUENCE: 449 | |
| KQSGSE | 6 |
| | |
| SEQ ID NO: 450 | moltype = AA  length = 8 |
| FEATURE | Location/Qualifiers |
| VARIANT | 3 |
| | note = /replace="T" |
| VARIANT | 6 |
| | note = /replace="K" or "R" |
| VARIANT | 8 |
| | note = /replace="Y" |
| SITE | 1..8 |
| | note = /note="Variant residues given in the sequence have no preference with respect to those in the annotations for variant positions" |
| REGION | 1..8 |
| | note = source = /note="Description of Artificial Sequence: Synthetic peptide" |
| source | 1..8 |
| | mol_type = protein |
| | organism = synthetic construct |
| SEQUENCE: 450 | |
| GFSFSSYW | 8 |
| | |
| SEQ ID NO: 451 | moltype = AA  length = 8 |

```
FEATURE              Location/Qualifiers
VARIANT              2
                     note = /replace="H"
VARIANT              4
                     note = /replace="Q" or "H"
VARIANT              5
                     note = /replace="A"
VARIANT              6
                     note = /replace="H" or "L"
VARIANT              8
                     note = /replace="K"
SITE                 1..8
                     note = /note="Variant residues given in the sequence have
                      no preference with respect to those in the annotations for
                      variant positions"
REGION               1..8
                     note = source = /note="Description of Artificial Sequence:
                      Synthetic peptide"
source               1..8
                     mol_type = protein
                     organism = synthetic construct
SEQUENCE: 451
IKQSGSET                                                                        8

SEQ ID NO: 452       moltype = AA  length = 10
FEATURE              Location/Qualifiers
VARIANT              6
                     note = /replace="R"
VARIANT              8
                     note = /replace="Y"
VARIANT              10
                     note = /replace="N"
SITE                 1..10
                     note = /note="Variant residues given in the sequence have
                      no preference with respect to those in the annotations for
                      variant positions"
REGION               1..10
                     note = source = /note="Description of Artificial Sequence:
                      Synthetic peptide"
source               1..10
                     mol_type = protein
                     organism = synthetic construct
SEQUENCE: 452
GFTFSSYWIS                                                                     10

SEQ ID NO: 453       moltype = AA  length = 17
FEATURE              Location/Qualifiers
VARIANT              5
                     note = /replace="H"
VARIANT              6
                     note = /replace="A"
VARIANT              7
                     note = /replace="L"
VARIANT              9
                     note = /replace="K"
VARIANT              10
                     note = /replace="R"
SITE                 1..17
                     note = /note="Variant residues given in the sequence have
                      no preference with respect to those in the annotations for
                      variant positions"
REGION               1..17
                     note = source = /note="Description of Artificial Sequence:
                      Synthetic peptide"
source               1..17
                     mol_type = protein
                     organism = synthetic construct
SEQUENCE: 453
SIHQQGHETK YVESVKG                                                             17

SEQ ID NO: 454       moltype = AA  length = 5
FEATURE              Location/Qualifiers
VARIANT              1
                     note = /replace="R"
VARIANT              3
                     note = /replace="Y"
VARIANT              5
                     note = /replace="N"
SITE                 1..5
```

```
                              note = /note="Variant residues given in the sequence have
                               no preference with respect to those in the annotations for
                               variant positions"
REGION                        1..5
                              note = source = /note="Description of Artificial Sequence:
                               Synthetic peptide"
source                        1..5
                              mol_type = protein
                              organism = synthetic construct
SEQUENCE: 454
SYWIS                                                                              5

SEQ ID NO: 455                moltype = AA  length = 7
FEATURE                       Location/Qualifiers
VARIANT                       6
                              note = /replace="R"
SITE                          1..7
                              note = /note="Variant residues given in the sequence have
                               no preference with respect to those in the annotations for
                               variant positions"
REGION                        1..7
                              note = source = /note="Description of Artificial Sequence:
                               Synthetic peptide"
source                        1..7
                              mol_type = protein
                              organism = synthetic construct
SEQUENCE: 455
GFTFSSY                                                                            7

SEQ ID NO: 456                moltype = AA  length = 6
FEATURE                       Location/Qualifiers
VARIANT                       3
                              note = /replace="H"
VARIANT                       4
                              note = /replace="A"
VARIANT                       5
                              note = /replace="L"
SITE                          1..6
                              note = /note="Variant residues given in the sequence have
                               no preference with respect to those in the annotations for
                               variant positions"
REGION                        1..6
                              note = source = /note="Description of Artificial Sequence:
                               Synthetic peptide"
source                        1..6
                              mol_type = protein
                              organism = synthetic construct
SEQUENCE: 456
HQQGHE                                                                             6

SEQ ID NO: 457                moltype = AA  length = 8
FEATURE                       Location/Qualifiers
VARIANT                       6
                              note = /replace="R"
VARIANT                       8
                              note = /replace="Y"
SITE                          1..8
                              note = /note="Variant residues given in the sequence have
                               no preference with respect to those in the annotations for
                               variant positions"
REGION                        1..8
                              note = source = /note="Description of Artificial Sequence:
                               Synthetic peptide"
source                        1..8
                              mol_type = protein
                              organism = synthetic construct
SEQUENCE: 457
GFTFSSYW                                                                           8

SEQ ID NO: 458                moltype = AA  length = 8
FEATURE                       Location/Qualifiers
VARIANT                       4
                              note = /replace="H"
VARIANT                       5
                              note = /replace="A"
VARIANT                       6
                              note = /replace="L"
VARIANT                       8
                              note = /replace="K"
```

|               |                                                                                                                                              |
|---------------|----------------------------------------------------------------------------------------------------------------------------------------------|
| SITE          | 1..8<br>note = /note="Variant residues given in the sequence have no preference with respect to those in the annotations for variant positions" |
| REGION        | 1..8<br>note = source = /note="Description of Artificial Sequence: Synthetic peptide"                                                         |
| source        | 1..8<br>mol_type = protein<br>organism = synthetic construct                                                                                  |
| SEQUENCE: 458 |                                                                                                                                              |
| IHQQGHET      | 8                                                                                                                                            |
|               |                                                                                                                                              |
| SEQ ID NO: 459 | moltype = AA  length = 11                                                                                                                   |
| FEATURE       | Location/Qualifiers                                                                                                                          |
| VARIANT       | 2<br>note = /replace="S"                                                                                                                     |
| VARIANT       | 3<br>note = /replace="L"                                                                                                                     |
| VARIANT       | 4<br>note = /replace="P"                                                                                                                     |
| VARIANT       | 6<br>note = /replace="L"                                                                                                                     |
| SITE          | 1..11<br>note = /note="Variant residues given in the sequence have no preference with respect to those in the annotations for variant positions" |
| REGION        | 1..11<br>note = source = /note="Description of Artificial Sequence: Synthetic peptide"                                                       |
| source        | 1..11<br>mol_type = protein<br>organism = synthetic construct                                                                                |
| SEQUENCE: 459 |                                                                                                                                              |
| GAVAGQLGFD H  | 11                                                                                                                                           |
|               |                                                                                                                                              |
| SEQ ID NO: 460 | moltype = AA  length = 7                                                                                                                    |
| FEATURE       | Location/Qualifiers                                                                                                                          |
| VARIANT       | 7<br>note = /replace="N"                                                                                                                     |
| SITE          | 1..7<br>note = /note="Variant residues given in the sequence have no preference with respect to those in the annotations for variant positions" |
| REGION        | 1..7<br>note = source = /note="Description of Artificial Sequence: Synthetic peptide"                                                        |
| source        | 1..7<br>mol_type = protein<br>organism = synthetic construct                                                                                 |
| SEQUENCE: 460 |                                                                                                                                              |
| GNSNRPS       | 7                                                                                                                                            |
|               |                                                                                                                                              |
| SEQ ID NO: 461 | moltype = AA  length = 11                                                                                                                   |
| FEATURE       | Location/Qualifiers                                                                                                                          |
| VARIANT       | 4<br>note = /replace="D" or "G"                                                                                                              |
| VARIANT       | 5<br>note = /replace="S" or "A"                                                                                                              |
| VARIANT       | 6<br>note = /replace="P" or "F"                                                                                                              |
| VARIANT       | 7<br>note = /replace="T" or "P"                                                                                                              |
| VARIANT       | 8<br>note = /replace="S" or "R"                                                                                                              |
| VARIANT       | 9<br>note = /replace="S" or "F"                                                                                                              |
| VARIANT       | 10<br>note = /replace="S" or "V"                                                                                                             |
| SITE          | 1..11<br>note = /note="Variant residues given in the sequence have no preference with respect to those in the annotations for variant positions" |
| REGION        | 1..11<br>note = source = /note="Description of Artificial Sequence: Synthetic peptide"                                                       |
| source        | 1..11<br>mol_type = protein<br>organism = synthetic construct                                                                                |

```
SEQUENCE: 461
QSYYTSSHGP V                                                                     11

SEQ ID NO: 462          moltype = AA  length = 8
FEATURE                 Location/Qualifiers
VARIANT                 2
                        note = /replace="D" or "G"
VARIANT                 3
                        note = /replace="S" or "A"
VARIANT                 4
                        note = /replace="P" or "F"
VARIANT                 5
                        note = /replace="T" or "P"
VARIANT                 6
                        note = /replace="S" or "R"
VARIANT                 7
                        note = /replace="S" or "F"
VARIANT                 8
                        note = /replace="S" or "V"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 462
YYTSSHGP                                                                          8

SEQ ID NO: 463          moltype = AA  length = 13
FEATURE                 Location/Qualifiers
VARIANT                 4
                        note = /replace="S"
VARIANT                 5
                        note = /replace="L"
VARIANT                 6
                        note = /replace="P"
VARIANT                 8
                        note = /replace="L"
SITE                    1..13
                        note = /note="Variant residues given in the sequence have
                         no preference with respect to those in the annotations for
                         variant positions"
REGION                  1..13
                        note = source = /note="Description of Artificial Sequence:
                         Synthetic peptide"
source                  1..13
                        mol_type = protein
                        organism = synthetic construct
SEQUENCE: 463
ARGAVAGQLG FDH                                                                   13

SEQ ID NO: 464          moltype = AA  length = 10
FEATURE                 Location/Qualifiers
VARIANT                 5
                        note = /replace="G"
VARIANT                 6
                        note = /replace="T"
VARIANT                 9
                        note = /replace="M"
VARIANT                 10
                        note = /replace="T"
SITE                    1..10
                        note = /note="Variant residues given in the sequence have
                         no preference with respect to those in the annotations for
                         variant positions"
REGION                  1..10
                        note = source = /note="Description of Artificial Sequence:
                         Synthetic peptide"
source                  1..10
                        mol_type = protein
                        organism = synthetic construct
SEQUENCE: 464
GFTFSSYAIS                                                                       10

SEQ ID NO: 465          moltype = AA  length = 17
```

```
FEATURE                 Location/Qualifiers
VARIANT                 1
                        note = /replace="S"
VARIANT                 4
                        note = /replace="S" or "G"
VARIANT                 5
                        note = /replace="H"
VARIANT                 7
                        note = /replace="Y"
VARIANT                 8
                        note = /replace="Y"
VARIANT                 9
                        note = /replace="A"
VARIANT                 10
                        note = /replace="R" or "N"
VARIANT                 13
                        note = /replace="G"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 465
AISASGGSTY YAESVKG                                                            17

SEQ ID NO: 466          moltype = AA  length = 5
FEATURE                 Location/Qualifiers
VARIANT                 1
                        note = /replace="T"
VARIANT                 4
                        note = /replace="M"
VARIANT                 5
                        note = /replace="T"
SITE                    1..5
                        note = /note="Variant residues given in the sequence have
                         no preference with respect to those in the annotations for
                         variant positions"
REGION                  1..5
                        note = source = /note="Description of Artificial Sequence:
                         Synthetic peptide"
source                  1..5
                        mol_type = protein
                        organism = synthetic construct
SEQUENCE: 466
SYAIS                                                                          5

SEQ ID NO: 467          moltype = AA  length = 7
FEATURE                 Location/Qualifiers
VARIANT                 5
                        note = /replace="G"
VARIANT                 6
                        note = /replace="T"
SITE                    1..7
                        note = /note="Variant residues given in the sequence have
                         no preference with respect to those in the annotations for
                         variant positions"
REGION                  1..7
                        note = source = /note="Description of Artificial Sequence:
                         Synthetic peptide"
source                  1..7
                        mol_type = protein
                        organism = synthetic construct
SEQUENCE: 467
GFTFSSY                                                                        7

SEQ ID NO: 468          moltype = AA  length = 6
FEATURE                 Location/Qualifiers
VARIANT                 2
                        note = /replace="S" or "G"
VARIANT                 3
                        note = /replace="H"
VARIANT                 5
                        note = /replace="Y"
VARIANT                 6
```

```
                        note = /replace="Y"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 468
SASGGS                                                                              6

SEQ ID NO: 469          moltype = AA  length = 8
FEATURE                 Location/Qualifiers
VARIANT                 5
                        note = /replace="G"
VARIANT                 6
                        note = /replace="T"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 469
GFTFSSYA                                                                            8

SEQ ID NO: 470          moltype = AA  length = 8
FEATURE                 Location/Qualifiers
VARIANT                 3
                        note = /replace="G"
VARIANT                 4
                        note = /replace="H"
VARIANT                 6
                        note = /replace="Y"
VARIANT                 7
                        note = /replace="Y"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 470
ISSSGGST                                                                            8

SEQ ID NO: 471          moltype = AA  length = 17
FEATURE                 Location/Qualifiers
VARIANT                 4
                        note = /replace="S"
VARIANT                 5
                        note = /replace="H"
VARIANT                 9
                        note = /replace="A"
VARIANT                 10
                        note = /replace="N"
VARIANT                 13
                        note = /replace="G"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 471
```

```
SISASGYYTR YAESVKG                                                                       17

SEQ ID NO: 472          moltype = AA  length = 6
FEATURE                 Location/Qualifiers
VARIANT                 2
                        note = /replace="S"
VARIANT                 3
                        note = /replace="H"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 472
SASGYY                                                                                    6

SEQ ID NO: 473          moltype = AA  length = 5
FEATURE                 Location/Qualifiers
VARIANT                 3
                        note = /replace="S" or "G"
VARIANT                 4
                        note = /replace="H"
SITE                    1..5
                        note = /note="Variant residues given in the sequence have
                         no preference with respect to those in the annotations for
                         variant positions"
REGION                  1..5
                        note = source = /note="Description of Artificial Sequence:
                         Synthetic peptide"
source                  1..5
                        mol_type = protein
                        organism = synthetic construct
SEQUENCE: 473
ISASG                                                                                     5
```

The invention claimed is:

1. An isolated nucleic acid or nucleic acids encoding the amino acid sequence of an anti-NPR1 antibody or antigen binding fragment, wherein the antibody or antigen binding fragment comprises three heavy chain complementarity determining regions (HCDR1, HCDR2, and HCDR3) and three light chain complementarity determining regions (LCDR1, LCDR2, and LCDR3) selected from:

```
                (I)
         SEQ ID NO: 28  (HCDR1),
         SEQ ID NO: 119 (HCDR2),
         SEQ ID NO: 30  (HCDR3),
         SEQ ID NO: 41  (LCDR1),
         SEQ ID NO: 42  (LCDR2), and
         SEQ ID NO: 134 (LCDR3);

(II)
         SEQ ID NO: 31  (HCDR1),
         SEQ ID NO: 119 (HCDR2),
         SEQ ID NO: 30  (HCDR3),
         SEQ ID NO: 41  (LCDR1),
         SEQ ID NO: 42  (LCDR2), and
         SEQ ID NO: 134 (LCDR3);

(III)
         SEQ ID NO: 32  (HCDR1),
         SEQ ID NO: 120 (HCDR2),
         SEQ ID NO: 30  (HCDR3),
         SEQ ID NO: 44  (LCDR1),
         SEQ ID NO: 45  (LCDR2), and
         SEQ ID NO: 135 (LCDR3); or (IV)
         SEQ ID NO: 34  (HCDR1),
         SEQ ID NO: 121 (HCDR2),
         SEQ ID NO: 36  (HCDR3),
         SEQ ID NO: 47  (LCDR1),
         SEQ ID NO: 45  (LCDR2), and
         SEQ ID NO: 134 (LCDR3).
```

2. A vector comprising the isolated nucleic acid(s) of claim 1.

3. A host cell comprising the isolated nucleic acid(s) of claim 1.

4. A method of producing an isolated anti-NPR1 antibody or antigen binding fragment, comprising culturing the host cell of claim 3 under conditions suitable for producing the antibody or antigen binding fragment.

5. The isolated nucleic acid(s) of claim 1, wherein the antibody or antigen binding fragment comprises:
   (a) a heavy chain variable region comprising an amino acid sequence of SEQ ID NO: 201, and a light chain variable region comprising an amino acid sequence of SEQ ID NO: 136; or
   (b) a heavy chain variable region comprising an amino acid sequence of SEQ ID NO: 122, and a light chain variable region comprising an amino acid sequence of SEQ ID NO: 136.

6. A vector comprising the isolated nucleic acid(s) of claim 5.

7. A host cell comprising the isolated nucleic acid(s) of claim 5.

8. A method of producing an isolated anti-NPR1 antibody or antigen binding fragment, comprising culturing the host cell of claim 7 under conditions suitable for producing the antibody or antigen binding fragment.

9. The isolated nucleic acid(s) of claim 1, wherein the antibody or antigen binding fragment comprises:
(a) a heavy chain comprising an amino acid sequence of SEQ ID NO: 203, and a light chain comprising an amino acid sequence of SEQ ID NO: 138; or
(b) a heavy chain comprising an amino acid sequence of SEQ ID NO: 208, and a light chain comprising an amino acid sequence of SEQ ID NO: 138.

10. A vector comprising the isolated nucleic acid(s) of claim 9.

11. A host cell comprising the isolated nucleic acid(s) of claim 9.

12. A method of producing an isolated anti-NPR1 antibody or antigen binding fragment, comprising culturing the host cell of claim 11 under conditions suitable for producing the antibody or antigen binding fragment.

\* \* \* \* \*